US011813272B2

(12) United States Patent
Taylor et al.

(10) Patent No.: US 11,813,272 B2
(45) Date of Patent: Nov. 14, 2023

(54) ACTIVE AGENTS AND METHODS OF THEIR USE FOR THE TREATMENT OF METABOLIC DISORDERS AND NONALCOHOLIC FATTY LIVER DISEASE

(71) Applicant: Flagship Pioneering Innovations V, Inc., Cambridge, MA (US)

(72) Inventors: Steven John Taylor, Winchester, MA (US); John Robert Proudfoot, Newtown, CT (US); Mi-Jeong Kim, Boston, MA (US); Kathleen Nudel, Jamaica Plain, MA (US); Timothy F. Briggs, Waltham, MA (US); Afrand Kamali Sarvestani, Somerville, MA (US); Leonard Buckbinder, East Greenwich, RI (US); Bernard Lanter, Somerville, MA (US); Ferdinand Edward Massari, Beverly, MA (US); Koji Yasuda, Boston, MA (US); Spencer Cory Peck, Watertown, MA (US); Cheri Snedeker, Boston, MA (US); Diana Le, Reading, MA (US); Jessica Alexander, Waltham, MA (US); Anna Liang, Everett, MA (US); Dinara Gunasekera, Cambridge, MA (US); David Arthur Berry, Waban, MA (US); John Patrick Casey, Jr., Boston, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 16/950,120

(22) Filed: Nov. 17, 2020

(65) Prior Publication Data

US 2021/0177877 A1 Jun. 17, 2021

Related U.S. Application Data

(63) Continuation of application No. 16/803,411, filed on Feb. 27, 2020, now Pat. No. 10,953,027, which is a continuation of application No. PCT/US2019/035680, filed on Jun. 5, 2019.

(60) Provisional application No. 62/828,958, filed on Apr. 3, 2019, provisional application No. 62/776,448, filed on Dec. 6, 2018, provisional application No. 62/776,455, filed on Dec. 6, 2018, provisional application No. 62/680,977, filed on Jun. 5, 2018, provisional application No. 62/680,976, filed on Jun. 5, 2018.

(51) Int. Cl.
*A61K 31/7028* (2006.01)
*A61P 3/10* (2006.01)
*A61K 45/06* (2006.01)

(52) U.S. Cl.
CPC .......... *A61K 31/7028* (2013.01); *A61K 45/06* (2013.01); *A61P 3/10* (2018.01)

(58) Field of Classification Search
CPC ........ A61K 31/7028; A61K 45/06; A61P 3/10
USPC .......................................................... 514/25
See application file for complete search history.

(56) References Cited

U.S. PATENT DOCUMENTS

| | | | |
|---|---|---|---|
| 4,696,919 A | 9/1987 | Hinohara et al. |
| 5,677,340 A | 10/1997 | Yu et al. |
| 6,075,132 A | 6/2000 | Mandai et al. |
| 6,784,177 B2 | 8/2004 | Cohn et al. |
| 7,544,816 B2 | 6/2009 | Chan et al. |
| 7,700,646 B2 | 4/2010 | Anderson et al. |
| 7,838,463 B2 | 11/2010 | Bickers et al. |
| 8,076,484 B2 | 12/2011 | Hsu |
| 8,304,551 B2 | 11/2012 | Milne et al. |
| 9,255,062 B2 | 2/2016 | Berni Canani et al. |
| 9,713,603 B2 | 7/2017 | Chan et al. |
| 10,953,027 B2 | 3/2021 | Taylor et al. |
| 2004/0033480 A1 | 2/2004 | Wong |
| 2006/0148758 A1 | 7/2006 | Anastassides |
| 2007/0082944 A1 | 4/2007 | Stapleton et al. |
| 2008/0004341 A1 | 1/2008 | Rosa Brunet et al. |
| 2010/0144651 A1 | 6/2010 | Nilsson et al. |
| 2010/0310615 A1 | 12/2010 | Vercauteren |
| 2012/0010284 A1 | 1/2012 | Bezwada |
| 2013/0030047 A1 | 1/2013 | Fereidoon et al. |
| 2013/0052285 A1 | 2/2013 | Song et al. |
| 2013/0261045 A1 | 10/2013 | Shytle et al. |
| 2014/0378541 A1 | 12/2014 | Chan et al. |
| 2015/0056194 A1 | 2/2015 | Hsu |

(Continued)

FOREIGN PATENT DOCUMENTS

| | | |
|---|---|---|
| CN | 104024213 A | 9/2014 |
| CN | 104940181 A | 9/2015 |

(Continued)

OTHER PUBLICATIONS

Van Hul et al. Reduced obesity, diabetes, and steatosis upon cinnamon and grape pomace are associated with changes in gut microbiota and markers of gut barrier. Am J Physiol Endocrinol Metab 314: E334-E352, 2018. First published Sep. 5, 2017. (Year: 2017).*

Porras et al. Protective effect of quercetin on high-fat diet-induced non-alcoholic fatty liver disease in mice is mediated by modulating intestinal microbiota imbalance and related gut-liver axis activation. Free Radical Biology and Medicine 102 (2017) 188-202. (Year: 2017).*

(Continued)

*Primary Examiner* — Yih-Horng Shiao
(74) *Attorney, Agent, or Firm* — Clark & Elbing LLP

(57) ABSTRACT

Disclosed herein are active agents, compositions containing them, unit dosage forms containing them, and methods of their use, e.g., for treating a metabolic disorder or nonalcoholic fatty liver disease or for modulating a metabolic marker or nonalcoholic fatty liver disease marker.

9 Claims, 48 Drawing Sheets

(56) References Cited

U.S. PATENT DOCUMENTS

| | | |
|---|---|---|
| 2016/0000753 A1 | 1/2016 | Rinsch et al. |
| 2016/0039781 A1 | 2/2016 | Dugar et al. |
| 2016/0144014 A1 | 5/2016 | Honda et al. |
| 2017/0143752 A1 | 5/2017 | Bernstein |
| 2020/0101030 A1 | 4/2020 | Casey, Jr. et al. |

FOREIGN PATENT DOCUMENTS

| | | | |
|---|---|---|---|
| CN | 106995474 A | | 8/2017 |
| CN | 107427489 A | | 12/2017 |
| DE | 19860698 A1 | | 7/2000 |
| EP | 3147279 A1 | | 3/2017 |
| KR | 10-2012-0088021 A | | 8/2012 |
| RO | 87311 A | | 11/1985 |
| WO | WO-2004/105779 A2 | | 12/2004 |
| WO | WO-2005/103026 A1 | | 11/2005 |
| WO | WO-2008/093984 A1 | | 8/2008 |
| WO | WO-2008/132552 A2 | | 11/2008 |
| WO | WO-2010/052356 A1 | | 5/2010 |
| WO | WO 2013/022846 | * | 2/2013 |
| WO | WO-2013022846 A2 | | 2/2013 |
| WO | WO-2013/115742 A1 | | 8/2013 |
| WO | WO-2015/019193 A2 | | 2/2015 |
| WO | WO-2016/013654 A1 | | 1/2016 |
| WO | WO-2016/025668 A1 | | 2/2016 |
| WO | WO-2016/086453 A1 | | 6/2016 |
| WO | WO-2016/137196 A1 | | 9/2016 |
| WO | WO-2017/114413 A1 | | 7/2017 |
| WO | WO-2017/122495 A1 | | 7/2017 |
| WO | WO-2017/132775 A1 | | 8/2017 |
| WO | WO-2018/226732 A1 | | 12/2018 |
| WO | WO-2019/236765 A1 | | 12/2019 |
| WO | WO-2019/236772 A1 | | 12/2019 |
| WO | WO-2020/037009 A1 | | 2/2020 |
| WO | WO-2021/222702 A1 | | 11/2021 |

OTHER PUBLICATIONS

"Glossary of Medical Education Terms," Institute of International Medical Education <http://www.iime.org/glossary.htm#P> retrieved Mar. 14, 2013 (23 pages).
Arpaia et al., "Metabolites Produced by Commensal Bacteria Promote Peripheral Regulatory T Cell Generation," available in PMC Jun. 19, 2014, published in final edited form as: Nature. 504(7480):451-455 (2013) (15 pages).
Besten et al., "Short-Chain Fatty Acids Protect Against High-Fat Diet-Induced Obesity via a PPAR-gamma-Dependent Switch From Lipogenesis to Fat Oxidation," Diabetes. 64(7):2398-408 (2015).
Bray et al., "A 6-month Randomized, Placebo-Controlled, Dose-Ranging Trial of Topiramate for Weight Loss in Obesity," Obes Res. 11(6):722-33 (2003).
Canfora et al., "Acetate: A Diet-Derived Key Metabolite in Energy Metabolism: Good or Bad in Context of Obesity and Glucose Homeostasis?" Curr Opin Clin Nutr Metab Care. 20(6):477-483 (2017).
Canfora et al., "Colonic Infusions of Short-Chain Fatty Acid Mixtures Promote Energy Metabolism in Overweight/Obese Men: A Randomized Crossover Trial," Sci Rep. 7:2360 (2017) (12 pages).
Canfora et al., "Short-chain Fatty Acids in Control of Body Weight and Insulin Sensitivity," Nat Rev Endocrinol. 11(10):577-91 (2015).
Chambers et al., "Control of appetite and energy intake by SCFA: what are the potential underlying mechanisms?," Proc Nutr Soc. 74(3):328-36 (2015).
Chambers et al., "Effects of targeted delivery of propionate to the human colon on appetite regulation, body weight maintenance and adiposity in overweight adults," Gut. 64(11):1744-54 (2015) (Supplementary Materials Included) (33 pages).
Cheng et al., "Synthesis and properties of macrocyclic butanoic acid conjugates as a promising delivery formulation for the nutrition of colon," Scientific World Journal. 2013:914234 (2013) (4 pages).

Extended European Seach Report for European Patent Application No. 19815045.0, dated Jun. 2, 2022 (30 pages).
Ferrannini et al., "How to measure insulin sensitivity," J Hypertens. 16(7):895-906 (1998).
Freeland et al., "Acute Effects of Intravenous and Rectal Acetate on Glucagon-Like peptide-1, Peptide YY, Ghrelin, Adiponectin and Tumour Necrosis Factor-Alpha," Br J Nutr. 103(3):460-6 (2010).
Greenblum et al., "Metagenomic Systems Biology of the Human Gut Microbiome Reveals Topological Shifts Associated With Obesity and Inflammatory Bowel Disease," Proc Natl Acad Sci USA. 109(2):594-9 (2012).
Hao et al., "Protective effects of L-arabinose in high-carbohydrate, high-fat diet-induced metabolic syndrome in rats," Food Nutr Res. 59:28886 (2015) (10 pages).
Herde et al., "Stereoselective acetylation of hemicellulosic C5-sugars," Carbohydr Res. 443-444:1-14 (2017).
International Search Report and Written Opinion for International Application No. PCT/US2019/035680, dated Oct. 9, 2019 (23 pages).
Kimura et al., "Free Fatty Acid Receptors in Health and Disease," Physiol Rev. 100(1):171-210 (2020).
Kimura et al., "The SCFA Receptor GPR43 and Energy Metabolism," Front Endocrinol (Lausanne). 5:85 (2014) (3 pages).
Kondo et al., "Vinegar Intake Reduces Body Weight, Body Fat Mass, and Serum Triglyceride Levels in Obese Japanese Subjects," Biosci Biotechnol Biochem. 73(8):1837-43 (2009) (8 pages).
Lim et al., "D-Xylose suppresses adipogenesis and regulates lipid metabolism genes in high-fat diet-induced obese mice," Nutr Res. 35(7):626-36 (2015).
Liu et al., "Small Molecules for Fat Combustion: Targeting Obesity," Acta Pharm Sin B. 9(2):220-236 (Mar. 2019).
Louchami et al., "Effects of the polyacetate esters of nutrient and nonnutrient monosaccharides on $^{45}$calcium efflux and insulin release from perifused rat pancreatic islets," Int J Pancreatol. 24(2):103-9 (1998).
Lu et al., "Tagatose, a new antidiabetic and obesity control drug," Diabetes Obes Metab. 10(2):109-34 (2008).
Mariño et al., "Gut Microbial Metabolites Limit the Frequency of Autoimmune T Cells and Protect Against Type 1 Diabetes," Nat Immunol. 18(5):552-562 (2017) (13 pages).
Partial Supplementary European Search Report for European Patent Application No. 19815045.0, dated Mar. 2, 2022 (32 pages).
Perry et al., "Acetate Mediates a Microbiome-Brain-beta-Cell Axis to Promote Metabolic Syndrome," available in PMC Dec. 8, 2016, published in final edited form as: Nature. 534(7606):213-7 (2016) (23 pages).
Petersen et al., "The Effects of Increased Acetate Turnover on Glucose-Induced Insulin Secretion in Lean and Obese Humans," J Clin Transl Sci. 3(1):18-20 (Jun. 2019).
Search Report and Written Opinion for Singaporean Patent Application No. 11202011698V, dated Apr. 4, 2022 (13 pages).
Sugiyama et al., "Bioavailability of Acetate From Two Vinegar Supplements: Capsule and Drink," J Nutr Sci Vitaminol (Tokyo). 56(4):266-9 (2010).
Thaiss et al., "Persistent Microbiome Alterations Modulate the Rate of Post-Dieting Weight Regain," Nature. 540(7634):544-551 (2016) (23 pages).
Topping et al., "Targeted delivery of short-chain fatty acids to the human large bowel," Am J Clin Nutr. 104(1):1-2 (2016).
Van der Beek et al., "Distal, Not Proximal, Colonic Acetate Infusions Promote Fat Oxidation and Improve Metabolic Markers in Overweight/Obese Men," Clin Sci (Lond). 130(22):2073-2082 (2016).
First Examination Report for Indian Application No. 202017057053, dated Aug. 17, 2022 (9 pages).
Hogg et al., "Resveratrol, Acetyl-Resveratrol, and Polydatin Exhibit Antigrowth Activity against 3D Cell Aggregates of the SKOV-3 and OVCAR-8 Ovarian Cancer Cell Lines," Obstet Gynecol Int. 2015:279591 (2015) (14 pages).
Oh et al., "Lipophilization of Resveratrol and Effects on Antioxidant Activities," J Agric Food Chem. 65(39):8617-25 (2017).
Che et al., "Effects of Astaxanthin and Docosahexaenoic-Acid-Acylated Astaxanthin on Alzheimer's Disease in APP/PS1 Double-Transgenic Mice," J Agric Food Chem. 66(19):4948-57 (2018).

(56) References Cited

OTHER PUBLICATIONS

"PubChem CID: 88064," PubChem, <https://pubchem.ncbi.nlm.nih.gov/compound/N-acetyl-l-alanine>, retrieved on Sep. 9, 2022 (48 pages).

Nomura et al., "Synthesis of L-Ascorbic Acid Acyl Derivatives stabilized against Oxidation," Chem Pharm Bull 14(9):1039-44 (1966).

Heebøll et al., "Effects of resveratrol in experimental and clinical non-alcoholic fatty liver disease," World J Hepatol. 6(4):188-98 (2014).

Preliminary Office Action for Brazilian Patent Application No. BR112020024695-6, dated May 6, 2023 (6 pages).

* cited by examiner

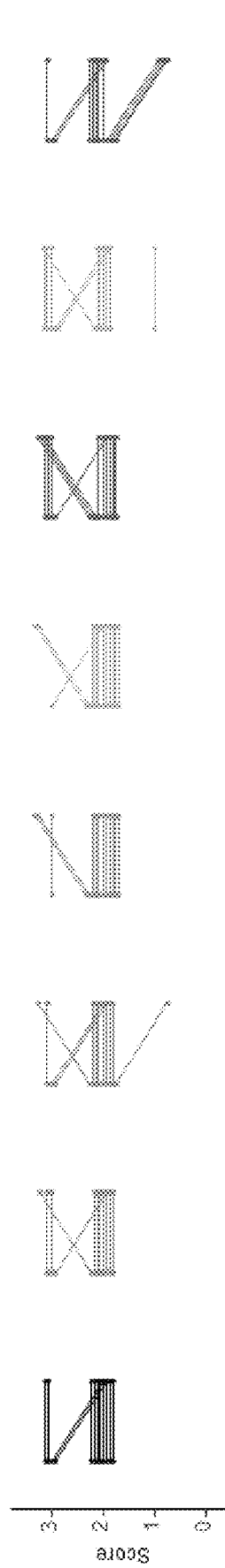
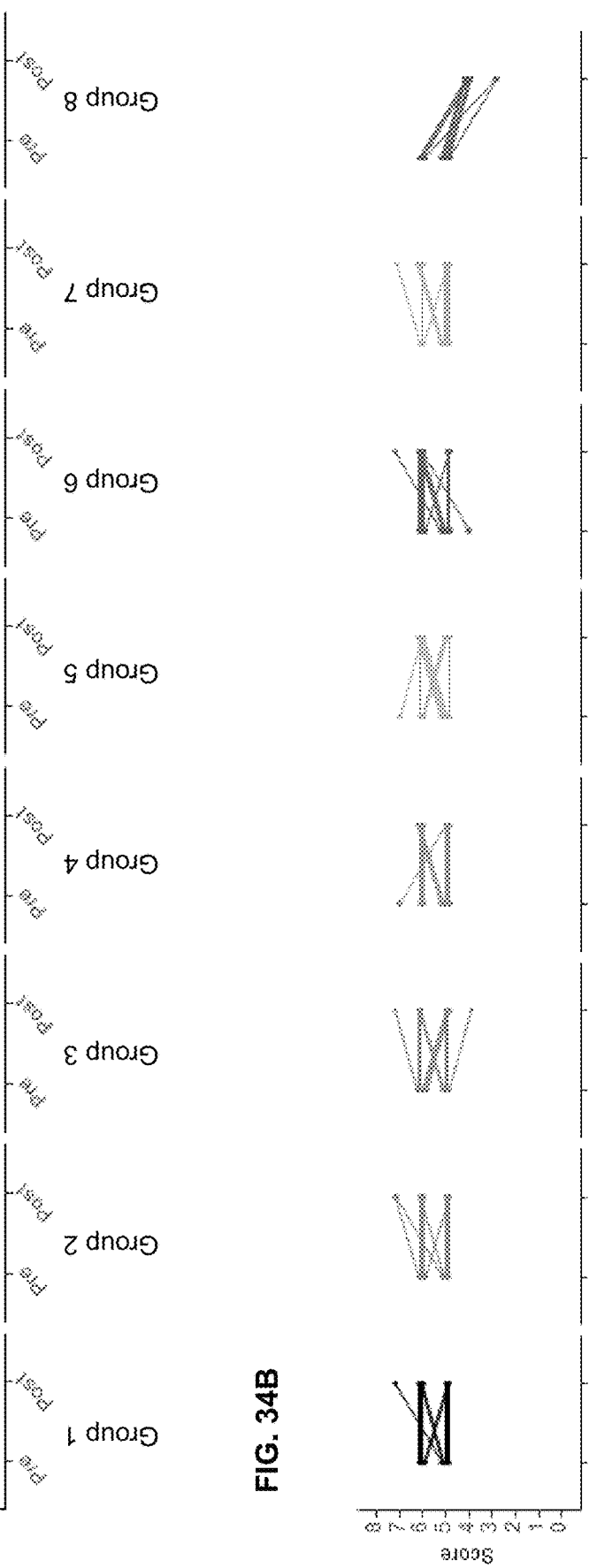
FIG. 34A
FIG. 34B

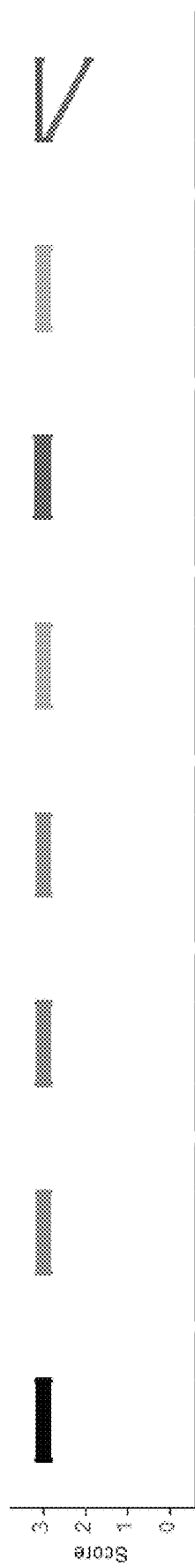
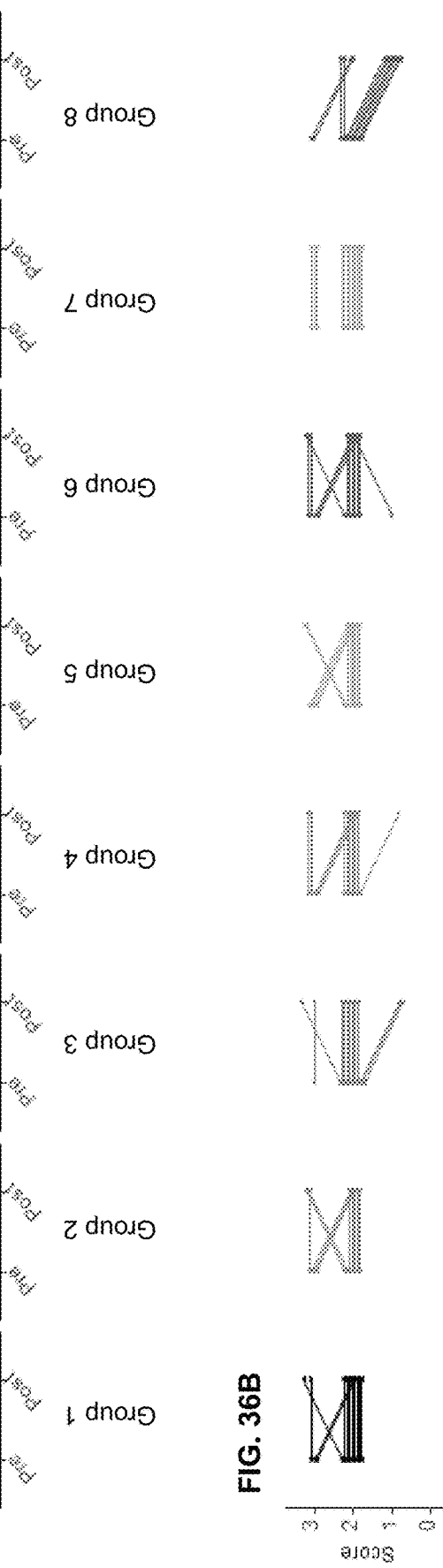
FIG. 36A
FIG. 36B

ACTIVE AGENTS AND METHODS OF THEIR USE FOR THE TREATMENT OF METABOLIC DISORDERS AND NONALCOHOLIC FATTY LIVER DISEASE

FIELD OF THE INVENTION

The invention relates compounds and methods of their medicinal use.

BACKGROUND

The increase in obesity incidence has reached epidemic proportions in the western world and more recently also in developing countries. Obesity is associated with significant co-morbidities such as cardiovascular diseases and type II diabetes. While bariatric surgery is a known treatment for obesity, this treatment is costly and risky. Pharmacological intervention is typically less efficacious and is often associated with adverse events.

Nonalcoholic fatty liver disease (NAFLD) is one of the most common forms of chronic liver disease, affecting an estimated 12% to 25% people in the United States. The main characteristic of NAFLD is fat accumulation (steatosis) in the liver. In NAFLD, the fat accumulation is not associated with excessive alcohol consumption.

Nonalcoholic steatohepatitis (NASH) is an advanced form of NAFLD. NASH is marked by liver inflammation, which may progress to scarring and irreversible liver damage. At its most severe, NASH can progress to cirrhosis and liver failure.

There is a need for methods and compositions useful for managing metabolic disorders and/or for treating NAFLD and NASH.

SUMMARY OF THE INVENTION

In general, the invention provides acylated active agents (e.g., an acylated catechin polyphenol, acylated carotenoid, acylated ellagic acid, acylated ellagic acid analogue, acylated ketone body or pre-ketone body, acylated stilbenoid, acylated S-adenosyl-L-methionine, acylated amino acid, acylated bile acid, acylated mesalamine, acylated metformin, acylated sugar, acylated shikimic acid, acylated vitamin, or acylated hydroxybenzoic acid), active agent combinations (e.g., combinations where a first agent is a stilbenoid, catechin polyphenol, carotenoid, bile acid, amino acid, hydroxybenzoic acid, shikimic acid, monosaccharide, or mesalamine, metformin, vitamin, S-adenosyl-L-methionine, and a second agent is a ketone body or pre-ketone body), compositions containing them (e.g., as unit dosage forms), and methods for modulating a metabolic marker or a nonalcoholic fatty liver disease marker in a subject or of treating a metabolic disorder or nonalcoholic fatty liver disease in a subject.

In some embodiments, the invention provides acylated active agents (e.g., acylated catechin polyphenols, acylated stilbenoids, acylated mesalamines, acylated sugars, acylated shikimic acids, and acylated hydroxybenzoic acids), active agent combinations (e.g., stilbenoid and pre-ketone body), compositions containing them (e.g., as unit dosage forms), and methods for modulating a metabolic marker in a subject or of treating a metabolic disorder in a subject. In certain embodiments, the invention provides acylated active agents (e.g., an acylated stilbenoid, acylated carotenoid, acylated vitamin, acylated catechin polyphenol, acylated S-adenosyl-L-methionine, acylated bile acid, acylated amino acid, acylated metformin, acylated sugar, or acylated ketone body or pre-ketone body), active agent combinations (e.g., stilbenoid and pre-ketone body), compositions containing them (e.g., as unit dosage forms), and methods for modulating a nonalcoholic fatty liver disease (e.g., nonalcoholic steatohepatitis) marker in a subject or of treating a nonalcoholic fatty liver disease (e.g., nonalcoholic steatohepatitis (NASH) with or without fibrosis, liver steatosis, or NASH with advanced fibrosis) in a subject.

In one aspect, the invention provides a method of modulating a metabolic marker or a nonalcoholic fatty liver disease marker in a subject in need thereof by administering to the subject an effective amount of an active agent. In a related aspect, the invention provides a method of treating a metabolic disorder or nonalcoholic fatty liver disease in a subject in need thereof by administering to the subject an effective amount of an active agent.

In some embodiments, the method is of modulating a metabolic marker. In certain embodiments, the method is of modulating a nonalcoholic fatty liver disease (e.g., nonalcoholic steatohepatitis) marker.

In another aspect, the invention provides a method of modulating a metabolic marker or a nonalcoholic fatty liver disease marker in a subject in need thereof by administering to the subject an effective amount of a first active agent and an effective amount of a second active agent. In another related aspect, the invention provides a method of treating a metabolic disorder or nonalcoholic fatty liver disease in a subject in need thereof by administering to the subject an effective amount of a first active agent and an effective amount of a second active agent.

In some embodiments, the method is of treating a metabolic disorder. In certain embodiments, the method is of treating nonalcoholic fatty liver disease (e.g., nonalcoholic steatohepatitis).

In some embodiments, the metabolic marker is for an obesity disorder. In other embodiments, the metabolic marker is for type II diabetes, prediabetes, insulin resistance, metabolic syndrome, hypercholesterolemia, atherosclerosis or hyperlipidemia.

In particular embodiments, the metabolic disorder is an obesity disorder. In certain embodiments, the metabolic disorder is type II diabetes, prediabetes, insulin resistance, metabolic syndrome, hypercholesterolemia, or hyperlipidemia.

In some embodiments, the total fat percentage, cellular adiposity, body mass index, rate of weight gain, abdominal fat quantity, ratio of white to brown fat, level of lipogenesis, or level of fat storage is reduced following the step of administering.

In certain embodiments, the subject is overweight. In further embodiments, the subject suffers from obesity. In yet further embodiments, the subject suffers from severe obesity, morbid obesity, or super obesity. In still further embodiments, the subject has a body mass index of at least 25 kg/m$^2$, at least 28 kg/m$^2$, at least 30 kg/m$^2$, at least 35 kg/m$^2$, or at least 45 kg/m$^2$.

In other embodiments, the level of insulin, GLP-1, or PYY is increased following the step of administering. In yet other embodiments, the level of blood sugar or hemoglobin A1c is reduced following the step of administering. In still other embodiments, the glucose tolerance is increased following the step of administering.

In some embodiments, the method reduces the level of alanine transaminase in the blood of the subject by at least 1% (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more; e.g., up to 100%) relative to the level of alanine transaminase in the blood of the subject prior to the administering step or relative to a control. In other embodiments, the method reduces the level of aspartate transaminase in the blood of the subject by at least 1% (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more; e.g., up to 100%) relative to the level of aspartate transaminase in the blood of the subject prior to the administering step or relative to a control. In yet other embodiments, the method reduces the liver weight of the subject by at least 1% relative to the liver weight of the subject prior to the administering step or relative to a control. In further embodiments, the method treats or reduces liver fibrosis.

In yet further embodiments, the subject suffers from nonalcoholic fatty liver disease (e.g., the subject is diagnosed with nonalcoholic fatty liver disease). In still further embodiments, the subject suffers from nonalcoholic steatohepatitis (e.g., the subject is diagnosed with nonalcoholic steatohepatitis).

In particular embodiments, the subject is a human. In certain embodiments, the subject is a cat or dog.

In some embodiments, the acylated active agent is an acylated stilbenoid, acylated carotenoid, acylated vitamin, acylated catechin polyphenol, acylated S-adenosyl-L-methionine, acylated bile acid, acylated amino acid, acylated metformin, acylated sugar, or acylated ketone body or pre-ketone body.

In some embodiments, the acylated active agent is an acylated stilbenoid. In further embodiments, the acylated stilbenoid is resveratrol having one, two, or three hydroxyl groups independently substituted with a fatty acid acyl or a group containing a ketone body or pre-ketone body.

In yet further embodiments, the acylated active agent is an acylated carotenoid. In still further embodiments, the acylated carotenoid is astaxanthin having one or two hydroxyl groups independently substituted with a fatty acid acyl or a group containing a ketone body or pre-ketone body.

In certain embodiments, the acylated active agent is an acylated vitamin. In particular embodiments, the acylated vitamin is a tocopherol or tocotrienol having a hydroxyl group substituted with a fatty acid acyl or a group containing a ketone body or pre-ketone body. In other embodiments, the acylated vitamin is ascorbic acid having one, two, three, or four hydroxyl groups independently substituted with a fatty acid acyl or a group containing a ketone body or pre-ketone body. In yet other embodiments, the acylated vitamin is a vitamin D having a hydroxyl group substituted with a fatty acid acyl or a group containing a ketone body or pre-ketone body. In still other embodiments, the vitamin D is cholecalciferol.

In some embodiments, the active agent is an acylated catechin polyphenol, acylated stilbenoid, acylated mesalamine, acylated sugar, acylated hydroxybenzoic acid, or acylated shikimic acid. In particular embodiments, following oral administration to the subject, the active agent is hydrolyzable in the gastrointestinal tract of the subject. In certain embodiments, the active agent releases at least one fatty acid. In further embodiments, the active agent is administered to the subject orally.

In certain embodiments, the active agent is acylated mesalamine. In some embodiments, the active agent is an acylated catechin polyphenol. In further embodiments, the active agent is an acylated stilbenoid. In yet further embodiments, the active agent is an acylated hydroxybenzoic acid.

In still further embodiments, the active agent is an acylated sugar. In particular embodiments, the active agent is an acylated shikimic acid.

In other embodiments, the acylated stilbenoid, acylated catechin polyphenol, acylated mesalamine, acylated sugar, acylated hydroxybenzoic acid, or acylated shikimic acid includes a group containing a fatty acid. In yet other embodiments, the group containing a fatty acid is a monosaccharide (e.g., arabinose, xylose, fructose, galactose, glucose, ribose, tagatose, fucose, and rhamnose), glucosinolate, sugar alcohol, or sugar acid having one or more hydroxyl groups substituted with a fatty acid acyl). In certain embodiments, the group containing a fatty acid is a monosaccharide (e.g., arabinose, xylose, fructose, galactose, glucose, ribose, tagatose, fucose, and rhamnose), sugar alcohol, or sugar acid having one or more hydroxyl groups substituted with a fatty acid acyl). In still other embodiments, the monosaccharide is L-arabinose, D-xylose, fructose, galactose, D-glucose, D-ribose, D-tagatose, L-fucose, or L-rhamnose (e.g., the monosaccharide is D-xylose). In further embodiments, the group containing a fatty acid is a fatty acid acyl. In yet further embodiments, the fatty acid is a short chain fatty acid (e.g., acetyl, propionyl, or butyryl). In still further embodiments, the short chain fatty acid is acetyl. In particular embodiments, the short chain fatty acid is butyryl.

In certain embodiments, the active agent (e.g., an acylated stilbenoid) includes at least one group containing a ketone body or pre-ketone body. In some embodiments, the active agent (e.g., acylated stilbenoid) includes at least one group containing a pre-ketone body. In further embodiments, the group containing a ketone body or pre-ketone body is a group containing a ketone body. In yet further embodiments, the group containing a ketone body or pre-ketone body is a group containing a pre-ketone body.

In particular embodiments, the acylated active agent is an acylated catechin polyphenol. In certain embodiments, the acylated catechin polyphenol is epigallocatechin gallate having one to eight hydroxyl groups independently substituted with a fatty acid acyl or a group containing a ketone body or pre-ketone body. In further embodiments, the acylated catechin polyphenol is silibinin having one to five hydroxyl groups independently substituted with a fatty acid acyl or a group containing a ketone body or pre-ketone body. In still further embodiments, the acylated catechin polyphenol is a compound of formula (I):

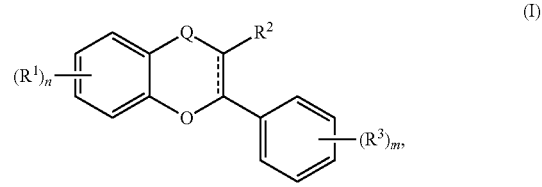

or a pharmaceutically acceptable salt thereof,
wherein
⫶ is a single carbon-carbon bond or double carbon-carbon bond;
Q is —CH$_2$— or —C(O)—;
each $R^1$ and each $R^3$ is independently H, halogen, —OR$^4$, phosphate, or sulfate;
$R^2$ is H or —OR$^4$;
each $R^4$ is independently H, optionally substituted alkyl, a monosaccharide, a sugar acid, a group containing a fatty acid, a group containing a ketone body or pre-ketone body, a group containing an amino acid metabolite, or benzoyl optionally substituted with 1, 2, 3, or 4 substituents independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate;

m is 0, 1, 2, 3, 4, or 5; and n is 1, 2, 3, or 4.

In further embodiments, each of n and m is independently 0, 1, 2, 3, or 4. In some embodiments, at least one $R^1$ is —$OR^A$. In yet further embodiments, each $R^A$ is independently H, optionally substituted alkyl, a monosaccharide, a sugar acid, a group containing a fatty acid, a group containing a ketone body or pre-ketone body, or benzoyl optionally substituted with 1, 2, 3, or 4 substituents independently selected from the group consisting of H, hydroxy, halogen, a group containing a fatty acid, a group containing a ketone body or pre-ketone body, an optionally substituted alkyl, an optionally substituted alkoxy, a monosaccharide, a sugar acid, phosphate, and sulfate. In still further embodiments, at least one $R^A$ is a group containing a fatty acid. In particular embodiments, at least one $R^A$ is a group containing a ketone body or pre-ketone body. In certain embodiments, at least one $R^A$ is benzoyl substituted with at least one group containing a fatty acid. In further embodiments, at least one $R^A$ is benzoyl substituted with at least one group containing a ketone body or pre-ketone body. In certain embodiments, at least one $R^A$ is benzoyl substituted with at least one group containing an amino acid metabolite.

In some embodiments, at least one $R^1$ is —$OR^A$, in which $R^A$ is a group containing a fatty acid, or provided that the compound comprises at least one group including a ketone body or pre-ketone body.

In certain embodiments, the acylated catechin polyphenol is a compound is of formula (I-a):

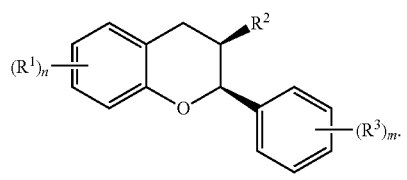

(I-a)

In particular embodiments, the acylated catechin polyphenol is a compound is of formula (I-b):

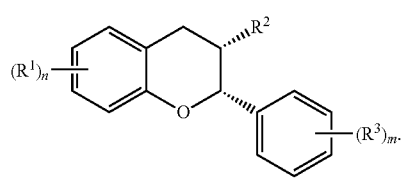

(I-b)

In further embodiments, the acylated catechin polyphenol is a compound is of formula (I-c):

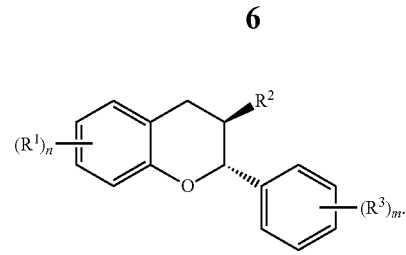

(I-c)

In yet further embodiments, the acylated catechin polyphenol is a compound is of formula (I-d):

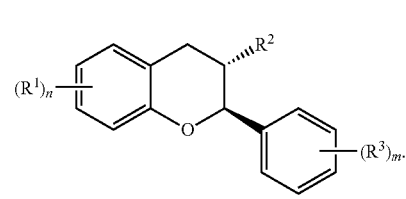

(I-d)

In certain embodiments, the acylated catechin polyphenol is a compound of formula (I-f):

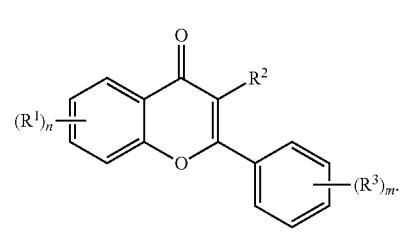

(I-f)

In still further embodiments, n is 2. In certain embodiments, m is 1. In particular embodiments, m is 2. In some embodiments, m is 3. In particular embodiments, each $R^1$ is independently —$OR^A$. In certain embodiments, each $R^3$ is independently H or —$OR^A$. In further embodiments, $R^2$ is H or —$OR^A$. In yet further embodiments, each $R^A$ is independently H, optionally substituted alkyl, a group containing a fatty acid, or a group containing a ketone body or pre-ketone body.

In other embodiments, the acylated catechin polyphenol is a compound of formula (I-e):

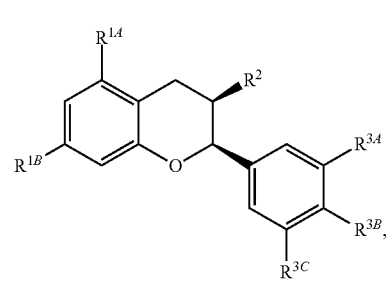

(I-e)

or a pharmaceutically acceptable salt thereof, wherein each of $R^{1A}$ and $R^{1B}$ is independently as defined for $R^1$; and each of $R^{3A}$, $R^{3B}$, and $R^{3C}$ is independently as defined for $R^3$.

In yet other embodiments, each of $R^{1A}$ and $R^{1B}$ is independently —$OR^A$. In still other embodiments, each of $R^{3A}$, $R^{3B}$, and $R^{3C}$ is independently H, halogen, or —$OR^A$. In some embodiments, $R^2$ is a group of formula:

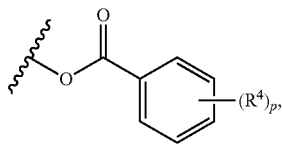

wherein p is 1, 2, 3, or 4, and each $R^4$ is independently selected from the group consisting of H, hydroxy, halogen, a group containing a fatty acid, a group containing a ketone body or pre-ketone body, an optionally substituted alkyl, an optionally substituted alkoxy, a monosaccharide, a sugar acid, phosphate, and sulfate.

In certain embodiments, p is 3. In particular embodiments, each $R^4$ is independently H, hydroxy, halogen, a group containing a fatty acid, a group containing a ketone body or pre-ketone body, or an optionally substituted alkoxy. In certain embodiments, $R^2$ is a group of formula:

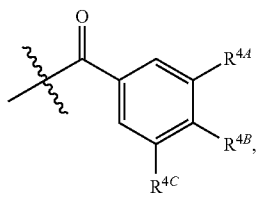

and
each of $R^{4A}$, $R^{4B}$, and $R^{4C}$ is as defined for $R^4$.

In further embodiments, each of $R^{4A}$, $R^{4B}$, and $R^{4C}$ is independently H, hydroxy, halogen, a group containing a fatty acid, a group containing a ketone body or pre-ketone body, or an optionally substituted alkoxy. In yet further embodiments, each $R^4$ is independently H, optionally substituted alkyl, fatty acid acyl, or optionally acylated monosaccharide.

In still further embodiments, the active agent (e.g., an acylated catechin polyphenol, acylated carotenoid, acylated ellagic acid, acylated ellagic acid analogue, acylated ketone body or pre-ketone body, acylated stilbenoid, acylated S-adenosyl-L-methionine, acylated amino acid, acylated bile acid, acylated mesalamine, acylated metformin, acylated sugar, acylated shikimic acid, acylated vitamin, or acylated hydroxybenzoic acid) includes at least one fatty acid acyl (e.g., a short chain fatty acid acyl or medium chain fatty acid acyl). In further embodiments, the active agent is an acylated catechin polyphenol, acylated stilbenoid, acylated mesalamine, acylated hydroxybenzoic acid, acylated sugar, or acylated shikimic acid. In certain embodiments, at least one fatty acid acyl is a short chain fatty acid acyl.

In some embodiments, the short chain fatty acid acyl is acetyl, propionyl, or butyryl. In certain embodiments, the short chain fatty acid acyl is acetyl. In particular embodiments, the short chain fatty acid acyl is butyryl. In further embodiments, the short chain fatty acid acyl is propionyl. In yet further embodiments, at least one fatty acid acyl is a medium chain fatty acid acyl (e.g., octanoyl).

In some embodiments, the active agent is an acylated sugar (e.g., an acylated sugar including a monosaccharide core). In certain embodiments, the monosaccharide core is xylose, arabinose, rhamnose, fucose, glucosamine, or tagatose. In particular embodiments, the active agent is a monosaccharide having one or more hydroxyls substituted with alkyl, acyl, a group containing a fatty acid, a group containing a ketone body or pre-ketone body, or a group containing an amino acid metabolite.

In certain embodiments, the active agent is an acylated hydroxybenzoic acid (e.g., an acylated hydroxybenzoic acid including gallic acid).

In some embodiments, the first active agent is a catechin polyphenol, stilbenoid, a monosaccharide, a hydroxybenzoic acid, shikimic acid, or mesalamine, and the second active agent is a ketone body or pre-ketone body. In certain embodiments, the first active agent is administered to the subject orally. In particular embodiments, the second active agent is administered to the subject orally. In further embodiments, the first and second active agents are administered to the subject separately (e.g., the first and second active agents are administered to the subject within 24 hours of each other). In yet further embodiments, the first and second active agents are administered to the subject concomitantly (e.g., the first and second active agents are administered to the subject in the same unit dosage form). In other embodiments, the first active agent is a stilbenoid (e.g., resveratrol). In yet other embodiments, the second active agent is a ketone body. In still other embodiments, the second active agent is a pre-ketone body. In some embodiments, the molar ratio of the first active agent to the second active agent is from 1:1 to 1:10.

In another aspect, the invention provides, a composition (e.g., a pharmaceutical composition, nutraceutical composition, food product, food additive, or dietary supplement) including an active agent. In some embodiments, the composition is provided in a unit dosage form. In other embodiments, the active agent is an acylated catechin polyphenol, acylated stilbenoid, acylated mesalamine, acylated hydroxybenzoic acid, acylated shikimic acid, or acylated sugar. In yet other embodiments, the active agent is a combination of a first active agent and a second active agent, where the first active agent is stilbenoid, catechin polyphenol, hydroxybenzoic acid, shikimic acid, monosaccharide, or mesalamine, and the second active agent is a ketone body or pre-ketone body.

In still other embodiments, the unit dosage form contains at least 0.5 g (e.g., at least 0.7 g, at least 1 g, or at least 2 g) of the active agent. In certain embodiments, the unit dosage form contains 10 g or less (e.g., 9 g or less, 8 g or less, 7 g or less, 6 g or less, 5 g or less) of the active agent. In particular embodiments, the unit dosage form contains 0.5-10 g (e.g., 0.7-10 g, 1-10 g, 2-10 g, 0.5-9 g, 0.7-9 g, 1-9 g, 2-9 g, 0.5-8 g, 0.7-8 g, 1-8 g, 2-8 g, 0.5-7 g, 0.7-7 g, 1-7 g, 2-7 g, 0.5-6 g, 0.7-6 g, 1-6 g, 2-6 g, 0.5-5 g, 0.7-5 g, 1-10 g, or 2-5 g) of the active agent.

In some embodiments, the unit dosage form is a pharmaceutical unit dosage form. In further embodiments, the unit dosage form is a nutraceutical dosage form. In yet further embodiments, the unit dosage form is a serving of a food product.

In still further embodiments, the active agent is the acylated catechin polyphenol. In some embodiments, the active agent is an acylated stilbenoid (e.g., an acylated resveratrol). In certain embodiments, the active agent is an acylated mesalamine. In certain embodiments, the active agent is an acylated hydroxybenzoic acid (e.g., an acylated hydroxybenzoic acid including gallic acid). In further embodiments, the active agent is an acylated sugar (e.g., an acylated sugar including a monosaccharide core, e.g., xylose, arabinose, rhamnose, fucose, glucosamine, tagatose, or ribose (e.g., xylose, arabinose, rhamnose, fucose, glucosamine, or tagatose)). In yet further embodiments, the active agent is an acylated shikimic acid.

In other embodiments, the acylated stilbenoid, acylated catechin polyphenol, or acylated mesalamine includes a group containing a fatty acid. In yet other embodiments, the group containing a fatty acid is a monosaccharide (e.g., arabinose, xylose, fructose, galactose, glucose, ribose, tagatose, fucose, and rhamnose), glucosinolate, sugar alcohol, or sugar acid having one or more hydroxyl groups substituted with a fatty acid acyl. In certain embodiments, the group containing a fatty acid is a monosaccharide (e.g., arabinose, xylose, fructose, galactose, glucose, ribose, tagatose, fucose, and rhamnose), sugar alcohol, or sugar acid having one or more hydroxyl groups substituted with a fatty acid acyl. In still other embodiments, the monosaccharide is L-arabinose, D-xylose, fructose, galactose, D-glucose, D-ribose, D-tagatose, L-fucose, or L-rhamnose (e.g., the monosaccharide is D-xylose). In further embodiments, the group containing a fatty acid is a fatty acid acyl. In yet further embodiments, the fatty acid is a short chain fatty acid (e.g., acetyl, propionyl, or butyryl). In still further embodiments, the short chain fatty acid is acetyl. In particular embodiments, the short chain fatty acid is butyryl.

In certain embodiments, the active agent (e.g., an acylated stilbenoid) includes at least one group containing a ketone body or pre-ketone body. In some embodiments, the active agent (e.g., acylated stilbenoid) includes at least one group containing a pre-ketone body. In further embodiments, the group containing a ketone body or pre-ketone body is a group containing a ketone body. In yet further embodiments, the group containing a ketone body or pre-ketone body is a group containing a pre-ketone body.

In still further embodiments, the acylated catechin polyphenol is a compound of formula (I):

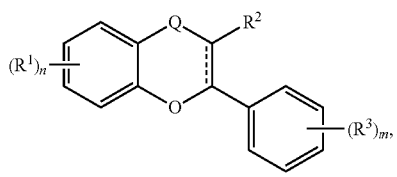

(I)

or a pharmaceutically acceptable salt thereof,
wherein
⫤ is a single carbon-carbon bond or double carbon-carbon bond;
Q is —$CH_2$— or —C(O)—;
each $R^1$ and each $R^3$ is independently H, halogen, —$OR^A$, phosphate, or sulfate;
$R^2$ is H or —$OR^A$;
each $R^A$ is independently H, optionally substituted alkyl, a monosaccharide, a sugar acid, a group containing a fatty acid, a group containing a ketone body or pre-ketone body, a group containing an amino acid metabolite, or benzoyl optionally substituted with 1, 2, 3, or 4 substituents independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate;
m is 0, 1, 2, 3, 4, or 5; and
n is 0, 1, 2, 3, or 4.

In some embodiments, at least one $R^1$ is —$OR^A$, in which $R^A$ is a group containing a fatty acid, a group containing a ketone body or pre-ketone body, a group containing an amino acid metabolite, or provided that the compound comprises at least one a group containing a fatty acid, a group containing a ketone body or pre-ketone body, or a group containing an amino acid metabolite. In some embodiments, at least one $R^1$ is —$OR^A$, in which $R^A$ is a group containing a fatty acid, or provided that the compound comprises at least one group including a ketone body or pre-ketone body.

In certain embodiments, the acylated catechin polyphenol is a compound is of formula (I-a):

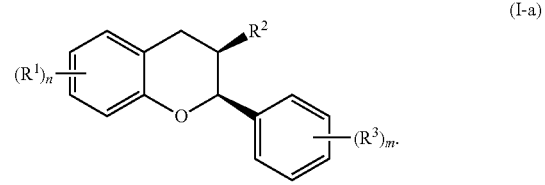

(I-a)

In particular embodiments, the acylated catechin polyphenol is a compound is of formula (I-b):

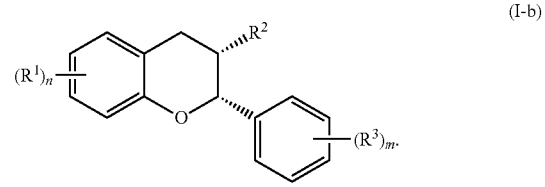

(I-b)

In further embodiments, the acylated catechin polyphenol is a compound is of formula (I-c):

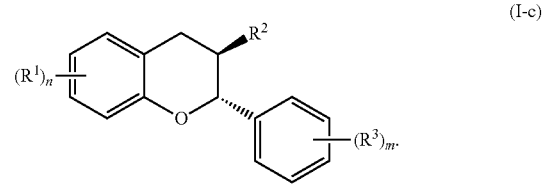

(I-c)

In yet further embodiments, the acylated catechin polyphenol is a compound is of formula (I-d):

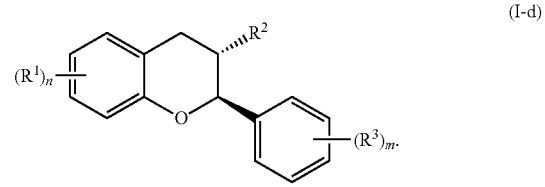

(I-d)

In certain embodiments, the acylated catechin polyphenol is a compound of formula (I-f):

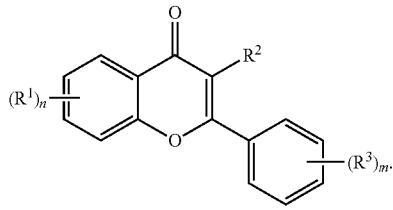

(I-f)

In still further embodiments, n is 2. In certain embodiments, m is 1. In particular embodiments, m is 2. In some embodiments, m is 3. In particular embodiments, each $R^1$ is independently —$OR^A$. In certain embodiments, each $R^3$ is independently H or —$OR^A$. In further embodiments, $R^2$ is H or —$OR^A$. In yet further embodiments, each $R^A$ is independently H, optionally substituted alkyl, a group containing a fatty acid, or a group containing a ketone body or pre-ketone body.

In other embodiments, the acylated catechin polyphenol is a compound is of formula (I-e):

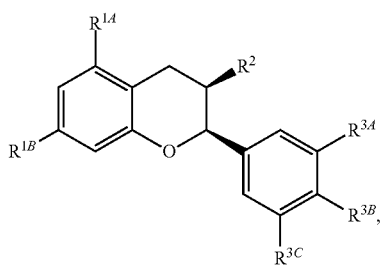

(I-e)

or a pharmaceutically acceptable salt thereof,
wherein each of $R^{1A}$ and $R^{1B}$ is independently as defined for $R^1$; and each of $R^{3A}$, $R^{3B}$, and $R^{3C}$ is independently as defined for $R^3$.

In yet other embodiments, each of $R^{1A}$ and $R^{1B}$ is independently —$OR^A$. In still other embodiments, each of $R^{3A}$, $R^{3B}$, and $R^{3C}$ is independently H, halogen, or —$OR^A$. In some embodiments, $R^2$ is a group of formula:

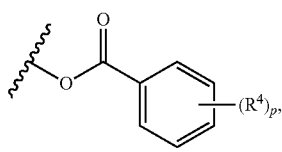

wherein p is 1, 2, 3, or 4, and each $R^4$ is independently selected from the group consisting of H, hydroxy, halogen, a group containing a fatty acid, a group containing a ketone body or pre-ketone body, an optionally substituted alkyl, an optionally substituted alkoxy, a monosaccharide, a sugar acid, phosphate, and sulfate.

In certain embodiments, p is 3. In particular embodiments, each $R^4$ is independently H, hydroxy, halogen, a group containing a fatty acid, a group containing a ketone body or pre-ketone body, or an optionally substituted alkoxy. In certain embodiments, $R^2$ is a group of formula:

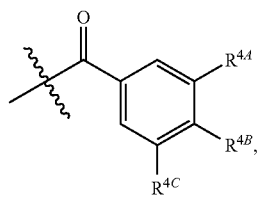

and
each of $R^{4A}$, $R^{4B}$, and $R^{4C}$ is as defined for $R^4$.

In further embodiments, each of $R^{4A}$, $R^{4B}$, and $R^{4C}$ is independently H, hydroxy, halogen, a group containing a fatty acid, a group containing a ketone body or pre-ketone body, or an optionally substituted alkoxy. In yet further embodiments, each $R^A$ is independently H, optionally substituted alkyl, fatty acid acyl, or optionally acylated monosaccharide.

In still further embodiments, the acylated catechin polyphenol includes at least one fatty acid acyl (e.g., a short chain fatty acid acyl). In some embodiments, the short chain fatty acid acyl is acetyl, propionyl, or butyryl. In certain embodiments, the short chain fatty acid acyl is acetyl. In particular embodiments, the short chain fatty acid acyl is butyryl.

In some embodiments, the active agent is a combination of a stilbenoid or catechin polyphenol with a ketone body or pre-ketone body. In certain embodiments, the molar ratio of the stilbenoid or catechin polyphenol to the ketone body or pre-ketone body is from 1:1 to 1:10. In particular embodiments, the active agent is a combination of a stilbenoid with a ketone body or pre-ketone body. In further embodiments, the active agent is a combination of a stilbenoid with a pre-ketone body. In yet further embodiments, the stilbenoid is resveratrol.

In yet another aspect, the invention provides an acylated stilbenoid of the following structure:

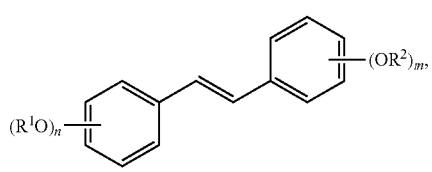

where
n is 1, 2, 3, or 4;
m is 1, 2, 3, or 4;
each $R^1$ is independently H, alkyl, acyl, a group containing a fatty acid, a group containing a ketone body or pre-ketone body, or a group containing an amino acid metabolite; and
each $R^2$ is independently H, alkyl, acyl, a group containing a fatty acid, a group containing a ketone body or pre-ketone body, or a group containing an amino acid metabolite;
wherein each group containing a fatty acid is independently a monosaccharide having one, two, three, or four hydroxyls substituted with fatty acid acyls;
provided that at least one $R^1$ or at least one $R^2$ is a group containing a fatty acid, a group containing a ketone body or pre-ketone body, or a group containing an amino acid metabolite.

In certain embodiments, n is 1. In particular embodiments, m is 2. In further embodiments, the acylated stilbenoid is a compound of the following structure:

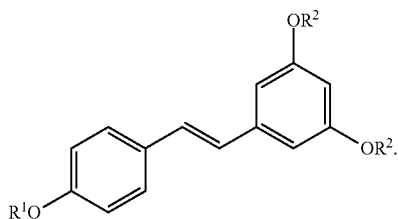

In yet further embodiments, at least one $R^1$ is a group containing a fatty acid. In still further embodiments, at least one $R^1$ is a group containing a ketone body or pre-ketone body. In particular embodiments, at least one $R^1$ is a group containing an amino acid metabolite. In certain embodiments, at least one $R^2$ is a group containing a fatty acid. In some embodiments, at least one $R^2$ is a group containing a ketone body or pre-ketone body. In further embodiments, at least one $R^2$ is a group containing an amino acid metabolite.

In still another aspect, the invention provides compounds and compositions (e.g., pharmaceutical compositions or nutraceutical compositions) containing the same. The compounds of the invention are the compounds described herein, e.g., an acylated catechin polyphenol, acylated carotenoid, acylated ellagic acid, acylated ellagic acid analogue, acylated ketone body or pre-ketone body, acylated stilbenoid, acylated S-adenosyl-L-methionine, acylated amino acid, acylated bile acid, acylated mesalamine, acylated metformin, acylated sugar, acylated shikimic acid, acylated vitamin, or acylated hydroxybenzoic acid.

Definitions

The term "active agent," as used herein, refers to an acylated active agent, catechin polyphenol, stilbenoid, ketone body, pre-ketone body, or fatty acid.

The term "active agent combination," as used herein, refers to a combination regimen including a first active agent and a second active agent. The first active agent may be, e.g., a catechin polyphenol, stilbenoid, mesalamine, hydroxybenzoic acid, shikimic acid, or monosaccharide. The second active agent may be, e.g., a ketone body or pre-ketone body. Non-limiting examples of active agent combinations include a stilbenoid (e.g., resveratrol) and a pre-ketone body (e.g., 1,3-butanediol). The first and second active agents may be administered together (e.g., in the same unit dosage form) or separately (e.g., within 24 hours of each other).

The term "acyl," as used herein, represents a chemical substituent of formula —C(O)—R, where R is alkyl, alkenyl, aryl, arylalkyl, cycloalkyl, heterocyclyl, heterocyclyl alkyl, heteroaryl, or heteroaryl alkyl. An optionally substituted acyl is an acyl that is optionally substituted as described herein for each group R. Additionally, an acyl may be a chemical substituent selected from the group consisting of a group containing a fatty acid, a group containing a ketone body or pre-ketone body, a group containing an amino acid metabolite, mesalamine acyl, and retinoic acid acyl. Non-limiting examples of acyl include fatty acid acyls (e.g., short chain fatty acid acyls (e.g., acetyl)), benzoyl (e.g., optionally substituted benzoyl), ketone body acyl, pre-ketone body acyl, sugar acid acyl (e.g., aldonyl, uronyl, ulosonyl), amino acid acyls, and amino acid metabolite acyls.

The term "acylated active agent," as used herein, represents a compound including two or more agents linked through ester bond(s), amide bond(s), carbonate linker(s), carbamate linker(s), and/or glycosidic bond(s). Non-limiting examples of acylated active agents include an acylated catechin polyphenol, acylated carotenoid, acylated ellagic acid, acylated ellagic acid analogue, acylated ketone body or pre-ketone body, acylated stilbenoid, acylated S-adenosyl-L-methionine, acylated amino acid, acylated bile acid, acylated mesalamine, acylated metformin, acylated shikimic acid, acylated sugar, acylated vitamin, or acylated hydroxybenzoic acid.

The term "acylated S-adenosyl-L-methionine," as used herein, represents S-adenosyl-L-methionine, in which at least one hydroxyl group is replaced with a substituent —OR, where each R is independently selected from the group consisting of an acyl, alkyl, a group containing a fatty acid, a group containing a ketone body or pre-ketone body, and a group containing an amino acid metabolite, provided that at least one R a group containing a fatty acid, a group containing a ketone body or pre-ketone body, or a group containing an amino acid metabolite.

The term "acylated amino acid," as used herein, represents an amino acid, in which at least one alcohol hydroxyl group, if present, or amino group is substituted with a group containing a fatty acid, a group containing a ketone body or pre-ketone body, or a group containing an amino acid metabolite. Non-limiting examples of an acylated amino acid include L-alanine having the amino group substituted with a group containing a fatty acid, a group containing a ketone body or pre-ketone body, or a group containing an amino acid metabolite.

The term "acylated bile acid," as used herein, represents a bile acid, in which at least one hydroxyl group is replaced with a substituent —OR, where each R is independently selected from the group consisting of an acyl, alkyl, a group containing a fatty acid, a group containing a ketone body or pre-ketone body, and a group containing an amino acid metabolite, provided that at least one R is a group containing a fatty acid, a group containing a ketone body or pre-ketone body, or a group containing an amino acid metabolite. Non-limiting examples of an acylated bile acid include ursodeoxycholic acid and obeticholic acid having one or two alcohol hydroxyl groups independent substituted with an acyl, alkyl, a group containing a ketone body or pre-ketone body, or a group containing an amino acid metabolite, provided that at least one hydroxyl group is substituted with a group containing a fatty acid, a group containing a ketone body or pre-ketone body, or a group containing an amino acid metabolite.

The term "acylated carotenoid," as used herein, represents a carotenoid, in which at least one hydroxyl group is replaced with a substituent —OR, where each R is independently selected from the group consisting of an acyl, alkyl, a group containing a fatty acid, a group containing a ketone body or pre-ketone body, and a group containing an amino acid metabolite, provided that at least one R is a group containing a ketone body or pre-ketone body, or a group containing an amino acid metabolite. Non-limiting examples of an acylated carotenoid include astaxanthin having one or both hydroxyl groups independently substituted with an acyl, alkyl, a group containing a ketone body or pre-ketone body, or a group containing an amino acid metabolite, provided that at least one hydroxyl is substituted with a group containing a fatty acid, a group containing a ketone body or pre-ketone body, or a group containing an amino acid metabolite.

The term "acylated catechin polyphenol," as used herein, represents a substituted compound having the core of formula (A):

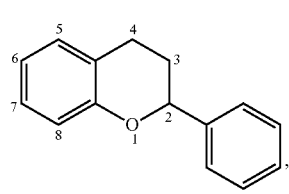

or a multimer thereof, or a salt thereof,
where the substituents are independently selected from the group consisting of —OR$^A$, —OCOO—R$^A$, —NHR$^B$, oxo, halogen, optionally substituted $C_{1-20}$ alkyl, optionally substituted $C_{2-20}$ alkenyl, optionally substituted thioalkyl, optionally substituted alkylsulfonyl, optionally substituted alkylsulfenyl, optionally substituted alkylsulfinyl, optionally substituted thioaryl, optionally substituted aryl thioalkyl, optionally substituted thioalkenyl, dialkylamino, sulfate, phosphate, ascorbic acid, optionally substituted heterocyclyl, nitro, amino acids, $C_{1-6}$ esters of amino acids, optionally acylated monosaccharide, and optionally acylated sugar acid, where each R$^A$ is independently H, optionally substituted alkyl, a group containing a fatty acid, a group containing a ketone body or pre-ketone body, a group containing an amino acid metabolite, or benzoyl optionally substituted with one, two, three, or four substituents independently selected from the group consisting of H, hydroxyl, halogen, a group containing a fatty acid, a group containing a ketone body or pre-ketone body, a group containing an amino acid metabolite, optionally substituted alkoxy, and optionally substituted alkyl, and where R$^B$ is independently H or optionally substituted alkyl;
where the carbon-carbon bond connecting carbon 2 and carbon 3 in formula (A) is a single bond or a double bond;
where the multimer includes a total of 2 or 3 cores of formula (A), each core substituted independently as described above; and
where two vicinal centers in core (A) may be further substituted with a group —(O)$_q$-L$^1$-L$^2$-, where q is 0 or 1, L1 is optionally substituted alkylene, optionally substituted alkenylene, or optionally substituted heterocyclylene; and L$^2$ is a covalent bond, optionally substituted heterocyclylene, or optionally substituted cycloalkylene;
provided that at least one of positions 5, 6, 7, and 8 is —OR$^A$, where R$^A$ is a group containing a fatty acid, a group containing a ketone body or pre-ketone body, a group containing an amino acid metabolite, or benzoyl optionally substituted with one, two, three, or four substituents independently selected from the group consisting of H, hydroxyl, a halogen, a group containing a fatty acid, a group containing a ketone body or pre-ketone body, an optionally substituted alkoxy, and an optionally substituted alkyl; and
provided that the substituted compound includes at least one group containing a fatty acid, group containing a ketone body or pre-ketone body, or group containing an amino acid metabolite.

The term "acylated catechin polyphenol" also represents a catechin polyphenol, in which at least one hydroxyl group is independently replaced with a substituent —OR, where each R is independently selected from the group consisting of an acyl, alkyl, group including a fatty acid, group including a ketone body or pre-ketone body, and group containing an amino acid metabolite, provided that at least one R is a group including a fatty acid, a group including a ketone body or pre-ketone body, or a group containing an amino acid metabolite. Non-limited examples of acylated catechin polyphenol include epigallocatechin gallate having one to eight hydroxyl groups independently substituted with an acyl, alkyl, group including a fatty acid, or group including a ketone body or pre-ketone body, provided that at least one hydroxyl is substituted with a group including a fatty acid or a group including a ketone body or pre-ketone body. For example, an acylated catechin polyphenol may be a compound of formula (I):

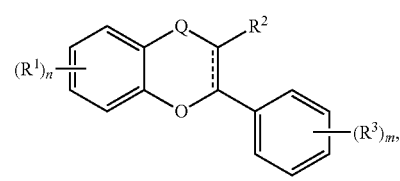

or a pharmaceutically acceptable salt thereof,
where
⫼ is a single carbon-carbon bond or double carbon-carbon bond;
Q is —CH$_2$— or —C(O)—;
each R$^1$ and each R$^3$ is independently H, halogen, —OR$^A$, phosphate, or sulfate;
R$^2$ is H or —OR$^A$;
each R$^A$ is independently H, optionally substituted alkyl, a monosaccharide, a sugar acid, a group containing a fatty acid, a group containing a ketone body or pre-ketone body, a group containing an amino acid metabolite, or benzoyl optionally substituted with 1, 2, 3, or 4 substituents independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate; and
each of n and m is independently 0, 1, 2, 3, or 4.

The term "acylated ellagic acid," as used herein, represents compounds of the following structures:

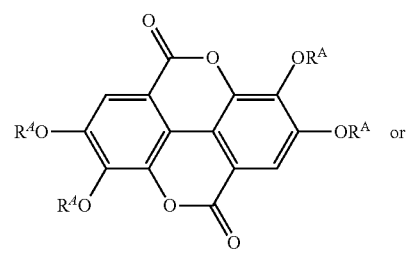

-continued

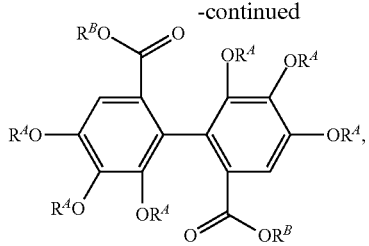

or a salt thereof, where each $R^A$ is independently H, alkyl, acyl, a group containing a fatty acid, a group containing a ketone body or pre-ketone body, or a group containing an amino acid metabolite; and each $R^B$ is independently H, alkyl, a group containing a fatty acid, a group containing a ketone body or pre-ketone body, or a group containing an amino acid metabolite; provided that at least one $R^A$ and/or at least one $R^B$, when present, is a group containing a fatty acid, a group containing a ketone body or pre-ketone body, or a group containing an amino acid metabolite.

The term "acylated ellagic acid analogue," as used herein, represents compounds of the following structure:

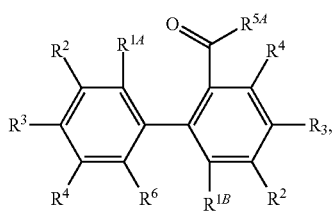

or a salt thereof,
where
each of $R^2$, $R^3$, and $R^4$ is independently H or $—OR^A$;
$R^6$ is H or $—(CO)—R^{5B}$;
$R^{1A}$ is H or $—OR^A$, and $R^{5A}$ is $—OH$ or $—OR^B$; or $R^{1A}$ and $R^{5A}$ combine to form $—O—$;
$R^{1B}$ is H or $—OR^A$, and $R^{5B}$ is absent, $—OH$, or $—OR^B$; or $R^{1B}$ and $R^{5B}$ combine to form $—O—$;
each $R^A$ is independently H, O-protecting group, alkyl, acyl, a group containing a fatty acid, a group containing a ketone body or pre-ketone body, or a group containing an amino acid metabolite;
each $R^B$ is independently H, O-protecting group, alkyl, a group containing a fatty acid, a group containing a ketone body or pre-ketone body, or a group containing an amino acid metabolite;
provided that at least one $R^A$ and/or at least one $R^B$ is a group containing a fatty acid, a group containing a ketone body or pre-ketone body, or a group containing an amino acid metabolite.

The term "acylated hydroxybenzoic acid," as used herein, represents a compound of formula:

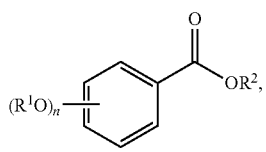

or a salt thereof, where
n is 1, 2, or 3;
each $R^1$ is independently H, acyl, alkyl, a group containing a fatty acid, a group containing a ketone body or pre-ketone body, or a group containing an amino acid metabolite; and
$R^2$ is H, alkyl, a group containing a fatty acid, a group containing a ketone body or pre-ketone body, or a group containing an amino acid metabolite;
provided that the compound includes at least one group containing a fatty acid, group containing a ketone body or pre-ketone body, or group containing an amino acid metabolite.

Non-limiting examples of acylated hydroxybenzoic acids include gallic acid, in which one, two, or three phenolic hydroxyls are independently substituted with groups containing a fatty acid, a group containing a ketone body or pre-ketone body, or a group containing an amino acid metabolite.

The term "acylated mesalamine," as used herein, represents a mesalamine, in which, one H in one or more of $—NH_2$, $—OH$, or $—COOH$ is replaced with an acyl, a group containing a fatty acid, a group containing a ketone body or pre-ketone body, or a group containing an amino acid metabolite, provided that acylated mesalamine contains at least one group containing a fatty acid, a group containing a ketone body or pre-ketone body, or a group containing an amino acid metabolite. In some embodiments, acylated mesalamine is a compound of formula (II):

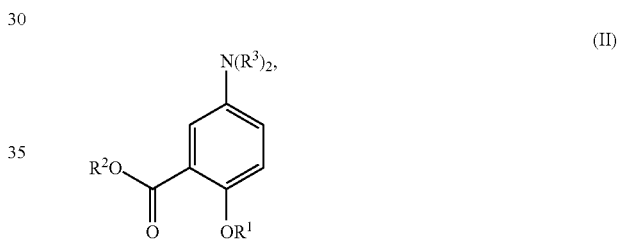

where
$R^1$ is H, alkyl, acyl, a group containing a fatty acid, a group containing a ketone body or pre-ketone body, or a group containing an amino acid metabolite;
$R^2$ is H, alkyl, a group containing a fatty acid, a group containing a ketone body or pre-ketone body, or a group containing an amino acid metabolite; and
each $R^3$ is independently H, alkyl, acyl, a group containing a fatty acid, a group containing a ketone body or pre-ketone body, or a group containing an amino acid metabolite; or both $R^3$ groups combine to form:

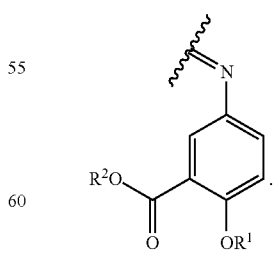

The acylated mesalamine includes at least one group containing a fatty acid, a group containing a ketone body or pre-ketone body, or a group containing an amino acid metabolite.

The term "acylated metformin," as used herein, represents metformin, in which at least one nitrogen is substituted with an acyl, alkyl, group containing a fatty acid, group containing a ketone body or pre-ketone body, or group containing an amino acid metabolite, provided that at least one R is a group containing a fatty acid, a group containing a ketone body or pre-ketone body, or a group containing an amino acid metabolite.

The term "acylated shikimic acid," as used herein, represents a compound of formula:

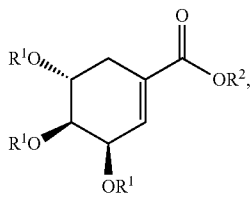

or a salt thereof,
where
each $R^1$ is independently H, acyl, alkyl, a group containing a fatty acid, a group containing a ketone body or pre-ketone body, or a group containing an amino acid metabolite; and
$R^2$ is H, alkyl, or a group containing a fatty acid;
provided that the compound includes at least one group containing a fatty acid, a group containing a ketone body or pre-ketone body, or a group containing an amino acid metabolite.

The term "acylated stilbenoid," as used herein, represents a stilbenoid, in which one, two, three, four, or five hydroxyl groups are independently replaced with a substituent —OR, where each R is independently selected from the group consisting of an acyl, alkyl, a group containing a fatty acid, a group containing a ketone body or pre-ketone body, or a group containing an amino acid metabolite, provided that at least one R is a group including a fatty acid, a group including a ketone body or pre-ketone body, or a group containing an amino acid metabolite.

The term "acylated sugar," as used herein, represents a monosaccharide or glucosinolate having one or more hydroxyls substituted with alkyl, acyl, a group containing a fatty acid, a group containing a ketone body or pre-ketone body, or a group containing an amino acid metabolite. A monosaccharide-based acylated sugar is an acylated monosaccharide. A glucosinolate-based acylated sugar is an acylated glucosinolate. Preferably, the acylated sugar is an acylated monosaccharide. The monosaccharide is present in the pyranose or furanose form. Preferably, the monosaccharide is present in the pyranose form. The monosaccharide may be an aldose or ketose. Non-limiting examples of monosaccharides are arabinose, xylose, fructose, galactose, glucose, ribose, tagatose, fucose, glucosamine, and rhamnose. In some embodiments, the monosaccharide is L-arabinose, D-xylose, fructose, galactose, D-glucose, D-ribose, D-tagatose, L-fucose, or L-rhamnose. Preferably, the monosaccharide is xylose, arabinose, rhamnose, fucose, glucosamine, or tagatose. The monosaccharide may include an anomeric carbon bonded to —OR, where R is H, alkyl, acyl, or a group containing a fatty acid, a group containing a ketone body or pre-ketone body, or a group containing an amino acid metabolite.

The term "acylated vitamin," as used herein, represents a vitamin, in which at least one hydroxyl is independently replaced with a substituent —OR, where each R is independently selected from the group consisting of an acyl, alkyl, group containing a fatty acid, group containing a ketone body or pre-ketone body, and group containing an amino acid metabolite, provided that at least one R is a group containing a fatty acid or a group containing a ketone body or pre-ketone body. Non-limiting examples of acylated vitamins include a tocopherol (e.g., α-tocopherol, β-tocopherol, γ-tocopherol, or δ-tocopherol), tocotrienol, or vitamin D (e.g., cholecalciferol) having a hydroxyl substituted with a group containing a fatty acid, a group containing a ketone body or pre-ketone body, or a group containing an amino acid metabolite. Another non-limiting example of an acylated vitamin is ascorbic acid having one, two, three, or four hydroxyl group substituted with an acyl, alkyl, group containing a fatty acid, and group containing a ketone body or pre-ketone body, provided that at least one R is a group containing a fatty acid, a group containing a ketone body or pre-ketone body, or a group containing an amino acid metabolite.

The term "acyloxy," as used herein, represents a chemical substituent of formula —OR, where R is acyl. An optionally substituted acyloxy is an acyloxy that is optionally substituted as described herein for acyl.

The term "alcohol oxygen atom," as used herein, refers to a divalent oxygen atom, where one valency of the alcohol oxygen atom is bonded to a first carbon atom, and another valency is bonded to a second carbon atom, where the first carbon atom is an $sp^3$-hybridized carbon atom, and the second carbon atom is an $sp^3$-hybridized carbon atom or an $sp^2$-hybridized carbon atom of a carbonyl group.

The term "aldonyl," as used herein, refers to a monovalent substituent that is aldonic acid in which a carboxylate hydroxyl is replaced with a valency.

The term "alkanoyl," as used herein, represents a chemical substituent of formula —C(O)—R, where R is alkyl. An optionally substituted alkanoyl is an alkanoyl that is optionally substituted as described herein for alkyl.

The term "alkoxy," as used herein, represents a chemical substituent of formula —OR, where R is a $C_{1-6}$ alkyl group, unless otherwise specified. An optionally substituted alkoxy is an alkoxy group that is optionally substituted as defined herein for alkyl.

The term "alkenyl," as used herein, represents acyclic monovalent straight or branched chain hydrocarbon groups containing one, two, or three carbon-carbon double bonds. Alkenyl, when unsubstituted, has from 2 to 22 carbons, unless otherwise specified. In certain preferred embodiments, alkenyl, when unsubstituted, has from 2 to 12 carbon atoms (e.g., 1 to 8 carbons). Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted as defined herein for alkyl.

The term "alkenylene," as used herein, refers to a straight or branched chain alkenyl group with one hydrogen removed, thereby rendering this group divalent. Non-limiting examples of the alkenylene groups include ethen-1,1-diyl; ethen-1,2-diyl; prop-1-en-1,1-diyl, prop-2-en-1,1-diyl; prop-1-en-1,2-diyl, prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en-1,3-diyl; but-3-en-2,3-diyl; buta-1,2-dien-1,1-diyl; buta-1,2-dien-1,3-diyl; buta-1,2-dien-1,4-diyl; buta-1,3-dien-1,1- diyl; buta-1,3-dien-1,2-diyl; buta-1,3-dien-1,3-diyl; buta-1,3-dien-1,4-diyl; buta-1,3-dien-2,3-diyl; buta-2,3-dien-1,1-diyl; and buta-2,3-dien-1,2-diyl. An optionally substituted alkenylene is an alkenylene that is optionally substituted as described herein for alkyl.

The term "alkyl," as used herein, refers to an acyclic straight or branched chain saturated hydrocarbon group, which, when unsubstituted, has from 1 to 22 carbons (e.g., 1 to 20 carbons), unless otherwise specified. In certain preferred embodiments, alkyl, when unsubstituted, has from 1 to 12 carbons (e.g., 1 to 8 carbons). Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: alkoxy; acyloxy; alkylsulfenyl; alkylsulfinyl; alkylsulfonyl; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; cyano; oxo (═O); thio (═S); and imino (═NR'), where R' is H, alkyl, aryl, or heterocyclyl. Each of the substituents may itself be unsubstituted or, valency permitting, substituted with unsubstituted substituent(s) defined herein for each respective group.

The term "alkylene," as used herein, refers to a saturated divalent hydrocarbon group that is a straight or branched chain saturated hydrocarbon, in which two valencies replace two hydrogen atoms. Non-limiting examples of the alkylene group include methylene, ethane-1,2-diyl, ethane-1,1-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, and butane-2,2-diyl, butane-2,3-diyl. An optionally substituted alkylene is an alkylene that is optionally substituted as described herein for alkyl.

The term "alkylsulfenyl," as used herein, represents a group of formula —S-(alkyl). An optionally substituted alkylsulfenyl is an alkylsulfenyl that is optionally substituted as described herein for alkyl.

The term "alkylsulfinyl," as used herein, represents a group of formula —S(O)-(alkyl). An optionally substituted alkylsulfinyl is an alkylsulfinyl that is optionally substituted as described herein for alkyl.

The term "alkylsulfonyl," as used herein, represents a group of formula —S(O)$_2$-(alkyl). An optionally substituted alkylsulfonyl is an alkylsulfonyl that is optionally substituted as described herein for alkyl.

The term "amide bond," as used herein, refers to a covalent bond between a nitrogen atom and a carbon atom of a carbonyl group that is further bonded to another carbon atom.

The term "amino acid," as used herein, represents proline, taurine, or a compound having an amino group and a carboxylate or sulfonate group separated by an optionally substituted alkylene or optionally substituted arylene. Amino acids are small molecules and have a molecular weight of <900 g/mol (preferably, <500 g/mol). Preferably, when the linker is alkylene, the linker may be optionally substituted as described herein for alkyl. In some embodiments, optionally substituted alkylene is an alkylene substituted with 1 or 2 groups that are independently hydroxyl, thiol, amino, guanidine, carbamoylamino, imidazolyl, indolyl, —SeH, oxo, 4-hydroxyphenyl, phenyl, or —SMe. Non-limiting examples of amino acids include alanine, arginine, asparagine, aspartic acid, cysteine, glutamic acid, glutamine, glycine, histidine, isoleucine, leucine, lysine, methionine, phenylalanine, proline, selenocysteine, serine, threonine, tyrosine, tryptophan, ornithine, citrulline, aminobenzoic acid, and taurine.

The term "amino acid metabolite," as used herein, represents proteinogenic amino acids, in which the α-amino group is replaced with —OH or —H, in which the 1-carboxyl group is replaced with H, in which the α-(CHNH$_2$) group is replaced with a carbonyl, in which the α-amino group and β-hydrogen atom are replaced with a double bond, or in which the 1-carboxyl group is replaced with hydroxyl and the α-(CHNH$_2$) group is replaced with a carbonyl. Non-limiting examples of amino acid metabolites include indole-3-acetic acid, indole-3-propionic acid, 3-(indole-3-yl)-acrylic acid, indole-3-pyruvic acid, and 3-(indol-3-yl)-2-hydroxypropionic acid.

The term "amino acid metabolite acyl," as used herein, represents an amino acid metabolite, in which carboxylate —OH is replaced with a valency.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkenyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; and cyano. Each of the substituents may itself be unsubstituted or substituted with unsubstituted substituent(s) defined herein for each respective group.

The term "aryl alkyl," as used herein, represents an alkyl group substituted with an aryl group. An optionally substituted aryl alkyl is an aryl alkyl, in which aryl and alkyl portions may be optionally substituted as the individual groups as described herein.

The term "arylene," as used herein, is a divalent group that is an aryl group, in which one hydrogen atom is replaced with a valency. Arylene may be optionally substituted as described herein for aryl. Non-limiting examples of arylenes include phenylene (e.g., 1,2-phenylene, 1,3-phenylene, and 1,4-phenylene).

The term "aryloxy," as used herein, represents a group —OR, where R is aryl. Aryloxy may be an optionally substituted aryloxy. An optionally substituted aryloxy is aryloxy that is optionally substituted as described herein for aryl.

The term "bile acid," as used herein, represents a compound of formula:

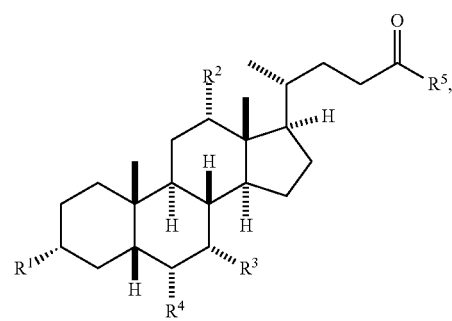

where
- $R^1$ is hydroxyl;
- each of $R^2$ and $R^3$ is independently H or hydroxyl;
- $R^4$ is H or alkyl;
- $R^5$ is hydroxyl, —NH—CH($R^{A}$)—COOH, or an amino sulfonic acid; and
- $R^{A}$, when present, is a side chain of a proteinogenic amino acid.

Non-limiting examples of bile acids are:

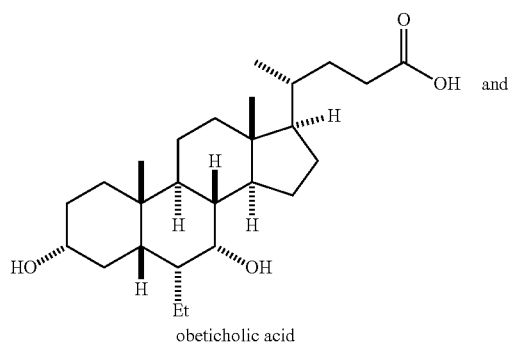
obeticholic acid

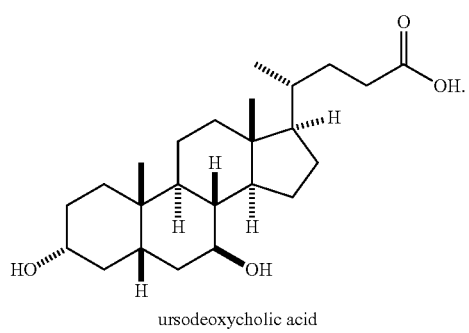
ursodeoxycholic acid

When the bile acid is acylated, one or more of the hydroxyl groups in the bile acid are independently substituted with substituted with a group containing a fatty acid acyl or a group containing a ketone body or pre-ketone body.

The term "bile acid acyl," as used herein, refers to a monovalent group that is a bile acid having a carboxylate, in which —OH is replaced with a valency.

The term "carbamate linker," as used herein, refers to a group $R^1$—(CO)—$R^2$, where $R^1$ is a bond to an alcohol or phenolic oxygen atom, and $R^2$ is a bond to a nitrogen atom.

The term "carbonate linker," as used herein, refers to a group $R^1$—C(O)—$R^2$, where $R^1$ is a bond to a first alcohol or phenolic oxygen atom, and $R^2$ is a bond to a second alcohol or phenolic oxygen atom.

The term "carbonyl," as used herein, refers to a divalent group —C(O)—.

The term "carboxylate," as used herein, represents group —COOH or a salt thereof.

The term "carotenoid," as used herein, represents a compound of formula:

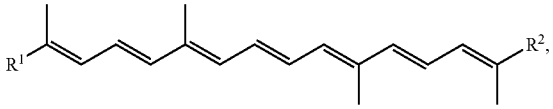

where

R is 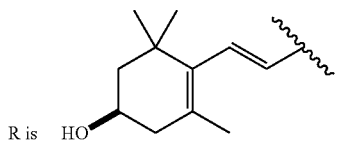,

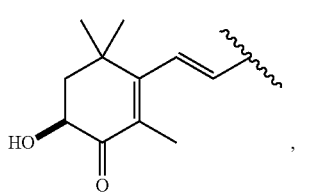,

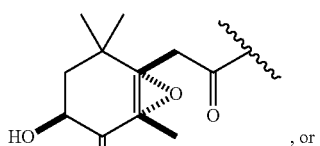, or

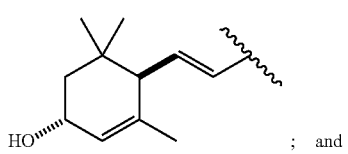; and $R^2$ is 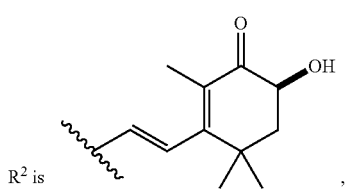,

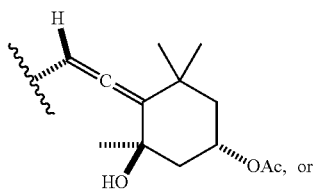, or

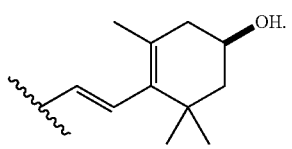.

Non-limiting examples of the carotenoid include:

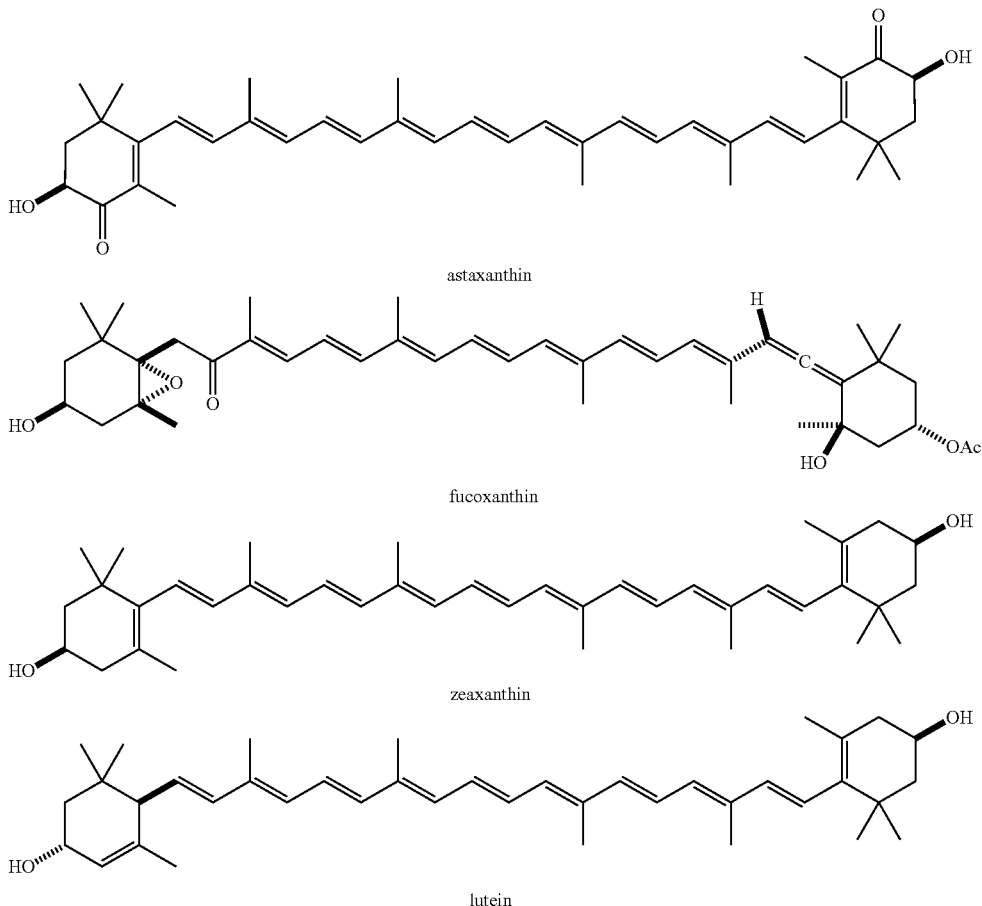

When the carotenoid is acylated, one or both of the hydroxyl groups in the carotenoid is independently substituted with a group containing a fatty acid acyl or a group containing a ketone body or pre-ketone body.

The term "catechin polyphenol," as used herein, refers to a compound of formula:

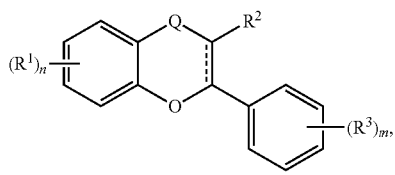

where

⫶ is a single carbon-carbon bond or double carbon-carbon bond;

Q is —CH$_2$— or —C(O)—;

each R$^1$ and each R$^3$ is independently H, halogen, —OR$^A$, phosphate, or sulfate;

R$^2$ is H or —OR$^A$;

each R$^A$ is independently H, optionally substituted alkyl, a monosaccharide, a sugar acid, or benzoyl optionally substituted with 1, 2, 3, or 4 substituents independently selected from the group consisting of H, hydroxy, halogen, optionally substituted alkyl, optionally substituted alkoxy, monosaccharide, sugar acid, phosphate, and sulfate;

m is 1, 2, 3, 4, or 5; and n is 1, 2, 3, or 4.

Preferably, each of n and m is independently 1, 2, 3, or 4. Non-limiting examples of catechin polyphenols include epigallocatechin gallate. When a catechin polyphenol is acylated, one or more of the hydroxyl groups in the catechin polyphenol are independently substituted with a group including a fatty acid or a group including a ketone body or pre-ketone body.

The expression "$C_{x-y}$," as used herein, indicates that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms. For example, ($C_{6-10}$-aryl)-$C_{1-6}$-alkyl is a group, in which the aryl portion, when unsubstituted, contains a total of from 6 to 10 carbon atoms, and the alkyl portion, when unsubstituted, contains a total of from 1 to 6 carbon atoms.

The term "cycloalkyl," as used herein, refers to a cyclic alkyl group having from three to ten carbons (e.g., a C3-C10 cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1]heptyl, 2-bicyclo[2.2.1]heptyl, 5-bicyclo[2.2.1]heptyl, 7-bicyclo[2.2.1]heptyl, and decalinyl. The cycloalkyl group may be unsubstituted or substituted (e.g., optionally substituted cycloalkyl) with one, two, three, four, or five substituents independently selected from the group consisting of: alkyl; alkenyl; alkoxy; acyloxy; alkylsulfenyl; alkylsulfinyl; alkylsulfonyl; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; cyano; oxo (=O); thio (=S); imino (=NR'), where R' is H, alkyl, aryl, or heterocyclyl. Each of the substituents may itself be unsubstituted or substituted with unsubstituted substituent(s) defined herein for each respective group.

The term "cycloalkylene," as used herein, represents a divalent group that is a cycloalkyl group, in which one hydrogen atom is replaced with a valency. An optionally substituted cycloalkylene is a cycloalkylene that is optionally substituted as described herein for cycloalkyl.

The term "cycloalkoxy," as used herein, represents a group —OR, where R is cycloalkyl. An optionally substituted cycloalkoxy is cycloalkoxy that is optionally substituted as described herein for cycloalkyl.

The term "dialkylamino," as used herein, refers to a group —NR$_2$, where each R is independently alkyl.

The terms "ellagic acid" and "ellagic acid analogue," as used herein, collectively refer to a compound of the structure:

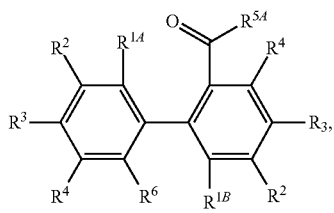

where
each of $R^2$, $R^3$, and $R^4$ is independently H or —OR$^A$;
$R^6$ is H or —(CO)—R$^{5B}$;
$R^{1A}$ is H or —OR$^A$, and $R^{5A}$ is —OH or —OR$^A$; or $R^{1A}$ and $R^{5A}$ combine to form —O—;
$R^{1B}$ is H or —OR$^A$, and $R^{5B}$ is absent, —OH, or —OR$^A$; or $R^{1B}$ and $R^{5B}$ combine to form —O—;
each $R^A$ is independently H or O-protecting group.

When the ellagic acid or its analogue is present in an acylated ellagic acid or an acylated ellagic acid analogue, from one to all hydroxyls in the ellagic acid or its analogue are substituted with a group containing a fatty acid. The term "ellagic acid analogue," refers to the compounds and groups of the above structure that are not ellagic acid. The term "ellagic acid" refers to the following two compounds:

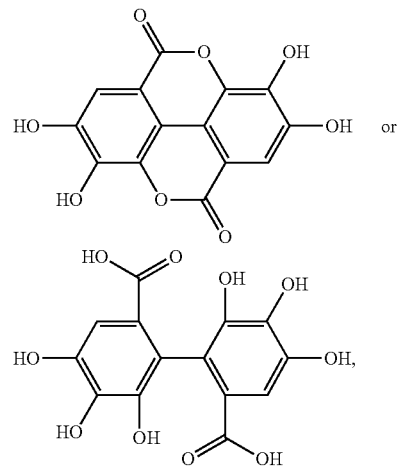

or these compounds within the structure of a conjugate.

Non-limiting examples of ellagic acid analogues include urolithin A, urolithin B, urolithin C, urolithin D, urolithin E, and urolithin M5.

The term "ester bond," as used herein, refers to a covalent bond between an alcohol or phenolic oxygen atom and a carbonyl group that is further bonded to a carbon atom.

The term "fatty acid," as used herein, refers to a short-chain fatty acid, a medium chain fatty acid, a long chain fatty acid, a very long chain fatty acid, or an unsaturated analogue thereof, or a phenyl-substituted analogue thereof. Short chain fatty acids contain from 1 to 6 carbon atoms, medium chain fatty acids contain from 7 to 13 carbon atoms, and a long-chain fatty acids contain from 14 to 22 carbon atoms. A fatty acid may be saturated or unsaturated. An unsaturated fatty acid includes 1, 2, 3, 4, 5, or 6 carbon-carbon double bonds. Preferably, the carbon-carbon double bonds in unsaturated fatty acids have Z stereochemistry.

The term "fatty acid acyl," as used herein, refers to a fatty acid, in which the hydroxyl group is replaced with a valency.

The term "fatty acid acyloxy," as used herein, refers to group —OR, where R is a fatty acid acyl.

The term "glycosidic bond," as used herein, refers to a covalent bond between an oxygen atom and an anomeric carbon atom in a monosaccharide or sugar acid having an anomeric carbon atom.

The terms "group containing an amino acid metabolite" and "group including an amino acid metabolite," as used interchangeably herein, represents a monovalent substituent including at least one amino acid metabolite within its structure and having the valency on a carbon atom of a carbonyl group or on an anomeric carbon atom. A group containing an amino acid metabolite bonds to a core through a carbonate linker, carbamate linker, ester bond, glycosidic bond, or amide bond. A group containing an amino acid metabolite may be a group selected from the group consisting of monosaccharide, ketone body, pre-ketone body, aldonyl, uronyl, ulosonyl, and amino acid metabolite acyl, and where each hydroxyl in the monosaccharide, ketone body, pre-ketone body, aldonyl, uronyl, and ulosonyl is optionally and independently substituted with an amino acid metabolite acyl.

The terms "group containing a fatty acid" and "group including a fatty acid," as used interchangeably herein, represents a monovalent substituent including at least one fatty acid within its structure and having the valency on a carbon atom of a carbonyl group or on an anomeric carbon atom. A group including a fatty acid bonds to a core through a carbonate linker, carbamate linker, ester bond, glycosidic bond, or amide bond. A group including a fatty acid may be a group selected from the group consisting of monosaccharide, ketone body, pre-ketone body, aldonyl, uronyl, ulosonyl, and fatty acid acyl, and where each hydroxyl in the monosaccharide, ketone body, pre-ketone body, aldonyl, uronyl, and ulosonyl is optionally and independently substituted with a fatty acid acyl.

The terms "group containing a ketone body or pre-ketone body" and "group including a ketone body or pre-ketone body," as used interchangeably herein, represents a monovalent substituent including at least one ketone body and/or at least one pre-ketone body within its structure and having the valency on a carbon atom of a carbonyl group or on an anomeric carbon atom. A group including a ketone body or pre-ketone body bonds to a core through a carbonate linker, ester bond, or glycosidic bond. A group including a ketone body or pre-ketone body may be a group selected from the group consisting of monosaccharide, ketone body, aldonyl, uronyl, ulosonyl, and —C(O)—R, where R is a pre-ketone body or ketone body, and where each hydroxyl in the monosaccharide, ketone body, pre-ketone body, aldonyl, uronyl, and ulosonyl is optionally and independently substituted with an acyl or ketone body, a hydroxyl group in which, if present, is optionally substituted with an acyl.

The term "halogen," as used herein, represents a halogen selected from bromine, chlorine, iodine, and fluorine.

The term "heteroaryl," as used herein, represents a monocyclic 5-, 6-, 7-, or 8-membered ring system, or a fused or bridging bicyclic, tricyclic, or tetracyclic ring system; the ring system contains one, two, three, or four heteroatoms independently selected from the group consisting of nitrogen, oxygen, and sulfur; and at least one of the rings is an aromatic ring. Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, dihydroindolyl, tetrahydroquinolyl, tetrahydroisoquinolyl, etc. The term bicyclic, tricyclic, and tetracyclic heteroaryls include at least one ring having at least one heteroatom as described above and at least one aromatic ring. For example, a ring having at least one heteroatom may be fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heteroaryls include 1,2,3,5,8,8a-hexahydroindolizine; 2,3-dihydrobenzofuran; 2,3-dihydroindole; and 2,3-dihydrobenzothiophene. Heteroaryl may be optionally substituted with one, two, three, four, or five substituents independently selected from the group consisting of: alkyl; alkenyl; alkoxy; acyloxy; aryloxy; alkylsulfenyl; alkylsulfinyl; alkylsulfonyl; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl.

Each of the substituents may itself be unsubstituted or substituted with unsubstituted substituent(s) defined herein for each respective group.

The term "heteroaryloxy," as used herein, refers to a structure —OR, in which R is heteroaryl. Heteroaryloxy can be optionally substituted as defined for heteroaryl.

The term "heterocyclyl," as used herein, represents a monocyclic, bicyclic, tricyclic, or tetracyclic non-aromatic ring system having fused or bridging 4-, 5-, 6-, 7-, or 8-membered rings, unless otherwise specified, the ring system containing one, two, three, or four heteroatoms independently selected from the group consisting of nitrogen, oxygen, and sulfur. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups have a carbon count of 1 to 16 carbon atoms unless otherwise specified. Certain heterocyclyl groups may have a carbon count up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, pyranyl, dihydropyranyl, dithiazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., a cyclohexane ring, a cyclohexene ring, a cyclopentane ring, a cyclopentene ring, or another heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkenyl; alkoxy; acyloxy; alkylsulfenyl; alkylsulfinyl; alkylsulfonyl; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; =S; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl.

The term "heterocyclyl alkyl," as used herein, represents an alkyl group substituted with a heterocyclyl group. The heterocyclyl and alkyl portions of an optionally substituted heterocyclyl alkyl are optionally substituted as the described for heterocyclyl and alkyl, respectively.

The term "heterocyclylene," as used herein, represents a heterocyclyl, in which one hydrogen atom is replaced with a valency. An optionally substituted heterocyclylene is a heterocyclylene that is optionally substituted as described herein for heterocyclyl.

The term "heterocyclyloxy," as used herein, refers to a structure —OR, in which R is heterocyclyl. Heterocyclyloxy can be optionally substituted as described for heterocyclyl.

The term "hydroxybenzoic acid," as used herein, represents a compound of the following structure:

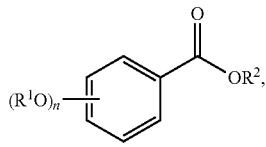

or a salt thereof,
where
n is 1, 2, or 3;
each $R^1$ is independently H or alkyl; and
$R^2$ is H or alkyl.

Non-limiting examples of hydroxybenzoic acids include gallic acid.

The terms "hydroxyl" and "hydroxy," as used interchangeably herein, represent —OH. A hydroxyl substituted with an acyl is an acyloxy. A protected hydroxyl is a hydroxyl, in which the hydrogen atom is replaced with an O-protecting group.

The term "hydroxymethyl," as used herein, refers to a group —CH$_2$OH.

The term "ketone body," as used herein, refers to (i) β-hydroxybutyric acid or acetoacetic acid, or (ii) a group that is β-hydroxybutyric acid or acetoacetic acid, where at least one hydroxyl hydrogen atom is replaced with a valency or a carboxylate —OH is replaced with a valency.

The term "ketone body acyl," as used herein, refers to a ketone body, in which the carboxylate —OH group is replaced with a valency.

The term "α-lipoic acid acyl," as used herein, refers to the monovalent group of formula:

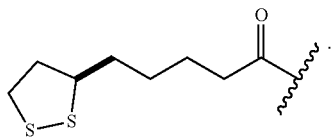 [SMILES: *C(=O)CCCC[C@@H]1CCSS1]

The term "metabolic marker," as used herein, refers to an observable indicative of the presence, absence, or risk of a metabolic disorder. The level of a metabolic marker may directly or inversely correlate with an obesity state. Non-limiting examples of the metabolic markers are a total fat percentage, cellular adiposity, rate of weight gain, abdominal fat quantity, subcutaneous fat quantity, inguinal fat quantity, epididymal fat quantity, ratio of white to brown fat, cholesterol (e.g., high density lipoprotein (HDL) or low density lipoprotein (LDL)) level, and level of triglycerides. In some embodiments, the metabolic marker is a total fat percentage, cellular adiposity, rate of weight gain, abdominal fat quantity, ratio of white to brown fat, cholesterol (e.g., high density lipoprotein (HDL) or low density lipoprotein (LDL)) level, and level of triglycerides. Total fat percentage can be assessed using body mass index. Abdominal fat can be assessed by measuring waist circumference. Ratio or white fat to brown fat can be assessed by measuring the miRNA-92a level, for example, using techniques and methods described in Chen et al., *Nat. Commun.*, 7:11420; $^{18}$F-fludeoxyglucose positron emission tomography/computed tomography, for example, using techniques and methods described in Gerngroß et al., *J. Nucl. Med.*, 58:1104-1110, 2017; magnetic resonance imaging, for example, using techniques and methods described in Chen et al., *J. Nucl. Med.*, 54:1584-1587, 2013.

The term "4-methyl-1,3-dioxan-2-yl," as used herein, refers to the monovalent group of formula:

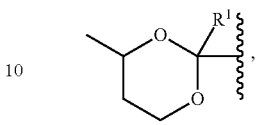

where $R^1$ is optionally substituted $C_{1-6}$ alkyl (e.g., methyl).

The term "modulating," as used herein, refers to an observable change in the level of a marker in a subject, as measured using techniques and methods known in the art for the measurement of the marker. Modulating the marker level in a subject may result in a change of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In some embodiments, modulating is increasing the level of a marker in a subject. Increasing the marker level in a subject may result in an increase of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In other embodiments, modulating is decreasing the level of a marker in a subject. Decreasing the marker level in a subject may result in a decrease of at least 1% relative to prior to administration (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration; e.g., up to 100% relative to prior to administration). In embodiments in which a parameter is increased or decreased (or reduced) in a subject following a step of administering a composition described herein, the increase or decrease may take place and/or be detectable within a range of time following the administration (e.g., within six hours, 24 hours, 3 days, a week or longer), and may take place and/or be detectable after one or more administrations (e.g., after 2, 3, 4, 5, 6, 7, 8, 9, 10 or more administrations, e.g., as part of a dosing regimen for the subject).

The term "nonalcoholic fatty disease marker," as used herein, represents an observable indicative of the presence or absence of a nonalcoholic fatty disease (e.g., nonalcoholic steatohepatitis). The level of a nonalcoholic disease marker may directly or inversely correlate with a nonalcoholic disease state. Non-limiting examples of the nonalcoholic disease markers are the alanine transaminase level (ALT), aspartate transaminase level (AST), γ-glutamyltransferase level, liver weight, and fibrotic markers. The alanine transaminase level, aspartate transaminase level, γ-glutamyltransferase level, and fibrotic markers can be measured in a blood sample from a subject using methods known in the art. Nonalcoholic fatty disease markers can be assessed using non-invasive tests, imaging methods, and biopsy. Liver fibrosis can be assessed invasively via liver biopsy or, alternatively, through non-invasive methods, e.g., composite scores/algorithms of serum markers (Fibrotest, Hepatscore, Fibrometet FIB-4 score, NAFLDD fibrosis score), or imaining techniques including transient elastography, magnetic resonance elastography, acoustic radiation force impulses, and sonography (Almpanis, Z., *Annals of Gastroenterology*, 29:1-9, 2016). BAAT is an overall clinical score that can be used to identify subjects who would benefit from a liver biopsy for the assessment of a subject for nonalcoholic fatty liver disease (e.g., nonalcoholic steatohepatitis). BAAT combines body mass index, age, ALT, and serum triglycerides. In addition, acoustic radiation force impulse can be used to measure liver stiffness, what correlates with fibrosis scoring. Magnetic Resonance Imaging (MRI) is also used to identify hepatic density and hepatic fat fraction; liver stiffness can be measured by MR elastography (Neuman et al., *J. Pharm. Pharm. Sci.*, 19:8-24, 2016).

The term "oxo," as used herein, represents a divalent oxygen atom (e.g., the structure of oxo may be shown as =O).

The term "phenolic oxygen atom," as used herein, refers to a divalent oxygen atom within the structure of a compound, where one valency of the phenolic oxygen atom is bonded to a first carbon atom, and another valency is bonded to a second carbon atom, where the first carbon atom is an $sp^2$-hybridized carbon atom within a benzene ring, and the second carbon atom is an $sp^3$-hybridized carbon atom or an $sp^2$-hybridized carbon atom.

The term "phosphate, as used herein, represents group —OPO(OH)$_2$ or a salt thereof.

The term "pre-ketone body," as used herein, represents (i) a ketone body having hydroxymethyl instead of a carboxylate, or (ii) a group that is a ketone body having hydroxymethyl instead of a carboxylate, where at least one hydroxyl is replaced with —OR, where R is a valency. The term "pre-ketone body," as used herein, also represents (4-methyl-1,3-dioxan-2-yl)-(alkylene)$_n$-CO—R$^A$, where n is 0 or 1, and R$^A$ is —OH, if the pre-ketone body is not part of an acylated active agent, or a valency if the pre-ketone body is part of a group including a pre-ketone body (e.g., a pre-ketone body acyl). A non-limiting example of a pre-ketone body is butane-1,3-diol or 4-hydroxybutan-2-one.

The term "pre-ketone body acyl," as used herein, refers to a pre-ketone body, in which the carboxylate —OH group is replaced with a valency.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," 3$^{rd}$ Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "stilbenoid," as used herein, represents a trans-stilbene that, when not acylated, is substituted with one, two, three, four, or five substituents independently selected from the group consisting of alkoxy (e.g., methoxy) and hydroxyl. Non-limiting examples of stilbenoids include resveratrol, pterostilbene, rhapontigenin, pinostilbene, oxyresveratrol, 4-methoxyresveratrol, and piceatannol. When the stilbenoid is acylated, one or both of the hydroxyl groups in the stilbenoid is independently substituted with a group including a fatty acid acyl or a group including a ketone body or pre-ketone body.

The term "subject," as used herein, represents a human or non-human animal (e.g., a mammal) that is suffering from, or is at risk of, disease, disorder, or condition, as determined by a qualified professional (e.g., a doctor or a nurse practitioner) with or without known in the art laboratory test(s) of sample(s) from the subject. Non-limiting examples of diseases, disorders, and conditions include metabolic disorders, nonalcoholic fatty liver disease, and nonalcoholic steatohepatitis (e.g., NASH with or without fibrosis, liver steatosis, or NASH with advanced fibrosis), as described herein.

Diagnosis may be performed by techniques and methods known in the art. A subject to be treated according to the methods of the invention may have been subjected to standard tests (e.g., tests for the levels of liver enzyme (e.g., alanine transaminase or aspartate transaminase) in the blood, tests for liver weight, tests for the levels of triglycerides and/or cholesterol in the blood, tests for body fat content, and/or tests for glucose tolerance and/or insulin resistance) or may have been identified, without such tests, as one at high risk due to the presence of one or more risk factors.

The term "sugar acid," as used herein, refers to a monosaccharide, in the linear form of which, one or both terminal positions are oxidized to a carboxylic acid. There are four classes of sugar acids: aldonic acid, ulosonic acid, uronic acid, and aldaric acid. Any of the four sugar acid classes may be used in acylated catechin polyphenol disclosed herein. Non-limiting examples of sugar acids include gluconic acid.

The term "sugar acid acyl," as used herein, refers to a monovalent group that is a sugar acid having a carboxylate, in which —OH is replaced with a valency.

The term "sulfate," as used herein, represents group —OSO$_3$H or a salt thereof.

The term "thioalkenyl," as used herein, represents a group —SR, where R is alkenyl. An optionally substituted thioalkenyl is thioalkenyl that is optionally substituted as described herein for alkenyl.

The term "thioalkyl," as used herein, represents a group —SR, where R is alkyl. An optionally substituted thioalkyl is thioalkyl that is optionally substituted as described herein for alkyl.

The term "thioaryl," as used herein, represents a group —SR, where R is aryl. An optionally substituted thioaryl is thioaryl that is optionally substituted as described herein for aryl.

"Treatment" and "treating," as used herein, refer to the medical management of a subject with the intent to improve, ameliorate, stabilize, prevent or cure a disease, disorder, or condition. This term includes active treatment (treatment directed to improve the disease, disorder, or condition); causal treatment (treatment directed to the cause of the associated disease, disorder, or condition); palliative treatment (treatment designed for the relief of symptoms of the disease, disorder, or condition); preventative treatment (treatment directed to minimizing or partially or completely inhibiting the development of the associated disease, disorder, or condition); and supportive treatment (treatment employed to supplement another therapy).

The term "trimethylglycine acyl," as used herein, refers to the monovalent group of formula:

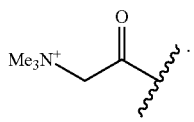

The term "ulosonyl," as used herein, refers to a monovalent substituent that is a ulosonic acid in which a carboxylate hydroxyl is replaced with a valency.

The term "uronyl," as used herein, refers to a monovalent substituent that is a uronic acid in which a carboxylate hydroxyl is replaced with a valency.

The term "vitamin," as used herein, refers to a tocopherol (e.g., α-tocopherol, β-tocopherol, γ-tocopherol, or δ-tocopherol), tocotrienol, vitamin D (e.g., cholecalciferol), and ascorbic acid. When the vitamin is acylated, one or more of the hydroxyl groups in the vitamin is independently substituted with a group containing a fatty acid acyl or a group containing a ketone body or pre-ketone body.

The compounds described herein, unless otherwise noted, encompass isotopically enriched compounds (e.g., deuterated compounds), tautomers, and all stereoisomers and conformers (e.g. enantiomers, diastereomers, E/Z isomers, atropisomers, etc.), as well as racemates thereof and mixtures of different proportions of enantiomers or diastereomers, or mixtures of any of the foregoing forms as well as salts (e.g., pharmaceutically acceptable salts).

Other features and advantages of the invention will be apparent from the Drawings, Detailed Description, and the Claims.

BRIEF DESCRIPTION OF THE DRAWINGS

FIG. 34A is chart showing overview of the result of fibrosis stage. For each animal the change from pre-study to post-study biopsy is indicated by a line. The points at each scoring step is slightly shifted to allow visual separation of the animals, this is only for visualization purposes and does not reflect any difference in score.

FIG. 34B is chart showing overview of the result of NAFLD Activity Scores. For each animal the change from pre-study to post-study biopsy is indicated by a line. The points at each scoring step is slightly shifted to allow visual separation of the animals, this is only for visualization purposes and does not reflect any difference in score.

FIG. 36A is a chart showing an overview of the result of steatosis scores. For each animal the change from pre-study to post-study biopsy is indicated by a line. The points at each scoring step is slightly shifted to allow visual separation of the animals, this is only for visualization purposes and does not reflect any difference in score.

FIG. 36B is a chart showing an overview of the result of inflammation scores. For each animal the change from pre-study to post-study biopsy is indicated by a line. The points at each scoring step is slightly shifted to allow visual separation of the animals, this is only for visualization purposes and does not reflect any difference in score.

DETAILED DESCRIPTION

Figure 1:
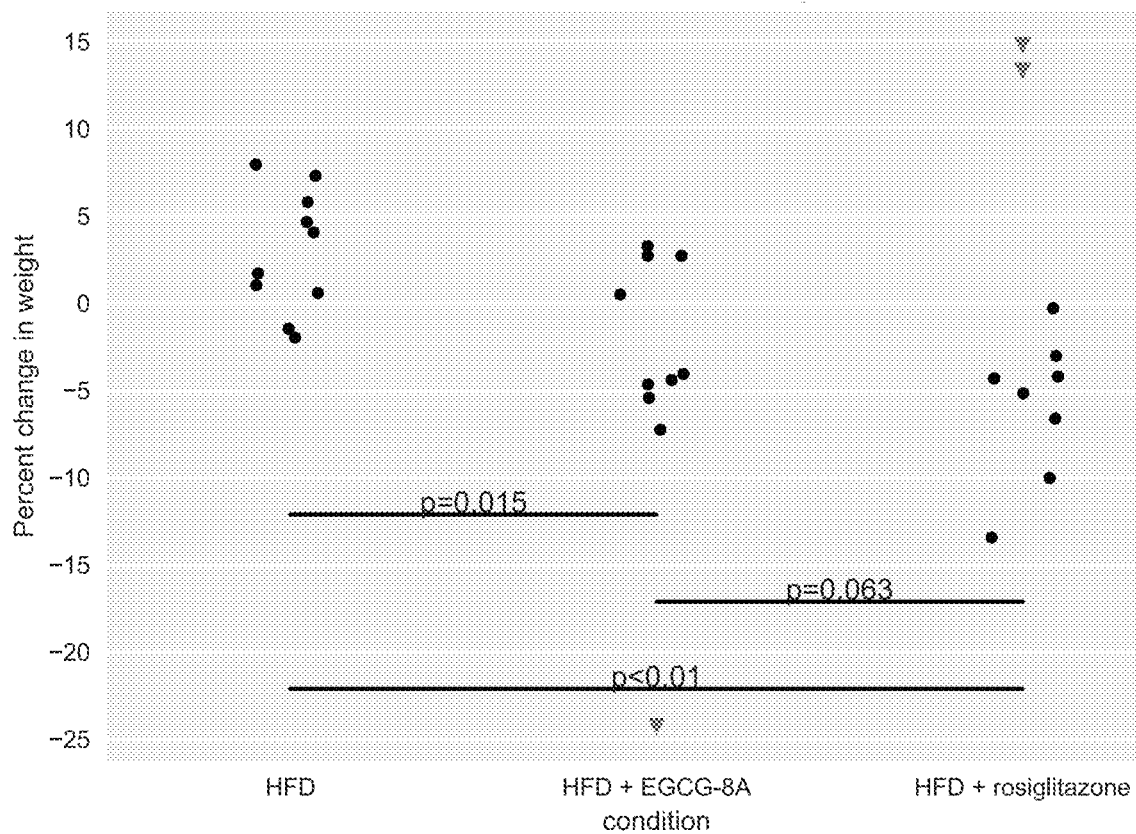
FIG. 1 is a chart showing the percentage change in weight of three animal cohorts: (1) untreated animals receiving a high-fat diet, (2) animals receiving epigallocatechin gallate octaacetate (EGCG-8A) along with a high-fat diet, and (3) animals receiving rosiglitazone with a high-fat diet.

The invention provides acylated active agents (e.g., an acylated catechin polyphenol, acylated carotenoid, acylated ellagic acid, acylated ellagic acid analogue, acylated ketone body or pre-ketone body, acylated stilbenoid, acylated S-adenosyl-L-methionine, acylated amino acid, acylated bile acid, acylated mesalamine, acylated metformin, acylated sugar, acylated shikimic acid, acylated vitamin, or acylated hydroxybenzoic acid), active agent combinations (e.g., combinations where a first agent is a stilbenoid, catechin polyphenol, carotenoid, bile acid, amino acid, hydroxybenzoic acid, shikimic acid, monosaccharide, or mesalamine, metformin, vitamin, S-adenosyl-L-methionine, and a second agent is a ketone body or pre-ketone body), compositions containing them (e.g., as unit dosage forms), and methods for modulating a metabolic marker or nonalcoholic fatty liver disease marker in a subject or of treating a metabolic disorder or nonalcoholic fatty liver disease (e.g., nonalcoholic steatohepatitis) in a subject. Without wishing to be bound by theory, the acylated active agents of the invention are believed to act in concert with, or in lieu of, the microbiota of a subject.

As described herein, the compounds and combination therapies of the invention were unexpectedly observed to exhibit activity in vivo for modulating a metabolic marker or for treating a metabolic disorder (e.g., obesity, type II diabetes, prediabetes, insulin resistance, metabolic syndrome, hypercholesterolemia, atherosclerosis or hyperlipidemia). It has been surprisingly found that administration of an acylated catechin polyphenol (e.g., epigallocatechin-3-gallate octaacetate) to a subject can induce weight loss, even if the subject is fed a high-fat diet. Surprisingly, administration of an acylated catechin polyphenol was found to produce superior activity relative to the administration of the same dose of acylated catechin polyphenol components as separate compounds.

The components of the acylated catechin polyphenol (e.g., short chain fatty acid acyls (e.g., acetyl) and epigallocatechin gallate) may act synergistically to modulate a metabolic marker, e.g., upon hydrolysis in the GI tract of the subject receiving the acylated catechin polyphenol. The components of the acylated catechin polyphenol (e.g., short chain fatty acid acyls (e.g., acetyl) and epigallocatechin gallate) may act synergistically to treat a metabolic disorder, e.g., upon hydrolysis in the GI tract of the subject receiving the acylated catechin polyphenol.

As described herein, the compounds and combination therapies of the invention were unexpectedly observed to exhibit activity in vivo for modulating a nonalcoholic fatty liver disease (e.g., nonalcoholic steatohepatitis) marker or for treating a nonalcoholic fatty liver disease (e.g., nonalcoholic steatohepatitis (NASH) with or without fibrosis, liver steatosis, NASH with advanced fibrosis). For example, FATZO mice (a disease model for NAFLD/NASH), administered the exemplary combination, a stilbenoid and a ketone body or pre-ketone body, exhibited statistically significant steatosis reduction, reduced liver weight, and reduced liver enzymes (e.g., reduced levels of alanine transaminase (ALT)) relative to FATZO mice not receiving the stilbenoid and the ketone body or pre-ketone body. In another study described herein, test mice, administered an acylated active agent disclosed herein (e.g., epigallocatechin gallate octaacetate), exhibited a statistically significant improvement in liver histology (e.g., steatosis reduction and ballooning degeneration reduction).

Further, and surprisingly, compounds and combination therapies disclosed herein may exhibit synergistic activity for modulating a nonalcoholic fatty liver disease (e.g., nonalcoholic steatohepatitis) marker or for treating a nonalcoholic fatty liver disease (e.g., nonalcoholic steatohepatitis (NASH) with or without fibrosis, liver steatosis, NASH with advanced fibrosis). For example, as described herein, FATZO mice, administered the exemplary combination, a stilbenoid and a pre-ketone body, exhibited steatosis reduction superior to those mice administered obeticholic acid—an agent under investigation for the treatment of NAFLD/NASH.

Advantageously, acylated active agents disclosed herein may have superior organoleptic properties (e.g., palatability). This provides an important advantage as the individual components (e.g., acetic acid or epigallocatechin gallate) may exhibit less desirable organoleptic properties (e.g., palatability). Improved organoleptic properties facilitate oral administration, and are particularly advantageous for delivery of high unit dosages (e.g., unit dosages of 0.5 g or higher).

The invention also provides active agent combinations.

Surprisingly, compounds and combination therapies disclosed herein may exhibit synergistic activity for modulating a metabolic disorder marker or for treating a metabolic disorder. For example, as described herein, FATZO mice, administered the exemplary combination, a stilbenoid and a pre-ketone body, exhibited reduction in the abdominal fat, blood triglycerides, and blood cholesterol relative to a control group of FATZO mice that was not administered the exemplary combination.

Acylated Active Agents

An acylated active agent disclosed herein may be an acylated catechin polyphenol, acylated carotenoid, acylated ellagic acid, acylated ellagic acid analogue, acylated ketone body or pre-ketone body, acylated stilbenoid, acylated S-adenosyl-L-methionine, acylated amino acid, acylated bile acid, acylated mesalamine, acylated metformin, acylated hydroxybenzoic acid, acylated shikimic acid, acylated vitamin, or acylated sugar.

Typically, an acylated active agent includes two or more active agents linked through ester bond(s), amide bond(s), carbonate linker(s), carbamate linker(s), and/or glycosidic bond(s). For example, an acylated active agent may include a core (e.g., a catechin polyphenol, stilbenoid, shikimic acid, hydroxybenzoic acid, monosaccharide, or glucosinolate), and the core may be substituted with one or more substituents independently selected from the group consisting of an alkyl, acyl, group including a fatty acid (e.g., a short chain fatty acid or a medium chain fatty acid), and group including a ketone body or pre-ketone body.

An acylated active agent disclosed herein may include, e.g., at least one group including a fatty acid. A group including a fatty acid may be, e.g., a fatty acid (e.g., short chain fatty acid or medium chain fatty acid), a monosaccharide having one or more hydroxyl groups substituted with fatty acid acyls (e.g., short chain fatty acid acyls or medium chain fatty acid acyls), or a sugar acid (e.g., aldonic acid) having one or more alcohol hydroxyl groups substituted with fatty acid acyls (e.g., short chain fatty acid acyls or medium chain fatty acid acyls).

An acylated active agent disclosed herein may include, e.g., at least one group including a ketone body or pre-ketone body. A group including a ketone body or pre-ketone body may be, e.g., a ketone body optionally having a hydroxyl group optionally substituted with an acyl (e.g., a fatty acid acyl (e.g., a short chain fatty acid acyl or medium chain fatty acid acyl)); a pre-ketone body optionally having a hydroxyl group optionally substituted with an acyl (e.g., a fatty acid acyl (e.g., a short chain fatty acid acyl or medium chain fatty acid acyl)); a monosaccharide having one or more hydroxyl groups substituted a ketone body acyl and/or pre-ketone body acyl, where each ketone body acyl and pre-ketone body acyl optionally has a hydroxyl group optionally substituted with a fatty acid acyl (e.g., a short chain fatty acid acyl or medium chain fatty acid acyl); or a sugar acid (e.g., aldonic acid or uronic acid) having one or more alcohol hydroxyl groups substituted with a ketone body acyl and/or pre-ketone body acyl, where each ketone body acyl and pre-ketone body acyl optionally has a hydroxyl group optionally substituted with a fatty acid acyl (e.g., a short chain fatty acid acyl or medium chain fatty acid acyl). A group including a ketone body or pre-ketone body may be, e.g., a group including a ketone body. A group including a ketone body or pre-ketone body may be, e.g., a group including a pre-ketone body. A group including a ketone body includes at least one ketone body residue. A group including a pre-ketone body includes at least one pre-ketone body residue.

An acylated active agent disclosed herein may include, e.g., at least one group containing an amino acid metabolite. A group containing an amino acid metabolite may be, e.g., an amino acid metabolite group (e.g., amino acid metabolite acyl). A group containing an amino acid metabolite may be, e.g., an amino acid metabolite acyl. Alternatively, an amino acid metabolite may be a pre-ketone body having a hydroxyl group substituted with an amino acid metabolite acyl; a monosaccharide having one or more hydroxyl groups substituted with an amino acid metabolite acyl, where each amino acid metabolite acyl optionally has a hydroxyl group optionally substituted with a fatty acid acyl (e.g., a short chain fatty acid acyl or medium chain fatty acid acyl), and the one or more remaining hydroxyls on the monosaccharide, if present, are optionally substituted with a fatty acid acyl (e.g., a short chain fatty acid acyl or medium chain fatty acid acyl); or a sugar acid (e.g., aldonic acid or uronic acid) having one or more alcohol hydroxyl groups substituted with an amino acid metabolite acyl, where each amino acid metabolite acyl optionally has a hydroxyl group optionally substituted with a fatty acid acyl (e.g., a short chain fatty acid acyl or medium chain fatty acid acyl), and the one or more remaining hydroxyls on the sugar acid, if present, are optionally substituted with a fatty acid acyl (e.g., a short chain fatty acid acyl or medium chain fatty acid acyl). A group containing an amino acid metabolite includes at least one amino acid metabolite residue.

In certain embodiments the group may be a monovalent group of the following formula:

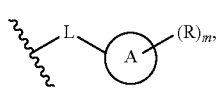

(B)

where
L is absent, carbamate linker, or carbonate linker;
group A is a fatty acid acyl, ketone body, pre-ketone body, monosaccharide, sugar acid, or glucosinolate (e.g., group A is a fatty acid acyl, ketone body, pre-ketone body, monosaccharide, or sugar acid);
each R is independently ketone body optionally having a hydroxyl group that is optionally substituted with an acyl (e.g., a fatty acid acyl), pre-ketone body optionally having a hydroxyl group that is optionally substituted with an acyl (e.g., a fatty acid acyl), an amino acid metabolite acyl optionally having a hydroxyl group that is optionally substituted with an acyl (e.g., a fatty acid acyl), or acyl; and
m is an integer from 0 to the total number of available hydroxyl groups in group A (e.g., 1, 2, 3, 4, or 5);
provided that
L is a carbonate linker or carbamate linker, if group A has a valency on a non-glycosidic alcohol oxygen atom; and
L is absent, if group A has a valency on a carbonyl carbon atom.

When the group formula (B) is a group including a fatty acid, the group of formula (B) includes at least one fatty acid. When the group of formula (B) is a group including a ketone body or pre-ketone body, the group includes at least one ketone body or pre-ketone body. When the group formula (B) is a group including an amino acid metabolite, the group of formula (B) includes at least one amino acid metabolite.

In some embodiments, the fatty acid(s) are short chain fatty acid acyls (e.g., butyryls). In particular embodiments, the fatty acid(s) in the group including a fatty acid are medium chain fatty acid acyls (e.g., octanoyl).

Non-limiting examples of a group including a fatty acid are:

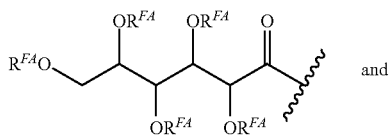

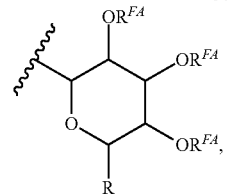

where
R is H, —CH$_3$, or —CH$_2$OR$^{FA}$;
each R$^{FA}$ is independently H or a fatty acid acyl (e.g., a short chain fatty acid acyl or medium chain fatty acid acyl);
provided that at least one R$^{FA}$ is fatty acid acyl(e.g., a short chain fatty acid acyl or medium chain fatty acid acyl).

Non-limiting examples of a group including a ketone body include:

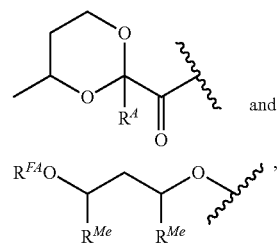

where R$^A$ is H or alkyl; R$^{FA}$ is fatty acid acyl; and one R$^{Me}$ is methyl and the remaining R$^{Me}$ is H.

Acylated Catechin Polyphenols

An acylated catechin polyphenol of the invention may be a substituted compound having the core of formula (A):

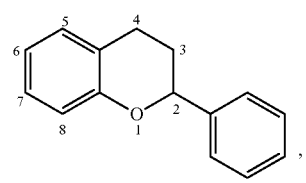

(A)

or a multimer thereof, or a salt thereof,
where the substituents are independently selected from the group consisting of —OR$^A$, —OCOO—R$^A$, —NHR$^B$, oxo, halogen, optionally substituted C$_{1-20}$ alkyl, optionally substituted C$_{2-20}$ alkenyl, optionally substituted thioalkyl, optionally substituted alkylsulfonyl, optionally substituted alkylsulfenyl, optionally substituted alkylsulfinyl, optionally substituted thioaryl, optionally substituted aryl thioalkyl, optionally substituted thioalkenyl, dialkylamino, sulfate, phosphate, ascorbic acid, optionally substituted heterocyclyl, nitro, amino acids, C$_{1-6}$ esters of amino acids, optionally acylated monosaccharide, and optionally acylated sugar acid, where each R$^A$ is independently H, optionally substituted alkyl, a group containing a fatty acid, a group containing a ketone body or pre-ketone body, or benzoyl optionally substituted with one, two, three, or four substituents independently selected from the group consisting of H, hydroxyl, halogen, a group containing a fatty acid, a group containing a ketone body or pre-ketone body, optionally substituted alkoxy, and optionally substituted alkyl, and where $R^B$ is independently H or optionally substituted alkyl;

where the carbon-carbon bond connecting carbon 2 and carbon 3 in formula (A) is a single bond or a double bond;

where the multimer includes a total of 2 or 3 cores of formula (A), each core substituted independently as described above; and where two vicinal centers in core (A) may be further substituted with a group —(O)$_q$-L$^1$-L$^2$-, where q is 0 or 1, L$^1$ is optionally substituted alkylene, optionally substituted alkenylene, or optionally substituted heterocyclylene; and L$^2$ is a covalent bond, optionally substituted heterocyclylene, or optionally substituted cycloalkylene.

In some embodiments, at least one of positions 5, 6, 7, and 8 is —OR$^A$, where R$^A$ is group containing a fatty acid, a group containing a ketone body or pre-ketone body, or benzoyl optionally substituted with one, two, three, or four substituents independently selected from the group consisting of H, hydroxyl, halogen, a group containing a fatty acid, a group containing a ketone body or pre-ketone body, optionally substituted alkoxy, and optionally substituted alkyl. In some embodiments, the compound of formula (A) includes at least one group containing a fatty acid or at least one group containing a ketone body or pre-ketone body.

An acylated catechin polyphenol of the invention may be a catechin polyphenol, in which one or more hydroxyl groups are independently replaced with —OR, where each R is independently selected from the group consisting of an acyl, alkyl, group including a fatty acid, and group including a ketone body or pre-ketone body, provided that at least one R is a group including a fatty acid or a group including a ketone body or pre-ketone body.

An acylated catechin polyphenol may be a compound of formula (I):

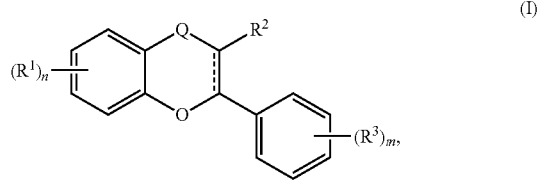

or a pharmaceutically acceptable salt thereof,
where
╎ is a single carbon-carbon bond or double carbon-carbon bond;
Q is —CH$_2$— or —C(O)—;
each R$^1$ and each R$^3$ is independently H, halogen, —OR$^A$, phosphate, or sulfate;
R$^2$ is H or —OR$^A$;
each R$^A$ is independently H, optionally substituted alkyl, a monosaccharide, a sugar acid, a group containing a fatty acid, a group containing a ketone body or pre-ketone body, a group containing an amino acid metabolite, or benzoyl optionally substituted with 1, 2, 3, or 4 substituents independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate;

m is 0, 1, 2, 3, 4, or 5; and
n is 0, 1, 2, 3, or 4.

Preferably, each of n and m is independently 0, 1, 2, 3, or 4. More preferably, each of n and m is independently 1, 2, 3, or 4.

In some embodiments, the compound includes at least one group containing a fatty acid or at least one group including a ketone body or pre-ketone body. In particular embodiments, at least one R$^1$ is —OR$^A$, in which R$^A$ is a group containing a fatty acid. In certain embodiments, the compound of formula (I) includes at least one group including a ketone body or pre-ketone body. In further embodiments, the compound includes at least one group including a ketone body or pre-ketone body. In yet further embodiments, the compound includes at least one group including a pre-ketone body.

In particular embodiments, ╎ is a single carbon-carbon bond. In certain embodiments, Q is —CH$_2$—.

In some embodiments, the acylated catechin polyphenol is of formula (I-a):

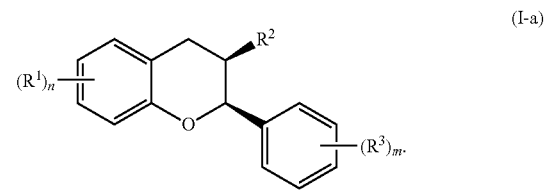

In certain embodiments, the acylated catechin polyphenol is of formula (I-b):

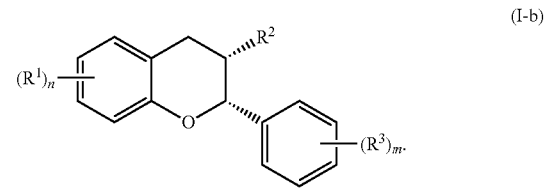

In particular embodiments, the acylated catechin polyphenol is of formula (I-c):

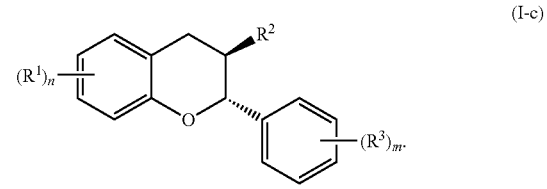

In further embodiments, the acylated catechin polyphenol is of formula (I-d):

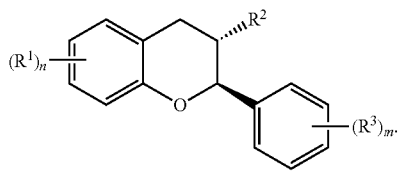

(I-d)

In certain embodiments, the acylated catechin polyphenol is a compound of formula (I-f):

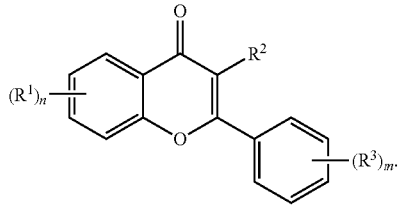

(I-f)

In still further embodiments, n is 2. In certain embodiments, m is 1. In particular embodiments, m is 2. In some embodiments, m is 3. In particular embodiments, each $R^1$ is independently —$OR^A$. In certain embodiments, each $R^3$ is independently H or —$OR^A$. In further embodiments, $R^2$ is H or —$OR^A$. In yet further embodiments, each $R^A$ is independently H, optionally substituted alkyl, a group containing a fatty acid, or a group containing a ketone body or pre-ketone body.

In some embodiments, $R^2$ is a group of formula:

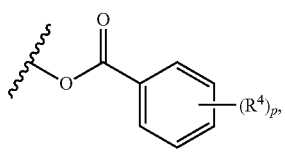

where p is 1, 2, 3, or 4, and each $R^4$ is independently selected from the group consisting of H, hydroxy, halogen, a group containing a fatty acid, a group containing a ketone body or pre-ketone body, a group containing an amino acid metabolite, an optionally substituted alkyl, an optionally substituted alkoxy, a monosaccharide, a sugar acid, phosphate, and sulfate.

In certain embodiments, p is 3. In particular embodiments, $R^4$ is independently H, hydroxy, halogen, a group containing a fatty acid, a group containing a ketone body or pre-ketone body, a group containing an amino acid metabolite, or an optionally substituted alkoxy.

In some embodiments, the acylated catechin polyphenol is of formula (I-e):

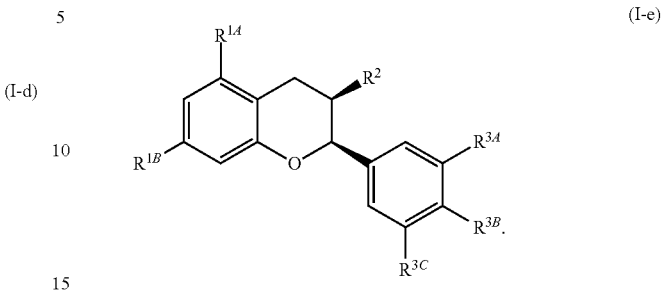

(I-e)

In certain embodiments, each of $R^{1A}$ and $R^{1B}$ is independently —$OR^A$. In particular embodiments each of $R^{3A}$, $R^{3B}$, and $R^{3C}$ is independently H, halogen, or —$OR^A$.

In further embodiments, $R^2$ is a group of formula:

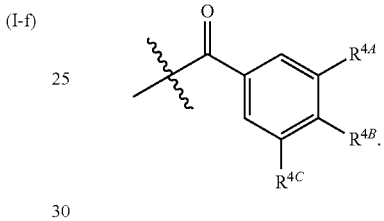

In yet further embodiments, $R^{4A}$, $R^{4B}$, and $R^{4C}$ is independently H, hydroxy, halogen, a group containing a fatty acid, a group containing a ketone body or pre-ketone body, a group containing an amino acid metabolite, or an optionally substituted alkoxy.

In some embodiments, each $R^A$ is independently H, optionally substituted alkyl, fatty acid acyl, or optionally acylated monosaccharide.

In certain embodiments, the acylated catechin polyphenol includes at least one fatty acid acyl (e.g., a short chain fatty acid acyl (e.g., the short chain fatty acid acyl is acetyl, propionyl, or butyryl)). In certain embodiments, the acylated catechin polyphenol includes at least one ketone body. In particular embodiments, the acylated catechin polyphenol includes at least one pre-ketone body. In further embodiments, the acylated catechin polyphenol includes at least one amino acid metabolite.

Acylated Stilbenoids

An acylated stilbenoid of the invention may be a stilbenoid, in which one, two, three, four, or five hydroxyl groups are independently replaced with a substituent —OR, where each R is independently selected from the group consisting of an acyl, alkyl, group including a fatty acid, and group including a ketone body or pre-ketone body, provided that at least one R is a group including a fatty acid or a group including a ketone body or pre-ketone body. Stilbenoids are trans-stilbenes that, when not acylated, are substituted with one, two, three, four, or five substituents independently selected from the group consisting of alkoxy (e.g., methoxy) and hydroxyl. Non-limiting examples of stilbenoids include resveratrol, pterostilbene, rhapontigenin, pinostilbene, oxyresveratrol, 4-methoxyresveratrol, and piceatannol. When the stilbenoid is acylated, one or both of the hydroxyl groups in the stilbenoid is independently substituted with a group including a fatty acid acyl or a group including a ketone body or pre-ketone body. In some embodiments, the acylated stilbenoid is an acylated resveratrol. In further embodiments, the acylated stilbenoid is an acylated piceatannol.

Acylated Mesalamines

An acylated mesalamine of the invention may be a mesalamine, in which one or more of —NH$_2$, —OH, or —COOH is replaced with an acyl, a group containing a fatty acid, a group containing a ketone body or pre-ketone body, or a group containing an amino acid metabolite, provided that acylated mesalamine contains at least one group containing a fatty acid, a group containing a ketone body or pre-ketone body, or a group containing an amino acid metabolite. A group containing a fatty acid, a group containing a ketone body or pre-ketone body, or a group containing an amino acid metabolite is bonded to mesalamine through a glycosidic bond, ester bond, amide bond, carbonate linker, or carbamate linker. In some embodiments, a group containing a fatty acid, a group containing a ketone body or pre-ketone body, or a group containing an amino acid metabolite is bonded to mesalamine through a glycosidic bond. In certain embodiments, an acylated mesalamine includes a group containing a ketone body or pre-ketone body. In further embodiments, an acylated mesalamine includes a group containing a fatty acid (e.g., a short chain fatty acid acyl (e.g., the short chain fatty acid acyl is acetyl, propionyl, or butyryl) or a medium chain fatty acid acyl (e.g., octanoyl)). In some embodiments, acylated mesalamine is a compound of formula (II):

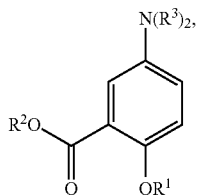

(II)

where
R$^1$ is H, alkyl, acyl, a group containing a fatty acid, a group containing a ketone body or pre-ketone body, or a group containing an amino acid metabolite;
R$^2$ is H, alkyl, a group containing a fatty acid, a group containing a ketone body or pre-ketone body, or a group containing an amino acid metabolite; and
each R$^3$ is independently H, alkyl, acyl, a group containing a fatty acid, a group containing a ketone body or pre-ketone body, or a group containing an amino acid metabolite; or both R$^3$ groups combine to form:

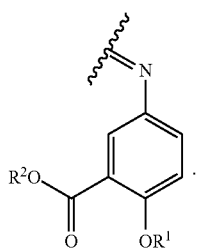

In some embodiments, the acylated mesalamine includes at least one group containing a fatty acid. In certain embodiments, the acylated mesalamine includes at least one group containing a ketone body or pre-ketone body. In further embodiments, the acylated mesalamine includes at least one group containing an amino acid metabolite.

In yet further embodiments,
R$^1$ is H, alkyl, acyl, or a group containing a fatty acid;
R$^2$ is H, alkyl, or a group containing a fatty acid; and
each R$^3$ is independently H, alkyl, acyl, or a group containing a fatty acid; or both R$^3$ groups combine to form:

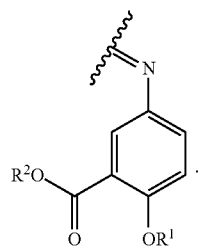

Acylated Ellagic Acid and Acylated Ellagic Acid Analogues

An acylated ellagic acid includes an ellagic acid core having one or more hydroxyls substituted with an acyl (e.g., a fatty acid acyl). An acylated ellagic acid analogue includes an ellagic acid analogue core having one or more hydroxyls substituted with an acyl (e.g., a fatty acid acyl).

An acylated ellagic acid is a compound of the following structures:

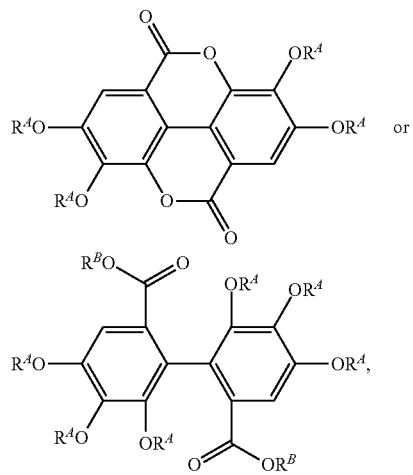

or a salt thereof, where each R$^A$ is independently H, alkyl, acyl, a group containing a fatty acid, a group containing a ketone body or pre-ketone body, or a group containing an amino acid metabolite; and each R$^B$ is independently H, alkyl, a group containing a fatty acid, a group containing a ketone body or pre-ketone body, or a group containing an amino acid metabolite; provided that at least one R$^A$ and/or at least one R$^B$, when present, is a group containing a fatty acid, a group containing a ketone body or pre-ketone body, or a group containing an amino acid metabolite.

An acylated ellagic acid analogue is a compound of the following structure:

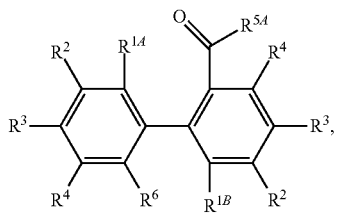

or a salt thereof,
where
each of $R^2$, $R^3$, and $R^4$ is independently H or —$OR^A$;
$R^6$ is H or —(CO)—$R^{5B}$;
$R^{1A}$ is H or —$OR^A$, and $R^{5A}$ is —OH or —$OR^B$; or $R^{1A}$ and $R^{5A}$ combine to form —O—;
$R^{1B}$ is H or —$OR^A$, and $R^{5B}$ is absent, —OH, or —$OR^B$; or $R^{1B}$ and $R^{5B}$ combine to form —O—;
each $R^A$ is independently H, O-protecting group, alkyl, acyl, a group containing a fatty acid, a group containing a ketone body or pre-ketone body, or a group containing an amino acid metabolite;
each $R^B$ is independently H, O-protecting group, alkyl, a group containing a fatty acid, a group containing a ketone body or pre-ketone body, or a group containing an amino acid metabolite;
provided that at least one $R^A$ and/or at least one $R^B$ is a group containing a fatty acid, a group containing a ketone body or pre-ketone body, or a group containing an amino acid metabolite.

Non-limiting examples of ellagic acid analogues include urolithin A, urolithin B, urolithin C, urolithin D, urolithin E, and urolithin M5.

Acylated Hydroxybenzoic Acids

An acylated active agent may be, e.g., an acylated hydroxybenzoic acid of the following structure:

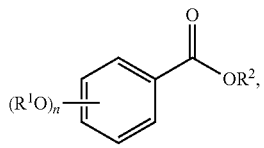

or a salt thereof,
where
n is 1, 2, or 3;
each $R^1$ is independently H, acyl, alkyl, a group containing a fatty acid, a group containing a ketone body or pre-ketone body, or a group containing an amino acid metabolite; and
$R^2$ is H, alkyl, a group containing a fatty acid, a group containing a ketone body or pre-ketone body, or a group containing an amino acid metabolite;
provided that the compound includes at least one group containing a fatty acid, at least one group containing a ketone body or pre-ketone body, or a group containing an amino acid metabolite.

Non-limiting examples of acylated hydroxybenzoic acids include gallic acid, in which one, two, or three phenolic hydroxyls are independently substituted with groups containing a fatty acid, groups containing a ketone body or pre-ketone body, or groups containing an amino acid metabolite.

Acylated Sugars

An acylated active agent may be, e.g., an acylated sugar. An acylated sugar may be a monosaccharide having one or more hydroxyls substituted with alkyl, acyl, a group containing a fatty acid, a group containing a ketone body or pre-ketone body, or group containing an amino acid metabolite. The monosaccharide is present in the pyranose or furanose form. Preferably, the monosaccharide is present in the pyranose form. The monosaccharide may be an aldose or ketose. Non-limiting examples of monosaccharides are arabinose, xylose, fructose, galactose, glucose, ribose, tagatose, fucose, and rhamnose. In some embodiments, the monosaccharide is L-arabinose, D-xylose, fructose, galactose, D-glucose, D-ribose, D-tagatose, L-fucose, or L-rhamnose. Preferably, the monosaccharide is xylose, arabinose, rhamnose, fucose, glucosamine, or tagatose. The monosaccharide may include an anomeric carbon bonded to —OR, where R is H, alkyl, acyl, a group containing a fatty acid, a group containing a ketone body or pre-ketone body, or a group containing an amino acid metabolite. Preferably, R is alkyl or a group containing a fatty acid. Alternatively, R is alkyl or a group containing an amino acid metabolite.

Acylated Shikimic Acid

An acylated active agent may be, e.g., an acylated shikimic acid of the following structure:

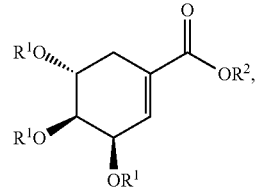

or a salt thereof,
where
each $R^1$ is independently H, acyl, alkyl, a group containing a fatty acid, a group containing a ketone body or pre-ketone body, or a group containing an amino acid metabolite; and
$R^2$ is H, alkyl, a group containing a fatty acid, a group containing a ketone body or pre-ketone body, or a group containing an amino acid metabolite;
provided that the compound includes at least one group containing a fatty acid, at least one group containing a ketone body or pre-ketone body, or a group containing an amino acid metabolite.

Combinations

The invention also provides combination regimens including a first active agent and a second active agent (e.g., as methods or unit dosage forms). The first active agent may be, e.g., a stilbenoid, catechin polyphenol, carotenoid, bile acid, amino acid, hydroxybenzoic acid, shikimic acid, monosaccharide, or mesalamine, metformin, vitamin, S-adenosyl-L-methionine. The second active agent may be, e.g., a ketone body or pre-ketone body, a nuclear receptor modulator (e.g., PPAR agonists (including alpha, delta/beta, gamma, and heterodimers thereof), FXR agonist, thyroid hormone receptor 1β agonist), GLP1R agonist, or ACC1 inhibitor. In some embodiments, the first active agent is a stilbenoid (e.g., resveratrol). In further embodiments, the second active agent is a pre-ketone body (e.g., 1,3-butanediol). The first active agent and the second active agent may act synergistically to modulate a metabolic marker or to treat a metabolic disorder. The first agent and the second agent may act synergistically to modulate a nonalcoholic fatty liver disease marker or to treat nonalcoholic fatty liver disease (e.g., nonalcoholic steatohepatitis). The first active agent and the second active agent may be provided in a dosage ratio of, e.g., from 2:1 to 1:20 (e.g., from 1:1 to 1:20, from 1:1 to 1:10, from 1:1 to 1:8, from 1:1 to 1:3, from 1:2 to 1:20, from 1:2 to 1:10, from 1:2 to 1:8, from 1:2 to 1:3, from 1:3 to 1:20, from 1:3 to 1:10, or from 1:3 to 1:8) of the first active agent to the second active agent.

Methods

Acylated active agents and active agent combinations described herein may be used to treat a metabolic disorder in a subject in need thereof. Additionally or alternatively, acylated active agents and active agent combinations described herein may be used to modulate a metabolic marker in a subject in need thereof.

Western diets—high in fats and refined carbohydrates—are associated with weight gain leading to obesity and risk for metabolic syndrome, type II diabetes, prediabetes, insulin resistance, hypercholesterolemia, and hyperlipidemia. Consumption of these diets may lead to accumulation of fat in the adipose tissue and liver. This may result in a change in the gut microbiome, elevation of the associated markers. In susceptible individuals, these dietary driven changes can lead to outright diabetes. Type II diabetes can cause cardiovascular and ophthalmic disease which can result in blindness, peripheral vascular insufficiency, cardiac disease and premature death. The dietary changes also correlate with changes in the gut microbiome termed dysbiosis. Correcting gut dysbiosis can lead to weight loss and improved glucose tolerance which, longer term, might be expected to abrogate many of the deleterious effects of an unhealthy diet. Metabolic products of the human gut microbiome, such as short chain fatty acids (SFCAs), may produce favorable metabolic effects upon the human host. In some cases, these molecules may work by binding to short chain fatty acid receptors. In other cases, the benefit may be produced via mechanisms such as peroxisome proliferator-activator receptor gamma (PPAR-gamma) or inhibition of histone deacetylase (HDACi).

A method of treating a metabolic disorder in a subject in need thereof may include administering an acylated active agent (e.g., a pharmaceutical or nutraceutical composition containing an acylated active agent) to the subject in need thereof. In some embodiments, the components of the acylated active agent (e.g., short chain fatty acid acyls (e.g., acetyl) or amino acid metabolites and epigallocatechin gallate or quercetin) may act synergistically to treat a metabolic disorder in a subject in need thereof.

Alternatively, a method of treating a metabolic disorder in a subject in need thereof may include administering a first active agent (e.g., a pharmaceutical or nutraceutical composition containing the first active agent) and a second active agent (e.g., a pharmaceutical or nutraceutical composition containing the second active agent) to the subject in need thereof. In certain embodiments, the first active agent and the second active agent (e.g., resveratrol and a pre-ketone body) may act synergistically to treat a metabolic disorder in a subject in need thereof. In some embodiments, a first active agent (e.g., a stilbenoid or catechin polyphenol) is co-administered with a second active agent (e.g., a pre-ketone body, ketone body, or fatty acid). The first and second active agent may be administered concomitantly. In certain embodiments, the second active agent may be administered before (e.g., within 12 hours, within 24 hours, within 3 days, or within 1 week), concomitantly with, or after (e.g., within 12 hours, within 24 hours, within 3 days, or within 1 week) the administration of the first active agent. When the first active agent and the second active agent are administered concomitantly, the two agents may be administered in separate unit dosages or in the same unit dosage. Preferably, the first active agent is a stilbenoid (e.g., resveratrol). Preferably, the second active agent is a pre-ketone body.

Non-limiting examples of metabolic disorders include obesity, metabolic syndrome, type II diabetes, prediabetes, insulin resistance, hypercholesterolemia, atherosclerosis and hyperlipidemia.

A method of modulating a metabolic marker in a subject in need thereof may include administering an acylated active agent (e.g., a pharmaceutical or nutraceutical composition containing an acylated active agent) to the subject. In some embodiments, the components of the acylated active agent (e.g., short chain fatty acid acyls (e.g., acetyl) or amino acid metabolites and a catechin polyphenol (e.g., epigallocatechin gallate or quercetin)) may act synergistically to modulate a metabolic marker in a subject in need thereof.

Alternatively, a method of modulating a metabolic marker in a subject in need thereof may include administering an active agent combination (e.g., a first active agent and a second active agent) to the subject. In certain embodiments, the first active agent and the second active agent (e.g., resveratrol and a pre-ketone body) may act synergistically to modulate a metabolic marker in a subject in need thereof.

Non-limiting examples of the metabolic markers include markers for obesity, type II diabetes, prediabetes, insulin resistance, metabolic syndrome, hypercholesterolemia, and hyperlipidemia. Obesity markers include, for example, total fat percentage, cellular adiposity, body mass index, rate of weight gain, abdominal fat quantity, subcutaneous fat quantity, inguinal fat quantity, epididymal fat quantity, ratio of white to brown fat, level of lipogenesis, and level of fat storage. Upon administration to a subject in need thereof, an acylated active agent or an active agent combination described herein may reduce the total fat percentage, cellular adiposity, body mass index, rate of weight gain, abdominal fat quantity, ratio of white to brown fat, level of lipogenesis, or level of fat storage. Markers for type II diabetes, prediabetes, insulin resistance, metabolic syndrome, hypercholesterolemia, and hyperlipidemia include, for example, an insulin level, GLP-1 level, PYY level, blood sugar level, hemoglobin A1c level, glucose tolerance level, cholesterol (e.g., HDL or LDL) level, and blood triglycerides level. Upon administration to a subject in need thereof, an acylated active agent or an active agent combination described herein may increase the insulin level, GLP-1 level, or PYY level. Additionally or alternatively, upon administration to a subject in need thereof, an acylated active agent or an active agent combination described herein may reduce the blood sugar level or hemoglobin A1c level. Additionally or alternatively, upon administration to a subject in need thereof, an acylated active agent or an active agent combination described herein may increase the glucose tolerance of the subject. Additionally or alternatively, upon administration to a subject in need thereof, an acylated active agent or an active agent combination described herein may reduce the blood cholesterol (e.g., LDL) level. Additionally or alternatively, upon administration to a subject in need thereof, an acylated active agent or an active agent combination described herein may reduce the blood triglycerides level. In some embodiments, the components of the acylated active agent (e.g., short chain fatty acid acyls (e.g., acetyl) or amino acid metabolites and a catechin polyphenol (e.g., epigallocatechin gallate or quercetin)) may act synergistically to modulate a metabolic marker, e.g., upon hydrolysis in the GI tract of the subject receiving the acylated active agent. In some embodiments, the active agents in an active agent combination (e.g., stilbenoid (e.g., resveratrol) and a pre-ketone body) may act synergistically to modulate a metabolic marker upon administration to a subject.

The markers described herein may be measured using methods known in the art. For example, glucose tolerance may be assessed using an oral glucose tolerance test (OGTT) described at MedlinePlus (medlineplus.gov). In this test, a subject drinks a liquid containing a predetermined amount of glucose (typically, 75 g of glucose), and blood glucose level is then measured at 15 minutes, 30 minutes, 60 minutes, 90 minutes, 120 minutes, 150 minutes, and 180 minutes after the glucose dosing. Insulin sensitivity can be measuring using an insulin clamp, for example, as described in Farrnnini and Mari, *J. Hypertens.*, 16:895-906, 1998. Lipogenesis may be measured using a hepatic de novo lipogenesis test, for example, as described in Rabøl et al., *Proc. Nat. Acad. Sci.*, 108:13705-13709, 2011. This test assesses the incorporation of deuterium into plasma very-low-density lipoprotein triglyceride (VLDL) during administration of deuterium-labeled water.

Acylated active agents and active agent combinations disclosed herein may be used in a method of treating a nonalcoholic fatty liver diseases (e.g., nonalcoholic steatohepatitis (NASH) with or without fibrosis, liver steatosis, NASH with advanced fibrosis) in a subject in need thereof. Additionally or alternatively, acylated active agents and active agent combinations disclosed herein may be used in a method of modulating a nonalcoholic fatty liver disease (e.g., nonalcoholic steatohepatitis) marker in a subject in need thereof.

Typically, the methods of treating NAFLD (e.g., NASH) or of modulating a NAFLD (e.g., NASH) marker include administration of acylated active agent or an active agent combination disclosed herein to a subject in need thereof (e.g., a subject diagnose with, or suffering from, NAFLD (e.g., NASH)). In some embodiments, the components of the acylated active agent (e.g., short chain fatty acid acyls (e.g., acetyl) or amino acid metabolites and a catechin polyphenol (e.g., epigallocatechin gallate or quercetin)) may act synergistically to treat NAFLD (e.g., NASH) in a subject in need thereof. In particular embodiments, the first active agent and the second active agent (e.g., resveratrol and a pre-ketone body) may act synergistically to treat NAFLD (e.g., NASH) in a subject in need thereof. In certain embodiments, the components of the acylated active agent (e.g., short chain fatty acid acyls (e.g., acetyl) or amino acid metabolites and a catechin polyphenol (e.g., epigallocatechin gallate or quercetin)) may act synergistically to modulate a NAFLD marker in a subject in need thereof. In further embodiments, the first active agent and the second active agent (e.g., resveratrol and a pre-ketone body) may act synergistically to modulate a NAFLD marker in a subject in need thereof.

In some embodiments, the method reduces the level of alanine transaminase in the blood of the subject by at least 1% (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more; e.g., up to 99% or 100%) relative to the level of alanine transaminase in the blood of the subject prior to the administering step. Certain methods disclosed herein may reduce the level of alanine transaminase in the blood of the subject to that which is considered normal for the subject (e.g., a human); a normal level of alanine transaminase in human blood is typically 7-56 units/L. In certain embodiments, the method reduces the level of aspartate transaminase in the blood of the subject by at least 1% (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more; e.g., up to 99% or 100%) relative to the level of aspartate transaminase in the blood of the subject prior to the administering step. Certain methods disclosed herein may reduce the level of aspartate transaminase in the blood of the subject to that which is considered normal for the subject (e.g., a human); a normal level of aspartate transaminase in human blood is typically 10-40 units/L. In particular embodiments, the method reduces the liver weight of the subject by at least 1% relative to the liver weight of the subject prior to the administering step.

Methods described herein may include administering multiple active agents (e.g., a stilbenoid, carotenoid, vitamin, catechin polyphenol, S-adenosyl-L-methionine, bile acid, or metformin in combination with, e.g., a pre-ketone body, ketone body, or fatty acid). In some embodiments, a first agent (e.g., a stilbenoid, carotenoid, vitamin, catechin polyphenol, S-adenosyl-L-methionine, bile acid, or metformin) is co-administered with a second agent (e.g., a pre-ketone body, ketone body, or fatty acid). The first and second agent may be administered concomitantly. In certain embodiments, the second agent may be administered before (e.g., within 12 hours, within 24 hours, within 3 days, or within 1 week), concomitantly with, or after (e.g., within 12 hours, within 24 hours, within 3 days, or within 1 week) the administration of the first agent. When the first and second agents are administered concomitantly, the two agents may be administered in separate unit dosages or in the same unit dosage. Preferably, the first agent is a stilbenoid (e.g., resveratrol). Preferably, the second agent is a pre-ketone body.

Pharmaceutical and Nutraceutical Compositions

The active agents disclosed herein (e.g., acylated active agents or active agents intended for combination regimens, e.g., a stilbenoid and a pre-ketone body) may be formulated into pharmaceutical or nutraceutical compositions for administration to human subjects in a biologically compatible form suitable for administration in vivo. Pharmaceutical and nutraceutical compositions typically include an active agent as described herein and a physiologically acceptable excipient (e.g., a pharmaceutically acceptable excipient).

The active agents described herein can also be used in the form of the free acid/base, in the form of salts, zwitterions, or as solvates. All forms are within the scope of the invention. The active agents, salts, zwitterions, solvates, or pharmaceutical or nutraceutical compositions thereof, may be administered to a subject in a variety of forms depending on the selected route of administration, as will be understood by those skilled in the art. The active agents described herein may be administered, for example, by oral, parenteral, buccal, sublingual, nasal, rectal, patch, pump, or transdermal administration, and the pharmaceutical or nutraceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, an active agent disclosed herein can be administered alone or in admixture with a pharmaceutical or nutraceutical carrier selected regarding the intended route of administration and standard pharmaceutical practice. Pharmaceutical and nutraceutical compositions for use in accordance with the present invention thus can be formulated in a conventional manner using one or more physiologically acceptable carriers comprising excipients and auxiliaries that facilitate processing of active agents disclosed herein into preparations which can be used pharmaceutically.

This disclosure also includes pharmaceutical and nutraceutical compositions which can contain one or more physiologically acceptable carriers. In making the pharmaceutical or nutraceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives. Nutraceutical compositions may be administered enterally (e.g., orally). A nutraceutical composition may be a nutraceutical oral formulation (e.g., a tablet, powder, lozenge, sachet, cachet, elixir, suspension, emulsion, solution, syrup, or soft or hard gelatin capsule), food additive (e.g., a food additive as defined in 21 C.F.R. § 170.3), food product (e.g., food for special dietary use as defined in 21 C.F.R. § 105.3), or dietary supplement (e.g., where the active agent is a dietary ingredient (e.g., as defined in 21 U.S.C. § 321(ff))). Active agents can be used in nutraceutical applications and as food additive or food products. Non-limiting examples of compositions including an active agent of the invention are a bar, drink, shake, powder, additive, gel, or chew.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* $21^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients,* $6^{th}$ Edition, Rowe et al., Eds., Pharmaceutical Press (2009).

These pharmaceutical and nutraceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy,* $21^{st}$ Ed., Gennaro, Ed., Lippencott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical and nutraceutical formulation. In preparing a formulation, the active agents can be milled to provide the appropriate particle size prior to combining with the other ingredients. If the active agent is substantially insoluble, it can be milled to a particle size of less than 200 mesh. If the active agent is substantially water soluble, the particle size can be adjusted by milling to provide a substantially uniform distribution in the formulation, e.g., about 40 mesh.

Dosages

The dosage of the active agent used in the methods described herein, or pharmaceutically acceptable salts or prodrugs thereof, or pharmaceutical or nutraceutical compositions thereof, can vary depending on many factors, e.g., the pharmacodynamic properties of the active agent; the mode of administration; the age, health, and weight of the recipient; the nature and extent of the symptoms; the frequency of the treatment, and the type of concurrent treatment, if any; and the clearance rate of the active agent in the subject to be treated. One of skill in the art can determine the appropriate dosage based on the above factors. The active agents used in the methods described herein may be administered initially in a suitable dosage that may be adjusted as required, depending on the clinical response. In general, a suitable daily dose of an active agent disclosed herein will be that amount of the active agent that is the lowest dose effective to produce a therapeutic effect. Such an effective dose will generally depend upon the factors described above.

An active agent disclosed herein may be administered to the subject in a single dose or in multiple doses. When multiple doses are administered, the doses may be separated from one another by, for example, 1-24 hours, 1-7 days, or 1-4 weeks. The active agent may be administered according to a schedule, or the active agent may be administered without a predetermined schedule. It is to be understood that, for any particular subject, specific dosage regimes should be adjusted over time according to the individual need and the professional judgment of the person administering or supervising the administration of the compositions.

The active agents may be provided in a unit dosage form. In some embodiments, the unit dosage form may be an oral unit dosage form (e.g., a tablet, capsule, suspension, liquid solution, powder, crystals, lozenge, sachet, cachet, elixir, syrup, and the like) or a food product serving (e.g., the active agents may be included as food additives or dietary ingredients). In certain embodiments, the unit dosage form is designed for administration of at least one active agent disclosed herein, where the total amount of an administered active agent(s) is from 0.1 g to 10 g (e.g., 0.5 g to 9 g, 0.5 g to 8 g, 0.5 g to 7 g, 0.5 g to 6 g, 0.5 g to 5 g, 0.5 g to 1 g, 0.5 g to 1.5 g, 0.5 g to 2 g, 0.5 g to 2.5 g, 1 g to 1.5 g, 1 g to 2 g, 1 g to 2.5 g, 1.5 g to 2 g, 1.5 g to 2.5 g, or 2 g to 2.5 g). When the administered active agents are provided as an active agent combination, the total amount may be, e.g., from 0.1 g to 10 g (e.g., 0.5 g to 9 g, 0.5 g to 8 g, 0.5 g to 7 g, 0.5 g to 6 g, 0.5 g to 5 g, 0.5 g to 1 g, 0.5 g to 1.5 g, 0.5 g to 2 g, 0.5 g to 2.5 g, 1 g to 1.5 g, 1 g to 2 g, 1 g to 2.5 g, 1.5 g to 2 g, 1.5 g to 2.5 g, or 2 g to 2.5 g). In other embodiments, the active agent is consumed at a rate of 0.1 g to 10 g per day (e.g., 0.5 g to 9 g, 0.5 g to 8 g, 0.5 g to 7 g, 0.5 g to 6 g, 0.5 g to 5 g, 0.5 g to 1 g per day, 0.5 g to 1.5 g per day, 0.5 g to 2 g per day, 0.5 g to 2.5 g per day, 1 g to 1.5 g per day, 1 g to 2 g per day, 1 g to 2.5 g per day, 1.5 g to 2 g per day, 1.5 g to 2.5 g per day, or 2 g to 2.5 g per day) or more. When the administered active agents are provided as an active agent combination, the total daily amount may be, e.g., 0.1 g to 10 g per day (e.g., 0.5 g to 9 g, 0.5 g to 8 g, 0.5 g to 7 g, 0.5 g to 6 g, 0.5 g to 5 g, 0.5 g to 1 g per day, 0.5 g to 1.5 g per day, 0.5 g to 2 g per day, 0.5 g to 2.5 g per day, 1 g to 1.5 g per day, 1 g to 2 g per day, 1 g to 2.5 g per day, 1.5 g to 2 g per day, 1.5 g to 2.5 g per day, or 2 g to 2.5 g per day) or more. The attending physician ultimately will decide the appropriate amount and dosage regimen, an effective amount of the active agent disclosed herein may be, for example, a total daily dosage of, e.g., between 0.5 g and 10 g (e.g., 0.5 to 5 g) of any of the acylated active agent or active agent combination described herein. Alternatively, the dosage amount can be calculated using the body weight of the subject. Preferably, when daily dosages exceed 5 g/day, the dosage of the active agents may be divided across two or three daily administration events.

In the methods of the invention, the time period during which multiple doses of an active agent disclosed herein are administered to a subject can vary. For example, in some embodiments doses of the active agents are administered to a subject over a time period that is 1-7 days; 1-12 weeks; or 1-3 months. In other embodiments, the active agents are administered to the subject over a time period that is, for example, 4-11 months or 1-30 years. In yet other embodiments, the active agents disclosed herein are administered to a subject at the onset of symptoms. In any of these embodiments, the amount of the active agent that is administered may vary during the time period of administration. When an active agent is administered daily, administration may occur, for example, 1, 2, 3, or 4 times per day.

Formulations

An active agent described herein may be administered to a subject with a pharmaceutically acceptable diluent, carrier, or excipient, in unit dosage form. Conventional pharmaceutical practice may be employed to provide suitable formulations or compositions to administer the active agent to subjects suffering from a disorder. Administration may begin before the subject is symptomatic.

Exemplary routes of administration of the active agents disclosed herein or pharmaceutical or nutraceutical compositions thereof, used in the present invention include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The active agents desirably are administered with a physiologically acceptable carrier (e.g., a pharmaceutically acceptable carrier). Pharmaceutical formulations of the active agents described herein formulated for treatment of the disorders described herein are also part of the present invention. In some preferred embodiments, the active agents disclosed herein are administered to a subject orally. In other preferred embodiments, the active agents disclosed herein are administered to a subject topically.

Formulations for Oral Administration

The pharmaceutical and nutraceutical compositions contemplated by the invention include those formulated for oral administration ("oral unit dosage forms"). Oral unit dosage forms can be, for example, in the form of tablets, capsules, a liquid solution or suspension, a powder, or liquid or solid crystals, which contain the active ingredient(s) in a mixture with physiologically acceptable excipients (e.g., pharmaceutically acceptable excipients). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other physiologically acceptable excipients (e.g., pharmaceutically acceptable excipients) can be colorants, flavoring agents, plasticizers, humectants, buffering agents, and the like.

Formulations for oral administration may also be presented as chewable tablets, as hard gelatin capsules where the active ingredient is mixed with an inert solid diluent (e.g., potato starch, lactose, microcrystalline cellulose, calcium carbonate, calcium phosphate or kaolin), or as soft gelatin capsules where the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of active agents, or by incorporating the active agent into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the active agents and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical and nutraceutical vehicles.

Formulations for Buccal Administration

Dosages for buccal or sublingual administration typically are 0.1 to 500 mg per single dose as required. In practice, the physician determines the actual dosing regimen which is most suitable for an individual subject, and the dosage varies with the age, weight, and response of the particular subject. The above dosages are exemplary of the average case, but individual instances exist where higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a active agent disclosed herein with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of active agents disclosed herein. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., U.S. Pat. Nos. 5,112,598 and 5,556,611, each of which is herein incorporated by reference).

Formulations for Nasal or Inhalation Administration

The active agents may also be formulated for nasal administration. Compositions for nasal administration also may conveniently be formulated as aerosols, drops, gels, and powders. The formulations may be provided in a single or multidose form. In the case of a dropper or pipette, dosing may be achieved by the subject administering an appropriate, predetermined volume of the solution or suspension. In the case of a spray, this may be achieved, for example, by means of a metering atomizing spray pump.

The active agents may further be formulated for aerosol administration, particularly to the respiratory tract by inhalation and including intranasal administration. The active agents for nasal or inhalation administration will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the active agent in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the unit dosage form comprises an aerosol dispenser, it will contain a propellant, which can be a compressed gas, e.g., compressed air or an organic propellant, e.g., fluorochlorohydrocarbon. The aerosol unit dosage forms can also take the form of a pump-atomizer.

Formulations for Parenteral Administration

The active agents described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in unit dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. For example, to prepare such a composition, the active agents disclosed herein may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., an active agent disclosed herein or a solution thereof);

(2) "Drug for Injection:" the drug substance (e.g., an active agent disclosed herein) as a dry solid that will be combined with the appropriate sterile vehicle for parenteral administration as a drug injection;

(3) "Drug Injectable Emulsion:" a liquid preparation of the drug substance (e.g., an active agent disclosed herein) that is dissolved or dispersed in a suitable emulsion medium;

(4) "Drug Injectable Suspension:" a liquid preparation of the drug substance (e.g., an active agent disclosed herein) suspended in a suitable liquid medium; and (5) "Drug for Injectable Suspension:" the drug substance (e.g., an active agent disclosed herein) as a dry solid that will be combined with the appropriate sterile vehicle for parenteral administration as a drug injectable suspension.

Exemplary formulations for parenteral administration include solutions of the active agents prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in *Remington: The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the active agents or biologically active agents within active agents. Other potentially useful parenteral delivery systems for active agents include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the active agent. Exemplary formulations for parenteral release of the active agent include: aqueous solutions, powders for reconstitution, cosolvent solutions, oil/water emulsions, suspensions, oil-based solutions, liposomes, microspheres, and polymeric gels.

Preparation of Acylated Active Agents

Acylated active agents may be prepared using synthetic methods and reaction conditions known in the art. Optimum reaction conditions and reaction times may vary depending on the reactants used. Unless otherwise specified, solvents, temperatures, pressures, and other reaction conditions may be selected by one of ordinary skill in the art.

Ester Preparation Strategy #1 (Acylation)

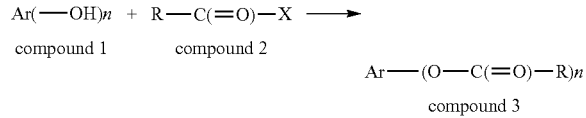

Scheme 1

In Scheme 1, a polyphenolic compound, compound 1 where n represents an integer from 1 to 15, is treated with an acylating agent, compound 2, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from $-10°$ C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by prior reaction of a carboxylic acid with an activating reagent such as EDC or EEDQ or the like. The acylating agents can be used in quantities ranging from 0.5 to 15 equivalents relative to compound 1.

The product, compound 3, can be purified by methods known to those of skill in the art.

Ester Preparation Strategy #2 (Acylation)

In some cases, the polyphenolic compound 1 may contain a functional group, Y, required to remain unreacted in the course of ester formation. In this case, it is appropriate to protect the functional group, Y, in the polyphenolic compound from acylation. This functional group may be an amino group or a hydroxyl group or other functionality with a labile hydrogen attached to a heteroatom. Such polyphenol esters can be prepared according to Scheme 2.

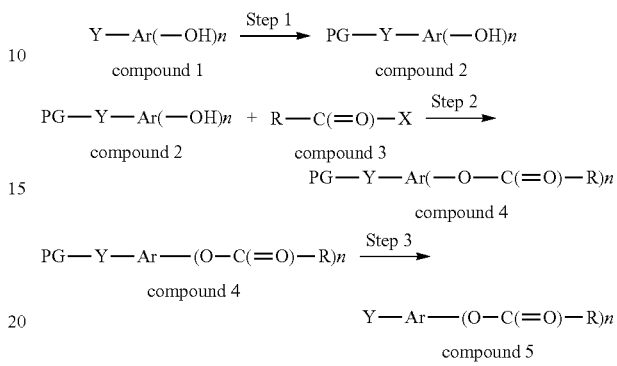

Scheme 2

In Scheme 2 Step 1, compound 1, a polyphenolic compound containing a functional group Y with a labile hydrogen in need of protection, is treated with a protecting reagent such as BOC anhydride, benzyoxycarbonyl chloride, FMOC chloride, benzyl bromide and the like in an appropriate solvent, optionally in the presence of a catalyst to provide compound 2 scheme 2. Compound 2 can be purified by methods known to those of skill in the art.

In Scheme 2 Step 2, compound 2 is treated with an acylating agent, compound 3, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from $-10°$ C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by prior reaction of a carboxylic acid with an activating reagent such as EDC or EEDQ or the like. The acylating agents can be used in quantities ranging from 0.5 to 15 equivalents, relative to compound 3. Compound 4 can be purified by methods known to those of skill in the art.

In Scheme 2 Step 3, compound 4 is subjected to conditions that cleave the protecting group, PG.

In the case of a BOC protecting group, the protecting group of compound 4 is removed under acidic conditions to give compound 5 of the invention. Suitable acids include trifluoroacetic acid, hydrochloric acid, p-toluenesulfonic acid and the like.

In the case of an FMOC protecting group, the protecting group of compound 4 is removed under basic conditions to give compound 5 of the invention. Suitable bases include piperidine, triethylamine and the like. Suitable solvents include DMF, NMP dichloromethane and the like. The FMOC group is also removed under non-basic conditions such as by treatment with tetrabutylammonium fluoride trihydrate in a suitable solvent such as DMF. The FMOC group is also removed by catalytic hydrogenation. Suitable catalysts for hydrogenation include 10% palladium-on-charcoal and palladium (II) acetate and the like. Suitable solvents for hydrogenation include DMF, ethanol, and the like In the case of a benzyloxycarbonyl or benzyl protecting group the protecting group of compound 4 is removed by hydrogenation to give compound 5. Suitable catalysts for hydrogenation include 10% Palladium-on-charcoal and Palladium acetate and the like. Suitable solvents for hydrogenation include DMF, ethanol, methanol, ethyl acetate, and the like. The product, compound 5, can be purified by methods known to those of skill in the art.

Ester Preparation Strategy #3 (Acylation)

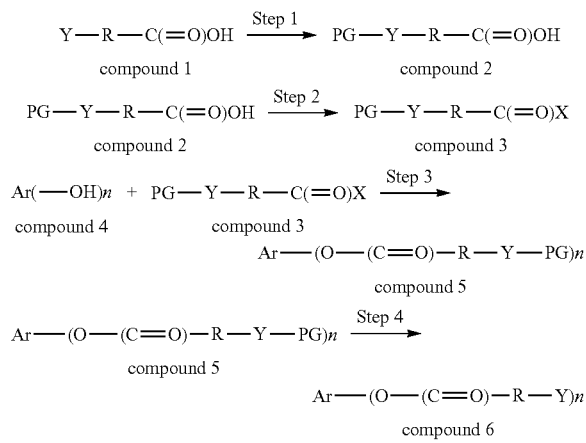

In Scheme 3 Step 1, compound 1, an acyl compound containing a functional group Y with a labile hydrogen in need on protection, is treated with a protecting reagent such as BOC anhydride, benzyoxycarbonyl chloride, FMOC chloride, benzyl bromide and the like in an appropriate solvent, optionally in the presence of a catalyst to provide compound 2 scheme 3. Compound 2 can be purified by methods known to those of skill in the art.

In Scheme 3 Step 2, compound 2 is treated with an activating reagent such as thionyl chloride, phosphorus oxychloride, EDC or EEDQ or the like to generate the activated acyl compound 3.

In Scheme 3 Step 3, the polyphenol compound 4 is treated with the activated acyl compound 3, in an appropriate solvent, optionally in the presence of a catalyst. Suitable catalysts include pyridine, dimethylaminopyridine, trimethylamine and the like to generate compound 5. The catalyst can be used in quantities ranging from 0.01 to 1.1 equivalents, relative to compound 3. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. The activated acyl compound 3 can be used in quantities ranging from 0.5 to 15 equivalents relative to compound 4.

In Scheme 3 Step 4, compound 5 is subjected to conditions designed to cleave the protecting group, PG, illustrated in Scheme 2 above. The product, compound 6, can be purified by methods known to those of skill in the art.

Ester Preparation Strategy #4 (Acylation)

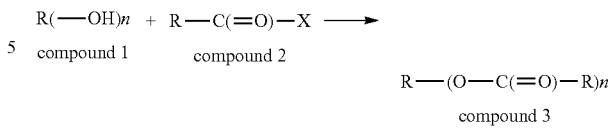

In Scheme 4 Step 1 a poly-ol compound, compound 1, where R represents a non-aromatic cyclic or acyclic moiety and n represents an integer from 1 to 15, is treated with an acylating agent, compound 2, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by prior reaction of a carboxylic acid with an activating reagent such as EDC or EEDQ or the like. The acylating agents can be used in quantities ranging from 0.5 to 15 equivalents, relative to compound 1. The product, compound 3, can be purified by methods known to those of skill in the art.

Ester Preparation Strategy #5 (Baeyer-Villiger Oxidation)

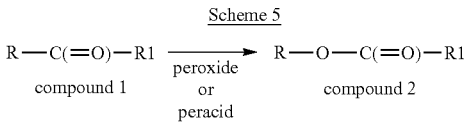

In Scheme 5 Step 1, a ketone compound, compound 1, where R and R1 represent non-aromatic cyclic or acyclic moieties, is treated with a peroxide or peroxyacid agent, such as meta-chloroperbenzoic acid, performic acid, peracetic acid, hydrogen peroxide, tert-butyl hydroperoxide and the like in an appropriate solvent, optionally in the presence of a catalyst. Suitable solvents include methylene chloride, diethyl ether, combinations thereof and the like. Suitable catalysts include $BF_3$, carboxylic acids and the like. Reaction temperatures range from −10° C. to the boiling point of the solvent used; reaction completion times range from 1 to 96 h. The product, compound 2, can be purified by methods known to those of skill in the art.

The R and R1 groups of compound 1 in Scheme 5 may optionally include additional ketone functionality that can undergo reaction. In addition the R and R1 groups of compound 1 may form a ring.

Ester Preparation Strategy #6 (Mitsunobu Reaction)

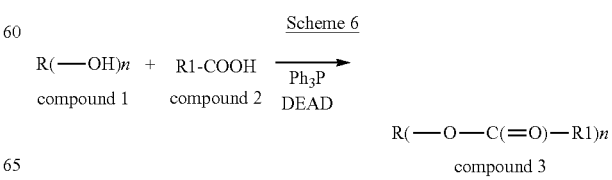

In Scheme 6 Step 1, a mixture of an alcohol compound, compound 1, where R represents a non-aromatic cyclic or acyclic moiety, and a carboxylic acid, compound 2 where R1 represents an alkanoyl group optionally substituted with one or more protected hydroxyl groups or oxo is treated with triphenylphosphine and a diazo compound such as diethylazodicarboxylate (DEAD) and the like in an appropriate solvent. Suitable solvents include methylene chloride, THF, acetonitrile, toluene, diethyl ether, combinations thereof and the like. Reaction temperatures range from −10° C. to the boiling point of the solvent used; reaction completion times range from 1 to 96 h. The product, compound 3 can be purified by methods known to those of skill in the art.

Where compound 3 is optionally substituted by one or more protected alcohol groups deprotection is accomplished by the methods illustrated in Scheme 2 above.

Ester Preparation Strategy #7 (Nucleophilic Alkylation)

Scheme 7

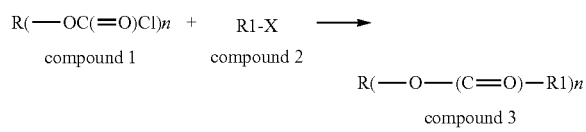

In Scheme 7 Step 1, a chloroformate compound, compound 1, where R represents an aromatic moiety or a non-aromatic cyclic or acyclic moiety, is treated, in an appropriate solvent, with an organometallic compound, compound 2 where R1 represents an alkyl group optionally substituted with one or more protected hydroxyl groups and X represents a metal such as Cu, Zn, Mg which is optionally coordinated by one or more counterions, such as chloride. Suitable solvents include methylene chloride, THF, acetonitrile, toluene, diethyl ether, combinations thereof, and the like. Reaction temperatures range from −10° C. to the boiling point of the solvent used; reaction completion times range from 1 to 96 h. The product, compound 3, can be purified by methods known to those of skill in the art.

Compound 1 can be prepared from the corresponding alcohol or polyol compounds by standard methods familiar to one skilled in the art.

Where compound 2 is optionally substituted by one or more protected alcohol groups deprotection is accomplished by the methods illustrated in Scheme 2 above.

Further modification of the initial product by methods known in the art and illustrated in the examples below, may be used to prepare additional compounds of this invention.

Ester Preparation Strategy #8 (Acylation)

Scheme 8

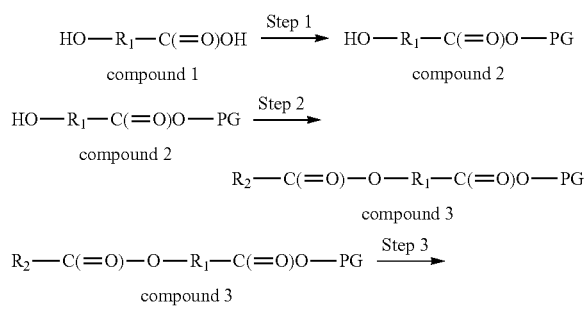

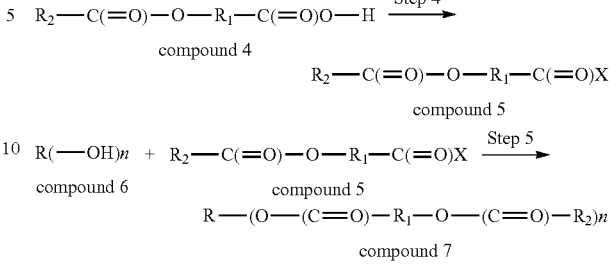

In Scheme 8 Step 1, compound 1, an acyl compound containing a hydroxyl group to be acylated, is treated with a protecting reagent such as benzyl bromide and the like in an appropriate solvent, optionally in the presence of a catalyst to provide compound 2 scheme 8. Compound 2 can be purified by methods known to those of skill in the art.

In scheme 8 Step 2, compound 2 is treated with an acylating agent, in an appropriate solvent, optionally in the presence of a catalyst. Suitable catalysts include pyridine, dimethylaminopyridine, trimethylamine and the like. The catalyst can be used in quantities ranging from 0.01 to 1.1 equivalents, relative to compound 2. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. Suitable acylating agents include acyl chlorides, acyl fluorides, acyl bromides, carboxylic acid anhydrides whether symmetrical or not. A suitable acylating agent may also be generated in situ by a reaction of a carboxylic acid with an activating reagent such as EDC or EEDQ or the like. The acylating agents can be used in quantities ranging from 0.5 to 15 equivalents relative to compound 1.

In Scheme 8 Step 3, compound 3 is subjected to conditions that cleave the protecting group, PG. In the case of a benzyl protecting group, the protecting group of compound 3 is removed by hydrogenation to give compound 4. Suitable catalysts for hydrogenation include 10% palladium-on-charcoal and palladium acetate and the like. Suitable solvents for hydrogenation include, DMF, ethanol, methanol, ethyl acetate and the like. The product, compound 4, can be purified by methods known to those of skill in the art.

In Scheme 8 Step 4, compound 4 is treated with an activating reagent such as thionyl chloride, phosphorus oxychloride, EDC or EEDQ or the like to generate the activated acyl compound 5.

In Scheme 8 Step 5, the poly-hydroxyl compound, compound 6, where R represents an aromatic or an aliphatic cyclic or acyclic core, is treated with the activated acyl compound 5, in an appropriate solvent, optionally in the presence of a catalyst. Suitable catalysts include pyridine, dimethylaminopyridine, trimethylamine and the like to generate compound 5. The catalyst can be used in quantities ranging from 0.01 to 1.1 equivalents, relative to compound 3. Suitable solvents include methylene chloride, ethyl acetate, diethyl ether, tetrahydrofuran, 1,4-dioxane, 1,2-dimethoxyethane, toluene, combinations thereof and the like. Reaction temperatures range from −10° C. to the boiling point of the solvent used; reaction completion times range from 1 to 96 h. The activated acyl compound 5 can be used in quantities ranging from 0.5 to 15 equivalents relative to compound 6.

The product, compound 7, can be purified by methods known in the art.

The following examples are meant to illustrate the invention. They are not meant to limit the invention in any way.

EXAMPLES

Example 1. Preparation of Exemplary Acylated Active Agents

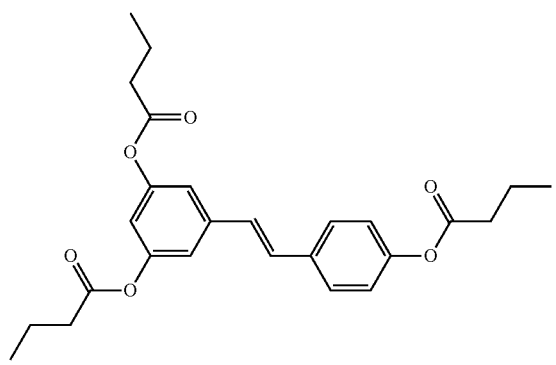 [SMILES: CCCC(=O)Oc1ccc(/C=C/c2cc(OC(=O)CCC)cc(OC(=O)CCC)c2)cc1]

Compound 1: [4-[(E)-2-[3,5-di(butanoyloxy)phenyl]vinyl]phenyl] butanoate

To a solution of 5-[(E)-2-(4-hydroxyphenyl)vinyl]benzene-1,3-diol (3 g, 13.14 mmol) and $K_2CO_3$ (4.54 g, 32.86 mmol) in acetonitrile (50 mL) was added butanoyl chloride (5.60 g, 52.58 mmol, 5.49 mL). The mixture was stirred at 20° C. for 10 h. The reaction mixture was filtered, and the filtrate was concentrated under reduced pressure to give a residue that was purified by column chromatography ($SiO_2$, Petroleum ether/Ethyl acetate=20/1 to 10:1). Compound 1 was obtained as a white solid. LC/MS: $(M+NH_4^+)$: 456.2

Compound 2: [4-[(E)-2-[3,5-bis(4-phenylbutanoyloxy)phenyl]vinyl]phenyl] 4-phenylbutanoate Step 1

To a solution of 4-phenylbutanoic acid (5 g, 30.45 mmol) in dichloromethane (50 mL) was added $SOCl_2$ (10.87 g, 91.35 mmol, 6.63 mL) at 0° C. The mixture is stirred at 20° C. for 10 h. The reaction mixture was concentrated under reduced pressure to give a residue that was dissolved in toluene (15 mL). The solution was concentrated under reduced pressure to afford 4-phenylbutanoyl chloride (4.32 g, crude) as a yellow oil, which was used in next step directly.

Step 2

To a solution of 5-[(E)-2-(4-hydroxyphenyl)vinyl]benzene-1,3-diol (0.278 g, 1.22 mmol) and $K_2CO_3$ (420.89 mg, 3.05 mmol) in acetonitrile (30 mL) was added 4-phenylbutanoyl chloride (1.00 g, 5.48 mmol). The mixture was stirred at 20° C. for 10 h, the reaction mixture was filtered, and the filtrate was concentrated under reduced pressure to give a residue. The residue was combined with another batch and purified by column chromatography ($SiO_2$, Petroleum ether/Ethyl acetate=20/1 to 8:1) to afford compound 2 (367 mg) as a white solid. LC/MS $(M+NH_4^+)$: 684.3

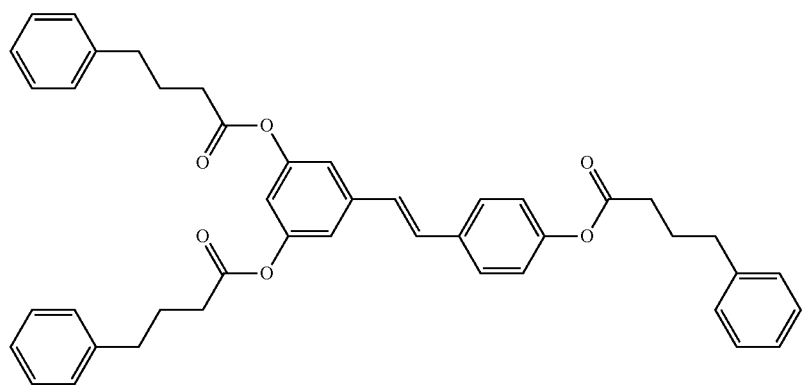 [SMILES: O=C(CCCc1ccccc1)Oc1ccc(/C=C/c2cc(OC(=O)CCCc3ccccc3)cc(OC(=O)CCCc3ccccc3)c2)cc1]

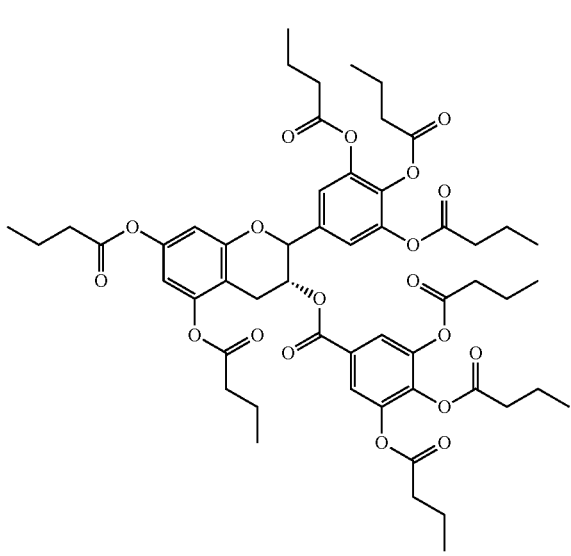 [SMILES: CCCC(=O)Oc1cc(OC(=O)CCC)c2c(c1)OC(c1cc(OC(=O)CCC)c(OC(=O)CCC)c(OC(=O)CCC)c1)[C@H](OC(=O)c1cc(OC(=O)CCC)c(OC(=O)CCC)c(OC(=O)CCC)c1)C2]

Compound 3: [(2R,3R)-5,7-di(butanoyloxy)-2-[3,4,5-tri(butanoyloxy)phenyl]chroman-3-yl] 3,4,5-tri(butanoyloxy)benzoate Butyryl chloride (6.03 mL) was added to a stirred solution of epigallocatechin gallate (2.0 g) and pyridine (6.28 mL) in dichloromethane (20 mL) over 2 h between −5° C. to 5° C. The resulting mixture was stirred overnight at room temperature. The reaction mixture was then diluted with dichloromethane (100 mL), washed sequentially with water (50 mL), 2N HCl (50 mL), saturated sodium bicarbonate (50 mL), and brine. The organic layer was evaporated in vacuo, and the resulting crude material was purified by flash chromatography (30% ethyl acetate/heptane) to give compound 3 (800 mg, 18%). $^1$H NMR (CDCl$_3$): δ 7.6 (s, 2H), 7.22 (s, 2H), 6.78 (s, 1H), 6.6 (s, 1H), 5.62 (t, 1H), 5.18 (s, 1H), 2.98-3.02 (m, 2H), 2.4-2.6 (m, 16H), 1.6-1.8 (m, 16H), 0.92-1.02 (m, 24H).

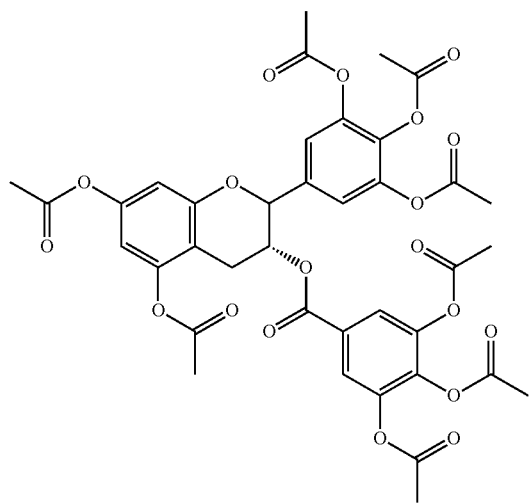 [SMILES: CC(=O)Oc1cc(OC(C)=O)c2c(c1)OC(c1cc(OC(C)=O)c(OC(C)=O)c(OC(C)=O)c1)[C@H](OC(=O)c1cc(OC(C)=O)c(OC(C)=O)c(OC(C)=O)c1)C2]

Compound 4: [(2R,3R)-5,7-diacetoxy-2-(3,4,5-triacetoxyphenyl)chroman-3-yl] 3,4,5-triacetoxybenzoate Acetic anhydride (6.1 mL) was added dropwise to epigallocatechin gallate (2.0 g) in pyridine (20 mL) at 0° C., and the resulting mixture was stirred overnight at room temperature. Water was added to the reaction mixture, and the solid was filtered and washed with aq. 1N HCl (10 mL) and heptane (20 mL). The solid was then dissolved in dichloromethane and passed through a silica gel filter column with dichloromethane as a mobile phase to furnish compound 4 (1.0 g, 28%) upon evaporation of volatiles. $^1$H NMR (CDCl$_3$): δ 7.6 (s, 2H), 7.2 (s, 2H), 6.75 (s, 1H), 6.6 (s, 1H), 5.6 (t, 1H), 5.19 (s, 1H), 2.98-3.02 (m, 2H), 2.18-2.28 (m, 24H).

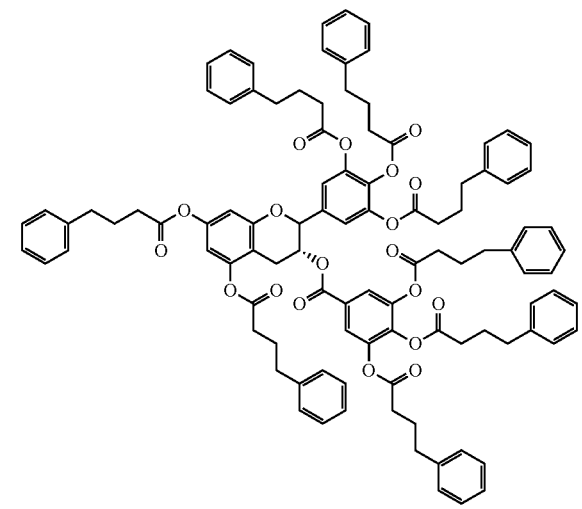 [SMILES: O=C(CCCc1ccccc1)Oc1cc(OC(=O)CCCc2ccccc2)c2c(c1)OC(c1cc(OC(=O)CCCc3ccccc3)c(OC(=O)CCCc3ccccc3)c(OC(=O)CCCc3ccccc3)c1)[C@H](OC(=O)c1cc(OC(=O)CCCc3ccccc3)c(OC(=O)CCCc3ccccc3)c(OC(=O)CCCc3ccccc3)c1)C2]

Compound 5: [(2R,3R)-5,7-bis(4-phenylbutanoyloxy)-2-[3,4,5-tris(4-phenylbutanoyloxy)phenyl]chroman-3-yl] 3,4,5-tris(4-phenylbutanoyloxy)benzoate Step 1

To a solution of 4-phenylbutanoic acid (3 g, 18.27 mmol) and SOCl$_2$ (10.87 g, 91.35 mmol, 6.63 mL) in dichloromethane (50 mL) is added one drop of DMF, then the mixture stirred at 20° C. for 5 h. The solvent is removed in vacuum and toluene (20 mL) added to the mixture. The mixture is concentrated in vacuo to afford 4-phenylbutanoyl chloride (3.5 g, crude).

Step 2

To a solution of [(2R,3R)-5,7-dihydroxy-2-(3,4,5-trihydroxyphenyl)chroman-3-yl] 3,4,5-trihydroxybenzoate (1 g, 2.18 mmol) and $K_2CO_3$ (4.52 g, 32.72 mmol) in acetonitrile (100 mL) was added a solution of 4-phenylbutanoyl chloride (7.97 g, 43.63 mmol) in acetonitrile (10 mL), then the mixture was stirred at 20° C. for 10 h. The mixture was filtered, and the filtrate was concentrated in vacuum. The crude product was purified by silica gel chromatography (petroleum ether/ethyl acetate=20:1-1:1) to afford compound 5 (2.2 g, 1.28 mmol, 58.7% yield) as a white solid. LC/MS (M+$H_3O^+$): 1645.1

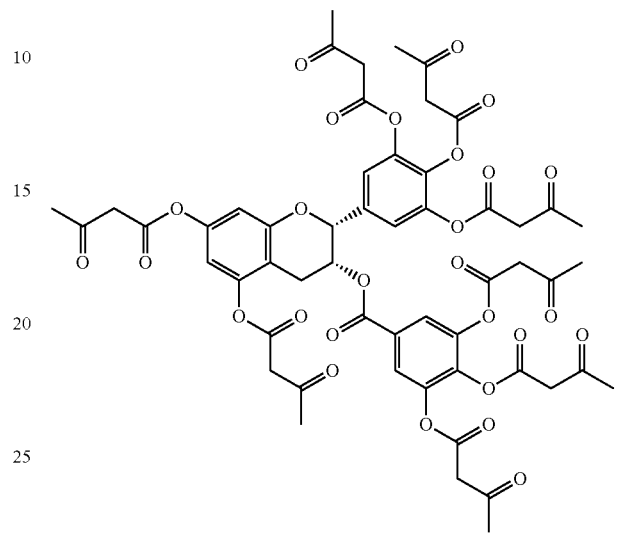

Compound 7:[4-[(E)-2-[3,5-bis[[(3R)-3-hydroxybutanoyl]oxy]phenyl]vinyl]phenyl](3R)-3-hydroxybutanoate

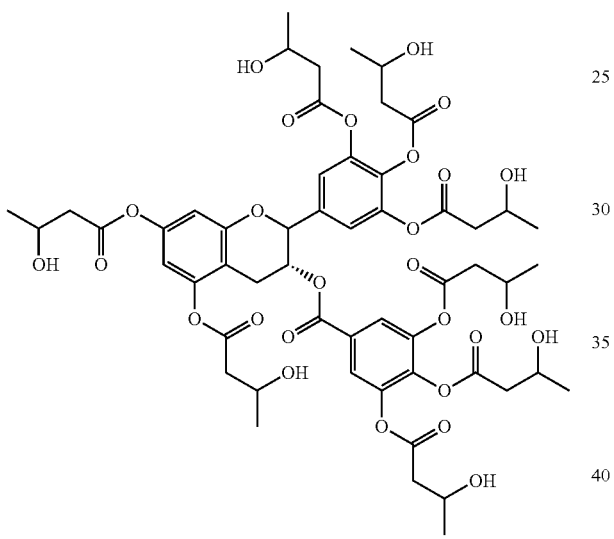

Compound 6: [(2R,3R)-5,7-bis(3-hydroxybutanoyloxy)-2-[3,4,5-tris(3-hydroxybutanoyloxy)phenyl]chroman-3-yl] 3,4,5-tris(3-hydroxybutanoyloxy)benzoate Compound 8:[(2R,3R)-5,7-bis(3-oxobutanoyloxy)-2-[3,4,5-tris(3-oxobutanoyloxy)phenyl]chroman-3-yl]3,4,5-tris(3-oxobutanoyloxy)benzoate

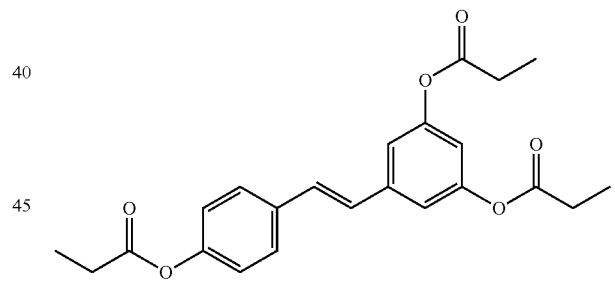

Compound 9: [4-[(E)-2-[3,5-di(propanoyloxy)phenyl]vinyl]phenyl] Propanoate

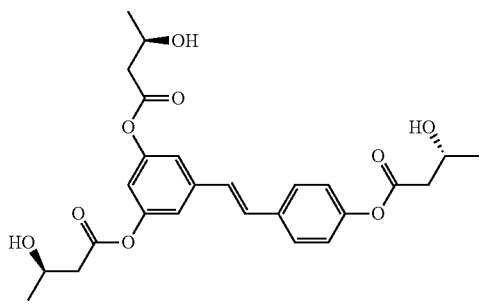 [SMILES: C[C@@H](O)CC(=O)Oc1ccc(/C=C/c2cc(OC(=O)C[C@@H](C)O)cc(OC(=O)C[C@@H](C)O)c2)cc1]

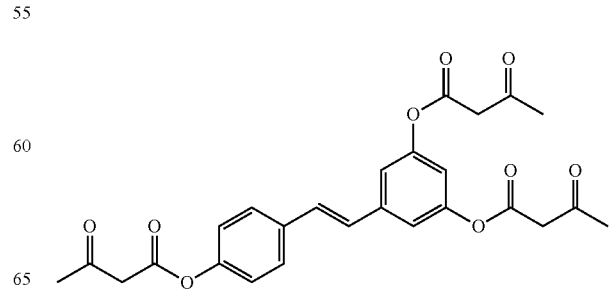

Compound 10:[4-[(E)-2-[3,5-bis(3-oxobutanoyloxy) phenyl]vinyl]phenyl]3-oxobutanoate

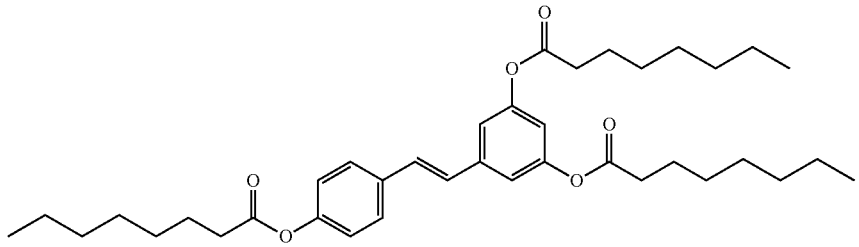 [SMILES: CCCCCCCC(=O)Oc1ccc(/C=C/c2cc(OC(=O)CCCCCCC)cc(OC(=O)CCCCCCC)c2)cc1]

Compound 11: [4-[(E)-2-[3,5-di(octanoyloxy)phenyl]vinyl]phenyl] octanoate

To a mixture of 5-[(E)-2-(4-hydroxyphenyl)vinyl]benzene-1,3-diol (1 g) and $K_2CO_3$ (1.8 g) in ACN (30 mL) was added octanoyl chloride (2.14 g) at 25° C. The mixture was stirred at 25° C. for 10 hours. Additional octanoyl chloride (1.42 g) was added and the mixture was stirred at 25° C. for 10 hours. The reaction mixture was concentrated under reduced pressure and the residue was purified by reverse phase prep-HPLC (C18, water (0.05% HCl)-ACN gradient) to give compound 11 (0.53 g, 20%) as colorless oil. $^1$H NMR (400 MHz, $CDCl_3$). 7.481 (m, 2H), 7.107-6.956 (m, 6H), 6.809, (m, 1H), 2.564 (m, 6H), 1.781 (m, 6H), 1.383 (m, 24H), 0.894 (m, 9H).

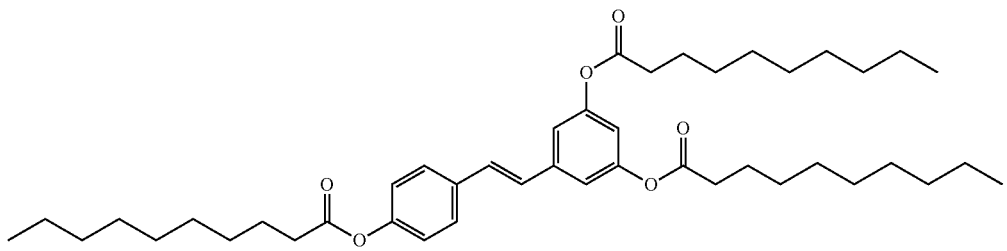 [SMILES: CCCCCCCCCC(=O)Oc1ccc(/C=C/c2cc(OC(=O)CCCCCCCCC)cc(OC(=O)CCCCCCCCC)c2)cc1]

Compound 12: [4-[(E)-2-[3,5-di(decanoyloxy)phenyl]vinyl]phenyl] Decanoate

To the solution of 5-[(E)-2-(4-hydroxyphenyl)vinyl]benzene-1,3-diol (1 g) and $K_2CO_3$ (3.0 g) in ACN (50 mL) was added decanoyl chloride (5.85 g) dropwise. Then the mixture was stirred at 25° C. for 16 h. The mixture was filtered and concentrated in and the residue was purified by silica gel chromatography (petroleum ether/EtOAc, 10:1) and then prep-TLC (petroleum ether/EtOAc, 5:1) to give compound 12 (0.062 g, 2%) as yellow oil. LCMS: 691.3 (M+H$^+$) $^1$H NMR (400 MHz, $CDCl_3$). δ 7.479 (m, 2H), 7.110-6.954 (m, 6H), 6.802, (m, 1H), 2.562 (m, 6H), 1.759 (m, 6H), 1.422-1.322 (m, 36H), 0.894 (m, 9H).

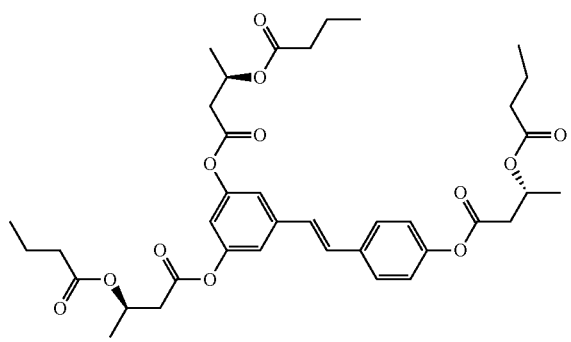 [SMILES: CCCC(=O)O[C@H](C)CC(=O)Oc1ccc(/C=C/c2cc(OC(=O)C[C@@H](C)OC(=O)CCC)cc(OC(=O)C[C@@H](C)OC(=O)CCC)c2)cc1]

Compound 13: [4-[(E)-2-[3,5-bis[[(3R)-3-butanoyloxybutanoyl]oxy]phenyl]vinyl]phenyl] (3R)-3-butanoyloxy-butanoate Step 1: Benzyl (3R)-3-hydroxybutanoate To a solution of sodium (3R)-3-hydroxybutanoate (50 g) in DMF (500 mL) was added dropwise bromomethylbenzene (67.8 g) at 25° C. Then the mixture was stirred at 60° C. for 12 h. Water (800 mL) was added to the reaction mixture, and the mixture was extracted with EtOAc (550 mL). The organic layer was washed with brine (230 mL) and dried over $Na_2SO_4$, filtered and concentrated. The residue was purified by flash silica gel chromatography (petroleum ether/ethyl acetate=100/1 to 40/1) to give benzyl (3R)-3-hydroxybutanoate (57 g, 66.6%) as a colorless oil which was used directly in the next step.

Step 2: Benzyl (3R)-3-butanoyloxybutanoate

To a solution of pyridine (55.7 g) in DCM (570 mL) was added benzyl (3R)-3-hydroxybutanoate (57 g) and DMAP (1.15 g) at 25° C. Butanoyl chloride (43.8 g) was added dropwise to the mixture under $N_2$ and then stirred at 25° C. for 12 h. The mixture was concentrated, the residue was diluted with EtOAc (300 mL) and the organic layer was washed with $H_2O$ (550 mL), brine (270 mL), dried over $Na_2SO_4$, filtered and concentrated. The residue was purified by flash silica gel chromatography (petroleum ether/ethyl acetate, 100:1 to 70:1) to give benzyl (3R)-3-butanoyloxybutanoate (54 g, 62.6%) as a colorless oil. LCMS: 265.1 (M+H$^+$)

Step 3: (3R)-3-butanoyloxybutanoic acid

To a suspension of Pd/C 10% (9 g) in EtOAc (1300 mL) was added benzyl (3R)-3-butanoyloxybutanoate (54 g) at 25° C. The reaction mixture was stirred at 25° C. under H$_2$ (15 Psi) for 4 h. The mixture was filtered and concentrated to give (3R)-3-butanoyloxybutanoic acid (30 g) as colorless oil.

Step 4: [4-[(E)-2-[3,5-bis[[(3R)-3-butanoyloxybutanoyl]oxy]phenyl]vinyl]phenyl] (3R)-3-butanoyloxy-butanoate To a solution of 5-[(E)-2-(4-hydroxyphenyl)vinyl]benzene-1,3-diol (0.25 g) and (3R)-3-butanoyloxybutanoic acid (0.76 g) in DCM (7.5 mL) was added DCC (0.29 g) in DCM (5 mL). DMAP (0.040 g) was added to the mixture at 25° C., and the mixture was stirred for 12 h. The mixture was cooled to 0° C., petroleum ether (10 mL) was added and the mixture was stirred for 15 min, then filtered and concentrated. The residue was dissolved in EtOAc (5 mL), washed with 0.5 N HC (18 mL) and brine (8 mL), dried over Na$_2$SO$_4$, filtered and concentrated. The residue was purified by reverse phase prep-HPLC (C18; water (0.05% HCl)-ACN gradient) to give compound 13 (0.060 g, 7%) as a colorless oil. LCMS: 697.4 (M+H$^+$) $^1$H NMR (400 MHz, CDCl$_3$). δ 7.494 (m, 2H), 7.12-7.042 (m, 6H), 6.824 (m, 1H), 5.428, (m, 3H), 2.909-2.785 (m, 6H), 2.303 (m, 6H), 1.696-1.658 (m, 6H), 1.527 (d, 9H), 0.956 (t, 9H).

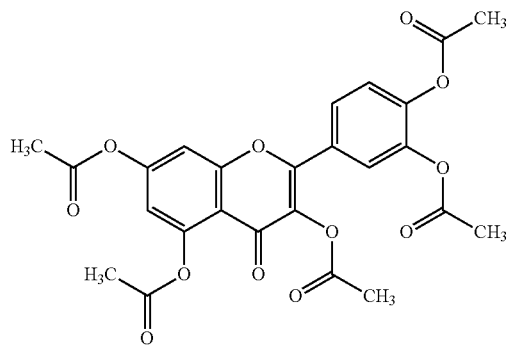 [SMILES: CC(=O)Oc1cc(OC(C)=O)c2c(=O)c(OC(C)=O)c(-c3ccc(OC(C)=O)c(OC(C)=O)c3)oc2c1]

Compound 14: [2-acetoxy-4-(3,5,7-triacetoxy-4-oxo-chromen-2-yl)phenyl] acetate

To a mixture of 2-(3,4-dihydroxyphenyl)-3,5,7-trihydroxy-chromen-4-one (1 g) and acetic anhydride (2.36 g) in THF (40 mL) was added K$_2$CO$_3$ (3.2 g) at 25° C., then the mixture was stirred at 55° C. for 12 h. Additional acetic anhydride was added (3 equiv.) and the mixture and stirred for another 3 h. The reaction mixture was concentrated in vacuum and purified by reverse phase prep-HPLC (C18; water (0.05% HCl)-ACN gradient) to give compound 14 (0.837 g, 49%) as a white solid. LCMS: 513.2 (M+H$^+$) $^1$H NMR (400 MHz, CDCl$_3$). δ 7.742-7.703 (m, 2H), 7.373-7.346 (m, 2H), 6.888 (s, 1H), 2.443, (s, 3H), 2.356 (s, 6H), 2.350 (s, 6H).

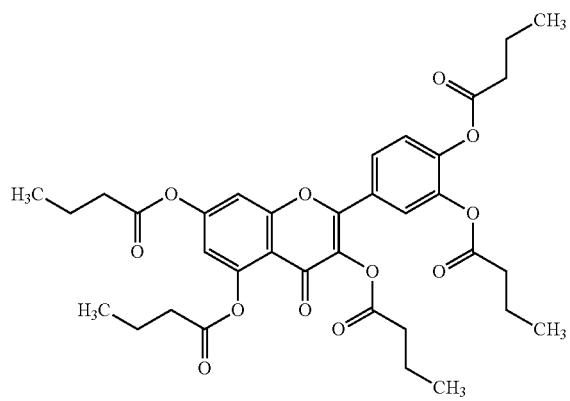 [SMILES: CCCC(=O)Oc1cc(OC(=O)CCC)c2c(=O)c(OC(=O)CCC)c(-c3ccc(OC(=O)CCC)c(OC(=O)CCC)c3)oc2c1]

Compound 15: [2-butanoyloxy-4-[3,5,7-tri(butanoyloxy)-4-oxo-chromen-2-yl]phenyl]butanoate To a mixture of 2-(3,4-dihydroxyphenyl)-3,5,7-trihydroxy-chromen-4-one (1 g) and butanoyl chloride (3.53 g) in THF (40 mL) was added TEA (3.35 g) at 25° C., then the mixture was stirred at 55° C. for 12 h. The reaction mixture was concentrated in vacuum and purified by reverse phase prep-HPLC (C18, water (0.05% HCl)-ACN gradient) to give compound 15 (1.13 g, 52% yield) as a colorless solid. LCMS: 653.3 (M+H$^+$) $^1$H NMR (400 MHz, CDCl$_3$). δ 7.666-7.608 (m, 2H), 7.292-7.210 (m, 2H), 6.880 (s, 1H), 2.542 (t, 2H), 2.535-2.484 (m, 8H), 1.753 (m, 10H), 1.020-0.997 (m, 12H), 0.949 (t, 3H).

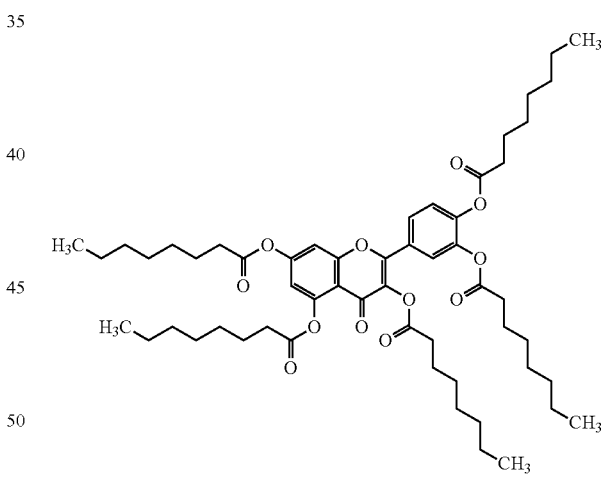

Compound 16: [2-octanoyloxy-4-[3,5,7-tri(octanoyloxy)-4-oxo-chromen-2-yl]phenyl]octanoate To a mixture of 2-(3,4-dihydroxyphenyl)-3,5,7-trihydroxy-chromen-4-one (0.32 g) and octanoyl chloride (1.72 g) in THF (20 mL) was added TEA (1.07 g) at 25° C. Then the mixture was stirred at 55° C. for 12 h. A portion of the solvent was removed in vacuum and the precipitate was collected by filtration to give compound 16 (0.20 g, 20%) as a white solid. $^1$H NMR (400 MHz, CDCl$_3$). δ 7.709-7.655 (m, 2H), 7.329-7.301 (m, 2H), 6.837 (s, 1H), 2.723 (t, 2H), 2.612-2.539 (m, 8H), 1.751 (m, 10H), 1.412-1.309 (m, 40H), 0.896 (m, 15H).

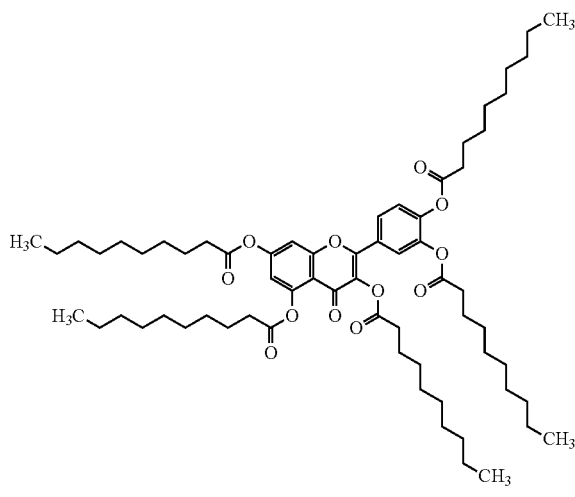 [SMILES: CCCCCCCCCC(=O)Oc1cc(OC(=O)CCCCCCCCC)c2c(=O)c(OC(=O)CCCCCCCCC)c(-c3ccc(OC(=O)CCCCCCCCC)c(OC(=O)CCCCCCCCC)c3)oc2c1]

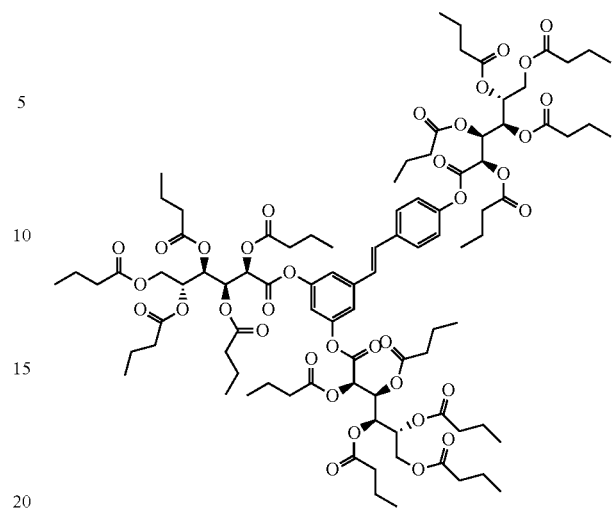

Compound 17:[2-decanoyloxy-4-[3,5,7-tris(decanoyloxy)-4-oxo-chromen-2-yl]phenyl]decanoate To a mixture of 2-(3,4-dihydroxyphenyl)-3,5,7-trihydroxy-chromen-4-one (1 g) and decanoyl chloride (6.31 g) in THF (50 mL) was added TEA (3.35 g) at 25° C., then the mixture was stirred at 55° C. for 12 h. A portion of the solvent was removed in vacuum and the precipitate was collected by filtration to give compound 17 (2.47 g, 69%) as a white solid. $^1$H NMR (400 MHz, CDCl$_3$). δ 7.772-7.669 (m, 2H), 7.343-7.321 (m, 2H), 6.685 (s, 1H), 2.736 (t, 2H), 2.610-2.551 (m, 8H), 1.762 (m, 10H), 1.557-1.295 (m, 50H), 0.899 (m, 15H).

Compound 19: [4-[(E)-2-[3,5-bis[[(2R,3S,4R,5R)-2,3,4,5,6-penta(butanoyloxy)hexanoyl]oxy]phenyl]vinyl]phenyl](2R,3S,4R,5R)-2,3,4,5,6-penta(butanoyloxy)hexanoate To a solution of 5-[(E)-2-(4-hydroxyphenyl)vinyl]benzene-1,3-diol (0.050 g), DCC (0.180 g) and DMAP (0.008 g) in THF (5 mL) was added (2R,3S,4R,5R)-2,3,4,5,6-penta(butanoyloxy)hexanoic acid (0.479 g) and the mixture was stirred at 40° C. for 12 h. The mixture reaction was filtered and concentrated. The residue was purified by column chromatography (SiO$_2$, petroleum ether/ethyl acetate gradient) to give compound 19 (0.080 g, 16% yield) as a colorless oil. $^1$H NMR (400 MHz, CDCl$_3$). δ 7.529-7.481 (m, 2H), 7.177-7.089 (m, 5H), 6.669 (m, 1H), 6.825 (m, 1H), 5.781 (m, 2H), 5.495-5.483 (m, 2H), 5.341-5.305 (m, 2H), 5.289-5.184 (m, 2H), 5.053 (d, 1H), 4.728 (dd, 1H), 4.375 (m, 2H), 4.156-3.989 (m, 4H), 2.474-2.221 (m, 30H), 1.597-1.566 (m, 30H), 0.923-0.847 (m, 45H)

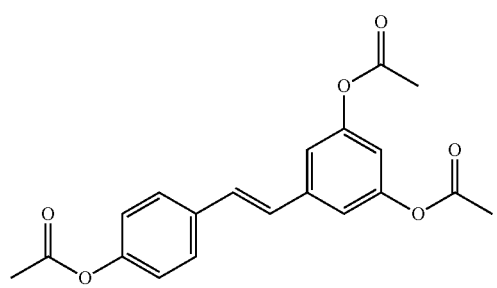 [SMILES: CC(=O)Oc1ccc(/C=C/c2cc(OC(C)=O)cc(OC(C)=O)c2)cc1]

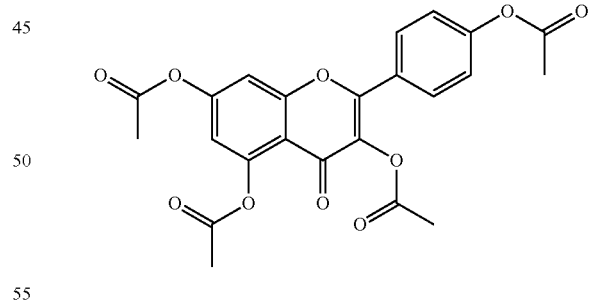

Compound 18: [4-[(E)-2-(3,5-diacetoxyphenyl)vinyl]phenyl] acetate $^1$H NMR (400 MHz, DMSO-d6). δ 7.635 (d, 2H), 7.322-6.915 (m, 6H), 6.910 (s, 1H), 3.327 (s, 3H), 2.291 (s, 3H), 2.275 (s, 3H). LCMS 355.0 (MH+)

Compound 20: [4-(3,5,7-triacetoxy-4-oxo-chromen-2-yl)phenyl] acetate

To a mixture of 3,5,7-trihydroxy-2-(4-hydroxyphenyl)chromen-4-one (2 g) in pyridine (15 mL) was added acetyl acetate (30 g), and then the mixture was stirred at 15° C. for 12 hr under N$_2$ atmosphere. The solvent was removed under reduced pressure and the residue was poured into crushed ice with vigorous stirring. The solid precipitate was collected by filtration and washed with cold water and then with methanol. Compound 20 (2.1 g, 65% yield) was obtained as a white solid. LCMS: 455.0 (M+H⁺) ¹H NMR (400 MHz, CDCl₃) δ 7.858 (d, 2H), 7.339 (d, 1H), 7.278-7.257 (m, 2H), 6.883 (d, 1H), 2.447 (s, 3H), 2.357 (s, 6H), 2.333 (s, 3H)

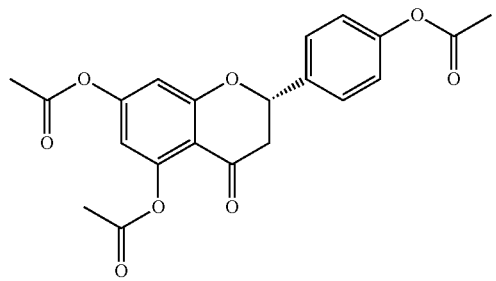 [SMILES: CC(=O)Oc1ccc([C@@H]2CC(=O)c3c(OC(C)=O)cc(OC(C)=O)cc3O2)cc1]

Compound 21: (S)-2-(4-acetoxyphenyl)-4-oxochromane-5,7-diyl diacetate 5,7-dihydroxy-2-(4-hydroxyphenyl)chroman-4-one (0.500 g) was dissolved with pyridine (10 mL), and then acetyl acetate (0.844 g) was added to the mixture reaction. The reaction mixture was stirred at 15° C. for 12 h. The mixture reaction was concentrated under reduced pressure. The residue was purified by column chromatography (SiO₂, petroleum ether/ethyl acetate gradient) to give compound 21 (0.300 g, 39% yield) as a white solid. LCMS: 416.1 (M+H₂O⁺) ¹H NMR (400 MHz, CDCl₃) δ 7.468 (d, 2H), 7.166 (d, 2H), 6.793 (d, 1H), 6.551 (d, 1H), 5.497 (dd, 1H), 3.039 (dd, 1H), 2.783 (dd, 1H), 2.393 (s, 3H), 2.326 (s, 3H), 2.308 (s, 3H).

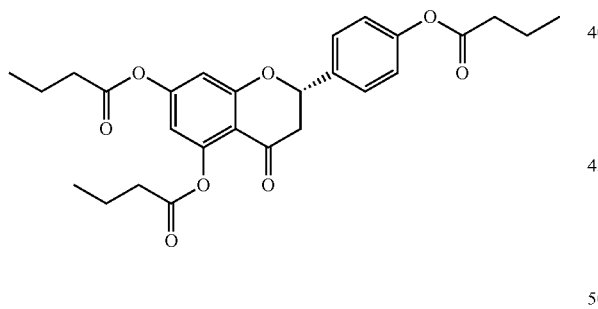

Compound 22: (S)-2-(4-(butyryloxy)phenyl)-4-oxochromane-5,7-diyl dibutyrate

To a solution of 5,7-dihydroxy-2-(4-hydroxyphenyl)chroman-4-one (0.500 g) in pyridine (10 mL), was added butanoyl butanoate (1.02 g). The reaction mixture was stirred at 15° C. for 12 h. The mixture was concentrated. The residue was purified by column chromatography (SiO₂, petroleum ether/ethyl acetate gradient) to give compound 22 (0.325 g, 34% yield) as a white solid. LCMS: 500.2 (M+H₂O⁺) ¹H NMR (400 MHz, CDCl₃) δ 7.463 (d, 2H), 7.158 (d, 2H), 6.786 (d, 1H), 6.536 (d, 1H), 5.483 (m, 1H), 3.031 (m, 1H), 2.662 (m, 1H), 2.586-2.524 (m, 6H), 1.837-1.785 (m, 6H), 1.089-1.021 (m, 9H)

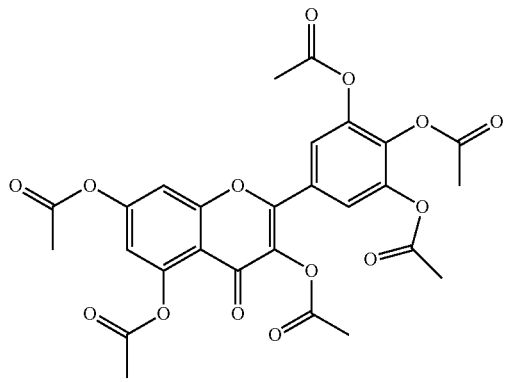 [SMILES: CC(=O)Oc1cc(OC(C)=O)c2c(=O)c(OC(C)=O)c(-c3cc(OC(C)=O)c(OC(C)=O)c(OC(C)=O)c3)oc2c1]

Compound 23: [3,5-diacetoxy-4-oxo-2-(3,4,5-triacetoxyphenyl)chromen-7-yl] acetate To a solution of 3,5,7-trihydroxy-2-(3,4,5-trihydroxyphenyl)chromen-4-one (1 g) in pyridine (10 mL) was added acetyl acetate (15.26 g), then the mixture was stirred at 15° C. for 16 h. The solvent was removed and the mixture was poured into ice water under stirring. The solid was filtered, washed with water and dried in vacuum to give compound 23 (1.1 g, 61% yield) as a gray solid. LCMS 571.1 (M+H⁺) ¹H NMR (400 MHz, CDCl₃) δ 7.260 (s, 2H), 7.349 (d, 1H), 6.886 (d, 1H), 2.441 (s, 3H), 2.372 (s, 3H), 2.353 (s, 3H), 2.341 (s, 3H), 2.333 (s, 6H)

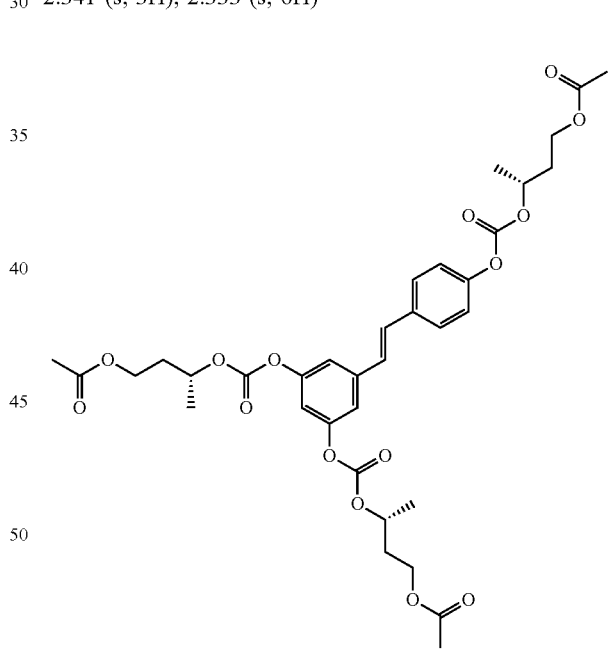

Compound 24: [(3R)-3-[4-[(E)-2-[3,5-bis[[(1R)-3-acetoxy-1-methyl-propoxy]carbonyloxy]phenyl]vinyl]phenoxy]carbonyloxybutyl] acetate Step 1: To a solution of (3R)-butane-1,3-diol (2.4 g) in pyridine (20 mL) was added Ac₂O (2.17 g) and the mixture was stirred at 15° C. for 12 h. The mixture reaction was concentrated. The residue was purified by column chromatography (SiO₂, petroleum ether/ethyl acetate gradient) to give [(3R)-3-hydroxybutyl] acetate (1.4 g, 35.8% yield) as a colorless oil.

Step 2: To a solution of triphosgene (0.269 g) in THF (5 mL) was added a solution of [(3R)-3-hydroxybutyl] acetate (0.300 g) and TEA (0.230 g) in THF (5 mL) at 0° C. and the mixture was stirred for 1 h at 15° C. A ~0.23 M of a solution (15 mL) of [(3R)-3-chlorocarbonyloxybutyl] acetate was obtained. The mixture reaction was used in the next step directly.

Step 3: To a solution of 5-[(E)-2-(4-hydroxyphenyl)vinyl]benzene-1,3-diol (0.090 g) and TEA (0.218 g) in THF (3 mL) was added a solution of [(3R)-3-chlorocarbonyloxybutyl] acetate (0.23 M, 10 mL) in THF. The reaction mixture was stirred for 5 h at 15° C. The mixture reaction was filtered and concentrated. The residue was purified by prep-TLC (SiO$_2$, petroleum ether/ethyl acetate, 4:1) to give compound 24 (0.085 g, 28.8% yield as a colorless oil. LCMS: 725.1 (M+Na$^+$) $^1$H NMR (400 MHz, CDCl$_3$) δ 7.520 (d, 2H), 7.244-7.192 (m, 4H), 7.114 (d, 1H), 7.036-6.979 (m, 2H), 5.019 (m, 3H), 4.226 (m, 6H), 2.099-1.995 (m, 6H), 2.055 (s, 6H), 1.442-1.422 (m, 9H).

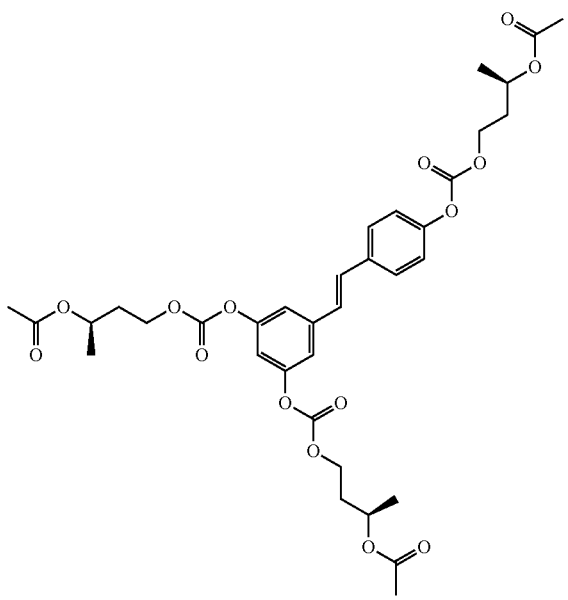 [SMILES: CC(=O)O[C@H](C)CCOC(=O)Oc1ccc(/C=C/c2cc(OC(=O)OCC[C@@H](C)OC(C)=O)cc(OC(=O)OCC[C@@H](C)OC(C)=O)c2)cc1]

Compound 25: [(1R)-3-[4-[(E)-2-[3,5-bis[[(3R)-3-acetoxybutoxy]carbonyloxy]phenyl]vinyl]phenoxy]carbonyloxy-1-methyl-propyl]acetate Step 1: To a solution of NaH (2.35 g, 60%) in THF (100 mL) was added (3R)-3-[tert-butyl (dimethyl)silyl]oxybutan-1-ol (10 g) at 0° C. The mixture was stirred at 15° C. for 1.5 h. Benzyl bromide (10.04 g) was added and the mixture was stirred at 15° C. for 16 h. The reaction mixture was filtered and concentrated under reduced pressure and the residue was purified by column chromatography (SiO$_2$, petroleum ether) to give [(1R)-3-benzyloxy-1-methyl-propoxy]-tert-butyl-dimethyl-silane (11 g, 55% yield) as a colorless oil.

Step 2: To a solution of [(1R)-3-benzyloxy-1-methyl-propoxy]-tert-butyl-dimethyl-silane (10 g) in THF (100 mL) was added pyridine hydrofluoride (8.41 g) at 15° C. The mixture was stirred for 2 h at 50° C. The reaction mixture was combined with another batch and concentrated under reduced pressure. The residue was diluted with H$_2$O (50 mL) and extracted four times with ethyl acetate (50 mL). The combined organic phase was washed with brine (50 mL), dried over Na$_2$SO$_4$, filtered and concentrated under reduced pressure. The residue was purified by column chromatography (SiO$_2$, petroleum ether/ethyl acetate gradient) to give (2R)-4-benzyloxybutan-2-ol (5.54 g) as a colorless oil.

Step 3: To a solution of (2R)-4-benzyloxybutan-2-ol (5.54 g) in pyridine (50 mL) was added Ac$_2$O (4.71 g) at 15° C. The mixture was stirred for 12 h at 15° C. The reaction mixture was concentrated under reduced pressure and the residue was purified by column chromatography (SiO$_2$, petroleum ether/ethyl acetate gradient) to give [(1R)-3-benzyloxy-1-methyl-propyl] acetate (4.7 g, 57% yield) as a colorless oil.

Step 4: To a solution of [(1R)-3-benzyloxy-1-methyl-propyl] acetate (2 g) in THF (20 mL) was added 10% Pd/C (0.027 g). The mixture was stirred under H$_2$ (30 psi) for 16 h at 30° C. The reaction mixture was filtered and concentrated under reduced pressure and the residue was purified by column chromatography (SiO$_2$, petroleum ether/ethyl acetate gradient) to give [(1R)-3-hydroxy-1-methyl-propyl] acetate (1.07 g, 65% yield) as a colorless oil.

Step 5: To a solution of [(1R)-3-hydroxy-1-methyl-propyl] acetate (0.300 g) in THF (5 mL) was added a solution of triphosgene (0.337 g) and TEA (0.230 g) in THF (5 mL) at 0° C. The mixture was stirred for 1 h at 15° C. The mixture reaction was filtered and used to next step directly.

Step 6: To a solution of 5-[(E)-2-(4-hydroxyphenyl)vinyl]benzene-1,3-diol (0.080 g) and TEA (0.194 g) in THF (3 mL) was added a solution of [(1R)-3-chlorocarbonyloxy-1-methyl-propyl] acetate (0.2 M, 10 mL) in THF. The reaction mixture was stirred for 5 h at 15° C. The mixture reaction was filtered and concentrated. The residue was purified by prep-TLC (SiO$_2$, petroleum ether/ethyl acetate, 4/1) to give compound 25 (0.056 g, 21% yield) as a colorless oil. LCMS: 703.1 (M+H$^+$) $^1$H NMR (400 MHz, CDCl$_3$) δ 7.513 (d, 2H), 7.232-7.181 (m, 4H), 7.154 (d, 1H), 7.129-7.002 (m, 2H), 5.106 (m, 3H), 4.340 (m, 6H), 2.072 (s, 9H), 2.078-1.995 (m, 6H), 1.323-1.282 (m, 9H)

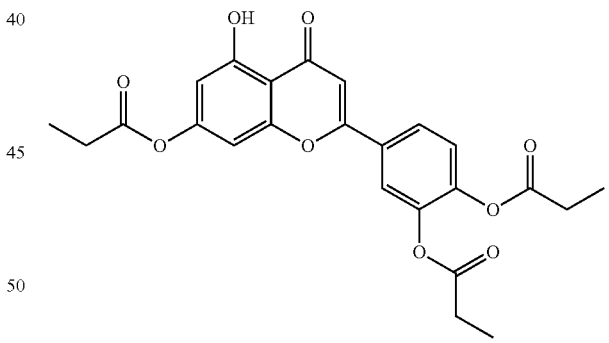

Compound 26: [4-[4-oxo-5,7-di(propanoyloxy)chromen-2-yl]-2-propanoyloxy-phenyl] Propanoate Propionic anhydride (1.33 mL, 10.4 mmol) was added dropwise to a stirred solution of luteolin (0.3 g, 1.04 mmol) in anhydrous pyridine (2.5 mL, 31.2 mmol) at 0° C. under N$_2$ atmosphere. The resulting stirred solution was allowed to come to room temperature and reaction was monitored to completion by LCMS. The solution was diluted with 30 mL ethyl acetate and washed with H$_2$O (30 mL), 1M HC (30 mL), H$_2$O (30 mL), and saturated NaHCO$_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield compound 26 (0.073 g, 15% yield) as an off-white solid. 1H-NMR (DMSO-d6, 400 MHz): δ 12.75 (s, 1H), 8.07 (m, 2H), 7.5 (m, 1H), 7.15 (s, 1H), 7.12 (d, 1H), 6.66 (d, 1H), 2.59-2.66 (m, 6H), 1.11-1.17 (m, 9H)

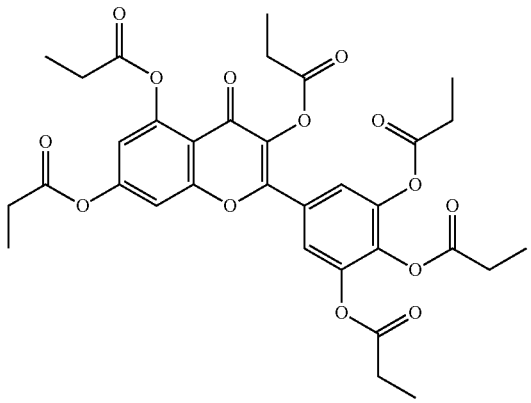 [SMILES: CCC(=O)Oc1cc(OC(=O)CC)c2c(=O)c(OC(=O)CC)c(-c3cc(OC(=O)CC)c(OC(=O)CC)c(OC(=O)CC)c3)oc2c1]

Compound 27: [4-oxo-3,5-di(propanoyloxy)-2-[3,4,5-tri(propanoyloxy)phenyl]chromen-7-yl] Propanoate Propionic anhydride (2 mL, 15.6 mmol) was added dropwise to a stirred solution of myricetin (0.5 g, 1.56 mmol) in anhydrous pyridine (2.78 mL, 47.1 mmol) at 0° C. under $N_2$ atmosphere. The resulting stirred solution was allowed to come to room temperature and reaction was monitored to completion by LCMS. The solution was diluted with 30 mL ethyl acetate and washed with $H_2O$ (30 mL), 1M HC (30 mL), $H_2O$ (30 mL), and saturated $NaHCO_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 27 (0.31 g, 30% yield) as a white solid. $^1$H-NMR (DMSO-d$_6$, 400 MHz): δ 7.77 (s, 2H), 7.64 (d, 1H), 7.16 (d, 1H), 2.60-2.70 (m, 12H), 1.07-1.17 (m, 18H)

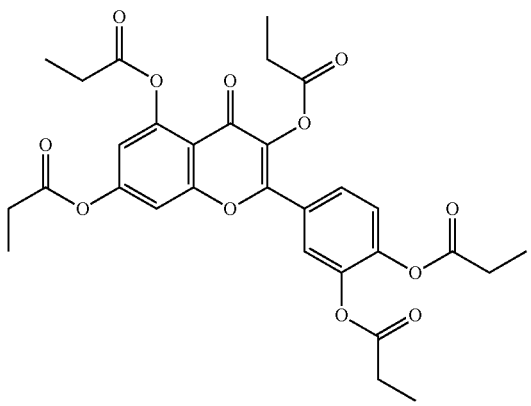 [SMILES: CCC(=O)Oc1cc(OC(=O)CC)c2c(=O)c(OC(=O)CC)c(-c3ccc(OC(=O)CC)c(OC(=O)CC)c3)oc2c1]

Compound 28: [4-[4-oxo-3,5,7-tri(propanoyloxy)chromen-2-yl]-2-propanoyloxy-phenyl] Propanoate Propionic anhydride (2.1 mL, 16.5 mmol) was added dropwise to a stirred solution of quercetin (0.5 g, 1.65 mmol) in anhydrous pyridine (3.98 mL, 49.5 mmol) at 0° C. under $N_2$ atmosphere. The resulting stirred solution was allowed to come to room temperature and reaction was monitored to completion by LCMS. The solution was diluted with 30 mL ethyl acetate and washed with $H_2O$ (30 mL), 1M HCl (30 mL), $H_2O$ (30 mL), and saturated $NaHCO_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 28 (0.1 g, 10% yield) as a white solid. $^1$H NMR (DMSO-d6, 400 MHz): δ 7.85 (m, 2H), 7.66 (d, 1H), 7.54 (d, 1H), 7.18 (d, 1H), 2.62-2.89 (m, 10H), 1.09-1.19 (m, 20H)

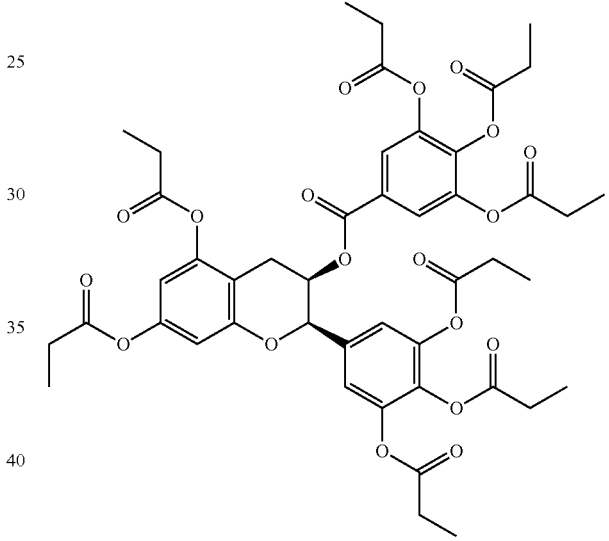

Compound 29: [(2R,3R)-5,7-di(propanoyloxy)-2-[3,4,5-tri(propanoyloxy)phenyl]chroman-3-yl] 3,4,5-tri(propanoyloxy)benzoate Propionic anhydride (2.78 mL, 21.8 mmol) was added dropwise to a stirred solution of epigallocatechin gallate (0.5 g, 1.09 mmol) in anhydrous pyridine (2.61 mL, 32.6 mmol) at 0° C. under $N_2$ atmosphere. The resulting stirred solution was allowed to come to room temperature and reaction was monitored to completion by LCMS. The solution was diluted with 30 mL ethyl acetate and washed with $H_2O$ (30 mL), 1M HCl (30 mL), $H_2O$ (30 mL), and saturated $NaHCO_3$ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 29 (0.695 g, 70% yield) as a white solid. $^1$H NMR (DMSO-d6, 400 MHz): δ 7.54 (s, 2H), 7.38 (s, 2H), 6.79 (m, 1H), 6.66 (m, 1H), 5.66 (m, 1H), 5.54 (s, 1H), 3.13-3.17 (m, 1H), 2.96 (d, 1H), 2.5-2.65 (m, 16H), 1.0-1.2 (m, 24H)

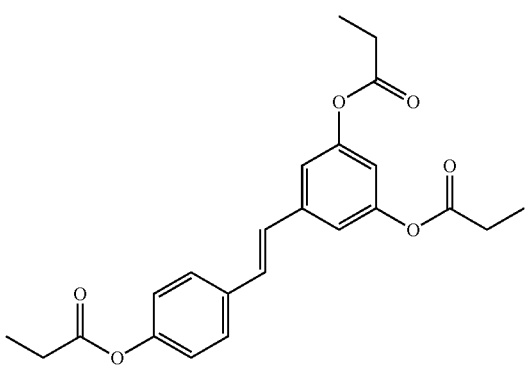 [SMILES: CCC(=O)Oc1ccc(/C=C/c2cc(OC(=O)CC)cc(OC(=O)CC)c2)cc1]

Compound 30: [4-[(E)-2-[3,5-di(propanoyloxy)phenyl]vinyl]phenyl] Propanoate

Propionic anhydride (0.56 mL, 4.4 mmol) was added dropwise to a stirred solution of resveratrol (0.1 g, 0.44 mmol) in anhydrous pyridine (1 mL, 12.4 mmol) at 0° C. under $N_2$ atmosphere. The resulting stirred solution was allowed to come to room temperature and reaction was monitored to completion by LCMS. The solution was diluted with 30 mL ethyl acetate and washed with $H_2O$ (30 mL), 1M HC (30 mL), $H_2O$ (30 mL), and saturated $NaHCO_3$ (30 mL). The organic layer was dried over sodium sulfate, filtered, and concentrated by rotary evaporation. The crude residue was purified by flash chromatography (silica, 10-60% ethyl acetate in hexanes) and fractions were concentrated by rotary evaporation to yield compound 30 (0.075 g, 43% yield) as a white solid. $^1$H-NMR (DMSO-$d_6$, 400 MHz): δ 7.65 (d, 2H), 7.2-7.3 (m, 4H), 7.13 (d, 2H), 6.92 (t, 1H), 2.6 (m, 6H), 1.1-1.3 (m, 9H)

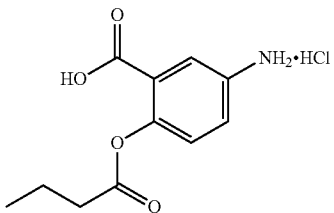

Compound 31: 5-amino-2-butanoyloxy-benzoic acid hydrochloride

Step 1

To a mixture of 5-amino-2-hydroxy-benzoic acid (3 g, 19.59 mmol) in methanol (50 mL) was added $Boc_2O$ (4.28 g, 19.59 mmol, 4.50 mL) in one portion at 15° C. under $N_2$. The mixture was stirred at 15° C. for 5 h. The residue was poured into water (100 mL). The aqueous phase was extracted with EtOAc (100 mL), and the organic phase was dried with anhydrous $Na_2SO_4$, filtered, and concentrated in vacuo. The residue was used in next step without further purification. 5-(tert-butoxycarbonylamino)-2-hydroxy-benzoic acid (4 g, crude) was obtained.

Step 2

To a solution of 5-(tert-butoxycarbonylamino)-2-hydroxy-benzoic acid (4 g, 15.79 mmol) and triethylamine (119.87 mg, 1.18 mmol, 164.88 μL) in THF (30 mL) was added butanoyl chloride (126.22 mg, 1.18 mmol, 123.74 μL) dropwise at 0° C., while the temperature was maintained below 0° C. The reaction mixture was warmed to 15° C. and stirred for 2 h. The reaction was quenched by slow addition of ice, and then the mixture was extracted with EtOAc (100 mL). The organic phase was dried over anhydrous $Na_2SO_4$, filtered, and concentrated in vacuo. The residue was purified by recrystallization with EtOAc (20 mL) to give the pure 2-butanoyloxy-5-(tert-butoxycarbonylamino)benzoic acid (1.5 g, 4.64 mmol, 29% yield) as white solid.

Step 3

A solution of 2-butanoyloxy-5-(tert-butoxycarbonylamino)benzoic acid (1.5 g, 4.64 mmol) in HCl-EtOAc (20 mL, 4 M) was stirred at 15° C. for 1 h. The mixture was filtered to obtain the product 5-amino-2-butanoyloxy-benzoic acid HCl salt as an off-white solid (0.74 g, 2.76 mmol, 59.58% yield). LC/MS: (M+H$^+$) 224.1

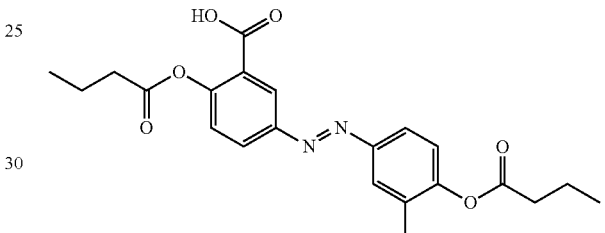

Compound 32: 2-butanoyloxy-5-[(E)-(4-butanoyloxy-3-carboxy-phenyl)azo]benzoic acid A solution of disodium (E)-4,4'-(diazene-1,2-diyl)bis(2-carboxyphenolate) (2 g, 5.78 mmol), butanoyl chloride (2.46 g, 23.11 mmol, 2.41 mL), and NaOH (462 mg, 11.55 mmol) in DMF (100 mL) was stirred at 50° C. for 0.5 h. The solid was filtered, water (150 mL) was added to the filtrate, and the mixture was filtered again. The resulting solids filter cake was dried in vacuo. 2-butanoyloxy-5-[(E)-(4-butanoyloxy-3-carboxy-phenyl)azo]benzoic acid (0.8 g) was obtained as brown solid. LC/MS: (M+H$^+$): 443.1

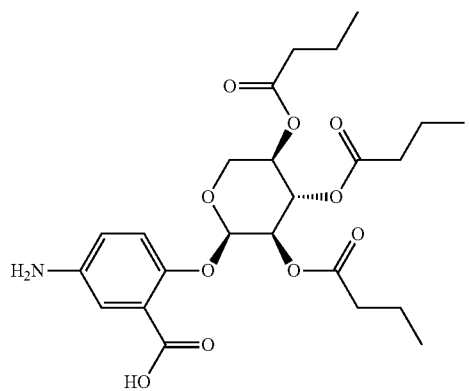 [SMILES: CCCC(=O)O[C@@H]1[C@@H](OC(=O)CCC)[C@@H](Oc2ccc(N)cc2C(=O)O)OC[C@H]1OC(=O)CCC]

Compound 33:5-amino-2-[(2R,3R,4S,5R)-3,4,5-tri(butanoyloxy)tetrahydropyran-2-yl]oxy-benzoic acid This compound was prepared according to a modified procedure described for the preparation of compound 34

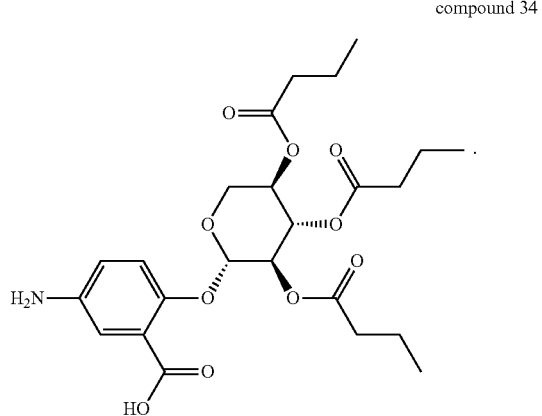 [SMILES: CCCC(=O)O[C@@H]1[C@@H](OC(=O)CCC)[C@H](Oc2ccc(N)cc2C(=O)O)OC[C@H]1OC(=O)CCC]

Compound 34: 5-amino-2-[(2S,3R,4S,5R)-3,4,5-tri(butanoyloxy)tetrahydropyran-2-yl]oxy-benzoic acid Step 1

5-Amino salicylic acid (10.0 g) was dissolved in a mixture of dioxane (100 mL), water (100 mL), and NaOH (2.60 g), and the resulting solution was cooled in an ice-bath. Di-tert-butyl dicarbonate (Boc anhydride) (15.60 g) was added, and the mixture was warmed to room temperature and stirred for 1.0 h. The solution was concentrated to 60 mL, diluted with ethyl acetate (100 mL), and the resulting mixture was cooled in an ice-bath. The mixture was acidified with aq. $KHSO_4$ to pH 2-3. The aqueous layer was extracted with EtOAc. The organic phase was washed with water, brine, dried over $Na_2SO_4$, filtered, and concentrated to afford 5-(tert-butoxycarbonylamino)-2-hydroxy-benzoic acid (7.0 g, 42%).

Step 2

5-(tert-butoxycarbonylamino)-2-hydroxy-benzoic acid (3 g) was dissolved in DMF, and the resulting solution was cooled to 0° C. 1,1'-Carbonyldiimidazole (CDI) was added, and the mixture was stirred at room temperature for 2 h. Then, tert-butylalcohol (1.7 g) and DBU (2.1 g) were added. The reaction was stirred at room temperature overnight. The reaction mixture was poured onto ice-water, and the solid product, tert-butyl 5-(tert-butoxycarbonylamino)-2-hydroxy-benzoate, was collected by filtration (3.0 g, 81.9%).

Step 3

To a mixture of tert-butyl 5-(tert-butoxycarbonylamino)-2-hydroxy-benzoate, [(3R,4S,5R)-4,5-di(butanoyloxy)-6-hydroxy-tetrahydropyran-3-yl] butanoate (1.2 g) and triphenylphosphene (1.2 g) in THF (50 mL) was added di-t-butyl azodicarboxylate (DTAD) (1.1 g), and the mixture was stirred overnight at room temperature. The product was purified by reverse phase chromatography using acetonitrile-water to afford tert-butyl 5-(tert-butoxycarbonylamino)-2-[(3R,4S,5R)-3,4,5-tri(butanoyloxy)tetrahydropyran-2-yl]oxy-benzoate as sticky solid (0.6 g, 30%).

Step 4

Tert-butyl 5-(tert-butoxycarbonylamino)-2-[(3R,4S,5R)-3,4,5-tri(butanoyloxy)tetrahydropyran-2-yl]oxy-benzoate (600 mg) was added to 4M HCl in dioxane (15 mL) and stirred at room temperature overnight. After the consumption of the starting material, the organic phase was evaporated, and the residue was co-evaporated with heptane and dichloromethane twice more. The solid obtained was dried under high vacuum to afford compound the title product as dark brown solid (200 mg, 43.8%). Fractionation of the product afforded two anomeric isomers (the compounds of Examples 33 and 34). $^1$H NMR (DMSO d6): Isomer 1: δ 7.62 (d, 1H), 7.45 (dd, 1H), 7.38 (d, 1H), 6 (d, 1H), 5.6 (t, 1H), 5.0-5.1 (m, 1H), 4.7-4.75 (m, 1H), 3.6-3.8 (m, 1H), 3.45-3.6 (1H), 2.1-2.3 (m, 6H), 1.4-1.6 (m, 6H), 0.75-0.85 (m, 9H). Isomer 2: δ 7.82 (d, 1H), 7.5 (dd, 1H), 7.05 (d, 1H), 5.5 (d, 1H), 5.3 (t, 1H), 5.1-5.15 (m, 1H), 4.9-5.0 (m, 1H), 4.0-4.08 (m, 1H), 3.7-3.8 (1H), 2.1-2.3 (m, 6H), 1.4-1.6 (m, 6H), 0.75-0.85 (m, 9H) ppm

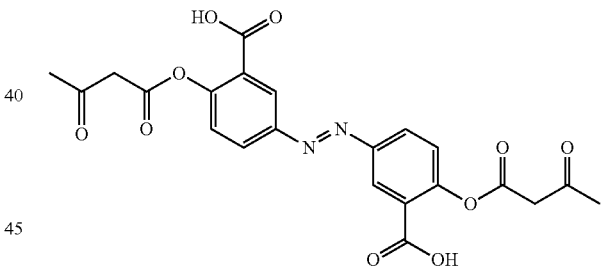

Compound 35: 5-[(E)-[3-carboxy-4-(3-oxobutanoyloxy)phenyl]azo]-2-(3-oxobutanoyloxy)benzoic acid

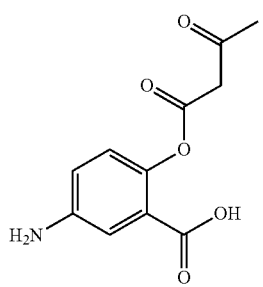 [SMILES: CC(=O)CC(=O)Oc1ccc(N)cc1C(=O)O]

Compound 36: 5-amino-2-(3-oxobutanoyloxy)benzoic acid

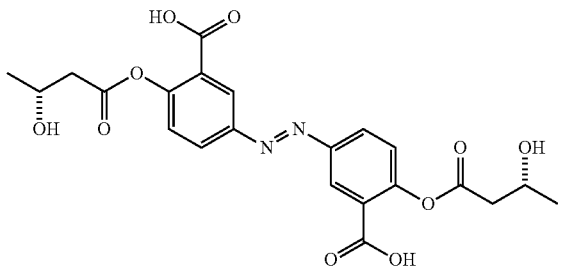 [SMILES: C[C@@H](O)CC(=O)Oc1ccc(/N=N/c2ccc(OC(=O)C[C@@H](C)O)c(C(=O)O)c2)cc1C(=O)O]

Compound 37: 5-[(E)-[3-carboxy-4-[(3R)-3-hydroxybutanoyl]oxy-phenyl]azo]-2-[(3R)-3-hydroxybutanoyl]oxy-benzoic acid

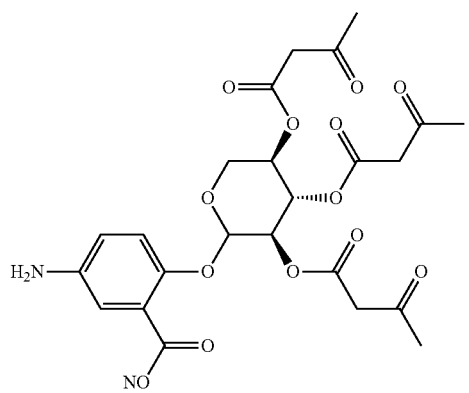

Compound 38: 5-amino-2-[(3R,4S,5R)-3,4,5-tris(3-oxobutanoyloxy)tetrahydropyran-2-yl]oxy-benzoic acid

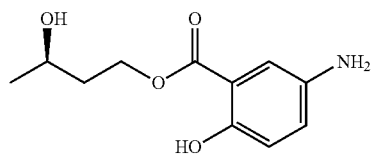 [SMILES: C[C@@H](O)CCOC(=O)c1cc(N)ccc1O]

Compound 39: [(3R)-3-hydroxybutyl] 5-amino-2-hydroxy-benzoate

Step 1: (3R)-3-benzyloxybutan-1-ol

To a suspension of LiAlH₄ (0.313 g) in dry THF (20 mL) was added dropwise a solution of (3R)-3-benzyloxybutanoic acid (2 g) in THF (20 mL) at 0° C. and the mixture was stirred at 0° C. for 2 h. The reaction mixture was added dropwise H₂O (1 mL) and 15% aq. NaOH (1 mL) and H₂O (3 mL), then dried over Na₂SO₄, filtered and concentrated. The residue was purified by column chromatography (SiO₂, petroleum ether/ethyl acetate, 50:1 to 20:1 to 15:1 to 10:1) to give (3R)-3-benzyloxybutan-1-ol (0.90 g, 43%) as a brown oil. LCMS: 181.2 (M+H⁺)

Step 2: Benzyl 2-benzyloxy-5-nitro-benzoate

To a solution of 2-hydroxy-5-nitro-benzoic acid (1 g) in DMF (16 mL) was added Cs₂CO₃ (4.45 g), followed by benzyl bromide (2.10 g) added dropwise and the reaction mixture was stirred at 80° C. for 10 h. Water (20 mL) was added and the mixture was extracted three times with EtOAc (10 mL). The organic layer was washed three times with brine (10 mL) and dried over Na₂SO₄, filtered and concentrated. The residue was purified by column chromatography (SiO₂, petroleum ether/ethyl acetate, 80:1 to 20:1) to give benzyl 2-benzyloxy-5-nitro-benzoate (1.3 g, 59%) as a yellow solid.

Step 3: 2-benzyloxy-5-nitro-benzoic acid

To a solution of benzyl 2-benzyloxy-5-nitro-benzoate (0.800 g,) in THF (50 mL) was added a solution of LiOH (0.527 g) in H₂O (50 mL). The mixture was stirred at 25° C. for 12 h. The mixture was concentrated, and the residue was acidified to pH 5 with 2N HCl (30 mL). The yellow precipitate was collected by filtration, washed with petroleum ether/ethyl acetate (30 ml, 30:1) and dried under reduced pressure to give 2-benzyloxy-5-nitro-benzoic acid (0.600 g, 90%) as a yellow solid.

Step 4: [(3R)-3-benzyloxybutyl] 2-benzyloxy-5-nitro-benzoate

To a solution of (3R)-3-benzyloxybutan-1-ol (0.195 g), N,N'-dicyclohexylcarbodiimide (0.335 g) and 4-dimethylaminopyridine (0.039 g) in CH₂Cl₂ (4 mL) was added 2-benzyloxy-5-nitro-benzoic acid (0.591 g). The mixture was degassed, purged with N₂ three times and stirred at 25° C. for 12 h. The reaction mixture was filtered and concentrated and the residue was purified by column chromatography (SiO₂, petroleum ether/ethyl acetate, 50:1 to 20:1) to give [(3R)-3-benzyloxybutyl] 2-benzyloxy-5-nitro-benzoate as a brown oil. LCMS: 458.2 (M+Na⁺).

Step 5: [(3R)-3-hydroxybutyl] 5-amino-2-hydroxy-benzoate

To solution of [(3R)-3-benzyloxybutyl] 2-benzyloxy-5-nitro-benzoate (0.450 g) in THF (20 mL) was added 10% Pd/C (0.200 g). The mixture was degassed, purged three times with H₂ and stirred at 50° C. for 5 h at 50 psi. The reaction mixture was filtered and concentrated and the residue was purified by column chromatography (SiO₂, petroleum ether/ethyl acetate, 50:1 to 0:1) to give [(3R)-3-hydroxybutyl]5-amino-2-hydroxy-benzoate (0.174 g, 71%) as yellow a solid. LCMS: 226.1 (M+H⁺) ¹H NMR (400 MHz, CDCl₃): δ 10.820 (s, 1H), 7.448 (m, 1H), 6.116 (m, 1H), 5.986 (m, 1H), 4.591 (m, 1H), 4.271 (m, 2H), 3.769 (m, 1H), 1.728 (m, 2H), 1.106 (d, 3H) ppm

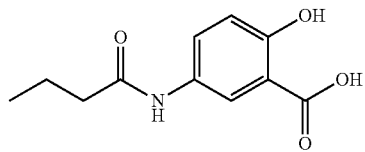 [SMILES: CCCC(=O)Nc1ccc(O)c(C(=O)O)c1]

Compound 40: 5-(butanoylamino)-2-hydroxy-benzoic acid

To a solution of 5-amino-2-hydroxy-benzoic acid (1 g) and triethylamine (0.991 g) in dioxane (20 mL) and H$_2$O (10 mL) was added butyric anhydride (1.24 g), and the mixture was stirred at 20° C. for 16 h. The dioxane was removed under reduced pressure and the pH was adjusted to 5-6 by adding aqueous 3N HCl at 0° C. The solid was filtered, washed three times with water (20 mL) and concentrated in vacuum. The crude product was purified by reverse phase prep-HPLC (C18, water (0.05% HCl)-acetonitrile gradient) to give 5-(butanoylamino)-2-hydroxy-benzoic acid (0.3 g, 20%) as a light pink solid. LCMS: 224.1 (M+H$^+$) $^1$H NMR (400 MHz, DMSO-d6): δ 11.015 (br, 1H), 9.807 (s, 1H), 8.106 (d, 1H), 7.652 (dd, 1H), 6.893 (d, 1H), 2.239 (m, 2H), 1.604 (m, 2H), 0.902 (t, 3H) ppm

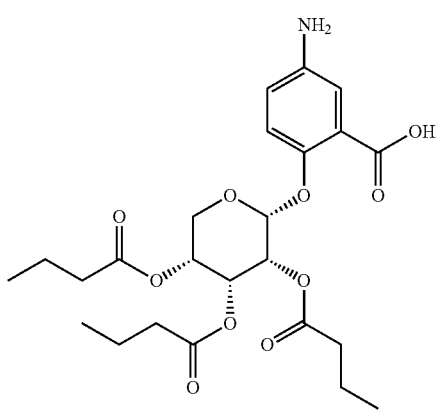 [SMILES: CCCC(=O)O[C@H]1[C@@H](Oc2ccc(N)cc2C(=O)O)OC[C@@H](OC(=O)CCC)[C@H]1OC(=O)CCC]

Compound 41: 5-amino-2-(((2R,3R,4R,5R)-3,4,5-tris(butyryloxy)tetrahydro-2H-pyran-2-yl)oxy)benzoic acid

Step 1. Ribose Tetrabutyrate

To a stirred solution of D-(+)-ribose 1 (5 g) in anhydrous pyridine (24.2 mL) was added solution of butyryl chloride (23.70 g) in dichloromethane (50 mL) at 0-5° C. The reaction mixture was brought to room temperature and stirred for 16 h. The mixture was diluted with dichloromethane (100 ml) and washed successively with water (100 mL), 2N aqueous HCl (300 mL), saturated sodium bicarbonate solution (300 mL) and brine (100 mL). The organic layer was dried over sodium sulfate and concentrated under reduced pressure. The residue was purified by column chromatography over silica gel (5-10% EtOAc-hexane gradient) to afford ribose tetrabutyrate as a colorless oil (7.5 g, 52%, mixture of a/p anomers).

Step 2. Ribose Tributyrate

Ammonium hydroxide (11 mL) was added slowly to a mixture of ribose tetrabutyrate 2 (7.5 g) in acetonitrile (60 mL) at room temperature and the resulting reaction mixture was stirred for 5 h. The mixture was diluted with MTBE (75 mL) and stirred for 15 minutes. The organic layer was separated and concentrated under reduced pressure and the residue was partitioned between MTBE (100 mL) and water (75 mL). The MTBE layer was separated, dried over sodium sulfate and concentrated under reduced pressure. The residue was purified by column chromatography [using silica gel 100-200 mesh and 10-20% EtOAc-Hexane as eluting solvent] to afford ribose tributyrate as a colorless oil (1.1 g, 17%).

Step 3. 5-tert-butoxycarbonylamino-2-hydroxy-benzoic acid

To the stirred solution of 5-amino salicylic acid 4 (5 g) in 1,4-dioxane and water (1:1, 100 mL) was added NaOH (1.3 g) and Boc-anhydride (7.83 g) at 0° C. and the resulting reaction mixture was stirred at room temperature for 1 h. The reaction mixture was concentrated under reduced pressure, the residue was diluted with EtOAc (50 mL) and the pH was adjusted to 3-4 by dropwise addition of 0.5N aqueous HCl at 0° C. The organic layer was separated, and the aqueous layer was extracted with EtOAc (50 mL). The combined organic layer was dried over sodium sulfate and concentrated under reduced pressure to provide 5-tert-butoxycarbonylamino-2-hydroxy-benzoic acid as off white solid (5.3 g, 64%).

Step 4. 5-tert-butoxycarbonylmethyl-2-hydroxy-benzoic acid tert-butyl Ester

To a stirred solution of 5-tert-butoxycarbonylamino-2-hydroxy-benzoic acid 5 (5.3 g) in DMF (50 mL) was added CDI (3.39 g) at 0-5° C. and the mixture was stirred for 2 h. tert-Butanol (4.025 mL) and DBU (2.54 mL) were then added and the mixture was stirred at room temperature for 16 h. The mixture was diluted with water (100 mL) and extracted with EtOAc (200 mL). The organic layer was separated, dried over sodium sulfate and concentrated under reduced pressure. The residue was purified by column chromatography using silica gel [100-200 mesh; under gradient elution of 5-10% EtOAc-Hexane] to afford 5-tert-butoxycarbonylmethyl-2-hydroxy-benzoic acid tert-butyl ester as off white solid (2 g, 31%).

Step 5. (2R,3R,4R,5R)-2-(2-(tert-butoxycarbonyl)-4-((tert-butoxycarbonyl)amino)phenoxy)tetrahydro-2H-pyran-3,4,5-triyl tributyrate Hydroxy-benzoic acid tert-butyl ester 6 (0.850 g) and ribose tributyrate (1.04 g) in THF (5 mL) was sequentially added triphenylphosphine (1.03 g) and di-tert-butyl azodicarboxylate (0.948 g) at room temperature and the mixture was stirred for 16 h. The mixture was concentrated under reduced pressure and the residue was purified by column chromatography over silica gel (5 to 18% EtOAc-Hexane gradient) to afford of crude (2R,3R,4R,5R)-2-(2-(tert-butoxycarbonyl)-4-((tert-butoxycarbonyl)amino)phenoxy)tetrahydro-2H-pyran-3,4,5-triyl tributyrate (1.3 g) which was used directly in the next step.

Step 6. 5-amino-2-[(2R,3R,4R,5R)-3,4,5-tri(butanoyloxy)tetrahydropyran-2-yl]oxy-benzoic acid To a stirred solution of crude (2R,3R,4R,5R)-2-(2-(tert-butoxycarbonyl)-4-((tert-butoxycarbonyl)amino)phenoxy)tetrahydro-2H-pyran-3,4,5-triyl tributyrate (1.3 g, crude from above experiment) in 1,4-dioxane (7 mL) was added 4N HCl in 1,4-dioxane (10 mL) at 0° C. and the resulting reaction mixture was stirred at room temperature for 16 h. Then reaction mixture was concentrated under reduced pressure and the residue was purified by reverse phase prep-HPLC to provide 5-amino-2-[(2R,3R,4R,5R)-3,4,5-tri(butanoyloxy)tetrahydropyran-2-yl]oxy-benzoic acid (0.05 g). LCMS: 496.5 (M+H⁺) ¹H NMR (400 MHz, DMSO-d6): δ 6.919-6.898 (m, 2H), 6.658 (m, 1H), 5.431 (m, 1H), 5.350 (m, 1H), 5.234 (m, 1H), 5.161 (m, 1H), 4.213 (m 1H), 3.749 (m, 1H), 2.497-2.268 (m, 4H), 2.197 (m, 1H), 1.620-1.487 (m, 6H), 0.926-0.888 (m, 9H) ppm

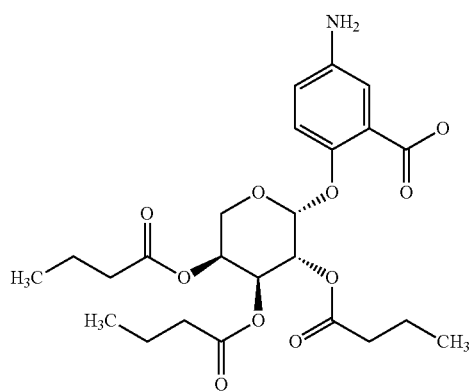

Compound 42: 5-amino-2-[(2R,3R,4S,5S)-3,4,5-tri(butanoyloxy)tetrahydropyran-2-yl]oxy-benzoic acid Step 1: 2-Hydroxy-4-nitro-benzoic acid (20 g) and KHCO₃ (13.1 g) were suspended in DMF (100 mL). To the suspension was added benzyl bromide (22.4 g) and the reaction mixture was stirred at room temperature overnight. Water (150 mL) was added and the resulting mixture was extracted with ethyl acetate (250 mL). The organic phase was separated and washed twice with water, brine, and dried over Na₂SO₄. The solvent was removed under reduced pressure and the residue was purified by column chromatography (hexanes/ethyl acetate gradient). Recrystallization from 15% ethyl acetate in hexanes provided benzyl 2-hydroxy-4-nitro-benzoate (10.5 g).

Step 2: Benzyl 2-hydroxy-4-nitro-benzoate (8.5 g), arabinose tributyrate (7.5 g) and triphenylphosphine (8.2 g) were dissolved in THF (150 mL) and stirred at 0° C. To this mixture was added di-t-butyl azodicarboxylate (7.2 g) and stirring was continued at 0° C. for 1 h, then at room temperature overnight. The reaction mixture was concentrated and purification by column chromatography (hexanes/ethyl acetate gradient) provided benzyl 5-nitro-2-[(2R,3R,4S,5S)-3,4,5-tri(butanoyloxy)tetrahydropyran-2-yl]oxy-benzoate (1.78 g, 14%).

Step 3: 5-nitro-2-[(2R,3R,4S,5S)-3,4,5-tri(butanoyloxy)tetrahydropyran-2-yl]oxy-benzoate (0.095 g) was dissolved in methanol (15 mL) and stirred at room temperature. To this mixture was added 10% Pd/C (0.05 g). The suspension was stirred under a hydrogen atmosphere at room temperature overnight. The reaction mixture was filtered through Celite and washed with methanol. The combined filtrate and washing were concentrated. The residue was purified by reverse phase chromatography (C-18, 0.1% trifluoroacetic acid in acetonitrile and 0.1% trifluoroacetic acid in water) to give 5-amino-2-[(2R,3R,4S,5S)-3,4,5-tri(butanoyloxy)tetrahydropyran-2-yl]oxy-benzoic acid (0.045 g, 59%). MS 494.2 (M-H) NMR (DMSO d6): δ 7.223 (m, 1H), 7.139 (m, 1H), 6.997 (s, 1H), 7.851 (d, 1H), 5.469 (m, 1H), 5.350 (m, 1H), 5.239 (m, 1H) 4.127 (d, 1H), 3.672 (d, 1H), 2.490-2.369 (M, 6H), 1.596-1.485 (m, 6H), 0.924-0.818 (m, 9H) ppm

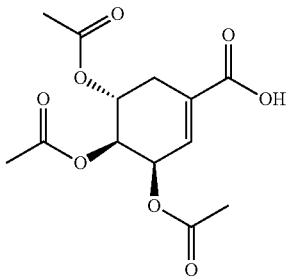 [SMILES: CC(=O)O[C@@H]1[C@H](OC(C)=O)C=C(C(=O)O)C[C@H]1OC(C)=O]

Compound 43: (3R,4S,5R)-3,4,5-triacetoxycyclohex-1-ene-1-carboxylic acid

Acetic anhydride (1.61 mL, 17.2 mmol) was added dropwise to a stirred solution of shikimic acid (0.300 g, 1.72 mmol) in anhydrous pyridine (1.38 mL, 17.2 mmol) at 0° C. under N₂ atmosphere. The resulting stirred solution was left to come to room temperature and reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% acetonitrile in water) and fractions were concentrated by rotary evaporation to yield compound 43 (0.18 g, 34.8% yield) as a white solid. ¹H-NMR (DMSO-d₆, 400 MHz): δ 12.90 (s, 1H), 6.61 (dt, 1H), 5.60 (m, 1H), 5.18 (dd, 1H), 5.12 (dt, 1H), 2.76 (m, 1H), 2.35 (m, 1H), 2.04 (s, 5H), 2.01 (s, 3H). LC-MS: 299.1 (M−H)⁻

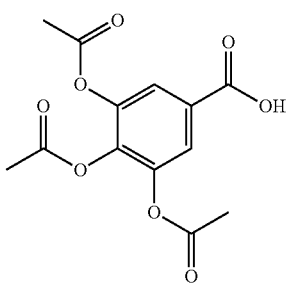 [SMILES: CC(=O)Oc1cc(C(=O)O)cc(OC(C)=O)c1OC(C)=O]

Compound 44: 3,4,5-triacetoxybenzoic acid

Acetic anhydride (1.65 mL, 17.6 mmol) was added dropwise to a stirred solution of gallic acid (0.300 g, 1.76 mmol) in anhydrous pyridine (1.41 mL, 17.6 mmol) at 0° C. under N₂ atmosphere. The resulting stirred solution was left to come to room temperature and reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% acetonitrile in water) and fractions were concentrated by rotary evaporation to yield compound 44 (0.259 g, 49.7% yield) as a white solid.

¹H-NMR (DMSO-d₆, 400 MHz): δ 13.44 (s, 1H), 7.75 (s, 1H), 2.33 (s, 3H), 2.30 (s, 6H). LC-MS: 319.0 (M+Na)⁺

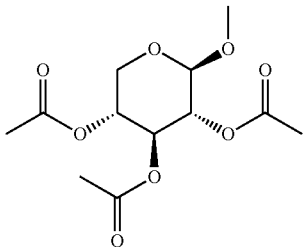 [SMILES: CO[C@@H]1OC[C@@H](OC(C)=O)[C@H](OC(C)=O)[C@H]1OC(C)=O]

Compound 45: (2R,3R,4S,5R)-2-methoxytetrahydro-2H-pyran-3,4,5-triyl triacetate

Acetic anhydride (2.28 mL, 24.2 mmol) was added dropwise to a stirred solution of (2R,3R,4S,5R)-2-methoxytetrahydropyran-3,4,5-triol (0.200 g, 1.21 mmol) in anhydrous pyridine (2.92 mL, 36.3 mmol) at 0° C. under N₂ atmosphere. The resulting stirred solution was left to come to room temperature and the reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 45 (0.217 g, 61.8% yield) as a white solid. 1H-NMR (DMSO-d6, 400 MHz): δ 5.21 (t, 1H), 4.87 (m, 1H), 4.79 (dd, 1H), 4.62 (d, 1H), 4.01 (dd, 1H), 3.53 (dd, 1H), 3.40 (s, 3H), 2.04 (s, 3H), 2.03 (s, 3H), 2.01 (s, 3H). LC-MS: 313.0 (M+Na)+

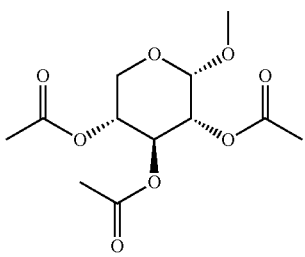 [SMILES: CO[C@H]1OC[C@@H](OC(C)=O)[C@H](OC(C)=O)[C@H]1OC(C)=O]

Compound 46: (2S,3R,4S,5R)-2-methoxytetrahydro-2H-pyran-3,4,5-triyl triacetate

Acetic anhydride (2.28 mL, 24.2 mmol) was added dropwise to a stirred solution of (2S,3R,4S,5R)-2-methoxytetrahydropyran-3,4,5-triol (0.200 g, 1.21 mmol) in anhydrous pyridine (2.92 mL, 36.3 mmol) at 0° C. under N₂ atmosphere. The resulting stirred solution was left to come to room temperature and the reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 46 (0.216 g, 61.5% yield) as a white solid. 1H-NMR (DMSO-d₆, 400 MHz): δ 5.30 (t, 1H), 4.92 (m, 1H), 4.88 (d, 1H), 4.84 (dd, 1H), 3.77 (dd, 1H), 1.27 (dd, 1H), 3.34 (s, 3H), 2.03 (s, 3H), 2.01 (s, 3H), 2.00 (s, 3H). LC-MS: 313.0 (M+Na)+

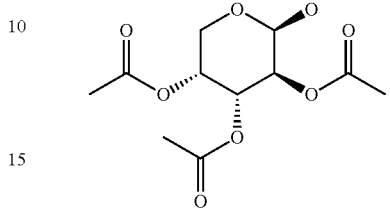

Compound 47: (2R,3S,4R,5R)-2-methoxytetrahydro-2H-pyran-3,4,5-triyl triacetate

Acetic anhydride (378 µL, 4.02 mmol) was added dropwise to a stirred solution (2R,3S,4R,5R)-2-methoxytetrahydropyran-3,4,5-triol (0.033 g, 201 µmol) in anhydrous pyridine (484 µL, 6.02 mmol) at 0° C. under N₂ atmosphere. The resulting stirred solution was left to come to room temperature and the reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 47 (0.0263 g, 45.1% yield) as a white solid. 1H-NMR (DMSO-d6, 400 MHz): δ 5.25 (m, 1H), 5.22 (dd, 1H), 5.02 (dd, 1H), 4.91 (d, 1H), 3.89 (dd, 1H), 3.64 (dd, 1H), 3.34 (s, 3H), 2.12 (s, 3H), 2.05 (s, 3H), 1.97 (s, 3H). LC-MS: 313.0 (M+Na)⁺

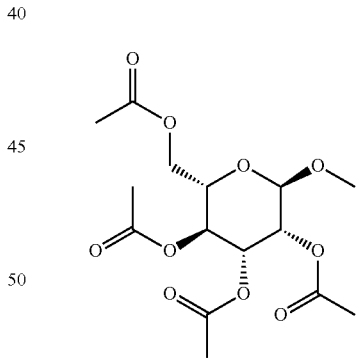

Compound 48: (2S,3S,4R,5R,6R)-2-(acetoxymethyl)-6-methoxytetrahydro-2H-pyran-3,4,5-triyl triacetate Acetic anhydride (1.92 mL, 20.4 mmol) was added dropwise to a stirred solution of (2S,3R,4R,5R,6R)-2-(hydroxymethyl)-6-methoxy-tetrahydropyran-3,4,5-triol (0.200 g, 1.02 mmol) in anhydrous pyridine (2.46 mL, 30.6 mmol) at 0° C. under N₂ atmosphere. The resulting stirred solution was left to come to room temperature and the reaction was monitored to completion by LCMS. The solution was diluted with 20 mL of ethyl acetate and washed with 1M HC (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 48 (0.197 g, 53.3% yield) as a white solid. $^1$H-NMR (DMSO-$d_6$, 400 MHz): δ 5.12 (m, 3H), 4.79 (d, 1H), 4.18 (dd, 1H), 4.08 (dd, 1H), 3.94-3.90 (m, 1H), 3.36 (s, 3H), 2.13 (s, 3H), 2.05 (s, 3H), 2.04 (s, 3H), 1.95 (s, 3H). LC-MS: 385.1 (M+Na)$^+$

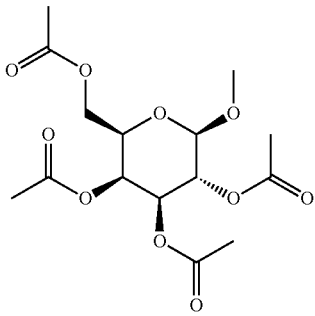 [SMILES: CO[C@@H]1O[C@H](COC(C)=O)[C@H](OC(C)=O)[C@H](OC(C)=O)[C@H]1OC(C)=O]

Compound 49: (2R,3S,4S,5R,6R)-2-(acetoxymethyl)-6-methoxytetrahydro-2H-pyran-3,4,5-triyl triacetate Acetic anhydride (1.92 mL, 20.4 mmol) was added dropwise to a stirred solution of (2R,3R,4S,5R,6R)-2-(hydroxymethyl)-6-methoxy-tetrahydropyran-3,4,5-triol (0.200 g, 1.02 mmol) in anhydrous pyridine (2.46 mL, 30.6 mmol) at 0° C. under $N_2$ atmosphere. The resulting stirred solution was left to come to room temperature and the reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 49 (0.153 g, 41.4% yield) as an oil. $^1$H-NMR (DMSO-$d_6$, 400 MHz): δ 5.28 (dd, 1H), 5.17 (dd, 1H), 4.95 (dd, 1H), 4.63 (d, 1H), 4.21 (m, 1H), 4.09 (m, 2H), 3.40 (s, 3H), 2.13 (s, 3H), 2.04 (s, 3H), 2.03 (s, 3H), 1.93 (s, 3H). LC-MS: 85.1 (M+Na)$^+$

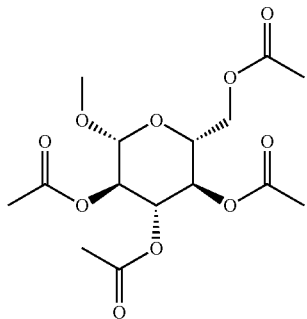 [SMILES: CO[C@@H]1O[C@H](COC(C)=O)[C@@H](OC(C)=O)[C@H](OC(C)=O)[C@H]1OC(C)=O]

Compound 50: (2R,3R,4S,5R,6R)-2-(acetoxymethyl)-6-methoxytetrahydro-2H-pyran-3,4,5-triyl triacetate Acetic anhydride (1.92 mL, 20.4 mmol) was added dropwise to a stirred solution of (2R,3S,4S,5R,6R)-2-(hydroxymethyl)-6-methoxy-tetrahydropyran-3,4,5-triol (0.200 g, 1.02 mmol) in anhydrous pyridine (2.46 mL, 30.6 mmol) at 0° C. under $N_2$ atmosphere. The resulting stirred solution was left to come to room temperature and the reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 50 (0.148 g, 40.1% yield) as a white solid. $^1$H-NMR (DMSO-$d_6$, 400 MHz): δ 5.27 (t, 1H), 4.91 (t, 1H), 4.75 (m, 2H), 4.20 (dd, 1H), 4.05-3.93 (m, 2H), 3.39 (s, 3H), 2.04 (s, 3H), 2.01 (s, 3H), 1.99 (s, 3H), 1.95 (s, 3H). LC-MS: 385.1 (M+Na)$^+$

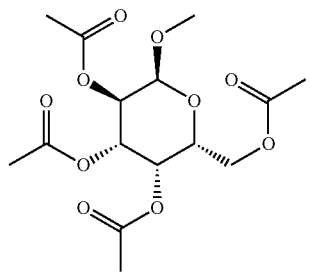 [SMILES: CO[C@H]1O[C@H](COC(C)=O)[C@H](OC(C)=O)[C@H](OC(C)=O)[C@H]1OC(C)=O]

Compound 51: (2R,3S,4S,5R,6S)-2-(acetoxymethyl)-6-methoxytetrahydro-2H-pyran-3,4,5-triyl triacetate Acetic anhydride (1.92 mL, 20.4 mmol) was added dropwise to a stirred solution of (2R,3R,4S,5R,6S)-2-(hydroxymethyl)-6-methoxy-tetrahydropyran-3,4,5-triol hydrate (1:1) (0.200 g, 1.02 mmol) in anhydrous pyridine (2.46 mL, 30.6 mmol) at 0° C. under $N_2$ atmosphere. The resulting stirred solution was left to come to room temperature and the reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 51 (0.157 g, 42.5% yield) as a white solid. 1H-NMR (DMSO-d6, 400 MHz): δ 5.36 (dd, 1H), 5.22 (dd, 1H), 4.99 (m, 2H), 4.18 (m, 1H), 4.06 (m, 2H), 3.34 (s, 3H), 2.13 (s, 3H), 2.04 (s, 3H), 2.01 (s, 3H), 1.95 (s, 3H). LC-MS: 385.1 (M+Na)$^+$

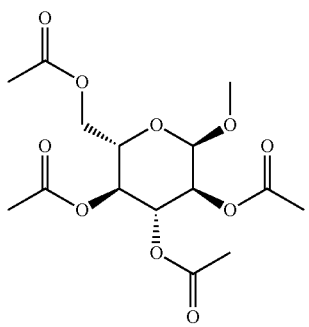 [SMILES: CO[C@@H]1O[C@@H](COC(C)=O)[C@H](OC(C)=O)[C@@H](OC(C)=O)[C@@H]1OC(C)=O]

Compound 52: (2S,3S,4R,5S,6R)-2-(acetoxymethyl)-6-methoxytetrahydro-2H-pyran-3,4,5-triyl triacetate Acetic anhydride (1.92 mL, 20.4 mmol) was added dropwise to a stirred solution of (2S,3R,4R,5S,6R)-2-(hydroxymethyl)-6-methoxy-tetrahydropyran-3,4,5-triol (0.200 g, 1.02 mmol) in anhydrous pyridine (2.46 mL, 30.6 mmol) at 0° C. under $N_2$ atmosphere. The resulting stirred solution was left to come to room temperature and the reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (silica, 10-90% ethyl acetate in hexanes) and fractions were concentrated by rotary evaporation to yield compound 52 (0.230 g, 62.3% yield) as a white solid. $^1$H-NMR (DMSO-$d_6$, 400 MHz): δ 5.29 (dd, 1H), 4.96 (dd, 1H), 4.92 (d, 1H), 4.82 (dd, 1H), 4.15 (dd, 1H), 4.05 (dd, 1H), 3.90 (m, 1H), 3.34 (s, 3H), 2.02 (s, 3H), 2.01 (s, 3H), 1.98 (s, 3H), 1.96 (s, 3H). LC-MS: 385.2 (M+Na)$^+$

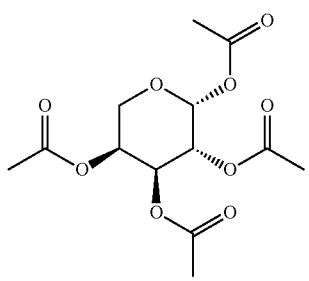 [SMILES: CC(=O)O[C@H]1OC[C@H](OC(C)=O)[C@H](OC(C)=O)[C@H]1OC(C)=O]

Compound 53: (2R,3R,4S,5S)-tetrahydro-2H-pyran-2,3,4,5-tetrayl tetraacetate

L-Arabinose (50 g), N,N-dimethylpyridin-4-amine (6 g), and triethylamine (367 mL) were dissolved in 700 mL DCM and stirred at 0° C. under $N_2$. Acetic anhydride (217 mL) was added dropwise over 30 minutes and the reaction mixture was stirred overnight. The solvent was removed under reduced pressure and the residue was redissolved in ethyl acetate, washed with 1M HCl, $H_2O$ and brine, dried over $MgSO_4$ and evaporated. Purification on normal phase with 0-100% ethyl acetate in hexanes gave Compound 53 as a waxy/amorphous solid (50% yield). 1H-NMR (DMSO-$d_3$, 400 MHz): δ 6.35 (d, 1H), 5.37 (m, 3H), 4.06 (dd, 1H), 3.82 (dd, 1H), 2.155 (s, 3H) 2.15 (s, 3H), 2.02 (s, 6H). LC-MS: 341.1 (M+Na)$^+$

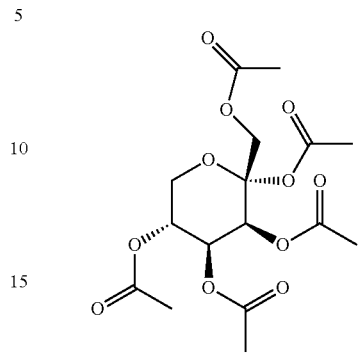

Compound 54: [(2R,3S,4S,5R)-2,3,4,5-tetraacetoxytetrahydropyran-2-yl]methyl acetate To a solution of (3S,4S, 5R)-2-(hydroxymethyl) tetrahydropyran-2, 3, 4, 5-tetrol (6 g, 33.3 mmol) in pyridine (50 mL) was added acetic anhydride (65.4 g, 640.6 mmol, 60.00 mL) and the mixture was stirred at 15° C. for 12 h. The reaction mixture was concentrated under reduced pressure. The residue was purified by column chromatography over silica gel, (eluent: petroleum ether/ethyl acetate=50:1 to 1:1 gradient) to give [(2R,3S,4S,5R)-2,3,4,5-tetraacetoxytetrahydropyran-2-yl]methyl acetate (6 g, 14.60 mmol, 43.85% yield) was obtained as a yellow solid. 1H-NMR (CDCl$_3$, 400 MHz): δ 5.461 (d, 1H), 5.336 (dd, 1H), 5.250 (m, 1H), 4.797 (d, 1H), 4.415 (d, 1H), 4.102 (d, 1H), 3.496 (t, 1H), 2.165 (s, 3H), 2.134 (s, 3H), 2.050 (s, 3H), 2.019 (s, 3H), 1.999 (s, 3H). LCMS: (M+Na$^+$): 413.1

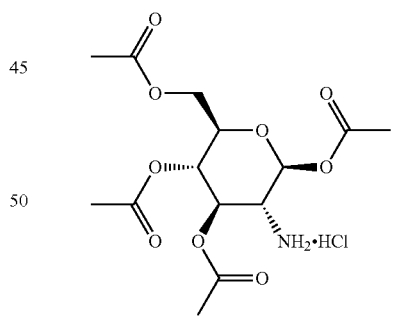

Compound 55: (2S,3R,4R,5S,6R)-6-(acetoxymethyl)-3-aminotetrahydro-2H-pyran-2,4,5-triyl triacetate HCl salt 1H-NMR (DMSO-d6, 400 MHz): δ 8.760-8.675 (br m, 3H), 5.901 (m, 1H), 5.346 (t, 1H), 4.932 (t, 1H), 4.190 (m, 1H), 4.051-3.976 (m, 3H), 3.582 (m, 1H), 2.170 (s, 3H), 2.028 (s, 3H), 1.996 (s, 3H), 1.977 (s, 3H). LCMS: (M+Na$^+$): 370.1

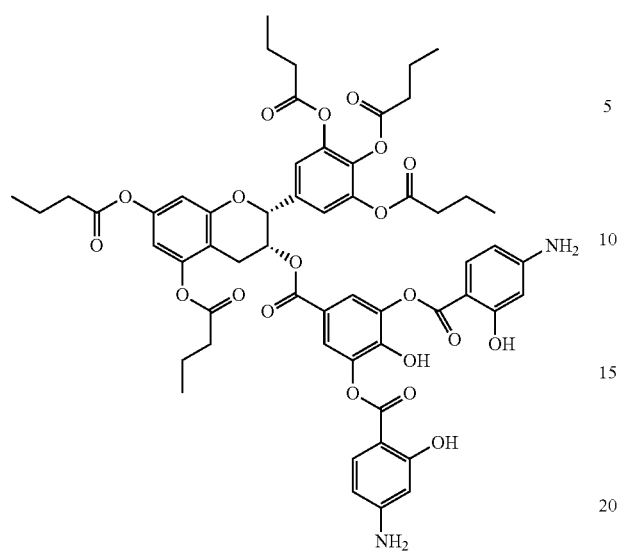
Compound 56: [(2R,3R)-5,7-di(butanoyloxy)-2-[3,4,5-tri(butanoyloxy)phenyl]chroman-3-yl] 3,5-bis[(4-amino-2-hydroxy-benzoyl)oxy]-4-hydroxy-benzoate
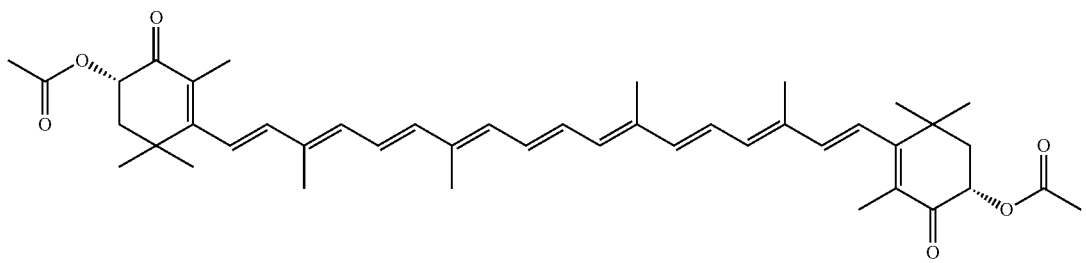 [SMILES: CC(=O)O[C@H]1CC(C)(C)C(/C=C/C(C)=C/C=C/C(C)=C/C=C/C=C(C)/C=C/C=C(C)/C=C/C2=C(C)C(=O)[C@@H](OC(C)=O)CC2(C)C)=C(C)C1=O]
Compound 57: [(1S)-4-[(1E,3E,5E,7E,9E,11E,13E,15E,17E)-18-[(4S)-4-acetoxy-2,6,6-trimethyl-3-oxo-cyclohexen-1-yl]-3,7,12,16-tetramethyl-octadeca-1,3,5,7,9,11,13,15,17-nonaenyl]-3,5,5-trimethyl-2-oxo-cyclohex-3-en-1-yl] acetate
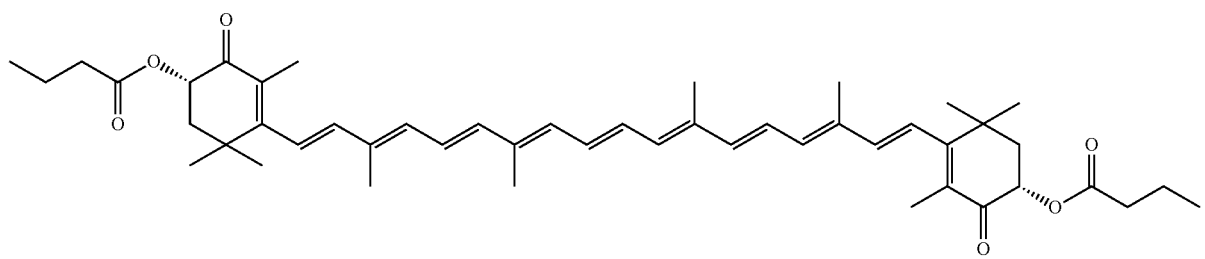 [SMILES: CCCC(=O)O[C@H]1CC(C)(C)C(/C=C/C(C)=C/C=C/C(C)=C/C=C/C=C(C)/C=C/C=C(C)/C=C/C2=C(C)C(=O)[C@@H](OC(=O)CCC)CC2(C)C)=C(C)C1=O]

Compound 58: [(1S)-4-[(1E,3E,5E,7E,9E,11E,13E,15E,17E)-18-[(4S)-4-butanoyloxy-2,6,6-trimethyl-3-oxo-cyclohexen-1-yl]-3,7,12,16-tetramethyl-octadeca-1,3,5,7,9,11,13,15,17-nonaenyl]-3,5,5-trimethyl-2-oxo-cyclohex-3-en-1-yl] butanoate

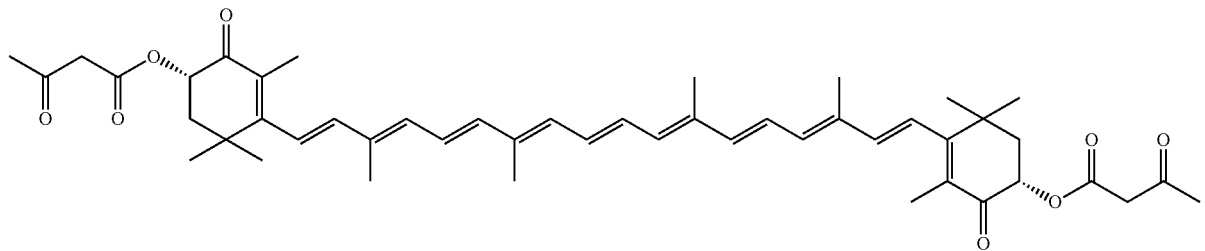 [SMILES: CC(=O)CC(=O)O[C@H]1CC(C)(C)C(/C=C/C(C)=C/C=C/C(C)=C/C=C/C=C(C)/C=C/C=C(C)/C=C/C2=C(C)C(=O)[C@@H](OC(=O)CC(C)=O)CC2(C)C)=C(C)C1=O]

Compound 59: [(1S)-3,5,5-trimethyl-2-oxo-4-[(1E,3E,5E,7E,9E,11E,13E,15E,17E)-3,7,12,16-tetramethyl-18-[(4S)-2,6,6-trimethyl-3-oxo-4-(3-oxobutanoyloxy)cyclohexen-1-yl]octadeca-1,3,5,7,9,11,13,15,17-nonaenyl]cyclohex-3-en-1-yl] 3-oxobutanoate

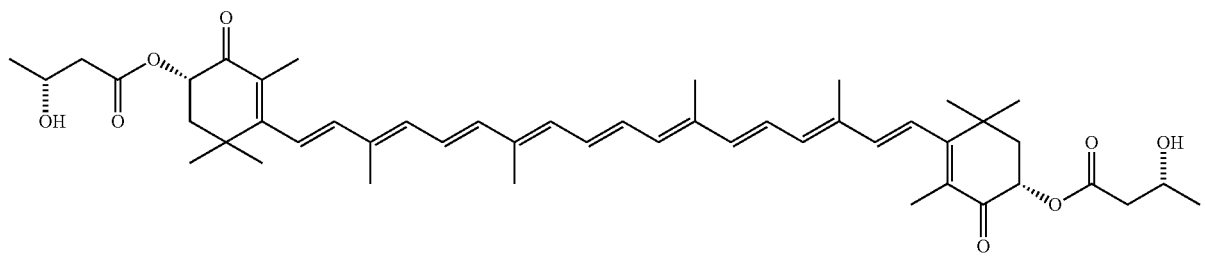 [SMILES: CC1=C(/C=C/C(C)=C/C=C/C(C)=C/C=C/C=C(C)/C=C/C=C(C)/C=C/C2=C(C)C(=O)[C@@H](OC(=O)C[C@@H](C)O)CC2(C)C)C(C)(C)C[C@H](OC(=O)C[C@@H](C)O)C1=O]

Compound 60: [(1S)-4-[(1E,3E,5E,7E,9E,11E,13E,15E,17E)-18-[(4S)-4-[(3R)-3-hydroxybutanoyl]oxy-2,6,6-trimethyl-3-oxo-cyclohexen-1-yl]-3,7,12,16-tetramethyl-octadeca-1,3,5,7,9,11,13,15,17-nonaenyl]-3,5,5-trimethyl-2-oxo-cyclohex-3-en-1-yl] (3R)-3-hydroxybutanoate

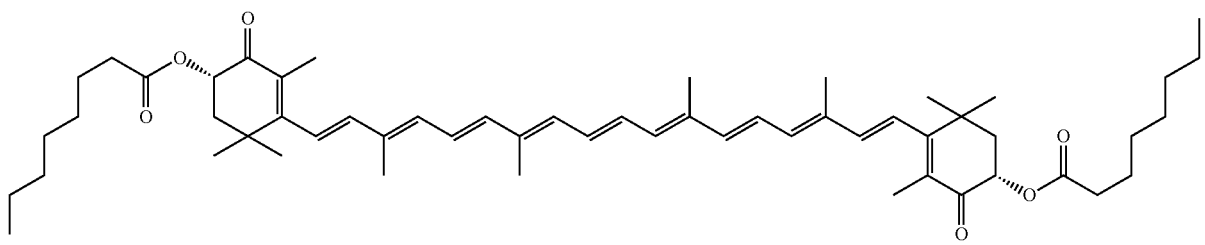 [SMILES: CCCCCCCC(=O)O[C@H]1CC(C)(C)C(/C=C/C(C)=C/C=C/C(C)=C/C=C/C=C(C)/C=C/C=C(C)/C=C/C2=C(C)C(=O)[C@@H](OC(=O)CCCCCCC)CC2(C)C)=C(C)C1=O]

Compound 61: [(1S)-3,5,5-trimethyl-2-oxo-4-[(1E,3E,5E,7E,9E,11E,13E,15E,17E)-3,7,12,16-tetramethyl-18-[(4S)-2,6,6-trimethyl-4-octanoyloxy-3-oxo-cyclohexen-1-yl]octadeca-1,3,5,7,9,11,13,15,17-nonaenyl]cyclohex-3-en-1-yl] octanoate

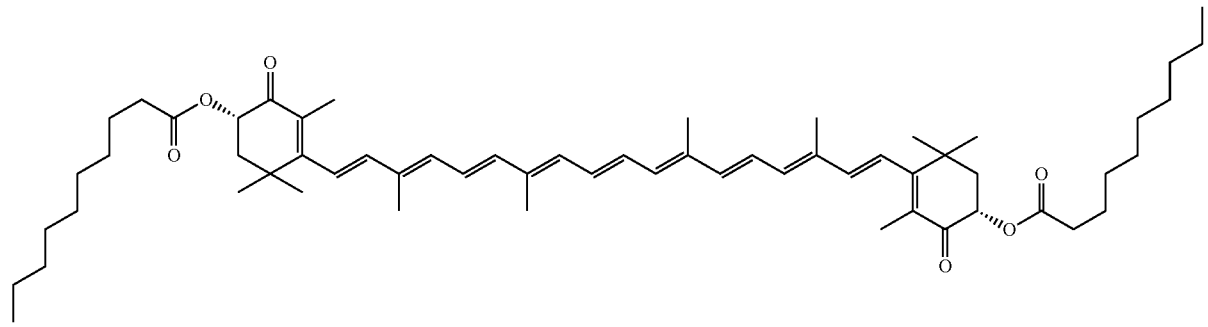 [SMILES: CCCCCCCCCC(=O)O[C@H]1CC(C)(C)C(/C=C/C(C)=C/C=C/C(C)=C/C=C/C=C(C)/C=C/C=C(C)/C=C/C2=C(C)C(=O)[C@@H](OC(=O)CCCCCCCCC)CC2(C)C)=C(C)C1=O]

Compound 62: [(1S)-4-[(1E,3E,5E,7E,9E,11E,13E,15E,17E)-18-[(4S)-4-decanoyloxy-2,6,6-trimethyl-3-oxo-cyclohexen-1-yl]-3,7,12,16-tetramethyl-octadeca-1,3,5,7,9,11,13,15,17-nonaenyl]-3,5,5-trimethyl-2-oxo-cyclohex-3-en-1-yl] Decanoate

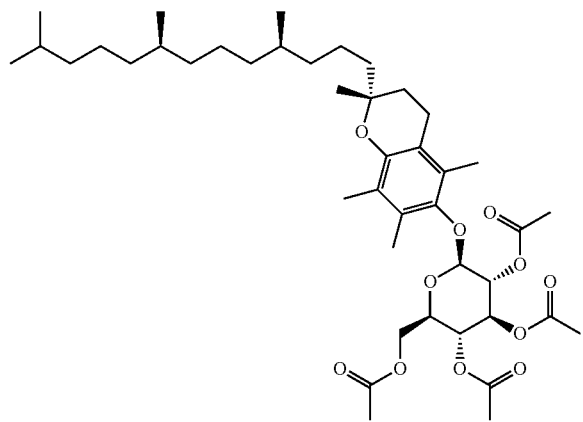 [SMILES: CC(=O)OC[C@H]1O[C@@H](Oc2c(C)c(C)c3c(c2C)CC[C@@](C)(CCC[C@H](C)CCC[C@H](C)CCCC(C)C)O3)[C@H](OC(C)=O)[C@@H](OC(C)=O)[C@@H]1OC(C)=O]

Compound 63: [(2R,3R,4S,5R,6S)-3,4,5-triacetoxy-6-[(2R)-2,5,7,8-tetramethyl-2-[(4R,8R)-4,8,12-trimethyltridecyl]chroman-6-yl]oxy-tetrahydropyran-2-yl]methyl acetate Step 1: 3-Bromopyridin-2-ol (5 g) was added to aqueous NaOH (0.34 M, 84.52 mL) and aqueous AgNO$_3$ (0.68 M, 42.26 mL) at 15° C. The mixture was stirred for 10 min. The reaction mixture was filtered and the solid was washed with H$_2$O (800 mL) and cooled methanol (200 mL) and dried under reduced pressure to give silver 3-bromopyridin-2-olate (6.5 g, 80.5% yield) as a white solid.

Step 2: To a solution of [(1R,2R,3S,4R,5S)-2,3,4-triacetoxy-5-bromo-cyclohexyl]methyl acetate (0.488 g) in toluene (10 mL) was added silver 3-bromopyridin-2-olate (1 g) at 15° C. The mixture was stirred for 3 hr at 120° C. The reaction mixture was filtered and concentrated under reduced pressure and the residue was purified by column chromatography (SiO$_2$, petroleum ether/ethyl acetate, 1:1) to give [(1R,2R,3S,4S,5S)-2,3,4-triacetoxy-5-[(3-bromo-2-pyridyl)oxy]cyclohexyl]methyl acetate (0.500 g, 75% yield) as a white solid.

Step 3: To a solution of [(1R,2R,3S,4S,5S)-2,3,4-triacetoxy-5-[(3-bromo-2-pyridyl)oxy]cyclohexyl]methyl acetate (0.350 g) and α-tocopherol (0.598 g) in DCM (5 mL) was added BF$_3$·Et$_2$O (47%, 0.629 g, 3 eq) at 15° C. The mixture was stirred for 5 hr at 15° C. The reaction mixture was quenched with sodium bicarbonate solution (5 mL), and extracted three times with dichloromethane (10 mL). The combined organic layers were washed with brine (10 mL), dried over Na$_2$SO$_4$, filtered and concentrated under reduced pressure. The residue was purified by prep-TLC (SiO$_2$, petroleum ether/Ethyl acetate, 5:1) to give [(2R,3R,4S,5R,6S)-3,4,5-triacetoxy-6-[(2R)-2,5,7,8-tetramethyl-2-[(4R,8R)-4,8,12-trimethyltridecyl]chroman-6-yl]oxy-tetrahydropyran-2-yl]methyl acetate (0.400 g, 75.7% yield) as a white solid. $^1$H NMR (400 MHz, CDCl$_3$) 5.362-5.179 (m, 3H), 4.724 (d, 1H), 4.191-4.049 (m, 3H), 3.536 (m, 1H), 2.568 (m, 2H), 2.152 (s, 3H), 2.120 (s, 3H), 2.105 (s, 3H), 2.082 (s, 3H), 2.054-2.027 (m, 9H), 1.838-1.737 (m, 2H), 1.572-1.042 (m, 24H), 0.882-0.842 (m, 12H)

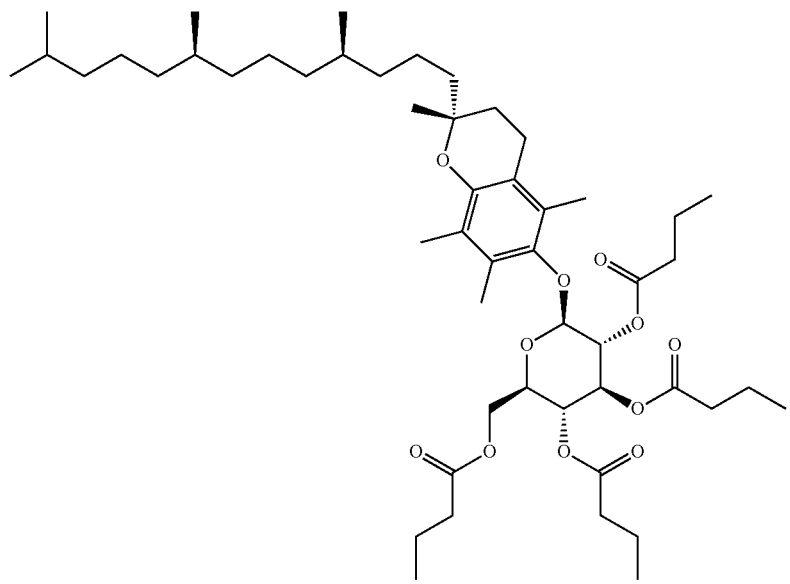 [SMILES: CCCC(=O)OC[C@H]1O[C@@H](Oc2c(C)c(C)c3c(c2C)CC[C@@](C)(CCC[C@H](C)CCC[C@H](C)CCCC(C)C)O3)[C@H](OC(=O)CCC)[C@@H](OC(=O)CCC)[C@@H]1OC(=O)CCC]

Compound 64: [(2R,3R,4S,5R,6S)-3,4,5-tri(butanoyloxy)-6-[(2R)-2,5,7,8-tetramethyl-2-[(4R,8R)-4,8,12-trimethyltridecyl]chroman-6-yl]oxy-tetrahydropyran-2-yl]methyl butanoate Step 1: To a solution of [(2R,3R,4S,5R,6S)-3,4,5-triacetoxy-6-[(2R)-2,5,7,8-tetramethyl-2-[(4R,8R)-4,8,12-trimethyltridecyl]chroman-6-yl]oxy-tetrahydropyran-2-yl] methyl acetate (2.7 g) in MeOH (30 mL) was added NaOMe in MeOH (25%, 192 mg) at 15° C. The mixture was stirred for 3 hr at 15° C. The reaction mixture was neutralized with cation exchange resin, filtered and concentrated under reduced pressure. The residue was purified by column chromatography (SiO$_2$, petroleum ether/ethyl acetate, 3:1 to ethyl acetate/MeOH, 20:1 gradient) to give (2R,3S,4S,5R,6S)-2-(hydroxymethyl)-6-[(2R)-2,5,7,8-tetramethyl-2-[(4R,8R)-4,8,12-trimethyltridecyl]chroman-6-yl]oxy-tetrahydropyran-3,4,5-triol (1.3 g, 62% yield) as a yellow solid.

Step 2: To a solution of (2R,3S,4S,5R,6S)-2-(hydroxymethyl)-6-[(2R)-2,5,7,8-tetramethyl-2-[(4R,8R)-4,8,12-trimethyltridecyl]chroman-6-yl]oxy-tetrahydropyran-3,4,5-triol in DCM (5 mL) was added pyridine (0.107 g) and butanoyl chloride (0.144 g) at 15° C. The mixture was stirred for 16 hr at 15° C. The reaction mixture was filtered and concentrated under reduced pressure. The residue was purified by prep-TLC (SiO$_2$, petroleum ether/ethyl acetate, 4:1) to give [(2R,3R,4S,5R,6S)-3,4,5-tri(butanoyloxy)-6-[(2R)-2,5,7,8-tetramethyl-2-[(4R,8R)-4,8,12-trimethyltridecyl]chroman-6-yl]oxy-tetrahydropyran-2-yl]methyl butanoate (0.075 g, 51% yield) as a colorless oil. $^1$H NMR (400 MHz, CDCl$_3$) 5.362 (m, 1H), 5.284 (m, 1H), 5.201 (m, 1H), 4.733 (d, 1H), 4.107 (m, 2H), 3.529 (m, 1H), 2.562 (m, 2H), 2.336 (m, 2H), 2.28-2.21 (m, 6H), 2.147 (s, 3H), 2.100 (s, 3H), 2.076 (s, 3H), 1.852-1.01 (m, 37H), 0.963-0.842 (m, 24H)

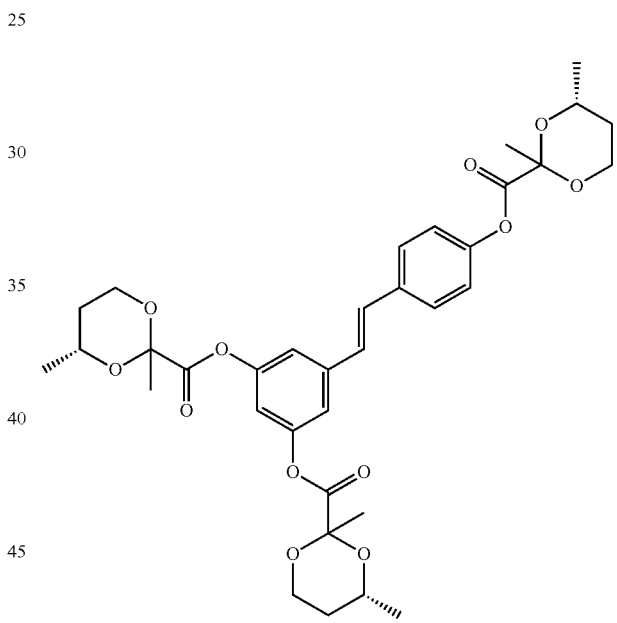

Compound 65:[4-[(E)-2-[3,5-bis[[(4R)-2,4-dimethyl-1,3-dioxane-2-carbonyl]oxy]phenyl]vinyl]phenyl](4R)-2,4-dimethyl-1,3-dioxane-2-carboxylate Step 1: To a solution of (3R)-butane-1,3-diol (2 g) and methyl 2-oxopropanoate (4.53 g) in ACN (100 mL) was added BF$_3$·Et$_2$O (47%, 13.40 g, 2 eq) dropwise, then the mixture was stirred at 15° C. for 16 h. The pH of the solution was adjusted to 7-8 with sat. NaHCO$_3$ and the aqueous phase was extracted three times with ethyl acetate (30 mL). The combined organic phase was washed with brine (20 mL), dried with anhydrous Na$_2$SO$_4$, filtered and concentrated in vacuum. The crude product was purified by silica gel chromatography (petroleum ether/ethyl acetate gradient) to give methyl (4R)-2,4-dimethyl-1,3-dioxane-2-carboxylate (2.5 g, 64.7% yield) as a yellow oil.

Step 2: To a solution of methyl (4R)-2,4-dimethyl-1,3-dioxane-2-carboxylate (2.5 g) in MeOH (40 mL) and H$_2$O (10 mL) was added NaOH (1.15 g), and the mixture was stirred at 80° C. for 16 h. The MeOH was removed and the pH of the mixture was adjusted to pH=2-3 with aqueous HCl (6M). The aqueous phase was extracted four times with ethyl acetate (30 mL). The combined organic phase was washed with brine (30 mL), dried with anhydrous $Na_2SO_4$, filtered and concentrated in vacuum to give (4R)-2,4-dimethyl-1,3-dioxane-2-carboxylic acid (1.5 g, 65% yield) as a yellow oil.

Step 3: A solution of resveratrol (0.2 g), (4R)-2,4-dimethyl-1,3-dioxane-2-carboxylic acid (0.561 g), DCC (0.723 g) and DMAP (0.054 g) in DCM (30 mL) was stirred at 15° C. for 16 h. The solid was removed by filtration and the solution was concentrated in vacuum. The crude product was purified by reverse phase prep-HPLC (C18, [water (0.1% TFA)-AC]0) to give [4-[(E)-2-[3,5-bis[[(4R)-2,4-dimethyl-1,3-dioxane-2-carbonyl]oxy]phenyl]vinyl]phenyl] (4R)-2,4-dimethyl-1,3-dioxane-2-carboxylate (0.1 g, 17% yield) as a colorless oil. LCMS: 672.3 (M+18) $^1$H NMR (400 MHz, $CDCl_3$) 7.552 (d, 2H), 7.211 (d, 2H), 7.170-7.104 (m, 3H), 7.034 (m, 1H), 6.944 (m, 1H), 4.163-4.005 (m, 9H), 1.975-1.709 (m, 12H), 1.549-1.513 (m, 3H), 1.318 (d, 9H)

Compound 66: [(2R)-2,5,7,8-tetramethyl-2-[(4R,8R)-4,8,12-trimethyltridecyl]chroman-6-yl](4R)-4-methyl-1,3-dioxane-2-carboxylate The solution of α-tocopherol (1 g), (4R)-2,4-dimethyl-1,3-dioxane-2-carboxylic acid (0.169 g), EDCl (0.223 g) and DMAP (0.071 g) in DCM (10 mL) was stirred at 15° C. for 16 h. The solvent was removed and the crude product was purified by prep-TLC (petroleum ether/ethyl acetate. 5:1) to give [(2R)-2,5,7,8-tetramethyl-2-[(4R,8R)-4,8,12-trimethyltridecyl]chroman-6-yl] (4R)-4-methyl-1,3-dioxane-2-carboxylate (0.12 g, 9% yield) as a yellow oil. LCMS: 576.4 (M+18) $^1$H NMR (400 MHz, $CDCl_3$) 5.297 (s, 1H), 4.306 (dd, 1H), 3.972-3.900 (m, 2H), 2.575 (t, 2H), 2.075 (s, 3H), 2.024 (s, 3H), 1.983 (s, 3H), 1.95-1.00 (m, 32H), 0.874-0.835 (m, 12H)

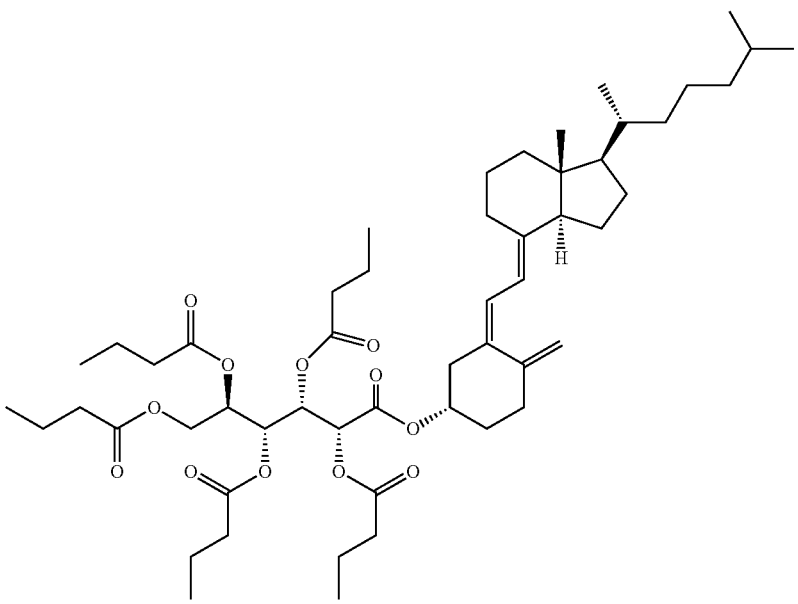

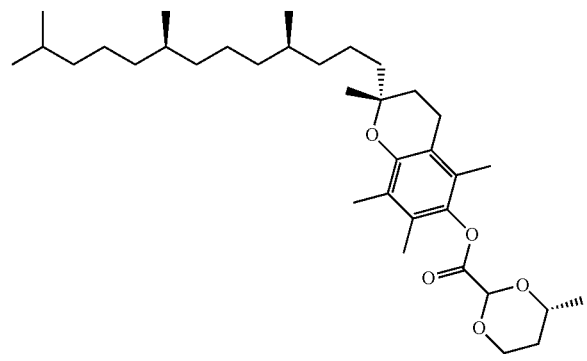 [SMILES: Cc1c(C)c2c(c(C)c1OC(=O)C1OCC[C@@H](C)O1)CC[C@@](C)(CCC[C@H](C)CCC[C@H](C)CCCC(C)C)O2]

Compound 67: [(1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl] (2R,3S,4R,5R)-2,3,4,5,6-penta(butanoyloxy)hexanoate To a solution of (1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexanol (0.200 g) and (2R,3S,4R,5R)-2,3,4,5,6-penta(butanoyloxy)hexanoic acid (0.341 g) in DCM (2 mL) was added DCC (0.129 g) and DMAP (0.013 g) at 15° C. The mixture was stirred at 15° C. for 16 h. The reaction mixture was filtered and concentrated under reduced pressure and the residue was purified by prep-TLC ($SiO_2$, petroleum ether/ethyl acetate, 5:1) to give [(1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl](2R,3S,4R,5R)-2,3,4,5,6-penta(butanoyloxy)hexanoate (0.300 g, 63% yield) as a colorless oil. $^1$H NMR (400 MHz, $CDCl_3$) 6.231 (d, 1H), 6.014 (d, 1H), 5.641 (dd, 1H), 5.511 (m, 1H), 5.262 (d, 1H), 5.121-5.066 (m, 2H), 4.967 (m, 1H), 4.847 (d, 1H), 4.317 (dd, 1H), 4.111 (m, 1H), 2.818 (m, 1H), 2.597 (m, 1H), 2.274-2.185 (m, 13H), 2.055-1.955 (m, 5H), 1.733-1.129 (m, 29H), 1.001-0.870 (m, 24H)

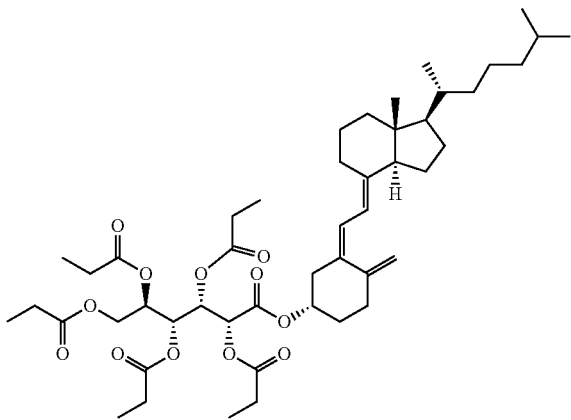 [SMILES: C=C1CC[C@H](OC(=O)[C@H](OC(=O)CC)[C@@H](OC(=O)CC)[C@H](OC(=O)CC)[C@@H](COC(=O)CC)OC(=O)CC)C/C1=C/C=C1\CCC[C@]2(C)[C@@H]([C@H](C)CCCC(C)C)CC[C@@H]12]

Compound 68: [(1 S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl] (2R,3S,4R,5R)-2,3,4,5,6-penta(propanoyloxy)hexanoate To a solution of (2R,3S,4R,5R)-2,3,4,5,6-penta(propanoyloxy) hexanoic acid (0.5 g) in DCM (5 mL) was added (1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexanol (0.484 g), DCC (0.433 g) and DMAP (0.038 g). The mixture was stirred at 15° C. for 12 hr. The reaction mixture was filtered and concentrated under reduced pressure to give a residue. The residue was purified by column chromatography (SiO$_2$, petroleum ether/ethyl acetate gradient) to give [(1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl] (2R,3S,4R,5R)-2,3,4,5,6-penta (propanoyloxy) hexanoate (0.24 g, 25% yield) as a colorless oil. $^1$H NMR (400 MHz, CDCl$_3$) 6.228 (d, 1H), 6.104 (d, 1H), 5.649 (m, 1H), 5.523 (m, 1H), 5.272 (d, 1H), 5.123-5.068 (m, 2H), 4.989 (m, 1H), 4.852 (m, 1H), 4.299 (m, 1H), 4.129 (m, 1H), 2.834 (m, 1H), 2.65-0.95 (m, 68H), 0.94-0.869 (m, 12H)

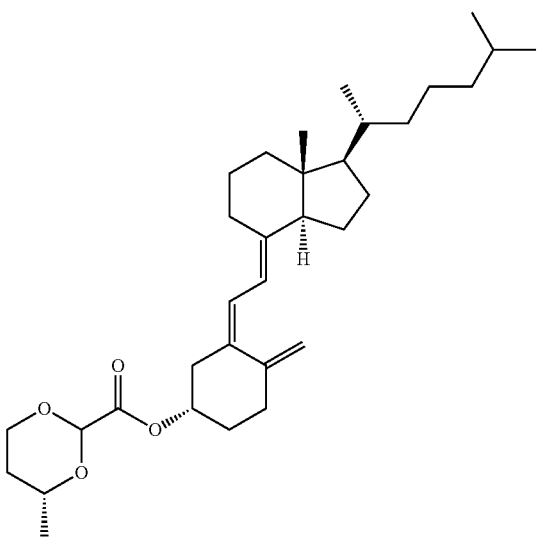 [SMILES: C=C1CC[C@H](OC(=O)C2OCC[C@@H](C)O2)C/C1=C/C=C1\CCC[C@]2(C)[C@@H]([C@H](C)CCCC(C)C)CC[C@@H]12]

Compound 69: [(1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl] (4R)-4-methyl-1,3-dioxane-2-carboxylate The solution of (1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexanol (0.3 g), (4R)-4-methyl-1,3-dioxane-2-carboxylic acid (0.228 g), DCC (0.322 g) and DMAP (0.095 g) in DCM (20 mL) was stirred at 15° C. for 16 h. The solid was filtered and the filtrate was concentrated in vacuum. The crude product was purified by prep-TLC (petroleum ether/ethyl acetate, 5:1) to give [(1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl] (4R)-4-methyl-1,3-dioxane-2-carboxylate (0.090 g, 21% yield) as a yellow solid. LCMS: 513.3 (M+H$^+$) $^1$H NMR (400 MHz, CDCl$_3$) 6.230 (d, 1H), 6.030 (d, 1H), 5.068-5.035 (m, 2H), 4.990 (s, 1H), 4.844 (s, 1H), 4.233 (m, 1H), 3.868-3.801 (m, 2H), 2.798 (m, 1H), 2.612 (m, 1H), 2.442 (m, 2H), 2.2 (m, 1H), 2.050-0.095 (m, 29H), 0.925 (d, 3H), 0.875 (d, 3H), 0.870 (d, 3H), 0.546 (s, 3H)

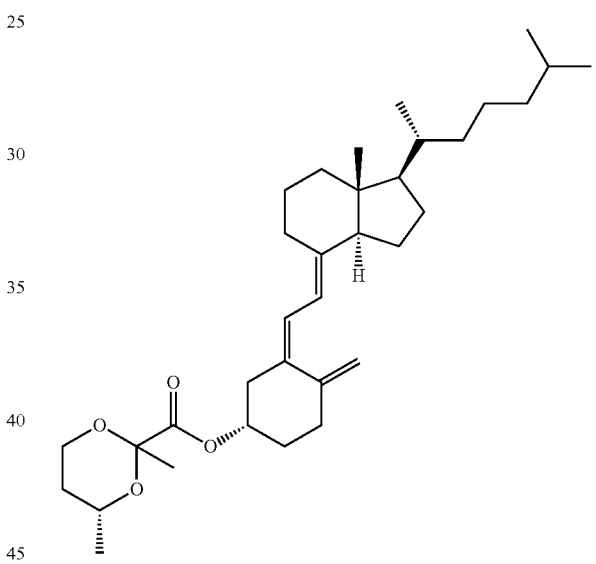

Compound 70: [(1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl] (4R)-2,4-dimethyl-1,3-dioxane-2-carboxylate A solution of (1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexanol (0.3 g), (4R)-2,4-dimethyl-1,3-dioxane-2-carboxylic acid (0.250 g), DCC (0.322 g) and DMAP (0.048 g) in DCM (20 mL) was stirred at 15° C. for 16 h. The solvent was removed under reduced pressure. The crude product was purified by silica gel chromatography (petroleum ether/ethyl acetate gradient) to give [(1S,3Z)-3-[(2E)-2-[(1R,3aS,7aR)-1-[(1R)-1,5-dimethylhexyl]-7a-methyl-2,3,3a,5,6,7-hexahydro-1H-inden-4-ylidene]ethylidene]-4-methylene-cyclohexyl] (4R)-2,4-dimethyl-1,3-dioxane-2-carboxylate (0.050 g, 12% yield) as yellow oil. LCMS: 549.4 (M+Na+) $^1$H NMR (400 MHz, CDCl$_3$) 6.130 (d, 1H), 5.938 (d, 1H), 5.026-4.978 (m, 2H), 4.784 (d, 1H), 3.843-3.772 (m, 3H), 2.730 (m, 1H), 2.552-0.995 (35H), 0.848 (d, 3H), 0.799 (d, 3H), 0.795 (d, 3HO, 0.469 (s, 3H)

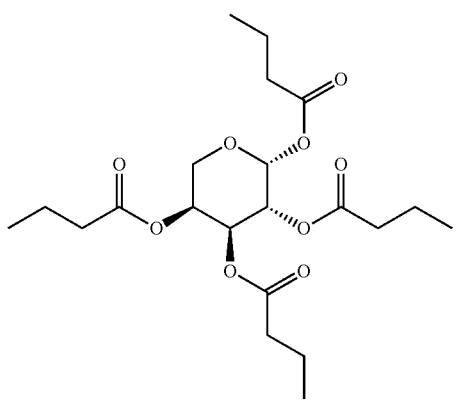 [SMILES: CCCC(=O)O[C@H]1OC[C@H](OC(=O)CCC)[C@H](OC(=O)CCC)[C@H]1OC(=O)CCC]

Compound 71: (2R,3R,4S,5S)-tetrahydro-2H-pyran-2,3,4,5-tetrayl tetrabutyrate

To the solution of (3R,4S,5S)-tetrahydro-2H-pyran-2,3,4,5-tetraol (3 g, 19.98 mmol, 1 eq), TEA (16.18 g, 159.86 mmol, 22.25 mL, 8 eq) and DMAP (488.25 mg, 4.00 mmol, 0.2 eq) in DCM (30 mL) was added butyric anhydride (19.34 g, 122.25 mmol, 20 mL, 6.12 eq) at 0° C. Then the solution was stirred 0° C. for 1 h and then stirred at 15° C. for another 15 h. LCMS showed the reaction was completed. The solvent was removed under reduced pressure. The crude product was purified by silica gel chromatography eluted with Petroleum ether/Ethyl acetate=1:0 to give (3R,4S,5S)-tetrahydro-2H-pyran-2,3,4,5-tetrayl tetrabutyrate (8 g, 18.58 mmol, 93.00% yield, 100% purity) as yellow oil. LCMS: (M+Na+): 453 1H-NMR (CDCl3, 400 MHz): δ 6.3 (1H, d) 5.3 (2H, M). 3.8-4.0 (dd, 2H), 2.2 (m, 8H), 1.6 (m, 8H), 0.97 (m, 12H).

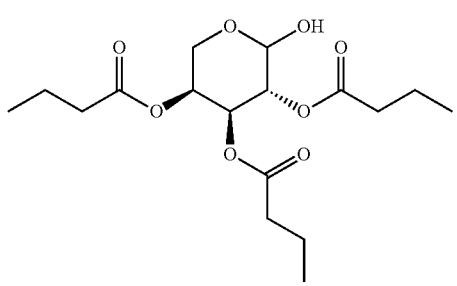 [SMILES: CCCC(=O)O[C@H]1[C@@H](OC(=O)CCC)COC(O)[C@@H]1OC(=O)CCC]

Compound 72: (3R,4S,5S)-2-hydroxytetrahydro-2H-pyran-3,4,5-triyl tributyrate

To a solution of [(3S,4S,5R)-4,5,6-tri(butanoyloxy)tetrahydropyran-3-yl] butanoate (1 g) in THF (20 mL) and H2O (1 mL) was added methanamine in THF (2 M, 1.51 mL) and the mixture was stirred at 15° C. for 24 h. The solvent was removed under reduced pressure. The crude product was purified by silica gel chromatography (petroleum ether/ethyl acetate gradient) to give [(3S,4S,5R)-4,5-di(butanoyloxy)-6-hydroxy-tetrahydropyran-3-yl] butanoate (0.15 g, 17.7% yield) as yellow oil. LCMS: 383.1 (M+Na+) 1H NMR (400 MHz, CDCl3) (mixture of anomers): δ 5.411 (d, 1H, major anomer), 5.370 (dd, 1H, major anomer), 5.300 (br, 1H, major anomer), 5.235 (br, 1H, minor anomer), 5.154 (dd, 1H, major anomer), 5.040 (m, 1H) 5.557 (br, 1H, minor anomer) 4.139 (d, 1H, major anomer) 3.959 (dd, 1H, minor anomer), 3.642 (dd, 1H, major anomer), 3.620 (d, 1H, minor anomer), 3.350 (br d, 1H, minor anomer), 2.619 (br, 2H, minor anomer), 2.330-2.116 (m, 6H, major and minor anomer), 1.666-1.496 (m, 6H, major and minor anomer), 0.931-0.834 (9H, major and minor anomer).

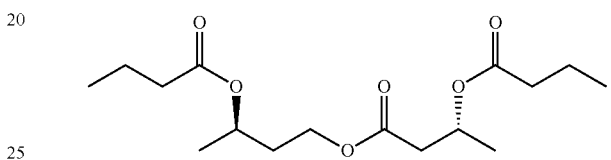

Compound 73: (R)-3-(butyryloxy)butyl (R)-3-(butyryloxy)butanoate

To a solution of [(3R)-3-hydroxybutyl] (3R)-3-hydroxybutanoate (0.400 g), K2CO3 (0.784 g) in acetonitrile (5 mL) was added butanoyl chloride (0.532 g), and the mixture was stirred at 15° C. for 12 h. The reaction mixture was concentrated and the residue was purified by column chromatography (SiO2, petroleum ether/ethyl acetate gradient) to give [(3R)-3-butanoyloxybutyl] (3R)-3-butanoyloxybutanoate (0.220 g, 27.5% yield) as a colorless oil. 1H NMR (400 MHz, CDCl3): δ 5.197 (m, 1H), 4.965 (m, 1H), 4.045 (m, 2H), 2.528 (m, 1H), 2.449 (m, 1H), 2.222-2.158 (m, 4H), 1.799 (m, 2H), 1.602-1.546 (m, 4H), 1.222 (d, 3H), 1.182 (d, 3H), 0.884 (t, 3H), 0.874 (t, 3H) ppm

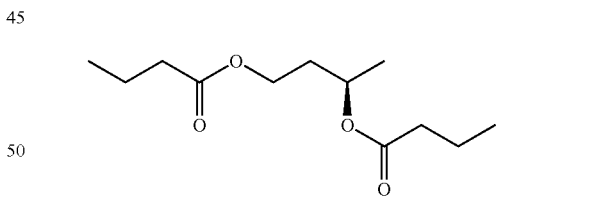

Compound 74: (R)-butane-1,3-diyl dibutyrate

To a solution of (3R)-butane-1,3-diol (6 g) and K2CO3 (23.92 g) in acetonitrile (50 mL) was added butanoyl chloride (18.44 g) and the mixture was stirred at 15° C. for 12 h. The mixture reaction was concentrated. The residue was purified by column chromatography (SiO2, petroleum ether/ethyl acetate gradient) to give [(3R)-3-butanoyloxybutyl] butanoate (11 g, 64.57% yield) as a colorless oil. LCMS: 248.1 (M+H3O+) 1H NMR (400 MHz, CDCl3): δ 5.022 (m, 1H), 4.101 (m, 2H), 2.300-2.247 (m, 4H), 1.885 (m, 2H), 1.679-1.594 (m, 4H), 1.260 (d, 3H), 0.949 (t, 6H) ppm

121

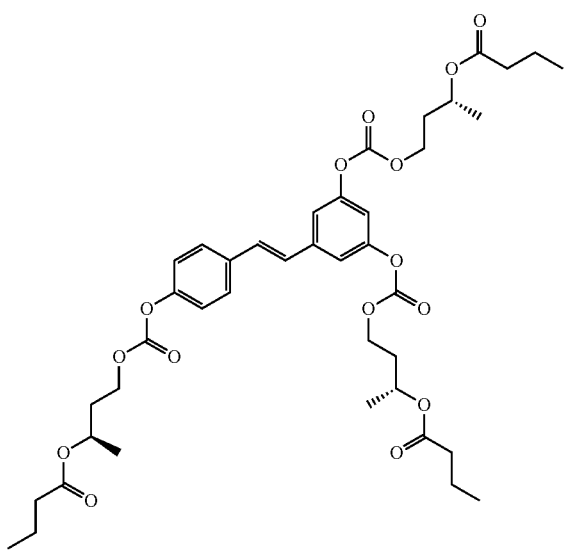 [SMILES: CCCC(=O)O[C@H](C)CCOC(=O)Oc1ccc(/C=C/c2cc(OC(=O)OCC[C@@H](C)OC(=O)CCC)cc(OC(=O)OCC[C@@H](C)OC(=O)CCC)c2)cc1]

Compound 75: (2R,2'R)-((((5-((E)-4-((((R)-3-(butyryloxy)butoxy)carbonyl)oxy)styryl)-1,3-phenylene)bis(oxy))bis(carbonyl))bis(oxy))bis(butane-4,2-diyl) dibutyrate To a solution of triphosgene (0.185 g, 0.624 mmol) in THF (10 mL) was added a solution of [(1R)-3-hydroxy-1-methyl-propyl] butanoate (0.200 g, 1.25 mmol) and TEA (0.189 g, 1.87 mmol) in THF (5 mL) at 0° C. The reaction was stirred for 1 h at 0° C. TLC showed the starting reactant was consumed. The reaction mixture was filtered and concentrated and used directly to next step.

Step 2

To a solution of 5-[(E)-2-(4-hydroxyphenyl)vinyl]benzene-1,3-diol (0.050 g, 0.219 mmol) and TEA (0.111 g, 1.10 mmol) in THF (5 mL) was added the solution above of [(1R)-3-chlorocarbonyloxy-1-methyl-propyl] butanoate in THF at 0° C. The reaction was stirred at 20° C. for 2 h, then filtered and concentrated. The residue was purified by prep-TLC to give [(1R)-3-[4-[(E)-2-[3,5-bis[[(3R)-3-butanoyloxybutoxy]carbonyloxy]phenyl]vinyl]phenoxy]carbonyloxy-1-methyl-propyl] butanoate (0.084 g, 41% yield) as colorless oil. LCMS: (M+H₂O⁺): 804.3 ¹H NMR (400 MHz, CDCl₃): δ 7.511 (m, 2H), 7.270-6.970 (m, 7H), 5.167-5.087 (m, 3H), 4.360-4.307 (m, 6H), 2.299 (t, 6H), 2.012 (m, 6H), 1.703-1.647 (m, 6H), 1.301 (d, 9H), 0.965 (t, 9H)

122

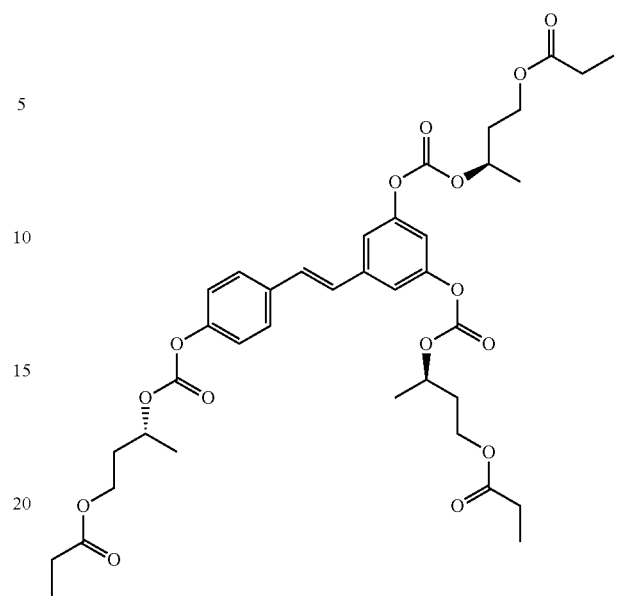

Compound 76: (3R,3'R)-((((5-((E)-4-(((((R)-4-(propionyloxy)butan-2-yl)oxy)carbonyl)oxy)styryl)-1,3-phenylene)bis(oxy))bis(carbonyl))bis(oxy))bis(butane-3,1-diyl) dipropionate To a solution of (3R)-butane-1,3-diol (2 g, 22.2 mmol) and TEA (2.47 g, 24.4 mmol) in DCM (10 mL) was added propanoyl propanoate (3.18 g, 24.4 mmol) and the mixture was stirred at 25° C. for 12 h. The mixture was concentrated and the residue was purified by column chromatography (SiO₂, petroleum ether/ethyl acetate=10/1 to 5:1) to give [(3R)-3-hydroxybutyl] propanoate (1.8 g, 55% yield) as a colorless oil.

To a solution of triphosgene (0.203 g, 0.68 mmol) in THF (10 mL) was added a solution of [(3R)-3-hydroxybutyl] propanoate (0.20 g, 1.37 mmol) and TEA (0.21 g, 2.1 mmol) in THF (5 mL) at 0° C. The mixture was stirred for 1 h at 0° C., then filtered and used directly to next step. To a solution of 5-[(E)-2-(4-hydroxyphenyl)vinyl]benzene-1,3-diol (0.050 g, 0.219 mmol) and TEA (0.111 g, 1.10 mmol) in THF (5 mL) was added the solution above of [(3R)-3-chlorocarbonyloxybutyl]propanoate in THF at 0° C. The reaction mixture was stirred at 20° C. for 2 h, then filtered and concentrated. The residue was purified by prep-TLC to give [(3R)-3-[4-[(E)-2-[3,5-bis[[(1R)-1-methyl-3-propanoyloxy-propoxy]carbonyloxy]phenyl]vinyl]phenoxy]carbonyloxybutyl]propanoate (0.060 g, 35% yield) as a colorless oil. LCMS: (M+Na⁺): 767.3 ¹H NMR (400 MHz, CDCl₃): δ 7.518 (d, 2H), 7.270-6.976 (m, 7H), 5.032-4.968 (m, 3H), 4.267-4.189 (m, 6H), 2.384-2.328 (m, 6H), 2.066-1.980 (m, 6H), 1.430 (d, 9H), 1.555 (t, 9H)

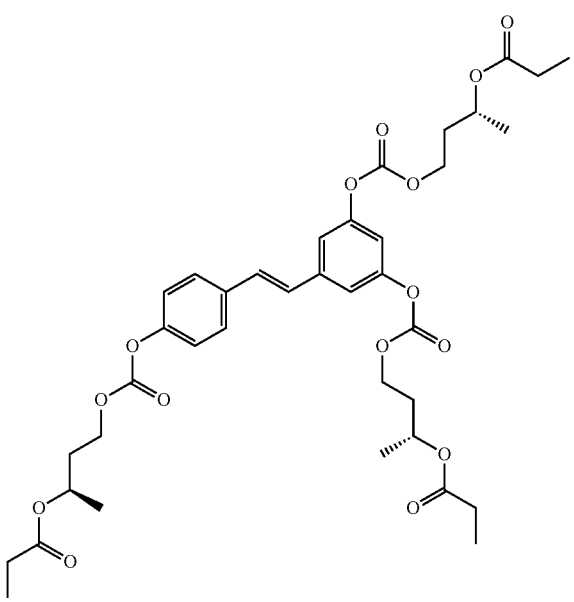 [SMILES: CCC(=O)O[C@H](C)CCOC(=O)Oc1ccc(/C=C/c2cc(OC(=O)OCC[C@@H](C)OC(=O)CC)cc(OC(=O)OCC[C@@H](C)OC(=O)CC)c2)cc1]

Compound 77: (2R,2'R)-((((5-((E)-4-((((R)-3-(propionyloxy)butoxy)carbonyl)oxy)styryl)-1,3-phenylene)bis(oxy))bis(carbonyl))bis(oxy))bis(butane-4,2-diyl) dipropionate

Step 1

To a solution of pyridine (1.05 g, 13.3 mmol) in DCM (10 mL) was added (2R)-4-benzyloxybutan-2-ol (1 g, 5.6 mmol) and DMAP (0.022 g, 0.18 mmol) at 0° C. Then propanoyl chloride (0.719 g, 7.77 mmol) was added to the mixture at 0° C. and the mixture was stirred at 25° C. for 3 h under $N_2$. The reaction mixture was concentrated under reduced pressure and the residue was purified by flash silica gel chromatography (petroleum ether/ethyl acetate=100/1 to 70/1) to give [(1R)-3-benzyloxy-1-methyl-propyl] propanoate (1.2 g, 4.6 mmol, 82% yield) as a colorless oil.

Step 2

To a solution of 10% Pd/C 0.4 g) in THF (200 mL) was added [(1R)-3-benzyloxy-1-methyl-propyl]propanoate (1.2 g, 5.1 mmol), and the mixture was degassed 3 times and purged with $H_2$, then stirred at 40° C. for 12 h under $H_2$, 15 Psi. The mixture reaction was filtered and concentrated to give [(1R)-3-hydroxy-1-methyl-propyl] propanoate (0.70 mg) as a colorless oil.

Step 3

To a solution of triphosgene (0.203 g, 0.684 mmol) in THF (10 mL) was added a solution of [(1R)-3-hydroxy-1-methyl-propyl] propanoate (0.200 g, 1.37 mmol) and TEA (0.208 g, 2.05 mmol) in THF (5 mL) at 0° C. The reaction was stirred for 1 h at 0° C. The reaction mixture was filtered and concentrated and used in next step directly.

Step 4

To a solution of 5-[(E)-2-(4-hydroxyphenyl)vinyl]benzene-1,3-diol (0.050 g, 0.219 mmol) and TEA (0.111 g, 1.10 mmol) in THF (5 mL) was added the above solution of [(1R)-3-chlorocarbonyloxy-1-methyl-propyl] propanoate in THF at 0° C. The reaction was stirred at 20° C. for 2 h. The mixture reaction was filtered and concentrated and the residue was purified by prep-TLC to give [(1R)-3-[4-[(E)-2-[3,5-bis[[(3R)-3-propanoyloxybutoxy]carbonyloxy]phenyl]vinyl]phenoxy]carbonyloxy-1-methyl-propyl]propanoate (0.030 g, 14.71% yield) as a colorless oil. LCMS: (M+Na⁺): 767.3 ¹H NMR (400 MHz, CDCl₃): δ 7.506 (d, 2H), 7.232-6.997 (m, 7H), 5.149-5.070 (m, 3H), 4.363-4.290 (m, 6H), 2.368-2.312 (m, 6H), 2.062-1.993 (m, 6H), 1.308 (d, 9H), 1.555 (t, 9H)

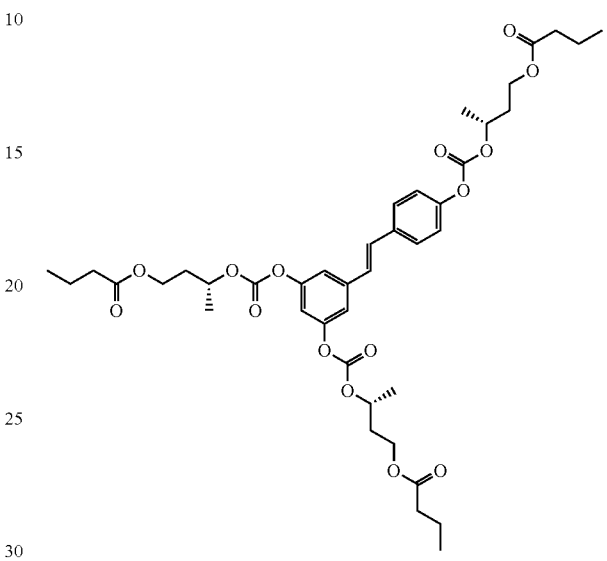

Compound 78: (3R,3'R)-((((5-((E)-4-(((((R)-4-(butyryloxy)butan-2-yl)oxy)carbonyl)oxy)styryl)-1,3-phenylene)bis(oxy))bis(carbonyl))bis(oxy))bis(butane-3,1-diyl) dibutyrate To a solution of triphosgene (0.185 g, 0.62 mmol) in THF (10 mL) was added a solution of [(3R)-3-hydroxybutyl] butanoate (0.200 g, 1.25 mmol and TEA (0.189 g, 1.87 mmol) in THF (5 mL) at 0° C. The reaction mixture was stirred for 1 h at 0° C. The mixture reaction was filtered and used directly to next step.

To a solution of 5-[(E)-2-(4-hydroxyphenyl)vinyl]benzene-1,3-diol (0.050 g, 0.219 mmol) and TEA (0.111 g, 1.10 mmol) in THF (5 mL) was added the solution above of [(3R)-3-chlorocarbonyloxybutyl]butanoate in THF at 0° C. The mixture was stirred at 20° C. for 2 h. The mixture reaction was filtered and concentrated and the residue was purified by prep-TLC (SiO₂, petroleum ether/ethyl acetate=5/1) to give [(3R)-3-[4-[(E)-2-[3,5-bis[[(1R)-3-butanoyloxy-1-methyl-propoxy]carbonyloxy]phenyl]vinyl]phenoxy]carbonyloxybutyl] butanoate (0.080 mg, 45% yield) as a colorless oil. LCMS: (M+H₂O⁺): 804.4 ¹H NMR (400 MHz, CDCl₃): δ 7.517 (m, 2H), 7.270-7.018 (m, 7H), 5.103 (m, 3H), 4.260-4.203 (m, 6H), 2.313 (m, 6H), 2.054 (m, 6H), 1.698-1.643 (m, 6H), 1.431 (d, 9H), 0.957 (t, 9H)

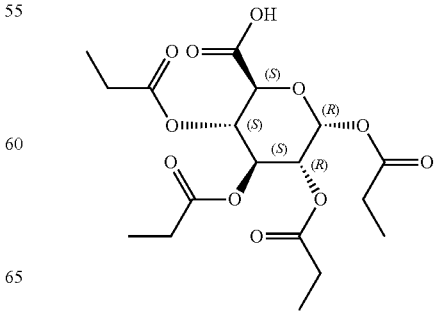

Compound 79: (2S,3S,4S,5R,6R)-3,4,5,6-tetrakis(propanoyloxy)oxane-2-carboxylic acid
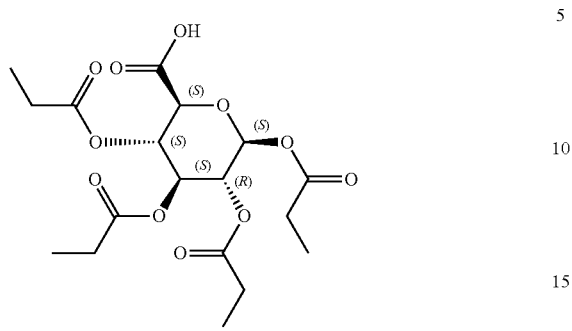
Compound 80: (2S,3S,4S,5R,6S)-3,4,5,6-tetrakis(propanoyloxy)oxane-2-carboxylic acid
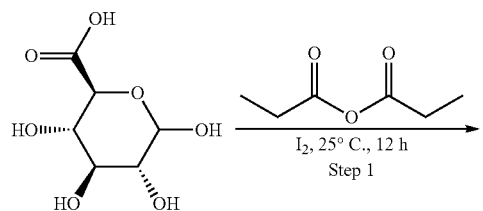
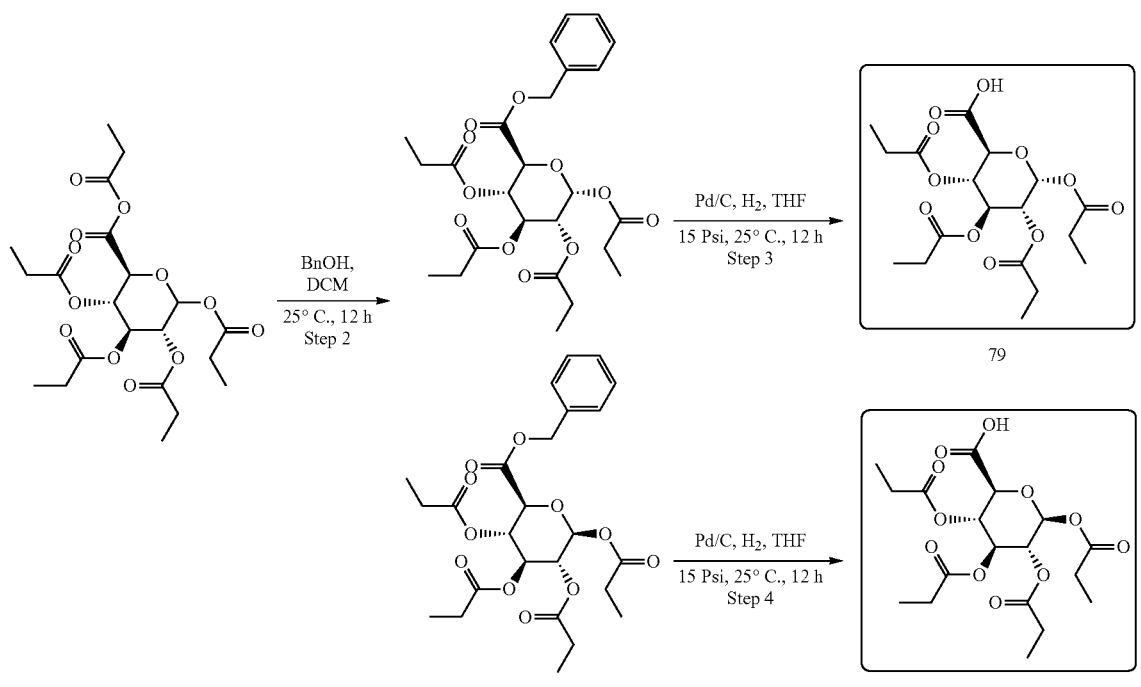

Step 1

To a solution of (2S,3S,4S,5R)-3,4,5,6-tetrahydroxytetrahydropyran-2-carboxylic acid (5 g, 25.75 mmol, 1 eq) in propionic anhydride (25 mL) was added I₂ (653.68 mg, 2.58 mmol, 518.79 uL, 0.1 eq). The mixture was stirred at 25° C. for 12 hr. TLC indicated (2S,3S,4S,5R)-3,4,5,6-tetrahydroxytetrahydropyran-2-carboxylic acid was consumed completely. The reaction mixture was concentrated under reduced pressure. Then the residue was taken up in toluene followed by distillation in vacuum. The crude product propionic (2S,3S,4S,5R)-3,4,5,6-tetrakis(propionyloxy) tetrahydro-2H-pyran-2-carboxylic anhydride (7 g, crude) was obtained as a brown liquid.

Step 2

To a solution of propionic (2S,3S,4S,5R)-3,4,5,6-tetrakis(propionyloxy)tetrahydro-2H-pyran-2-carboxylic anhydride (7 g, 16.73 mmol, 1 eq) in DCM (70 mL) was added BnOH (3.62 g, 33.46 mmol, 3.48 mL, 2 eq). The mixture was stirred at 25° C. for 12 hr. TLC indicated (propionic (2S,3S,4S,5R)-3,4,5,6-tetrakis(propionyloxy)tetrahydro-2H-pyran-2-carboxylic anhydride was consumed completely and one major new spot was detected. The reaction mixture was concentrated under reduced pressure. The residue was purified by column chromatography (SiO₂, Petroleum ether/Ethyl acetate=20/1 to 6:1). Compound benzyl (2S,3S,4S,5R)-3,4,5,6-tetra(propanoyloxy)tetrahydropyran-2-carboxylate (1.5 g, crude) was obtained as a yellow oil. The residue was purified by prep-HPLC ([water (10 mM NH₄HCO₃)-ACN]). Benzyl (2S,3S,4S,5R,6R)-3,4,5,6-tetra(propanoyloxy) tetrahydropyran-2-carboxylate (30 mg) was obtained as a white solid. Benzyl (2S,3S,4S,5R,6S)-3,4,5,6-tetra(propanoyloxy)tetrahydropyran-2-carboxylate (100 mg) was obtained as a white solid. The compound ID was temporary assigned.

Step 3

To a solution of benzyl (2S,3S,4S,5R,6R)-3,4,5,6-tetra(propanoyloxy)tetrahydropyran-2-carboxylate (30 mg, 59.00 umol, 1 eq) in THF (5 mL) was added Pd/C (3 mg, 59.00 umol, 10% purity, 1.00 eq). The suspension was degassed and purged with H₂ for 3 times. The mixture was stirred under H₂ (15 Psi) at 25° C. for 12 hr. LC-MS showed the desired compound was detected. Filtered and concentrated under reduced pressure to give a residue. The residue was purified by prep-HPLC ([water (0.1% TFA)-ACN]). Compound 79 for (2S,3S,4S,5R,6R)-3,4,5,6-tetra (propanoyloxy) tetrahydropyran-2-carboxylic acid (5.3 mg, 12.67 umol, 21.47% yield, 100% purity) was obtained as a yellow solid. The compound ID was temporary assigned. The structure was not further confirmed by 2D NMR. LCMS: (M+18)+:436.1. @3.215 min. ¹H NMR (400 MHz, CDCl₃): δ 6.35 (s, 1H), 5.49 (t, J=9.6 Hz, 1H), 5.22 (t, J=9.8 Hz, 1H), 5.07 (d, J=10.1 Hz, 1H), 4.42 (s, 1H), 2.50-2.36 (m, 2H), 2.34-2.14 (m, 6H), 1.13 (t, J=7.6 Hz, 3H), 1.07-0.97 (m, 9H)

Step 4

To a solution of benzyl (2S,3S,4S,5R,6S)-3,4,5,6-tetra(propanoyloxy)tetrahydropyran-2-carboxylate (50.00 mg, 98.33 umol, 1 eq) in THF (5 mL) was added Pd/C (3 mg, 98.33 umol, 10% purity, 1.00 eq). The suspension was degassed and purged with H₂ for 3 times. The mixture was stirred under H₂ (15 Psi) at 25° C. for 12 hr. LC-MS showed the desired compound was detected. The reaction mixture was filtered and concentrated under reduced pressure. The residue was purified by prep-HPLC ([water (0.1% TFA)-ACN]). Compound 80 for (2S,3S,4S,5R,6R)-3,4,5,6-tetra (propanoyloxy)tetrahydropyran-2-carboxylic acid (11 mg, 26.29 umol, 26.74% yield, 100% purity) was obtained as yellow oil. The compound ID was temporary assigned. The structure was not further confirmed by 2D NMR. LCMS: (M+18)+: 436.1 @ 3.125 min. ¹H NMR (400 MHz, CDCl₃): δ 5.84 (d, J=7.6 Hz, 1H), 5.42-5.27 (m, 2H), 5.19 (t, J=8.3 Hz, 1H), 4.28 (d, J=9.2 Hz, 1H), 2.46-2.24 (m, 8H), 1.18-1.06 (m, 12H)

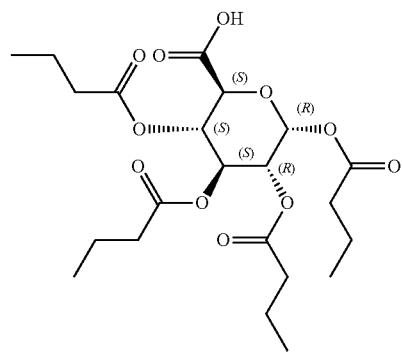

Compound 81: (2S,3S,4S,5R,6R)-3,4,5,6-tetrakis(butanoyloxy)oxane-2-carboxylic acid This compound was prepared according to a modified procedure described for the preparation of compounds 79 and 80. LCMS: (M+Na⁺): 492.2. ¹H-NMR (400 MHz, CDCl₃): δ 6.26 (d, J=3.7 Hz, 1H), 5.49 (t, J=9.9 Hz, 1H), 5.16 (t, J=10.0 Hz, 1H), 5.05 (dd, J=10.2, 3.7 Hz, 1H), 4.12 (d, J=10.3 Hz, 1H), 2.34 (t, J=7.4 Hz, 2H), 2.28-2.09 (m, 6H), 1.69-1.58 (m, 2H), 1.58-1.42 (m, 6H), 0.95-0.78 (m, 12H)

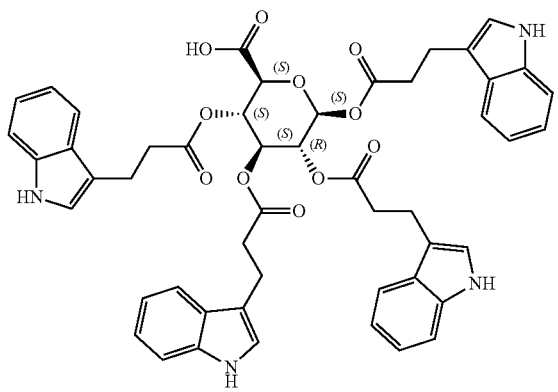

Compound 82: (2S,3S,4S,5R,6S)-3,4,5,6-tetrakis({[3-(1H-indol-3-yl)propanoyl]oxy})oxane-2-carboxylic acid

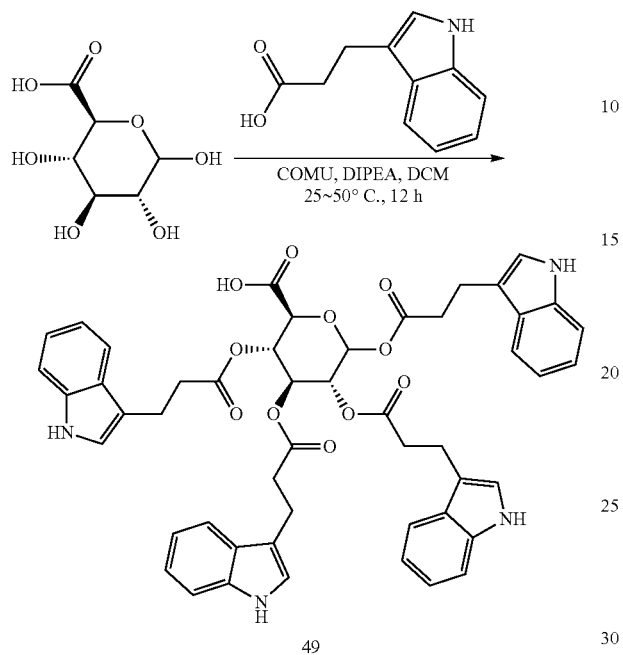

To a mixture of (2S,3S,4S,5R)-3,4,5,6-tetrahydroxytetrahydropyran-2-carboxylic acid (0.2 g, 1.03 mmol, 1 eq) and 3-(1H-indol-3-yl)propanoic acid (1.17 g, 6.18 mmol, 6 eq) in DCM (10 mL) was added DIPEA (1.07 g, 8.24 mmol, 1.44 mL, 8 eq) and COMU (2.65 g, 6.18 mmol, 6 eq) in one portion at 25° C. under $N_2$. The mixture was stirred at 50° C. for 12 hours. LCMS showed the desired mass was detected. The reaction mixture was filtered and concentrated under reduced pressure to give a residue. The residue was purified by prep-HPLC (column: Waters Xbridge Prep OBD C18 150*40 10 u; mobile phase: [water (10 mM $NH_4HCO_3$)-ACN]; B %: 30%-55%,11 min) to give (2S,3S,4S,5R)-3,4,5,6-tetrakis[3-(1H-indol-3-yl)propanoyloxy]tetrahydropyran-2-carboxylic acid (88 mg, 8.77 umol, 8.51e-1% yield, 96.37% purity) as a white solid. LCMS: (M−H$^+$) 877.2 @ 1.375 min. LCMS: (M+18) 896.3 @ 2.832 min. $^1$H NMR: (400 MHz, Methanol-d4): δ 7.5-6.8 (m, 20H), 5.8 (d, 1H), 5.4-5.3 (m, 1H), 5.3-5.2 (m, 1H), 5.2-5.1 (m, 1H), 4.1 (d, 1H), 3.0-2.0 (m, 16H)

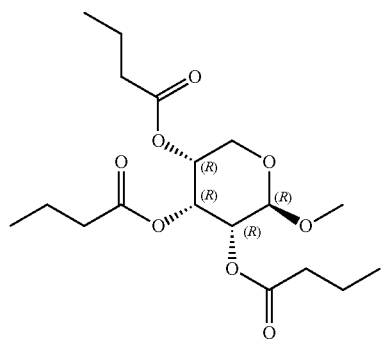

Compound 83: (2R,3R,4R,5R)-3,5-bis(butanoyloxy)-2-methoxyoxan-4-yl butanoate This compound was prepared according to a modified procedure described for the preparation of compound 53.

LCMS: (m+H+)=375.4. $^1$H NMR (400 MHz, DMSO-d6) δ 5.28 (t, 1H), 5.08 (q, 1H), 4.90 (td, 1H), 4.69 (d, 1H), 3.92 (dd, 1H), 3.68 (dd, 1H), 3.34 (s, 3H), 2.39-2.16 (m, 6H), 1.54 (m, 6H), 0.88 (m, 9H).

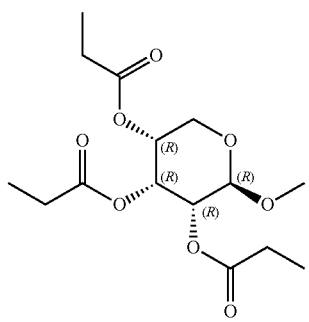

Compound 84: (2R,3R,4R,5R)-2-methoxy-3,5-bis(propanoyloxy)oxan-4-yl propanoate This compound was prepared according to a modified procedure described for the preparation of compound 53.

LCMS: (m+H+)=355.3. $^1$H NMR (400 MHz, DMSO-d6) δ 5.26 (t, 1H), 5.07 (q, 1H), 4.94-4.84 (m, 1H), 4.71 (d, 1H), 3.92 (dd, 1H), 3.69 (dd, 1H), 3.35 (s, 3H), 2.45-2.17 (m, 6H), 1.02 (dt, 9H)

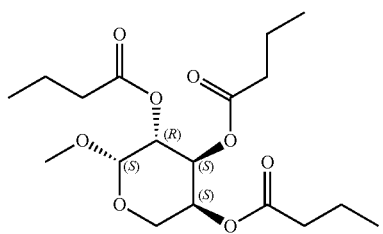

Compound 85: (2S,3R,4S,5S)-3,5-bis(butanoyloxy)-2-methoxyoxan-4-yl butanoate This compound was prepared according to a modified procedure described for the preparation of compound 53.

LCMS: (M+Na+) 397.3. $^1$H NMR (400 MHz, DMSO-d6) δ 5.27 (dt, 1H), 5.24 (dd, 1H), 5.04 (dd, 1H), 4.90 (d, 1H), 3.89 (dd, 1H), 3.61 (dd, 1H), 3.32 (s, 3H), 2.39-2.13 (m, 6H), 1.65-1.42 (m, 6H), 0.97-0.80 (m, 9H).

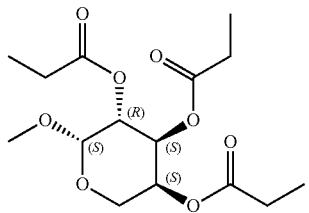

Compound 86: (2S,3R,4S,5S)-2-methoxy-3,5-bis(propanoyloxy)oxan-4-yl propanoate This compound was prepared according to a modified procedure described for the preparation of compound 53.

LCMS: (M+Na+) 355.3. $^1$H NMR (400 MHz, DMSO-d6) δ 5.27 (dt, 1H), 5.23 (dd, 1H), 5.04 (dd, 1H), 4.90 (d, 1H), 3.89 (dd, 1H), 3.62 (dd, 1H), 3.32 (s, 3H), 2.45-2.10 (m, 6H), 1.12-0.91 (m, 9H).

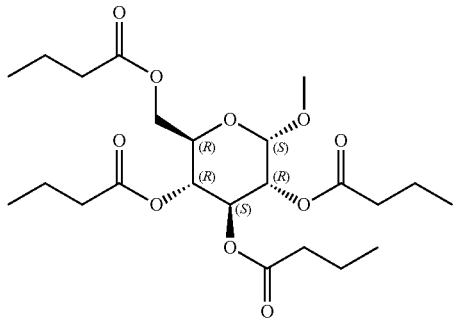

Compound 87: [(2R,3R,4S,5R,6S)-3,4,5-tris(butanoyloxy)-6-methoxyoxan-2-yl]methyl butanoate This compound was prepared according to a modified procedure described for the preparation of compound 53.

LCMS: (M+Na+) 497.2. $^1$H NMR (400 MHz, DMSO-d$_6$) δ 5.34 (dd, 1H), 5.00 (t, 1H), 4.92 (d, 1H), 4.83 (dd, 1H), 4.14 (dd, 1H), 4.10-3.88 (m, 2H), 3.34 (s, 3H), 2.35-2.08 (m, 8H), 1.60-1.40 (m, 8H), 0.93-0.78 (m, 12H)

Compound 88: [(2R,3R,4S,5R,6S)-6-methoxy-3,4,5-tris(propanoyloxy)oxan-2-yl]methyl propanoate This compound was prepared according to a modified procedure described for the preparation of compound 53.

LCMS: (M+Na+) 441.2. $^1$H NMR (400 MHz, DMSO-d6) δ 5.32 (dd, 1H), 4.99 (t, 1H), 4.92 (d, 1H), 4.85 (dd, 1H), 4.17 (dd, 1H), 4.06 (dd, 1H), 3.93 (ddd, 1H), 3.34 (s, 3H), 2.39-2.11 (m, 8H), 1.09-0.92 (m, 12H)

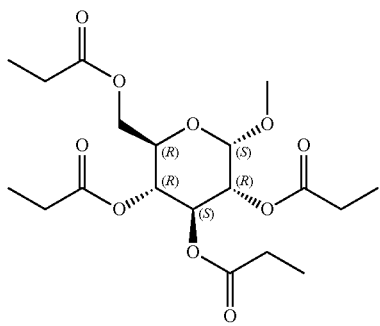

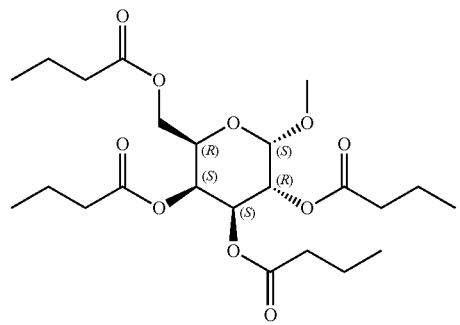

Compound 89: [(2R,3S,4S,5R,6S)-3,4,5-tris(butanoyloxy)-6-methoxyoxan-2-yl]methyl butanoate This compound was prepared according to a modified procedure described for the preparation of compound 53.

LCMS: (M+Na+) 497.2. $^1$H NMR (400 MHz, DMSO-d$_6$) δ 5.40 (dd, 1H), 5.27 (dd, 1H), 5.04 (dd, 1H), 4.97 (d, 1H), 4.22 (t, 1H), 4.15-3.97 (m, 2H), 3.35 (s, 3H), 2.47-2.07 (m, 8H), 1.69-1.38 (m, 8H), 1.01-0.77 (m, 12H)

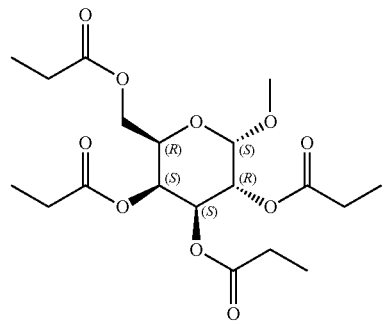

Compound 90: [(2R,3S,4S,5R,6S)-6-methoxy-3,4,5-tris(propanoyloxy)oxan-2-yl]methyl propanoate This compound was prepared according to a modified procedure described for the preparation of compound 53.

LCMS: (M+Na+): 441.1. $^1$H NMR (400 MHz, DMSO-d$_6$) δ 5.40 (dd, 1H), 5.27 (dd, 1H), 5.05 (dd, 1H), 4.98 (d, 1H), 4.22 (ddd, 1H), 4.07 (d, 2H), 3.36 (s, 3H), 2.49-2.11 (m, 8H), 1.15-0.94 (m, 12H)

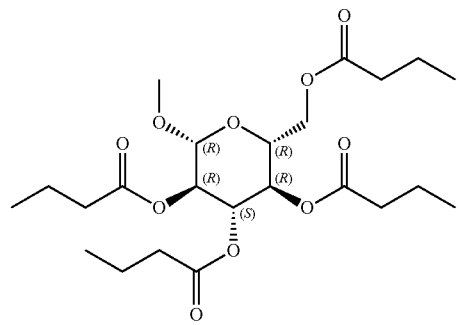

Compound 91: [(2R,3R,4S,5R,6R)-3,4,5-tris(butanoyloxy)-6-methoxyoxan-2-yl]methyl butanoate This compound was prepared according to a modified procedure described for the preparation of compound 53.

LCMS: (M+Na+): 497.1. $^1$H NMR (400 MHz, DMSO-d$_6$) δ 5.33 (t, 1H), 4.96 (t, 1H), 4.81 (dd, 1H), 4.19 (dd, 1H), 4.12-3.97 (m, 2H), 3.39 (s, 3H), 2.38-2.10 (m, 8H), 1.64-1.38 (m, 8H), 0.97-0.77 (m, 12H)

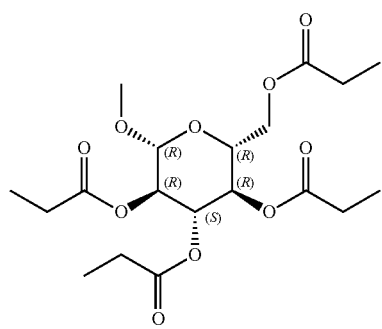

Compound 92: [(2R,3R,4S,5R,6R)-6-methoxy-3,4,5-tris(propanoyloxy)oxan-2-yl]methyl propanoate This compound was prepared according to a modified procedure described for the preparation of compound 53.

LCMS: (M+Na+) 441.1. $^1$H NMR (400 MHz, DMSO-d$_6$) δ 5.31 (t, 1H), 4.95 (t, 1H), 4.80 (dd, 1H), 4.74 (d, 1H), 4.24 (dd, 1H), 4.10-3.99 (m, 2H), 3.39 (s, 3H), 2.41-2.13 (m, 8H), 1.09-0.91 (m, 12H)

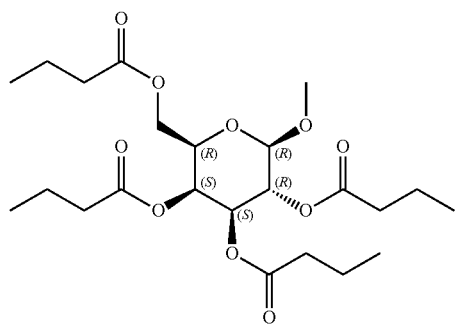

Compound 93: [(2R,3S,4S,5R,6R)-3,4,5-tris(butanoyloxy)-6-methoxyoxan-2-yl]methyl butanoate This compound was prepared according to a modified procedure described for the preparation of compound 53.

LCMS: (M+Na+) 497.1. $^1$H NMR (400 MHz, DMSO-d6) δ 5.30 (dd, 1H), 5.22 (dd, 1H), 4.99 (dd, 1H), 4.64 (d, 1H), 4.28-4.20 (m, 1H), 4.15-3.96 (m, 2H), 3.38 (s, 3H), 2.43-2.06 (m, 8H), 1.53 (ddq, 8H), 0.99-0.79 (m, 12H).

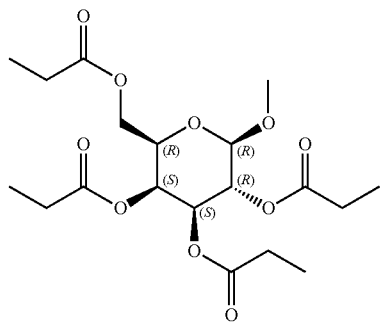

Compound 94: [(2R,3S,4S,5R,6R)-6-methoxy-3,4,5-tris(propanoyloxy)oxan-2-yl]methyl propanoate This compound was prepared according to a modified procedure described for the preparation of compound 53.

LCMS (M+Na): 441.1. $^1$H NMR (400 MHz, DMSO-d6) δ 5.30 (dd, 1H), 5.20 (dd, 1H), 4.98 (dd, 1H), 4.65 (d, 1H), 4.24 (td, 1H), 4.18-4.01 (m, 2H), 3.39 (s, 3H), 2.48-2.08 (m, 8H), 1.03 (ddt, 12H)

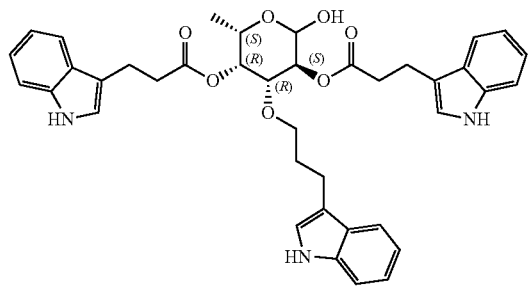

Compound 95: (2S,3R,4R,5S)-6-hydroxy-4,5-bis({[3-(1H-indol-3-yl)propanoyl]oxy})-2-methyloxan-3-yl 3-(1H-indol-3-yl)propanoate This compound was prepared according to a procedure described for compound 197 with the exception that the synthesis was stopped at the stage when compound 95 was produced. LCMS: (M−H): 676.3. $^1$H NMR (400 MHz, Chloroform-d) δ 7.77-6.47 (m, 18H), 5.42-5.32 (m, 1H), 5.29-5.22 (m, 1H), 5.12-5.03 (m, 1H), 4.69-4.62 (m, 1H), 4.41-4.35 (m, 1H), 3.87-3.81 (m, 1H), 3.20-3.00 (m, 4H), 2.90-2.75 (m, 4H), 2.74-2.59 (m, 2H), 2.12-1.97 (m, 2H), 1.22-1.07 (m, 3H)

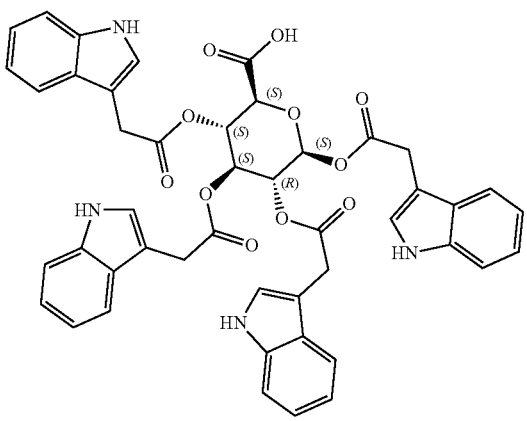

Compound 96: (2S,3S,4S,5R,6S)-3,4,5,6-tetrakis({[2-(1H-indol-3-yl)acetyl]oxy})oxane-2-carboxylic acid

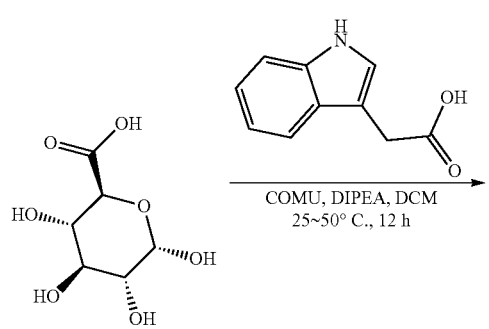

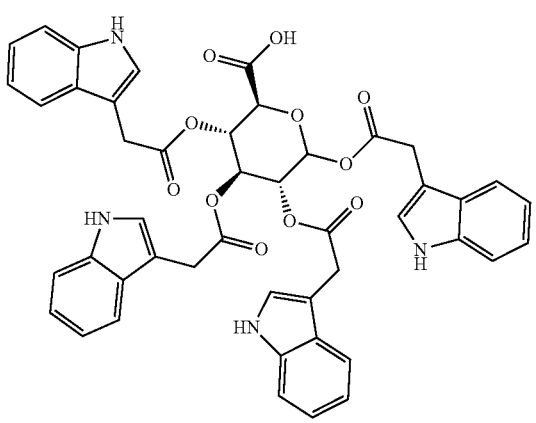

63

To a mixture of (2S,3S,4S,5R,6S)-3,4,5,6-tetrahydroxytetrahydropyran-2-carboxylic acid (200 mg, 1.03 mmol, 1 eq) and 2-(1H-indol-3-yl)acetic acid (1.08 g, 6.18 mmol, 6 eq) in DCM (10 mL) was added COMU (2.65 g, 6.18 mmol, 6 eq) and DIPEA (1.07 g, 8.24 mmol, 1.44 mL, 8 eq) in one portion at 25° C. under $N_2$. The mixture was stirred at 50° C. for 12 hours. LCMS showed the desired mass was detected. The reaction mixture was filtered and concentrated under reduced pressure to give a residue. The residue was purified by prep-HPLC (column: Waters Xbridge Prep OBD C18 150*40 10 u; mobile phase: [water (10 mM $NH_4HCO_3$)-MeOH]; B %: 25%-45%,11 min) to give compound 96 (2S,3S,4S,5R)-3,4,5,6-tetrakis(2-(1H-indol-3-yl)acetoxy)tetrahydro-2H-pyran-2-carboxylic acid (5 mg, 5.48 μmol, 0.532% yield, 90.23% purity) as alight yellow solid. LCMS: (M+18)$^+$ 840.2@2.594 min. $^1$H NMR (400 MHz, Methanol-$d_4$) δ 7.53-6.79 (m, 20H), 5.69 (d, J=8.3 Hz, 1H), 5.39-5.02 (m, 3H), 4.61 (s, 1H), 3.67-3.18 (m, 4H), 3.15-2.90 (m, 4H).

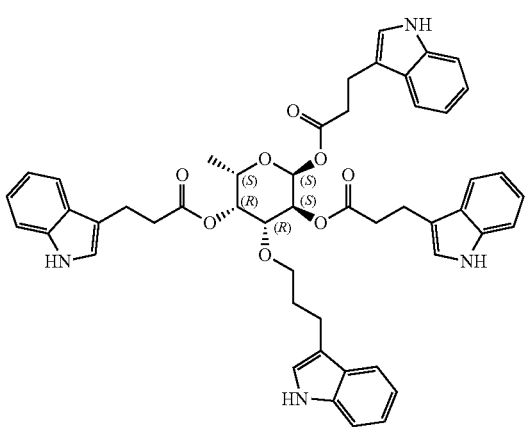

Compound 97: (2S,3S,4R,5R,6S)-3,4,5-tris({[3-(1H-indol-3-yl)propanoyl]oxy})-6-methyloxan-2-yl 3-(1H-indol-3-yl)propanoate This compound was prepared following a modified procedure described for compound 96. $^1$H NMR (400 MHz, Chloroform-d) δ 7.88-6.20 (m, 24H), 5.45-5.20 (m, 3H), 5.15-4.88 (m, 1H), 4.16-3.89 (m, 1H), 3.24-2.99 (m, 4H), 2.99-2.65 (m, 8H), 2.41-1.99 (m, 4H), 1.37-0.91 (m, 3H).

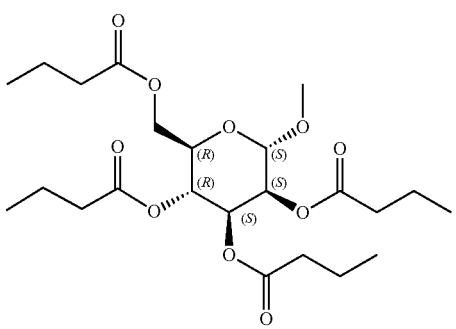

Compound 98:[(2R,3R,4S,5S,6S)-3,4,5-tris(butanoyloxy)-6-methoxyoxan-2-yl]methyl butanoate This compound was prepared according to a modified procedure described for the preparation of compound 53.

LCMS: (M+Na+) 497.2. $^1$H NMR (400 MHz, DMSO-d6) δ 5.28-5.08 (m, 3H), 4.78 (d, 1H), 4.21-4.07 (m, 2H), 3.94 (ddd, 1H), 3.36 (s, 3H), 2.44-2.11 (m, 8H), 1.69-1.40 (m, 8H), 0.89 (m, 12H)

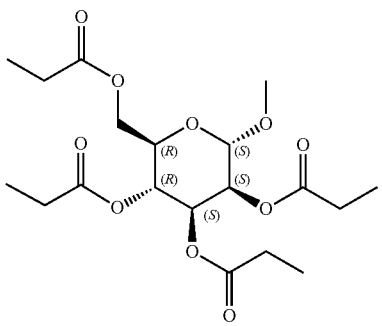

Compound 99: [(2R,3R,4S,5S,6S)-6-methoxy-3,4,5-tris(propanoyloxy)oxan-2-yl]methyl propanoate This compound was prepared according to a modified procedure described for the preparation of compound 53.
LCMS: (M+Na+) 441.1. $^1$H NMR (400 MHz, DMSO-d6) δ 5.25-5.15 (m, 1H), 5.14 (m, 2H), 4.80 (d, 1H), 4.20 (dd, 1H), 4.10 (dd, 1H), 3.95 (m, 1H), 3.37 (s, 3H), 2.48-2.18 (m, 8H), 1.14-0.93 (m, 12H)

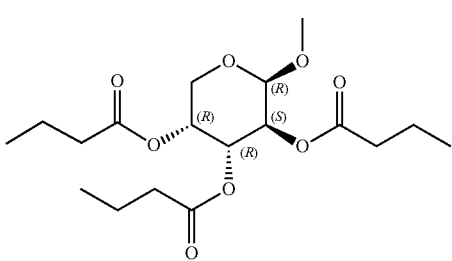

Compound 100: (2R,3S,4R,5R)-4,5-bis(butanoyloxy)-2-methoxyoxan-3-yl butanoate

This compound was prepared according to a modified procedure described for the preparation of compound 53.
LCMS: (M+Na+) 397.2. $^1$H NMR (400 MHz, DMSO-d6) δ 5.31-5.20 (m, 2H), 5.04 (dd, 1H), 4.90 (d, 1H), 3.89 (dd, 1H), 3.62 (dd, 1H), 3.32 (s, 3H), 2.40-2.13 (m, 6H), 1.65-1.42 (m, 6H), 0.97-0.78 (m, 9H)

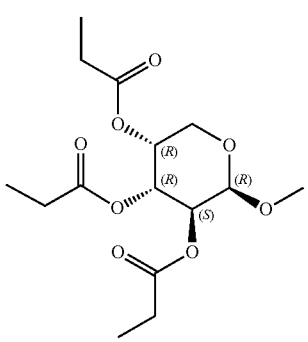

Compound 101: (2R,3S,4R,5R)-2-methoxy-3,5-bis(propanoyloxy)oxan-4-yl propanoate

This compound was prepared according to a modified procedure described for the preparation of compound 53.

LCMS: (M+Na+) 355.1. $^1$H NMR (400 MHz, DMSO-d6) δ 5.31-5.22 (m, 2H), 5.06 (dd, 1H), 4.92 (d, 1H), 3.91 (dd, 1H), 3.64 (dd, 1H), 3.34 (s, 3H), 2.47-2.12 (m, 6H), 1.13-0.95 (m, 9H)

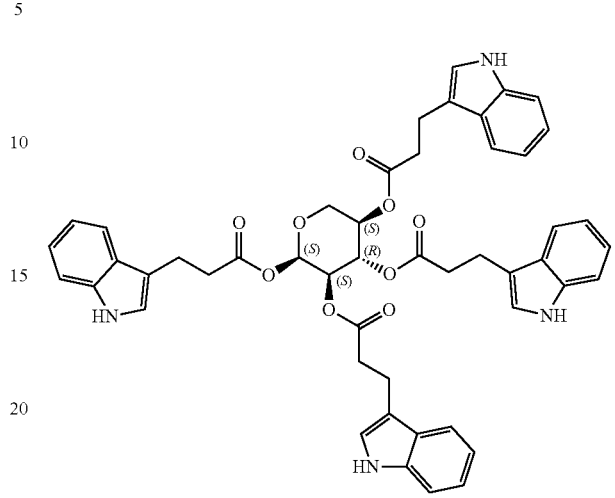

Compound 102: (2S,3R,4S,5S)-3,4,5-tris({[3-(1H-indol-3-yl)propanoyl]oxy})oxan-2-yl 3-(1H-indol-3-yl)propanoate This compound was prepared following a modified procedure described for compound 96. LCMS: (M+H$^+$): 835.3. $^1$H NMR (400 MHz, Chloroform-d) δ 7.84 (d, J=6.9 Hz, 2H), 7.69 (s, 1H), 7.59-7.45 (m, 5H), 7.34-7.25 (m, 2H), 7.22-7.06 (m, 10H), 7.03 (d, J=2.4 Hz, 1H), 6.92 (d, J=2.3 Hz, 1H), 6.76 (d, J=2.3 Hz, 1H), 6.49 (d, J=2.3 Hz, 1H), 5.68 (d, J=6.9 Hz, 1H), 5.37-5.28 (m, 2H), 5.07 (dd, J=9.2, 3.4 Hz, 1H), 3.95 (dd, J=13.0, 3.7 Hz, 1H), 3.74 (dd, J=13.0, 2.0 Hz, 1H), 3.20-2.57 (m, 12H), 2.55-2.39 (m, 2H), 2.24-1.98 (m, 2H).

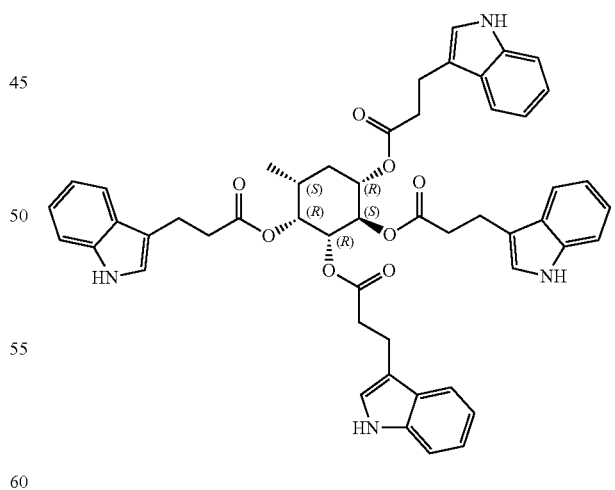

Compound 103: (2R,3S,4R,5R,6S)-3,4,5-tris({[3-(1H-indol-3-yl)propanoyl]oxy})-6-methyloxan-2-yl 3-(1H-indol-3-yl)propanoate This compound was prepared following a modified procedure described for compound 96. $^1$H NMR (400 MHz, Chloroform-d) δ 7.78 (s, 1H), 7.74 (s, 1H), 7.66 (s, 1H), 7.54-7.46 (m, 2H), 7.51-7.37 (m, 2H), 7.29 (s, 1H), 7.26-7.16 (m, 2H), 7.16-6.92 (m, 11H), 6.87 (d, J=2.3 Hz, 1H), 6.61 (d, J=2.3 Hz, 1H), 6.30 (d, J=2.4 Hz, 1H), 5.67 (d, J=8.3 Hz, 1H), 5.36 (dd, J=10.5, 8.3 Hz, 1H), 5.27-5.21 (m, 1H), 4.98 (dd, J=10.5, 3.3 Hz, 1H), 3.98-3.86 (m, 1H), 3.18-2.51 (m, 12H), 2.40-2.22 (m, 2H), 1.99-1.76 (m, 2H), 1.21-1.11 (m, 3H)

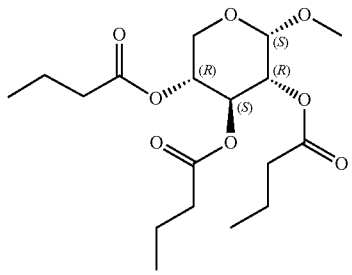

Compound 104: (2S,3R,4S,5R)-4,5-bis(butanoyloxy)-2-methoxyoxan-3-yl butanoate

This compound was prepared according to a modified procedure described for the preparation of compound 53.

LCMS: (M+Na+) 397.2. $^1$H NMR (400 MHz, DMSO-$d_6$) δ 5.37 (t, 1H), 4.97 (ddd, 1H), 4.91 (d, 1H), 4.86 (dd, 1H), 3.80 (dd, 1H), 3.50 (t, 1H), 3.36 (s, 3H), 2.37-2.13 (m, 6H), 1.53 (qd, 6H), 0.89 (td, 9H)

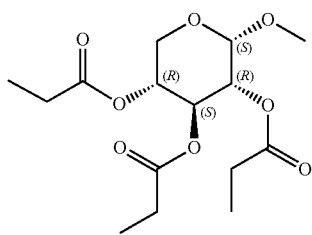

Compound 105: (2S,3R,4S,5R)-2-methoxy-4,5-bis(propanoyloxy)oxan-3-yl propanoate

This compound was prepared according to a modified procedure described for the preparation of compound 53.

LCMS: (M+Na+) 355.1. $^1$H NMR (400 MHz, DMSO-$d_6$) δ 5.35 (t, 1H), 4.96 (ddd, 1H), 4.91 (d, 1H), 4.87 (dd, 1H), 3.80 (dd, 1H), 3.51 (t, 1H), 3.36 (s, 3H), 2.37-2.23 (m, 6H), 1.02 (td, 9H)

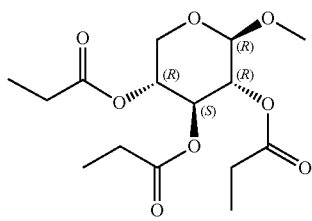

Compound 106: (2R,3R,4S,5R)-2-methoxy-4,5-bis(propanoyloxy)oxan-3-yl propanoate

This compound was prepared according to a modified procedure described for the preparation of compound 53.

LCMS: (M+Na+) 355.1. $^1$H NMR (400 MHz, DMSO-d6) δ 5.24 (t, 1H), 4.90 (td, 1H), 4.81 (dd, 1H), 4.64 (d, 1H), 4.01 (dd, 1H), 3.55 (dd, 1H), 3.40 (s, 3H), 2.38-2.22 (m, 6H), 1.08-0.96 (m, 9H).

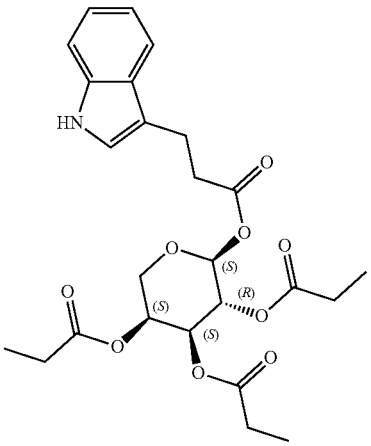

Compound 107: (2S,3R,4S,5S)-3,4,5-tris(propanoyloxy)oxan-2-yl 3-(1H-indol-3-yl)propanoate Step 1

Propionic anhydride (500 mL, 4 mol, 10 eq) was added to L-arabinose (60 g, 0.4 mol, 1 eq) in a 2 L round bottom flask equipped with a stirbar. Pyridine (320 mL, 4 mol, 10 eq) was added to the flask, and the reaction was stirred overnight at room temperature. The reaction was washed with 1M HCl, saturated sodium bicarbonate, and brine. Next the propionic anhydride was removed by rotary evaporation to yield 170 g of crude (2S,3R,4S,5S)-tetrahydro-2H-pyran-2,3,4,5-tetrayl tetrapropionate. Product was taken forward to next step without further purification.

Step 2

Benzylamine (78.5 mL, 720 mmol, 5 equiv) was added to a stirred solution of (2S,3R,4S,5S)-tetrahydro-2H-pyran-2,3,4,5-tetrayl tetrapropionate (62 g, 144 mmol, 1 equiv) in THF (500 mL) at RT. When the TLC indicated complete disappearance of starting material (4-8 h), the reaction was quenched by addition of 1M HCl (375 mL), and the mixture was extracted with ethyl acetate (3×500 mL). The organic phase was dried, pulled through a plug of silica, and concentrated. The crude product was purified by using column chromatography (100% hexanes to 50% Ethyl acetate in hexanes) to yield (3R,4S,5S)-2-hydroxytetrahydro-2H-pyran-3,4,5-triyl tripropionate (16 g, 44.3 mmol, 30.8% yield).

Step 3

Indole-propionic acid (23.0 g, 122 mmol, 1.5 eq), EDC HCl (23.4 g, 122 mmol, 1.5 eq), and DMAP (15 g, 122 mmol, 1.5 eq) were stirred in DCM (200 mL) at room temperature for a few minutes. Compound (3R,4S,5S)-2-hydroxytetrahydro-2H-pyran-3,4,5-triyl tripropionate (26 g, 81.6 mmol, 1 eq) was added and the solution was stirred overnight. The solution was washed with saturated ammonium chloride, saturated sodium bicarbonate, and brine, then loaded onto silica and purified by column chromatography (100% hexanes to 50% Ethyl acetate in hexanes) to yield the title compound (10.7 g, 21.8 mmol, 26.8% yield) as a gooey solid. LCMS (M+Na$^+$): 512.2. $^1$H NMR (400 MHz, DMSO-d$_6$) δ 10.78 (s, 1H), 7.48 (dd, J=7.7, 1.0 Hz, 1H), 7.31 (dd, J=8.1, 1.1 Hz, 1H), 7.10-7.01 (m, 2H), 7.00-6.91 (m, 1H), 5.77 (d, J=7.6 Hz, 1H), 5.28 (dd, J=9.7, 3.6 Hz, 1H), 5.22-5.16 (m, 1H), 5.09 (dd, J=9.7, 7.6 Hz, 1H), 3.98 (dd, J=13.2, 1.7 Hz, 1H), 3.87 (dd, J=13.0, 2.8 Hz, 1H), 2.92 (t, J=7.4 Hz, 2H), 2.70 (td, J=7.8, 7.4, 2.9 Hz, 2H), 2.37 (q, J=7.5 Hz, 2H), 2.27-2.05 (m, 4H), 1.04 (t, J=7.5 Hz, 3H), 0.95 (t, J=7.5 Hz, 3H), 0.89 (t, J=7.5 Hz, 3H).

Compound 109: (2S,3R,4S,5R)-2-{[2-(1H-indol-3-yl)acetyl]oxy}-4,5-bis(propanoyloxy)oxan-3-yl propanoate This compound was prepared following a modified procedure described for compound 107. LCMS: (M+Na+): 498.2. $^1$H NMR (400 MHz, Chloroform-d) δ 8.07 (s, 1H), 7.60-7.53 (m, 1H), 7.35 (dt, J=8.2, 1.0 Hz, 1H), 7.24-7.16 (m, 2H), 7.16-7.09 (m, 1H), 5.74 (d, J=7.1 Hz, 1H), 5.19 (t, J=8.4 Hz, 1H), 5.05 (dd, J=8.6, 7.0 Hz, 1H), 5.02-4.93 (m, 1H), 4.11 (dd, J=12.0, 5.0 Hz, 1H), 3.81 (d, J=0.9 Hz, 2H), 3.49 (dd, J=12.0, 8.7 Hz, 1H), 2.36-2.17 (m, 4H), 2.12-1.85 (m, 2H), 1.14-1.03 (m, 6H), 0.94 (t, J=7.6 Hz, 3H).

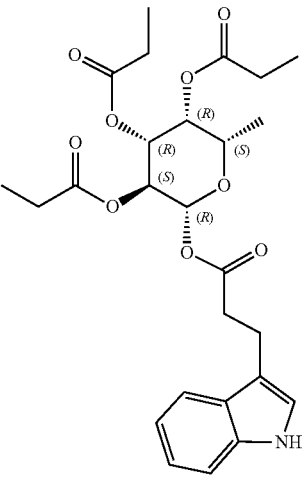

Compound 110: (2R,3S,4R,5R,6S)-6-methyl-3,4,5-tris(propanoyloxy)oxan-2-yl 3-(1H-indol-3-yl)propanoate This compound was prepared following a modified procedure described for compound 107. LCMS: (M+Na+): 526.2. $^1$H NMR (400 MHz, Chloroform-d) δ 7.97 (s, 1H), 7.57-7.47 (m, 1H), 7.32-7.23 (m, 1H), 7.11 (ddd, J=8.1, 7.1, 1.3 Hz, 1H), 7.04 (ddd, J=8.0, 7.0, 1.1 Hz, 1H), 6.97-6.89 (m, 1H), 5.66 (d, J=8.4 Hz, 1H), 5.28 (dd, J=10.4, 8.3 Hz, 1H), 5.21 (dd, J=3.5, 1.1 Hz, 1H), 5.03 (dd, J=10.4, 3.4 Hz, 1H), 3.89 (qd, J=6.4, 1.2 Hz, 1H), 3.13-2.95 (m, 2H), 2.79-2.61 (m, 2H), 2.49-2.30 (m, 2H), 2.21-1.93 (m, 4H), 1.26-1.09 (m, 6H), 1.00 (t, J=7.5 Hz, 3H), 0.91 (t, J=7.6 Hz, 3H)

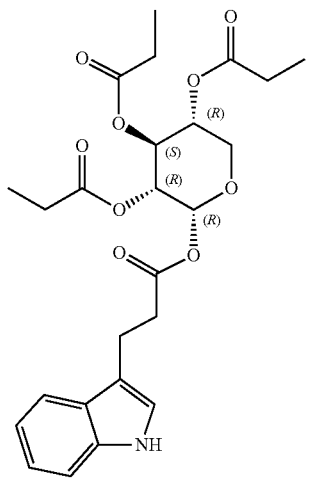

Compound 108: (2R,3R,4S,5R)-3,4,5-tris(propanoyloxy)oxan-2-yl 3-(1H-indol-3-yl)propanoate This compound was prepared following a modified procedure described for compound 107. $^1$H NMR (400 MHz, DMSO-d6) δ 10.79 (s, 1H), 7.56-7.43 (m, 1H), 7.31 (m, 1H), 7.13 (d, 1H), 7.05 (ddd, 1H), 6.96 (ddd, 1H), 6.13 (d, 1H), 5.33 (t, 1H), 5.06-4.92 (m, 2H), 3.80 (dd, 1H), 3.52 (t, 1H), 3.05-2.79 (m, 4H), 2.32-2.03 (m, 6H), 0.97 (m, 6H), 0.89 (t, 3H)

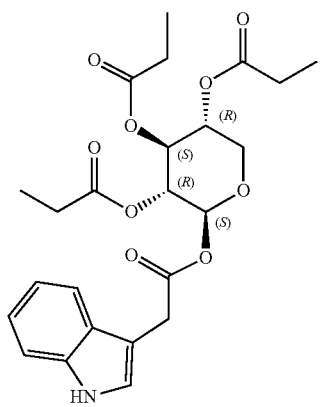

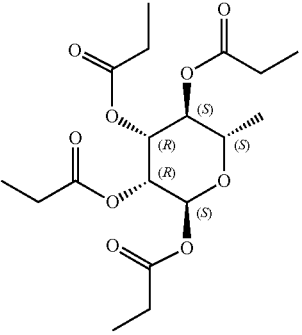

Compound 111: (2S,3R,4R,5S,6S)-6-methyl-3,4,5-tris(propanoyloxy)oxan-2-yl propanoate This compound was prepared according to a modified procedure described for the preparation of compound 53.

LCMS: (M+Na$^+$): 411.1. $^1$H NMR (400 MHz, Chloroform-d) δ 6.03 (d, J=1.9 Hz, 1H), 5.33 (dd, J=10.1, 3.5 Hz, 1H), 5.27 (dd, J=3.5, 2.0 Hz, 1H), 5.15 (t, J=10.0 Hz, 1H), 4.00-3.88 (m, 1H), 2.51-2.37 (m, 4H), 2.37-2.19 (m, 4H), 1.27-1.04 (m, 15H).

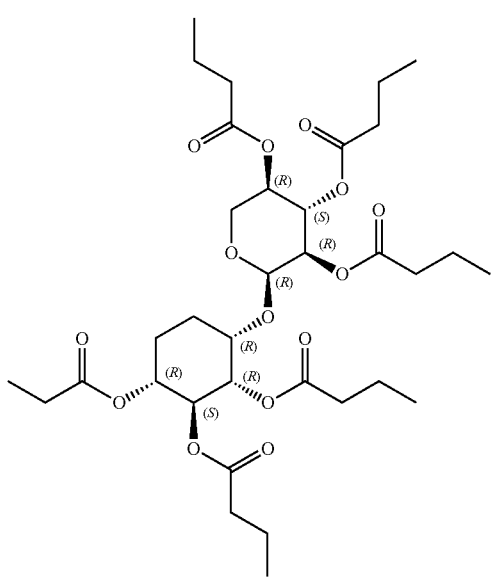

Compound 112: (2R,3R,4S,5R)-4,5-bis(butanoyloxy)-2-{[(2R,3R,4S,5R)-3,4,5-tris(butanoyloxy)oxan-2-yl]oxy}oxan-3-yl butanoate This compound was prepared according to a modified procedure described for the preparation of compound 53.

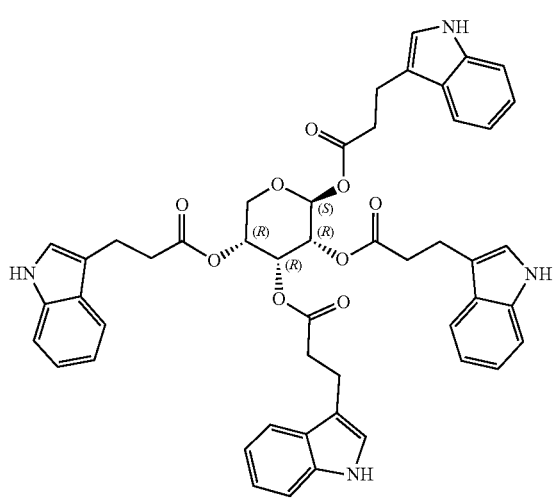

Compound 113: (2S,3R,4R,5R)-3,4,5-tris({[3-(1H-indol-3-yl)propanoyl]oxy})oxan-2-yl 3-(1H-indol-3-yl)propanoate This compound was prepared following a modified procedure described for compound 96. LCMS: (M+H$^+$): 835.3. $^1$H NMR (400 MHz, Chloroform-d) δ 7.77 (s, 1H), 7.73 (s, 1H), 7.49 (d, J=8.1 Hz, 3H), 7.46-7.38 (m, 2H), 7.25 (t, J=8.4 Hz, 3H), 7.19-6.92 (m, 10H), 6.83 (d, J=2.3 Hz, 1H), 6.77 (d, J=2.3 Hz, 1H), 6.75-6.67 (m, 1H), 6.65-6.60 (m, 1H), 6.03 (d, J=3.7 Hz, 1H), 5.52 (s, 1H), 5.08 (t, J=3.5 Hz, 1H), 5.03-4.94 (m, 1H), 3.76 (t, J=10.4 Hz, 1H), 3.51 (dd, J=11.2, 4.7 Hz, 1H), 3.06-2.86 (m, 8H), 2.67-2.38 (m, 8H).

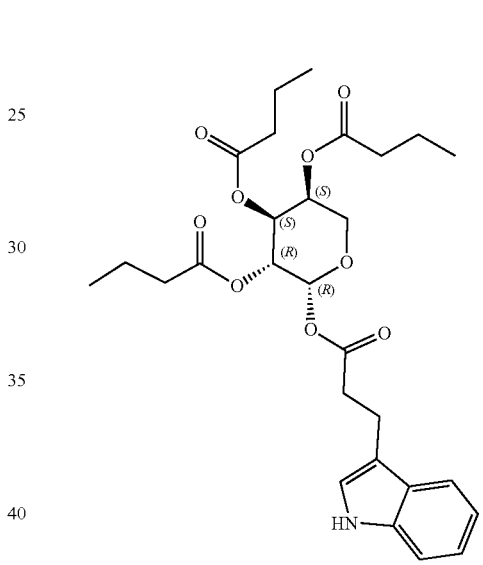

Compound 114: (2R,3R,4S,5S)-4,5-bis(butanoyloxy)-2-{[3-(1H-indol-3-yl)propanoyl]oxy}oxan-3-yl butanoate This compound was prepared following a modified procedure described for compound 107. LCMS: (M+H$^+$): 532.2. $^1$H NMR (400 MHz, Methanol-d$_4$) δ 7.56 (d, J=7.8 Hz, 1H), 7.32 (d, J=8.1 Hz, 1H), 7.12-7.05 (m, 2H), 7.05-6.97 (m, 1H), 6.26 (d, J=3.6 Hz, 1H), 5.36-5.26 (m, 2H), 5.21 (dd, J=10.5, 3.6 Hz, 1H), 3.80 (dd, J=13.4, 1.3 Hz, 1H), 3.62 (dd, J=13.4, 1.9 Hz, 1H), 3.21-3.04 (m, 2H), 2.87 (t, J=6.9 Hz, 2H), 2.44-2.34 (m, 2H), 2.22 (t, J=7.2 Hz, 2H), 2.06-1.95 (m, 2H), 1.73-1.61 (m, 2H), 1.64-1.52 (m, 2H), 1.45 (h, J=7.3 Hz, 2H), 0.98 (t, J=7.4 Hz, 3H), 0.91 (t, J=7.4 Hz, 3H), 0.80 (t, J=7.4 Hz, 3H).

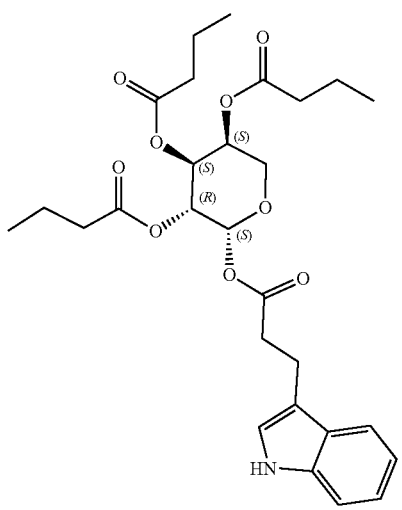

Compound 115: (2S,3R,4S,5S)-4,5-bis(butanoyloxy)-2-{[3-(1H-indol-3-yl)propanoyl]oxy}oxan-3-yl butanoate This compound was prepared following a modified procedure described for compound 107. LCMS: (M+H⁺): 532.2. ¹H NMR (400 MHz, Methanol-d₄) δ 7.41 (dt, J=7.9, 1.1 Hz, 1H), 7.21 (dt, J=8.2, 1.0 Hz, 1H), 7.02-6.94 (m, 1H), 6.93-6.85 (m, 2H), 5.63 (d, J=7.2 Hz, 1H), 5.24-5.17 (m, 1H), 5.17-5.05 (m, 2H), 3.83 (dd, J=13.1, 3.3 Hz, 1H), 3.76 (dd, J=13.1, 1.9 Hz, 1H), 3.03-2.89 (m, 2H), 2.73-2.58 (m, 2H), 2.34-1.90 (m, 6H), 1.64-1.53 (m, 2H), 1.52-1.43 (m, 2H), 1.41-1.31 (m, 2H), 0.94-0.84 (m, 3H), 0.84-0.76 (m, 3H), 0.73 (t, J=7.4 Hz, 3H).

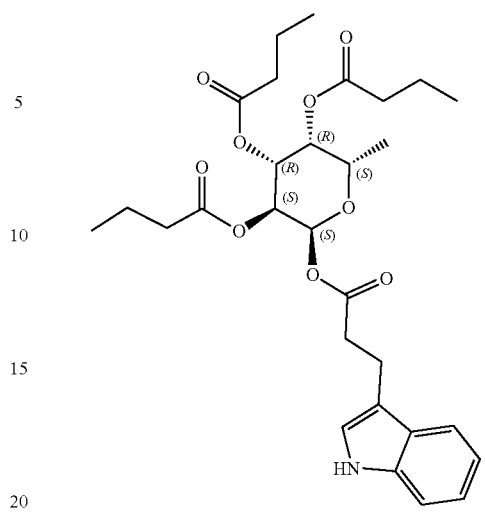

Compound 117: (2S,3S,4R,5R,6S)-4,5-bis(butanoyloxy)-2-{[3-(1H-indol-3-yl)propanoyl]oxy}-6-methyloxan-3-yl butanoate This compound was prepared following a modified procedure described for compound 107. ¹H NMR (400 MHz, Chloroform-d) δ 8.05 (s, 1H), 7.61 (d, J=7.8 Hz, 1H), 7.39-7.32 (m, 1H), 7.19 (ddd, J=8.2, 7.0, 1.3 Hz, 1H), 7.13 (td, J=7.5, 1.2 Hz, 1H), 7.08 (d, J=2.3 Hz, 1H), 6.33 (d, J=3.2 Hz, 1H), 5.40-5.22 (m, 3H), 4.01-3.91 (m, 1H), 3.20-3.08 (m, 2H), 2.84 (t, J=7.3 Hz, 2H), 2.47-2.32 (m, 2H), 2.20 (td, J=7.3, 1.8 Hz, 2H), 2.04 (td, J=7.3, 1.2 Hz, 2H), 1.76-1.41 (m, 6H), 1.04-0.87 (m, 9H), 0.83 (t, J=7.4 Hz, 3H)

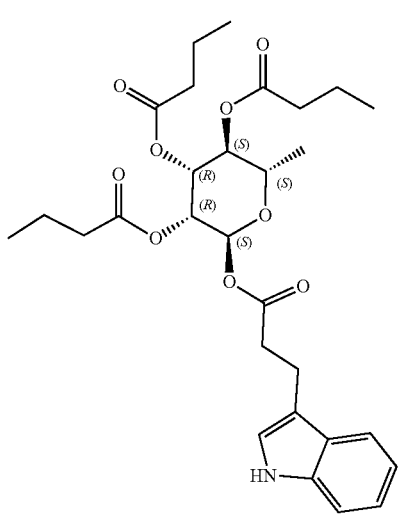

Compound 116: (2S,3R,4R,5S,6S)-4,5-bis(butanoyloxy)-2-{[3-(1H-indol-3-yl)propanoyl]oxy}-6-methyloxan-3-yl butanoate This compound was prepared following a modified procedure described for compound 107.

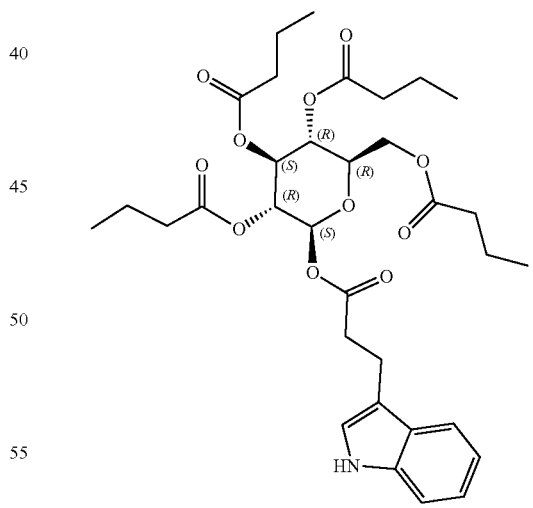

Compound 118: [(2R,3R,4S,5R,6S)-3,4,5-tris(butanoyloxy)-6-{[3-(1H-indol-3-yl)propanoyl]oxy}oxan-2-yl]methyl butanoate This compound was prepared following a modified procedure described for compound 107. ¹H NMR (400 MHz, Chloroform-d) δ 7.93 (s, 1H), 7.49 (dd, J=7.8, 1.1 Hz, 1H), 7.28 (dt, J=8.1, 1.0 Hz, 1H), 7.12 (ddd, J=8.1, 7.0, 1.3 Hz, 1H), 7.04 (ddd, J=8.1, 7.0, 1.1 Hz, 1H), 6.92 (d, J=2.4 Hz, 1H), 5.68 (d, J=8.2 Hz, 1H), 5.26-5.17 (m, 1H), 5.14-5.05 (m, 2H), 4.14 (qd, J=12.5, 3.4 Hz, 2H), 3.77 (ddd, J=10.0, 4.5, 2.4 Hz, 1H), 3.06-2.97 (m, 2H), 2.78-2.61 (m, 2H), 2.30-2.22 (m, 2H), 2.24-2.09 (m, 4H), 2.03 (td, J=7.4, 2.7 Hz, 2H), 1.63-1.36 (m, 8H), 0.91-0.72 (m, 12H).

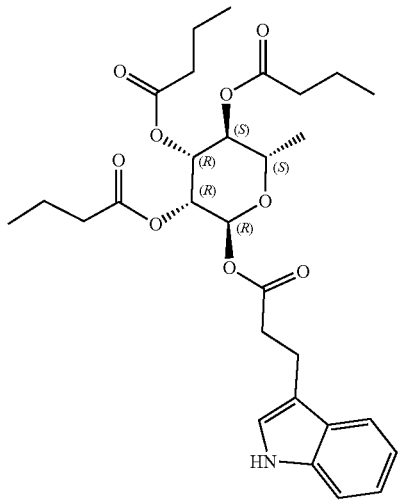

Compound 119: (2R,3R,4R,5S,6S)-4,5-bis(butanoyloxy)-2-{[3-(1H-indol-3-yl)propanoyl]oxy}-6-methyloxan-3-yl butanoate This compound was prepared following a modified procedure described for compound 107.

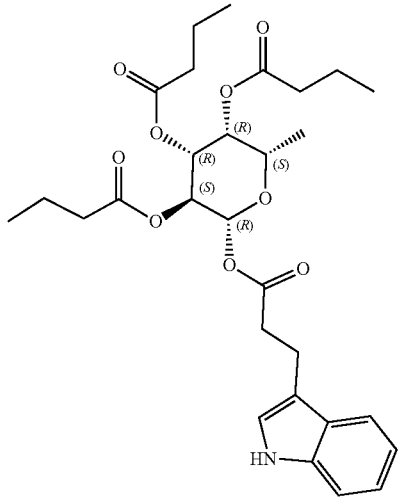

Compound 120: (2R,3S,4R,5R,6S)-4,5-bis(butanoyloxy)-2-{[3-(1H-indol-3-yl)propanoyl]oxy}-6-methyloxan-3-yl butanoate This compound was prepared following a modified procedure described for compound 107. ¹H NMR (400 MHz, Chloroform-d) δ 7.96 (s, 1H), 7.57 (d, J=7.9 Hz, 1H), 7.35 (d, J=8.1 Hz, 1H), 7.23-7.15 (m, 1H), 7.15-7.07 (m, 1H), 7.04 (d, J=2.3 Hz, 1H), 5.73 (d, J=8.4 Hz, 1H), 5.41-5.30 (m, 1H), 5.32-5.27 (m, 1H), 5.10 (dd, J=10.4, 3.4 Hz, 1H), 4.02-3.93 (m, 1H), 3.15-3.00 (m, 2H), 2.87-2.68 (m, 2H), 2.51-2.34 (m, 2H), 2.27-2.16 (m, 2H), 2.16-2.00 (m, 2H), 1.78-1.66 (m, 2H), 1.62-1.43 (m, 4H), 1.27-1.18 (m, 3H), 0.99 (t, J=7.4 Hz, 3H), 0.89 (t, J=7.4 Hz, 3H), 0.83 (t, J=7.4 Hz, 3H)

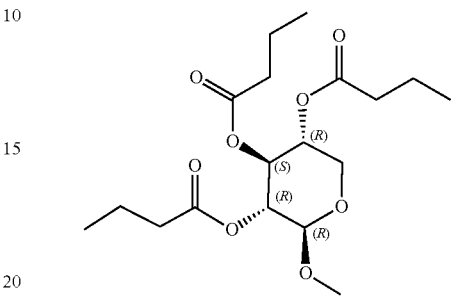

Compound 121: (2R,3R,4S,5R)-4,5-bis(butanoyloxy)-2-methoxyoxan-3-yl butanoate

This compound was prepared following a modified procedure described for compounds 79 and 80. LCMS: (M+Na+) 397.2. ¹H NMR (400 MHz, DMSO-d6) δ 5.26 (t, 1H), 4.90 (td, 1H), 4.82 (dd, 1H), 4.63 (d, 1H), 4.00 (dd, 1H), 3.54 (dd, 1H), 3.40 (s, 3H), 2.34-2.18 (m, 6H), 1.59-1.48 (m, 6H), 0.97-0.81 (m, 9H)

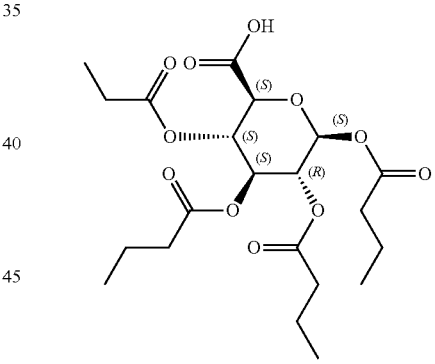

Compound 122: [(2R,3R,4S,5R,6R)-3,4,5-tris(butanoyloxy)-6-{[3-(1H-indol-3-yl)propanoyl]oxy}oxan-2-yl]methyl butanoate This compound was prepared following a modified procedure described for compound 107. ¹H NMR (400 MHz, Chloroform-d) δ 8.04 (s, 1H), 7.54 (dd, J=7.8, 1.2 Hz, 1H), 7.29 (dt, J=8.2, 1.0 Hz, 1H), 7.12 (ddd, J=8.2, 7.0, 1.3 Hz, 1H), 7.09-7.00 (m, 2H), 6.26 (d, J=3.7 Hz, 1H), 5.37 (t, J=9.9 Hz, 1H), 5.05 (t, J=9.9 Hz, 1H), 4.97 (dd, J=10.3, 3.7 Hz, 1H), 3.97 (dd, J=12.5, 3.9 Hz, 1H), 3.86 (dd, J=12.5, 2.3 Hz, 1H), 3.71 (ddd, J=10.3, 4.0, 2.2 Hz, 1H), 3.17-3.00 (m, 2H), 2.81 (t, J=7.2 Hz, 2H), 2.23 (td, J=7.4, 1.7 Hz, 2H), 2.20-2.08 (m, 4H), 2.00-1.87 (m, 2H), 1.62-1.46 (m, 6H), 1.47-1.34 (m, 2H), 0.91-0.80 (m, 9H), 0.74 (t, J=7.4 Hz, 3H).

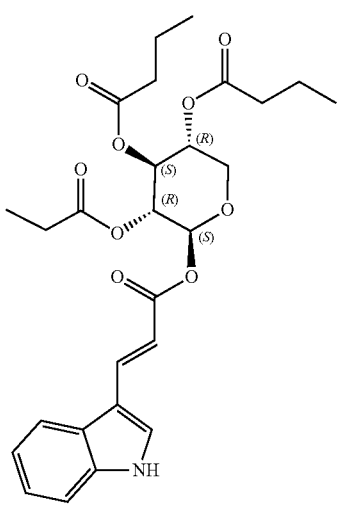

Compound 123: (2S,3R,4S,5R)-3,4,5-tris(propanoyloxy)oxan-2-yl (2E)-3-(1H-indol-3-yl)prop-2-enoate This compound was prepared following a modified procedure described for compound 107. ¹H NMR (400 MHz, Chloroform-d) δ 8.50 (s, 1H), 7.98 (d, J=15.9 Hz, 1H), 7.94-7.88 (m, 1H), 7.54 (d, J=2.8 Hz, 1H), 7.46-7.39 (m, 1H), 7.35-7.24 (m, 2H), 6.41 (d, J=15.9 Hz, 1H), 5.87 (d, J=7.2 Hz, 1H), 5.31 (t, J=8.6 Hz, 1H), 5.21 (dd, J=8.8, 7.2 Hz, 1H), 5.07 (td, J=8.7, 5.2 Hz, 1H), 4.20 (dd, J=11.9, 5.2 Hz, 1H), 3.58 (dd, J=11.9, 9.0 Hz, 1H), 2.38-2.25 (m, 6H), 1.22-1.04 (m, 9H).

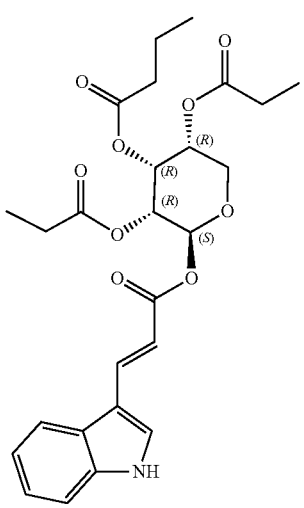

Compound 124: (2S,3R,4R,5R)-3,4,5-tris(propanoyloxy)oxan-2-yl (2E)-3-(1H-indol-3-yl)prop-2-enoate This compound was prepared following a modified procedure described for compound 107. ¹H NMR (400 MHz, Chloroform-d) δ 8.58 (s, 1H), 7.99 (d, J=15.9 Hz, 1H), 7.95-7.89 (m, 1H), 7.55 (d, J=2.8 Hz, 1H), 7.48-7.38 (m, 1H), 7.35-7.24 (m, 2H), 6.44 (d, J=15.9 Hz, 1H), 6.19 (d, J=4.8 Hz, 1H), 5.62 (t, J=3.5 Hz, 1H), 5.27-5.18 (m, 2H), 4.11 (dd, J=12.3, 3.4 Hz, 1H), 3.95 (dd, J=12.4, 5.8 Hz, 1H), 2.39 (ddd, J=9.8, 4.8, 2.2 Hz, 6H), 1.21-1.10 (m, 9H)

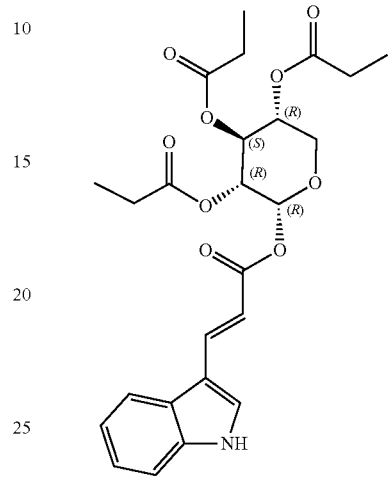

Compound 125: (2R,3R,4S,5R)-3,4,5-tris(propanoyloxy)oxan-2-yl (2E)-3-(1H-indol-3-yl)prop-2-enoate This compound was prepared following a modified procedure described for compound 107.

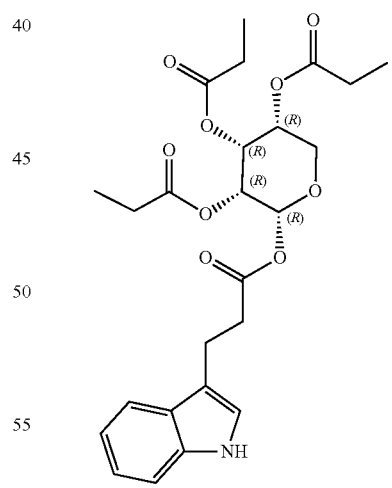

Compound 126: (2R,3R,4R,5R)-3,4,5-tris(propanoyloxy)oxan-2-yl 3-(1H-indol-3-yl)propanoate This compound was prepared following a modified procedure described for compound 107.

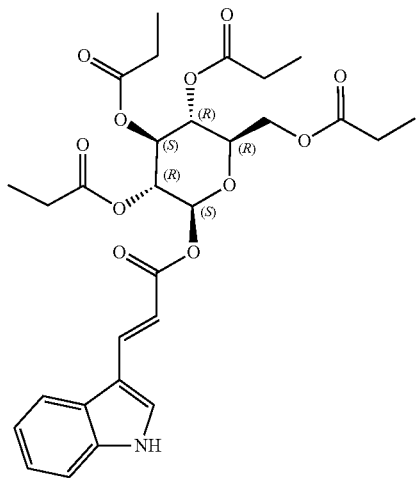

Compound 127: (2S,3R,4S,5R,6R)-3,4,5-tris(propanoyloxy)-6-[(propanoyloxy)methyl]oxan-2-yl (2E)-3-(1H-indol-3-yl)prop-2-enoate This compound was prepared following a modified procedure described for compound 107. $^1$H NMR (400 MHz, Chloroform-d) δ 8.48 (s, 1H), 7.91 (d, J=15.9 Hz, 1H), 7.87-7.79 (m, 1H), 7.47 (d, J=2.9 Hz, 1H), 7.41-7.32 (m, 1H), 7.28-7.16 (m, 2H), 6.33 (d, J=16.0 Hz, 1H), 5.84 (d, J=7.8 Hz, 1H), 5.32-5.19 (m, 2H), 5.15 (t, J=9.5 Hz, 1H), 4.27 (dd, J=12.5, 4.6 Hz, 1H), 4.08 (dd, J=12.5, 2.2 Hz, 1H), 3.86 (ddd, J=10.0, 4.6, 2.2 Hz, 1H), 2.37-2.14 (m, 8H), 1.11-0.95 (m, 12H).

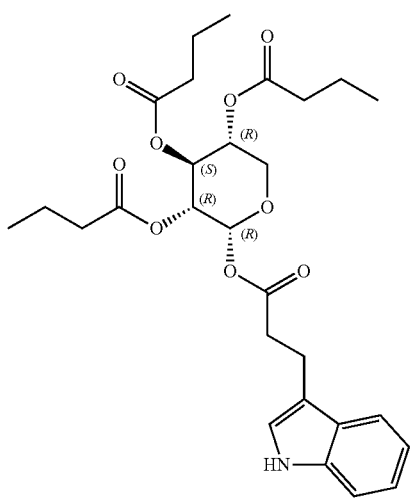

Compound 128: (2R,3R,4S,5R)-4,5-bis(butanoyloxy)-2-{[3-(1H-indol-3-yl)propanoyl]oxy}oxan-3-yl butanoate This compound was prepared following a modified procedure described for compound 107. $^1$H NMR (400 MHz, Methanol-d$_4$) δ 7.58 (dt, J=7.8, 1.1 Hz, 1H), 7.34 (dt, J=8.1, 1.0 Hz, 1H), 7.15-7.07 (m, 2H), 7.03 (ddd, J=8.0, 7.0, 1.1 Hz, 1H), 6.28 (d, J=3.5 Hz, 1H), 5.41-5.28 (m, 2H), 5.23 (dd, J=10.5, 3.6 Hz, 1H), 3.83 (dd, J=13.3, 1.4 Hz, 1H), 3.65 (dd, J=13.3, 2.0 Hz, 1H), 3.23-3.05 (m, 2H), 2.89 (t, J=6.9 Hz, 2H), 2.49-2.31 (m, 2H), 2.24 (t, J=7.2 Hz, 2H), 2.08-1.98 (m, 2H), 1.76-1.54 (m, 4H), 1.54-1.41 (m, 2H), 1.06-0.89 (m, 6H), 0.83 (t, J=7.4 Hz, 3H).

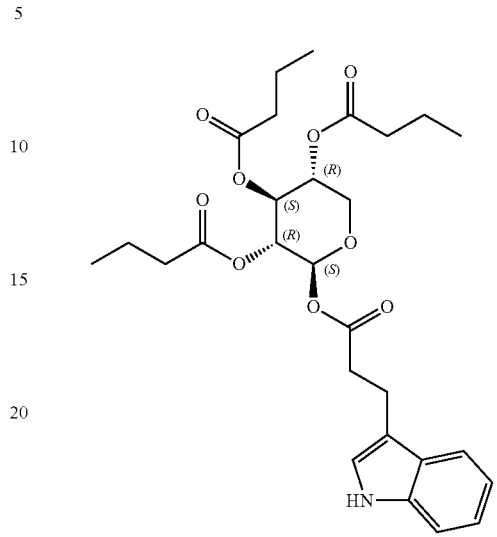

Compound 129: (2S,3R,4S,5R)-4,5-bis(butanoyloxy)-2-{[3-(1H-indol-3-yl)propanoyl]oxy}oxan-3-yl butanoate This compound was prepared following a modified procedure described for compound 107. $^1$H NMR (400 MHz, Methanol-d$_4$) δ 7.56-7.47 (m, 1H), 7.37-7.30 (m, 1H), 7.10 (ddd, J=8.1, 6.9, 1.3 Hz, 1H), 7.06-6.97 (m, 2H), 5.79-5.70 (m, 1H), 5.37-5.29 (m, 1H), 5.29-5.17 (m, 2H), 3.95 (dd, J=13.1, 3.3 Hz, 1H), 3.88 (dd, J=13.1, 1.9 Hz, 1H), 3.15-3.00 (m, 2H), 2.83-2.72 (m, 2H), 2.48-2.34 (m, 2H), 2.22 (t, J=7.3 Hz, 2H), 2.18-2.00 (m, 2H), 1.76-1.65 (m, 2H), 1.68-1.52 (m, 2H), 1.55-1.42 (m, 2H), 1.06-0.96 (m, 3H), 0.99-0.80 (m, 6H).

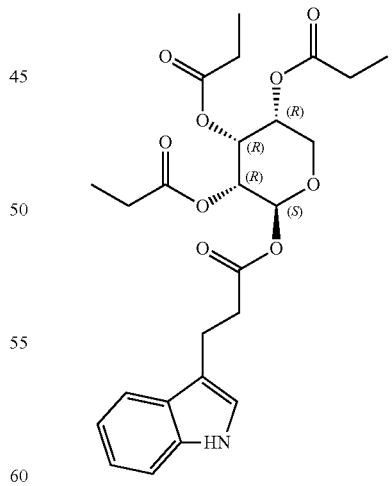

Compound 130: (2S,3R,4R,5R)-3,4,5-tris(propanoyloxy)oxan-2-yl 3-(1H-indol-3-yl)propanoate This compound was prepared following a modified procedure described for compound 107.

Compound 131: (2R,3R,4S,5R,6R)-3,4,5-tris(propanoyloxy)-6-[(propanoyloxy)methyl]oxan-2-yl (2E)-3-(1H-indol-3-yl)prop-2-enoate This compound was prepared following a modified procedure described for compound 107. ¹H NMR (400 MHz, Chloroform-d) δ 8.59 (s, 1H), 8.09-7.99 (m, 2H), 7.61 (d, J=2.8 Hz, 1H), 7.52-7.43 (m, 1H), 7.39-7.31 (m, 2H), 6.58-6.49 (m, 2H), 5.68 (t, J=9.9 Hz, 1H), 5.29-5.18 (m, 2H), 4.33 (dd, J=12.4, 4.2 Hz, 1H), 4.26 (ddd, J=10.3, 4.2, 2.1 Hz, 1H), 4.15 (dd, J=12.3, 2.1 Hz, 1H), 2.46-2.25 (m, 8H), 1.20-1.07 (m, 12H).

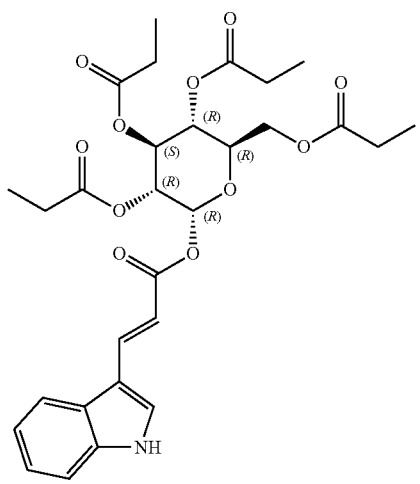

Compound 132: (2S,3R,4S,5S)-3,4,5-tris(propanoyloxy)oxan-2-yl(2E)-3-(1H-indol-3-yl)prop-2-enoate This compound was prepared following a modified procedure described for compound 107.

Compound 133: (2R,3R,4R,5R)-3,4,5-tris(propanoyloxy)oxan-2-yl propanoate

This compound was prepared according to a modified procedure described for the preparation of compound 53.

Compound 134: (2S,3R,4R,5S,6S)-6-methyl-3,4,5-tris(propanoyloxy)oxan-2-yl (2E)-3-(1H-indol-3-yl)prop-2-enoate This compound was prepared following a modified procedure described for compound 107.

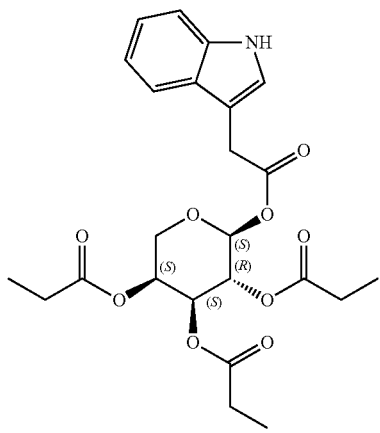

Compound 135: (3S,4S,5R,6S)-6-{[2-(1H-indol-3-yl)acetyl]oxy}-4,5-bis(propanoyloxy)oxan-3-yl propanoate This compound was prepared following a modified procedure described for compound 107.

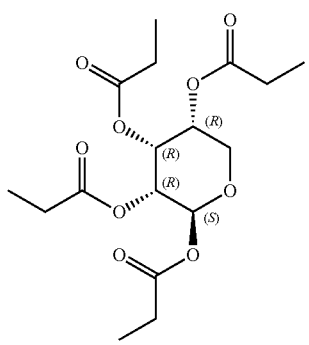

Compound 136: (2S,3R,4R,5R)-3,4,5-tris(propanoyloxy)oxan-2-yl propanoate

This compound was prepared according to a modified procedure described for the preparation of compound 53.

Compound 137: (3R,4R,5R)-2-hydroxy-4,5-bis(propanoyloxy)oxan-3-yl propanoate

This compound was prepared according to a modified procedure described for the preparation of compound 21.

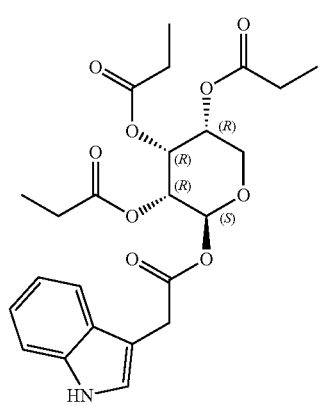

Compound 138: (2S,3R,4R,5R)-2-{[2-(1H-indol-3-yl)acetyl]oxy}-4,5-bis(propanoyloxy)oxan-3-yl propanoate This compound was prepared following a modified procedure described for compound 107.

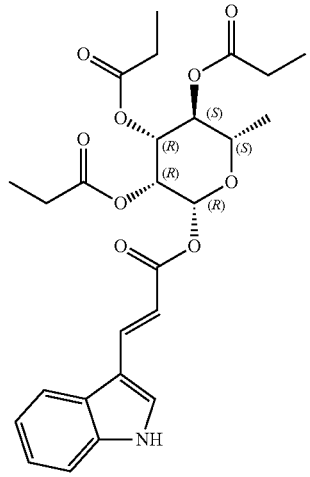

Compound 139: (2R,3R,4R,5S,6S)-6-methyl-3,4,5-tris(propanoyloxy)oxan-2-yl (2E)-3-(1H-indol-3-yl)prop-2-enoate This compound was prepared following a modified procedure described for compound 107.

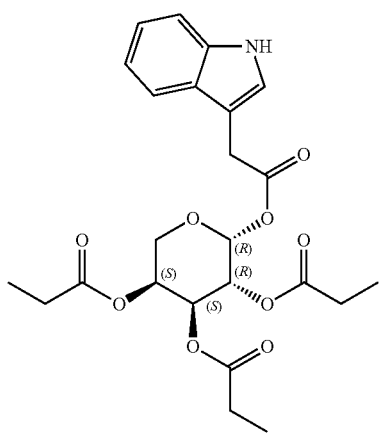

Compound 140: (3S,4S,5R,6R)-6-{[2-(1H-indol-3-yl)acetyl]oxy}-4,5-bis(propanoyloxy)oxan-3-yl propanoate This compound was prepared following a modified procedure described for compound 107.

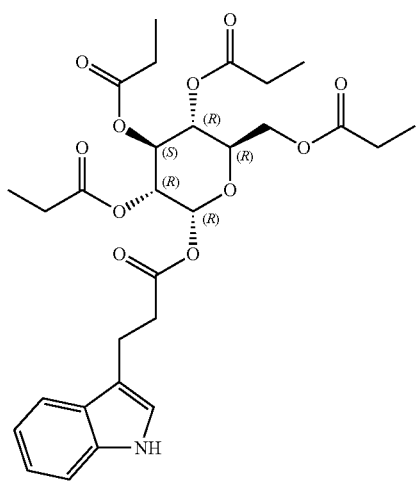

Compound 141: [(2R,3R,4S,5R,6R)-6-{[3-(1H-indol-3-yl)propanoyl]oxy}-3,4,5-tris(propanoyloxy)oxan-2-yl]methyl propanoate This compound was prepared following a modified procedure described for compound 107.

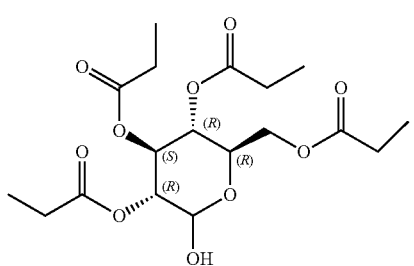

Compound 142: [(2R,3R,4S,5R)-6-hydroxy-3,4,5-tris(propanoyloxy)oxan-2-yl]methyl propanoate This compound was prepared according to a modified procedure described for the preparation of compound 21.

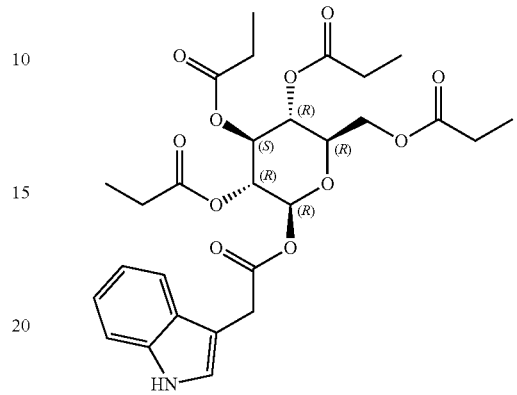

Compound 143: [(2R,3R,4S,5R,6S)-6-{[2-(1H-indol-3-yl)acetyl] oxy}-3,4,5-tris(propanoyloxy)oxan-2-yl]methyl propanoate This compound was prepared following a modified procedure described for compound 107.

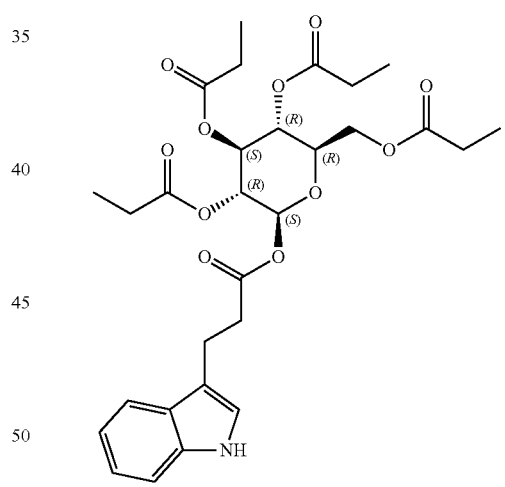

Compound 144: [(2R,3R,4S,5R,6S)-6-{[3-(1H-indol-3-yl)propanoyl]oxy}-3,4,5-tris(propanoyloxy) oxan-2-yl]methyl propanoate This compound was prepared following a modified procedure described for compound 107. LCMS (M+Na$^+$): 598.2. $^1$H NMR (400 MHz, DMSO-d$_6$) δ 10.78 (d, J=2.4 Hz, 1H), 7.50-7.44 (m, 1H), 7.34-7.27 (m, 1H), 7.09-7.00 (m, 2H), 6.95 (ddd, J=7.9, 6.9, 1.1 Hz, 1H), 5.99 (d, J=8.3 Hz, 1H), 5.45 (t, J=9.6 Hz, 1H), 5.02-4.89 (m, 2H), 4.27-4.15 (m, 2H), 4.03-3.94 (m, 1H), 2.97-2.84 (m, 2H), 2.79-2.63 (m, 2H), 2.34-1.98 (m, 8H), 1.05-0.82 (m, 12H).

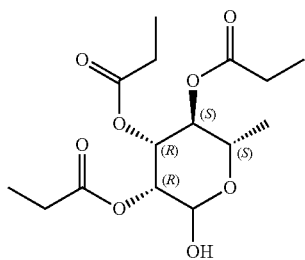

Compound 145: (3R,4R,5S,6S)-2-hydroxy-6-methyl-4,5-bis(propanoyloxy)oxan-3-yl propanoate This compound was prepared according to a modified procedure described for the preparation of compound 21.

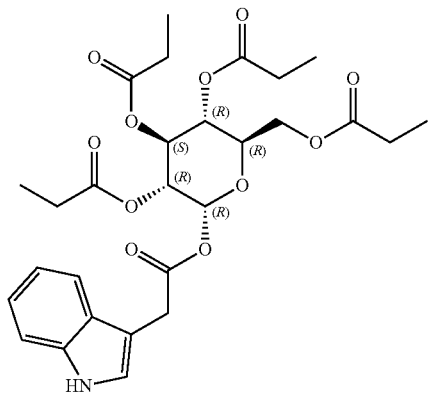

Compound 146:[(2R,3R,4S,5R,6R)-6-{[2-(1H-indol-3-yl)acetyl]oxy}-3,4,5-tris(propanoyloxy)oxan-2-yl]methyl propanoate This compound was prepared following a modified procedure described for compound 107.

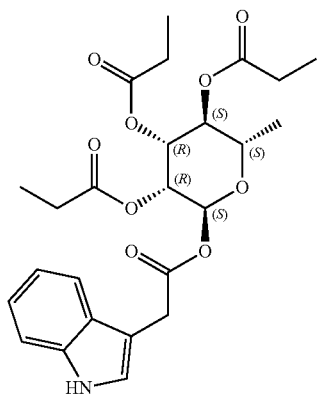

Compound 147: (2S,3R,4R,5S,6S)-2-{[2-(1H-indol-3-yl)acetyl]oxy}-6-methyl-4,5-bis(propanoyloxy)oxan-3-yl propanoate This compound was prepared following a modified procedure described for compound 107.

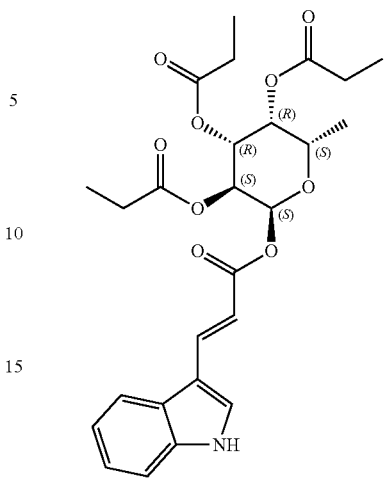

Compound 148: (2S,3S,4R,5R,6S)-6-methyl-3,4,5-tris(propanoyloxy)oxan-2-yl (2E)-3-(1H-indol-3-yl)prop-2-enoate This compound was prepared following a modified procedure described for compound 107.

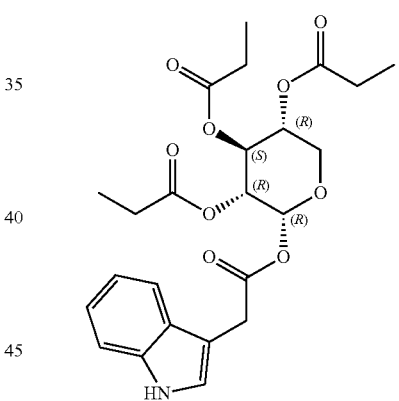

Compound 149: (2R,3R,4S,5R)-2-{[2-(1H-indol-3-yl)acetyl]oxy}-4,5-bis(propanoyloxy)oxan-3-yl propanoate This compound was prepared following a modified procedure described for compound 107. LCMS (M+Na$^+$): 498.2. $^1$H NMR (400 MHz, Chloroform-d) δ8.10 (s, 1H), 7.63-7.56 (m, 1H), 7.33-7.26 (m, 1H), 7.18 (d, J=2.4 Hz, 1H), 7.17-7.06 (m, 2H), 6.21 (d, J=3.6 Hz, 1H), 5.42 (t, J=9.9 Hz, 1H), 4.98-4.87 (m, 2H), 3.82 (s, 2H), 3.74 (dd, J=11.1, 5.9 Hz, 1H), 3.40 (t, J=11.0 Hz, 1H), 2.22 (qd, J=7.6, 1.9 Hz, 4H), 1.96 (qd, J=7.5, 4.2 Hz, 2H), 1.08-0.99 (m, 6H), 0.88 (t, J=7.6 Hz, 3H).

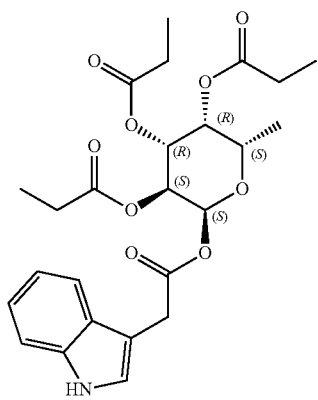

Compound 150: (2S,3S,4R,5R,6S)-2-{[2-(1H-indol-3-yl)acetyl]oxy}-6-methyl-4,5-bis(propanoyloxy)oxan-3-yl propanoate

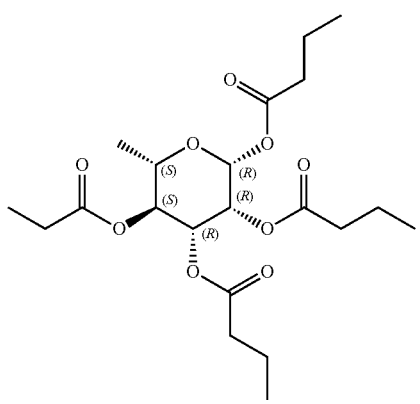

Compound 151: (2R,3R,4R,5S,6S)-3,4,5-tris(butanoyloxy)-6-methyloxan-2-yl butanoate This compound was prepared according to a modified procedure described for the preparation of compound 53. $^1$H NMR (400 MHz, DMSO-d$_6$) δ 6.05 (d, J=1.3 Hz, 1H), 5.38 (dd, J=3.5, 1.2 Hz, 1H), 5.31 (dd, J=10.1, 3.4 Hz, 1H), 4.89 (t, J=9.9 Hz, 1H), 3.90-3.81 (m, 1H), 2.41-2.36 (m, 2H), 2.33-2.22 (m, 4H), 2.15 (td, J=7.2, 1.2 Hz, 2H), 1.65-1.56 (m, 2H), 1.55-1.41 (m, 6H), 1.11 (d, J=6.2 Hz, 3H), 0.94 (t, J=7.4 Hz, 3H), 0.88-0.80 (m, 9H)

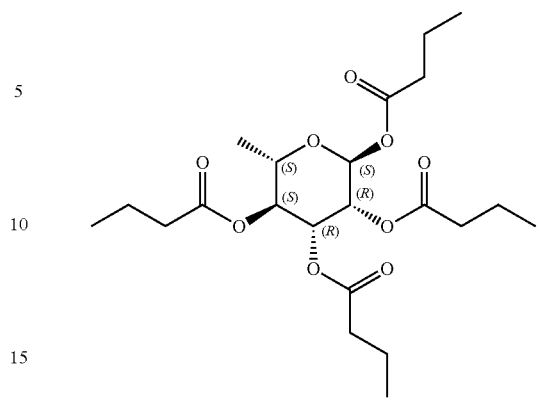

Compound 152: (2S,3R,4R,5S,6S)-3,4,5-tris(butanoyloxy)-6-methyloxan-2-yl butanoate This compound was prepared according to a modified procedure described for the preparation of compound 53.

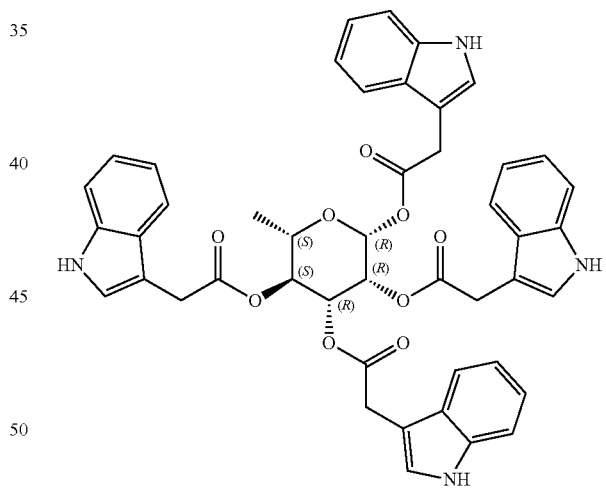

Compound 153: (2R,3R,4R,5S,6S)-3,4,5-tris({[2-(1H-indol-3-yl)acetyl]oxy})-6-methyloxan-2-yl 2-(1H-indol-3-yl)acetate This compound was prepared following a modified procedure described for compound 63.

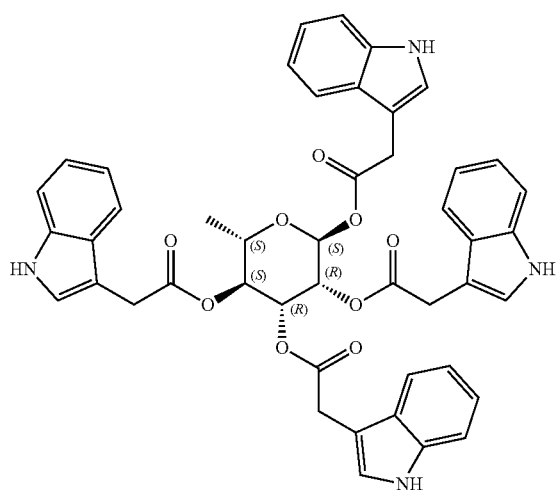

Compound 154: (2S,3R,4R,5S,6S)-3,4,5-tris({[2-(1H-indol-3-yl)acetyl]oxy})-6-methyloxan-2-yl 2-(1H-indol-3-yl)acetate This compound was prepared following a modified procedure described for compound 96.

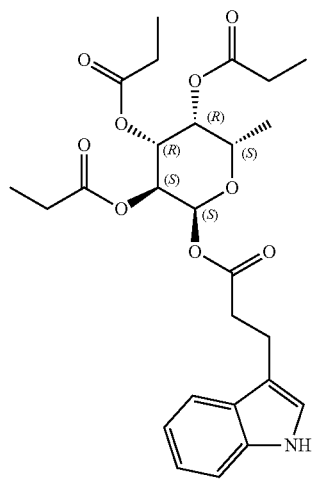

Compound 155: (2S,3S,4R,5R,6S)-6-methyl-3,4,5-tris(propanoyloxy)oxan-2-yl 3-(1H-indol-3-yl)propanoate This compound was prepared following a modified procedure described for compound 107. LCMS (M+Na⁺): 526.2. ¹H NMR (400 MHz, Chloroform-d) δ 8.08 (s, 1H), 7.65-7.57 (m, 1H), 7.35 (dt, J=8.1, 1.0 Hz, 1H), 7.24-7.09 (m, 2H), 7.09-7.04 (m, 1H), 6.33 (d, J=2.5 Hz, 1H), 5.36-5.26 (m, 2H), 5.26-5.22 (m, 1H), 4.01-3.91 (m, 1H), 3.20-3.08 (m, 2H), 2.84 (t, J=7.1 Hz, 2H), 2.44 (qd, J=7.6, 0.9 Hz, 2H), 2.24 (q, J=7.5 Hz, 2H), 2.09 (qd, J=7.6, 1.8 Hz, 2H), 1.18 (t, J=7.6 Hz, 3H), 1.09 (t, J=7.6 Hz, 3H), 1.05-0.96 (m, 6H)

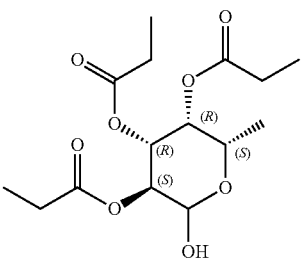

Compound 156: (3S,4R,5R,6S)-2-hydroxy-6-methyl-4,5-bis(propanoyloxy)oxan-3-yl propanoate This compound was prepared according to a modified procedure described for the preparation of compound 21.

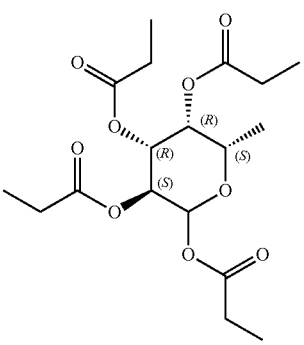

Compound 157: (3S,4R,5R,6S)-6-methyl-3,4,5-tris(propanoyloxy)oxan-2-yl propanoate This compound was prepared according to a modified procedure described for the preparation of compound 53.

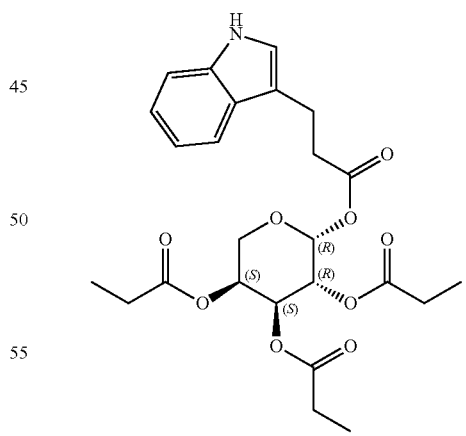

Compound 158: (2R,3R,4S,5S)-3,4,5-tris(propanoyloxy)oxan-2-yl 3-(1H-indol-3-yl)propanoate This compound was prepared following a modified procedure described for compound 107. LCMS (M+Na⁺): 512.2. ¹H NMR (400 MHz, Chloroform-d) δ 8.00 (s, 1H), 7.57-7.48 (m, 1H), 7.32-7.25 (m, 1H), 7.19 (s, 1H), 7.17-

6.93 (m, 3H), 6.28 (d, J=3.1 Hz, 1H), 5.32-5.21 (m, 3H), 3.74 (dd, J=13.2, 1.4 Hz, 1H), 3.62 (dd, J=13.2, 1.9 Hz, 1H), 3.11-3.01 (m, 2H), 2.77 (t, J=7.4 Hz, 2H), 2.35 (q, J=7.5 Hz, 2H), 2.19 (q, J=7.6 Hz, 2H), 2.04 (qd, J=7.6, 1.6 Hz, 2H), 1.15-1.00 (m, 6H), 0.94 (t, J=7.6 Hz, 3H)

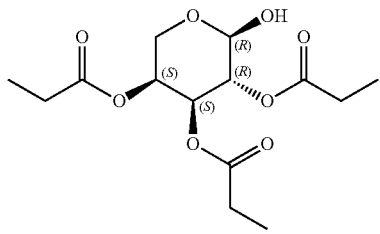

Compound 159: (3S,4S,5R,6R)-6-hydroxy-4,5-bis(propanoyloxy)oxan-3-yl propanoate

This compound was prepared according to a modified procedure described for the preparation of compound 21.

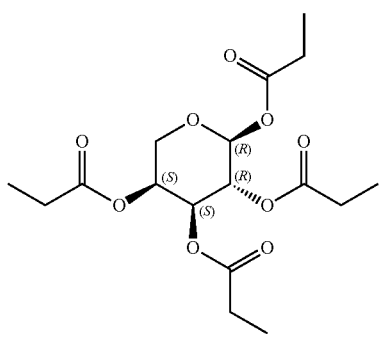

Compound 160: (2S,3R,4S,5S)-3,4,5-tris(propanoyloxy)oxan-2-yl propanoate

This compound was prepared according to a modified procedure described for the preparation of compound 53.

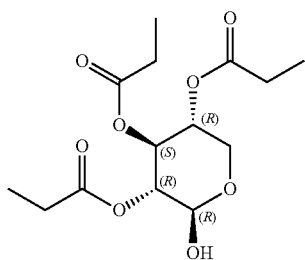

Compound 161: (2R,3R,4S,5R)-2-hydroxy-4,5-bis(propanoyloxy)oxan-3-yl propanoate

This compound was prepared according to a modified procedure described for the preparation of compound 21.

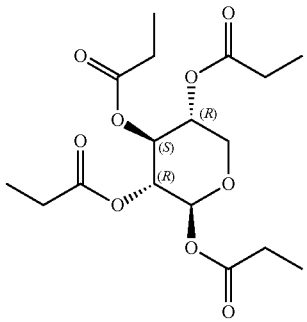

Compound 162: (3R,4S,5R)-3,4,5-tris(propanoyloxy)oxan-2-yl propanoate

This compound was prepared according to a modified procedure described for the preparation of compound 53.

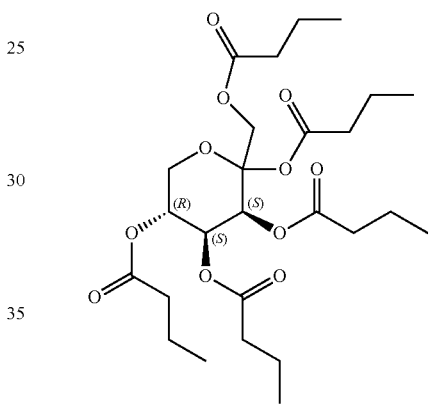

Compound 163: [(3S,4S,5R)-2,3,4,5-tetrakis(butanoyloxy)oxan-2-yl]methyl butanoate This compound was prepared according to a modified procedure described for the preparation of compound 53.

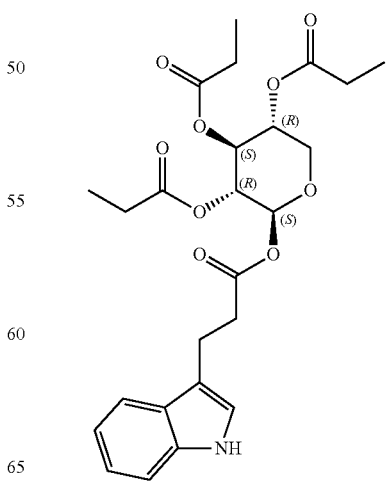

167

Compound 164: (2S,3R,4S,5R)-3,4,5-tris(propanoyloxy)oxan-2-yl 3-(1H-indol-3-yl)propanoate This compound was prepared following a modified procedure described for compound 107. LCMS: (m+Na+) 512.2. ¹H NMR (400 MHz, DMSO-d6) δ 10.89-10.66 (m, 1H), 7.52-7.44 (m, 1H), 7.30 (m, 1H), 7.10-7.01 (m, 2H), 6.95 (m, 1H), 5.84 (d, 1H), 5.30 (t, 1H), 4.96-4.84 (m, 2H), 3.97 (dd, 1H), 3.67 (dd, 1H), 2.92 (t, 2H), 2.70 (td, 2H), 2.31-2.10 (m, 6H), 1.05-0.85 (m, 9H)

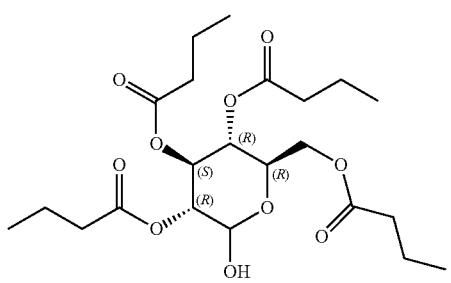

Compound 165:[(2R,3R,4S,5R)-3,4,5-tris(butanoyloxy)-6-hydroxyoxan-2-yl]methyl butanoate

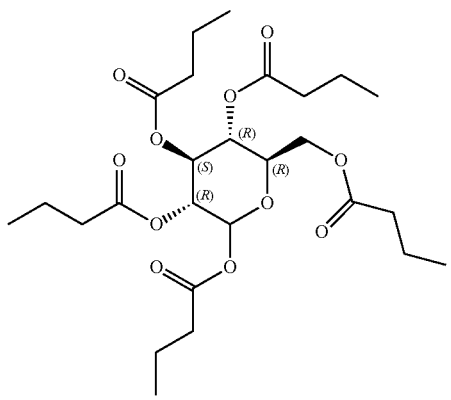

Compound 166:[(2R,3R,4S,5R)-3,4,5,6-tetrakis(butanoyloxy)oxan-2-yl]methyl butanoate

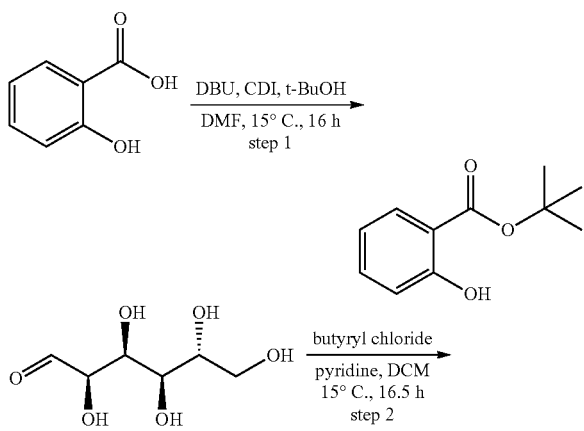

168

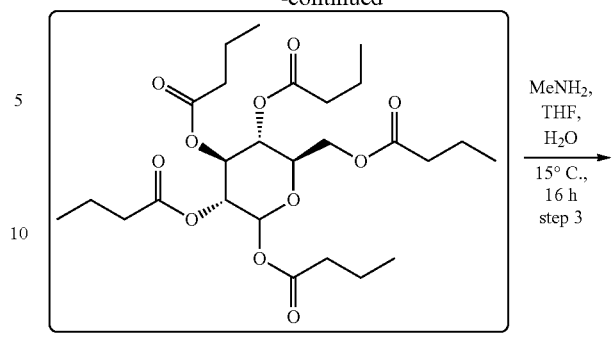

166

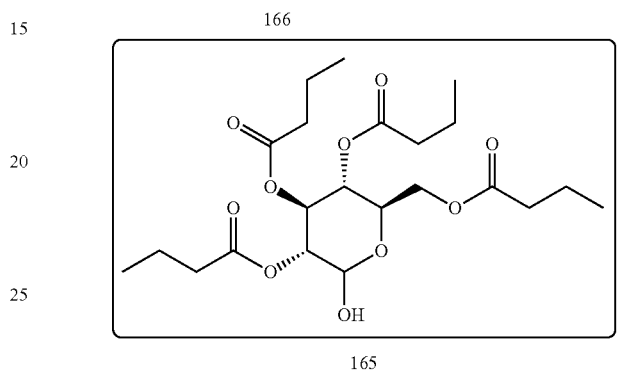

165

Step 1

To the solution of 2-hydroxybenzoic acid (6 g, 43.44 mmol, 7.50 mL, 1 eq) and CDI (8.45 g, 52.13 mmol, 1.2 eq) in DMF (50 mL) was added DBU (7.94 g, 52.13 mmol, 7.86 mL, 1.2 eq) and t-BuOH (6.47 g, 87.32 mmol, 8.35 mL, 2.01 eq). The mixture was stirred at 15° C. for 16 h. LCMS (ET14826-364-P1A) showed the reaction was completed. The solvent was removed under reduced pressure. The crude product was purified by silica gel chromatography eluted with Petroleum ether/Ethyl acetate=1:0-2:1 to give tert-butyl 2-hydroxybenzoate (5 g, 25.74 mmol, 59.26% yield) as colorless oil showed by ¹H NMR. LCMS: (M–H⁺): 193.1 @ 1.988 min

Step 2

To the solution of (2R,3S,4R,5R)-2,3,4,5,6-pentahydroxyhexanal (20 g, 111.02 mmol, 1 eq) in DCM (500 mL) was added butyryl chloride (94.63 g, 888.12 mmol, 92.77 mL, 8 eq) and the mixture was stirred at 15° C. for 0.5 h. Then pyridine (70.25 g, 888.12 mmol, 71.68 mL, 8 eq) was added to the solution dropwise slowly. After the addition, the mixture was stirred at 15° C. for another 16 h. LCMS (ET14826-367-P1A) showed the reaction was completed. The solvent was removed under reduced pressure. The crude product was purified by silica gel chromatography eluted with Petroleum ether/Ethyl acetate=1:0-5:1 to give (3R,4S,5R,6R)-6-((butyryloxy)methyl) tetrahydro-2H-pyran-2,3,4,5-tetrayl tetrabutyrate (58 g, 109.31 mmol, 98.46% yield) as yellow oil showed by ¹H NMR. LCMS: (M+18): 548.3 @ 1.640 min

Step 3

To the solution of (3R,4S,5R,6R)-6-((butyryloxy)methyl) tetrahydro-2H-pyran-2,3,4,5-tetrayl tetrabutyrate (10 g, 18.85 mmol, 1 eq) in THF (85 mL) and H$_2$O (5 mL) was added methanamine/THF (2 M, 12.25 mL, 1.3 eq). Then the mixture was stirred at 15° C. for 16 h. LCMS (ET14826-370-P1A2) showed most of the starting material was consumed and the desired MS was detected. The solvent was removed under reduced pressure. The crude product was purified by silica gel chromatography eluted with Petroleum ether/Ethyl acetate=10:1-1:1 to give (2R,3R,4S,5R)-2-((butyryloxy)methyl)-6-hydroxytetrahydro-2H-pyran-3,4,5-triyl tributyrate (10 g, 21.50 mmol, 57.03% yield, 99% purity) as yellow oil. LCMS: (M+18): 478.3 @ 1.478 min; LCMS: (M+Na$^+$): 483.1 @ 3.678, 3.742 min

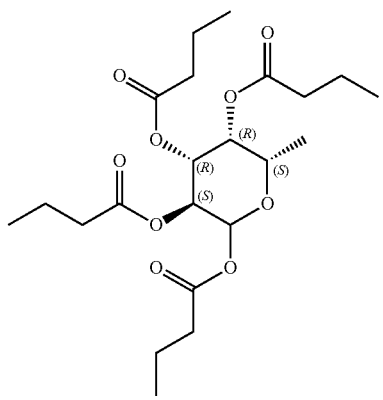

Compound 169: (3S,4R,5R,6S)-3,4,5-tris(butanoyloxy)-6-methyloxan-2-yl butanoate

This compound was prepared according to a modified procedure described for the preparation of compound 53.

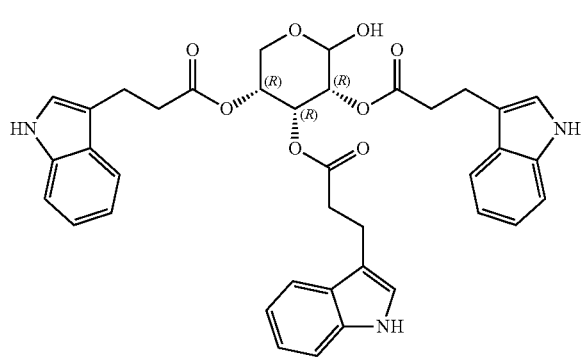

Compound 167: (3R,4R,5R)-6-hydroxy-4,5-bis({[3-(1H-indol-3-yl)propanoyl]oxy})oxan-3-yl 3-(1H-indol-3-yl)propanoate This compound was prepared following a modified procedure described for compound 197 with the exception that the synthesis was stopped at the stage producing the title compound.

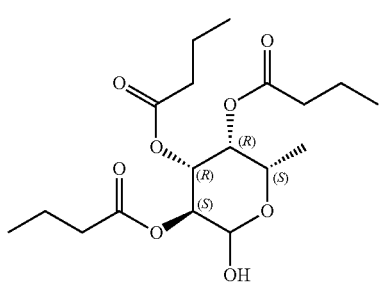

Compound 168: (3S,4R,5R,6S)-4,5-bis(butanoyloxy)-2-hydroxy-6-methyloxan-3-yl butanoate This compound was prepared according to a modified procedure described for the preparation of compound 21.

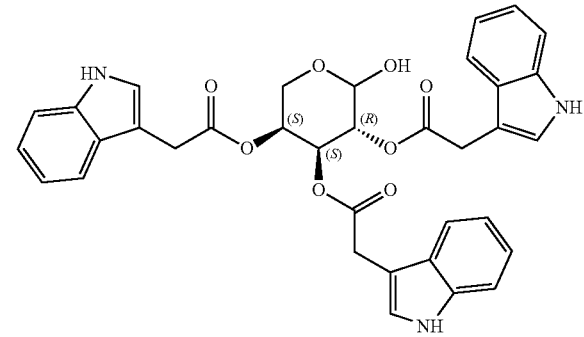

Compound 170: (3R,4R,5R)-6-hydroxy-4,5-bis({[2-(1H-indol-3-yl)acetyl]oxy})oxan-3-yl 2-(1H-indol-3-yl)acetate This compound was prepared following a modified procedure described for compound 197 with the exception that the synthesis was stopped at the stage producing the title compound.

Compound 171: (3S,4S,5R)-6-hydroxy-4,5-bis({[2-(1H-indol-3-yl)acetyl]oxy})oxan-3-yl 2-(1H-indol-3-yl)acetate This compound was prepared following a modified procedure described for compound 197 with the exception that the synthesis was stopped at the stage producing the title compound.

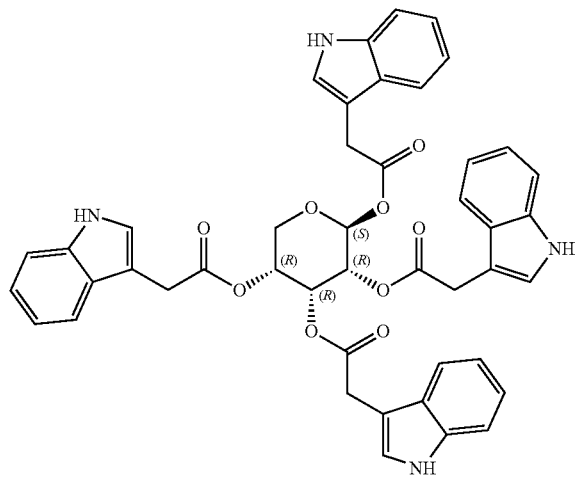

Compound 172: (2S,3R,4R,5R)-3,4,5-tris({[2-(1H-indol-3-yl)acetyl]oxy})oxan-2-yl 2-(1H-indol-3-yl)acetate This compound was prepared following a modified procedure described for compound 107.

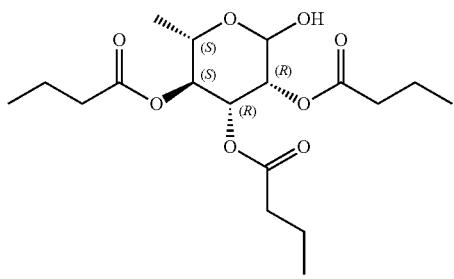

Compound 173: (2S,3S,4R,5R)-4,5-bis(butanoyloxy)-6-hydroxy-2-methyloxan-3-yl butanoate This compound was prepared according to a modified procedure described for the preparation of compound 21.

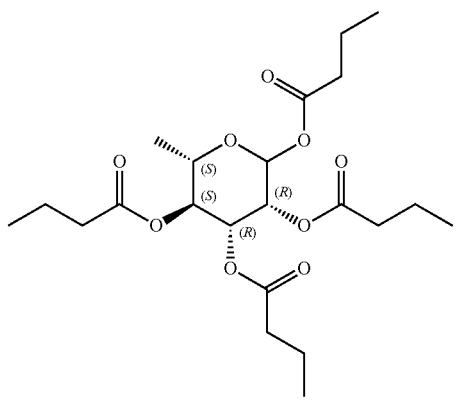

Compound 174: (3R,4R,5S,6S)-3,4,5-tris(butanoyloxy)-6-methyloxan-2-yl butanoate This compound was prepared according to a modified procedure described for the preparation of compound 53.

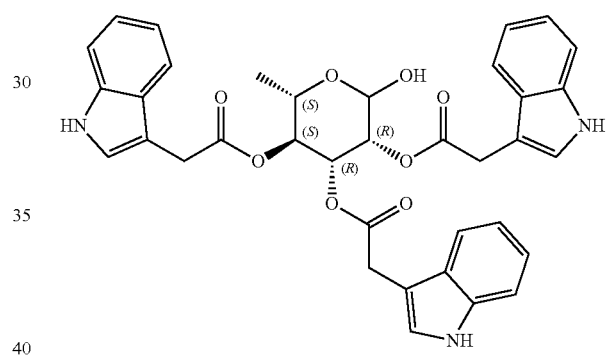

Compound 175: (2S,3S,4R,5R)-6-hydroxy-4,5-bis({[2-(1H-indol-3-yl)acetyl]oxy})-2-methyloxan-3-yl 2-(1H-indol-3-yl)acetate This compound was prepared following a modified procedure described for compound 197 with the exception that the synthesis was stopped at the stage producing the title compound.

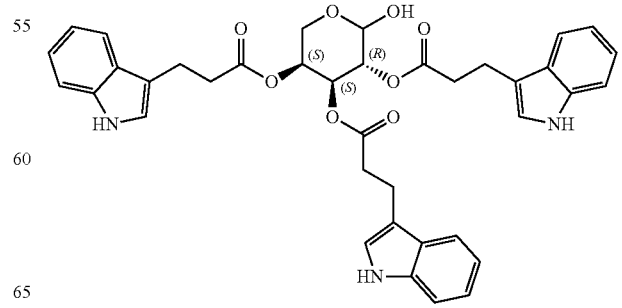

Compound 176: (3S,4S,5R)-6-hydroxy-4,5-bis({[3-(1H-indol-3-yl)propanoyl]oxy})oxan-3-yl 3-(1H-indol-3-yl)propanoate This compound was prepared following a modified procedure described for compound 197 with the exception that the synthesis was stopped at the stage producing the title compound.

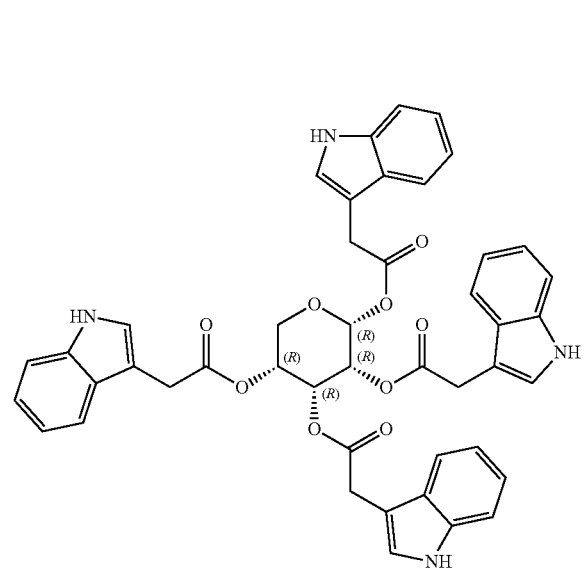

Compound 177: (2R,3R,4R,5R)-3,4,5-tris({[2-(1H-indol-3-yl)acetyl]oxy})oxan-2-yl 2-(1H-indol-3-yl)acetate This compound was prepared following a modified procedure described for compound 96.

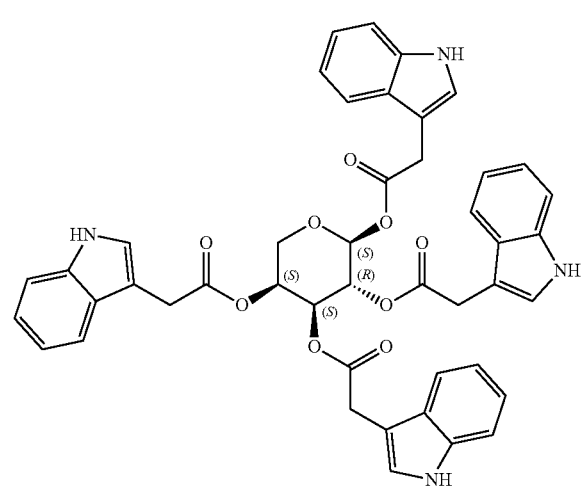

Compound 178: (2S,3R,4S,5S)-3,4,5-tris({[2-(1H-indol-3-yl)acetyl]oxy})oxan-2-yl 2-(1H-indol-3-yl)acetate This compound was prepared following a modified procedure described for compound 96.

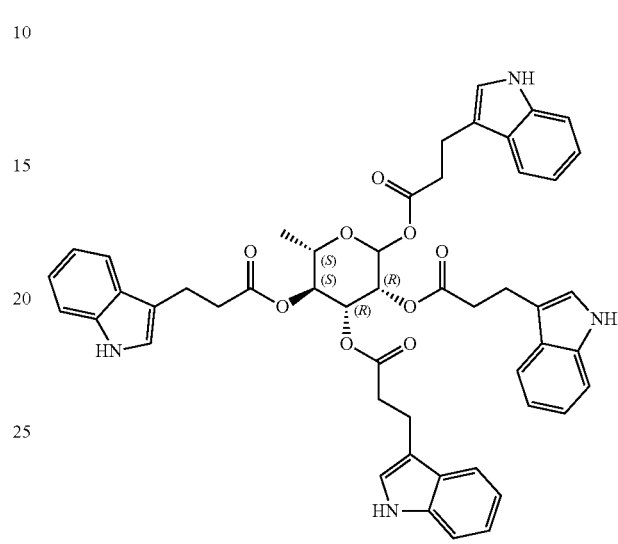

Compound 179: (3R,4R,5S,6S)-3,4,5-tris({[3-(1H-indol-3-yl)propanoyl]oxy})-6-methyloxan-2-yl 3-(1H-indol-3-yl)propanoate This compound was prepared following a modified procedure described for compound 96.

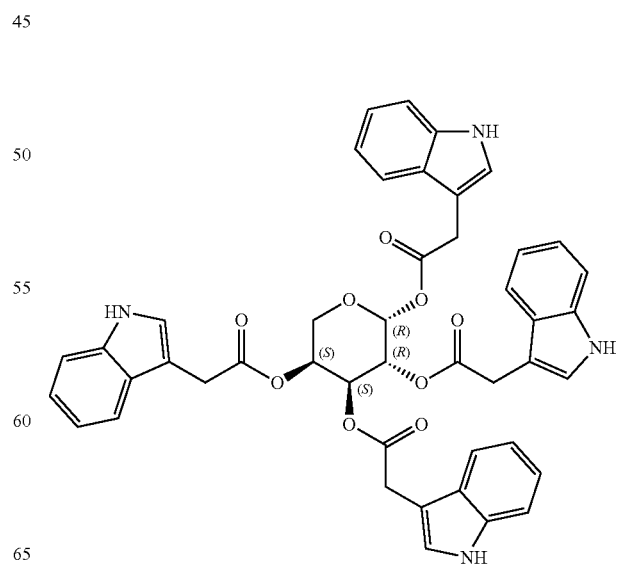

Compound 180: (2R,3R,4S,5S)-3,4,5-tris({[2-(1H-indol-3-yl)acetyl]oxy})oxan-2-yl 2-(1H-indol-3-yl)acetate This compound was prepared following a modified procedure described for compound 96.

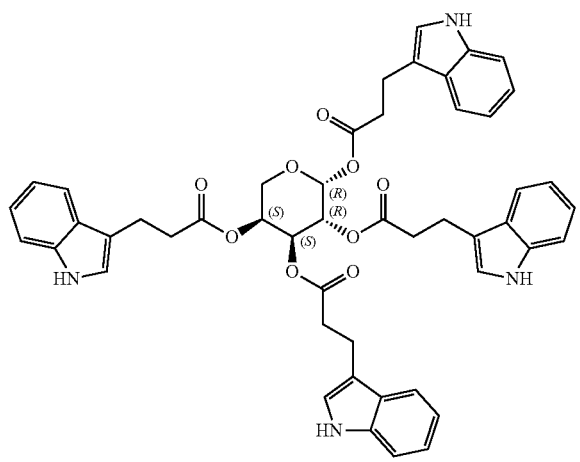

Compound 181: (2R,3R,4S,5S)-3,4,5-tris({[3-(1H-indol-3-yl)propanoyl]oxy})oxan-2-yl 3-(1H-indol-3-yl)propanoate This compound was prepared following a modified procedure described for compound 96. LCMS (M+H$^+$): 835.3. $^1$H NMR (400 MHz, Chloroform-d) δ 7.68 (d, J=7.1 Hz, 2H), 7.57 (d, J=10.5 Hz, 2H), 7.54-7.48 (m, 2H), 7.48-7.41 (m, 2H), 7.20-6.98 (m, 12H), 6.92 (dd, J=13.6, 2.4 Hz, 2H), 6.60 (d, J=2.3 Hz, 1H), 6.49 (d, J=2.3 Hz, 1H), 6.27 (d, J=3.6 Hz, 1H), 5.32 (dd, J=10.7, 3.5 Hz, 1H), 5.25 (s, 1H), 5.24-5.17 (m, 1H), 3.75 (d, J=13.2 Hz, 1H), 3.59 (dd, J=13.2, 2.0 Hz, 1H), 3.13-2.94 (m, 4H), 2.90-2.67 (m, 8H), 2.31-2.02 (m, 4H)

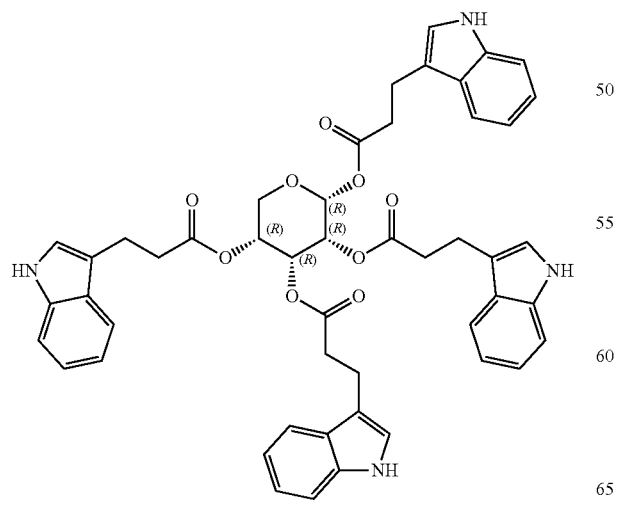

Compound 182: (2R,3R,4R,5R)-3,4,5-tris({[3-(1H-indol-3-yl)propanoyl]oxy})oxan-2-yl 3-(1H-indol-3-yl)propanoate This compound was prepared following a modified procedure described for compound 96. LCMS (M+H$^+$): 835.3. $^1$H NMR (400 MHz, Chloroform-d) δ 7.79 (d, J=15.3 Hz, 3H), 7.69 (s, 1H), 7.53-7.43 (m, 4H), 7.27-7.14 (m, 4H), 7.14-7.06 (m, 4H), 7.02 (t, J=7.4 Hz, 4H), 6.82 (s, 2H), 6.76 (s, 2H), 5.97 (s, 1H), 5.17 (d, J=4.7 Hz, 1H), 5.06 (t, J=6.1 Hz, 1H), 4.04 (s, 1H), 4.01-3.93 (m, 1H), 3.81 (dd, J=12.1, 5.7 Hz, 1H), 3.03-2.88 (m, 8H), 2.65-2.56 (m, 6H), 2.44 (t, J=7.5 Hz, 2H)

Compound 183: (3S,4S,5R)-4,5-bis(butanoyloxy)-6-hydroxyoxan-3-yl butanoate

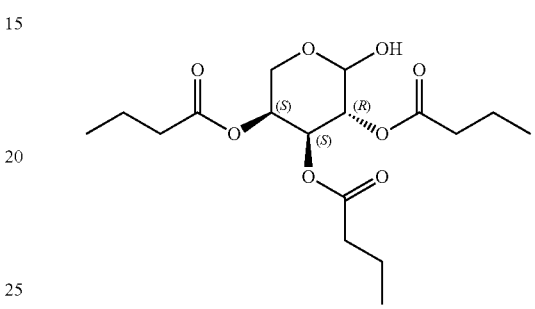

Compound 184: (2R,3R,4S,5S)-3,4,5-tris(butanoyloxy)oxan-2-yl butanoate

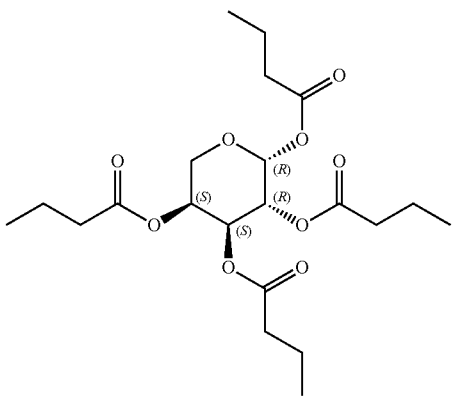

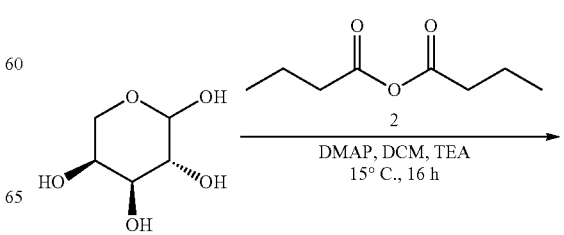

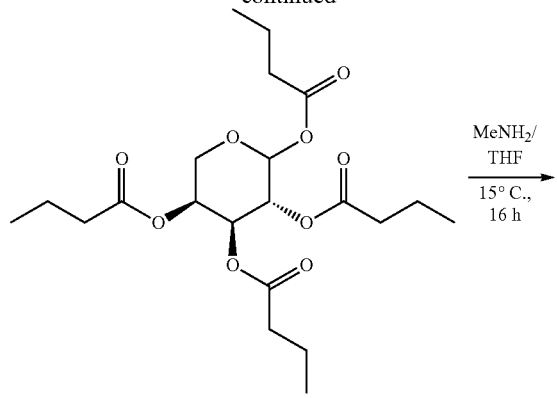

184

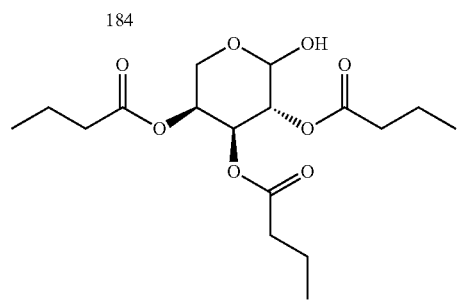

183

Step 1

To the solution of (3R,4S,5S)-tetrahydro-2H-pyran-2,3,4,5-tetraol (10 g, 66.61 mmol, 1 eq), TEA (53.92 g, 532.87 mmol, 74.17 mL, 8 eq) and DMAP (1.63 g, 13.32 mmol, 0.2 eq) in DCM (100 mL) was added butyric anhydride (52.69 g, 333.05 mmol, 54.48 mL, 5 eq) at 0° C. Then the solution was stirred 0° C. for 1 h and stirred at 15° C. for another 15 h. TLC showed the reaction was completed. The solvent was removed under reduced pressure. The crude product was purified by silica gel chromatography eluted with Petroleum ether/Ethyl acetate=1:0 to give compound 184 (3R,4S,5S)-tetrahydro-2H-pyran-2,3,4,5-tetrayl tetrabutyrate (28 g, 65.04 mmol, 97.65% yield, 100% purity) as yellow oil. LCMS: (M+Na$^+$): 453 @ 1.592 min. $^1$H NMR (400 MHz, Chloroform-d) δ 6.4 (m, 1H), 5.4-5.3 (m, 3H), 4.1-3.8 (m, 2H), 3.7-3.3 (m, 2H), 2.4-2.2 (m, 8H), 1.7-1.6 (m, 8H), 1.0-0.9 (m, 12H).

Step 2

To the solution of compound 184 (3R,4S,5S)-tetrahydro-2H-pyran-2,3,4,5-tetrayl tetrabutyrate (25 g, 58.07 mmol, 1 eq) in THF (200 mL) and H$_2$O (10 mL) was added methanamine/THF (2 M, 37.75 mL, 1.3 eq). Then the mixture was stirred at 15° C. for 16 h. LCMS showed the desired MS. The solvent was removed under reduced pressure. The crude product was purified by silica gel chromatography eluted with Petroleum ether/Ethyl acetate=1:0-2:1 to give compound 183 (3R,4S,5S)-2-hydroxytetrahydro-2H-pyran-3,4,5-triyl tributyrate (14 g, 38.85 mmol, 33.45% yield) as yellow oil. LCMS: (M+H$_2$O$^+$): 378 @2.833, 2.934 min. $^1$H NMR (400 MHz, Chloroform-d) δ 5.5-5.4 (m, 1H), 5.4-5.3 (m, 1H), 5.3-5.1 (m, 2H), 4.6 (m, 1H) 4.3-4.0 (m, 1H), 3.7-3.6 (m, 1H), 2.4-2.3 (m, 6H), 1.7-1.6 (m, 6H), 1.0-0.9 (m, 9H)

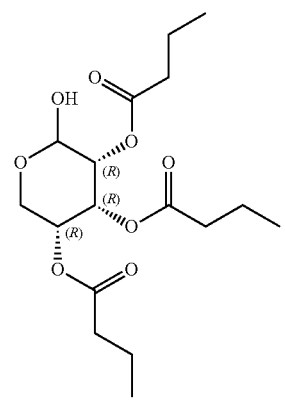

Compound 185:
(3R,4R,5R)-4,5-bis(butanoyloxy)-2-hydroxyoxan-3-yl butanoate

This compound was prepared according to a modified procedure described for the preparation of compound 21.

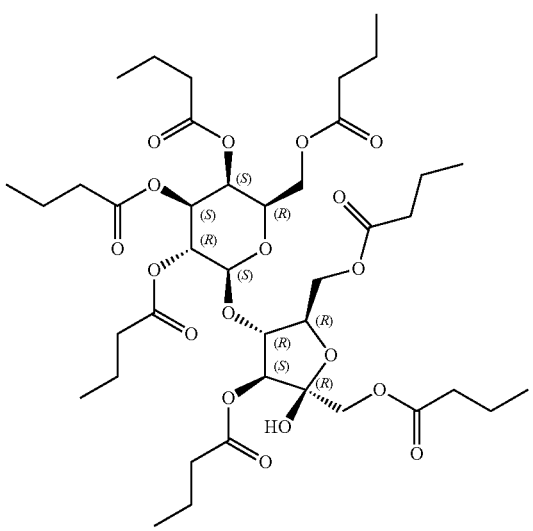

Compound 186:[(2R,3R,4S,5R)-4-(butanoyloxy)-5-[(butanoyloxy)methyl]-5-hydroxy-3-{[(2S,3R,4S,5S,6R)-3,4,5-tris(butanoyloxy)-6-[(butanoyloxy)methyl]oxan-2-yl]oxy}oxolan-2-yl]methyl butanoate This compound was prepared according to a modified procedure described for the preparation of compound 53.

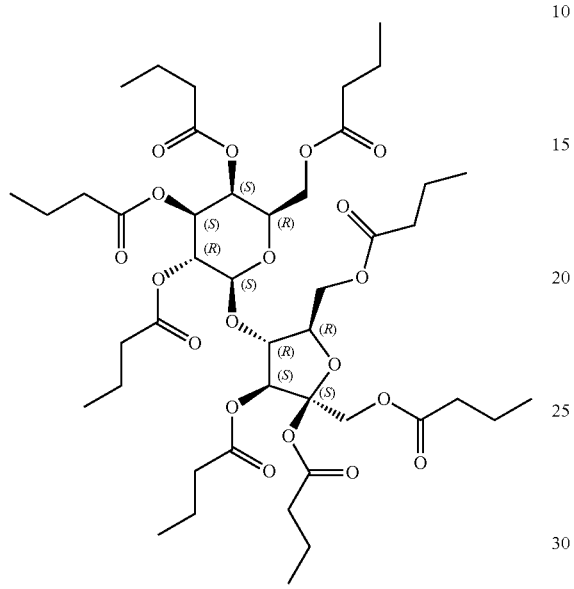

Compound 187: [(2R,3R,4S,5)-4,5-bis(butanoyloxy)-5-[(butanoyloxy)methyl]-3-{[(2S,3R,4S,5S,6R)-3,4,5-tris(butanoyloxy)-6-[(butanoyloxy)methyl]oxan-2-yl]oxy}oxolan-2-yl]methyl butanoate This compound was prepared according to a modified procedure described for the preparation of compound 53.

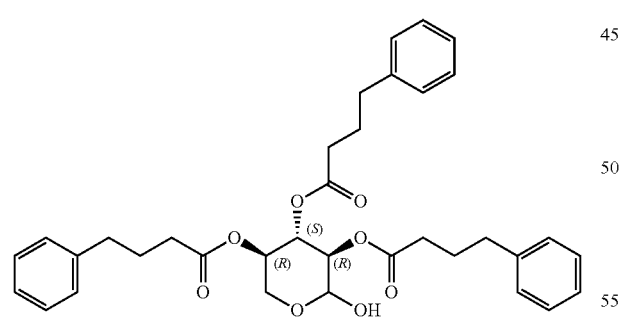

Compound 188: (3R,4S,5R)-6-hydroxy-4,5-bis[(4-phenylbutanoyl)oxy]oxan-3-yl 4-phenyl butanoate This compound was prepared according to the description in WO 2018/226732. $^1$H NMR (CDCl$_3$): δ 7.0-7.2 (m, 15H) 5.5 (dd, 1H), 5.4 (m, 1H), 4.8-5.0 (m, 2H), 4.1 (brs, 1H), 3.8, (dd, 2H), 2.5-2.6 (m, 6H), 2.2-2.3 (m, 6H), 1.8-0.9 (m, 6H) ppm

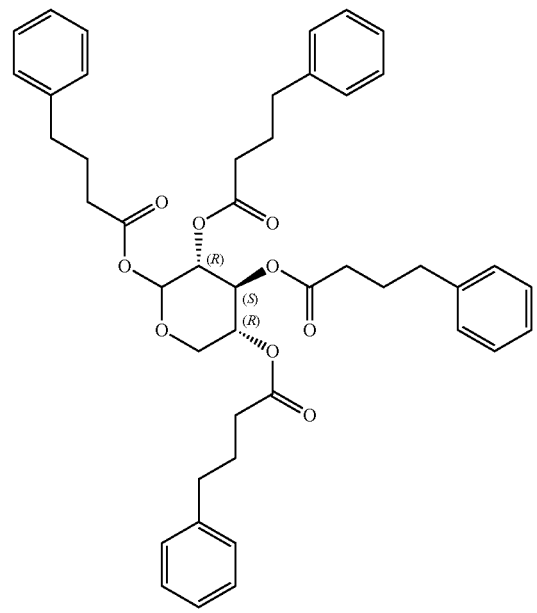

Compound 189: (3R,4S,5R)-4,5,6-tris[(4-phenylbutanoyl)oxy]oxan-3-yl 4-phenyl butanoate This compound was prepared according to a modified procedure described for the preparation of compound 53.

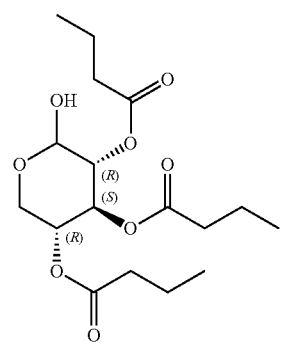

Compound 190: (3R,4S,5R)-4,5-bis(butanoyloxy)-2-hydroxyoxan-3-yl butanoate

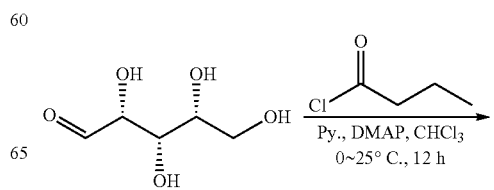

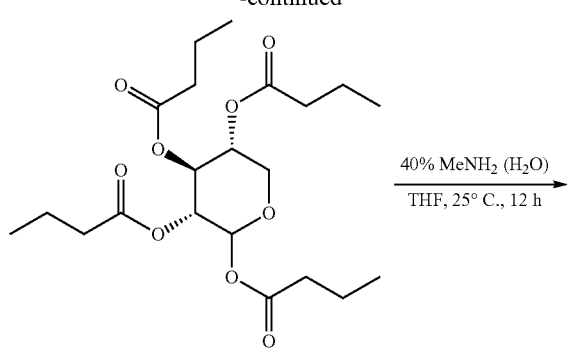

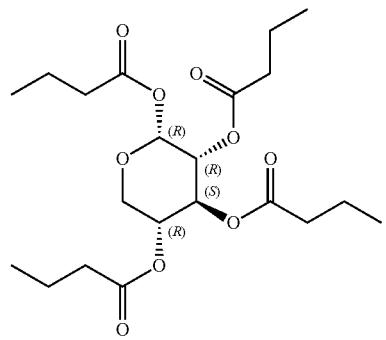

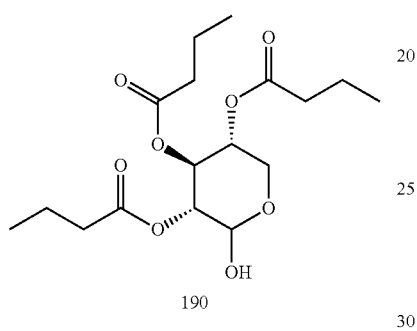

190

Step 1

To a solution of pyridine (316.13 g, 4.00 mol, 322.58 mL, 6 eq) in CHCl₃ (1 L) was added butanoyl chloride (425.83 g, 4.00 mol, 417.48 mL, 6 eq) and DMAP (2.44 g, 19.98 mmol, 0.03 eq) at 0° C. (2R,3S,4R)-2,3,4,5-tetrahydroxypentanal (100 g, 666.09 mmol, 1 eq) was added into the mixture at 0° C. and the mixture was stirred at 25° C. for 12 h. TLC showed the starting reactant consumed. The mixture reaction was concentrated. The residue was purified by column chromatography (SiO₂, Petroleum ether/Ethyl acetate=20/1 to 10:1 to 3/1). [(3R,4S,5R)-4,5,6-tri(butanoyloxy)tetrahydropyran-3-yl]butanoate (165 g, 325.79 mmol, 48.91% yield, 85% purity) was obtained as colorless oil.

Step 2

To a solution of [(3R,4S,5R)-4,5,6-tri(butanoyloxy)tetrahydropyran-3-yl] butanoate (55 g, 127.76 mmol, 1 eq) in THF (800 mL) was added MeNH₂ in H₂O (14.88 g, 191.64 mmol, 40% purity, 1.5 eq). The mixture was stirred at 25° C. for 12 h. TLC showed the starting reactant consumed. The mixture reaction was concentrated. The residue was purified by column chromatography (SiO₂, Petroleum ether/Ethyl acetate=10/1 to 5:1). [(3R,4S,5R)-4,5-di(butanoyloxy)-6-hydroxy-tetrahydropyran-3-yl] butanoate (50 g, 124.86 mmol, 48.87% yield, 90% purity) was obtained. The compound was combined with other batches. In total, 99 g was obtained as a yellow solid. LCMS: (M+Na⁺): 383.1 @ 3.490 min. ¹H NMR (400 MHz, DMSO-d₆) δ 7.2-7.0 (m, 1H), 5.4-5.1 (m, 2H), 4.9-4.7 (m, 2H), 3.7-3.3 (m, 2H), 2.4-2.2 (m, 6H), 1.5-1.4 (m, 6H), 0.9-0.8 (m, 9H)

Compound 191:
(2R,3R,4S,5R)-3,4,5-tris(butanoyloxy)oxan-2-yl butanoate

This compound was prepared according to a modified procedure described for the preparation of compound 53.

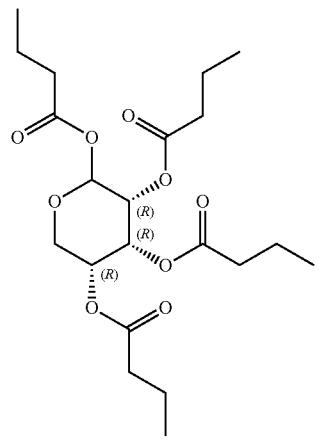

Compound 192:
(3R,4R,5R)-3,4,5-tris(butanoyloxy)oxan-2-yl butanoate

This compound was prepared according to a modified procedure described for the preparation of compound 53.

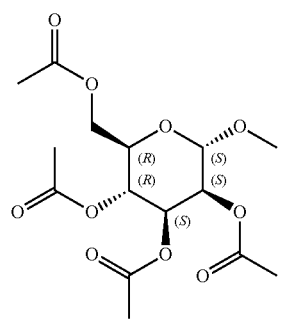

Compound 193: (2R,3R,4S,5S,6S)-2-(acetoxymethyl)-6-methoxytetrahydro-2H-pyran-3,4,5-triyl triacetate This compound was prepared according to a modified procedure described for the preparation of compound 53.

LCMS: (m+Na+) 385.1. $^1$H NMR (400 MHz, DMSO-d6) δ 5.16-5.07 (m, 3H), 4.79 (d, 1H), 4.17 (dd, 1H), 4.07 (dd, 1H), 3.95-3.87 (m, 1H), 3.36 (s, 3H), 2.12 (s, 3H), 2.04 (d, 6H), 1.95 (s, 3H)

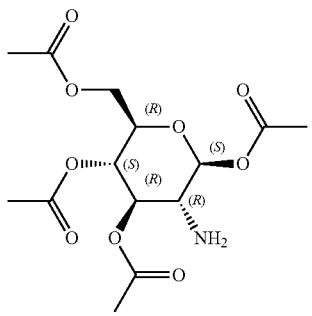

Compound 194: (2S,3R,4R,5S,6R)-6-(acetoxymethyl)-3-aminotetrahydro-2H-pyran-2,4,5-triyl triacetate Stir Boc-protected glucosamine in acetic anhydride and purify. Then, deprotect with HCl in dioxane to yield the title compound as the HCl salt. LCMS: (M+Na+): 370.1. $^1$H NMR (400 MHz, DMSO-d$_6$) δ 8.94-8.54 (m, 3H), 6.01-5.82 (m, 1H), 5.42-5.27 (m, 1H), 4.94 (t, J=9.6 Hz, 1H), 4.20 (dd, J=12.5, 4.4 Hz, 1H), 4.13-3.92 (m, 2H), 3.67-3.51 (m, 1H), 2.18 (s, 3H), 2.08-1.95 (m, 9H)

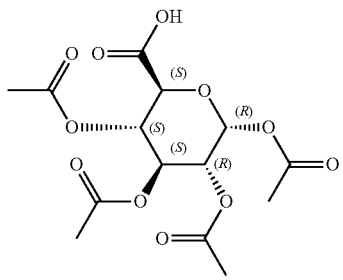

Compound 195: (2S,3S,4S,5R,6R)-3,4,5,6-tetraacetoxytetrahydro-2H-pyran-2-carboxylic acid This compound was prepared following a modified procedure described for compounds 79 and 80. LCMS: (M+NH$_4^+$): 380.1. $^1$H NMR (400 MHz, Chloroform-d) δ 6.40 (s, 1H), 5.52 (t, J=9.5 Hz, 1H), 5.32-5.22 (m, 1H), 5.16-5.08 (m, 1H), 4.46 (d, J=9.7 Hz, 1H), 2.20 (s, 3H), 2.08-2.00 (m, 9H).

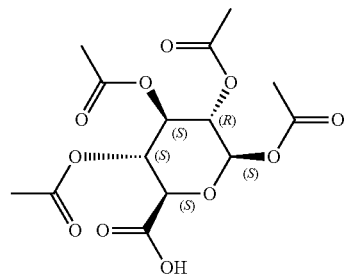

Compound 196: (2S,3S,4S,5R,6S)-3,4,5,6-tetraacetoxytetrahydro-2H-pyran-2-carboxylic acid This compound was prepared following a modified procedure described for compounds 79 and 80. LCMS: (M+NH$_4$+): 380.0. $^1$H NMR (400 MHz, Chloroform-d) δ 5.81 (d, J=7.6 Hz, 1H), 5.39-5.26 (m, 2H), 5.22-5.10 (m, 1H), 4.32-4.22 (m, 1H), 2.14 (s, 3H), 2.12-2.03 (m, 9H).

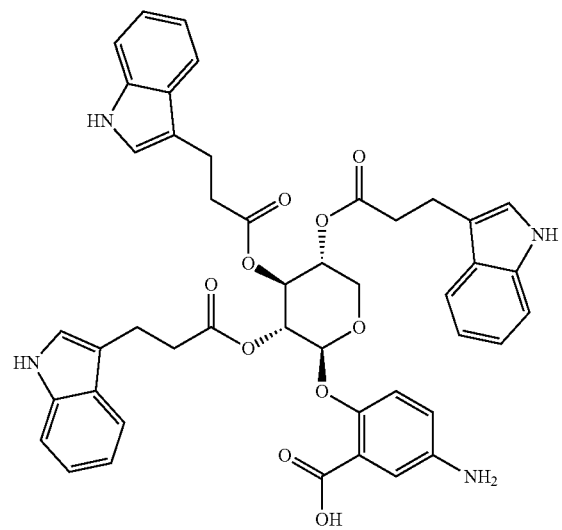 [SMILES: Nc1ccc(O[C@@H]2OC[C@@H](OC(=O)CCc3c[nH]c4ccccc34)[C@H](OC(=O)CCc3c[nH]c4ccccc34)[C@H]2OC(=O)CCc2c[nH]c3ccccc23)c(C(=O)O)c1]

Compound 197: 5-amino-2-(((2S,3R,4S,5R)-3,4,5-tris((3-(1H-indol-3-yl)propanoyl)oxy)tetrahydro-2H-pyran-2-yl)oxy)benzoic acid 3-Indolepropionic acid (20.0 g, 104 mmol) and dicyclohexylcarbodiimide (10.3 g, 49.3 mmol) were dissolved in tetrahydrofuran (345 mL). The reaction was stirred under nitrogen for 2 d. The solution was filtered, washed with tetrahydrofuran and the filtrate was concentrated to give crude 3-(1H-indol-3-yl)propanoic anhydride (26 g, 69%).

Crude 3-(1H-indol-3-yl)propanoic anhydride (26.0 g, 72.1 mmol) was dissolved in pyridine (150 mL) under nitrogen. 4-dimethylaminopyridine (450 mg, 3.61 mmol) and d-(+)-xylose (1.11 g, 7.43 mmol) were added. The mixture was stirred for 24 h. 1 N aqueous hydrochloric acid was added and the aqueous layer was extracted with ethyl acetate. The combined organic layers were concentrated. The crude material was purified by automated reverse phase chromatography (C18, 60 to 65% acetonitrile in 10 mM aqueous ammonium formate) to afford (3R,4S,5R)-tetrahydro-2H-pyran-2,3,4,5-tetrayl tetrakis(3-(1H-indol-3-yl)

propanoate (3.49 g, 58%) as a yellow suspension. LCMS calcd for $C_{49}H_{46}N_4O_9$ 834.33, found 833.6 [M−H] at 2.05 min.

(3R,4S,5R)-tetrahydro-2H-pyran-2,3,4,5-tetrayl tetrakis (3-(1H-indol-3-yl)propanoate) (1.06 g, 1.27 mmol) was dissolved in acetonitrile (13.0 mL) at room temperature. Aqueous perchloric acid (70% wt., 110 µL, 1.27 mmol) was added and the mixture was stirred for 3 h. The mixture was washed with saturated aqueous $NaHCO_3$, water and brine and dried over anhydrous $Na_2SO_4$, filtered and concentrated. The crude material was purified by automated reverse phase chromatography (C18, acetonitrile in 10 mM aqueous ammonium formate). After lyophilisation, (3R,4S,5R)-2-hydroxytetrahydro-2H-pyran-3,4,5-triyl tris(3-(1H-indol-3-yl)propanoate (121 mg, 14%) was obtained as a yellow solid. $^1$H NMR (400 MHz, DMSO-$d_6$) δ 10.75 (s, 3H), 7.46-7.34 (m, 3H), 7.25 (d, J=10.6 Hz, 3H), 7.02 (m, 8H), 6.94-6.82 (m, 4H), 5.41 (t, J=9.8 Hz, 0.5H), 5.26 (s, 0.3H), 5.16 (s, 1H), 4.92-4.69 (m, 2H), 3.64 (m, 2H), 2.84 (dd, J=15.8, 7.8 Hz, 6H), 2.53-2.49 (m, 6H). LCMS calcd for $C_{38}H_{37}N_3O_8$ 663.26, found 681.2 [M+$NH_4$] at 1.80 min.

(3R,4S,5R)-2-hydroxytetrahydro-2H-pyran-3,4,5-triyl tris(3-(1H-indol-3-yl)propanoate) (121 mg, 182 µmol) was dissolved in N N-dimethylformamide (600 µL). The solution was stirred at room temperature when benzyl 2-fluoro-5-nitrobenzoate (65.2 mg, 237 µmol) and then 1,4-diazabicyclo[2.2.2]octane (102 mg, 912 µmol) were added. Stirring was continued for 2 d. Then, water was added. The aqueous layer was extracted with ethyl acetate. The combined organic layers were washed with brine, dried over anhydrous $Na_2SO_4$, filtered and concentrated to give a brown oil. The crude material was adsorbed on celite and purified by automated chromatography ($SiO_2$, ethyl acetate gradient in hexanes) to afford (3R,4S,5R)-2-(2-((benzyloxy)carbonyl)-4-nitrophenoxy)tetrahydro-2H-pyran-3,4,5-triyl tris(3-(1H-indol-3-yl)propanoate) (36.0 mg, 21%) as a yellow oil. LCMS calcd for $C52H_{46}N_4O_{12}$ 918.31, found 936 [M+$NH_4$] at 2.10 min.

(3R,4S,5R)-2-(2-((benzyloxy)carbonyl)-4-nitrophenoxy) tetrahydro-2H-pyran-3,4,5-triyl tris(3-(1H-indol-3-yl)propanoate) (36.0 mg, 39.2 µmol) was dissolved in methanol (800 µL) and stirred at room temperature under nitrogen. To this stirring solution, palladium on carbon (10% wt. 4.17 mg, 3.92 µmol) was added. The suspension was degassed with hydrogen and allowed to stir under hydrogen for 2 h. The mixture was filtered through celite and washed with methanol. The filtrate was concentrated under vacuo. The crude material was purified by preparative HPLC-MS (CSH column, acetonitrile in 10 mM aqueous ammonium formate). After lyophilisation, 3-carboxy-4-(((2S,3R,4S,5R)-3,4,5-tris((3-(1H-indol-3-yl)propanoyl)oxy)tetrahydro-2H-pyran-2-yl)oxy)benzenaminium formate (4.20 mg, 13%) was obtained as a white solid. $^1$H NMR (400 MHz, DMSO-$d_6$) δ 10.77 (t, J=12.5 Hz, 3H), 8.40 (s, 3H), 7.53-7.38 (m, 3H), 7.28 (dd, J=8.0, 4.8 Hz, 3H), 7.03 (dd, J=13.2, 4.9 Hz, 6H), 6.96-6.85 (m, 3H), 6.82-6.67 (m, 2H), 6.53 (d, J=7.0 Hz, 1H), 5.29 (t, J=8.5 Hz, 1H), 5.18 (d, J=6.7 Hz, 1H), 5.06-5.01 (m, 1H), 4.91 (dd, J=13.5, 8.3 Hz, 1H), 3.98 (dd, J=11.6, 4.9 Hz, 1H), 3.60-3.51 (m, 1H), 2.91-2.79 (m, 7H), 2.74-2.67 (m, 1H), 2.63-2.54 (m, 4H). LCMS calcd for $C_{45}H_{42}N_4O_{10}$ 798.29, found 816 [M+$NH_4$] at 1.80 min.

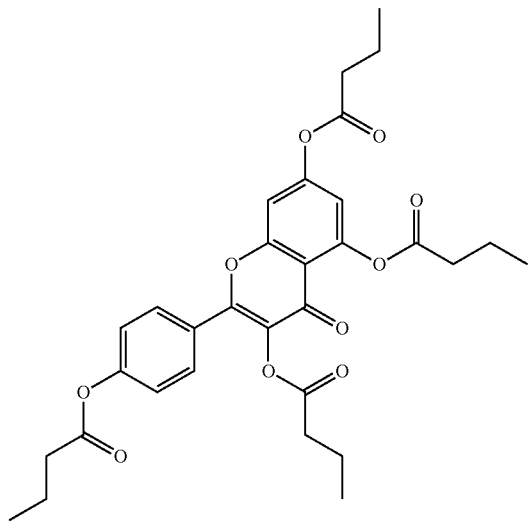 [SMILES: CCCC(=O)Oc1ccc(-c2oc3cc(OC(=O)CCC)cc(OC(=O)CCC)c3c(=O)c2OC(=O)CCC)cc1]

Compound 198: 4-[3,5,7-tris(butanoyloxy)-4-oxo-4H-chromen-2-yl]phenyl butanoate

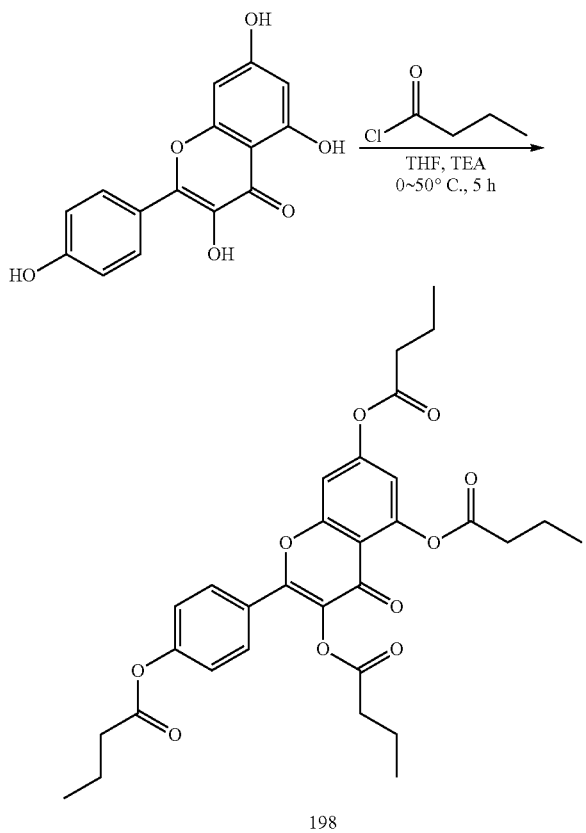

198

To a mixture of 3,5,7-trihydroxy-2-(4-hydroxyphenyl) chromen-4-one (500 mg, 1.75 mmol, 1 eq), TEA (883.80 mg, 8.73 mmol, 1.22 mL, 5 eq) in THF (20 mL) was added butanoyl chloride (930.62 mg, 8.73 mmol, 912.37 uL, 5 eq) slowly at 0° C. And then the mixture was stirred at 50° C. for 5 hr under $N_2$ atmosphere. LC-MS showed reactant was consumed completely and one main peak with desired mass was detected. The reaction mixture was quenched by addition H₂O 200 mL at 25° C. and then extracted with EtOAc 180 mL (60 mL*3). The combined organic layers were washed with brine 20 mL, dried over Na₂SO₄, filtered and concentrated under reduced pressure to give a residue. The residue was purified by column chromatography (SiO₂, Petroleum ether/Ethyl acetate=5/1 to 3:1). [4-[3,5,7-tri(butane-yloxy)-4-oxo-chromen-2-yl]phenyl]butanoate (437 mg, 734.02 umol, 42.02% yield, 95.17% purity) was obtained as a white solid. LCMS: (M+H⁺) 567.2 @ 1.577 min, LCMS: (M+H⁺) 567.2 @ 3.520 min. ¹H NMR (400 MHz, Chloroform-d) δ 12.10 (s, 1H), 7.88-7.58 (m, 2H), 7.36 (d, J=8.3 Hz, 1H), 6.86 (d, J=2.0 Hz, 1H), 6.59 (d, J=2.0 Hz, 1H), 2.87-2.37 (m, 8H), 1.41-1.12 (m, 12H)

Compound 199: 5-hydroxy-4-oxo-2-[4-(propanoyloxy)phenyl]-4H-chromen-7-yl propanoate Propionic anhydride (641 uL, 5.03 mmol) was added dropwise to a stirred solution of 5,7-dihydroxy-2-(4-hydroxyphenyl)-4H-chromen-4-one (170 mg, 0.63 mmol) in 1 mL pyridine at 0° C. under nitrogen. The reaction was stirred at room temperature for 16 hours then diluted with 20 mL ethyl acetate. The organic layer was washed with 10 mL 1M HCl twice followed by brine, dried over MgSO4, filtered and concentrated. The residue was dissolved in DMSO and purified by reverse phase flash chromatography (10-90% acetonitrile in water). Fraction was concentrated by lyophilization to yield 5-hydroxy-4-oxo-2-[4-(propanoyloxy)phenyl]-4H-chromen-7-yl propanoate (48 mg, 20% yield) as a white solid. LCMS: (M+H) 383.1. ¹H NMR (400 MHz, DMSO-d6) δ 12.83 (s, 1H), 8.21-8.15 (m, 2H), 7.40-7.34 (m, 2H), 7.14 (s, 1H), 7.11 (d, 1H), 6.68 (d, 1H), 2.65 (qd, 4H), 1.16 (t, 6H)

Compound 200: 3,5-bis(butanoyloxy)-4-oxo-2-[3,4,5-tris(butanoyloxy)phenyl]-4H-chromen-7-yl butanoate

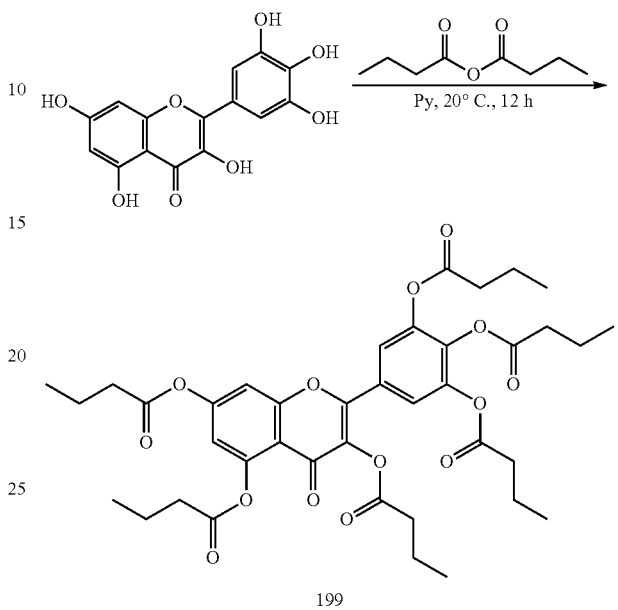

A mixture of 3,5,7-trihydroxy-2-(3,4,5-trihydroxyphenyl) chromen-4-one (0.2 g, 628.47 umol, 1 eq), butanoyl butanoate (795.36 mg, 5.03 mmol, 822.50 uL, 8 eq) in Pyridine (5 mL) was degassed and purged with N₂ for 3 times, and then the mixture was stirred at 20° C. for 12 hr under N₂ atmosphere. TLC indicated the reaction was completed and one new spot formed. The reaction mixture was washed with H₂O (5 mL), filtered and the filter cake was concentrated under reduced pressure to give a residue. Compound [3,5-di(butanoyloxy)-4-oxo-2-[3,4,5-tri(butanoyloxy)phenyl] chromen-7-yl] butanoate (0.378 g, 501.43 μmol, 79.79% yield, 98% purity) was obtained as off-white solid. LCMS: (M+H⁺) 739.2 @ 3.587 min. ¹H NMR (400 MHz, Chloroform-d) δ 7.62 (s, 2H), 7.35 (d, J=2.2 Hz, 1H), 6.88 (d, J=2.2 Hz, 1H), 2.74 (t, J=7.5 Hz, 2H), 2.69-2.52 (m, 10H), 1.91-1.70 (m, 12H), 1.12-0.98 (m, 18H).

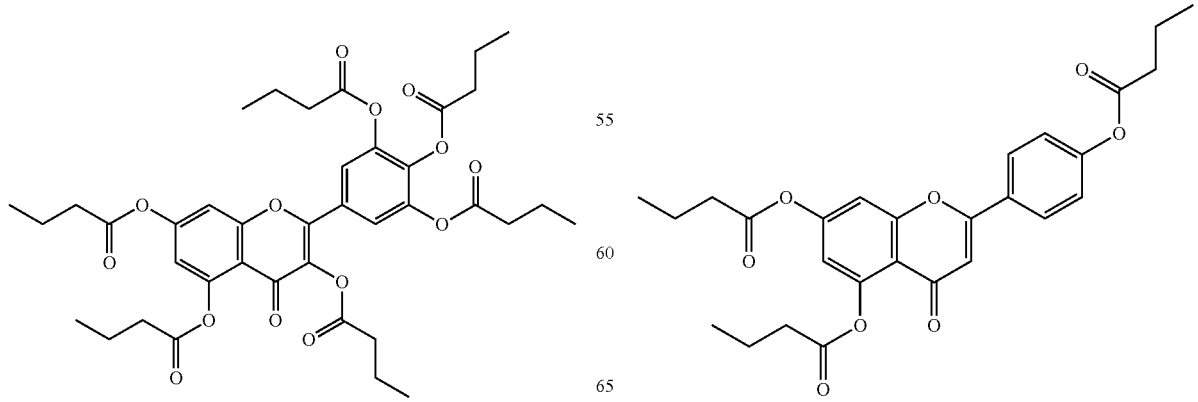

Compound 201: 5-(butanoyloxy)-2-[4-(butanoyloxy)phenyl]-4-oxo-4H-chromen-7-yl butanoate Compound 202: 2-[3,4-bis(butanoyloxy)phenyl]-5-(butanoyloxy)-4-oxo-4H-chromen-7-yl butanoate

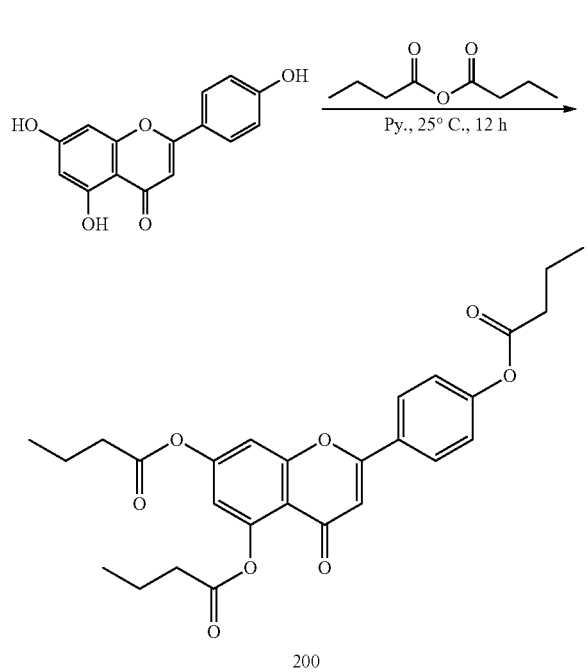

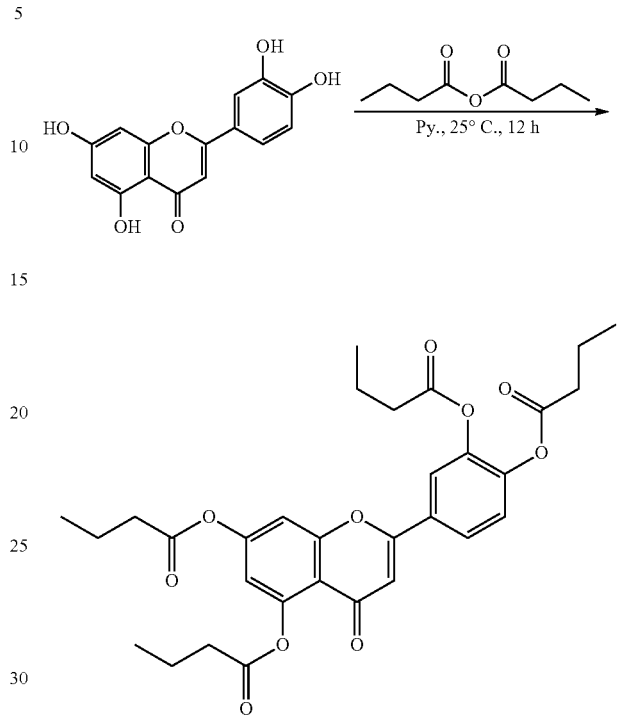

To a solution of 5,7-dihydroxy-2-(4-hydroxyphenyl)chromen-4-one (500 mg, 1.85 mmol, 1 eq) in Py. (5 mL) was added butanoyl butanoate (1.76 g, 11.10 mmol, 1.82 mL, 6 eq) at 25° C. The mixture was stirred at 25° C. for 12 hr. LCMS showed the desired compound was detected. The reaction mixture was concentrated under reduced pressure to give a residue. The residue were washed with $H_2O$ (20 mL) and petroleum ether (20 mL), and concentrated under reduced pressure to give a residue. Compound [4-[5,7-di(butanoyloxy)-4-oxo-chromen-2-yl]phenyl] butanoate (167 mg, 340.60 umol, 18.41% yield, 98% purity) was obtained as a yellow solid. LCMS: (M+H$^+$) 481.1 @ 3.244 min. $^1$H NMR (400 MHz, Chloroform-d) δ 7.92-7.83 (m, 2H), 7.34 (d, J=2.3 Hz, 1H), 7.28-7.22 (m, 2H), 6.83 (d, J=2.2 Hz, 1H), 6.62 (s, 1H), 2.72 (t, J=7.5 Hz, 2H), 2.58 (td, J=7.4, 1.8 Hz, 4H), 1.87-1.74 (m, 6H), 1.12-1.02 (m, 9H)

To a solution of 2-(3,4-dihydroxyphenyl)-5,7-dihydroxychromen-4-one (500 mg, 1.75 mmol, 1 eq) in Pyridine (10 mL) was added butanoyl butanoate (2.21 g, 13.97 mmol, 2.29 mL, 8 eq) at 25° C. The mixture was stirred at 25° C. for 12 hr. LCMS showed the desired compound was detected. The reaction mixture was concentrated under reduced pressure to give a residue. The residue were washed with $H_2O$ (20 mL) and petroleum ether (20 mL), and concentrated under reduced pressure to give a residue. Compound [2-butanoyloxy-4-[5,7-di(butanoyloxy)-4-oxo-chromen-2-yl]phenyl] butanoate (155 mg, 270.83 umol, 15.50% yield, 99% purity) was obtained as a yellow solid. LCMS: (M+H$^+$) 567.1 @3.385 min. $^1$H NMR (400 MHz, Chloroform-d) δ 7.76-7.66 (m, 2H), 7.40-7.32 (m, 2H), 6.83 (d, J=2.2 Hz, 1H), 6.60 (s, 1H), 2.72 (t, J=7.5 Hz, 2H), 2.62-2.51 (m, 6H), 1.91-1.72 (m, 8H), 1.11-1.01 (m, 12H).

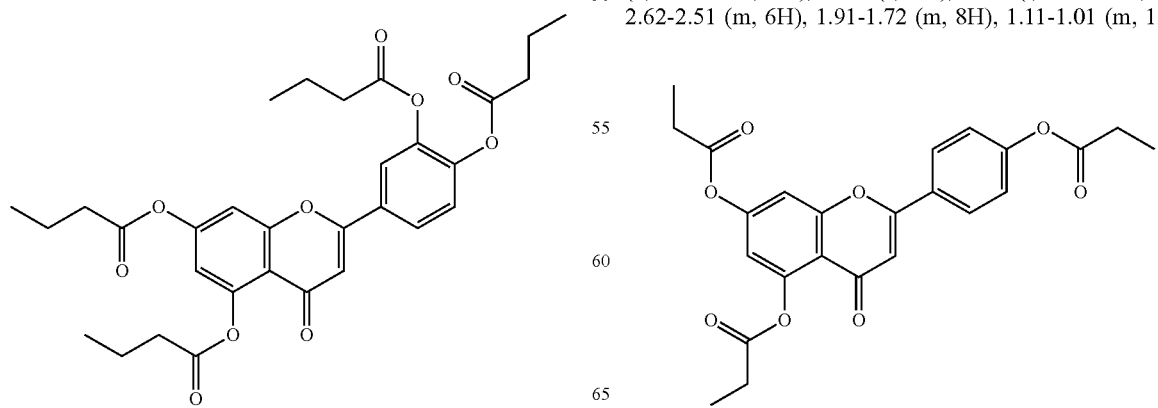

Compound 203: 4-oxo-7-(propanoyloxy)-2-[4-(propanoyloxy)phenyl]-4H-chromen-5-yl propanoate

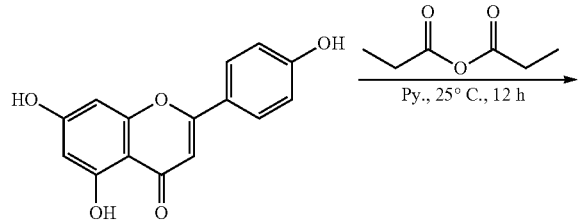

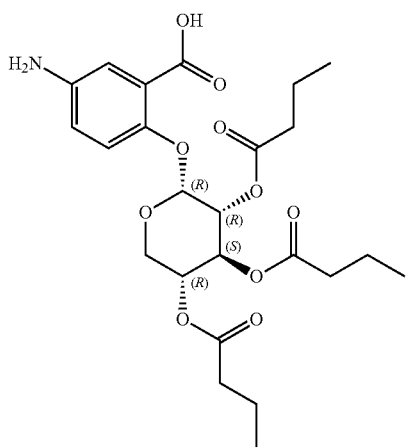

202

To a solution of 5,7-dihydroxy-2-(4-hydroxyphenyl) chromen-4-one (500 mg, 1.85 mmol, 1 eq) in Pyridine (5 mL) was added propanoyl propanoate (1.44 g, 11.10 mmol, 1.43 mL, 6 eq) at 25° C. The mixture was stirred at 25° C. for 12 hr. LCMS showed the desired compound was detected. The reaction mixture was concentrated under reduced pressure to give a residue. The residue were washed with H$_2$O (20 mL) and petroleum ether (20 mL), and concentrated under reduced pressure to give a residue. Compound [4-[4-oxo-5,7-di(propanoyloxy)chromen-2-yl] phenyl] propanoate (156 mg, 351.73 umol, 19.01% yield, 98.85% purity) was obtained as a yellow solid. LCMS: (M+H$^+$) 439.1 @ 3.130 min. $^1$H NMR (400 MHz, Chloroform-d) δ 7.94-7.86 (m, 2H), 7.38 (d, J=2.2 Hz, 1H), 7.32-7.24 (m, 2H), 6.87 (d, J=2.2 Hz, 1H), 6.64 (s, 1H), 2.80 (q, J=7.5 Hz, 2H), 2.66 (qd, J=7.5, 1.8 Hz, 4H), 1.38-1.26 (m, 9H)

Compound 204: 5-amino-2-[(2R,3R,4S,5R)-3,4,5-tri(butanoyloxy)tetrahydropyran-2-yl]oxy-benzoic acid This compound was prepared according to a modified procedure described for the preparation of compound 34. LCMS [M−H]$^-$: 494.5. $^1$H NMR (400 MHz, DMSO-d$_6$) δ 6.83-6.75 (m, 2H), 6.64-6.53 (m, 1H), 5.58 (d, J=3.6 Hz, 1H), 5.53 (t, J=9.9 Hz, 1H), 5.03-4.90 (m, 2H), 3.89 (t, J=10.9 Hz, 1H), 3.73 (dd, J=10.9, 5.9 Hz, 1H), 2.38-2.12 (m, 6H), 1.58-1.39 (m, 6H), 0.92-0.76 (m, 9H)

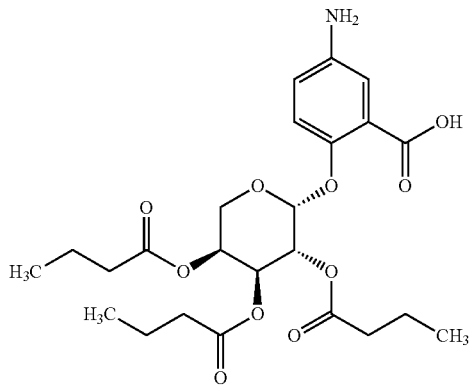 [SMILES: CCCC(=O)O[C@@H]1[C@@H](OC(=O)CCC)[C@@H](Oc2ccc(N)cc2C(=O)O)OC[C@@H]1OC(=O)CCC]

Compound 205: 5-amino-2-[(2R,3R,4S,5S)-3,4,5-tri(butanoyloxy)tetrahydropyran-2-yl]oxy-benzoic acid Step 1: 2-Hydroxy-4-nitro-benzoate (20 g) and KHCO$_3$ (13.1 g) were suspended in DMF (100 mL). To the suspension was added benzyl bromide (22.4 g) and the reaction mixture was stirred at room temperature overnight. Water (150 mL) was added and the resulting mixture was extracted with ethyl acetate (250 mL). The organic phase was separated and washed twice with water, brine, and dried over Na$_2$SO$_4$. The solvent was removed under reduced pressure and the residue was purified by column chromatography (hexanes/ethyl acetate gradient). Recrystallization from 15% ethyl acetate in hexanes provided benzyl 2-hydroxy-4-nitro-benzoate (10.5 g).

Step 2: Benzyl 2-hydroxy-4-nitro-benzoate (8.5 g), arabinose tributyrate (7.5 g) and triphenylphosphine (8.2 g) were dissolved in THF (150 mL) and stirred at 0° C. To this mixture was added di-t-butyl azodicarboxylate (7.2 g) and stirring was continued at 0° C. for 1 h, then at room temperature overnight. The reaction mixture was concentrated and purification by column chromatography (hexanes/ethyl acetate gradient) provided benzyl 5-nitro-2-[(2R,3R,4S,5S)-3,4,5-tri(butanoyloxy)tetrahydropyran-2-yl]oxy-benzoate (1.78 g, 14%).

Step 3: 5-nitro-2-[(2R,3R,4S,5S)-3,4,5-tri(butanoyloxy)tetrahydropyran-2-yl]oxy-benzoate (0.095 g) was dissolved in methanol (15 mL) and stirred at room temperature. To this mixture was added 10% Pd/C (0.05 g). The suspension was stirred under a hydrogen atmosphere at room temperature overnight. The reaction mixture was filtered through Celite and washed with methanol. The combined filtrate and washing were concentrated. The residue was purified by reverse phase chromatography (C-18, 0.1% trifluoroacetic acid in acetonitrile and 0.1% trifluoroacetic acid in water) to give 5-amino-2-[(2R,3R,4S,5S)-3,4,5-tri(butanoyloxy)tetrahydropyran-2-yl]oxy-benzoic acid (0.045 g, 59%). MS 494.2 (M−H) NMR (DMSO d6): δ 7.223 (m, 1H), 7.139 (m, 1H), 6.997 (s, 1H), 7.851 (d, 1H), 5.469 (m, 1H), 5.350 (m, 1H), 5.239 (m, 1H) 4.127 (d, 1H), 3.672 (d, 1H), 2.490-2.369 (M, 6H), 1.596-1.485 (m, 6H), 0.924-0.818 (m, 9H) ppm

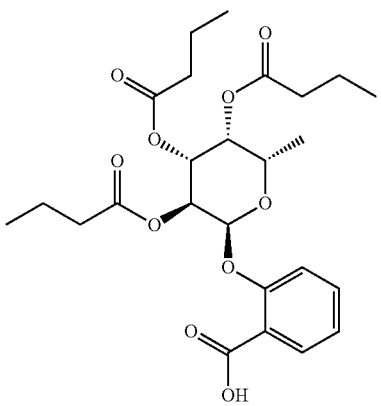 [SMILES: CCCC(=O)O[C@H]1[C@H](OC(=O)CCC)[C@H](Oc2ccccc2C(=O)O)O[C@@H](C)[C@H]1OC(=O)CCC]

Compound 206: 2-(((2S,3S,4R,5R,6S)-3,4,5-tris (butyryloxy)-6-methyltetrahydro-2H-pyran-2-yl) oxy)benzoic acid Step 1

To a mixture of [(2S,3R,4R,5S)-4,5-di(butanoyloxy)-6-hydroxy-2-methyl-tetrahydropyran-3-yl]butanoate (0.95 g, 2.54 mmol) and tert-butyl 2-hydroxybenzoate (0.468 g, 2.41 mmol) in THF (10 mL) was added tert-butyl (NE)-N-tert-butoxycarbonyliminocarbamate (0.876 g, 3.81 mmol) and PPh₃ (0.952 g, 3.63 mmol) in one portion at 15° C. under N₂. The mixture was stirred at 15° C. for 12 h. The reaction mixture was filtered and concentrated under reduced pressure to give a residue which was purified by prep-HPLC [water (10 mM NH₄HCO₃)-ACN] to give tert-butyl 2-[(3S, 4R,5R,6S)-3,4,5-tri(butanoyloxy)-6-methyl-tetrahydropyran-2-yl]oxybenzoate (0.3 g, 0.544 mmol, 21% yield) as a white solid.

Step 2

To a solution of tert-butyl 2-[(3S,4R,5R,6S)-3,4,5-tri(butanoyloxy)-6-methyl-tetrahydropyran-2-yl]oxybenzoate (0.15 g, 0.272 mmol) in DCM (5 mL) was added TFA (0.031 g, 0.27 mmol). The mixture was stirred at 15° C. for 12 hr. The reaction mixture was filtered and concentrated under reduced pressure to give a residue. The residue was purified by prep-HPLC [water (0.1% TFA)-ACN] to give compound 205 and compound 211.

Compound 205 was prepared as a colorless oil (0.003 g, 1.9% yield). LCMS: 517.2 (M+Na⁺); ¹H NMR CDCl3 8.192 (m, 1H), 7.565 (m, 1 HO, 7.441 (m, 1H), 7.255 (m, 1H), 5.813 (m, 1H), 5.525-5.444 (m, 3H), 4.413 (m, 1H), 2.460 (t, 2H), 2.356 (t, 2H), 2.233 (t, 2H), 1.627 (m, 6H), 1.225 (d, 3H), 1.028 (t, 3H), 0.938 (t, 3H), 0.919 (t, 3H)

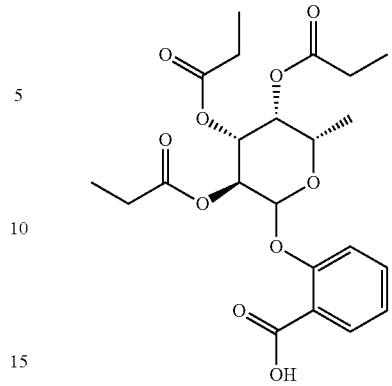

Compound 207: 2-(((3S,4R,5R,6S)-6-methyl-3,4,5-tris(propionyloxy)tetrahydro-2H-pyran-2-yl)oxy) benzoic acid Step 1

To a mixture of [(2S,3R,4R,5S)-6-hydroxy-2-methyl-4,5-di(propanoyloxy)tetrahydropyran-3-yl]propanoate (1 g, 3.01 mmol) and tert-butyl 2-hydroxybenzoate (1.17 g, 6.02 mmol) in THF (10 mL) was added di-tert-butyl azodicarboxylate (1.04 g, 4.51 mmol) and triphenylphosphine (2.77 g, 4.51 mmol) in one portion at 15° C. under N₂. The mixture was stirred at 15° C. for 12 h. The reaction mixture was filtered and concentrated under reduced pressure and the residue was purified by prep-HPLC. [water (10 mM NH₄HCO₃)-ACN] to give tert-butyl 2-[(3S,4R,5R,6S)-6-methyl-3,4,5-tri(propanoyloxy)tetrahydropyran-2-yl]oxybenzoate (0.6 g, 39% yield) as a yellow solid.

Step 2

To a mixture of tert-butyl 2-[(3S,4R,5R,6S)-6-methyl-3,4,5-tri(propanoyloxy)tetrahydropyran-2-yl]oxybenzoate (0.44 g, 0.865 mmol) in DCM (5 mL) was added TFA (0.099 g, 0.865 mmol) in one portion at 15° C. under N₂. The mixture was stirred 12 h. The reaction mixture was filtered and concentrated under reduced pressure to give a residue. The residue was purified by prep-HPLC [water (0.1% TFA)-ACN]. 2-[(3S,4R,5R,6S)-6-methyl-3,4,5-tri(propanoyloxy) tetrahydropyran-2-yl]oxybenzoic acid (0.067 g, 15% yield) as a white solid. MS 475.1 (M+Na) NMR (DMSO d6): δ 8.1 (m, 1H), 7.5 (m, 1H), 7.1 (m, 2H), 5.6 (m, 1H), 5.4 (m, 1H), 5.3 (m, 1H), 5.1 (m, 1H) 4.0 (m, 1H), 2.2 (m, 6H), 1.2 (m, 12H).

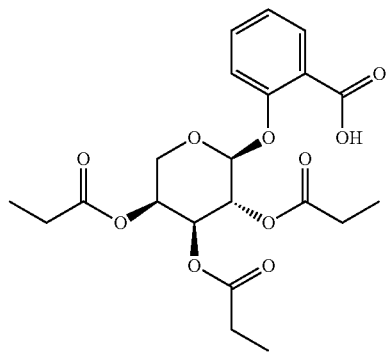 [SMILES: CCC(=O)O[C@@H]1[C@@H](OC(=O)CC)[C@H](Oc2ccccc2C(=O)O)OC[C@@H]1OC(=O)CC]

Compound 208: 2-(((2S,3R,4S,5S)-3,4,5-tris(propionyloxy)tetrahydro-2H-pyran-2-yl)oxy)benzoic acid

Step 1

To a solution of (3R,4S,5S)-2-hydroxytetrahydro-2H-pyran-3,4,5-triyl tripropionate (188.47 mg, 592.09 umol, 1 eq), tert-butyl 2-hydroxybenzoate (230 mg, 1.18 mmol, 2 eq) and triphenylphosphine (545.97 mg, 888.14 umol, 1.5 eq) in THF (10 mL) was added di-tertbutyazodicarboxylate (204.50 mg, 888.14 umol, 1.5 eq) at 0° C. The mixture was stirred at 15° C. for 16 hr. TLC indicated new spot formed. The reaction mixture was concentrated under reduced pressure to give a residue. The residue was purified by column chromatography (SiO$_2$, Petroleum ether/Ethyl acetate=10:1 to 1:1). Compound tert-butyl tert-butyl 2-[(3R,4S,5S)-3,4,5-tri(propanoyloxy)tetrahydropyran-2-yl]oxybenzoate (200 mg, 404.42 umol, 68.30% yield) was obtained as a white solid.

Step 2

To a solution of tert-butyl 2-[(3R,4S,5S)-3,4,5-tri(propanoyloxy)tetrahydropyran-2-yl] oxybenzoate (100 mg, 202.21 umol, 1 eq) in CH$_2$Cl$_2$ (1 mL) was added TFA (138.34 mg, 1.21 mmol, 89.83 uL, 6 eq) at 15° C. The mixture was stirred at 15° C. for 2 hr. LCMS showed desired MS was detected. The reaction mixture was concentrated under reduced pressure to give a residue. The residue was purified by prep-TLC (SiO$_2$, Petroleum ether/Ethyl acetate=1:1). Compound 2-[(3R,4S,5S)-3,4,5-tri(propanoyloxy)tetrahydropyran-2-yl]oxybenzoic acid (30 mg, 32.84 μmol, 16.24% yield, 46.66% purity) was obtained as a colorless oil. LCMS: (M−1) 437.1 NMR (CDCl$_3$): δ8.2 (m, 1H), 7.4 (m, 1H), 7.2 (m, 2H), 5.3 (m, 4H), 4.0 (dd, 2H), 2.47-1.1 (m, 9H) ppm.

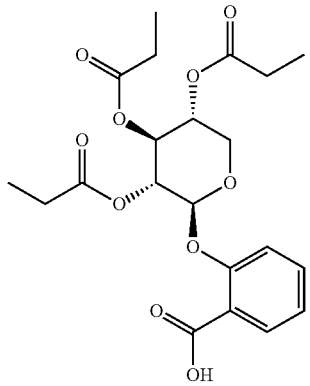 [SMILES: CCC(=O)O[C@@H]1[C@@H](OC(=O)CC)[C@H](Oc2ccccc2C(=O)O)OC[C@H]1OC(=O)CC]

Compound 209: 2-(((2S,3R,4S,5R)-3,4,5-tris(propionyloxy)tetrahydro-2H-pyran-2-yl)oxy)benzoic acid

Step 1

To a solution of [(3R,4S,5R)-6-hydroxy-4,5-di(propanoyloxy)tetrahydropyran-3-yl] propanoate (0.500 g, 1.57 mmol), tert-butyl 2-hydroxybenzoate (0.610 g, 3.14 mmol) and PPh$_3$ (0.824 g, 3.14 mmol) in THF (10 mL) was added di-tert-butyl azodicarboxylate (0.723 g, 3.14 mmol) at 0° C. The reaction was stirred for 12 h at 15° C. The mixture reaction was concentrated under reduced pressure. The residue was purified by column chromatography (SiO$_2$, petroleum ether/ethyl acetate=30/1 to 5:1) to give tert-butyl 2-[(3R,4S, 5R)-3,4,5-tri(propanoyloxy)tetrahydropyran-2-yl]oxybenzoate (0.320 g, 37% yield) as a brown solid.

Step 2

To a solution of TFA (10 mL) in CH$_2$Cl$_2$ (30 mL) was added tert-butyl 2-[(3R,4S,5R)-3,4,5-tri(propanoyloxy)tetrahydropyran-2-yl]oxybenzoate (0.300 g, 606 mmol) and the mixture was stirred at 15° C. for 2 h. The mixture reaction was concentrated under reduced pressure. The residue was purified by prep-HPLC (column: Waters Xbridge Prep OBD C18 150*40 10 u; mobile phase: [water (10 mM NH4HCO3)-ACN]; B %: 1%-50%,11 min) to give 2-[(3R,4S,5R)-3,4,5-tri(propanoyloxy)tetrahydropyran-2-yl]oxybenzoic acid (0.010 g, 3.4% yield) as a yellow oil. MS 437.1 (M−H) NMR (DMSO d6): δ 7.5 (m, 1H), 7.3 (m, 1H), 7.1 (m, 1H), 7.0 (m, 1H), 5.9 (m, 1H), 5.6 (1H) 5.0 (m, 2H), 4.0 (m, 1H), 3.7 (m, 1H), 2.2 (m, 6H), 0.97 (m, 9H).

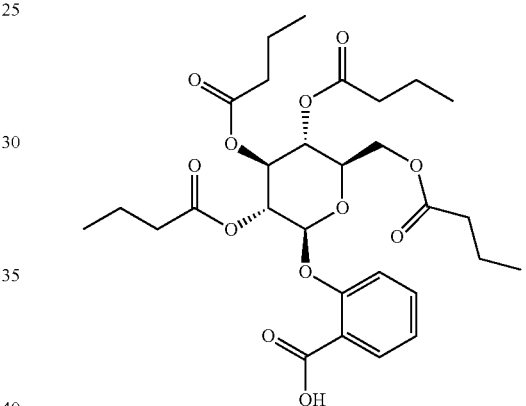

Compound 210: 2-(((2S,3R,4S,5R,6R)-3,4,5-tris(butyryloxy)-6-((butyryloxy)methyl)tetrahydro-2H-pyran-2-yl)oxy)benzoic acid To the solution of 2-hydroxybenzoic acid (6 g, 43.44 mmol, 7.50 mL, 1 eq) and CDI (8.45 g, 52.13 mmol, 1.2 eq) in DMF (50 mL) was added DBU (7.94 g, 52.13 mmol, 7.86 mL, 1.2 eq) and t-BuOH (6.47 g, 87.32 mmol, 8.35 mL, 2.01 eq). The mixture was stirred at 15° C. for 16 h. LCMS (ET14826-364-P1A) showed the reaction was completed. The solvent was removed under reduced pressure. The crude product was purified by silica gel chromatography eluted with Petroleum ether/Ethyl acetate=1:0-2:1 to give tert-butyl 2-hydroxybenzoate (5 g, 25.74 mmol, 59.26% yield)

To the solution of (2R,3S,4R,5R)-2,3,4,5,6-pentahydroxyhexanal (20 g, 111.02 mmol, 1 eq) in DCM (500 mL) was added butyryl chloride (94.63 g, 888.12 mmol, 92.77 mL, 8 eq) and the mixture was stirred at 15° C. for 0.5 h. Then pyridine (70.25 g, 888.12 mmol, 71.68 mL, 8 eq) was added to the solution dropwise slowly. After the addition, the mixture was stirred at 15° C. for another 16 h. LCMS (ET14826-367-P1A) showed the reaction was completed. The solvent was removed under reduced pressure. The crude product was purified by silica gel chromatography eluted with Petroleum ether/Ethyl acetate=1:0-5:1 to give (3R,4S, 5R,6R)-6-((butyryloxy)methyl) tetrahydro-2H-pyran-2,3,4,5-tetrayl tetrabutyrate (58 g, 109.31 mmol, 98.46% yield) as yellow oil To the solution of (3R,4S,5R,6R)-6-((butyryloxy)methyl) tetrahydro-2H-pyran-2,3,4,5-tetrayl tetrabutyrate (10 g, 18.85 mmol, 1 eq) in THF (85 mL) and H₂O (5 mL) was added methanamine/THF (2 M, 12.25 mL, 1.3 eq). Then the mixture was stirred at 15° C. for 16 h. LCMS (ET14826-370-P1A2) showed most of the starting material was consumed and the desired MS was detected. The solvent was removed under reduced pressure. The crude product was purified by silica gel chromatography eluted with Petroleum ether/Ethyl acetate=10:1-1:1 to give (2R,3R,4S,5R)-2-((butyryloxy)methyl)-6-hydroxytetrahydro-2H-pyran-3,4,5-triyl tributyrate (10 g, 21.50 mmol, 57.03% yield, 99% purity) as yellow oil.

To the solution of (2R,3R,4S,5R)-2-((butyryloxy)methyl)-6-hydroxytetrahydro-2H-pyran-3,4,5-triyl tributyrate (0.85 g, 1.85 mmol, 1 eq) and tert-butyl 2-hydroxybenzoate (340.57 mg, 1.75 mmol, 0.95 eq) in THF (20 mL) was added PPh₃ (692.29 mg, 2.64 mmol, 1.43 eq) and di-tert-butyl azodicarboxylate (637.51 mg, 2.77 mmol, 1.5 eq). Then the mixture was stirred at 15° C. for 16 h. LCMS showed the reaction was completed and the desired MS was detected. The solvent was removed under reduced pressure. The crude product was purified by p-HPLC (column: Phenomenex Luna C18 200*40 mm*10 um; mobile phase: [water (0.1% TFA)-ACN]; B %: 75%-95%,10 min) to give (3R,4S,5R,6R)-2-(2-(tert-butoxycarbonyl)phenoxy)-6-((butyryloxy)methyl)tetrahydro-2H-pyran-3,4,5-triyl tributyrate (0.2 g, 314.11 umol, 17.02% yield) as brown oil.

To the solution of (3R,4S,5R,6R)-2-(2-(tert-butoxycarbonyl)phenoxy)-6-((butyryloxy)methyl) tetrahydro-2H-pyran-3,4,5-triyl tributyrate (0.2 g, 314.11 umol, 1 eq) in DCM (10 mL) was added TFA (1.54 g, 13.51 mmol, 1 mL, 43.00 eq). Then the solution was stirred at 15° C. for 16 h. LCMS showed the reaction was completed and the desired MS was detected. The solvent was removed under reduced pressure. The crude product was purified by p-HPLC (column: Nanomicro Kromasil C18 100*30 mm 5 um; mobile phase: [water (0.1% TFA)-ACN]; B %: 60%-78%,10 min) to afford the title compound (24 mg, 40.10 umol, 12.76% yield, 97% purity, temporary assigned) as yellow oil. LCMS: (M+18): 598.2 NMR (DMSO d6): δ 8.1 (d, 1H), 7.5 (dd, 1H), 7.4 (d, 1H), 7.2 (m, 1H), 5.8 (m, 1H), 5.6 (t, 1H), 5.2 (m, 2H), 4.1 (m, 3H), 2.3 (m, 8H), 1.6 (m, 8H), 0.87 (m, 12H) ppm.

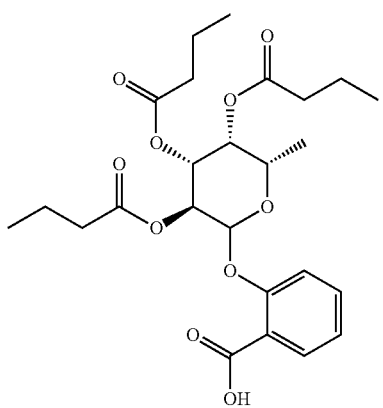 [SMILES: CCCC(=O)O[C@@H]1[C@H](OC(=O)CCC)[C@H](C)OC(Oc2ccccc2C(=O)O)[C@H]1OC(=O)CCC]

Compound 211: 2-(((3S,4R,5R,6S)-3,4,5-tris(butyryloxy)-6-methyltetrahydro-2H-pyran-2-yl)oxy)benzoic acid Compound 211 was prepared as a colorless oil (0.03 g, 22% yield). LCMS: 517.2 (M+Na⁺); ¹H NMR CDCl₃ 8.080 (m, 1H), 7.491 (m, 1H), 7.164 (m, 1H), 7.086 (m, 1H), 5.494 (m, 1H), 5.292 (m, 1H), 5.197 (m, 1H), 5.133 (m, 1H), 3.946 (m, 1H), 2.413-2.153 (m, 6H), 1.653-1.546 (m, 6H), 1.204 (d, 3H), 0.946 (t, 3H), 0.869 (t, 3H), 0.850 (t, 3H).

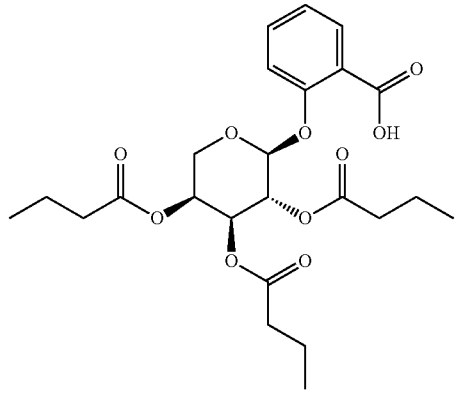 [SMILES: CCCC(=O)O[C@@H]1[C@@H](OC(=O)CCC)[C@H](Oc2ccccc2C(=O)O)OC[C@@H]1OC(=O)CCC]

Compound 212: 2-(((2S,3R,4S,5S)-3,4,5-tris(butyryloxy)tetrahydro-2H-pyran-2-yl)oxy)benzoic acid Compound 212 was prepared in an analogous matter to compound 211. Compound 212 was prepared in 27% yield (15 mg). LCMS: 503 (M+Na⁺); ¹H NMR CDCl3 8,095 (m, 1H), 7.484 (m, 1H), 7.326 (m, 1H), 7.154 (m, 1H), 5.775 (d, 1H), 5.482-5.404 (m, 3H), 4.084 (d, 1H), 3.840 (d, 1H), 2.372-2.276 (m, 6H), 1.658-1.497 (m, 6H), 0.937 (t, 3H), 0.863 (t, 3H), 0.823 (t, 3H).

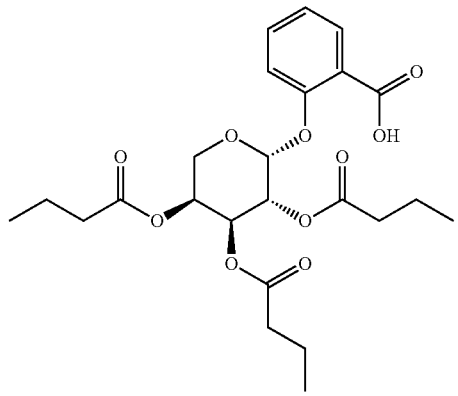 [SMILES: CCCC(=O)O[C@@H]1[C@@H](OC(=O)CCC)[C@@H](Oc2ccccc2C(=O)O)OC[C@@H]1OC(=O)CCC]

Compound 213: 2-(((2R,3R,4S,5S)-3,4,5-tris(butyryloxy)tetrahydro-2H-pyran-2-yl)oxy)benzoic acid Step 1

A solution of DCC (8 g, 38.8 mmol) in THF (50 mL) was added dropwise to a solution of 2-hydroxybenzoic acid (5 g, 36.2 mmol) and DMAP (0.17 g, 1.39 mmol) in t-BuOH (100 mL) and the mixture was stirred at 15° C. for 16 h. The crude product was purified by silica gel chromatography (petroleum ether/ethyl acetate=1:0) to give tert-butyl 2-hydroxybenzoate (3 g, 42.7%) as colorless oil.

Step 2

To a solution of (3R,4S,5S)-2-hydroxytetrahydro-2H-pyran-3,4,5-triyl tributyrate (0.7 g, 1.94 mmol) and tert-butyl 2-hydroxybenzoate (0.358 g, 1.85 mmol) in THF (30 mL) was added PPh$_3$ (0.728 g, 2.78 mmol) and DBAD (0.671 g, 2.91 mmol) in portions. Then the mixture was stirred at 15° C. for 16 h. The solvent was removed under reduced pressure. The crude product was purified by prep-HPLC (column: Agela innoval ods-2 250*80 mm; mobile phase: [water (0.1% TFA)-ACN]; B %: 37%-67%,20 min) to give (3R,4S,5S)-2-(2-(tert-butoxycarbonyl)phenoxy)tetrahydro-2H-pyran-3,4,5-triyl tributyrate (0.4 g, 0.745 mmol, 38.4%) as a yellow oil.

Step 3

To a solution of (3R,4S,5S)-2-(2-(tert-butoxycarbonyl)phenoxy)tetrahydro-2H-pyran-3,4,5-triyl tributyrate (0.2 g, 0.37 mmol) in DCM (10 mL) was added TFA (3.08 g, 27 mmol). Then the mixture was stirred at 15° C. for 16 h under N$_2$. The solvent was removed under reduced pressure. The crude product was purified by prep-HPLC (column: Waters Xbridge 150*25 5 u; mobile phase: [water (0.1% TFA)-ACN]; B %: 47%-67%,12 min) to give the title compound. LCMS: 503 (M+Na$^+$); $^1$H NMR CDCl$_3$ 8.202 (m, 1H), 7.567 (m, 1H), 7.264-7.213 (m, 2H), 5.480-5.351 (m, 4H), 4.061 (m, 1H), 3.8 (m, 1H), 2.425-2.297 (m, 6H), 1.688-1.650 (m, 6H), 0.959 (m, 9H)

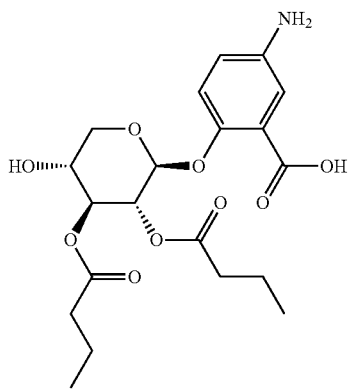 [SMILES: CCCC(=O)O[C@@H]1[C@@H](OC(=O)CCC)[C@H](Oc2ccc(N)cc2C(=O)O)OC[C@H]1O]

Compound 214:5-amino-2-(((2S,3R,4S,5R)-3,4-bis(butyryloxy)-5-hydroxytetrahydro-2H-pyran-2-yl)oxy)benzoic acid Pancreatin from porcine pancreas (200 mg) and FaSSIF/FeSSIF/FaSSGF powder (44.8 mg, sourced from biorelevant.com) were suspended in 20 mL of SIF buffer (10.5 mM sodium hydroxide, 28.6 mM monobasic sodium phosphate monohydrate, 106 mM sodium chloride, pH 6.5) and incubated at 37° C. on a laboratory rocker for 30 minutes. Compound 34 (200 mg, 0.404 mmol, 1 eq) was then added to 20 mL of the SIF suspension and rocked at 37° C. overnight. The suspension was added to a separatory funnel and diluted with additional water (20 mL). Product was extracted with dichloromethane (40 mL) three times, then the organic layer was dried over magnesium sulfate. After filtering out the salts, the solution was concentrated by rotary evaporation and re-dissolved in DMSO before injection and purification by reverse phase C18 column chromatography (gradient: 10% acetonitrile in deionized water to 100% acetonitrile). Fractions containing product were lyophilized to yield the title compound as a white powder (95 mg, 0.223 mmol, 55% yield). LCMS [M–H]$^-$: 424.2. $^1$H NMR (400 MHz, DMSO-d$_6$) δ 6.84 (d, J=8.7 Hz, 1H), 6.76 (d, J=2.8 Hz, 1H), 6.60 (dd, J=8.7, 2.9 Hz, 1H), 5.41 (d, J=5.3 Hz, 1H), 5.02-4.93 (m, 2H), 4.84 (dd, J=9.7, 7.8 Hz, 1H), 3.83 (dd, J=11.3, 5.5 Hz, 1H), 3.71-3.59 (m, 1H), 3.38 (t, J=10.8 Hz, 1H), 2.33-2.08 (m, 4H), 1.56-1.40 (m, 4H), 0.89-0.77 (m, 6H).

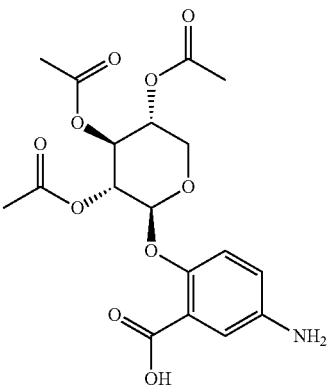 [SMILES: CC(=O)O[C@@H]1[C@@H](OC(C)=O)[C@H](Oc2ccc(N)cc2C(=O)O)OC[C@H]1OC(C)=O]

Compound 215:5-amino-2-(((2S,3R,4S,5R)-3,4,5-triacetoxytetrahydro-2H-pyran-2-yl)oxy)benzoic acid (3R,4S,5R)-tetrahydro-2H-pyran-2,3,4,5-tetrayl tetraacetate (3.90 g, 12.3 mmol) was dissolved in tetrahydrofuran (80.0 mL). The solution was stirred at room temperature when methylamine (40% wt. in water, 1.59 mL, 18.4 mmol) was added dropwise. The mixture was stirred overnight and concentrated to give crude (3R,4S,5R)-2-hydroxytetrahydro-2H-pyran-3,4,5-triyl triacetate as a brown oil.

Crude (3R,4S,5R)-2-hydroxytetrahydro-2H-pyran-3,4,5-triyl triacetate (500 mg, 1.81 mmol) was dissolved in N N-dimethylformamide (4.00 mL) at room temperature. The solution was stirred when benzyl 2-fluoro-5-nitrobenzoate (752 mg, 2.73 mmol) and then 1,4-diazabicyclo[2.2.2]octane (1.06 g, 9.36 mmol) were added. Stirring was continued for 90 h. Water (50 mL) was added and the mixture was extracted with ethyl acetate (5×20 mL). The combined organic layers were washed with water (20 mL), brine (2×20 mL), dried over anhydrous Na$_2$SO$_4$, filtered and concentrated to give a brown oil. The crude material was adsorbed on celite and purified by automated chromatography (40 g, SiO$_2$, 0 to 60% ethyl acetate in hexanes) to afford (2S,3R,4S,5R)-2-(2-((benzyloxy)carbonyl)-4-nitrophenoxy)tetrahydro-2H-pyran-3,4,5-triyl triacetate (413 mg, 43%) as a pale yellow foam. LCMS calcd for C$_{25}$H$_{25}$O$_{12}$ 531.14, found 554.4 [M+Na] at 1.86 min.

(2S,3R,4S,5R)-2-(2-((benzyloxy)carbonyl)-4-nitrophenoxy)tetrahydro-2H-pyran-3,4,5-triyl triacetate (413 mg, 0.777 mmol) was dissolved in methanol (3.00 mL) at room temperature. The solution was stirred under nitrogen when palladium on carbon (10% wt., 50.0 mg, 0.0470 mmol) was added. The mixture was degassed with hydrogen and then stirred under hydrogen overnight. The mixture was filtered on celite and concentrated to give a brown oil. The crude material was purified by automated reverse phase chromatography (24 g, C18, 5 to 40% acetonitrile in 10 mM aqueous ammonium formate) as a solution in N N-dimethylformamide (10% water). After lyophilization, 5-amino-2-(((2S,3R,4S,5R)-3,4,5-triacetoxytetrahydro-2H-pyran-2-yl)oxy)benzoic acid (59.8 mg, 19%) was obtained as a white solid. $^1$H NMR (400 MHz, DMSO-d$_6$) δ 6.87 (d, J=8.8 Hz, 1H), 6.79 (d, J=2.9 Hz, 1H), 6.62 (dd, J=8.7, 2.9 Hz, 1H), 5.21 (t, J=8.8 Hz, 1H), 5.11 (d, J=7.0 Hz, 1H), 4.96 (dd, J=9.0, 7.0 Hz, 1H), 4.89 (td, J=8.9, 5.2 Hz, 1H), 4.04 (dd, J=11.6, 5.2 Hz, 1H), 3.62 (dd, J=11.6, 9.1 Hz, 1H), 2.02-1.97 (m, 9H). LCMS calcd for $C_{18}H_{21}O_{10}$ 411.12, found 410.3 [M−H] at 1.10 min.

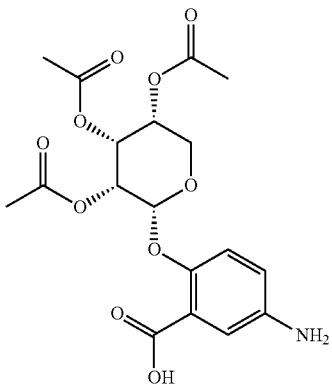 [SMILES: CC(=O)O[C@H]1[C@@H](Oc2ccc(N)cc2C(=O)O)OC[C@@H](OC(C)=O)[C@H]1OC(C)=O]

Compound 216: 5-amino-2-(((2R,3R,4R,5R)-3,4,5-triacetoxytetrahydro-2H-pyran-2-yl)oxy)benzoic acid D-(−)-ribose (1.99 g, 13.1 mmol) was dissolved in pyridine (40 mL) under nitrogen. The solution was stirred when acetic acid (10.0 mL, 106 mmol) and then 4-dimethylaminopyridine (126 mg, 1.01 mmol) were added. Stirring was continued overnight Water (150 mL) was added and after 1 h of additional stirring, the mixture was extracted with ethyl acetate (3×40 mL). The combined organic layers were washed with saturated aqueous NaHCO$_3$ (3×50 mL), water (50 mL), brine (2×50 mL), dried over anhydrous Na$_2$SO$_4$, filtered and concentrated to give a pale yellow oil. The crude material was adsorbed on celite and purified by automated chromatography (80 g, SiO$_2$, 0 to 80% ethyl acetate in heptanes) to afford (3R,4R,5R)-tetrahydro-2H-pyran-2,3,4,5-tetrayl tetraacetate (3.90 g, 93%) as a colorless oil. (3R,4R,5R)-tetrahydro-2H-pyran-2,3,4,5-tetrayl tetraacetate (3.6 g, 11.3 mmol) was dissolved in acetonitrile (14.0 mL) at room temperature. Aqueous perchloric acid (70% wt., 974 μL, 11.3 mmol) was added in one portion and the mixture was stirred for 1 h. The mixture was washed with aqueous saturated NaHCO$_3$, water and brine, dried over anhydrous Na$_2$SO$_4$, filtered and concentrated to give crude (3R,4R,5R)-2-hydroxytetrahydro-2H-pyran-3,4,5-triyl triacetate (1.11 g, 36%). $^1$H NMR (400 MHz, DMSO-d$_6$) δ 7.02 (s, 1H, OH), 5.93-5.82 (m, 1H), 5.51-5.04 (m, 1H), 4.99-4.44 (m, 2H), 3.98-3.38 (m, 2H), 2.12-1.91 (m, 9H).

(3R,4R,5R)-2-hydroxytetrahydro-2H-pyran-3,4,5-triyl triacetate (1.11 g, 4.02 mmol) was dissolved in N N-dimethylformamide (7.0 mL). The solution was stirred at room temperature when benzyl 2-fluoro-5-nitrobenzoate (1.11 g, 4.02 mmol) and then 1,4-diazabicyclo[2.2.2]octane (2.28 g, 20.1 mmol) were added. Stirring was continued for 2 d. Then, water was added. The aqueous layer was extracted with ethyl acetate. The combined organic layers were washed with brine, dried over anhydrous Na$_2$SO$_4$, filtered and concentrated to give a brown oil. The crude material was adsorbed on celite and purified by automated chromatography (SiO$_2$, ethyl acetate gradient in hexanes) to give (3R,4R,5R)-2-(2-((benzyloxy)carbonyl)-4-nitrophenoxy)tetrahydro-2H-pyran-3,4,5-triyl triacetate (295 mg, 14%) as a yellow oil. $^1$H NMR (400 MHz, CDCl$_3$) δ 8.70 (d, J=2.9 Hz, 1H), 8.31 (dd, J=9.2, 2.9 Hz, 1H), 7.44-7.27 (m, 6H), 6.00 (d, J=4.8 Hz, 0.5 Ha), 5.73 (d, J=2.7 Hz, 1Ha'), 5.46 (t, J=3.6 Hz, 1H), 5.38 (app q, J=12.1 Hz, 2H), 5.29-5.26 (m, 1H), 5.15-4.99 (m, 2H), 4.02-3.94 (m, 2H), 3.80 (dd, J=12.9, 3.1 Hz, 1H), 2.20-1.97 (m, 9H). LCMS calcd for $C_{25}H_{25}NO_{12}$ 531.14, found 554.3 [M+Na] at 1.79 min.

(3R,4R,5R)-2-(2-((benzyloxy)carbonyl)-4-nitrophenoxy)tetrahydro-2H-pyran-3,4,5-triyl triacetate (280 mg, 527 μmol) was dissolved in methanol (5.0 mL). Palladium on carbon (10% wt., 22.4 mg, 21.1 μmol) was added to the stirring solution under nitrogen. The mixture was degassed with hydrogen and allowed to stir under hydrogen for 2 h. The mixture was filtered through a pad of celite and washed with methanol and dichloromethane. The filtrate was concentrated and purified by automated reverse phase chromatography (C18, 15 to 25% acetonitrile in 10 mM aqueous ammonium formate). After lyophilisation, 5-amino-2-(((2R,3R,4R,5R)-3,4,5-triacetoxytetrahydro-2H-pyran-2-yl)oxy) benzoic acid (26.7 mg, 12%) as a white solid. $^1$H NMR (400 MHz, DMSO-d$_6$) δ 6.85 (dd, J=5.6, 2.7 Hz, 2H), 6.60 (dd, J=8.6, 2.5 Hz, 1H), 5.36 (t, J=3.6 Hz, 1H), 5.31 (d, J=3.0 Hz, 1H), 5.15 (t, J=3.3 Hz, 1H), 5.09 (d, J=3.2 Hz, 1H), 4.18 (dd, J=12.8, 1.9 Hz, 1H), 3.73 (dd, J=12.7, 3.7 Hz, 1H), 2.04 (d, J=4.3 Hz, 7H), 1.93 (s, 3H). LCMS calcd for $C_{18}H_{21}NO_{10}$ 411.12, found 412.1 [M+H] at 1.02 min.

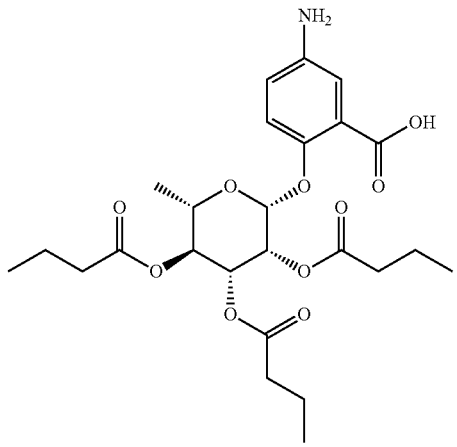 [SMILES: CCCC(=O)O[C@@H]1[C@@H](OC(=O)CCC)[C@H](C)O[C@H](Oc2ccc(N)cc2C(=O)O)[C@@H]1OC(=O)CCC]

Compound 217: 5-amino-2-(((2R,3R,4R,5S,6S)-3,4,5-tris(butyryloxy)-6-methyltetrahydro-2H-pyran-2-yl)oxy)benzoic acid (3R,4R,5S,6S)-2-hydroxy-6-methyltetrahydro-2H-pyran-3,4,5-triyl tributyrate (316 mg, 0.844 mmol), benzyl 2-hydroxy-5-nitrobenzoate (355 mg, 1.30 mmol) and triphenylphosphine (374 mg, 1.43 mmol) were dissolved in dry tetrahydrofuran (2.50 mL) under nitrogen at room temperature. The solution was stirred at 0° C. when di-tert-butyl azodicarboxylate (299 mg, 1.27 mmol) was added in one portion. After 30 min of additional stirring, the flask was removed from the cooling bath, the mixture was allowed to warm up till room temperature and stir overnight. The mixture was adsorbed on celite and purified by automated chromatography (40 g, SiO$_2$, 0 to 30% ethyl acetate in hexanes) to afford (2R,3R,4R,5S,6S)-2-(2-((benzyloxy)carbonyl)-4-nitrophenoxy)-6-methyltetrahydro-2H-pyran-3,4,5-triyl tributyrate (197 mg, 37%). LCMS calcd for C$_{32}$H$_{39}$NO$_{12}$ 629.25, found 647.0 [M+NH$_4$] at 2.20 min.

(2R,3R,4R,5S,6S)-2-(2-((benzyloxy)carbonyl)-4-nitrophenoxy)-6-methyltetrahydro-2H-pyran-3,4,5-triyl tributyrate (197 mg, 0.313 mmol) was dissolved in methanol (2.50 mL) at room temperature. The solution was stirred under nitrogen when palladium on carbon (10% wt., 2.30 mg, 0.0216 mmol) was added in one portion. The suspension was stirred, degassed with hydrogen and allowed to stir under hydrogen overnight. The mixture was diluted with dichloromethane and filtered on celite. The crude material was concentrated and purified by automated reverse phase chromatography (12 g, C18, 10 to 60% acetonitrile in 10 mM aqueous ammonium formate) as a solution in N N-dimethylformamide (10% water). After lyophilisation, 5-amino-2-(((2R,3R,4R,5S,6S)-3,4,5-tris(butyryloxy)-6-methyltetrahydro-2H-pyran-2-yl)oxy)benzoic acid (78.4 mg, 49%) was obtained as a white solid. $^1$H NMR (400 MHz, DMSO-d$_6$) δ 6.89 (d, J=2.9 Hz, 1H), 6.87 (d, J=8.7 Hz, 1H), 6.65 (dd, J=8.7, 2.9 Hz, 1H), 5.58 (dd, J=3.3, 0.9 Hz, 1H), 5.30 (d, J=1.0 Hz, 1H), 5.18 (dd, J=10.2, 3.4 Hz, 1H), 5.05 (br s, 2H), 4.90 (t, J=9.9 Hz, 1H), 3.80-3.70 (m, J=6.2 Hz, 1H), 2.41-2.34 (m, 2H), 2.33-2.22 (m, 2H), 2.14 (td, J=7.2, 3.2 Hz, 2H), 1.66-1.56 (m, 2H), 1.56-1.42 (m, 4H), 1.12 (d, J=6.2 Hz, 3H), 0.94 (t, J=7.4 Hz, 3H), 0.89-0.80 (m, 6H). LCMS calcd for C$_{25}$H$_{35}$NO$_{10}$ 509.23, found 508.3 [M−H] at 1.74 min.

bined organic layers were washed with brine, dried over anhydrous Na$_2$SO$_4$, filtered and concentrated to give a brown oil. The crude material was adsorbed on celite to be purified by automated chromatography (SiO$_2$, ethyl acetate gradient in hexanes) to afford (3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 45%). LCMS calcd for C$_{36}$H$_{45}$NO$_{14}$ 715.28, found 733.6 [M+NH$_4$] at 2.26 min.

(3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 236 μmol) was dissolved in methanol (5.0 mL) at room temperature. The solution was stirred under nitrogen when palladium on carbon (10% wt., 25.1 mg, 23.6 μmol) was added in one portion. Then, the solvent was degassed with hydrogen and the reaction was allowed to stir under hydrogen for 2 h. The mixture was diluted with dichloromethane and filtered on celite. The crude material was purified by automated reverse phase chromatography (C18, 25% to 65% acetonitrile in 10 mM aqueous ammonium formate). After lyophilisation, 5-amino-2-(((2S,3R,4S,5R,6R)-3,4,5-tris(butyryloxy)-6-((butyryloxy)methyl)tetrahydro-2H-pyran-2-yl)oxy)benzoic acid (32.3 mg, 23%) was obtained as a white solid $^1$H NMR (400 MHz, DMSO-d$_6$) δ 6.88 (d, J=8.8 Hz, 1H), 6.76 (d, J=2.8 Hz, 1H), 6.60 (dd, J=8.8, 2.8 Hz, 1H), 5.36 (t, J=9.6 Hz, 1H), 5.21 (d, J=8.0 Hz, 1H), 5.03-4.93 (m, 3H), 4.18-4.05 (m, 2H, H), 2.30-2.09 (m, 8H), 1.58-1.39 (m, 8H), 0.90-0.77 (m, 12H). LCMS calcd for C$_{29}$H$_{41}$N$_{12}$ 595.26, found 613.3 [M+NH$_4$].

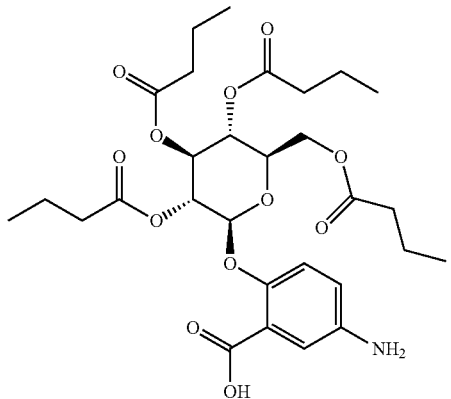 [SMILES: CCCC(=O)OC[C@H]1O[C@@H](Oc2ccc(N)cc2C(=O)O)[C@H](OC(=O)CCC)[C@@H](OC(=O)CCC)[C@@H]1OC(=O)CCC]

Compound 218: 5-amino-2-(((2S,3R,4S,5R,6R)-3,4,5-tris(butyryloxy)-6-((butyryloxy)methyl)tetrahydro-2H-pyran-2-yl)oxy)benzoic acid 2R,3R,4S,5R)-2-((butyryloxy)methyl)-6-hydroxytetrahydro-2H-pyran-3,4,5-triyl tributyrate (239 mg, 519 μmol) was dissolved in N N-dimethylformamide (1 mL). The solution was stirred at room temperature when benzyl 2-fluoro-5-nitrobenzoate (186 mg, 675 μmol) and then 1,4-diazabicyclo[2.2.2]octane (294 mg, 2.59 mmol) were added. Stirring was continued for 2 d and water was added. The aqueous layer was extracted with ethyl acetate. The com-

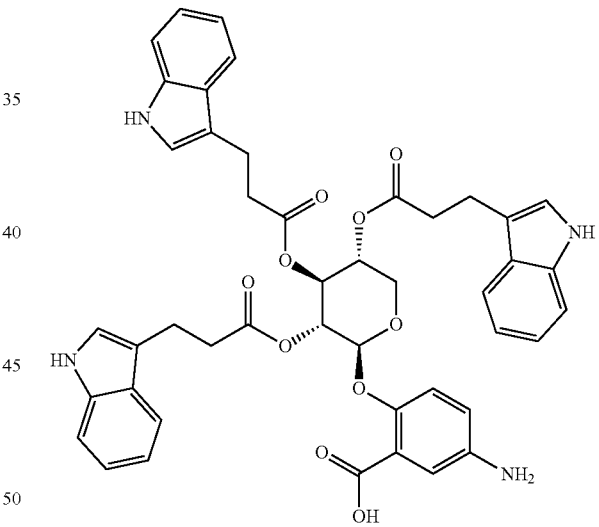

Compound 219: 5-amino-2-(((2S,3R,4S,5R)-3,4,5-tris((3-(1H-indol-3-yl)propanoyl)oxy)tetrahydro-2H-pyran-2-yl)oxy)benzoic acid 3-Indolepropionic acid (20.0 g, 104 mmol) and dicyclohexylcarbodiimide (10.3 g, 49.3 mmol) were dissolved in tetrahydrofuran (345 mL). The reaction was stirred under nitrogen for 2 d. The solution was filtered, washed with tetrahydrofuran and the filtrate was concentrated to give crude 3-(1H-indol-3-yl)propanoic anhydride (26 g, 69%).

Crude 3-(1H-indol-3-yl)propanoic anhydride (26.0 g, 72.1 mmol) was dissolved in pyridine (150 mL) under nitrogen. 4-dimethylaminopyridine (450 mg, 3.61 mmol) and d-(+)-xylose (1.11 g, 7.43 mmol) were added. The mixture was stirred for 24 h. 1 N aqueous hydrochloric acid was added and the aqueous layer was extracted with ethyl acetate. The combined organic layers were concentrated. The crude material was purified by automated reverse phase chromatography (C18, 60 to 65% acetonitrile in 10 mM aqueous ammonium formate) to afford (3R,4S,5R)-tetrahydro-2H-pyran-2,3,4,5-tetrayl tetrakis(3-(1H-indol-3-yl)propanoate (3.49 g, 58%) as a yellow suspension. LCMS calcd for $C_{49}H_{46}N_4O_9$ 834.33, found 833.6 [M–H] at 2.05 min.

(3R,4S,5R)-tetrahydro-2H-pyran-2,3,4,5-tetrayl tetrakis (3-(1H-indol-3-yl)propanoate) (1.06 g, 1.27 mmol) was dissolved in acetonitrile (13.0 mL) at room temperature. Aqueous perchloric acid (70% wt., 110 μL, 1.27 mmol) was added and the mixture was stirred for 3 h. The mixture was washed with saturated aqueous $NaHCO_3$, water and brine and dried over anhydrous $Na_2SO_4$, filtered and concentrated. The crude material was purified by automated reverse phase chromatography (C18, acetonitrile in 10 mM aqueous ammonium formate). After lyophilisation, (3R,4S,5R)-2-hydroxytetrahydro-2H-pyran-3,4,5-triyl tris(3-(1H-indol-3-yl)propanoate (121 mg, 14%) was obtained as a yellow solid. $^1$H NMR (400 MHz, DMSO-$d_6$) δ 10.75 (s, 3H), 7.46-7.34 (m, 3H), 7.25 (d, J=10.6 Hz, 3H), 7.02 (m, 8H), 6.94-6.82 (m, 4H), 5.41 (t, J=9.8 Hz, 0.5H), 5.26 (s, 0.3H), 5.16 (s, 1H), 4.92-4.69 (m, 2H), 3.64 (m, 2H), 2.84 (dd, J=15.8, 7.8 Hz, 6H), 2.53-2.49 (m, 6H). LCMS calcd for $C_{38}H_{37}N_3O_8$ 663.26, found 681.2 [M+$NH_4$] at 1.80 min.

(3R,4S,5R)-2-hydroxytetrahydro-2H-pyran-3,4,5-triyl tris(3-(1H-indol-3-yl)propanoate) (121 mg, 182 μmol) was dissolved in N N-dimethylformamide (600 μL). The solution was stirred at room temperature when benzyl 2-fluoro-5-nitrobenzoate (65.2 mg, 237 μmol) and then 1,4-diazabicyclo[2.2.2]octane (102 mg, 912 μmol) were added. Stirring was continued for 2 d. Then, water was added. The aqueous layer was extracted with ethyl acetate. The combined organic layers were washed with brine, dried over anhydrous $Na_2SO_4$, filtered and concentrated to give a brown oil. The crude material was adsorbed on celite and purified by automated chromatography ($SiO_2$, ethyl acetate gradient in hexanes) to afford (3R,4S,5R)-2-(2-((benzyloxy)carbonyl)-4-nitrophenoxy)tetrahydro-2H-pyran-3,4,5-triyl tris(3-(1H-indol-3-yl)propanoate) (36.0 mg, 21%) as a yellow oil. LCMS calcd for $C_{52}H_{46}N_4O_{12}$ 918.31, found 936 [M+$NH_4$] at 2.10 min.

(3R,4S,5R)-2-(2-((benzyloxy)carbonyl)-4-nitrophenoxy) tetrahydro-2H-pyran-3,4,5-triyl tris(3-(1H-indol-3-yl)propanoate) (36.0 mg, 39.2 μmol) was dissolved in methanol (800 μL) and stirred at room temperature under nitrogen. To this stirring solution, palladium on carbon (10% wt. 4.17 mg, 3.92 μmol) was added. The suspension was degassed with hydrogen and allowed to stir under hydrogen for 2 h. The mixture was filtered through celite and washed with methanol. The filtrate was concentrated under vacuo. The crude material was purified by preparative HPLC-MS (CSH column, acetonitrile in 10 mM aqueous ammonium formate). After lyophilisation, 3-carboxy-4-(((2S,3R,4S,5R)-3,4,5-tris((3-(1H-indol-3-yl)propanoyl)oxy)tetrahydro-2H-pyran-2-yl)oxy)benzenaminium formate (4.20 mg, 13%) was obtained as a white solid. $^1$H NMR (400 MHz, DMSO-$d_6$) δ 10.77 (t, J=12.5 Hz, 3H), 8.40 (s, 3H), 7.53-7.38 (m, 3H), 7.28 (dd, J=8.0, 4.8 Hz, 3H), 7.03 (dd, J=13.2, 4.9 Hz, 6H), 6.96-6.85 (m, 3H), 6.82-6.67 (m, 2H), 6.53 (d, J=7.0 Hz, 1H), 5.29 (t, J=8.5 Hz, 1H), 5.18 (d, J=6.7 Hz, 1H), 5.06-5.01 (m, 1H), 4.91 (dd, J=13.5, 8.3 Hz, 1H), 3.98 (dd, J=11.6, 4.9 Hz, 1H), 3.60-3.51 (m, 1H), 2.91-2.79 (m, 7H), 2.74-2.67 (m, 1H), 2.63-2.54 (m, 4H). LCMS calcd for $C_{45}H_{42}N_4O_{10}$ 798.29, found 816 [M+$NH_4$] at 1.80 min.

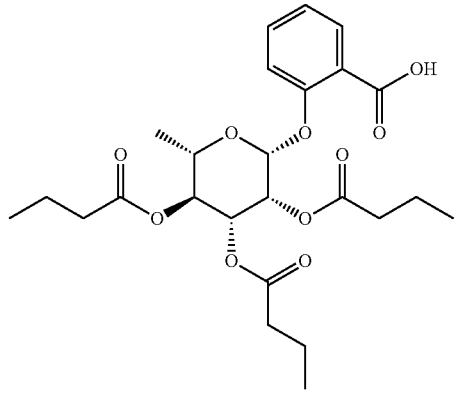 [SMILES: CCCC(=O)O[C@@H]1[C@@H](OC(=O)CCC)[C@H](C)O[C@H](Oc2ccccc2C(=O)O)[C@@H]1OC(=O)CCC]

Compound 220: 2-(((2R,3R,4R,5S,6S)-3,4,5-tris (butyryloxy)-6-methyltetrahydro-2H-pyran-2-yl) oxy)benzoic acid (3R,4R,5S,6S)-2-hydroxy-6-methyltetrahydro-2H-pyran-3,4,5-triyl tributyrate (1.20 g, 3.20 mmol), benzyl 2-hydroxybenzoate (1.10 g, 4.81 mmol) and triphenylphosphine (1.27 g, 4.81 mmol) were dissolved in tetrahydrofuran (54.0 mL) and stirred at 0° C. Di-tert-butyl azodicarboxylate (1.11 g, 4.81 mmol) was added portion wise and the reaction mixture was stirred at 0° C. for 1 h and allowed to warm up till room temperature to stir overnight. The mixture was adsorbed on silica to be purified by automated chromatography (100 g, $SiO_2$, 0 to 35% ethyl acetate in hexanes). (2S,3R,4R,5S,6S)-2-(2-((benzyloxy)carbonyl)phenoxy)-6-methyltetrahydro-2H-pyran-3,4,5-triyl tributyrate (165 mg, 8.1%) and (2R,3R,4R,5S,6S)-2-(2-((benzyloxy)carbonyl) phenoxy)-6-methyltetrahydro-2H-pyran-3,4,5-triyl tributyrate (427 mg, 21%) were separated but containing other impurities.

(2S,3R,4R,5S,6S)-2-(2-((benzyloxy)carbonyl)phenoxy)-6-methyltetrahydro-2H-pyran-3,4,5-triyl tributyrate (166 mg, 284 μmol) was dissolved in methanol (9.00 mL) and stirred at room temperature under nitrogen. To this mixture was added palladium on carbon (10% wt., 11.0 mg, 73.0 μmol). The suspension was degassed with hydrogen and stir under hydrogen overnight. The mixture was filtered through celite and washed with methanol. The filtrate was concentrated under vacuo. The crude material was purified by automated chromatography (25 g, $SiO_2$, 0 to 100% ethyl acetate in hexanes) as a solution in dichloromethane to afford 2-(((2S,3R,4R,5S,6S)-3,4,5-tris(butyryloxy)-6-methyltetrahydro-2H-pyran-2-yl)oxy)benzoic acid (9 mg, 6%) as a white solid. $^1$H NMR (400 MHz, DMSO-$d_6$) δ 7.71 (d, J=8.2 Hz, 1H), 7.51 (t, J=8.1 Hz, 1H), 7.29 (d, J=8.0 Hz, 1H), 7.14 (t, J=7.9 Hz, 1H), 5.76 (d, J=3.1 Hz, 2H), 5.43 (d, J=8.3 Hz, 2H), 5.02 (t, J=9.8 Hz, 1H), 1.54 (ddt, J=22.7, 14.8, 7.4 Hz, 6H), 1.05 (d, J=6.3 Hz, 3H), 0.95 (t, J=7.4 Hz, 3H), 0.85 (q, J=7.4 Hz, 6H). LCMS calcd for $C_{25}H_{34}O_{10}$ 494.22, found 512.3 [M+$NH_4$] at 1.94 min.

(2R,3R,4R,5S,6S)-2-(2-((benzyloxy)carbonyl)phenoxy)-6-methyltetrahydro-2H-pyran-3,4,5-triyl tributyrate (427 mg, 711 μmol) was dissolved methanol (9.00 mL) and stirred at room temperature under nitrogen. To this mixture was added palladium on carbon (10% wt., 11.0 mg, 73.0 μmol). The suspension was degassed with hydrogen and stir under hydrogen overnight. The mixture was filtered through celite and washed with methanol. The filtrate was concentrated under vacuo. The crude material was purified by automated chromatography (50 g, SiO$_2$, 0 to 100% ethyl acetate in hexanes) as a solution in dichloromethane to afford 2-(((2R,3R,4R,5S,6S)-3,4,5-tris(butyryloxy)-6-methyltetrahydro-2H-pyran-2-yl)oxy)benzoic acid (18 mg, 5%) as a white solid. $^1$H NMR (400 MHz, DMSO-d$_6$) δ 7.62 (dd, J=7.5, 1.6 Hz, 1H), 7.46 (t, J=7.9 Hz, 1H), 7.14 (d, J=7.8 Hz, 1H), 7.08 (td, J=7.6, 0.8 Hz, 1H), 5.68 (d, J=0.8 Hz, 1H), 5.55 (dd, J=3.5, 1.0 Hz, 1H), 5.22 (dd, J=10.2, 3.4 Hz, 1H), 4.90 (t, J=9.9 Hz, 1H), 3.90-3.82 (m, 1H), 2.38 (t, J=7.1 Hz, 2H), 2.27 (m, 2H), 2.13 (td, J=7.2, 2.7 Hz, 2H), 1.60 (m, 2H), 1.48 (m, 4H), 1.12 (d, J=6.2 Hz, 3H), 0.93 (t, J=7.4 Hz, 3H), 0.85 (t, J=8.5 Hz, 3H), 0.83 (t, J=8.1 Hz, 3H). LCMS calcd for C$_{25}$H$_{34}$O$_{10}$ 494.22, found 493.3 [M−H] at 1.87 min.

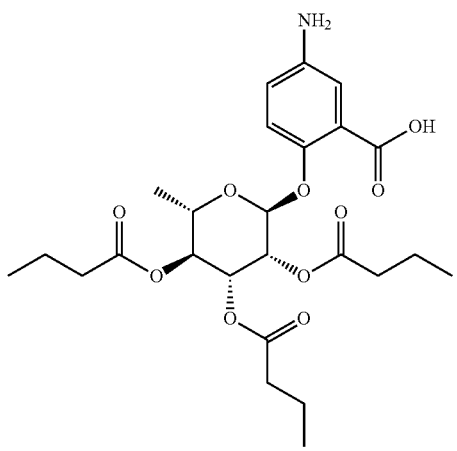 [SMILES: CCCC(=O)O[C@@H]1[C@@H](OC(=O)CCC)[C@H](C)O[C@@H](Oc2ccc(N)cc2C(=O)O)[C@@H]1OC(=O)CCC]

Compound 221: 5-amino-2-(((2S,3R,4R,5S,6S)-3,4,5-tris(butyryloxy)-6-methyltetrahydro-2H-pyran-2-yl)oxy)benzoic acid (3R,4R,5S,6S)-2-hydroxy-6-methyltetrahydro-2H-pyran-3,4,5-triyl tributyrate (197 mg, 0.526 mmol) and benzyl 2-fluoro-5-nitrobenzoate (194 mg, 0.705 mmol) were dissolved in N N-dimethylformamide (1.0 mL) at room temperature. The solution was stirred when 1,4-diazabicyclo[2.2.2]octane (282 mg, 2.51 mmol) was added in one portion and stirring was continued for 88 h. Water (60 mL) was added and the aqueous layer was extracted with ethyl acetate (3×20 mL). The combined organic layers were washed with brine (3×20 mL), dried over anhydrous Na$_2$SO$_4$, filtered and concentrated. The crude material was adsorbed on celite and purified by automated chromatography (12 g, SiO$_2$, 0 to 20% ethyl acetate in hexanes) to afford (2S,3R,4R,5S,6S)-2-(2-((benzyloxy)carbonyl)-4-nitrophenoxy)-6-methyltetrahydro-2H-pyran-3,4,5-triyl tributyrate (136 mg, 41%) as a colorless gum. $^1$H NMR (400 MHz, CDCl$_3$) δ 8.75 (d, J=2.9 Hz, 1H), 8.33 (dd, J=9.2, 2.9 Hz, 1H), 7.51-7.46 (m, 2H), 7.41-7.30 (m, 4H), 5.66 (d, J=1.9 Hz, 1H), 5.61 (dd, J=10.2, 3.5 Hz, 1H), 5.58-5.44 (m, 3H), 5.23 (t, J=10.0 Hz, 1H), 3.99-3.91 (m, 1H), 2.51-2.38 (m, 2H), 2.31-2.20 (m, 4H), 1.77-1.67 (m, 2H), 1.67-1.57 (m, 4H), 1.18 (d, J=6.3 Hz, 3H), 1.01 (t, J=7.4 Hz, 3H), 0.97-0.90 (m, 6H). LCMS calcd for C$_{32}$H$_{39}$NO$_{12}$ 629.25, found 647.1 [M+NH$_4$] at 2.25 min.

(2S,3R,4R,5S,6S)-2-(2-((benzyloxy)carbonyl)-4-nitrophenoxy)-6-methyltetrahydro-2H-pyran-3,4,5-triyl tributyrate (136 mg, 0.216 mmol) was dissolved in methanol (2.00 mL) at room temperature under nitrogen. Palladium on carbon (10% wt., 2.30 mg, 0.0216 mmol) was added in one portion. The suspension was stirred, degassed with hydrogen and allowed to stir under hydrogen overnight. The mixture was diluted with dichloromethane and filtered on celite. The filtrate was concentrated and this material was purified by preparative HPLC-MS (CSH column, 40 to 60% acetonitrile in 10 mM aqueous ammonium formate) as a solution in N N-dimethylformamide (10% water). After lyophilization, 5-amino-2-(((2S,3R,4R,5S,6S)-3,4,5-tris(butyryloxy)-6-methyltetrahydro-2H-pyran-2-yl)oxy)benzoic acid (70.9 mg, 64%) was obtained as a white solid. $^1$H NMR (400 MHz, DMSO-d$_6$) δ 6.93 (d, J=2.9 Hz, 1H), 6.90 (d, J=8.7 Hz, 1H), 6.66 (dd, J=8.7, 2.9 Hz, 1H), 5.45 (dd, J=3.4, 1.8 Hz, 1H), 5.32 (dd, J=10.2, 3.4 Hz, 1H), 5.30 (d, J=1.4 Hz, 1H), 5.21-5.03 (m, 2H), 5.00 (t, J=10.1 Hz, 1H), 4.20-4.12 (m, 1H), 2.40-2.22 (m, 4H), 2.15 (td, J=7.2, 1.3 Hz, 2H), 1.64-1.43 (m, 6H), 1.08 (d, J=6.3 Hz, 3H), 0.93 (t, J=7.4 Hz, 3H), 0.89-0.81 (m, 6H). LCMS calcd for C$_{25}$H$_{35}$NO$_{10}$ 509.23, found 508.3 [M−H] at 1.78 min.

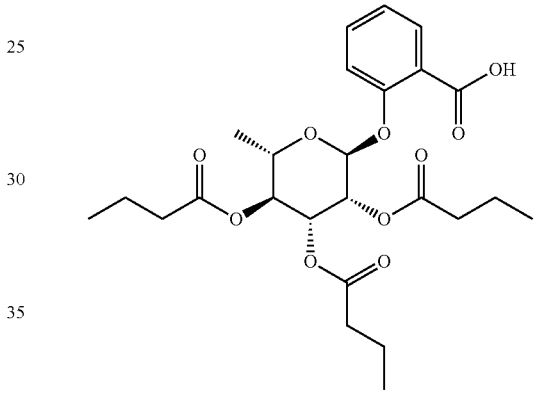

Compound 222: 2-(((2S,3R,4R,5S,6S)-3,4,5-tris(butyryloxy)-6-methyltetrahydro-2H-pyran-2-yl)oxy)benzoic acid (3R,4R,5S,6S)-2-hydroxy-6-methyltetrahydro-2H-pyran-3,4,5-triyl tributyrate (1.20 g, 3.20 mmol), benzyl 2-hydroxybenzoate (1.10 g, 4.81 mmol) and triphenylphosphine (1.27 g, 4.81 mmol) were dissolved in tetrahydrofuran (54.0 mL) and stirred at 0° C. Di-tert-butyl azodicarboxylate (1.11 g, 4.81 mmol) was added portion wise and the reaction mixture was stirred at 0° C. for 1 h and allowed to warm up till room temperature to stir overnight. The mixture was adsorbed on silica to be purified by automated chromatography (100 g, SiO$_2$, 0 to 35% ethyl acetate in hexanes). (2S,3R,4R,5S,6S)-2-(2-((benzyloxy)carbonyl)phenoxy)-6-methyltetrahydro-2H-pyran-3,4,5-triyl tributyrate (165 mg, 8.1%) and (2R,3R,4R,5S,6S)-2-(2-((benzyloxy)carbonyl)phenoxy)-6-methyltetrahydro-2H-pyran-3,4,5-triyl tributyrate (427 mg, 21%) were separated but containing other impurities.

(2S,3R,4R,5S,6S)-2-(2-((benzyloxy)carbonyl)phenoxy)-6-methyltetrahydro-2H-pyran-3,4,5-triyl tributyrate (166 mg, 284 μmol) was dissolved in methanol (9.00 mL) and stirred at room temperature under nitrogen. To this mixture was added palladium on carbon (10% wt., 11.0 mg, 73.0 μmol). The suspension was degassed with hydrogen and stir under hydrogen overnight. The mixture was filtered through celite and washed with methanol. The filtrate was concentrated under vacuo. The crude material was purified by automated chromatography (25 g, SiO2, 0 to 100% ethyl acetate in hexanes) as a solution in dichloromethane to afford 2-(((2S,3R,4R,5S,6S)-3,4,5-tris(butyryloxy)-6-methyltetrahydro-2H-pyran-2-yl)oxy)benzoic acid (9 mg, 6%) as a white solid. 1H NMR (400 MHz, DMSO-d6) δ 7.71 (d, J=8.2 Hz, 1H), 7.51 (t, J=8.1 Hz, 1H), 7.29 (d, J=8.0 Hz, 1H), 7.14 (t, J=7.9 Hz, 1H), 5.76 (d, J=3.1 Hz, 2H), 5.43 (d, J=8.3 Hz, 2H), 5.02 (t, J=9.8 Hz, 1H), 1.54 (ddt, J=22.7, 14.8, 7.4 Hz, 6H), 1.05 (d, J=6.3 Hz, 3H), 0.95 (t, J=7.4 Hz, 3H), 0.85 (q, J=7.4 Hz, 6H). LCMS calcd for C25H34O10 494.22, found 512.3 [M+NH4] at 1.94 min.

(2R,3R,4R,5S,6S)-2-(2-((benzyloxy)carbonyl)phenoxy)-6-methyltetrahydro-2H-pyran-3,4,5-triyl tributyrate (427 mg, 711 μmol) was dissolved methanol (9.00 mL) and stirred at room temperature under nitrogen. To this mixture was added palladium on carbon (10% wt., 11.0 mg, 73.0 μmol). The suspension was degassed with hydrogen and stir under hydrogen overnight. The mixture was filtered through celite and washed with methanol. The filtrate was concentrated under vacuo. The crude material was purified by automated chromatography (50 g, SiO2, 0 to 100% ethyl acetate in hexanes) as a solution in dichloromethane to afford 2-(((2R,3R,4R,5S,6S)-3,4,5-tris(butyryloxy)-6-methyltetrahydro-2H-pyran-2-yl)oxy)benzoic acid (18 mg, 5%) as a white solid. 1H NMR (400 MHz, DMSO-d6) δ 7.62 (dd, J=7.5, 1.6 Hz, 1H), 7.46 (t, J=7.9 Hz, 1H), 7.14 (d, J=7.8 Hz, 1H), 7.08 (td, J=7.6, 0.8 Hz, 1H), 5.68 (d, J=0.8 Hz, 1H), 5.55 (dd, J=3.5, 1.0 Hz, 1H), 5.22 (dd, J=10.2, 3.4 Hz, 1H), 4.90 (t, J=9.9 Hz, 1H), 3.90-3.82 (m, 1H), 2.38 (t, J=7.1 Hz, 2H), 2.27 (m, 2H), 2.13 (td, J=7.2, 2.7 Hz, 2H), 1.60 (m, 2H), 1.48 (m, 4H), 1.12 (d, J=6.2 Hz, 3H), 0.93 (t, J=7.4 Hz, 3H), 0.85 (t, J=8.5 Hz, 3H), 0.83 (t, J=8.1 Hz, 3H). LCMS calcd for C25H34O10 494.22, found 493.3 [M−H].

was concentrated. The crude material was purified by automated chromatography (SiO2, 30% ethyl acetate in hexanes) to afford (3S,4R,5R,6S)-2-(2-(tert-butoxycarbonyl)-4-((tert-butoxycarbonyl)amino)phenoxy)-6-methyltetrahydro-2H-pyran-3,4,5-triyl tributyrate (213 mg, 24%). [M+NH4+]= 683, room temperature=2.21. 1H NMR (400 MHz, CDCl3) δ 7.58-6.95 (m, 3H), 5.48 (dd, J=10.5, 8.0 Hz, 1H), 5.28 (d, J=3.4 Hz, 1H), 5.10 (dd, J=10.4, 3.4 Hz, 1H), 5.00 (d, J=8.0 Hz, 1H), 3.88 (q, J=6.5 Hz, 1H), 2.55-2.15 (m, 2H), 1.76-1.56 (m, 3H), 1.55 (s, 4H), 1.49 (s, 3H), 1.46 (s, 2H), 1.26-1.14 (m, 2H), 0.99 (t, J=7.4 Hz, 1H), 0.89 (t, J=7.4 Hz, 2H).

(3S,4R,5R,6S)-2-(2-(tert-butoxycarbonyl)-4-((tert-butoxycarbonyl)amino)phenoxy)-6-methyltetrahydro-2H-pyran-3,4,5-triyl tributyrate (200 mg, 300 μmol) was dissolved in dichloromethane (2.00 mL) at 0° C. To the solution was added hydrochloric acid (4 M in 1,4-dioxane, 158 μL, 631 μmol). The resulting mixture was stirred at 0° C. for 30 min, then at room temperature for 2 h. Solvents were evaporated and the residue was purified by automated reverse phase chromatography (C18, acetonitrile in 10 mM aqueous ammonium formate) After lyophilisation, 5-amino-2-(((3S,4R,5R,6S)-3,4,5-tris(butyryloxy)-6-methyltetrahydro-2H-pyran-2-yl)oxy)benzoic acid (10.0 mg, 13%) was obtained as a white solid. 1H NMR (400 MHz, DMSO-d6) δ 6.86 (d, J=9.1 Hz, 1H), 6.74 (d, J=2.9 Hz, 1H), 6.60 (dd, J=9.8, 2.1 Hz, 1H), 5.21-5.06 (m, 4H), 5.01-4.91 (m, 1H), 2.67-2.63 (m, 1H), 2.53 (s, 1H), 2.45-2.07 (m, 7H), 1.60 (dt, J=14.6, 7.3 Hz, 2H), 1.52-1.39 (m, 4H), 1.07 (d, J=6.4 Hz, 3H), 0.92 (t, J=7.4 Hz, 3H), 0.80 (t, J=7.4 Hz, 6H). LCMS calcd for C25H35NO10 509.23, found 508.2 [M−H] at 1.68 min.

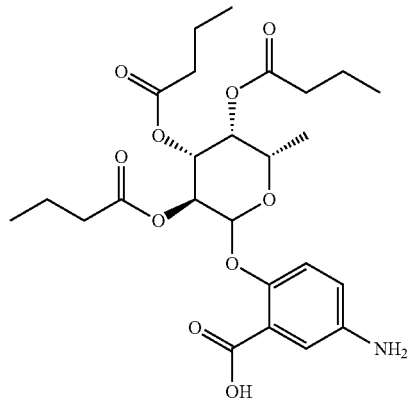 [SMILES: CCCC(=O)O[C@@H]1[C@H](OC(=O)CCC)[C@H](C)OC(Oc2ccc(N)cc2C(=O)O)[C@H]1OC(=O)CCC]

Compound 223: 5-amino-2-(((3S,4R,5R,6S)-3,4,5-tris(butyryloxy)-6-methyltetrahydro-2H-pyran-2-yl)oxy)benzoic acid (3S,4R,5R,6S)-2-hydroxy-6-methyltetrahydro-2H-pyran-3,4,5-triyl tributyrate (500 mg, 1.34 mmol), tert-butyl 5-((tert-butoxycarbonyl)amino)-2-hydroxybenzoate (620 mg, 2.00 mmol) and triphenylphosphine (531 mg, 2.00 mmol) were dissolved in tetrahydrofuran (22.0 mL) and stirred at 0° C. Di-tert-butyl azodicarboxylate (471 mg, 2.00 mmol) was added and stirring was continued at 0° C. for 1 h, then at room temperature overnight. The reaction mixture

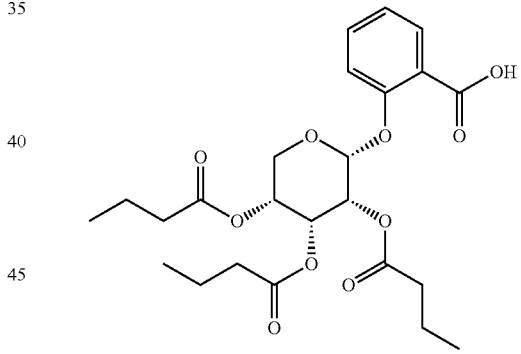

Compound 224: 2-(((3R,4R,5R)-3,4,5-tris(butyryloxy)tetrahydro-2H-pyran-2-yl)oxy)benzoic acid (3R,4R,5R)-2-hydroxytetrahydro-2H-pyran-3,4,5-triyl tributyrate (200 mg, 555 μmol), benzyl 2-hydroxybenzoate (190 mg, 832 μmol) and triphenylphosphine (221 mg, 832 μmol) were dissolved in tetrahydrofuran (4.0 mL) and stirred at 0° C. Di-tert-butyl azodicarboxylate (196 mg, 832 μmol) was added and stirring continued at 0° C. for 1 h, then at room temperature overnight. The reaction mixture was concentrated and purified by automated chromatography (SiO2, ethyl acetate gradient in hexanes) to afford (2R,3R,4R,5R)-2-(2-((benzyloxy)carbonyl)phenoxy)tetrahydro-2H-pyran-3,4,5-triyl tributyrate (229 mg, 72%) as a colorless oil. 1H NMR (400 MHz, CDCl3) δ 7.74 (dd, J=7.7, 1.8 Hz, 1H), 7.46-7.31 (m, 6H), 7.19 (d, J=8.3 Hz, 1H), 7.08 (t, J=7.5 Hz, 1H), 5.57 (broad s, 1H), 5.51 (d, J=3.4 Hz, 1H), 5.31 (dd, J=29.5, 12.5 Hz, 2H), 5.22 (broad s, 1H), 5.15-5.09 (m, 1H), 4.21 (dd, J=11.3, 8.8 Hz, 1H), 3.65 (dd, J=11.3, 4.2 Hz, 1H), 2.50-2.26 (m, 6H), 1.74-1.57 (m, 6H), 1.01-0.84 (m, 9H). LCMS calcd for $C_{31}H_{38}O_{10}$ 570.25, found 588.4 [M+NH$_4$] at 2.19 min.

(2R,3R,4R,5R)-2-(2-((benzyloxy)carbonyl)phenoxy)tetrahydro-2H-pyran-3,4,5-triyl tributyrate (229 mg, 401 µmol) was dissolved in methanol (4.0 mL) at room temperature. The solution was stirred under nitrogen when palladium on carbon (10% wt., 42.7 mg, 40.1 µmol) was added in one portion. The mixture was degassed with hydrogen and allowed to stir under hydrogen for 3 h. The mixture was diluted with dichloromethane and filtered on celite. The crude material was adsorbed on celite and purified by automated reverse phase chromatography (C18, acetonitrile in 10 mM aqueous ammonium formate). After lyophilisation, 2-(((2R,3R,4R,5R)-3,4,5-tris(butyryloxy)tetrahydro-2H-pyran-2-yl)oxy)benzoic acid obtained as an oil (92.0 mg, 48%). $^1$H NMR (400 MHz, DMSO-d$_6$) δ 7.61 (dd, J=7.7, 1.7 Hz, 1H), 7.51-7.44 (m, 1H), 7.18 (d, J=8.4 Hz, 1H), 7.09 (t, J=7.5 Hz, 1H), 5.63 (broad d, J=2.7 Hz, 1H), 5.45 (broad t, J=3.4 Hz, 1H), 5.31 (broad t, J=2.9 Hz, 1H), 5.09 (broad dt, J=6.6, 3.5 Hz, 1H), 4.00 (dd, J=12.0, 6.3 Hz, 1H), 3.81 (dd, J=12.0, 3.2 Hz, 1H), 2.38-2.19 (m, 6H), 1.62-1.44 (m, 6H), 0.86 (td, J=7.4, 2.9 Hz, 9H). UP-LCMS calcd for $C_{24}H_{32}O_{10}$ 480.20, found 503.2 [M+Na] at 1.72 min.

Compound 225 5-amino-2-(((2R,3R,4S,5R,6R)-3,4,5-tris(butyryloxy)-6-((butyryloxy)methyl)tetrahydro-2H-pyran-2-yl)oxy)benzoic acid Compound 225 was isolated as a minor isomer during the preparation of compound 218.

(2R,3R,4S,5R)-2-((butyryloxy)methyl)-6-hydroxytetrahydro-2H-pyran-3,4,5-triyl tributyrate (239 mg, 519 µmol) was dissolved in N N-dimethylformamide (1 mL). The solution was stirred at room temperature when benzyl 2-fluoro-5-nitrobenzoate (186 mg, 675 µmol) and then 1,4-diazabicyclo[2.2.2]octane (294 mg, 2.59 mmol) were added. Stirring was continued for 2 d and water was added. The aqueous layer was extracted with ethyl acetate. The combined organic layers were washed with brine, dried over anhydrous Na$_2$SO$_4$, filtered and concentrated to give a brown oil. The crude material was adsorbed on celite to be purified by automated chromatography (SiO$_2$, ethyl acetate gradient in hexanes) to afford (3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 45%). LCMS calcd for $C_{36}H_{45}NO_{14}$ 715.28, found 733.6 [M+NH$_4$] at 2.26 min.

(3R,4S,5R,6R)-2-(2-((benzyloxy)carbonyl)-4-nitrophenoxy)-6-((butyryloxy)methyl)tetrahydro-2H-pyran-3,4,5-triyl tributyrate (169 mg, 236 µmol) was dissolved in methanol (5.0 mL) at room temperature. The solution was stirred under nitrogen when palladium on carbon (10% wt., 25.1 mg, 23.6 µmol) was added in one portion. Then, the solvent was degassed with hydrogen and the reaction was allowed to stir under hydrogen for 2 h. The mixture was diluted with dichloromethane and filtered on celite. The crude material was purified by automated reverse phase chromatography (C18, 25% to 65% acetonitrile in 10 mM aqueous ammonium formate). After lyophilisation, 5-amino-2-(((2R,3R,4S,5R,6R)-3,4,5-tris(butyryloxy)-6-((butyryloxy)methyl)tetrahydro-2H-pyran-2-yl)oxy)benzoic acid (9 mg, 6%) was obtained as a white solid. $^1$H NMR (400 MHz, DMSO-d$_6$) δ 6.82 (d, J=8.5 Hz, 1H), 6.79 (s, 1H), 6.58 (d, J=8.3 Hz, 1H), 5.56 (d, J=3.6 Hz, 1H), 5.52 (t, J=9.9 Hz, 1H), 5.04 (t, J=9.9 Hz, 1H), 4.93 (dd, J=10.3, 3.6 Hz, 1H), 4.38 (broad s, 1H), 4.10 (dd, J=12.4, 5.1 Hz, 1H), 3.98 (dd, J=12.4, 2.0 Hz, 1H), 2.37-2.15 (m, 8H), 1.56-1.39 (m, 8H), 0.90-0.73 (m, 12H). LCMS calcd for $C_{29}H_{41}NO_{12}$ 595.26, found 613.3 [M+NH$_4$] at 1.84 min.

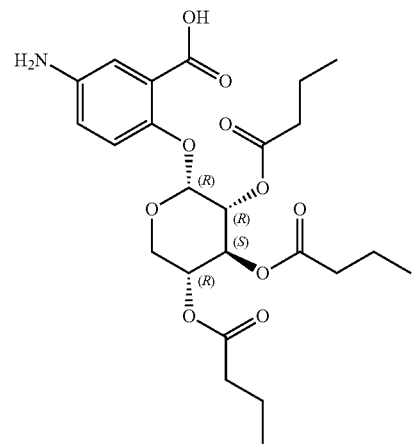

Compound 226: 5-amino-2-[(2R,3R,4S,5R)-3,4,5-tri(butanoyloxy)tetrahydropyran-2-yl]oxy-benzoic acid This compound was prepared according to a modified procedure described for the preparation of compound 34. LCMS [M−H]$^-$: 494.5. $^1$H NMR (400 MHz, DMSO-d$_6$) δ 6.83-6.75 (m, 2H), 6.64-6.53 (m, 1H), 5.58 (d, J=3.6 Hz, 1H), 5.53 (t, J=9.9 Hz, 1H), 5.03-4.90 (m, 2H), 3.89 (t, J=10.9 Hz, 1H), 3.73 (dd, J=10.9, 5.9 Hz, 1H), 2.38-2.12 (m, 6H), 1.58-1.39 (m, 6H), 0.92-0.76 (m, 9H).

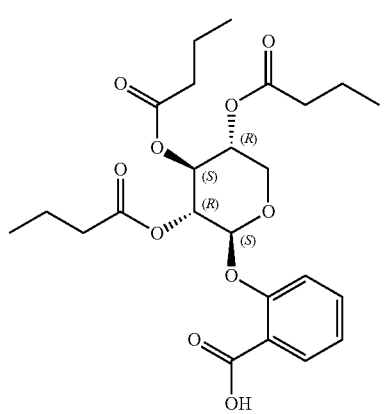

Compound 227: 2-{[(2S,3R,4S,5R)-3,4,5-tris(butanoyloxy)oxan-2-yl]oxy}benzoic acid
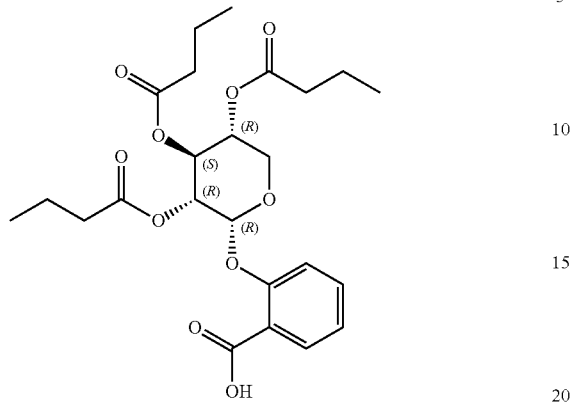
Compound 228: 2-{[(2R,3R,4S,5R)-3,4,5-tris(butanoyloxy)oxan-2-yl]oxy}benzoic acid
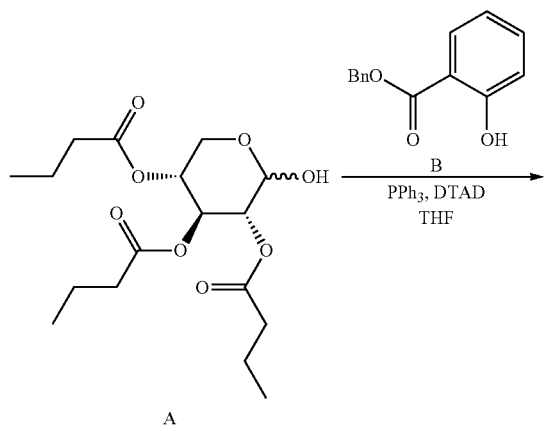
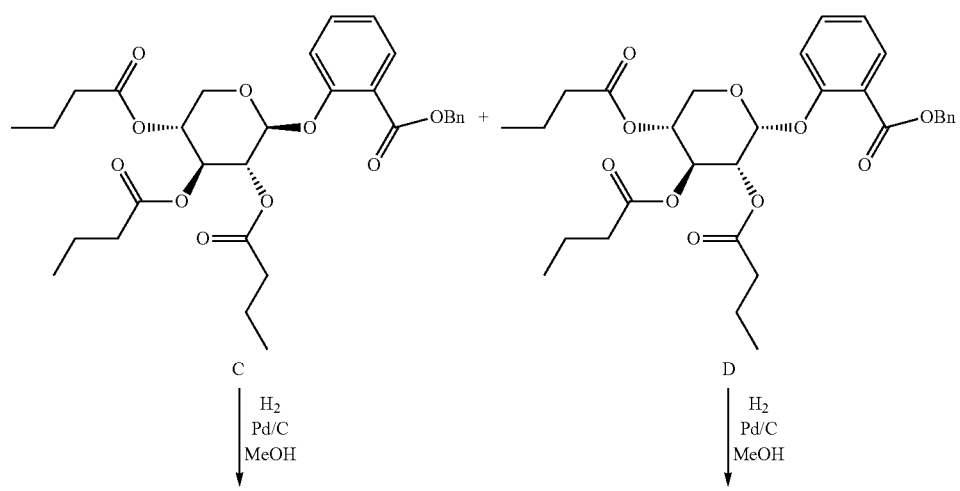

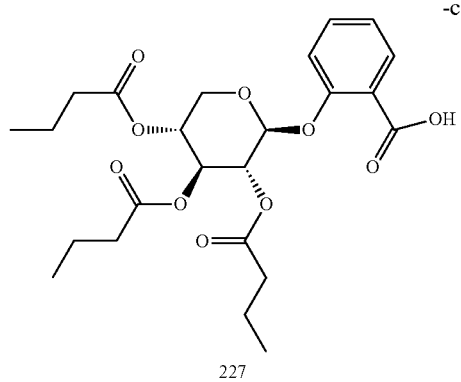

227

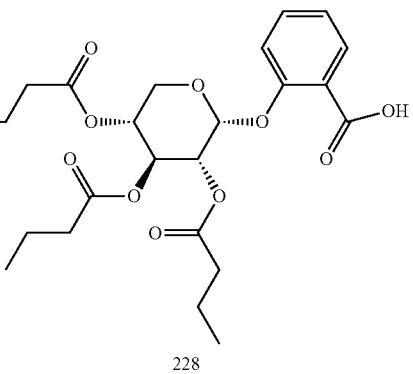

228

Step 1

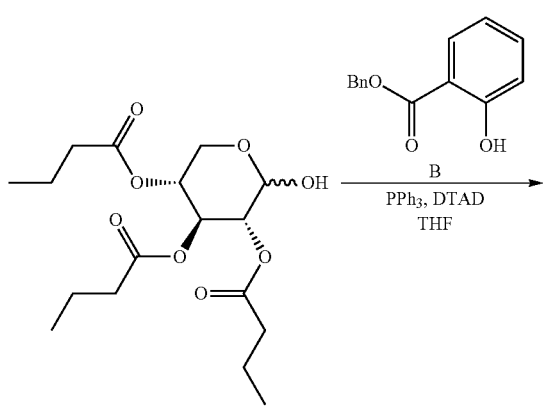

A

| S.N. | Materials | MW/d | Amount/ mmol | Equiv/ Vol |
|------|-----------|------|--------------|------------|
| 1 | Xylose Tributyrate (X3B) A | 360 | 12 g/33.3 | 1.0 |
| 2 | Compound B | 228 | 11.4 g/50 | 1.5 |
| 3 | Triphenylphosphine | 262 | 13.1 g/50 | 1.5 |
| 4 | Di-t-butyl azodicarboxylate (DTAD) | 230 | 11.5 g/50 | 1.5 |
| 5 | THF | | 240 mL | 20 Vol |

Compound A, B and TPP were dissolved in THF and stirred at 0° C. To this mixture was added DTAD and stirring was continued at 0° C. for 1 h, then at room temperature overnight. The reaction mixture was concentrated. NMR of the crude product showed a mixture of C and D (ratio 1:0.9). Multiple purifications by column chromatography using 0-30% ethyl acetate in hexanes provided the desired β isomer C (7 g, 32%) and α isomer D (4.6 g, 21%).

Step 2A

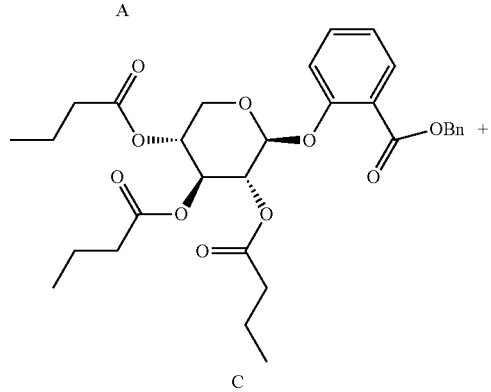

D

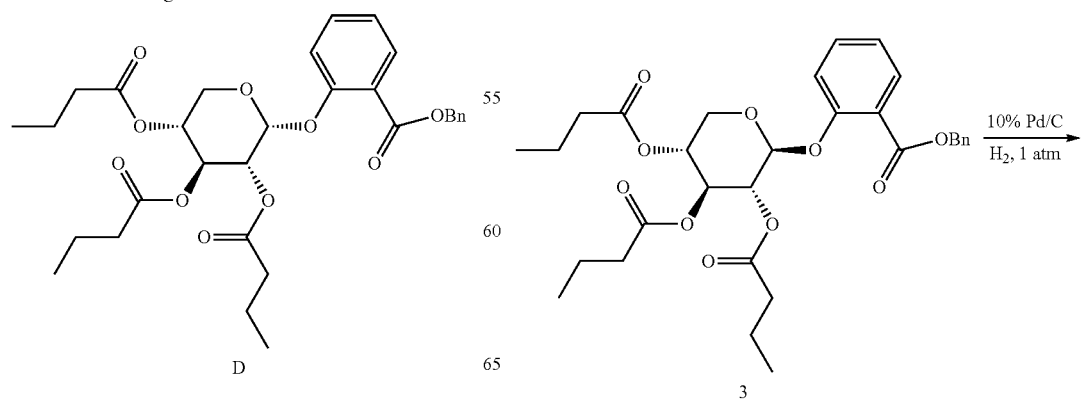

-continued

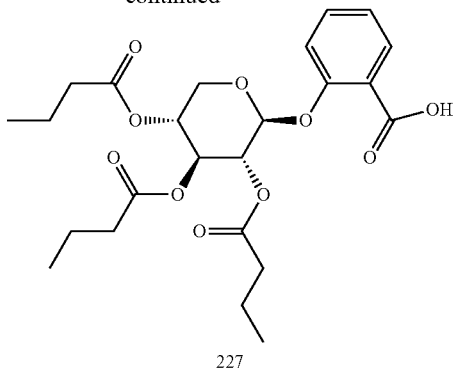

227

| S.N. | Materials | MW/d | Amount/ mmol | Equiv/ Vol |
|---|---|---|---|---|
| 1 | Compound C | 570 | 4.2 g/7.37 | 1.0 |
| 2 | 10% Pd/C | | 200 mg | |
| 3 | MeOH | | 50 mL | 12 Vol |

Compound C was dissolved in methanol and stirred at room temperature. To this mixture was added 10% Pd/C. The suspension was stirred under a hydrogen atmosphere at room temperature overnight. The reaction mixture was filtered through Celite and washed with methanol. The combined filtrate and washing were concentrated. The residue was purified by ISCO using 0-5% MeOH in DCM to give 2.1 g (60%) of pure product 227 and 850 mg of impure product.

Step 2B

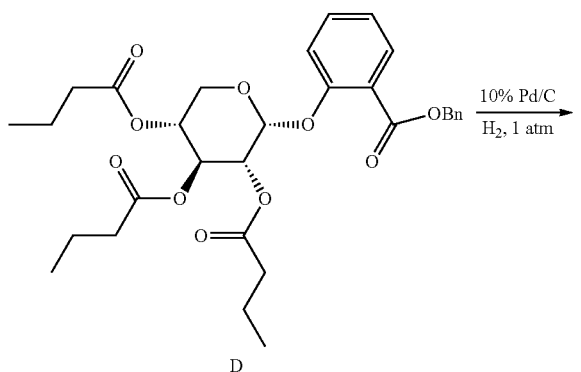

D

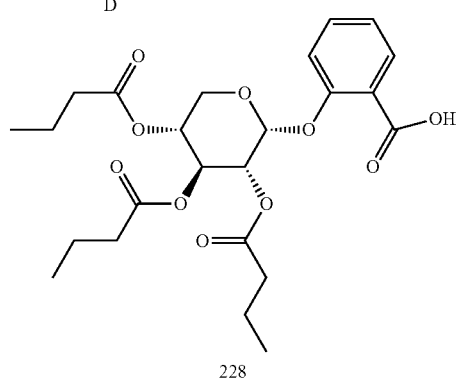

228

| S.N. | Materials | MW/d | Amount/ mmol | Equiv/ Vol |
|---|---|---|---|---|
| 1 | Compound 4 | 570 | 2.8 g/4.9 | 1.0 |
| 2 | 10% Pd/C | | 150 mg | |
| 3 | MeOH | | 40 mL | 14 Vol |

Compound 4 was dissolved in methanol and stirred at room temperature. To this mixture was added 10% Pd/C. The suspension was stirred under hydrogen atmosphere at room temperature overnight. The reaction mixture was filtered through Celite and washed with methanol. The combined filtrate and washing were concentrated. The residue was purified by ISCO using 0-5% MeOH in DCM to give 936 mg (40%) of pure product 228.

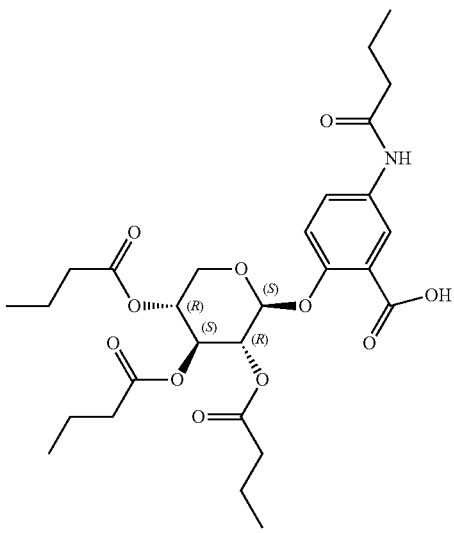

Compound 229: 5-butanamido-2-{[(2S,3R,4S,5R)-3,4,5-tris(butanoyloxy)oxan-2-yl]oxy}benzoic acid Compound 34 (50 mg, 0.10 mmol, 1 equiv) was dissolved in 0.25 mL of DCM, followed by addition of butyric anhydride (0.05 mL, 0.3 mmol, 3 equiv). The reaction was stirred at room temperature for 40 minutes, then purified by column chromatography (0-100% EtOAc in hexanes) to yield the title compound as a white solid (42.5 mg, 0.075 mmol, 75% yield). $^1$H NMR (400 MHz, DMSO-$d_6$) δ 12.71 (s, 1H), 9.90 (s, 1H), 7.86 (d, J=2.8 Hz, 1H), 7.65 (dd, J=9.0, 2.7 Hz, 1H), 7.10 (d, J=9.0 Hz, 1H), 5.36 (d, J=7.2 Hz, 1H), 5.29 (t, J=9.0 Hz, 1H), 5.04 (dd, J=9.2, 7.2 Hz, 1H), 4.94 (td, J=9.2, 5.4 Hz, 1H), 4.04 (dd, J=11.5, 5.4 Hz, 1H), 3.70 (dd, J=11.6, 9.4 Hz, 1H), 2.33-2.11 (m, 8H), 1.65-1.41 (m, 8H), 0.93-0.77 (m, 12H).

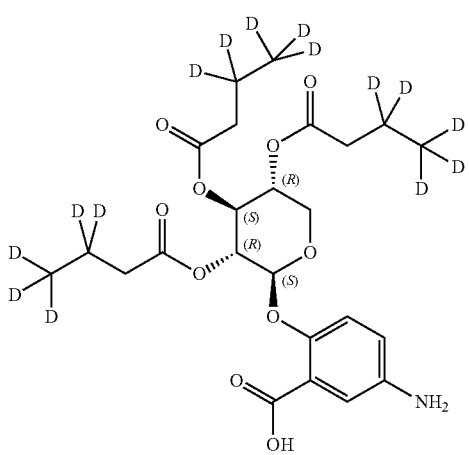

Compound 230: 5-amino-2-{[(2S,3R,4S,5R)-3,4,5-tris[(3,3,4,4,4-²H₅)butanoyloxy]oxan-2-yl]oxy}benzoic acid This compound was prepared as described for compound 34 with the exception that starting materials appropriately enriched in deuterium. LCMS: (M+H+) 511.3. 1H NMR (400 MHz, DMSO-d6) δ 12.41 (s, 1H), 6.86 (d, 1H), 6.81 (d, 1H), 6.64 (dd, 1H), 5.27 (t, 1H), 5.14 (d, 1H), 5.00 (dd, 1H), 4.92 (td, 1H), 4.02 (dd, 1H), 3.63 (dd, 1H), 2.33-2.14 (m, 6H)

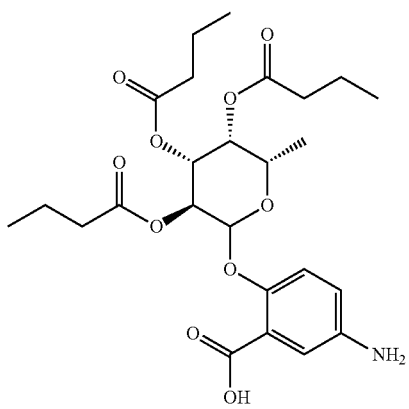 [SMILES: CCCC(=O)O[C@@H]1[C@H](OC(=O)CCC)[C@H](C)OC(Oc2ccc(N)cc2C(=O)O)[C@H]1OC(=O)CCC]

Compound 231:5-amino-2-(((3S,4R,5R,6S)-3,4,5-tris(butyryloxy)-6-methyltetrahydro-2H-pyran-2-yl)oxy)benzoic acid (3S,4R,5R,6S)-2-hydroxy-6-methyltetrahydro-2H-pyran-3,4,5-triyl tributyrate (500 mg, 1.34 mmol), tert-butyl 5-((tert-butoxycarbonyl)amino)-2-hydroxybenzoate (620 mg, 2.00 mmol) and triphenylphosphine (531 mg, 2.00 mmol) were dissolved in tetrahydrofuran (22.0 mL) and stirred at 0° C. Di-tert-butyl azodicarboxylate (471 mg, 2.00 mmol) was added and stirring was continued at 0° C. for 1 h, then at room temperature overnight. The reaction mixture was concentrated. The crude material was purified by automated chromatography (SiO₂, 30% ethyl acetate in hexanes) to afford (3S,4R,5R,6S)-2-(2-(tert-butoxycarbonyl)-4-((tert-butoxycarbonyl)amino)phenoxy)-6-methyltetrahydro-2H-pyran-3,4,5-triyl tributyrate (213 mg, 24%). [M+NH₄⁺]=683, room temperature=2.21. ¹H NMR (400 MHz, CDCl₃) δ 7.58-6.95 (m, 3H), 5.48 (dd, J=10.5, 8.0 Hz, 1H), 5.28 (d, J=3.4 Hz, 1H), 5.10 (dd, J=10.4, 3.4 Hz, 1H), 5.00 (d, J=8.0 Hz, 1H), 3.88 (q, J=6.5 Hz, 1H), 2.55-2.15 (m, 2H), 1.76-1.56 (m, 3H), 1.55 (s, 4H), 1.49 (s, 3H), 1.46 (s, 2H), 1.26-1.14 (m, 2H), 0.99 (t, J=7.4 Hz, 1H), 0.89 (t, J=7.4 Hz, 2H).

(3S,4R,5R,6S)-2-(2-(tert-butoxycarbonyl)-4-((tert-butoxycarbonyl)amino)phenoxy)-6-methyltetrahydro-2H-pyran-3,4,5-triyl tributyrate (200 mg, 300 µmol) was dissolved in dichloromethane (2.00 mL) at 0° C. To the solution was added hydrochloric acid (4 M in 1,4-dioxane, 158 µL, 631 µmol). The resulting mixture was stirred at 0° C. for 30 min, then at room temperature for 2 h. Solvents were evaporated and the residue was purified by automated reverse phase chromatography (C18, acetonitrile in 10 mM aqueous ammonium formate) After lyophilisation, 5-amino-2-(((3S,4R,5R,6S)-3,4,5-tris(butyryloxy)-6-methyltetrahydro-2H-pyran-2-yl)oxy)benzoic acid (10.0 mg, 13%) was obtained as a white solid. ¹H NMR (400 MHz, DMSO-d₆) δ 6.86 (d, J=9.1 Hz, 1H), 6.74 (d, J=2.9 Hz, 1H), 6.60 (dd, J=9.8, 2.1 Hz, 1H), 5.21-5.06 (m, 4H), 5.01-4.91 (m, 1H), 2.67-2.63 (m, 1H), 2.53 (s, 1H), 2.45-2.07 (m, 7H), 1.60 (dt, J=14.6, 7.3 Hz, 2H), 1.52-1.39 (m, 4H), 1.07 (d, J=6.4 Hz, 3H), 0.92 (t, J=7.4 Hz, 3H), 0.80 (t, J=7.4 Hz, 6H). LCMS calcd for C₂₅H₃₅NO₁₀ 509.23, found 508.2 [M−H] at 1.68 min.

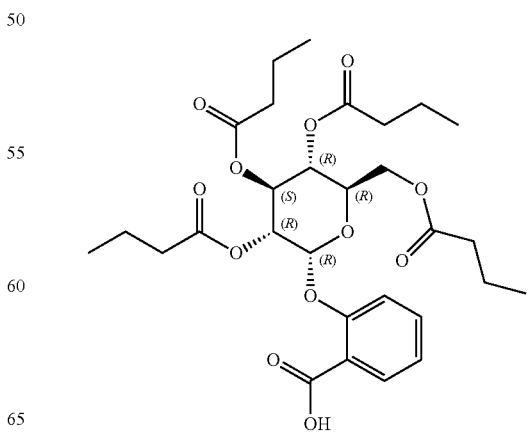

Compound 232: 2-{[(2R,3R,4S,5R,6R)-3,4,5-tris(butanoyloxy)-6-[(butanoyloxy)methyl]oxan-2-yl]oxy}benzoic acid This compound was prepared according to a modified procedure for the preparation of compound 223.

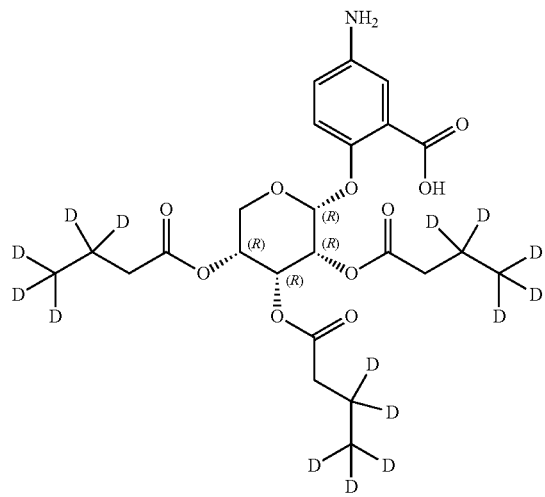

Compound 233: 5-amino-2-{[(2R,3R,4R,5R)-3,4,5-tris[(3,3,4,4,4-²H₅)butanoyloxy]oxan-2-yl]oxy}benzoic acid This compound was prepared according to a modified procedure for the preparation of compound 41.

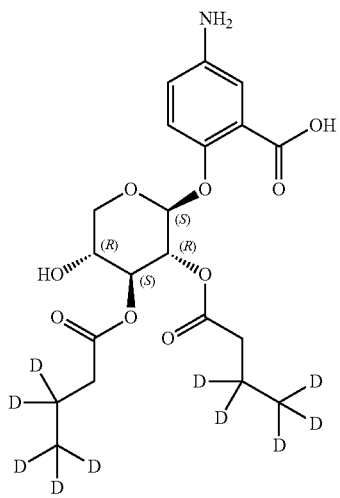

Compound 234: 5-amino-2-{[(2S,3R,4S,5R)-3,4-bis[(3,3,4,4,4-²H)butanoyloxy]-5-hydroxyoxan-2-yl]oxy}benzoic acid This compound was prepared according to a modified procedure for the preparation of compound 214. LCMS: (M−H−) 434.2. $^1$H NMR (400 MHz, Chloroform-d) δ 7.46 (d, 1H), 7.04 (d, 1H), 6.85 (dd, 1H), 5.35 (d, 1H), 5.15 (dd, 1H), 5.06 (t, 1H), 4.17 (dd, 1H), 3.84 (td, 1H), 3.61 (dd, 1H), 2.41 (s, 2H), 2.36 (s, 2H)

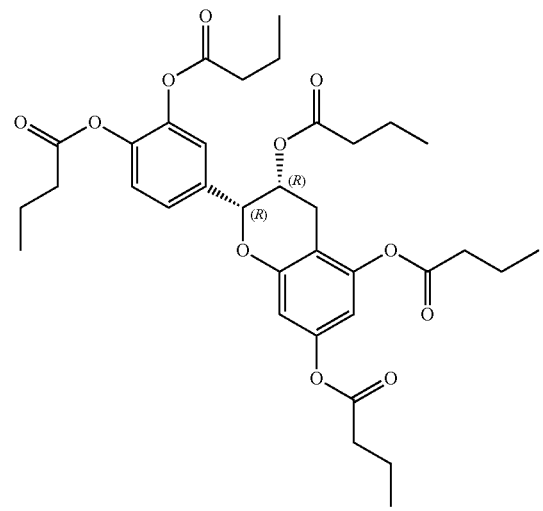

Compound 235: (2R,3R)-2-[3,4-bis(butanoyloxy)phenyl]-5,7-bis(butanoyloxy)-3,4-dihydro-2H-1-benzopyran-3-yl butanoate

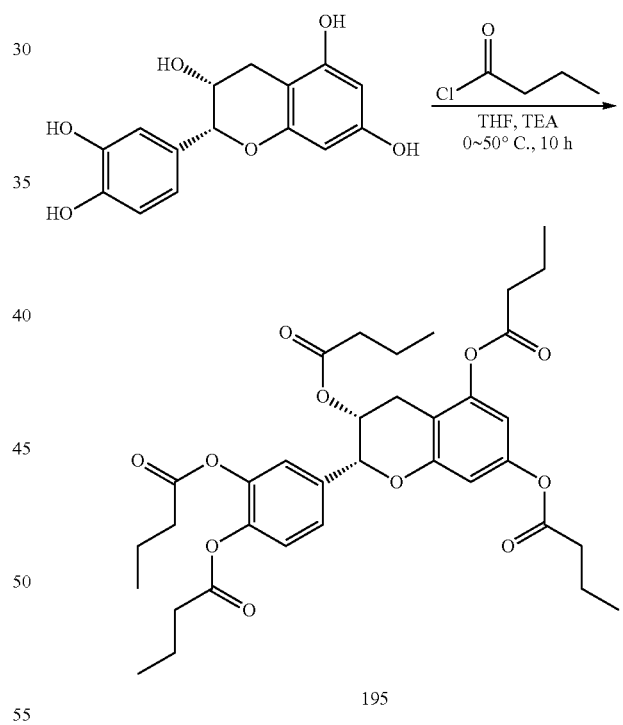

195

A mixture of (2R,3R)-2-(3,4-dihydroxyphenyl)chromane-3,5,7-triol (300 mg, 1.03 mmol, 1 eq) and TEA (627.50 mg, 6.20 mmol, 863.13 uL, 6 eq) in THF (8 mL) was cooled to 0° C. and stirred under N₂. Then butanoyl chloride (110.12 mg, 1.03 mmol, 107.96 μL, 1.00 eq) was dropped to the mixture and then heated to 50° C. and stirred for 10 hours. LCMS showed desired compound was detected. The reaction mixture was concentrated under reduced pressure to give a residue. The residue was purified by prep-HPLC (column: Phenomenex Luna C18 200*40 mm*10 um; mobile phase: [water (0.05% HCl)-ACN]; B %: 70%-90%, 10 min) to give WX-0637 (2R,3R)-2-(3,4-bis(butyryloxy) phenyl)chroman-3,5,7-triyl tributyrate (154 mg, 216.61 umol, 20.96% yield, 90.12% purity) as a white solid. LCMS: (M+H$^+$) 641.4 @ 1.476 min; LCMS: (M+Na$^+$) 663.3 @ 2.346 min. $^1$H NMR (400 MHz, Chloroform-d) δ 7.32 (d, J=2.0 Hz, 1H), 7.30-7.23 (m, 1H), 7.19 (d, J=8.4 Hz, 1H), 6.67 (d, J=2.3 Hz, 1H), 6.54 (d, J=2.3 Hz, 1H), 5.43-5.37 (m, 1H), 5.12 (s, 1H), 2.97 (dd, J=17.8, 4.5 Hz, 1H), 2.86 (dd, J=17.9, 2.3 Hz, 1H), 2.57-2.47 (m, 8H), 2.14 (t, J=7.4 Hz, 2H), 1.77 (hd, J=7.4, 2.3 Hz, 8H), 1.44 (h, J=7.3 Hz, 2H), 1.08-0.99 (m, 12H), 0.74 (t, J=7.4 Hz, 3H)

and the mixture heated to 50° C. and stirred for 10 hours. LCMS showed desired compound was detected. The reaction mixture was concentrated under reduced pressure to give a residue. The residue was purified by prep-HPLC (column: Phenomenex Luna C18 200*40 mm*10 um; mobile phase: [water (0.05% HCl)-ACN]; B %: 55%-75%, 10 min) to give [2-propanoyloxy-4-[(2R,3R)-3,5,7-tri(propanoyloxy)chroman-2-yl]phenyl] propanoate (151 mg, 258.48 umol, 25.01% yield, 97.67% purity) as a white solid. LCMS: (M+H+) 571.3 @ 1.342 min; LCMS: (M+Na$^+$) 593.3 @ 2.147 min. $^1$H NMR (400 MHz, Chloroform-d) δ 7.33 (d, J=2.0 Hz, 1H), 7.30-7.23 (m, 1H), 7.19 (d, J=8.4 Hz, 1H), 6.67 (d, J=2.3 Hz, 1H), 6.56 (d, J=2.3 Hz, 1H), 5.43-5.37 (m, 1H), 5.12 (s, 1H), 2.97 (dd, J=17.8, 4.5 Hz, 1H), 2.86 (dd, J=17.9, 2.3 Hz, 1H), 2.63-2.51 (m, 8H), 2.18 (q, J=7.5 Hz, 2H), 1.30-1.20 (m, 12H), 0.95 (t, J=7.5 Hz, 3H)

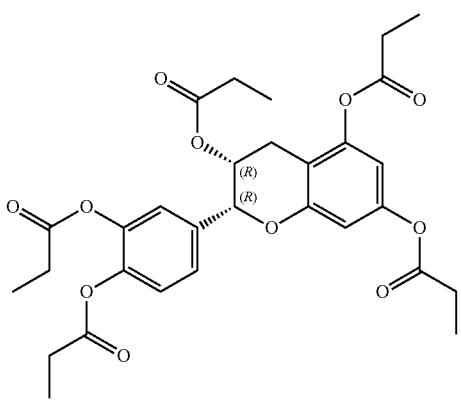

Compound 236: (2R,3R)-2-[3,4-bis(propanoyloxy) phenyl]-5,7-bis(propanoyloxy)-3,4-dihydro-2H-1-benzopyran-3-yl propanoate

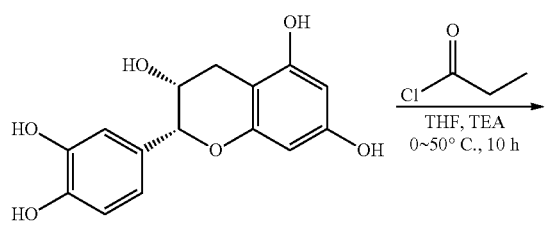

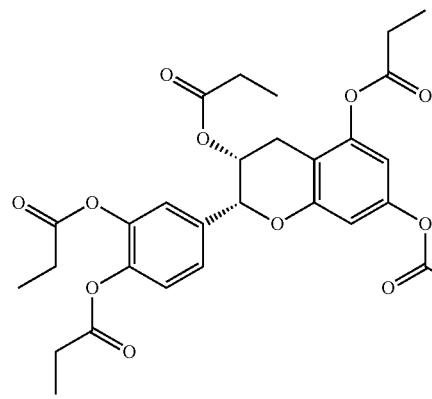

196

A mixture of (2R,3R)-2-(3,4-dihydroxyphenyl)chromane-3,5,7-triol (300 mg, 1.03 mmol, 1 eq) and TEA (627.50 mg, 6.20 mmol, 863.13 uL, 6 eq) in THF (8 mL) was cooled to 0° C. and stirred under N$_2$. Then propanoyl chloride (573.76 mg, 6.20 mmol, 573.76 uL, 6 eq) was dropped to the mixture

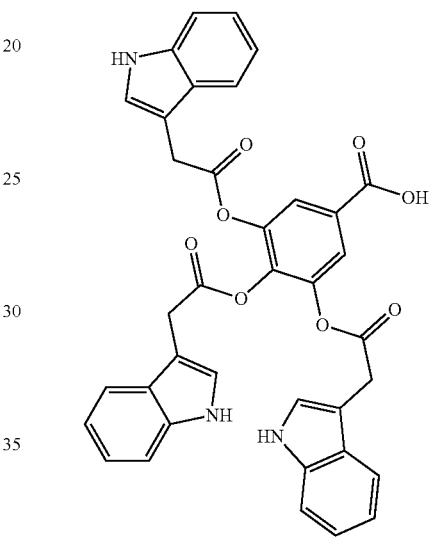

Compound 237: 3,4,5-tris({[2-(1H-indol-3-yl) acetyl]oxy})benzoic acid

This compound was prepared following a modified procedure described for compound 96. LCMS: (M+H+) 642.2. $^1$H NMR (400 MHz, DMSO-d6) δ 11.06 (dd, 3H), 7.65 (s, 2H), 7.46 (dd, 3H), 7.37 (dd, 3H), 7.22 (dd, 3H), 7.14-7.07 (m, 3H), 7.05-6.97 (m, 3H), 3.71 (s, 4H), 3.43 (s, 2H)

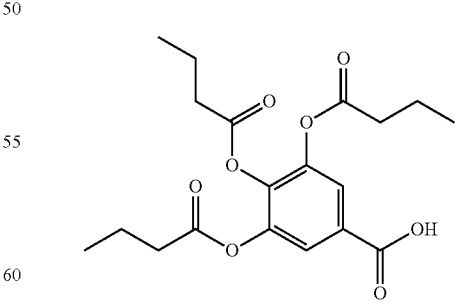

Compound 238: 3,4,5-tris(butyryloxy)benzoic acid

Gallic Acid (400 mg, 2.35 mmol) was dissolved in pyridine (15 eq, 2.83 mL, 35.2 mmol) in a dry round bottom flask. The flask was flushed with N₂ and the solution was chilled to 0° C. in an ice bath. Butyric anhydride (6 eq, 2.30 mL, 14.1 mmol) was added dropwise under N₂. The resulting stirred solution was allowed to come to room temperature and reaction was monitored to completion by LCMS. The solution was diluted with 20 mL of ethyl acetate and washed with 1M HCl (20 mL) and saturated NaCl (20 mL). The organic layer was dried over magnesium sulfate, filtered, and concentrated by rotary evaporation. The crude residue was purified by flash chromatography (C18, 10-90% acetonitrile in water) and fractions were concentrated and fully dried by lyophilization to yield compound 238 (740 mg, 82.8% yield) as a white solid. LCMS [M−H]⁻: 379.1. ¹H NMR (400 MHz, DMSO-d₆) δ 13.45 (bs, 1H), 7.74 (s, 2H), 2.62-2.55 (m, 6H), 1.70-1.58 (m, 6H), 0.99-0.93 (m, 9H).

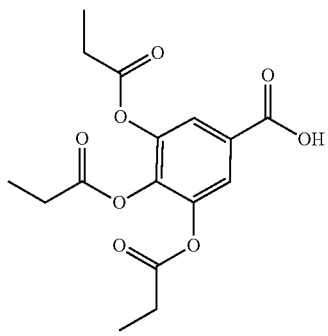 [SMILES: CCC(=O)Oc1cc(C(=O)O)cc(OC(=O)CC)c1OC(=O)CC]

Compound 239: 3,4,5-tris(propanoyloxy)benzoic acid

This compound was prepared following a modified procedure described for compound 44. LCMS (M−H−) 337.1. ¹H NMR (400 MHz, DMSO-d₆) δ 13.43 (s, 1H), 7.75 (s, 2H), 2.62 (m, 6H), 1.13 (m, 9H)

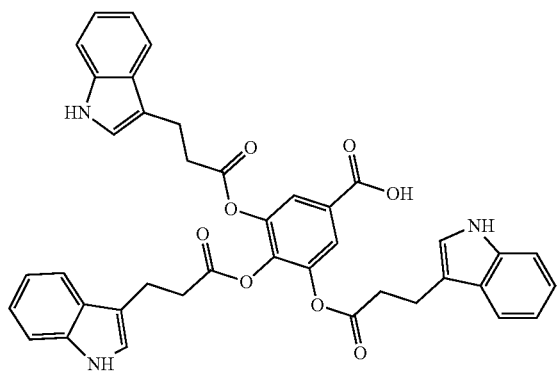 [SMILES: O=C(CCc1c[nH]c2ccccc12)Oc1cc(C(=O)O)cc(OC(=O)CCc2c[nH]c3ccccc23)c1OC(=O)CCc1c[nH]c2ccccc12]

Compound 240: 3,4,5-tris({[3-(1H-indol-3-yl)propanoyl]oxy})benzoic acid

This compound was prepared following a modified procedure described for compound 44. LCMS: (m+H+) 684.2. ¹H NMR (400 MHz, DMSO-d6) δ 13.48 (s, 1H), 10.85 (d, 3H), 7.70 (s, 2H), 7.50 (dd, 3H), 7.38-7.29 (m, 3H), 7.13 (dd, 3H), 7.10-7.02 (m, 3H), 6.94 (m, 3H), 3.00 (m, 6H), 2.83 (m, 6H)

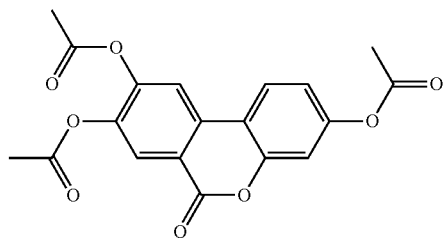 [SMILES: CC(=O)Oc1ccc2c(c1)oc(=O)c1cc(OC(C)=O)c(OC(C)=O)cc12]

Compound 241:
6-oxo-6H-benzo[c]chromene-3,8,9-triyl triacetate

To a mixture of 3,8,9-trihydroxybenzo[c]chromen-6-one (0.3 g, 1.23 mmol, 1 eq) and acetyl acetate (501.67 mg, 4.91 mmol, 460.25 uL, 4 eq) in DCM (10 mL) was added triethylamine (TEA) (372.94 mg, 3.69 mmol, 512.98 uL, 3 eq). The mixture was stirred at 25° C. for 10 hours. TLC indicated one new spot was detected. The reaction mixture was quenched by addition water 10 mL and extracted with EtOAc (10 mL×3). The combined organic layers were washed with brine 20 mL, dried over Na₂SO₄, filtered and concentrated under reduced pressure to give the residue. The residue was purified by column chromatography (SiO₂, Petroleum ether/Ethyl acetate=3/1 to 1:1). Compound (8,9-diacetoxy-6-oxo-benzo[c]chromen-3-yl) acetate (0.36 g) was obtained as a gray solid. LCMS: (M+H⁺): 371.0 ¹H NMR (400 MHz, CDCl₃) δ 8.2 (s, 1H), 9.9 m, 2H), 7.1 (m, 2H), 2.3 (s, 9H).

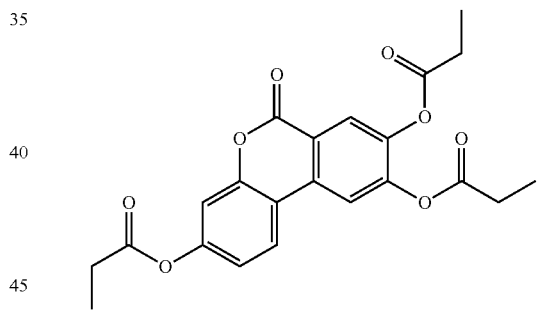

Compound 242: [6-oxo-8,9-di(propanoyloxy)benzo[c]chromen-3-yl] Propanoate

Propionic anhydride (2.61 mL, 20.4 mmol) was added dropwise to a stirred solution of urolithin C (0.5 g, 2.04 mmol) in anhydrous pyridine (4.92 mL, 61.2 mmol) at 0° C. under N₂ atmosphere. The resulting stirred solution was allowed to come to room temperature and reaction was monitored to completion by LCMS. The solution was diluted with 30 mL ethyl acetate and washed with H₂O (30 mL), 1M HCl (30 mL), H₂O (30 mL), and saturated NaHCO₃ (30 mL). The organic layer was dried over sodium sulfate, filtered, and concentrated by rotary evaporation. The crude residue was purified by flash chromatography (silica, 10-100% ethyl acetate in hexanes) and fractions were concentrated by rotary evaporation to yield Compound 242 (0.05 g, 6% yield) as a pink solid. ¹H NMR (DMSO-d6, 400 MHz): δ 8.4 (s, 1H), 8.35 (d, 1H), 8.14 (s, 1H), 7.31 (d, 1H), 7.23 (m, 1H), 2.73-2.63 (m, 6H), 1.21-1.14 (m, 9H) ppm.

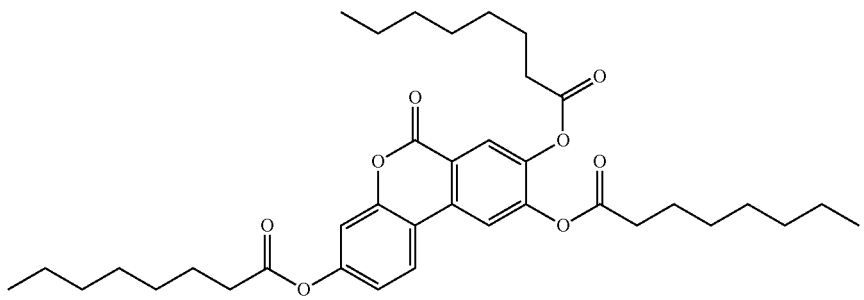 [SMILES: CCCCCCCC(=O)Oc1ccc2c(c1)oc(=O)c1cc(OC(=O)CCCCCCC)c(OC(=O)CCCCCCC)cc12]

Compound 243: [8,9-di(octanoyloxy)-6-oxo-benzo[c]chromen-3-yl] octanoate

To a solution of 3,8,9-trihydroxybenzo[c]chromen-6-one (0.3 g) in acetonitrile (10 mL) was added K$_2$CO$_3$ (0.68 g) followed by octanoyl chloride (0.8 g). The resulting mixture was stirred at 50° C. for 24 hours. Additional octanoyl chloride (0.8 g) was added and the mixture was stirred at 50° C. for 12 hours. The reaction mixture was quenched by addition of water (10 mL) and extracted three times with ethyl acetate (10 mL). The combined organic layers were dried over Na$_2$SO$_4$, filtered and concentrated under reduced pressure. The residue was purified by column chromatography (SiO$_2$, petroleum ether/ethyl acetate, 9:1 to 1:1) to give [8,9-di(octanoyloxy)-6-oxo-benzo[c]chromen-3-yl]octanoate (0.45 g, 55.5%) as a white solid. $^1$H NMR (400 MHz, CDCl$_3$): δ 8.186 (s, 1H), 7.926 (d, 1H), 7.908 (s, 1H), 7.157-7.096 (m, 2H), 2.621-2.573 (m, 6H), 1.79-1.75 (6H, m), 1.5-1.25 (m, 24H), 0.916-0.878 (m, 9H) ppm

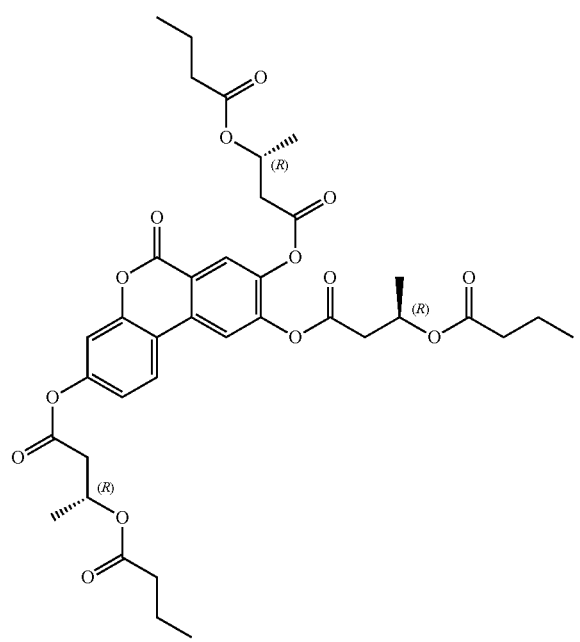

Compound 244: 8,9-bis({[(3R)-3-(butanoyloxy)butanoyl]oxy})-6-oxo-6H-benzo[c]chromen-3-yl (3R)-3-(butanoyloxy)butanoate This compound was prepared following a modified procedure described for compound 242.

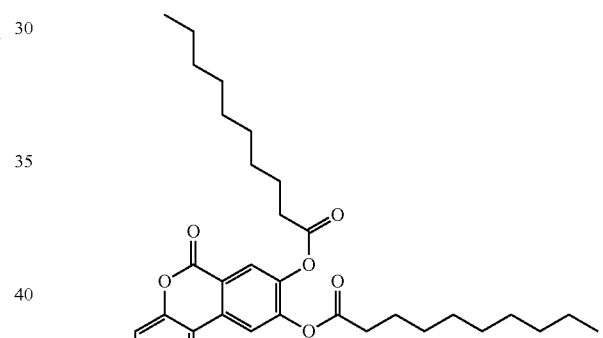

Compound 245: 8,9-bis(decanoyloxy)-6-oxo-6H-benzo[c]chromen-3-yl decanoate

This compound was prepared following a modified procedure described for compound 242.

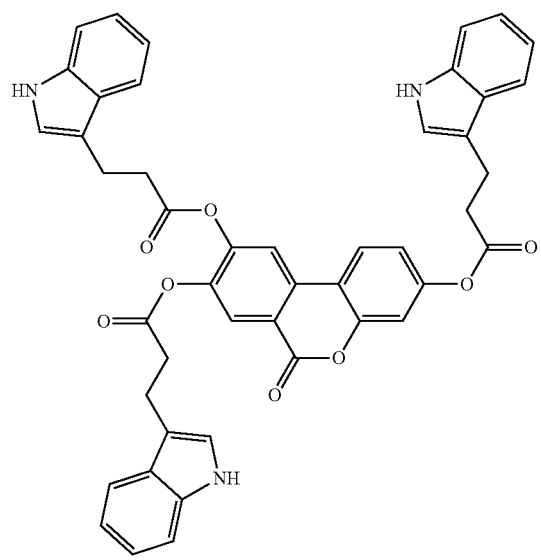 [SMILES: O=C(CCc1c[nH]c2ccccc12)Oc1ccc2c(c1)oc(=O)c1cc(OC(=O)CCc3c[nH]c4ccccc34)c(OC(=O)CCc3c[nH]c4ccccc34)cc12]

Compound 246: 8,9-bis({[3-(1H-indol-3-yl)propanoyl]oxy})-6-oxo-6H-benzo[c]chromen-3-yl 3-(1H-indol-3-yl)propanoate This compound was prepared following a modified procedure described for compound 96.

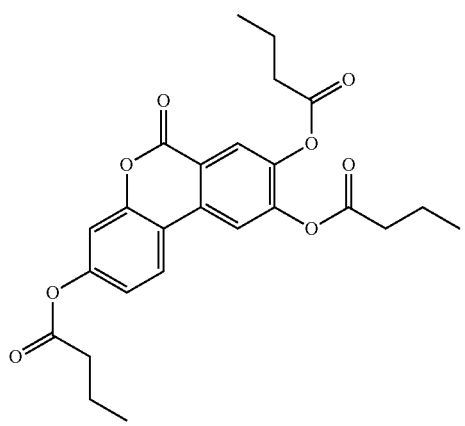 [SMILES: CCCC(=O)Oc1ccc2c(c1)oc(=O)c1cc(OC(=O)CCC)c(OC(=O)CCC)cc12]

Compound 248: 8,9-bis(butanoyloxy)-6-oxo-6H-benzo[c]chromen-3-yl butanoate

This compound was prepared following a modified procedure described for compound 242.

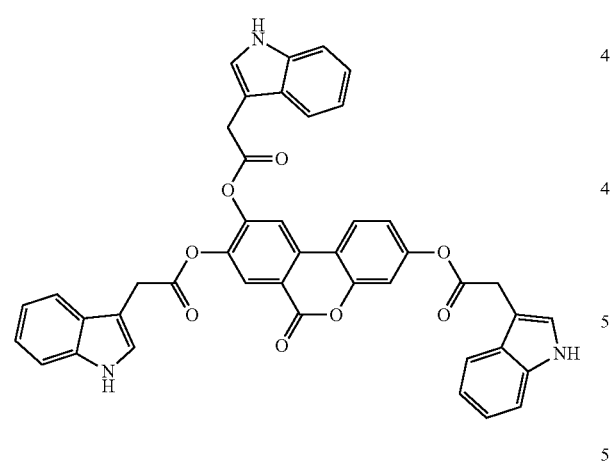

Compound 247: 8,9-bis({[2-(1H-indol-3-yl)acetyl]oxy})-6-oxo-6H-benzo[c]chromen-3-yl 2-(1H-indol-3-yl)acetate This compound was prepared following a modified procedure described for compound 96.

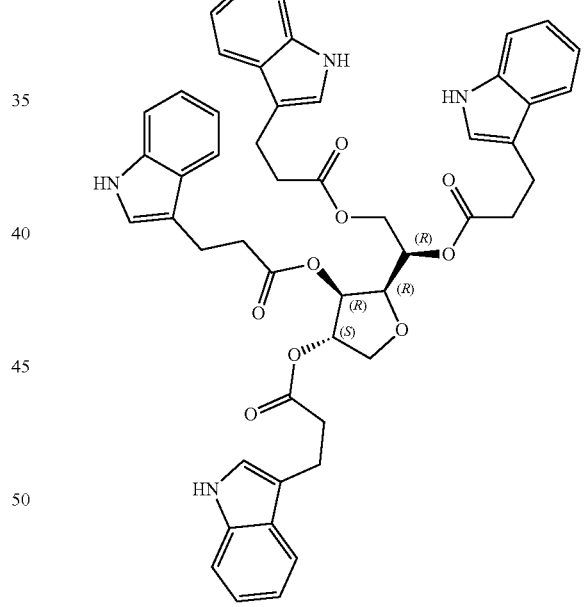

Compound 249: (1R)-1-[(2R,3R,4S)-3,4-bis({[3-(1H-indol-3-yl)propanoyl]oxy})oxolan-2-yl]-2-{[3-(1H-indol-3-yl)propanoyl]oxy}ethyl 3-(1H-indol-3-yl)propanoate This compound was prepared following a modified procedure described for compound 96.

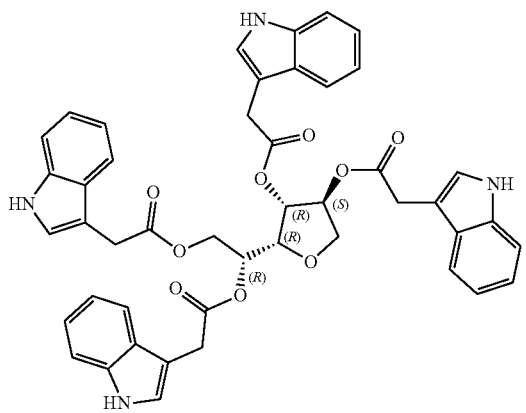

Compound 250: (1R)-1-[(2R,3R,4S)-3,4-bis({[2-(1H-indol-3-yl)acetyl]oxy})oxolan-2-yl]-2-{[2-(1H-indol-3-yl)acetyl]oxy}ethyl 2-(1H-indol-3-yl)acetate This compound was prepared following a modified procedure described for compound 96.

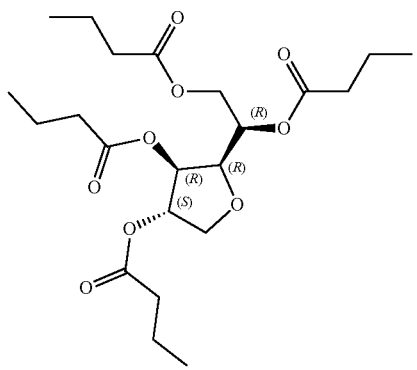

Compounds 251: (1R)-1-[(2R,3R,4S)-3,4-bis(butanoyloxy)oxolan-2-yl]-2-(butanoyloxy)ethyl butanoate This compound was prepared following a modified procedure described for compound 242.

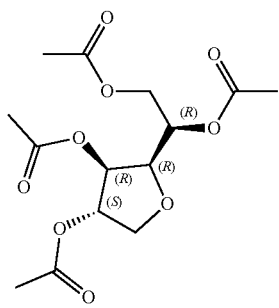

Compound 252: (1R)-2-(acetyloxy)-1-[(2R,3R,4S)-3,4-bis(acetyloxy)oxolan-2-yl]ethylacetate This compound was prepared following a modified procedure described for compound 242.

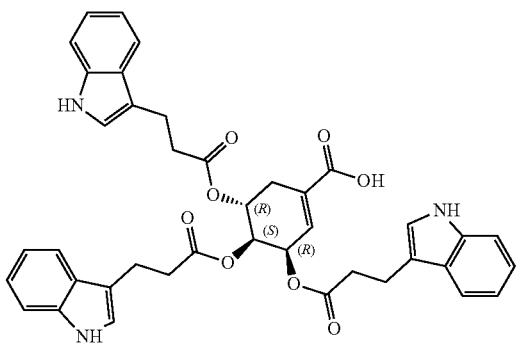

Compound 253: (3R,4S,5R)-3,4,5-tris({[3-(1H-indol-3-yl)propanoyl]oxy})cyclohex-1-ene-1-carboxylic acid This compound was prepared following a modified procedure described for compound 96.

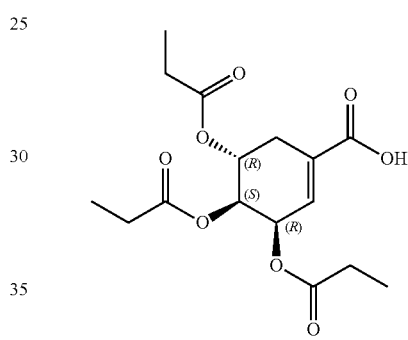

Compound 254: (3R,4S,5R)-3,4,5-tris(propanoyloxy)cyclohex-1-ene-1-carboxylic acid This compound was prepared following a modified procedure described for compound 43.

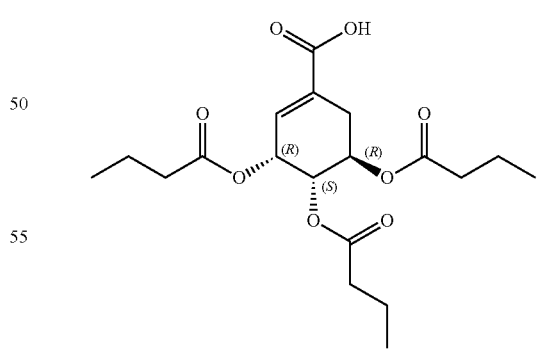

Compound 255: (3R,4S,5R)-3,4,5-tris(butanoyloxy)cyclohex-1-ene-1-carboxylic acid This compound was prepared following a modified procedure described for compound 43.

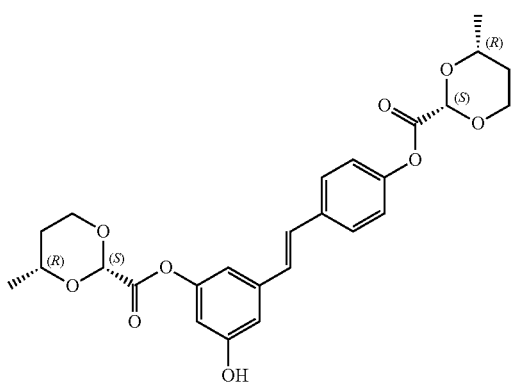

Compound 256: 4-[(1E)-2-{3-hydroxy-5-[(2S,4R)-4-methyl-1,3-dioxane-2-carbonyloxy]phenyl}ethenyl]phenyl (2S,4R)-4-methyl-1,3-dioxane-2-carboxylate

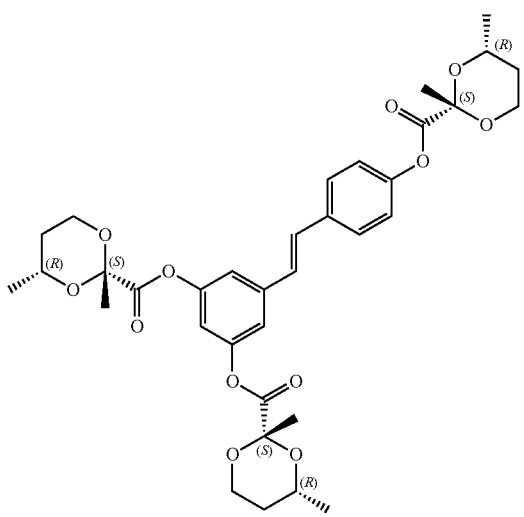

Compound 257:3-[(2S,4R)-2,4-dimethyl-1,3-dioxane-2-carbonyloxy]-5-[(1E)-2-{4-[(2S,4R)-2,4-dimethyl-1,3-dioxane-2-carbonyloxy]phenyl}ethenyl]phenyl(2S,4R)-2,4-dimethyl-1,3-dioxane-2-carboxylate

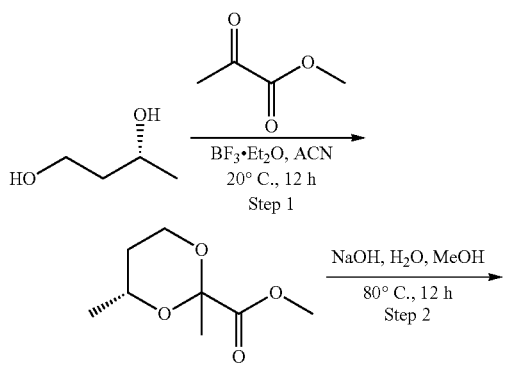

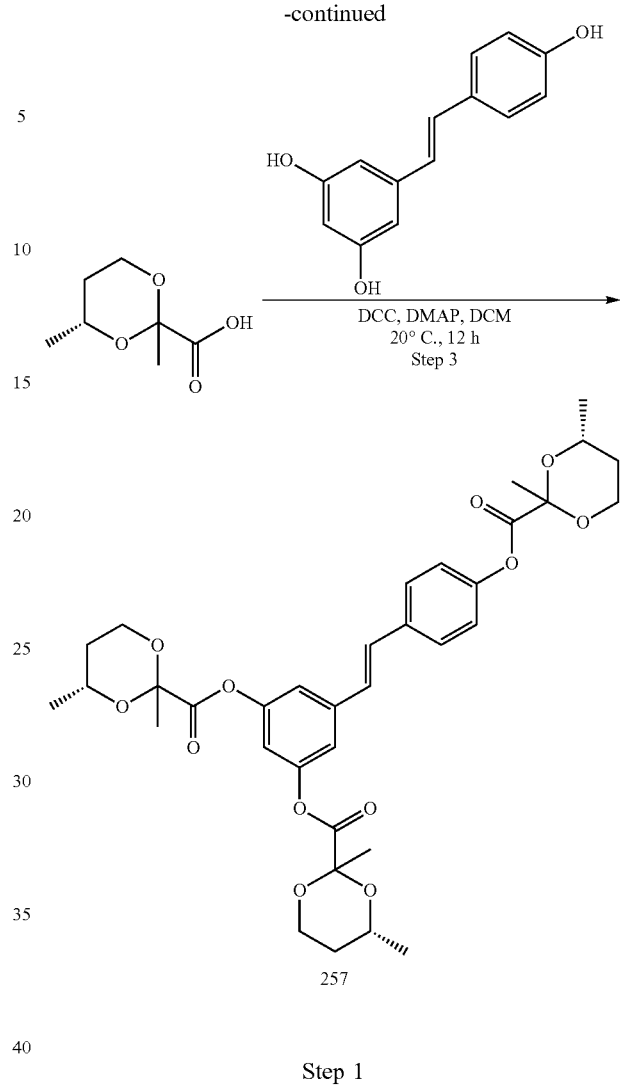

Step 1

To a mixture of (3R)-butane-1,3-diol (10 g, 110.96 mmol, 1 eq) and methyl 2-oxopropanoate (22.66 g, 221.92 mmol, 20.05 mL, 2 eq) in ACN (500 mL) was added BF$_3$·Et$_2$O (67.02 g, 221.92 mmol, 58.27 mL, 47% purity, 2 eq) dropwise in at 20° C. under N$_2$. The mixture was stirred at 20° C. for 12 hours. TLC indicated one new spot formed. The pH of the solution was adjusted to 7-8 by added sat. NaHCO$_3$ solution. The aqueous phase was extracted with ethyl acetate (100 mL*3). The combined organic phase was washed with brine (50 mL), dried with anhydrous Na$_2$SO$_4$, filtered and concentrated in vacuum. The residue was purified by column chromatography (SiO$_2$, Petroleum ether/Ethyl acetate=100/1 to 10:1). $^1$H NMR indicated desired compound methyl (4R)-2,4-dimethyl-1,3-dioxane-2-carboxylate (13.8 g, 79.22 mmol, 71.40% yield) was obtained as yellow oil.

Step 2

To a mixture of methyl (4R)-2,4-dimethyl-1,3-dioxane-2-carboxylate (13.8 g, 79.22 mmol, 1 eq) in MeOH (220 mL) and H$_2$O (55 mL) was added NaOH (6.34 g, 158.44 mmol, 2 eq) in one portion at 80° C. under N$_2$. The mixture was stirred at 80° C. for 12 hours. TLC showed the reaction was completed. MeOH was removed under reduced pressure. The pH of the mixture was adjusted to 2-3 by added aq. HCl (6 M). The aqueous phase was extracted with ethyl acetate (100 mL*4). The combined organic phase was washed with brine (100 mL), dried with anhydrous Na$_2$SO$_4$, filtered and concentrated in vacuum. Compound (4R)-2,4-dimethyl-1,3-dioxane-2-carboxylic acid (12 g, 74.92 mmol, 94.57% yield) was obtained as yellow solid.

Step 3

To a mixture of 5-[(E)-2-(4-hydroxyphenyl)vinyl]benzene-1,3-diol (2 g, 8.76 mmol, 1 eq) and (4R)-2,4-dimethyl-1,3-dioxane-2-carboxylic acid (5.61 g, 35.05 mmol, 4 eq) in DCM (40 mL) was added DCC (7.23 g, 35.05 mmol, 7.09 mL, 4 eq) and DMAP (535.25 mg, 4.38 mmol, 0.5 eq) in one portion at 20° C. under N$_2$. The mixture was stirred at 20° C. for 12 hours. LCMS showed starting material was consumed completely. The reaction mixture was filtered and concentrated under reduced pressure to give a residue. The residue was purified by prep-HPLC [water (0.1% TFA)-ACN]. [4-[(E)-2-[3,5-bis[[(4R)-2,4-dimethyl-1,3-dioxane-2-carbonyl]oxy] phenyl]vinyl]phenyl](4R)-2,4-dimethyl-1,3-dioxane-2-carboxylate (2.8 g, 3.64 mmol, 41.49% yield, 85% purity) was obtained as white solid. LCMS: (M+H$_3$O$^+$): 672.2 @2.990

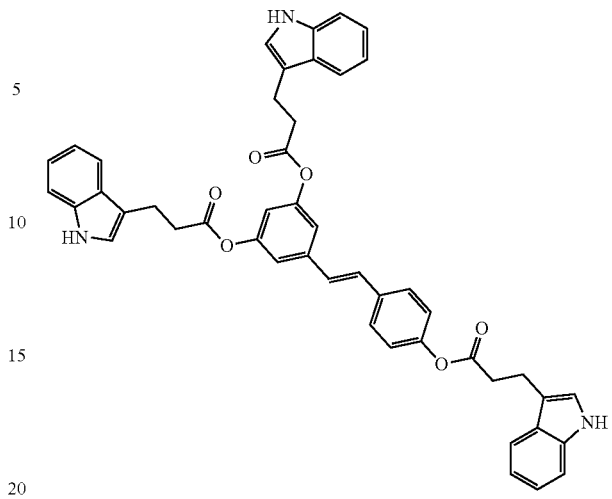

Compound 259: 4-[(1E)-2-[3,5-bis({[3-(1H-indol-3-yl)propanoyl]oxy})phenyl]ethenyl]phenyl 3-(1H-indol-3-yl)propanoate This compound was prepared according to a modified procedure described for the preparation of compound 2.

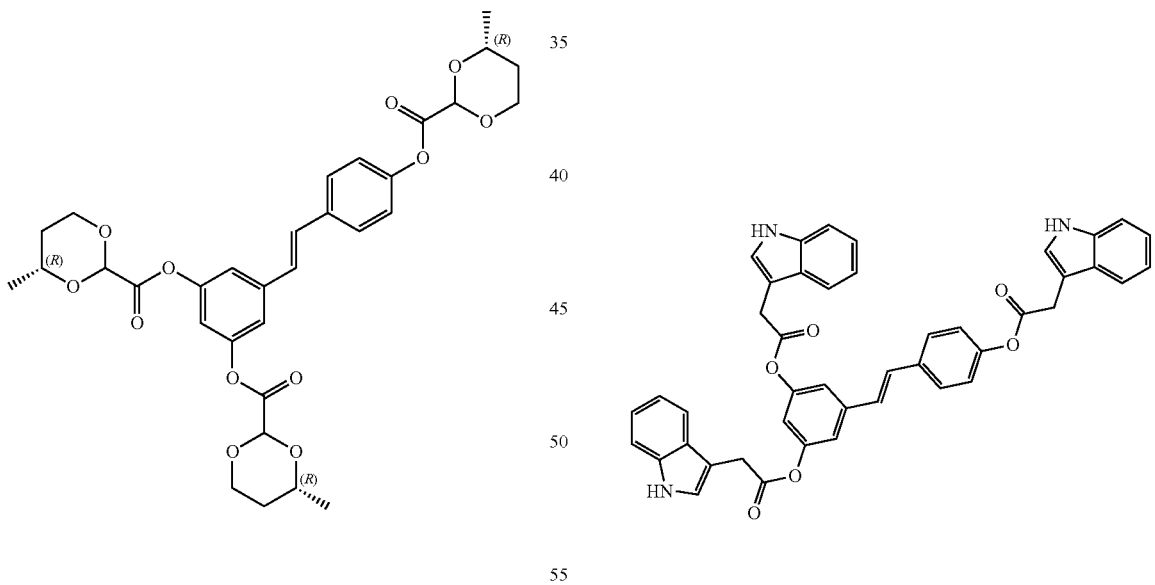

Compound 258: 3-[(4R)-4-methyl-1,3-dioxane-2-carbonyloxy]-5-[(1E)-2-{4-[(4R)-4-methyl-1,3-dioxane-2-carbonyloxy]phenyl}ethenyl]phenyl (4R)-4-methyl-1,3-dioxane-2-carboxylate This compound was prepared according to a modified procedure described for the preparation of compound 257.

Compound 260: 4-[(1E)-2-[3,5-bis({[2-(1H-indol-3-yl)acetyl]oxy})phenyl]ethenyl]phenyl 2-(1H-indol-3-yl)acetate This compound was prepared according to a modified procedure described for the preparation of compound 2.

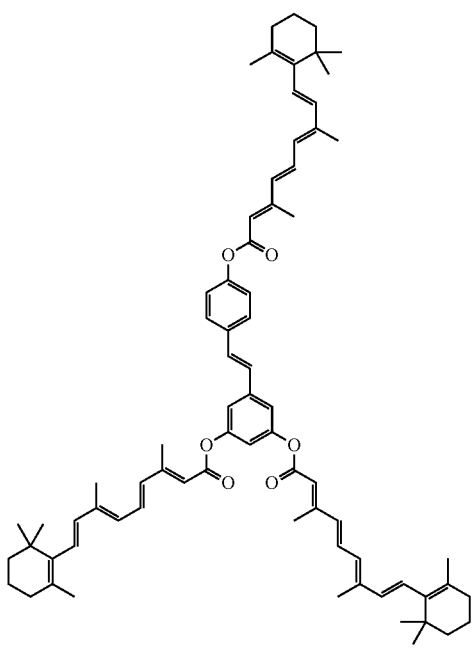 [SMILES: CC1=C(/C=C/C(C)=C/C=C/C(C)=C/C(=O)Oc2ccc(/C=C/c3cc(OC(=O)/C=C(C)/C=C/C=C(C)/C=C/C4=C(C)CCCC4(C)C)cc(OC(=O)/C=C(C)/C=C/C=C(C)/C=C/C4=C(C)CCCC4(C)C)c3)cc2)C(C)(C)CCC1]

Compound 261: 3-{[(2E,4E,6E,8E)-3,7-dimethyl-9-(2,6,6-trimethylcyclohex-1-en-1-yl)nona-2,4,6,8-tetraenoyl]oxy}-5-[(1E)-2-(4-{[(2E,4E,6E,8E)-3,7-dimethyl-9-(2,6,6-trimethylcyclohex-1-en-1-yl)nona-2,4,6,8-tetraenoyl]oxy}phenyl)ethenyl]phenyl (2E,4E,6E,8E)-3,7-dimethyl-9-(2,6,6-trimethylcyclohex-1-en-1-yl)nona-2,4,6,8-tetraenoate The following compound may be prepared using the synthesis strategies described herein:

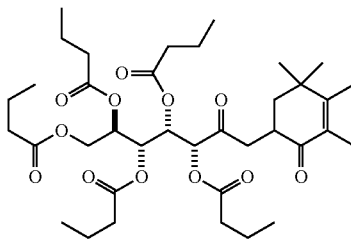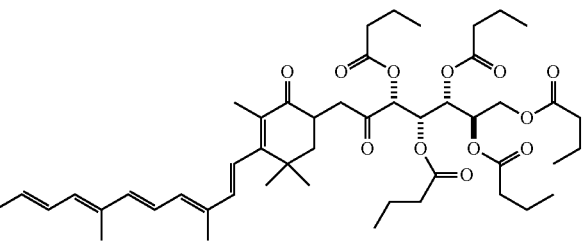

Example 2. In Vitro Assays

Acylated active agents disclosed herein may be stable under a range of physiological pH levels and cleaved selectively at a desired site of action (for example, in the GI tract, e.g., in the stomach, small intestine, or large intestine) by enzymes present in the local microenvironment. Acylated active agents are tested for chemical stability at a range of pH levels as well as their ability to be degraded in representative in vitro systems. Data for select acylated active agents are shown below.

Assay 1. Stability of acylated active agents in Simulated Gastric Fluid (SGF). This assay was used to assess the stability of an acylated active agent in a stomach.

Medium was prepared by dissolving 2 g of sodium chloride in 0.6 L of ultrapure water (MilliQ®, Millipore Sigma, Darmstadt, Germany). The pH was adjusted to 1.6 with 1N hydrochloric acid, and the volume was then adjusted to 1 L with purified water.

60 mg FaSSIF powder (Biorelevant™, London, UK) were dissolved in 500 mL buffer (above). Pepsin was added (0.1 mg/mL) (Millipore Sigma, Darmstadt, Germany), and the solution was stirred. The resulting SGF media were used fresh for each experiment.

Test compounds were dissolved in DMSO stock to 1 mM. An aliquot of the DMSO stock solution was removed and diluted in the SGF Media in 15 mL falcon tubes to generate a compound concentration of 1 µM. A 1 mL aliquot was immediately removed and diluted once with 1 volume of acetonitrile for T0 timepoint. The mixture was sealed and mixed at 37° C. in an incubator. Aliquots (1 mL) were removed at regular intervals and immediately quenched by the addition of 1 volume of acetonitrile. The resulting samples were analyzed by LC/MS to determine degradation rates in SGF.

Assay 2. Stability of acylated active agents in Simulated Intestinal Fluid (SIF). This assay was used to assess the stability of an acylated active agent in a small intestine.

Phosphate buffer was prepared by dissolving 0.42 g of sodium hydroxide pellets and 3.95 g of monobasic sodium phosphate monohydrate and 6.19 g of sodium chloride in ultrapure water (MilliQ®, Millipore Sigma, Darmstadt, Germany). The pH was adjusted to 6.7 using aq. HCl and aq. NaOH, as necessary, and the solution was diluted with ultrapure water to produce 1 L of the pH 6.7 buffer.

112 mg FaSSIF powder (Biorelevant™, London, UK) was dissolved in 50 mL of the pH 6.7 buffer. 2 to 3 mL of the resulting solution were then added to 500 mg pancreatin (Millipore Sigma, Darmstadt, Germany). The resulting mixture was agitated by finger tapping the vessel containing the mixture until milky suspension formed. At this time, the remainder of the 50 mL FaSSiF/pH 6.7 buffer solution was added. The resulting suspension was flipped upside down 10 times to produce SIF, which was used fresh.

Test compounds were dissolved in DMSO stock to 1 mM. An aliquot of the DMSO stock solution was removed and diluted in the SIF media in 15 mL falcon tubes to produce a mixture with a tested compound concentration of 1 µM. A 1 mL aliquot was immediately removed and diluted once with 1 volume of acetonitrile for T0 timepoint. The mixture was sealed and agitated at 37° C. in an incubator. Aliquots (1 mL) were removed at regular intervals and immediately quenched by the addition of 1 volume of acetonitrile. The resulting samples were analyzed by LC/MS to determine degradation rates.

Assay 3. Fecal Incubation Stability. This assay was used to assess the stability of an acylated active agent in a large intestine. All experiments were performed in an anaerobic chamber containing 90% nitrogen, 5% hydrogen and 5% carbon dioxide. Human fecal matter in a slurry (15% WV) is added to 96 well plates containing YCFA media or other suitable media (1.6 mL). Compounds were added to each individual well to reach a final analyte concentration of 1 or 10 μM, and the material was mixed by pipetting. At set time points a sample was removed, quenched with acetonitrile, and analyzed by LC/MS.

Buffer Assay. Stability of acylated active agents in a buffer. This assay provides for the assessment of the stability of an acylated active agent at different physiological pH levels.

Compounds are diluted in DMSO, and added in the appropriate quantity to phosphate buffer (pH levels 2, 4, 6, and 8) to reach a total sample concentration of 2 μM. Compounds are incubated at RT, and aliquots are removed at time points 0, 60, 120, 360 and 1440 minutes and analyzed for purity by LC/MS/MS.

TABLE 1

| Compound | Assay 1 (SGF) (% Remaining @ 1 hours) | Assay 2 (SIF) (% @ Remaining 4 hours) | Assay 3 (% Remaining at 24 h) |
|---|---|---|---|
| 1 | C | B | |
| 2 | | C | |
| 3 | C | C | C |
| 4 | C | A | A |
| 11 | C | | |
| 12 | C | | |
| 13 | C | B | |
| 14 | C | A | |
| 15 | C | B | |
| 18 | C | C | |
| 19 | B | B | |
| 20 | C | A | |
| 21 | C | A | |
| 22 | B | A | |
| 23 | C | A | |
| 24 | C | A | |
| 31 | C | C | |
| 32 | A | A | |
| 33 | C | C | |
| 34 | C | C | |
| 39 | C | C | |
| 40 | C | C | |
| 41 | C | C | |
| 42 | | C | |
| 43 | C | C | B |
| 44 | C | B | |
| 45 | C | B | B |
| 46 | C | B | B |
| 53 | C | A | A |
| 63 | C | C | |
| 65 | C | C | |
| 66 | C | A | |
| 67 | B | A | |
| 69 | C | C | |
| 70 | B | C | |
| 72 | C | A | |
| 75 | C | B | |
| 76 | B | A | |
| 77 | B | A | |
| 78 | C | A | |
| 79 | C | A | A |
| 80 | C | A | A |
| 82 | Run 1: B, Run 2: C | A | A |
| 83 | C | A | A |
| 84 | C | C | B |
| 85 | B | B | B |
| 86 | C | B | C |
| 87 | B | A | A |
| 88 | C | A | A |
| 89 | | A | A |
| 90 | C | A | A |
| 91 | | A | A |
| 92 | | A | A |
| 93 | | A | A |
| 94 | | A | A |
| 95 | C | A | C |
| 97 | | A | A |
| 101 | C | A | B |
| 102 | B | A | A |
| 103 | B | A | Run 1: A, Run 2: B |
| 104 | B | A | A |
| 105 | C | B | A |
| 106 | C | A | A |
| 107 | C | A | A |
| 108 | C | | |
| 109 | C | A | A |
| 110 | C | C | A |
| 111 | B | A | A |
| 113 | C | A | A |
| 114 | B | A | |
| 116 | C | A | A |
| 117 | C | A | A |
| 118 | B | A | A |
| 119 | B | | A |
| 120 | B | | A |
| 121 | | A | A |
| 122 | C | B | A |
| 123 | C | A | A |
| 124 | C | A | A |
| 125 | C | A | A |
| 126 | C | A | A |
| 127 | B | | |
| 128 | C | A | A |
| 129 | B | | A |
| 130 | B | A | A |
| 131 | B | | A |
| 132 | B | | A |
| 133 | C | A | A |
| 134 | C | B | A |
| 135 | C | A | A |
| 136 | C | A | A |
| 137 | C | B | B |
| 138 | C | A | A |
| 139 | B | A | B |
| 140 | C | A | A |
| 141 | C | A | A |
| 142 | C | A | |
| 143 | C | A | A |
| 144 | C | A | A |
| 145 | C | A | C |
| 146 | C | A | A |
| 147 | C | A | A |
| 148 | C | | |
| 149 | C | A | A |
| 150 | C | A | |
| 151 | | A | |
| 152 | | A | |
| 153 | | A | |
| 154 | | A | |
| 155 | Batch 1: C; Batch 2: B | C | A |
| 156 | C | A | |
| 157 | C | A | |

TABLE 1-continued

| Compound | Assay 1 (SGF) (% Remaining @ 1 hours) | Assay 2 (SIF) (% Remaining 4 hours) | Assay 3 (% Remaining at 24 h) |
|---|---|---|---|
| 158 | C | A | A |
| 159 | C | B |   |
| 160 | C |   |   |
| 161 | C | A |   |
| 162 | C | A |   |
| 162 |   | A |   |
| 163 | C |   |   |
| 167 | C | A |   |
| 172 |   | C |   |
| 178 |   |   | A |
| 180 | B | A | A |
| 181 |   | A | A |
| 182 | C | A |   |
| 190 |   | A | A |
| 191 |   | C |   |
| 193 | C | C | B |
| 194 | C | A | C |
| 195 | C | C | B |
| 199 | B | A | A |
| 200 | C | C |   |
| 201 | B | A | A |
| 202 | C | A |   |
| 203 | C | A | B |
| 204 |   | B |   |
| 227 | C | A | A |
| 229 |   | A |   |
| 230 |   |   | B |
| 234 |   |   | B |
| 235 | C | A | A |
| 236 | B | A | A |
| 237 | C | A | A |
| 239 | C | A | A |
| 240 | A | C |   |
| 242 | C | A |   |
| 246 |   | B | B |
| 248 |   |   | A |
| 253 | B | B |   |
| 254 |   |   | B |
| 255 | C | C | B |
| 256 | A |   |   |
| 257 | C | A | A |
| 258 | A |   |   |
| 259 | C | C | B |
| 260 |   |   | A |

In Table 1,
A: <25% of the tested compound remaining;
B: 25-75% of the tested compound remaining; and
C: >75% of the tested compound remaining.

Table 1 shows that, for example, compounds 1, 4, 13-15, 20-24, 44-46, 53, 66, 67, 72, and 75-78 can be selectively delivered to an upper intestine.

Example 3. In Vivo Evaluation of an Acylated Catechin Polyphenol for Metabolic Disorders Active agents (e.g., acylated active agents or active agent combinations) disclosed herein may be useful in modulating metabolic markers and for treating metabolic disorders. Active agents (e.g., acylated active agents or active agent combinations) disclosed herein may also be useful in modulating NAFLD markers and for treating NAFLD (e.g., NASH). This example demonstrates the capability of an exemplary acylated active agent, compound 4, to induce weight loss and improve metabolic markers (e.g., improve glucose tolerance) in a subject. This example also demonstrates the capability of an exemplary active agent combination, resveratrol and a pre-ketone body, to improve NAFLD markers (e.g., liver weight, steatosis, ballooning, liver inflammation, or liver enzyme levels) in a subject.

C57BL/6 mice were divided into seven cohorts, as listed in Table 2.

TABLE 2

| Model | Treatment* | # of animals | Dose** | Frequency | Route |
|---|---|---|---|---|---|
| HFD-fed C57BL/6 mice | ND | 10 |   | Ad libitum | Diet |
|   | HFD | 10 |   | Ad libitum | Diet |
|   | HFD + Acetate | 10 | 5% | Ad libitum | Diet |
|   | HFD + EGCG | 10 | 1% | Ad libitum | Diet |
|   | HFD + Acetate + EGCG | 10 | 5% + 1% | Ad libitum | Diet |
|   | HFD + Compound 4 | 10 | 6% | Ad libitum | Diet |
|   | HFD + rosiglitazone | 10 | 0.45 mg/g | Ad libitum | Diet |

*In Table 2, ND means normal diet, HFD means high-fat diet, and EGCG means epigallocatechin gallate.
**In Table 2, dose percentages refer to weight percentage relative to the high fat diet.

Animals were allowed free access to food and drinking water for the entire 8 week study. Animals were weighed on a weekly basis, and food and drinking water consumption monitored. Plasma and stool samples were collected at the beginning of the study, mid-study, and day of termination. These samples were used for the measurement of the disease makers.

Figure 2:
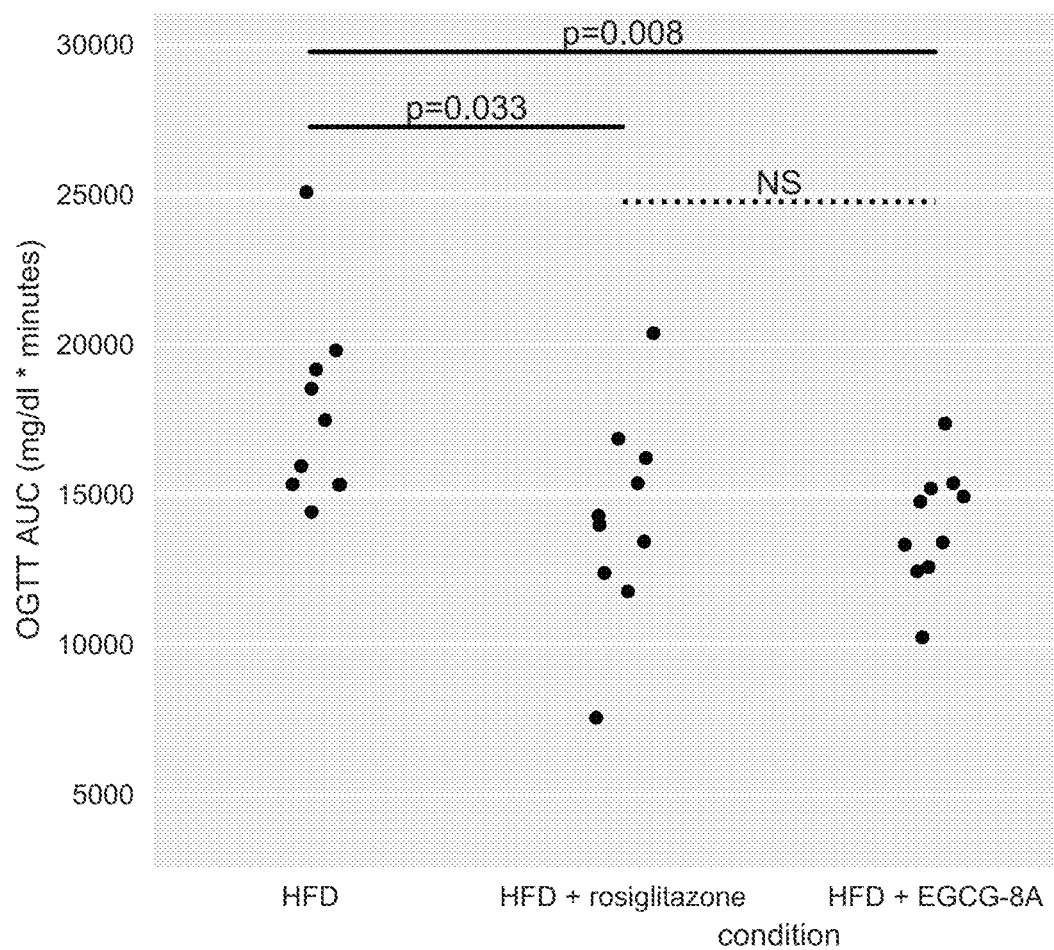
FIG. 2 is a chart showing the glucose tolerance levels in three animal cohorts: (1) untreated animals receiving a high-fat diet, (2) animals receiving rosiglitazone with a high-fat diet, and (3) animals receiving epigallocatechin gallate octaacetate (EGCG-8A) along with a high-fat diet.

The results of this study are illustrated in FIGS. 1 and 2. FIG. 1 shows that animals in the HFD+compound 4 cohort underwent weight loss despite being fed a high-fat diet. FIG. 2 shows that glucose tolerance of animals in the HFD+ Compound 4 cohort exceeded that of animals in the HFD+ rosiglitazone; the latter is a known insulin sensitizer drug approved for use as an antidiabetic drug.

The results of this study show that an exemplary acylated active agent, compound 4, can induce weight loss and improve metabolic markers (e.g., glucose tolerance) in a subject.

Disease markers were also assessed in liver tissues collected from mice as follows. Liver tissues from mice were collected, fixed by immersion in 10% neutral buffered formalin. Fixed tissue specimens were sent to a histological processing laboratory (Premier Laboratory, Longmont, CO), where they were paraffin embedded, sectioned (approximately 4 μm), mounted, and stained with hematoxylin and eosin (H&E) using standard methods.

Liver sections (2) for each animal were scored from a scan of the H&E-stained slide for inflammation, steatosis (macrovesicular vacuolation) and ballooning (microvascular vacuolation) using a modified grading scale based on human biopsy scoring (Brunt et al., Am J Clin Pathol, 128:837-47, 2007). Inflammation was scored 0=no inflammation, 1=minimal (1-3 foci of scattered (lobar) inflammatory cells), 2=mild (3 to 10 scattered foci of inflammatory cells with or without portal/periportal inflammation), 3=moderate (>10 scattered (lobar) foci of inflammatory cells and/or marked portal/periportal inflammation. Steatosis was graded (as in Brunt et al., Am J Clin Pathol, 128:837-47, 2007) as follows: 0=no steatosis, grade 1: ≤33%; grade 2: >33%, <66%; 3: ≥66%. Ballooning was scored as follows: 0=no ballooning, 1=rare/few, and 2=many hepatocytes with microvesicular vacuolation.

Figure 3:
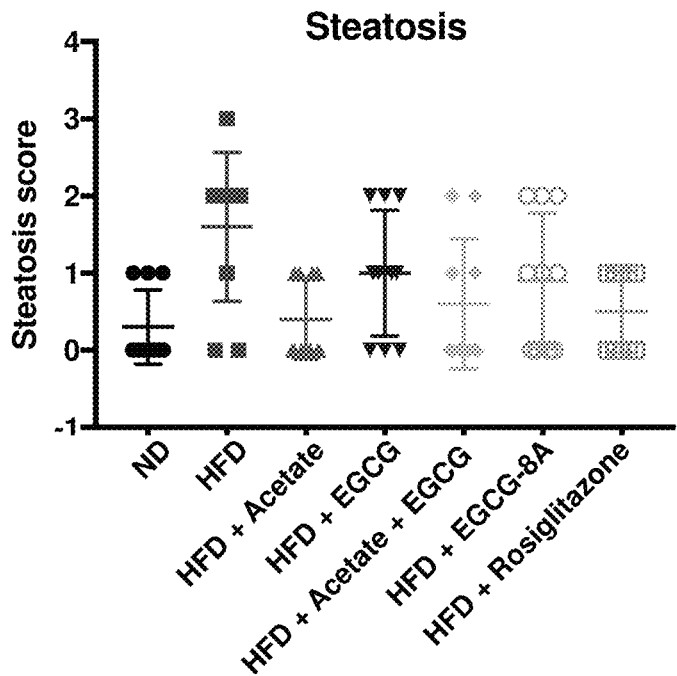
FIG. 3 is a graph showing steatosis scores for mice divided into the following cohorts: (ND) the normal diet group, (HFD) high fat diet group, (HFD+Acetate) high fat diet group administered acetic acid, (HFD+EGCG) high fat diet group administered epigallocatechin gallate, (HFD+Acetate+EGCG) high fat diet group administered a combination of epigallocatechin gallate and acetic acid, (HFD+EGCG-8A) high fat diet group administered epigallocatechin gallate octaacetate, and (HFD+Rosiglitazone) high fat diet group receiving rosiglitazone.
Figure 4:
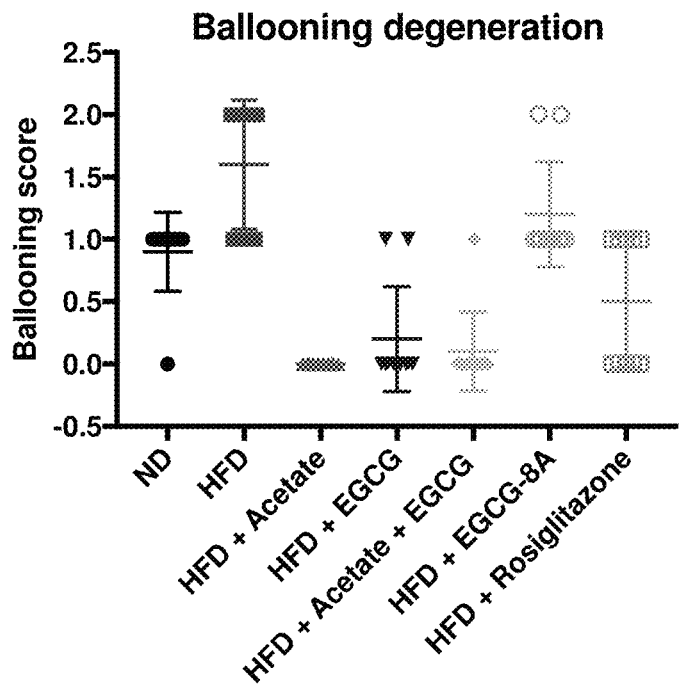
FIG. 4 is a graph showing ballooning degeneration scores for mice divided into the following cohorts: (ND) the normal diet group, (HFD) high fat diet group, (HFD+Acetate) high fat diet group administered acetic acid, (HFD+EGCG) high fat diet group administered epigallocatechin gallate, (HFD+Acetate+EGCG) high fat diet group administered a combination of epigallocatechin gallate and acetic acid, (HFD+EGCG-8A) high fat diet group administered epigallocatechin gallate octaacetate, and (HFD+Rosiglitazone) high fat diet group receiving rosiglitazone.
Figure 5A:
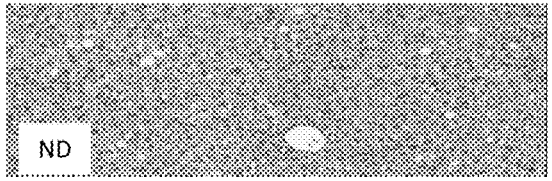
FIG. 5A is an image from the histological analysis of the livers from the (ND) normal diet group in FIG. 4.
Figure 5B:
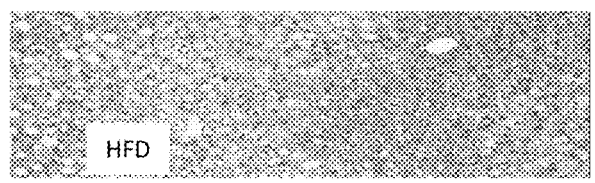
FIG. 5B is an image from the histological analysis of the livers from the (HFD) high fat diet group in FIG. 4.
Figure 5C:
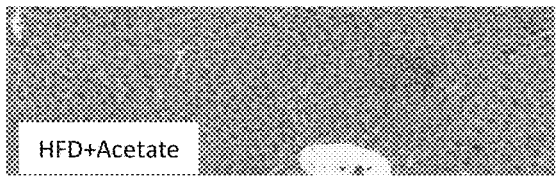
FIG. 5C is an image from the histological analysis of the livers from the (HFD+Acetate) high fat diet group administered acetic acid in FIG. 4.
Figure 5D:
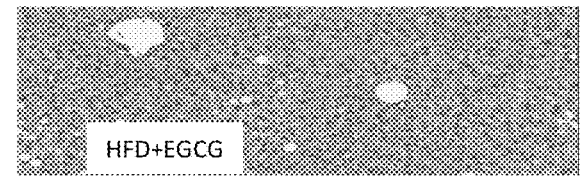
FIG. 5D is an image from the histological analysis of the livers from the (HFD+EGCG) high fat diet group administered epigallocatechin gallate in FIG. 4.
Figure 5E:
FIG. 5E is an image from the histological analysis of the livers from the (HFD+Acetate+EGCG) high fat diet group administered a combination of epigallocatechin gallate and acetic acid in FIG. 4.
Figure 5F:
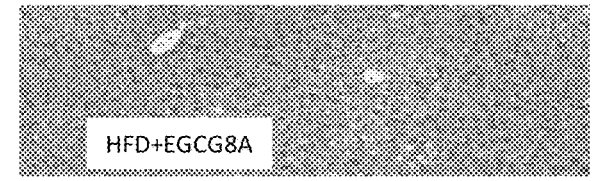
FIG. 5F is an image from the histological analysis of the livers from the (HFD+EGCG-8A) high fat diet group administered epigallocatechin gallate octaacetate in FIG. 4.
Figure 5G:
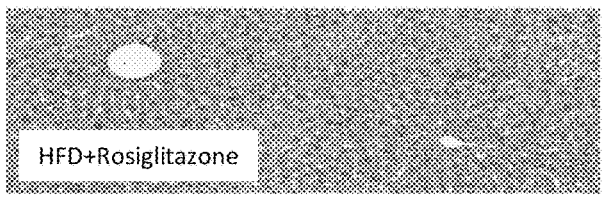
FIG. 5G is an image from the histological analysis of the livers from the (HFD+Rosiglitazone) high fat diet group receiving rosiglitazone in FIG. 4.

Results of this study are shown in FIGS. 3-5G. FIG. 3 shows that animals receiving a high fat diet and an exemplary acylated active agent, compound 4 (EGCG-8A), exhibited a lower steatosis score than the animals fed high fat diet only; the steatosis score observed for the animals receiving high fat diet and compound 4 (EGCG-8A) were similar to a control group of animals fed a normal diet. FIG. 4 shows that animals receiving a high fat diet and an exemplary acylated active agent, compound 4 (EGCG-8A), exhibited a lower ballooning score than the animals fed a high fat diet only; the ballooning score observed for the animals receiving a high fat diet and compound 4 (EGCG-8A) were similar to a control group of animals fed a normal diet. FIGS. 5A-5G show the histological analysis of the livers from the tested animals; the livers from the animals receiving a high fat diet exhibited significant steatosis (FIG. 5B), whereas the livers from the animals receiving a high fat diet and compound 4 (EGCG-8A) exhibited significantly lower steatosis.

Example 4. In Vivo Evaluation of an Active Agent Combination

Active agents (e.g., acylated active agents or active agent combinations) disclosed herein may be useful in modulating metabolic markers and for treating metabolic disorders. This example demonstrates the capability of an exemplary active agent combination, resveratrol and a pre-ketone body, to improve metabolic markers (e.g., abdominal fat accumulation, as well as triglyceride and cholesterol levels) in a subject.

Standard husbandry practices of the facility were followed, including free access to feed and reverse osmosis drinking water. Primary enclosure was either contact or suspended caging. Water was supplied in bottles or automatic racking system. Room was maintained at 22-25° C. and under the 12-hour light cycle. Each animal was observed daily from time of arrival to study end for clinical signs of ill health. Each group consisted of 8 FATZO mice (inbred AKR/J and C57BL/6J). Mice were provided 5% Fructose in their drinking water. For animals receiving 1,3-butanediol or p-hydroxybutyrate, compound was dissolved at 4.2% (w/v) or 3% (w/v) respectively in the drinking water in addition to the fructose. Resveratrol was delivered in the diet at a dose level of 0.78% (w/w). Positive control used in the study was obeticholic acid, 0.0523% (w/w) in diet. On Day 1, animals were weighed and randomized into treatment group. Animals were allowed free access to food and drinking water for entire 8 week of the study. Animals were weighed on a weekly basis, and food and drinking water consumption monitored. Plasma and stool samples were collected at the beginning of the study, mid-study, and day of termination. These samples were used for the measurement of the disease makers. Results of this study are shown in FIGS. 6-15.

Figure 6:
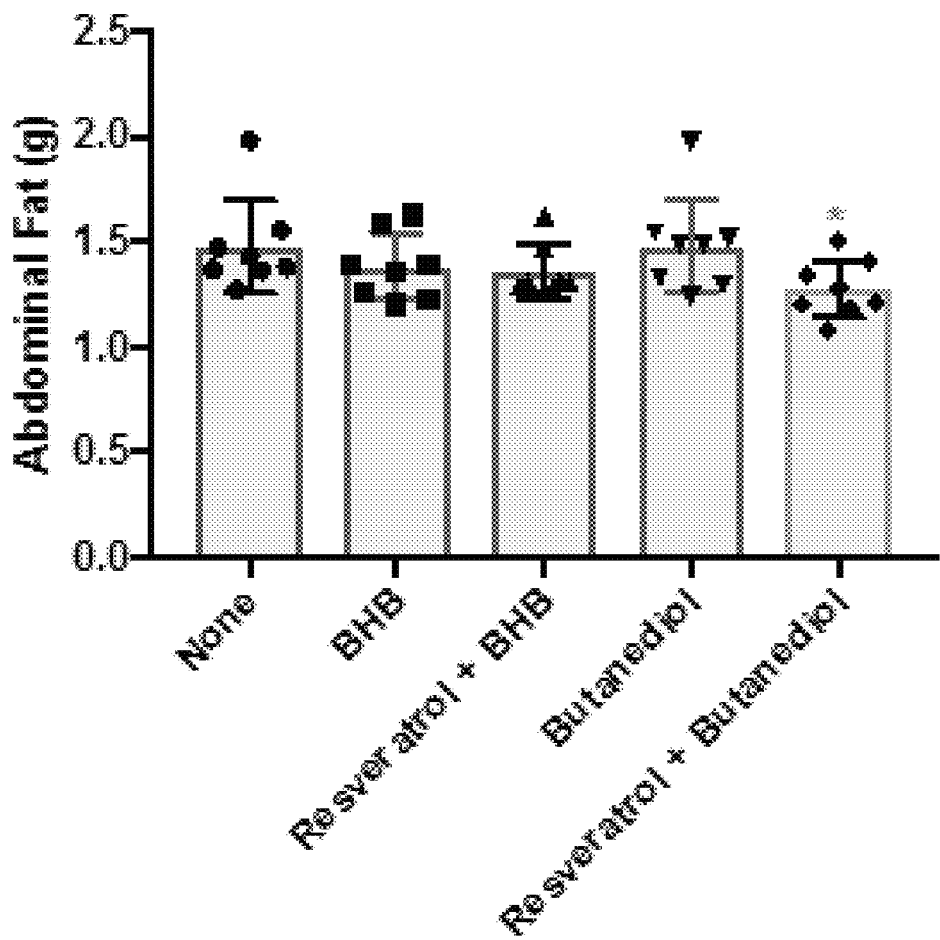
FIG. 6 is a chart showing the abdominal fat levels in five animal cohorts: (None) control group animals, (BHB) animals receiving β-hydroxybutyrate, (Resveratrol+BH) animals receiving a combination of resveratrol and β-hydroxybutyrate, (Butanediol) animals receiving 1,3-butanediol, and (Resveratrol+Butanediol) animals receiving resveratrol and 1,3-butanediol.
Figure 7:
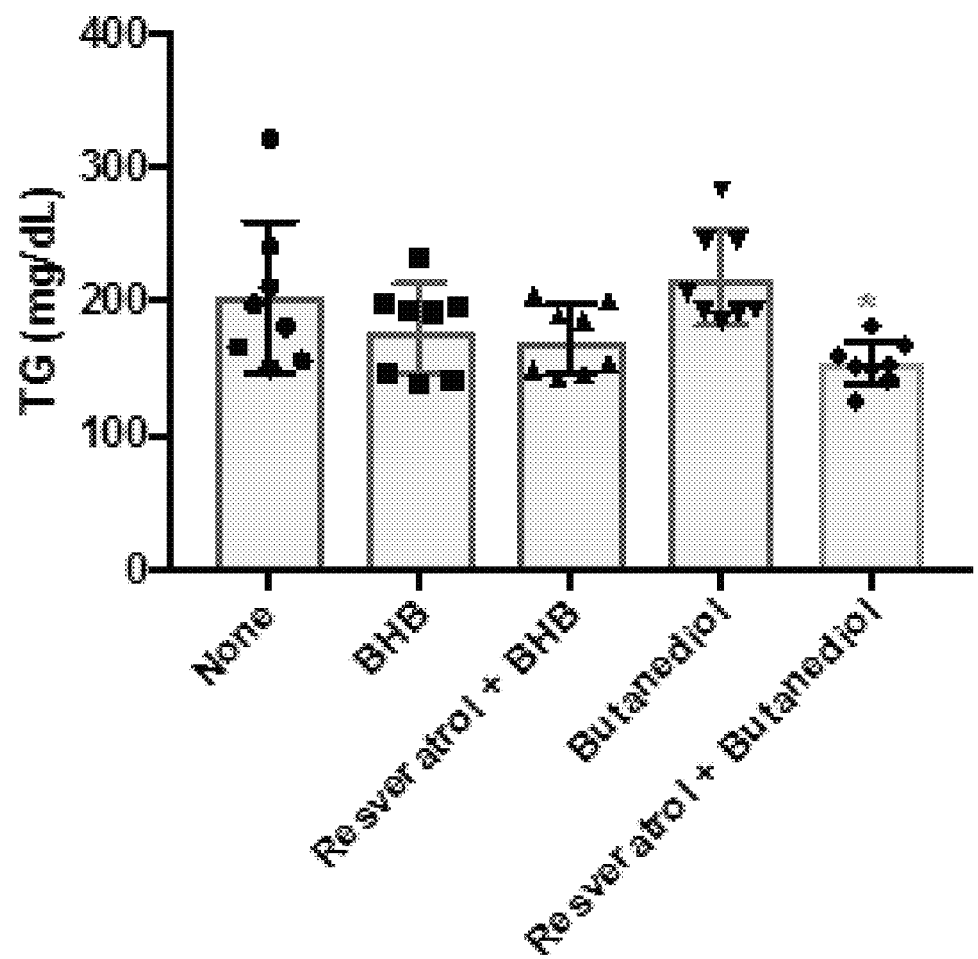
FIG. 7 is a chart showing the triglyceride levels in five animal cohorts: (None) control group animals, (BHB) animals receiving β-hydroxybutyrate, (Resveratrol+BH) animals receiving a combination of resveratrol and β-hydroxybutyrate, (Butanediol) animals receiving 1,3-butanediol, and (Resveratrol+Butanediol) animals receiving resveratrol and 1,3-butanediol.
Figure 8:
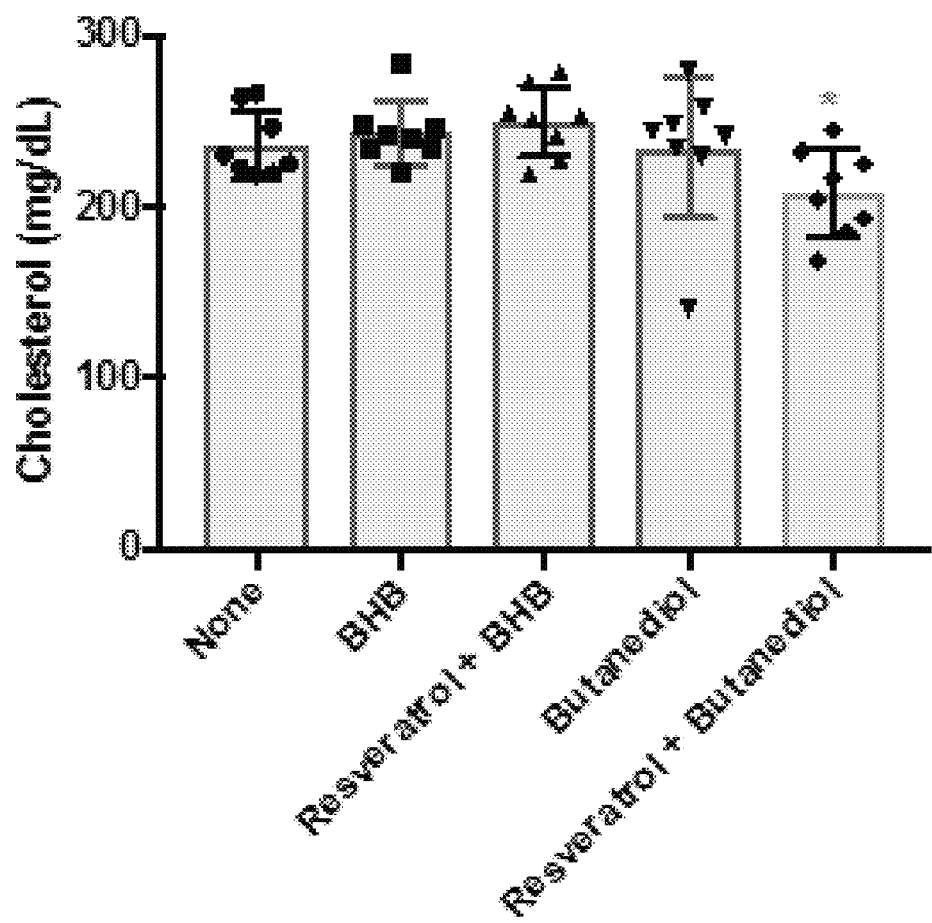
FIG. 8 is a chart showing the cholesterol levels in five animal cohorts: (None) control group animals, (BHB) animals receiving β-hydroxybutyrate, (Resveratrol+BH) animals receiving a combination of resveratrol and β-hydroxybutyrate, (Butanediol) animals receiving 1,3-butanediol, and (Resveratrol+Butanediol) animals receiving resveratrol and 1,3-butanediol.
Figure 9:
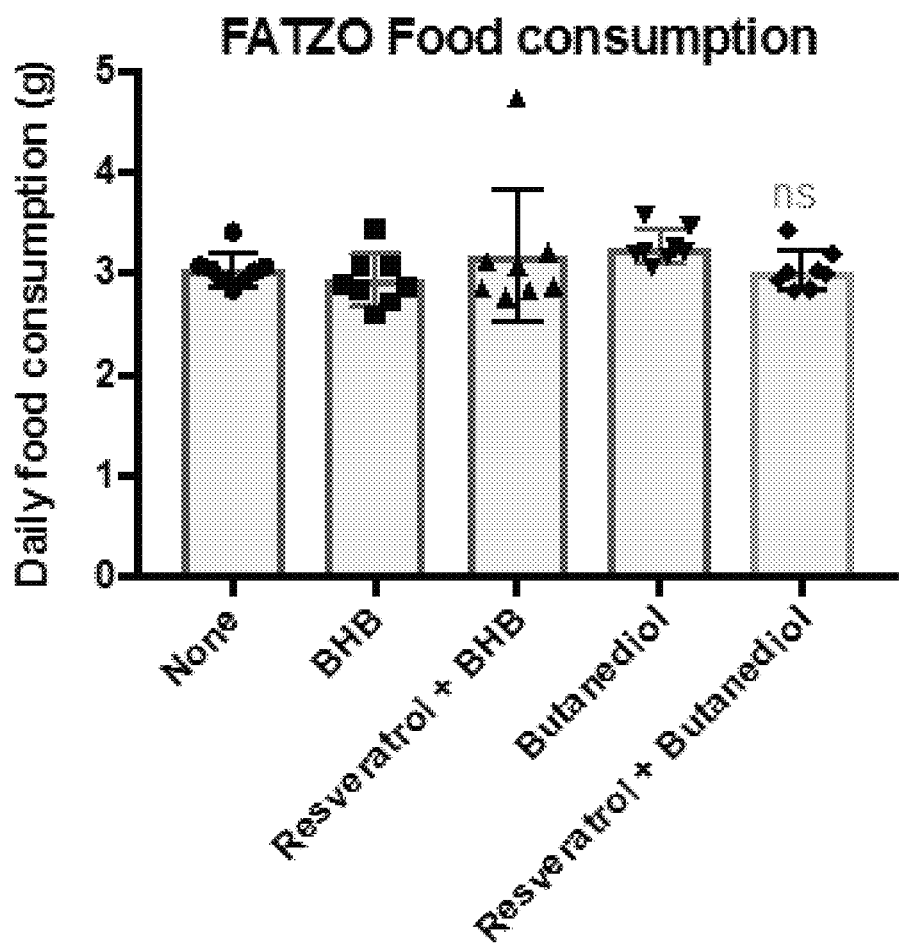
FIG. 9 is a chart showing the daily food consumption for five animal cohorts: (None) control group animals, (BHB) animals receiving β-hydroxybutyrate, (Resveratrol+BH) animals receiving a combination of resveratrol and β-hydroxybutyrate, (Butanediol) animals receiving 1,3-butanediol, and (Resveratrol+Butanediol) animals receiving resveratrol and 1,3-butanediol.
Figure 10:
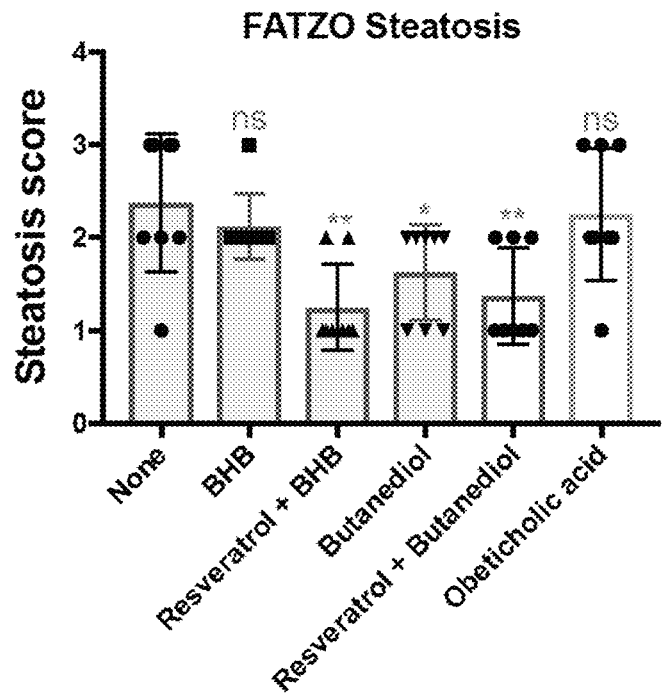
FIG. 10 is a graph showing steatosis scores for FATZO mice divided into the following cohorts: (None) control group, (BHB) β-hydroxybutyrate group, (Resveratrol+BHB) resveratrol and β-hydroxybutyrate combination group, (Butanediol) 1,3-butanediol group, (Resveratrol+Butanediol) resveratrol and 1,3-butanediol combination group, and (Obeticholic acid) obeticholic acid group.
Figure 11:
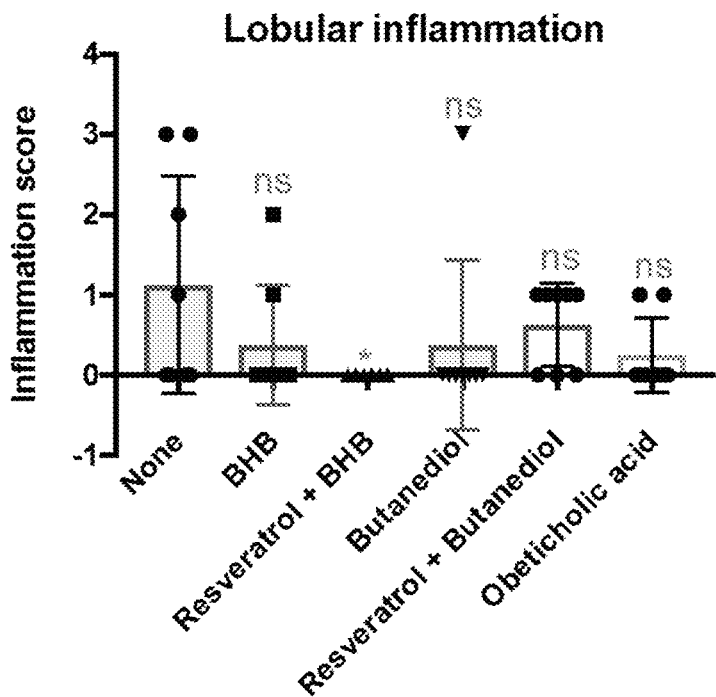
FIG. 11 is a graph showing lobular inflammation scores for FATZO mice divided into the following cohorts: (None) control group, (BHB) β-hydroxybutyrate group, (Resveratrol+BHB) resveratrol and β-hydroxybutyrate combination group, (Butanediol) 1,3-butanediol group, (Resveratrol+Butanediol) resveratrol and 1,3-butanediol combination group, and (Obeticholic acid) obeticholic acid group.
Figure 12:
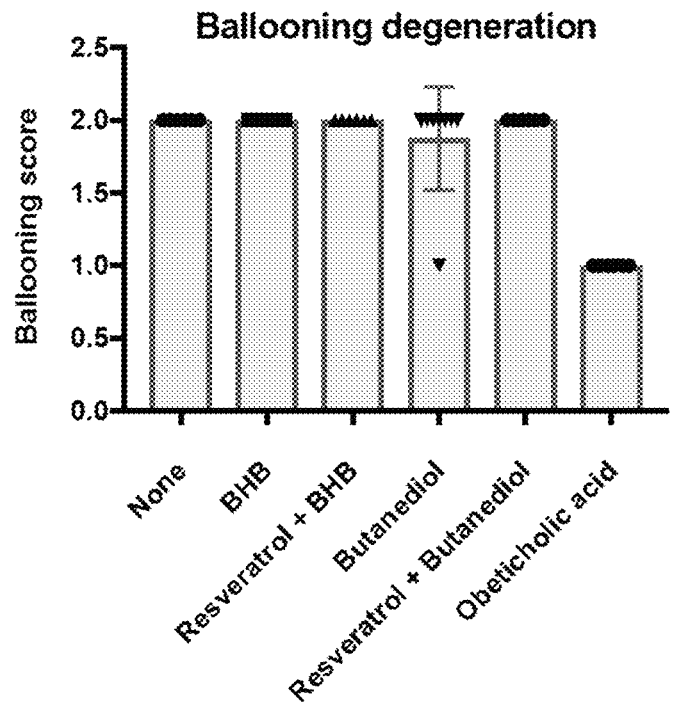
FIG. 12 is a graph showing ballooning degeneration scores for FATZO mice divided into the following cohorts: (None) control group, (BHB) β-hydroxybutyrate group, (Resveratrol+BHB) resveratrol and β-hydroxybutyrate combination group, (Butanediol) 1,3-butanediol group, (Resveratrol+Butanediol) resveratrol and 1,3-butanediol combination group, and (Obeticholic acid) obeticholic acid group.
Figure 13:
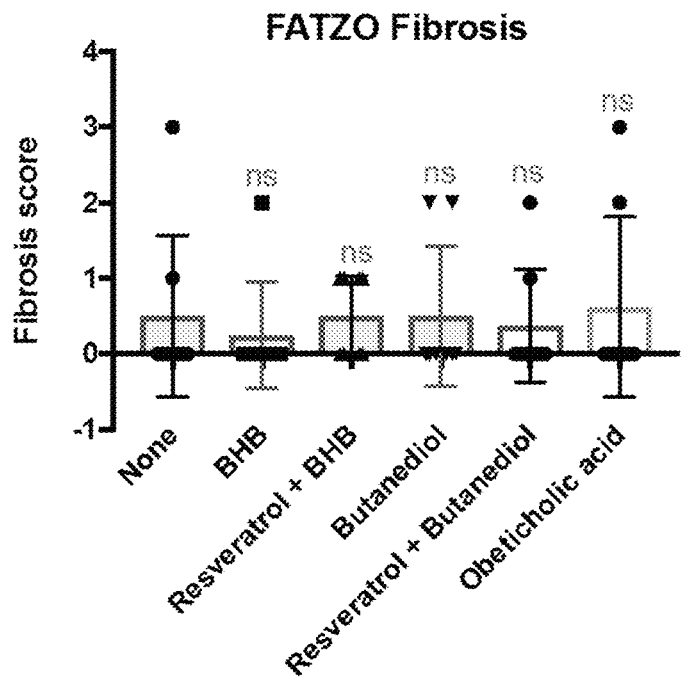
FIG. 13 is a graph showing fibrosis scores for FATZO mice divided into the following cohorts: (None) control group, (BHB) β-hydroxybutyrate group, (Resveratrol+BHB) resveratrol and β-hydroxybutyrate combination group, (Butanediol) 1,3-butanediol group, (Resveratrol+Butanediol) resveratrol and 1,3-butanediol combination group, and (Obeticholic acid) obeticholic acid group.
Figure 14:
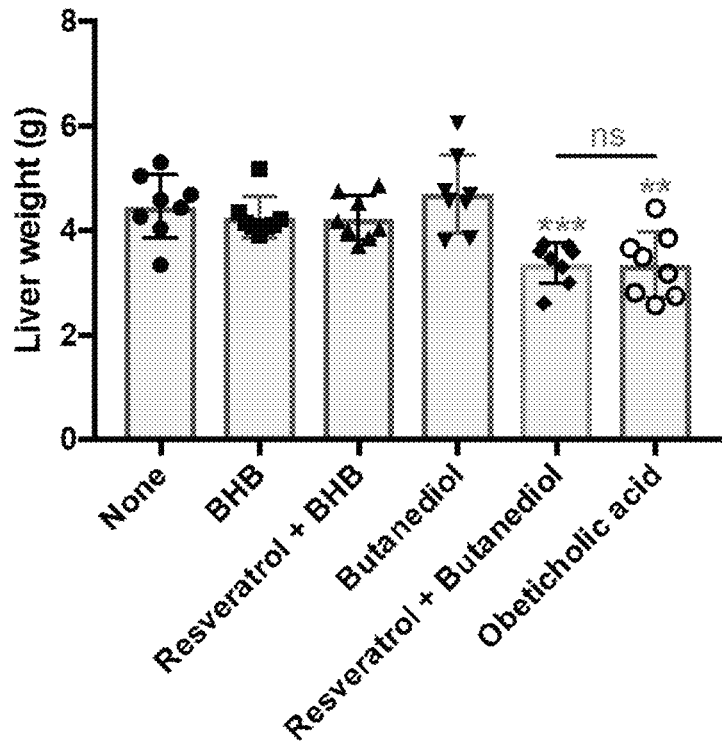
FIG. 14 is a graph showing liver weights for FATZO mice divided into the following cohorts: (None) control group, (BHB) β-hydroxybutyrate group, (Resveratrol+BHB) resveratrol and β-hydroxybutyrate combination group, (Butanediol) 1,3-butanediol group, (Resveratrol+Butanediol) resveratrol and 1,3-butanediol combination group, and (Obeticholic acid) obeticholic acid group.
Figure 15:
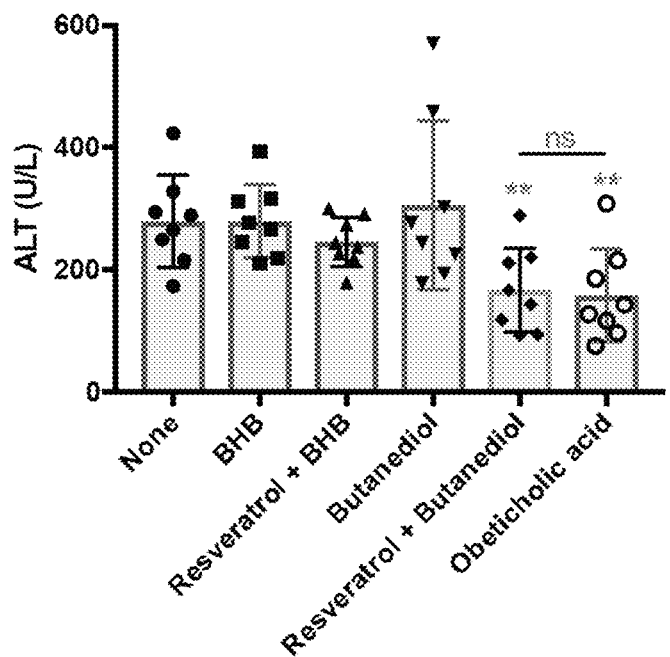
FIG. 15 is a graph showing alanine transaminase blood levels for FATZO mice divided into the following cohorts: (None) control group, (BHB) β-hydroxybutyrate group, (Resveratrol+BHB) resveratrol and β-hydroxybutyrate combination group, (Butanediol) 1,3-butanediol group, (Resveratrol+Butanediol) resveratrol and 1,3-butanediol combination group, and (Obeticholic acid) obeticholic acid group.
Figure 16:
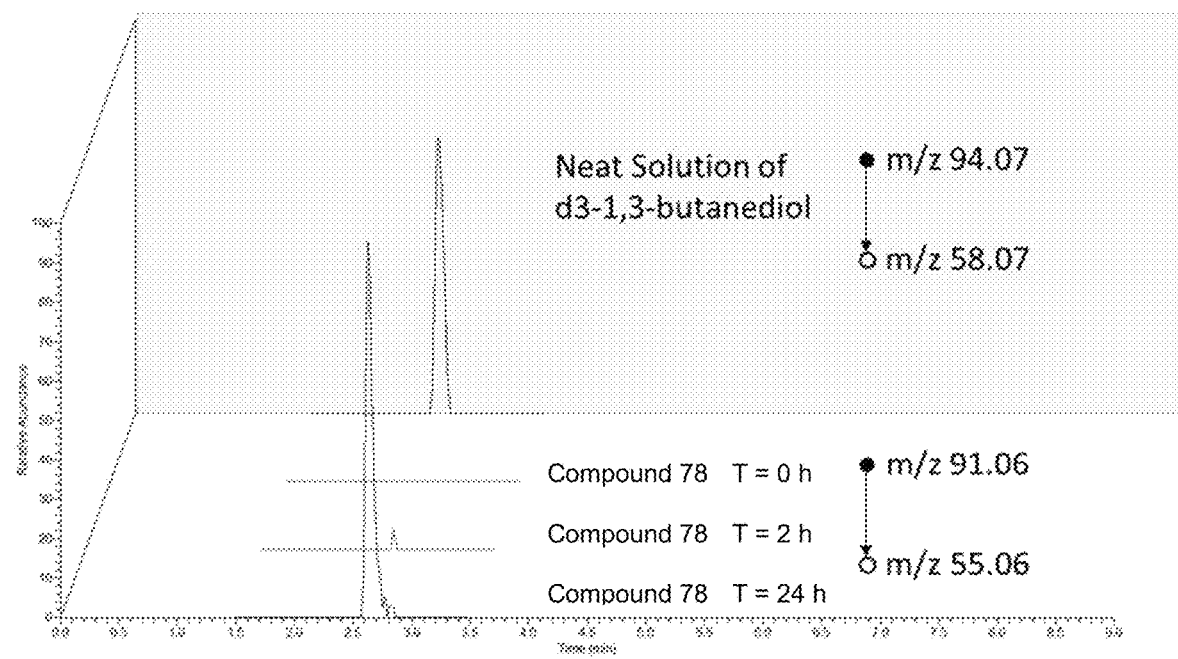
FIG. 16 is a graph showing the HPLC traces for 1,3-butanediol produced by compound 78 cleavage in simulated intestinal fluid.
Figure 17:
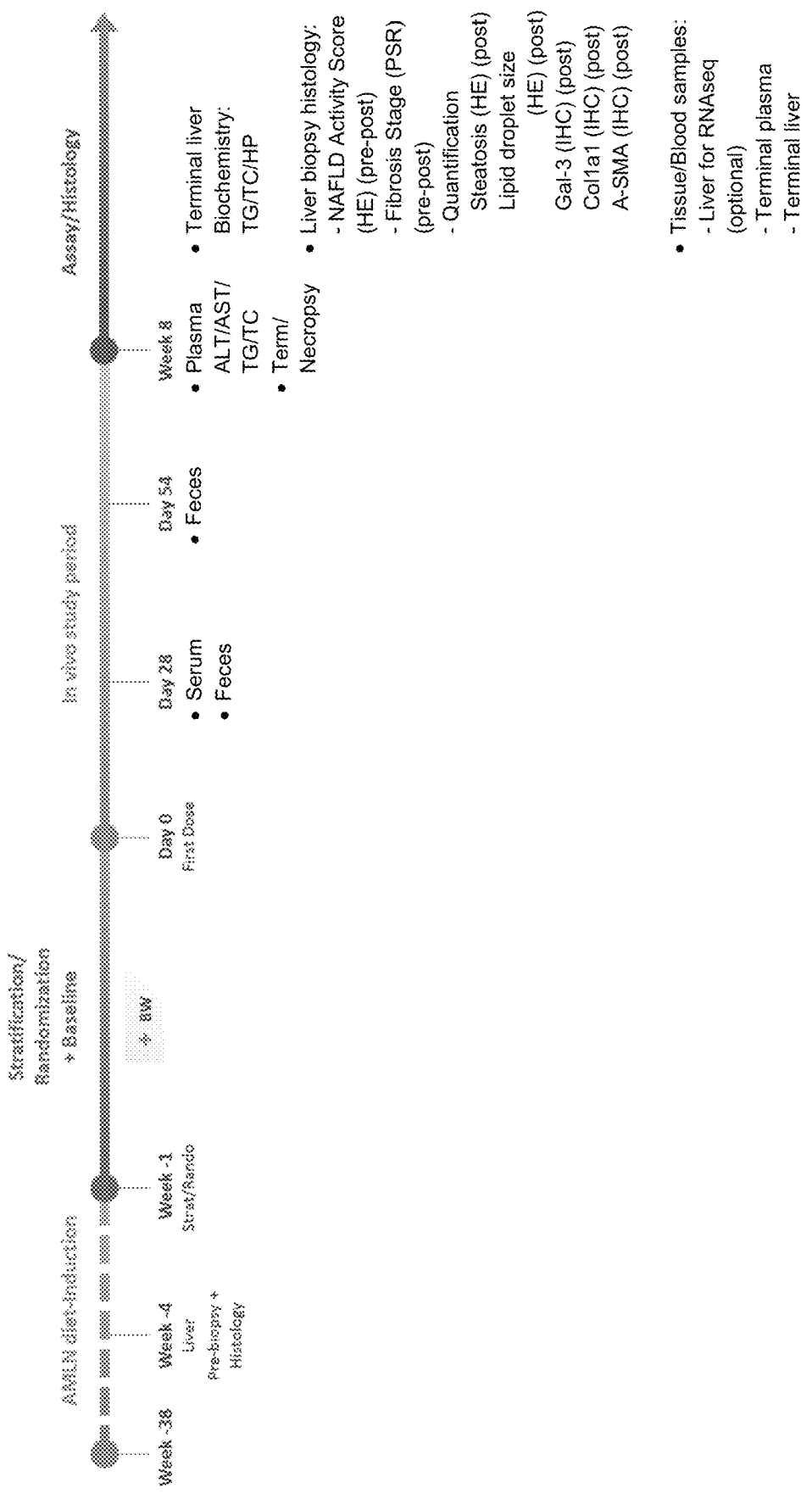
FIG. 17 is a scheme showing an outline of the study described in Example 15. The abbreviations are as follows: QD means once a day; BIW means twice weekly; BW means Body weight; FI means Food intake; WI means Water intake; ALT means Alanine transaminase; AST means Aspartate transaminase; TG means Triglycerides; TC means Total cholesterol; HP means Hydroxyproline; HE means Hematoxylin and eosin; PSR means Picrosirius red; IHC means Immunohistochemistry; Gal-3 means Galectin-3; Col1a1 means Collagen 1a1; and α-SMA means Alpha-smooth muscle actin.
Figure 18A:
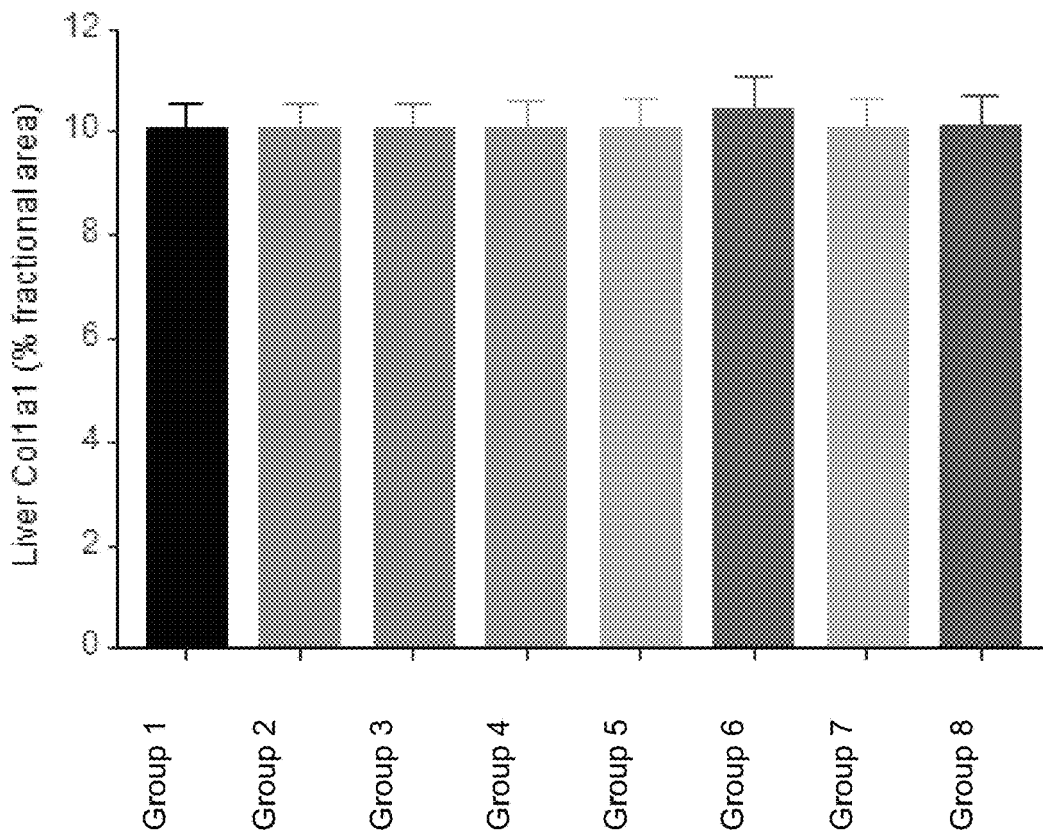
FIG. 18A is a chart showing liver collagen 1a1 (Col1a1) in liver biopsy taken 4 weeks before the Example 15 study commenced. Values expressed as mean of n=12-13+SEM. Dunnett's test one-factor linear model. No differences at significance level 0.05 compared to Control.
Figure 18B:
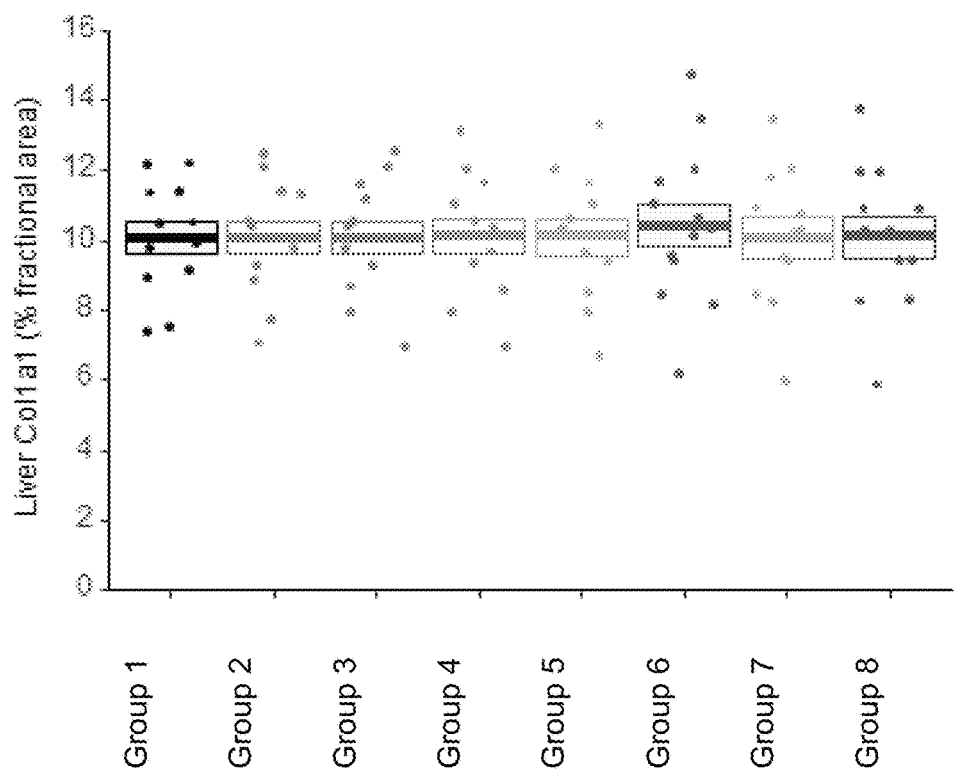
FIG. 18B is a chart showing individual liver collagen 1a1 (Col1a1) in liver biopsy taken 4 weeks before the Example 15 study commenced. Points show individual measurements. Box indicate position of mean (middle line) and SEM (top and bottom).
Figure 19A:
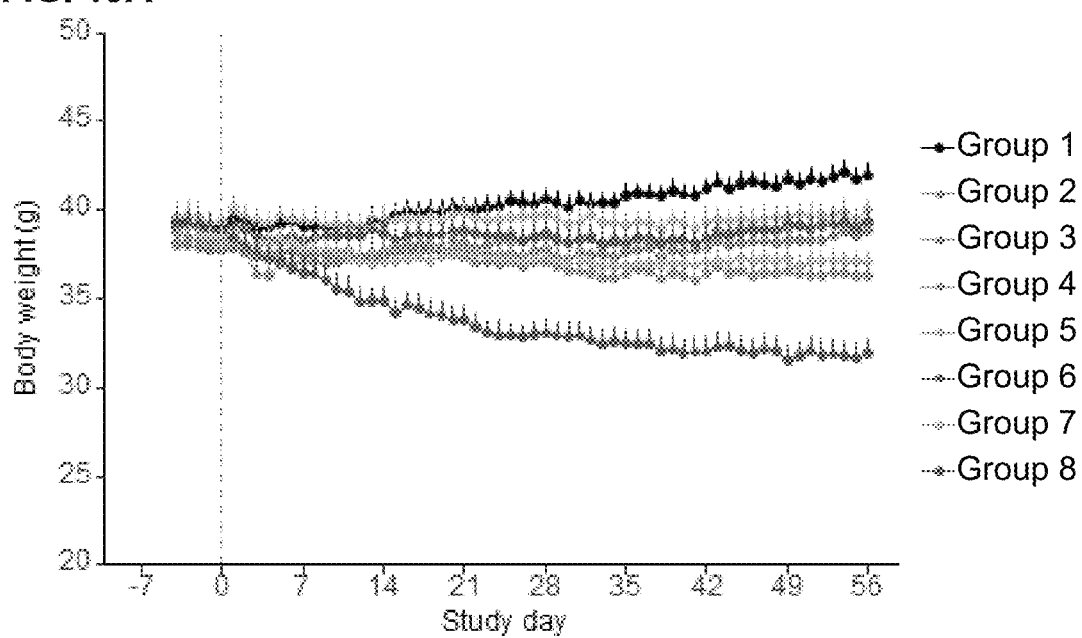
FIG. 19A is a chart showing absolute body weight throughout the study period. Values expressed as mean of n=10-13+SEM. No statistical analysis conducted.
Figure 19B:
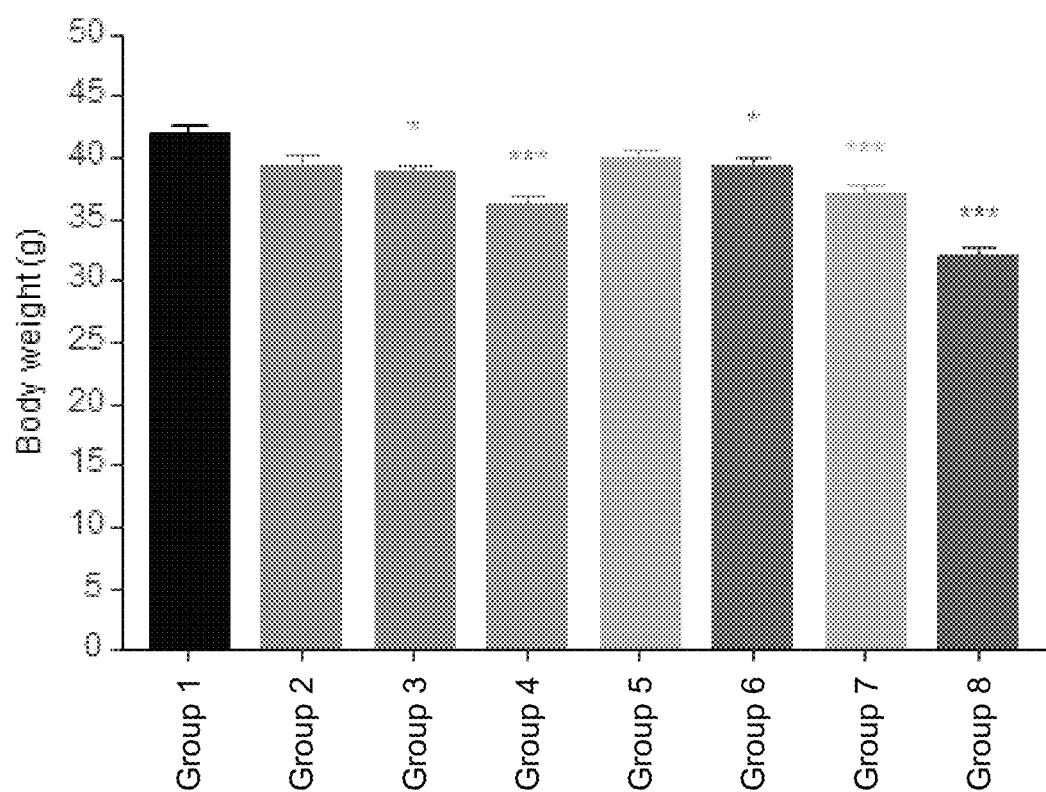
FIG. 19B is a chart showing absolute body weight at study termination. Values expressed as mean of n=11-13+SEM. Dunnett's test one-factor linear model. *: $P<0.05$, ***: $P<0.001$ compared to Control.
Figure 20A:
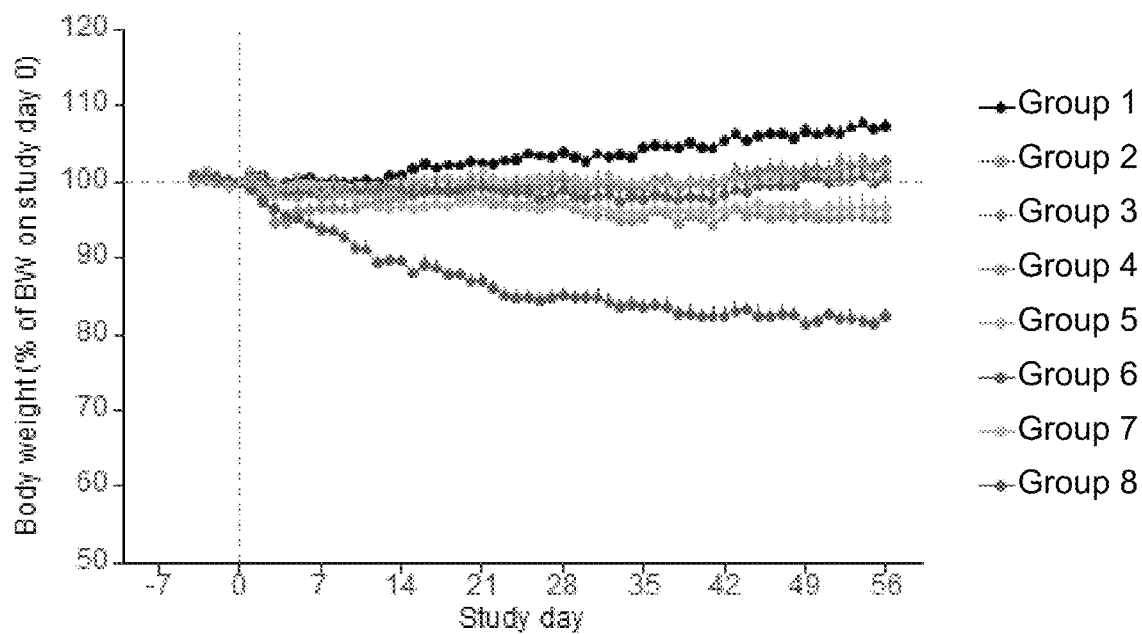
FIG. 20A is a chart showing relative body weight (BW) throughout the study period. Values expressed as mean of n=10-12+SEM. No statistical analysis conducted.
Figure 20B:
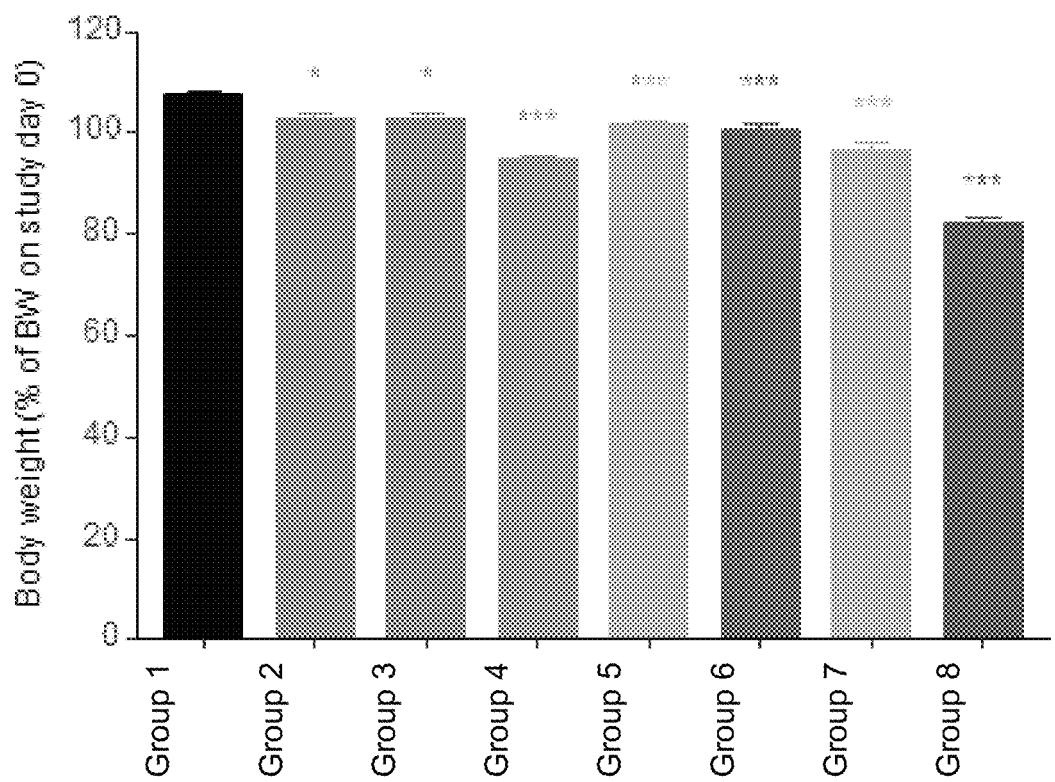
FIG. 20B is a chart showing relative body weight (BW) at study termination. Values expressed as mean of n=11-13+SEM. Dunnett's test one-factor linear model. *: $P<0.05$, ***: $P<0.001$ compared to Control.
Figure 21A:
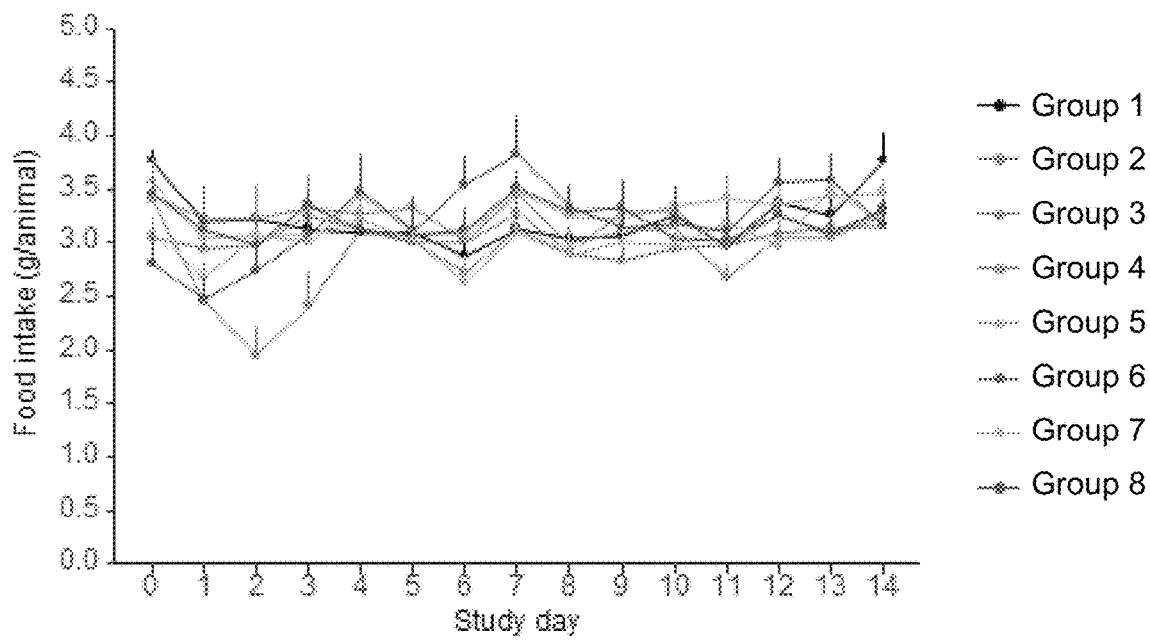
FIG. 21A is a chart showing daily food intake during study week 1-2. Values expressed as mean of n=11-13+SEM. No statistical analysis conducted.
Figure 21B:
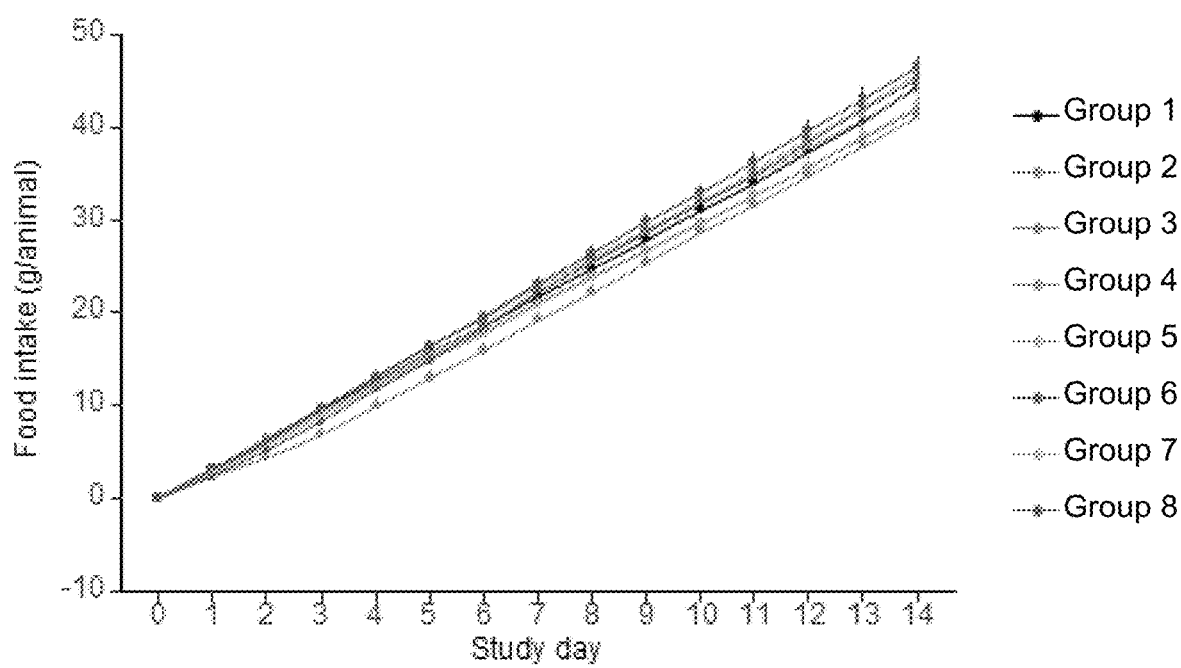
FIG. 21B is a chart showing cumulative food intake during study week 1-2. Values expressed as mean of n=10-12+SEM. No statistical analysis conducted.
Figure 22:
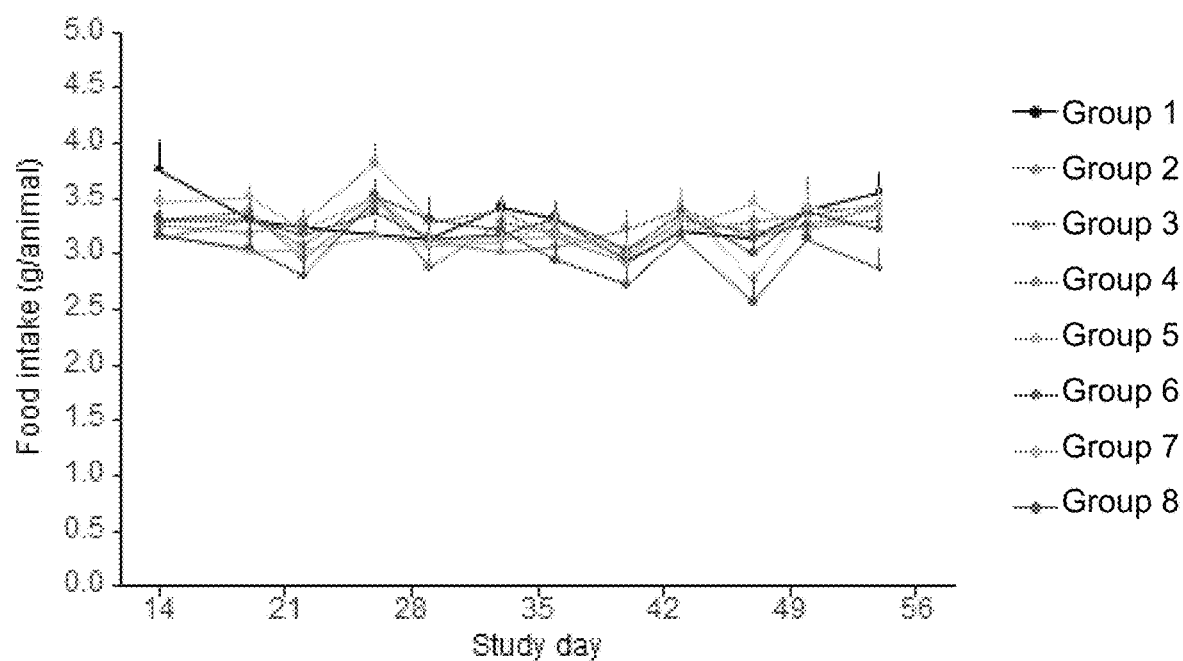
FIG. 22 is a chart showing Weekly food intake measured twice weekly during study week 3-8. Values expressed as mean of n=11-13+SEM. No statistical analysis conducted.
Figure 23A:
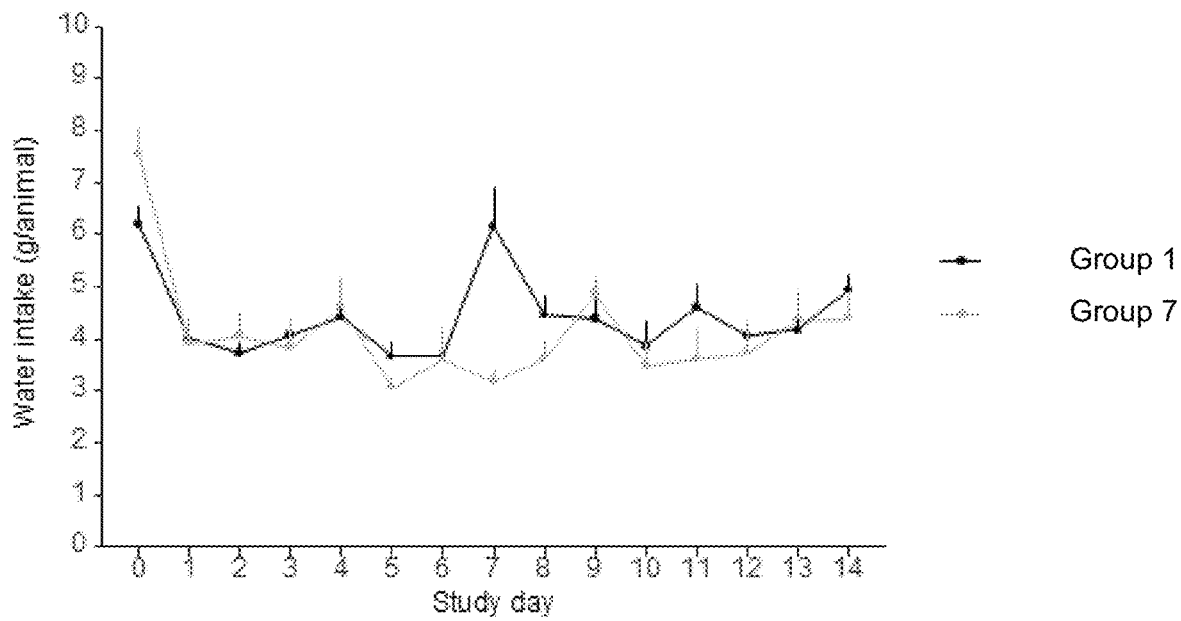
FIG. 23A is a chart showing daily water intake in treatment during study week 1-2. Values expressed as mean of n=10-12+SEM. No statistical analysis conducted.
Figure 23B:
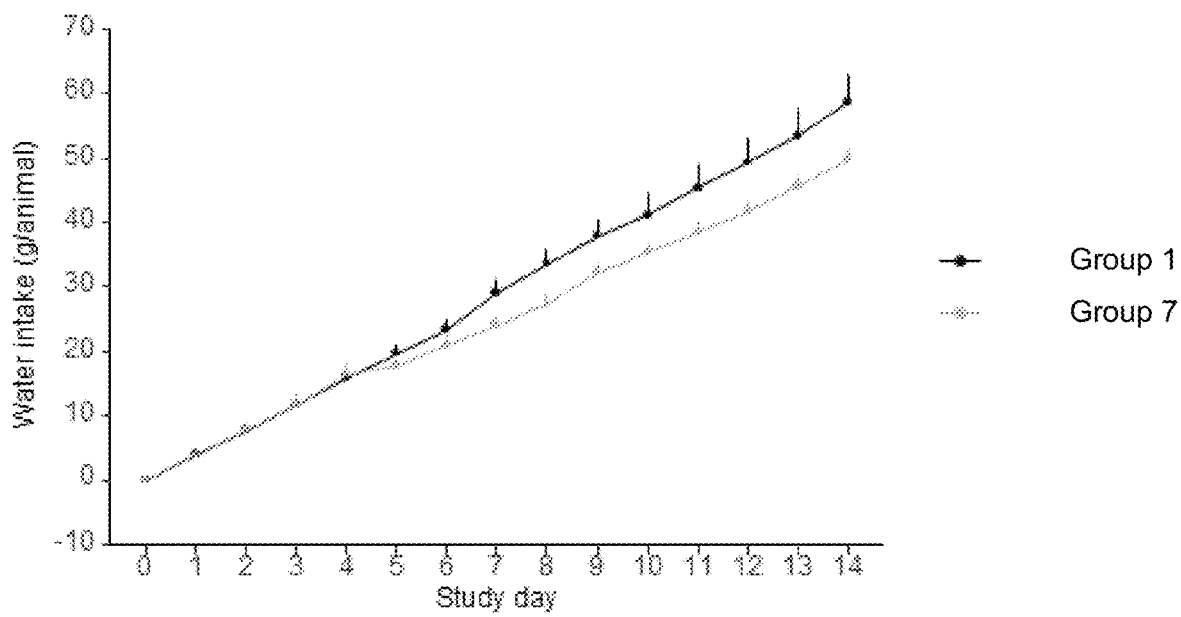
FIG. 23B is a chart showing cumulative water intake during study week 1-2. Values expressed as mean of n=9-12+SEM. No statistical analysis conducted.
Figure 24:
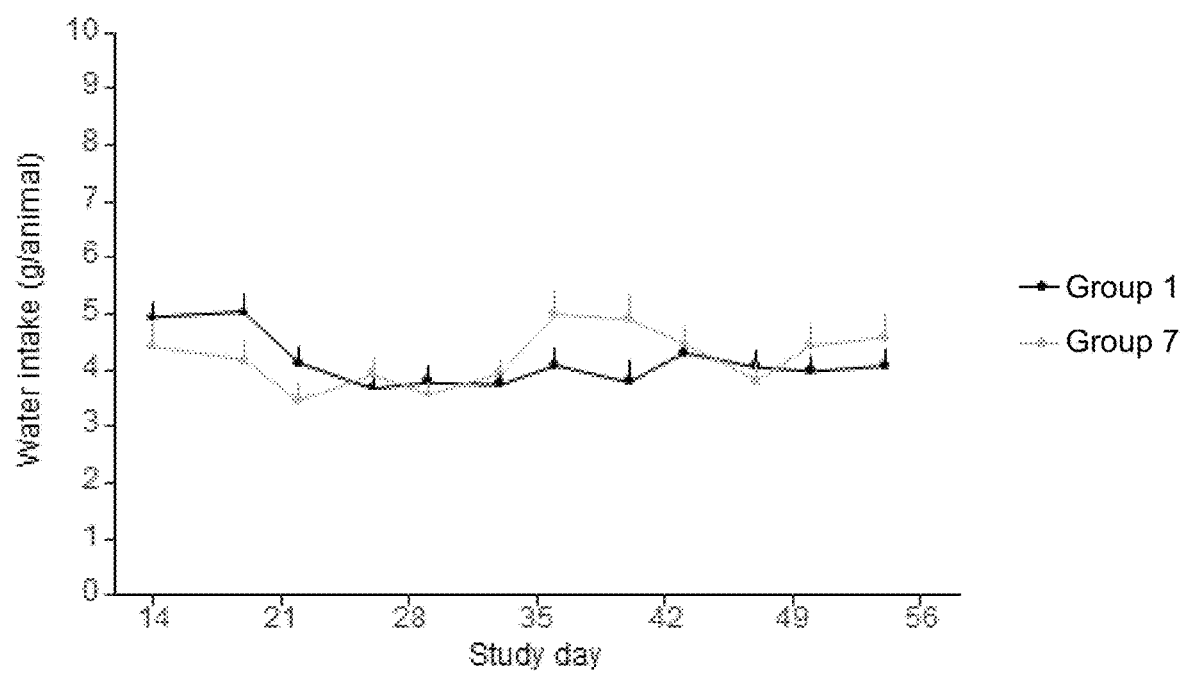
FIG. 24 is a chart showing weekly water intake (24-hour measured) measured twice weekly during study week 3-8. Values expressed as mean of n=10-12+SEM. No statistical analysis conducted.
Figure 25A:
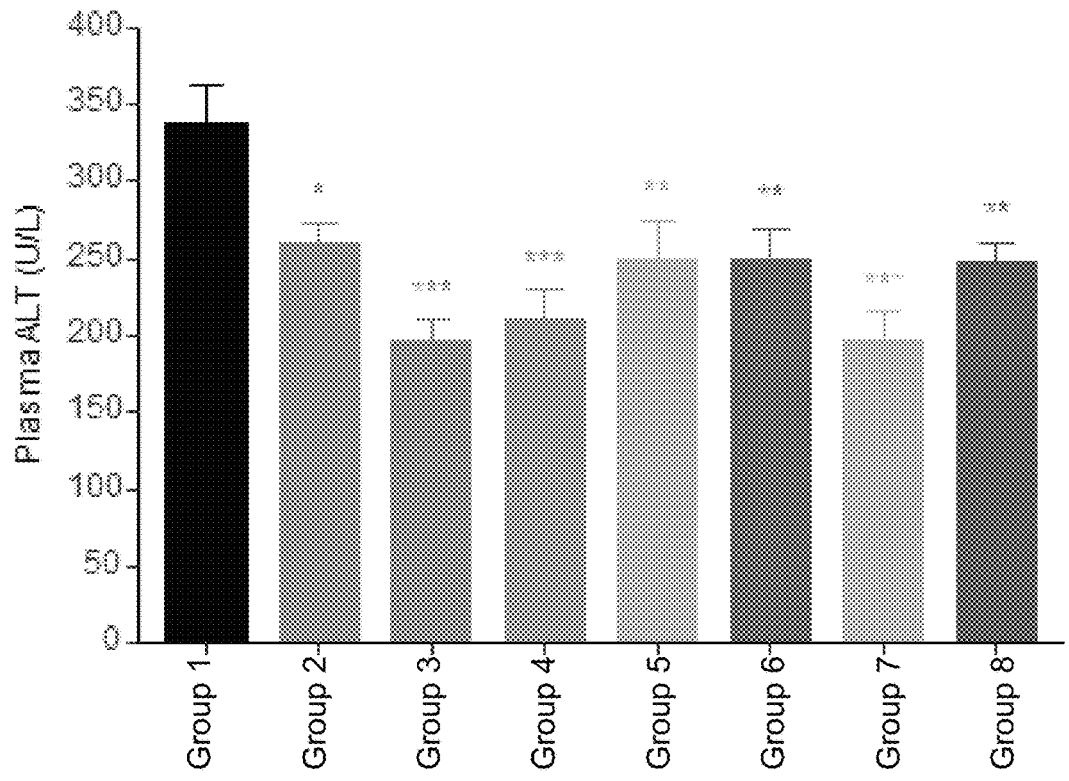
FIG. 25A is a chart showing plasma alanine transaminase (ALT) at termination. Values expressed as mean of n=11-13+SEM. Dunnett's test one-factor linear model. *: $P<0.05$, : $P<0.01$, *: $P<0.001$ compared to Control.
Figure 25B:
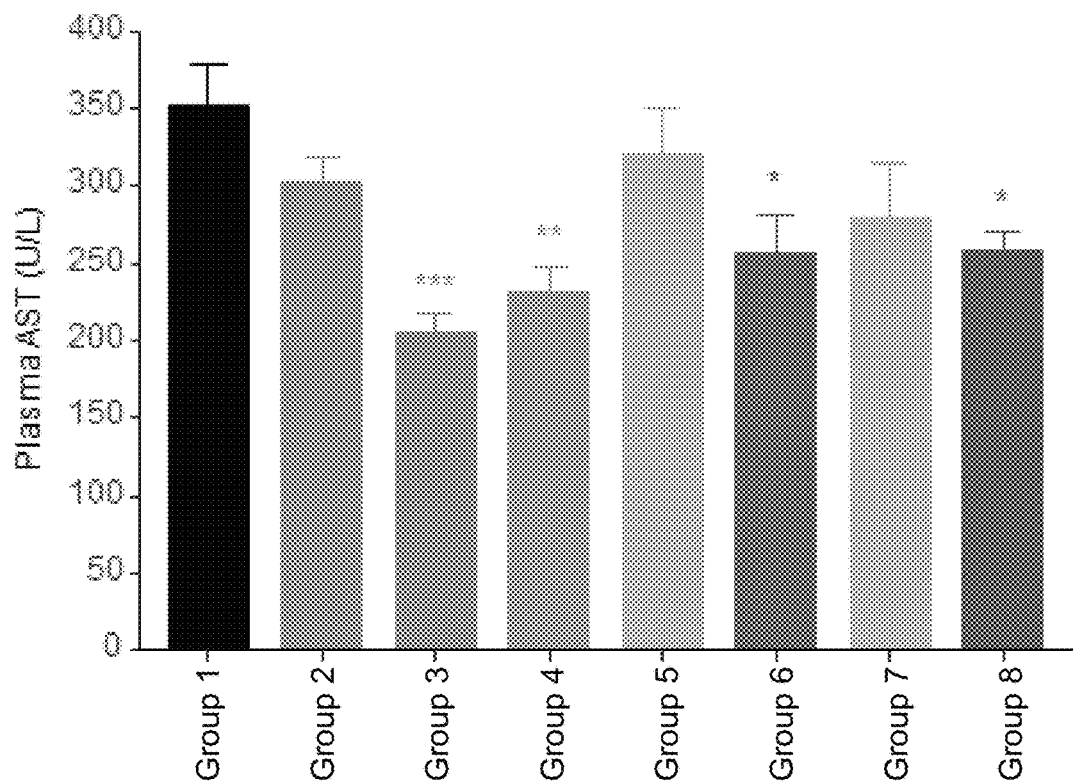
FIG. 25B is a chart showing plasma aspartate transaminase (AST) at termination. Values expressed as mean of n=11-13+SEM. Dunnett's test one-factor linear model. *: P<0.05, : P<0.01, *: P<0.001 compared to Control.
Figure 26A:
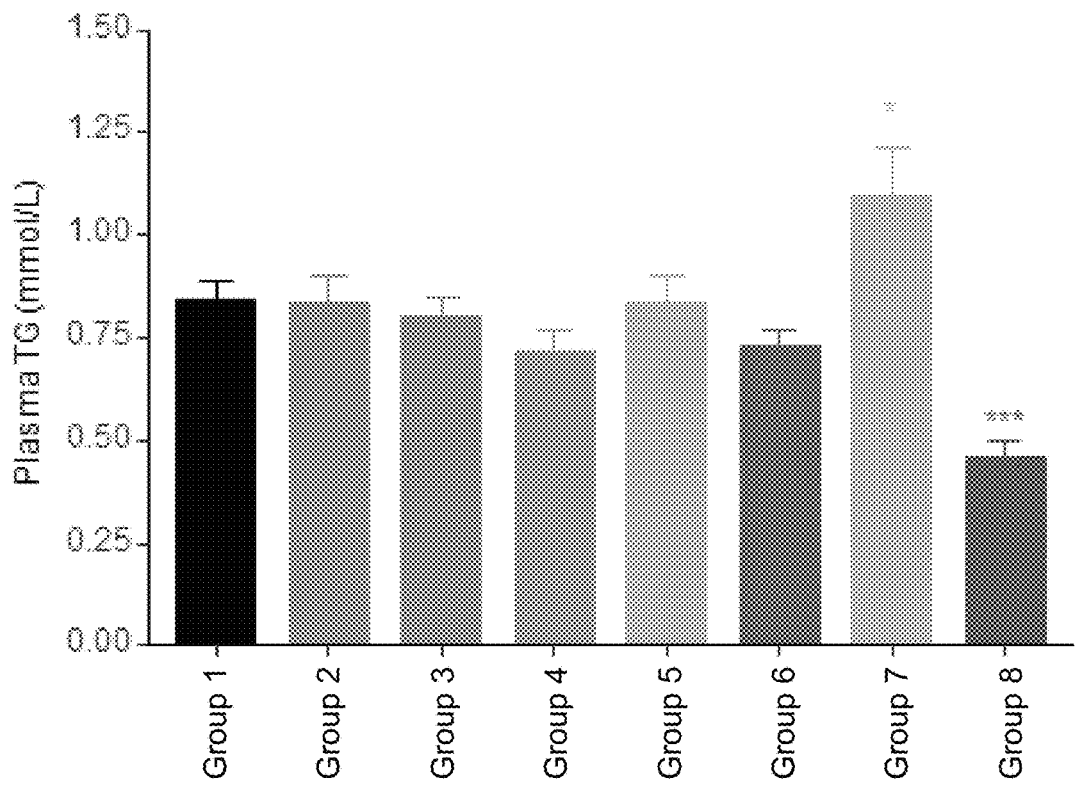
FIG. 26A is a chart showing plasma triglycerides (TG) at termination. Values expressed as mean of n=11-13+SEM. Dunnett's test one-factor linear model. *: P<0.05, ***: P<0.001 compared to Control.
Figure 26B:
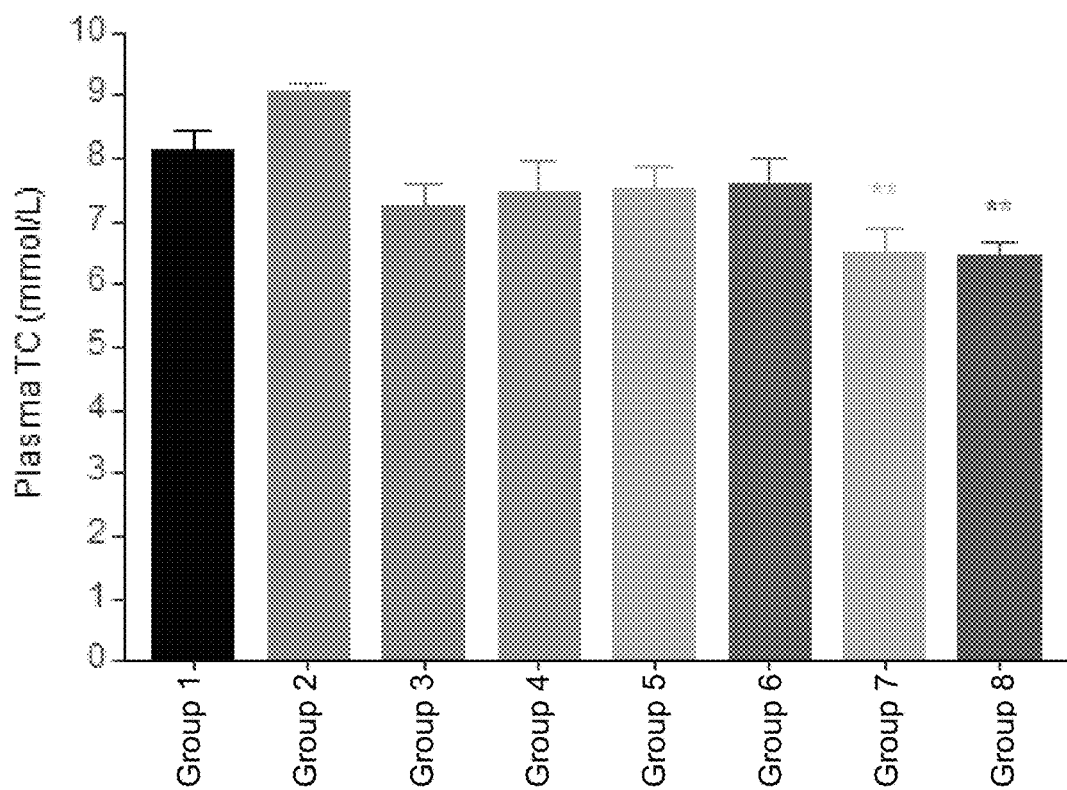
FIG. 26B is a chart showing plasma total cholesterol (TC) at termination. Values expressed as mean of n=11-13+SEM. Dunnett's test one-factor linear model. **: P<0.01 compared to Control.
Figure 27A:
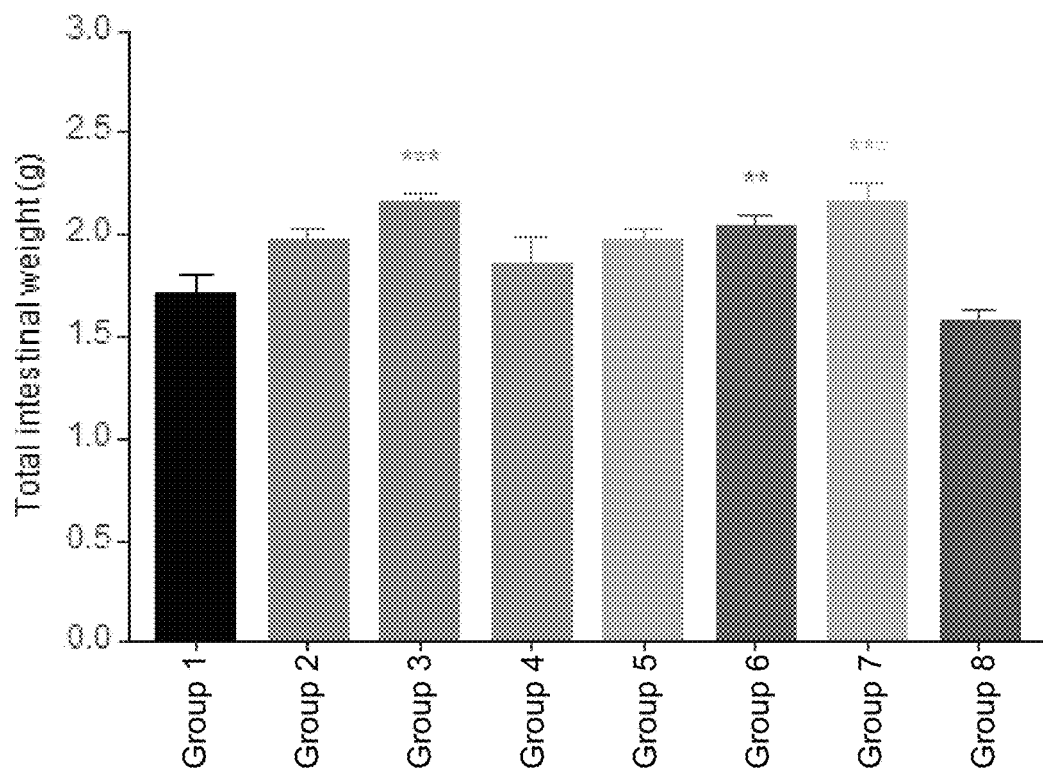
FIG. 27A is a chart showing total intestinal weight (including content) at termination. Values expressed as mean of n=11-13+SEM. Dunnett's test one-factor linear model. : P<0.01, *: P<0.001 compared to Control.
Figure 27B:
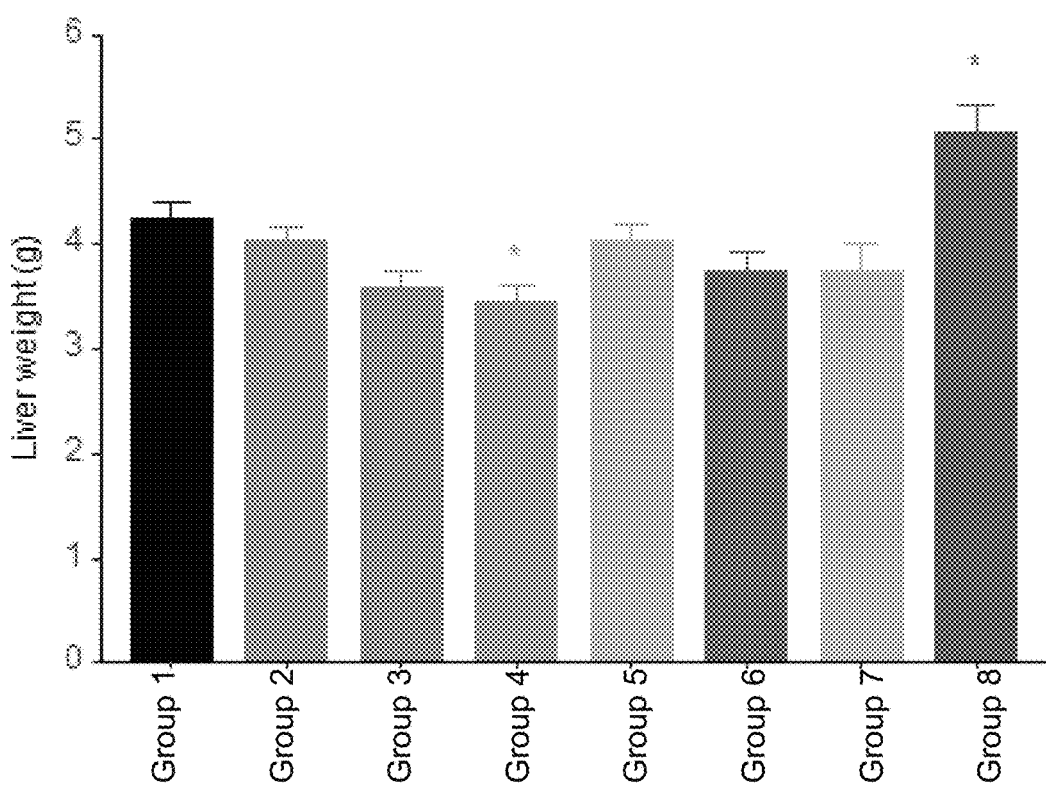
FIG. 27B is a chart showing liver weight at termination. Values expressed as mean of n=11-13+SEM. Dunnett's test one-factor linear model. *: P<0.05 compared to Control.
Figure 28A:
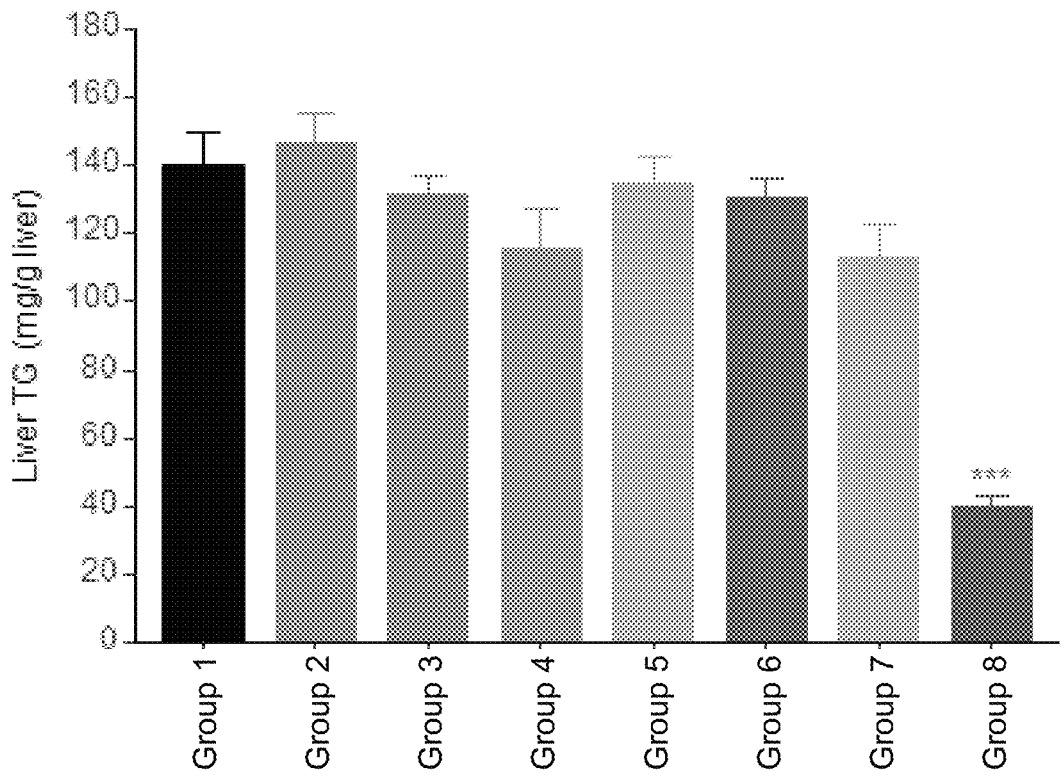
FIG. 28A is a chart showing relative liver triglycerides (TG) at termination. Values expressed as mean of n=11-13+SEM. Dunnett's test one-factor linear model. ***: P<0.001 compared to Control.
Figure 28B:
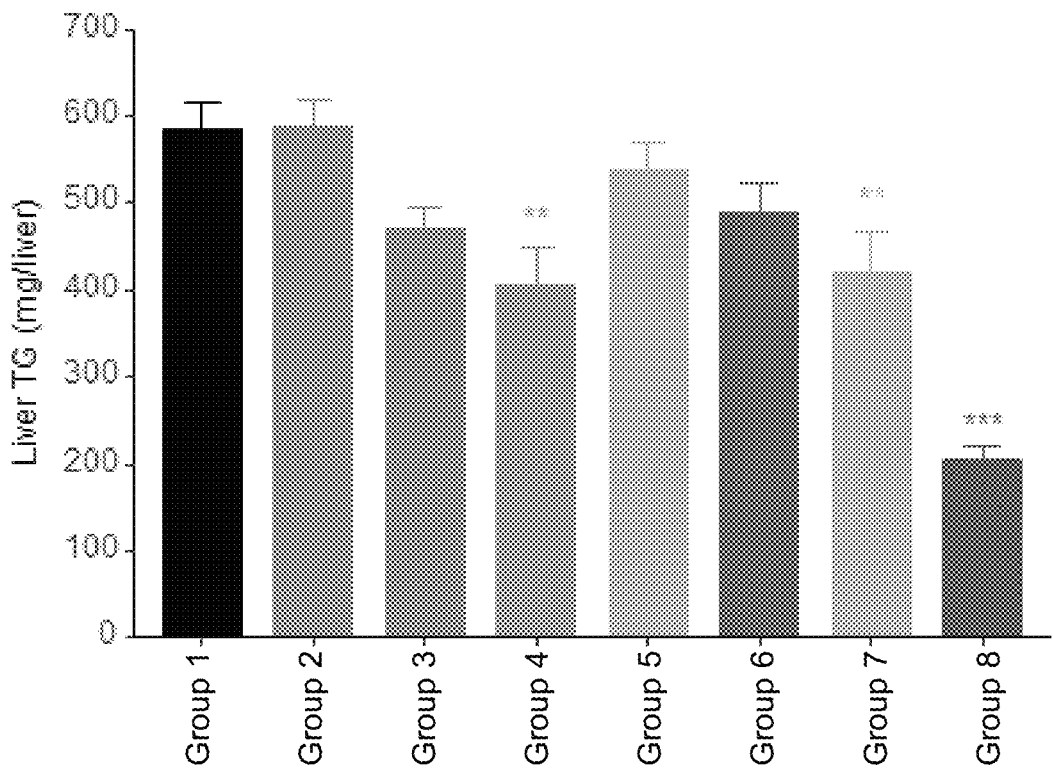
FIG. 28B is a chart showing total liver triglycerides (TG) at termination. Values expressed as mean of n=11-13+SEM. Dunnett's test one-factor linear model. : P<0.01, *: P<0.001 compared to Control.
Figure 29A:
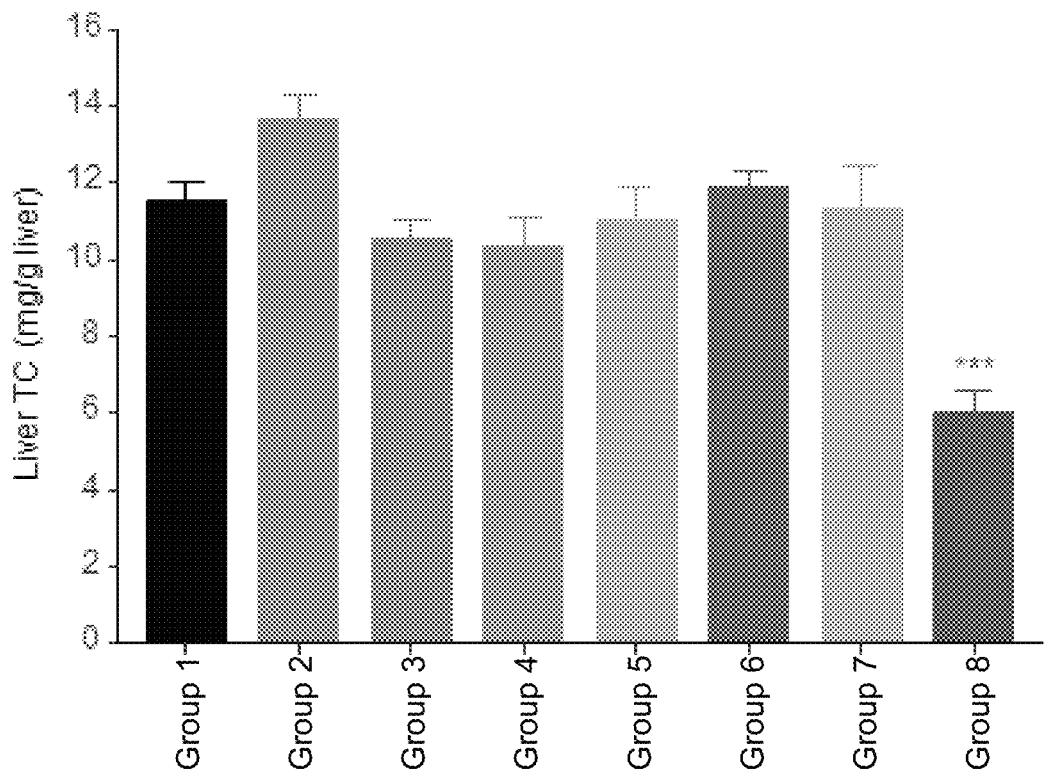
FIG. 29A is a chart showing relative liver total cholesterol (TC) at termination. Values expressed as mean of n=11-13+SEM. Dunnett's test one-factor linear model. ***: P<0.001 compared to Control.
Figure 29B:
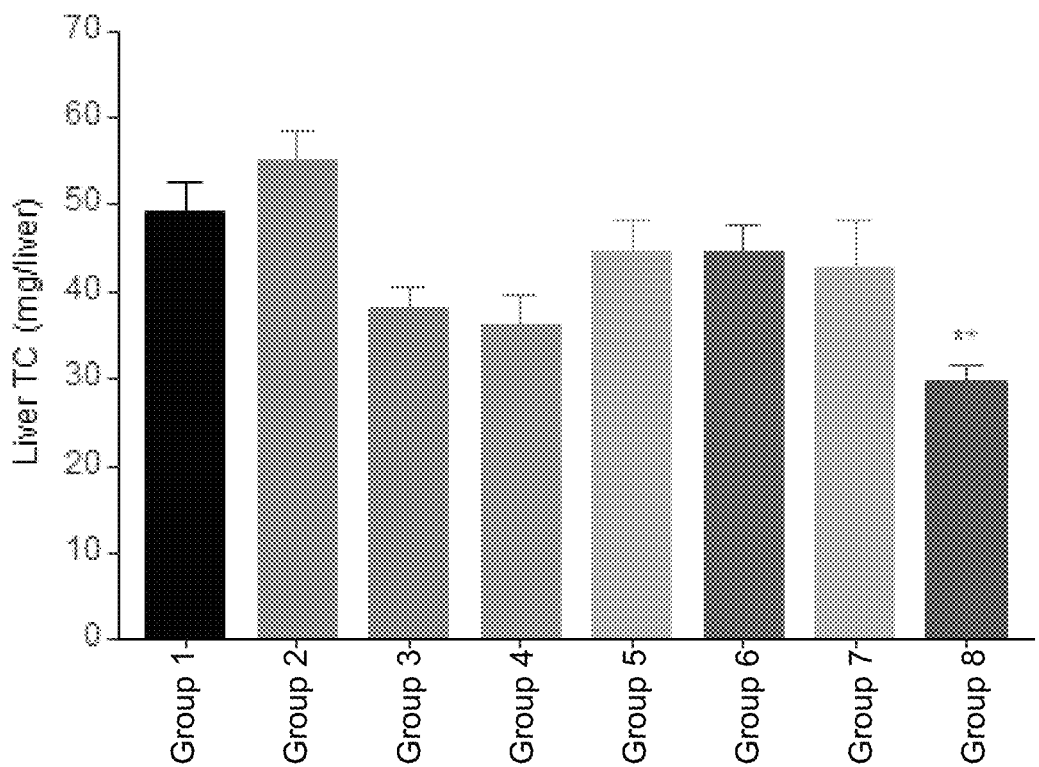
FIG. 29B is a chart showing total liver total cholesterol (TC) at termination. Values expressed as mean of n=11-13+SEM. Dunnett's test one-factor linear model. **: P<0.01 compared to Control.
Figure 30A:
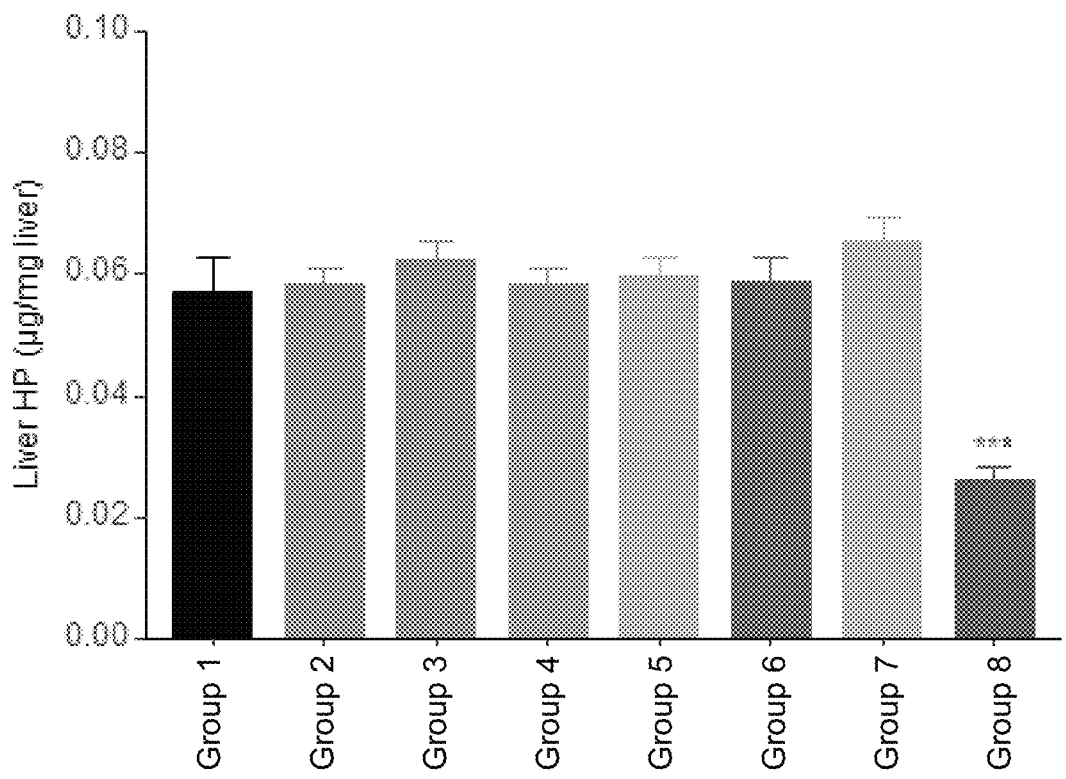
FIG. 30A is a chart showing relative liver hydroxyproline (HP) at termination. Values expressed as mean of n=11-13+SEM. Dunnett's test one-factor linear model. ***: P<0.001 compared to Control.
Figure 30B:
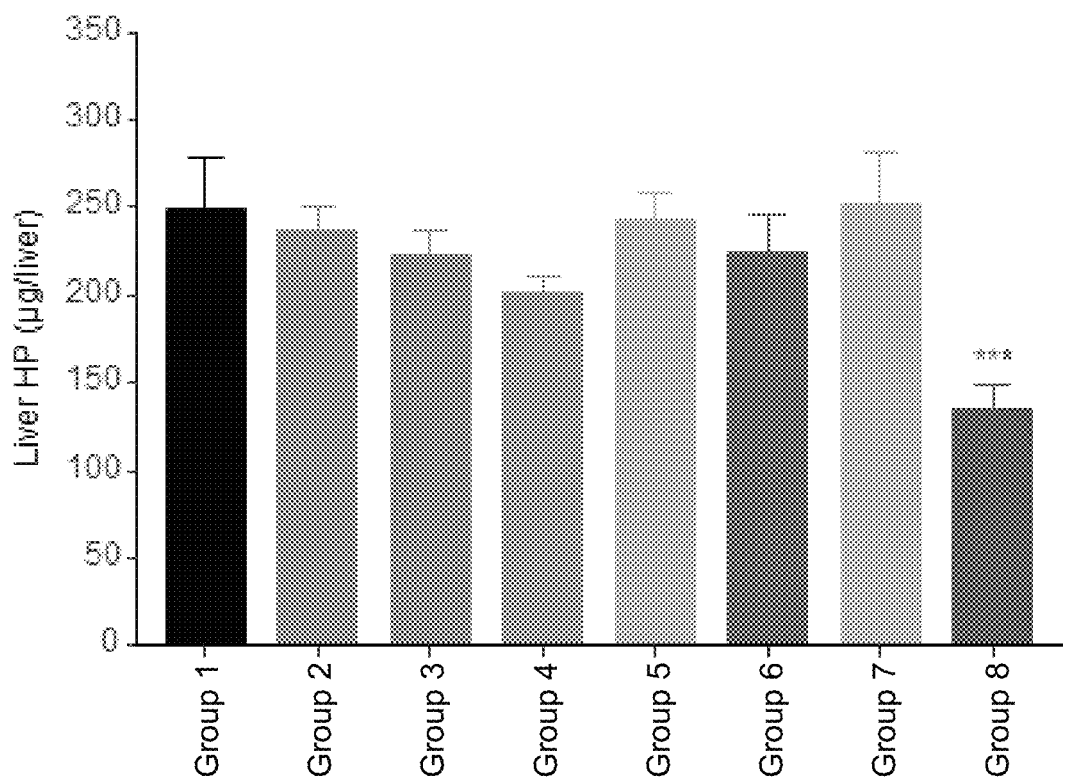
FIG. 30B is a chart showing total liver hydroxyproline (HP) at termination. Values expressed as mean of n=11-13+SEM. Dunnett's test one-factor linear model. ***: P<0.001 compared to Control.
Figure 31A:
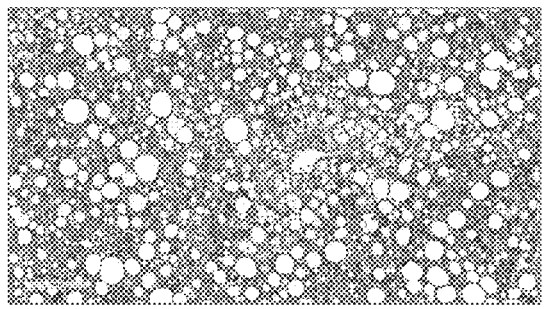
FIG. 31A is an image of liver morphology (liver HE staining) at termination (magnification 20×, scale bar=100 μm) for Group 1.
Figure 31B:
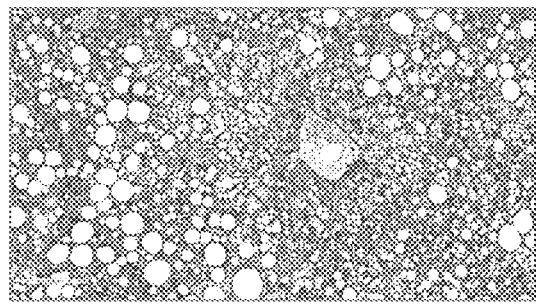
FIG. 31B is an image of liver morphology (liver HE staining) at termination (magnification 20×, scale bar=100 μm) for Group 2.
Figure 31C:
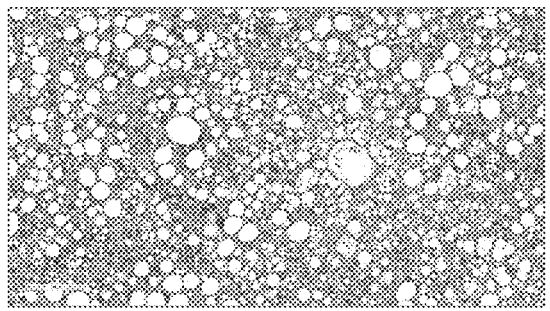
FIG. 31C is an image of liver morphology (liver HE staining) at termination (magnification 20×, scale bar=100 μm) for Group 3.
Figure 31D:
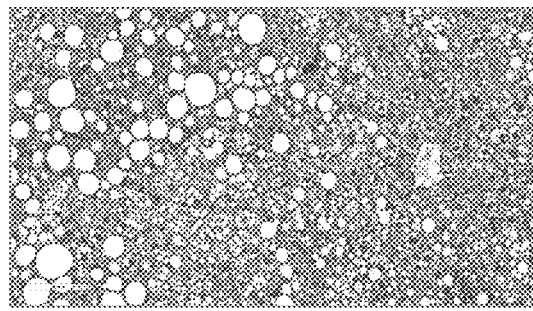
FIG. 31D is an image of liver morphology (liver HE staining) at termination (magnification 20×, scale bar=100 μm) for Group 4.
Figure 31E:
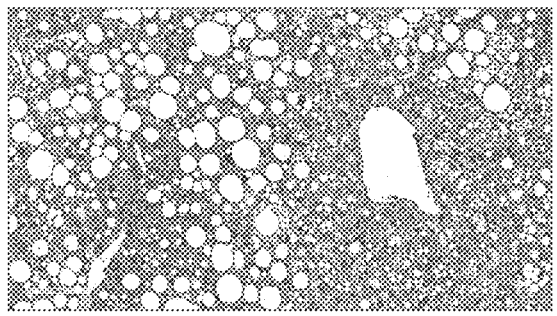
FIG. 31E is an image of liver morphology (liver HE staining) at termination (magnification 20×, scale bar=100 μm) for Group 5.
Figure 31F:
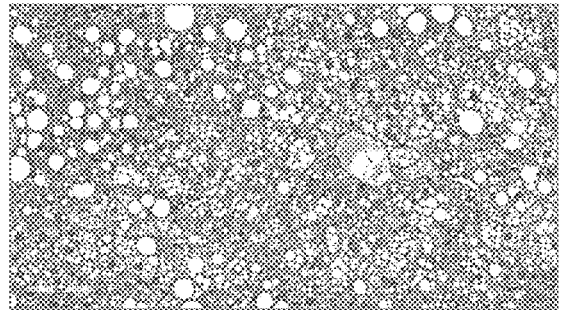
FIG. 31F is an image of liver morphology (liver HE staining) at termination (magnification 20×, scale bar=100 μm) for Group 6.
Figure 31G:
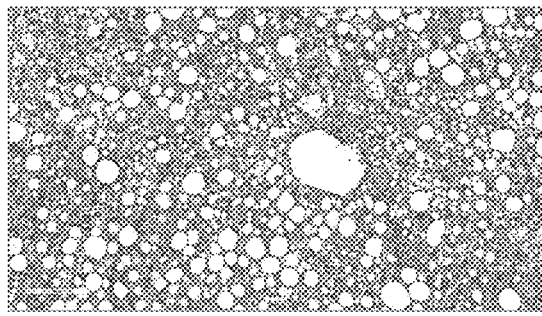
FIG. 31G is an image of liver morphology (liver HE staining) at termination (magnification 20×, scale bar=100 μm) for Group 7.
Figure 31H:
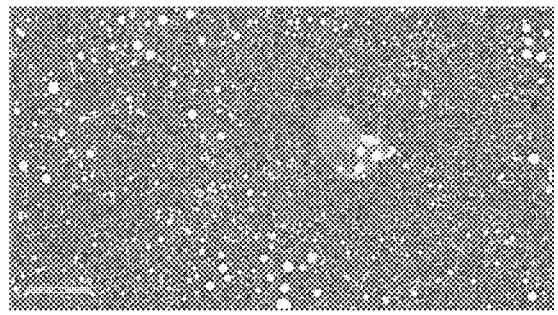
FIG. 31H is an image of liver morphology (liver HE staining) at termination (magnification 20×, scale bar=100 μm) for Group 8.
Figure 32A:
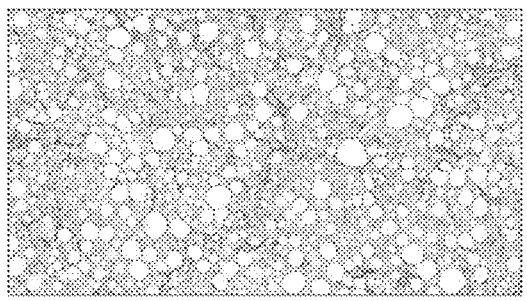
FIG. 32A is an image of liver morphology (liver Picro Sirius Red staining) at termination (magnification 20×, scale bar=100 μm) for Group 1.
Figure 32B:
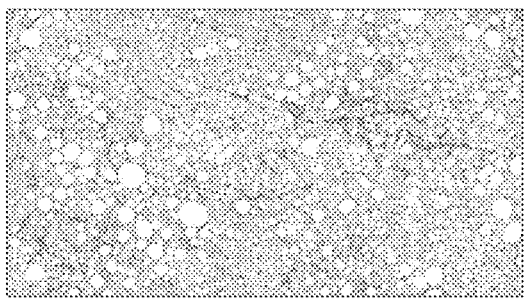
FIG. 32B is an image of liver morphology (liver Picro Sirius Red staining) at termination (magnification 20×, scale bar=100 μm) for Group 2.
Figure 32C:
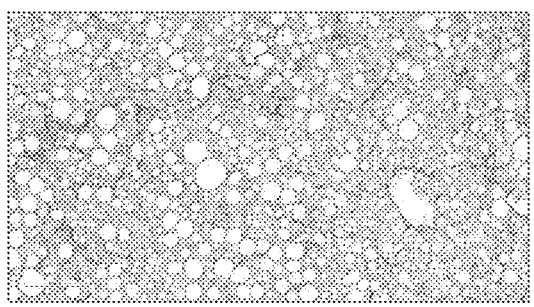
FIG. 32C is an image of liver morphology (liver Picro Sirius Red staining) at termination (magnification 20×, scale bar=100 μm) for Group 3.
Figure 32D:
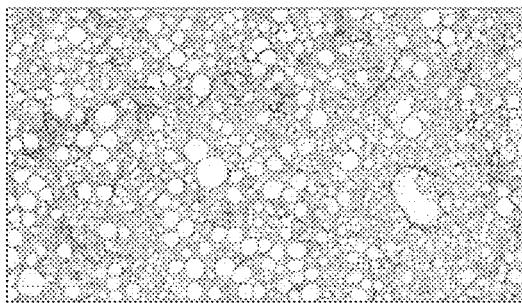
FIG. 32D is an image of liver morphology (liver Picro Sirius Red staining) at termination (magnification 20×, scale bar=100 μm) for Group 4.
Figure 32E:
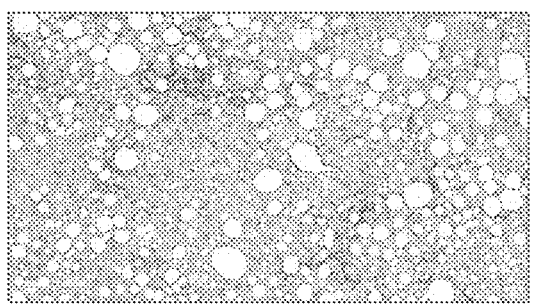
FIG. 32E is an image of liver morphology (liver Picro Sirius Red staining) at termination (magnification 20×, scale bar=100 μm) for Group 5.
Figure 32F:
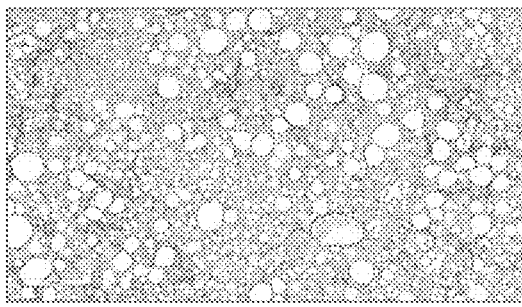
FIG. 32F is an image of liver morphology (liver Picro Sirius Red staining) at termination (magnification 20×, scale bar=100 μm) for Group 6.
Figure 32G:
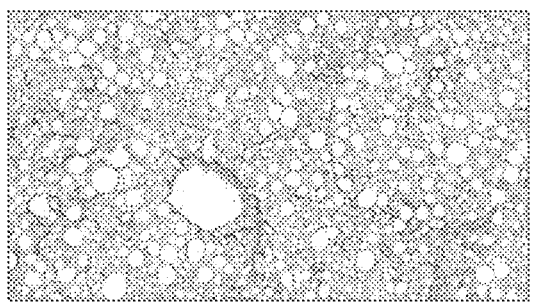
FIG. 32G is an image of liver morphology (liver Picro Sirius Red staining) at termination (magnification 20×, scale bar=100 μm) for Group 7.
Figure 32H:
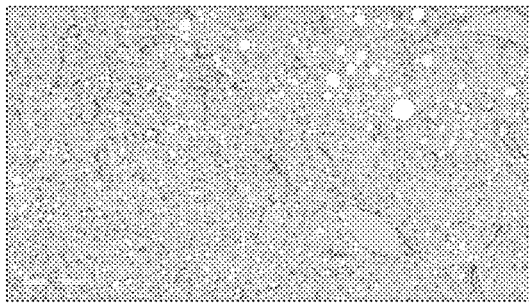
FIG. 32H is an image of liver morphology (liver Picro Sirius Red staining) at termination (magnification 20×, scale bar=100 μm) for Group 8.
Figure 33A:
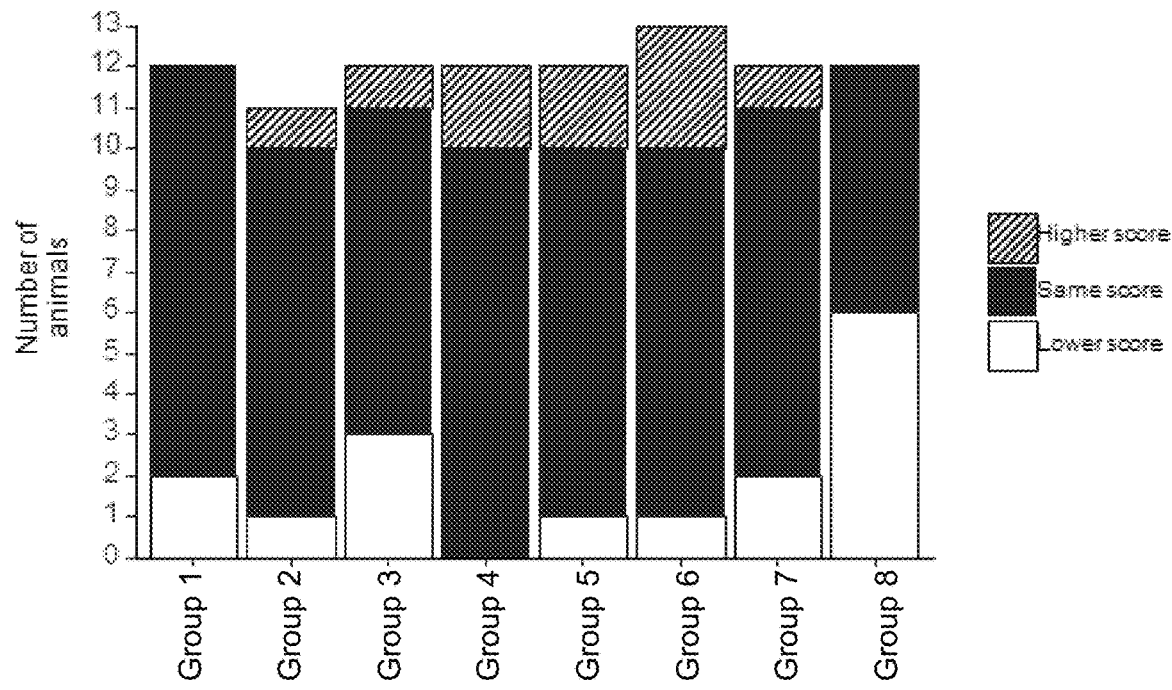
FIG. 33A is chart showing summary of histopathological scoring (fibrosis stage) of pre- and post-study biopsies. For each group the number of animals with a higher (worsening), same or lower (improvement) in score at post-compared to pre-study is indicated by the height of the bar. For each compound group significance of number of animals with a lower score versus appropriate vehicle was assessed using Fisher's Exact Test followed by correction for multiple comparisons using the Bonferroni method. ***: P<0.001 compared to Control.
Figure 33B:
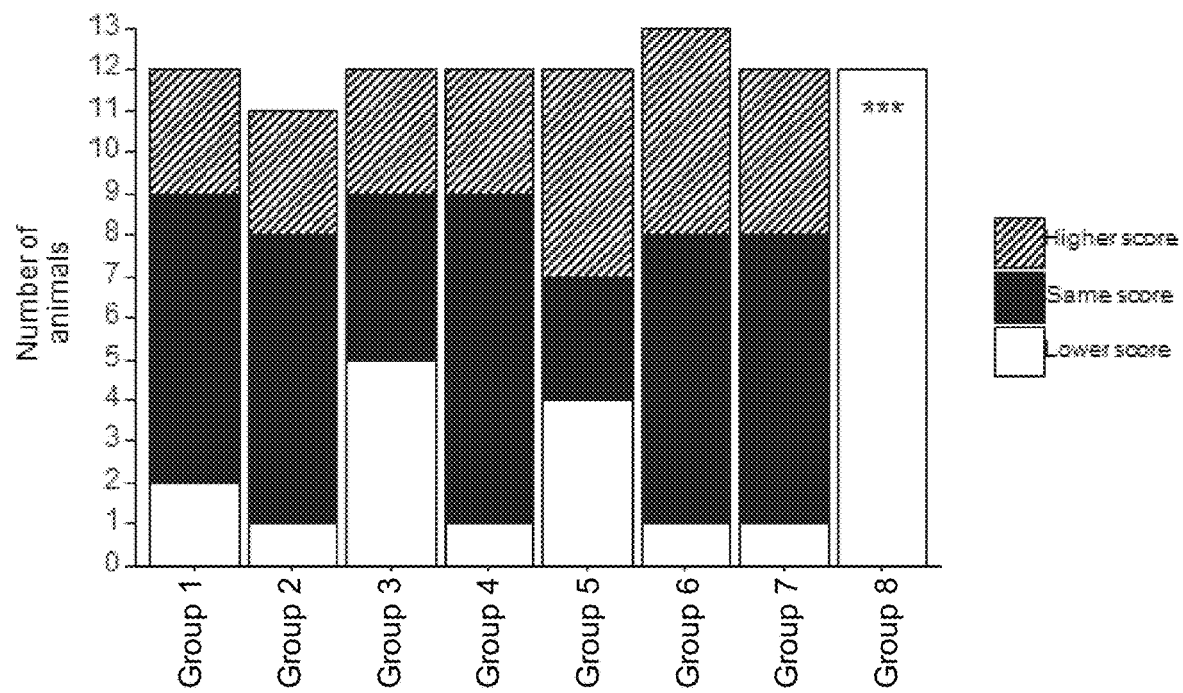
FIG. 33B is chart showing summary of histopathological scoring (NAFLD activity score) of pre- and post-study biopsies. For each group the number of animals with a higher (worsening), same or lower (improvement) in score at post- compared to pre-study is indicated by the height of the bar. For each compound group significance of number of animals with a lower score versus appropriate vehicle was assessed using Fisher's Exact Test followed by correction for multiple comparisons using the Bonferroni method. ***: P<0.001 compared to Control.
Figure 35A:
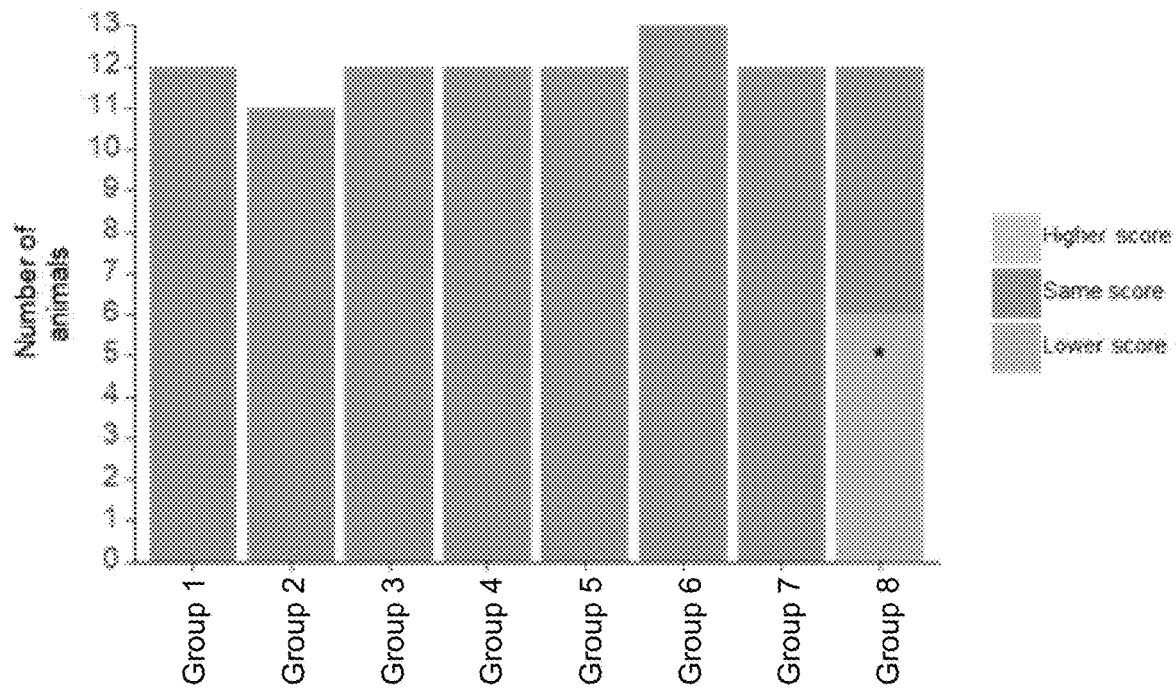
FIG. 35A is chart showing summary of NAFLD activity score (seatosis score) showing individual scores for steatosis, lobular inflammation and ballooning degeneration of pre- and post-study biopsies. For each group the number of animals with a higher (worsening), same or lower (improvement) in score at post- compared to pre-study is indicated by the height of the bar. One-sided Fisher's exact test with Bonferroni correction. *: P<0.05 compared to Control.
Figure 35B:
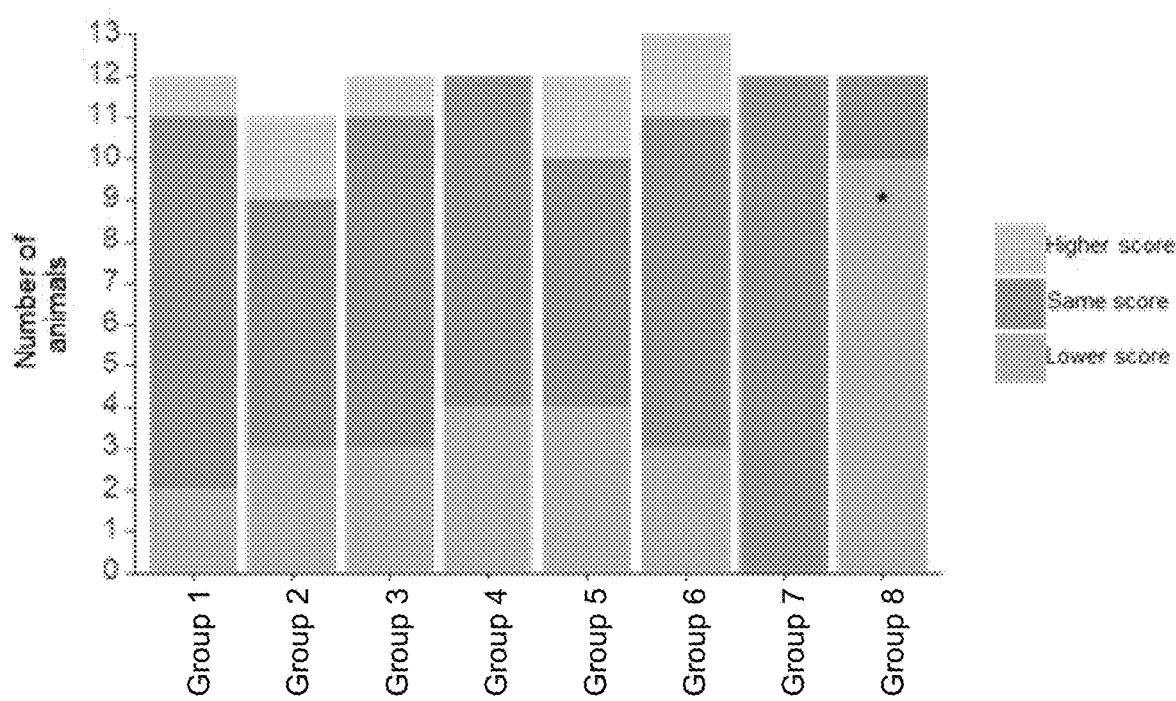
FIG. 35B is chart showing summary of NAFLD activity score (lobular inflammation) showing individual scores for steatosis, lobular inflammation and ballooning degeneration of pre- and post-study biopsies. For each group the number of animals with a higher (worsening), same or lower (improvement) in score at post- compared to pre-study is indicated by the height of the bar. One-sided Fisher's exact test with Bonferroni correction. *: P<0.05 compared to Control.
Figure 35C:
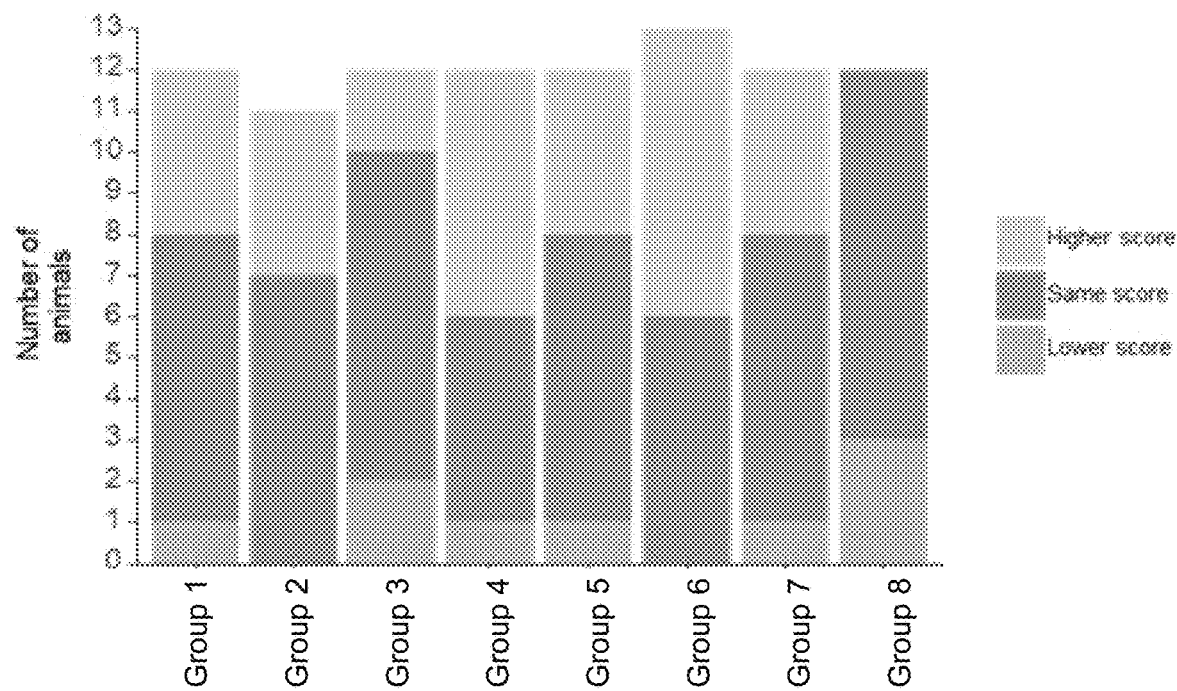
FIG. 35C is chart showing summary of NAFLD activity score (hepatocellular ballooning) showing individual scores for steatosis, lobular inflammation and ballooning degeneration of pre- and post-study biopsies. For each group the number of animals with a higher (worsening), same or lower (improvement) in score at post- compared to pre-study is indicated by the height of the bar. One-sided Fisher's exact test with Bonferroni correction. *: P<0.05 compared to Control.
Figure 36C:
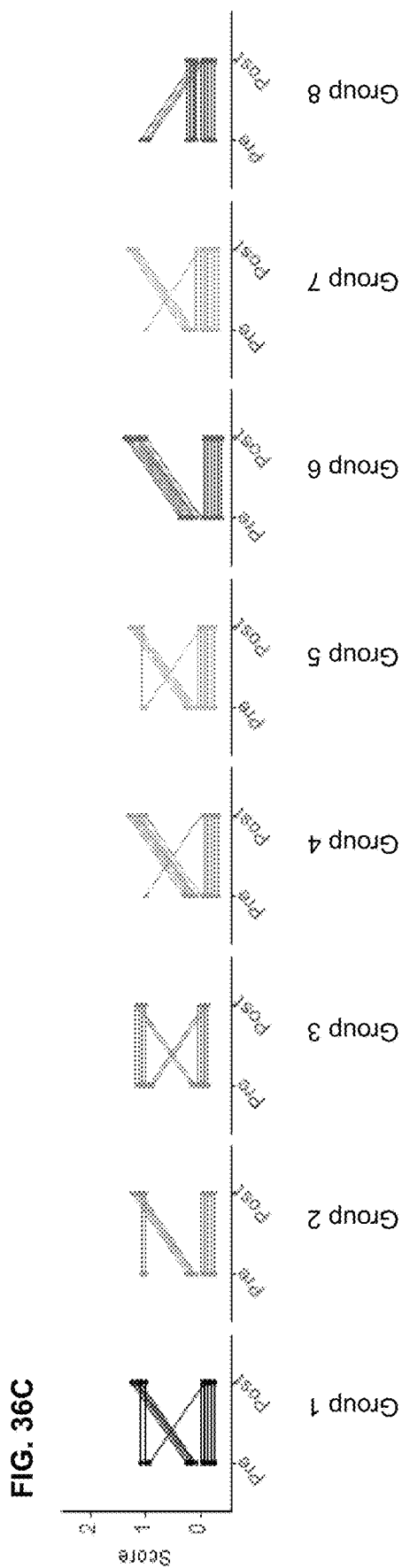
FIG. 36C is a chart showing an overview of the result of ballooning degeneration scores. For each animal the change from pre-study to post-study biopsy is indicated by a line. The points at each scoring step is slightly shifted to allow visual separation of the animals, this is only for visualization purposes and does not reflect any difference in score.
Figure 37A:
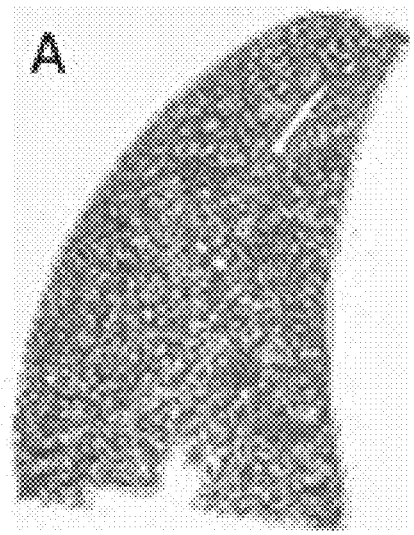
FIG. 37A is an image showing crude detection of tissue at low magnification (first step of histological quantitative assessment).
Figure 37B:
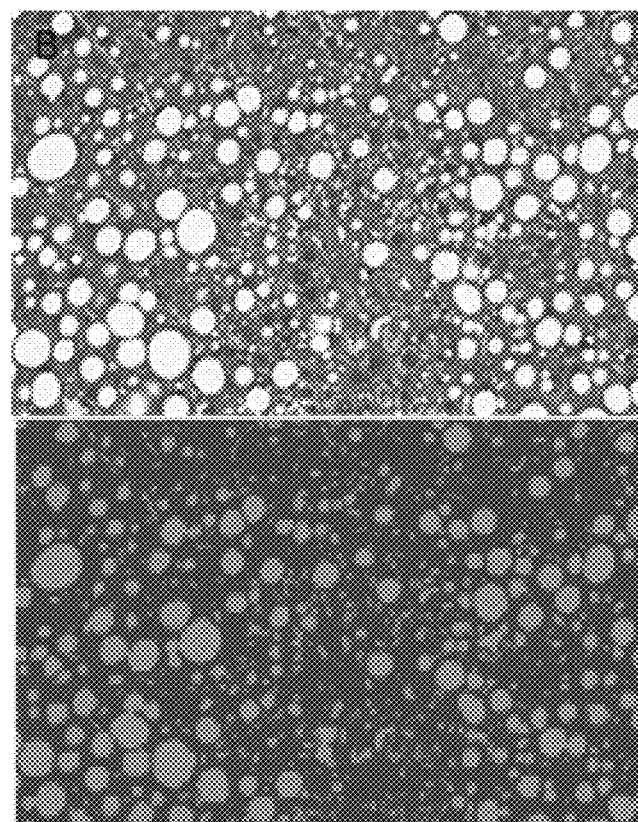
FIG. 37B is an image showing detection of steatosis (pink) and tissue (blue) at high magnification.
Figure 38A:
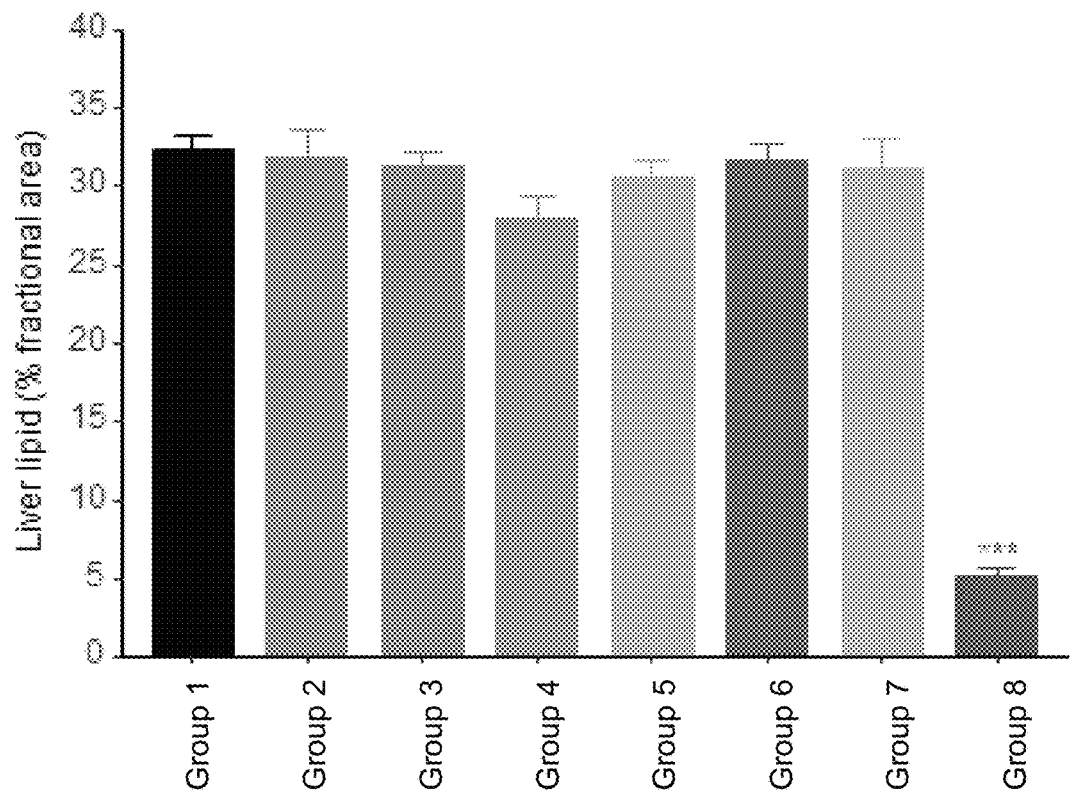
FIG. 38A is a chart showing terminal relative steatosis quantified by morphometry. Values expressed as mean of n=11-13+SEM. Dunnett's test one-factor linear model. ***: P<0.001 compared to Control.
Figure 38B:
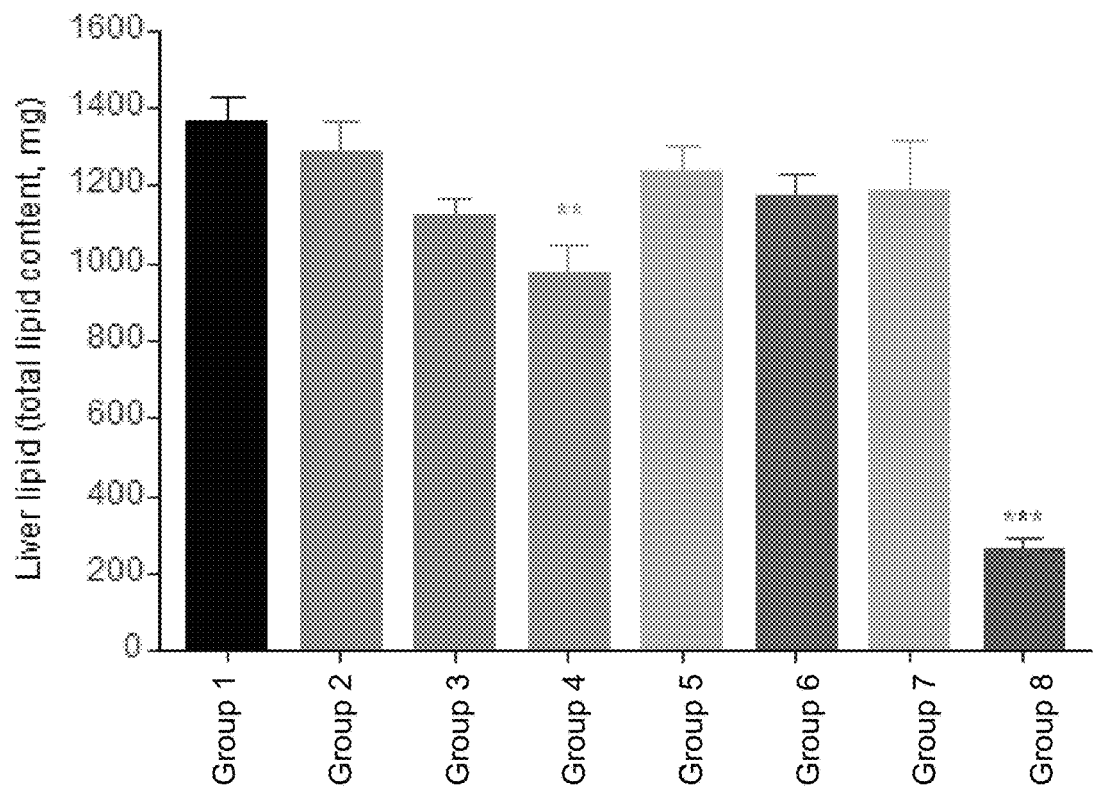
FIG. 38B is a chart showing terminal total liver steatosis quantified by morphometry. Values expressed as mean of n=11-13+SEM. Dunnett's test one-factor linear model. : P<0.01, *: P<0.001 compared to Control.
Figure 38C:
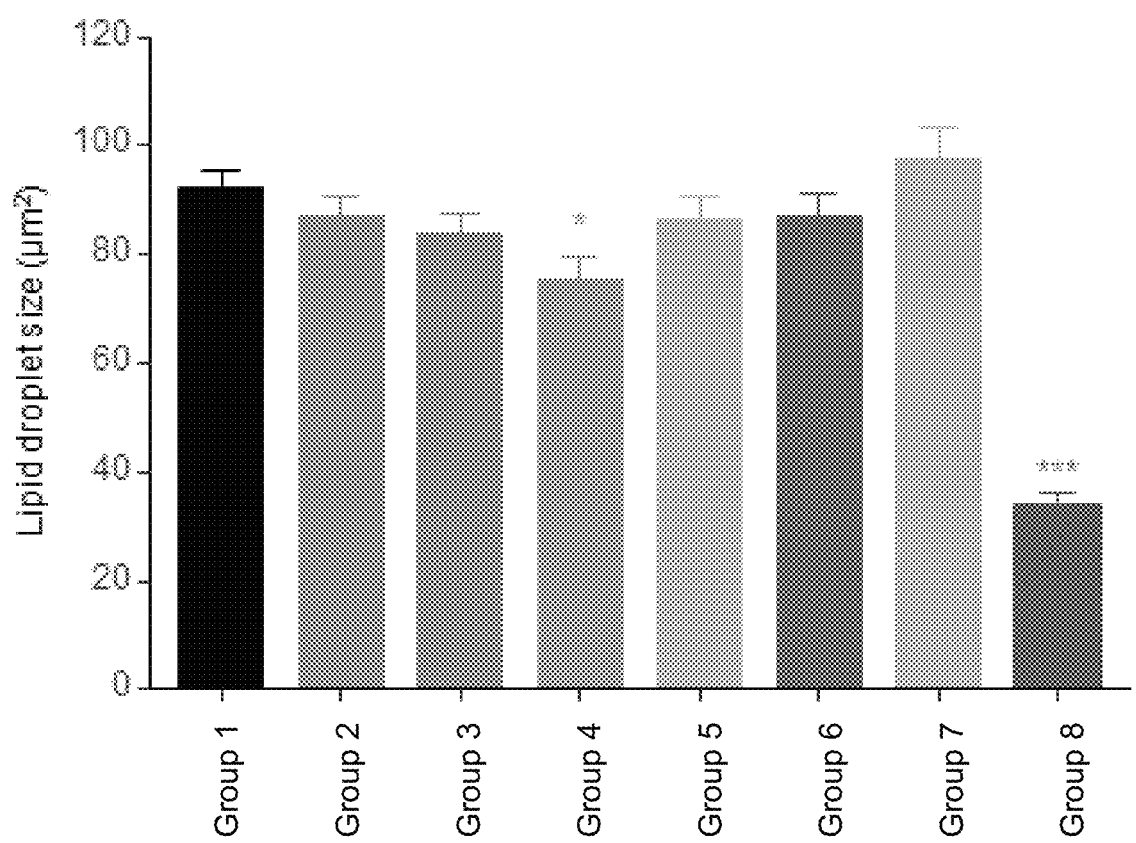
FIG. 38C is a chart showing lipid droplet size quantified by morphometry. Values expressed as mean of n=11-13+SEM. Dunnett's test one-factor linear model. *: P<0.05, ***: P<0.001 compared to Control.
Figure 39A:
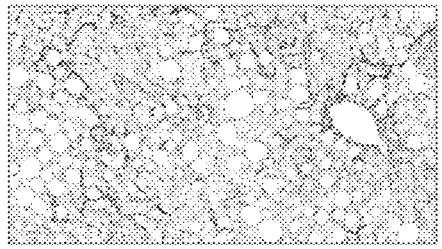
FIG. 39A is an image of liver morphology (liver stained with anti-type I collagen (Southern Biotech, cat. no. 1310-01) at termination (magnification 20×, scale bar=100 μm) for Group 1.
Figure 39B:
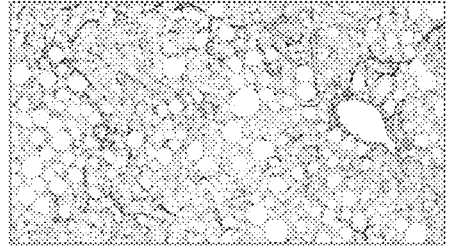
FIG. 39B is an image of liver morphology (liver stained with anti-type I collagen (Southern Biotech, cat. no. 1310-01) at termination (magnification 20×, scale bar=100 μm) for Group 2.
Figure 39C:
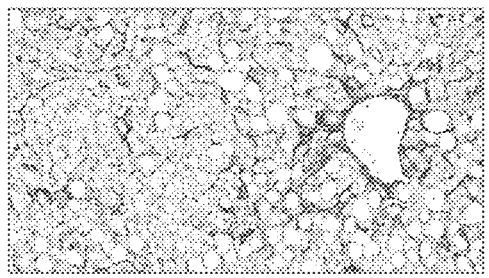
FIG. 39C is an image of liver morphology (liver stained with anti-type I collagen (Southern Biotech, cat. no. 1310-01) at termination (magnification 20×, scale bar=100 μm) for Group 3.
Figure 39D:
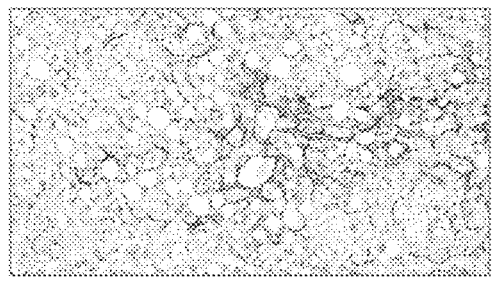
FIG. 39D is an image of liver morphology (liver stained with anti-type I collagen (Southern Biotech, cat. no. 1310-01) at termination (magnification 20×, scale bar=100 μm) for Group 4.
Figure 39E:
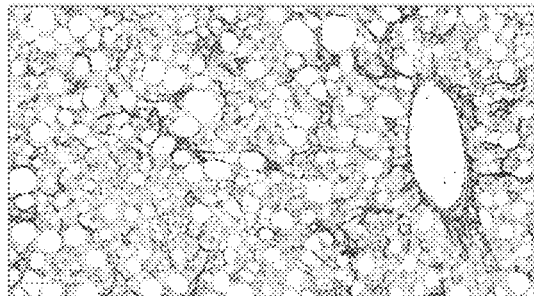
FIG. 39E is an image of liver morphology (liver stained with anti-type I collagen (Southern Biotech, cat. no. 1310-01) at termination (magnification 20×, scale bar=100 μm) for Group 5.
Figure 39F:
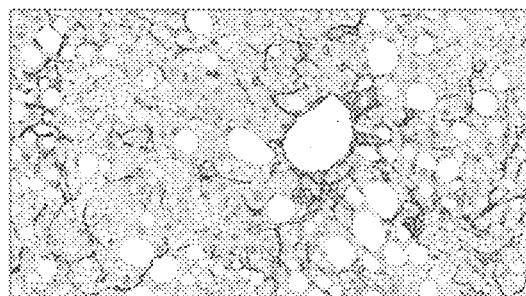
FIG. 39F is an image of liver morphology (liver stained with anti-type I collagen (Southern Biotech, cat. no. 1310-01) at termination (magnification 20×, scale bar=100 μm) for Group 6.
Figure 39G:
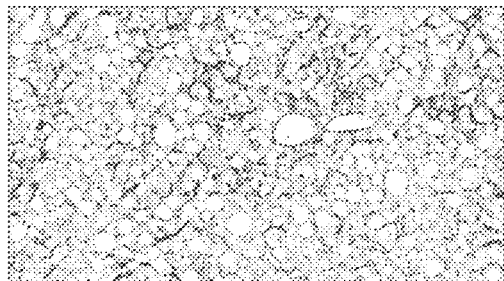
FIG. 39G is an image of liver morphology (liver stained with anti-type I collagen (Southern Biotech, cat. no. 1310-01) at termination (magnification 20×, scale bar=100 μm) for Group 7.
Figure 39H:
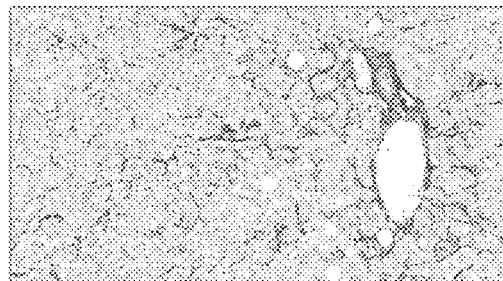
FIG. 39H is an image of liver morphology (liver stained with anti-type I collagen (Southern Biotech, cat. no. 1310-01) at termination (magnification 20×, scale bar=100 μm) for Group 8.
Figure 40A:
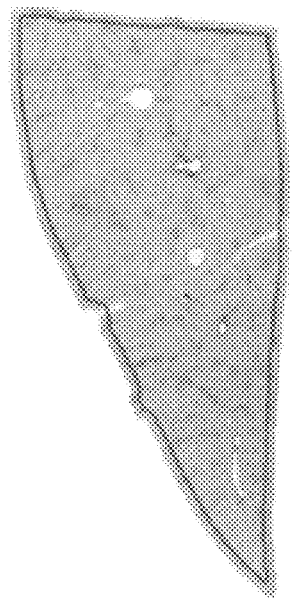
FIG. 40A is an image showing crude detection of tissue at low magnification (first step of histological quantitative assessment).
Figure 40B:
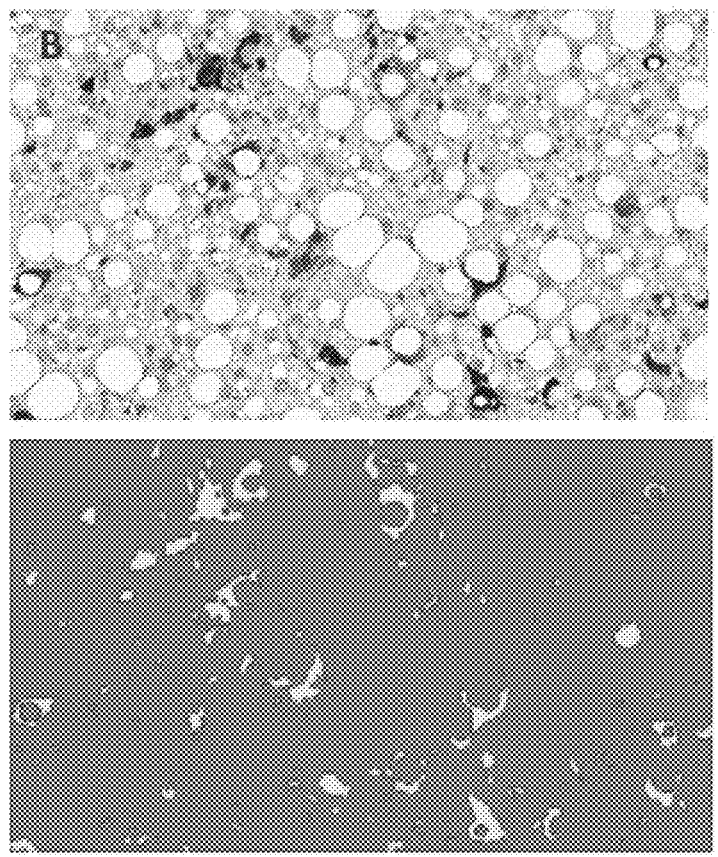
FIG. 40B is an image showing detection of collagen 1A1 (green) and tissue (red) at high magnification.
Figure 41A:
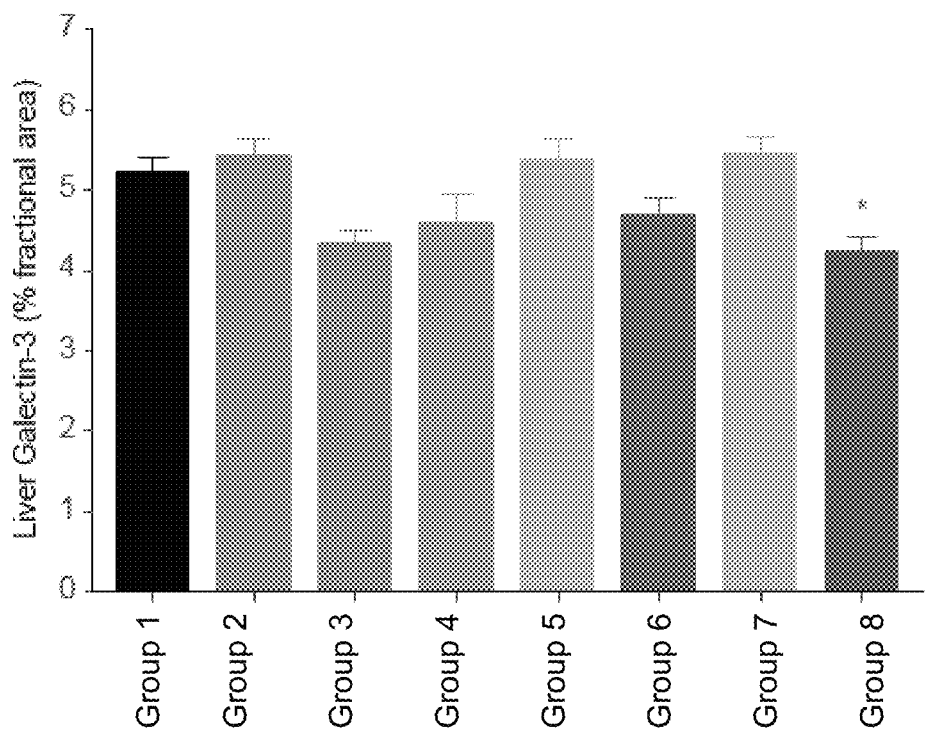
FIG. 41A is a chart showing terminal relative Collagen 1A1 (Col1a1) quantified by morphometry. Values expressed as mean of n=11-13+SEM. Dunnett's test one-factor linear model. No differences at significance level 0.05 compared to Control.
Figure 41B:
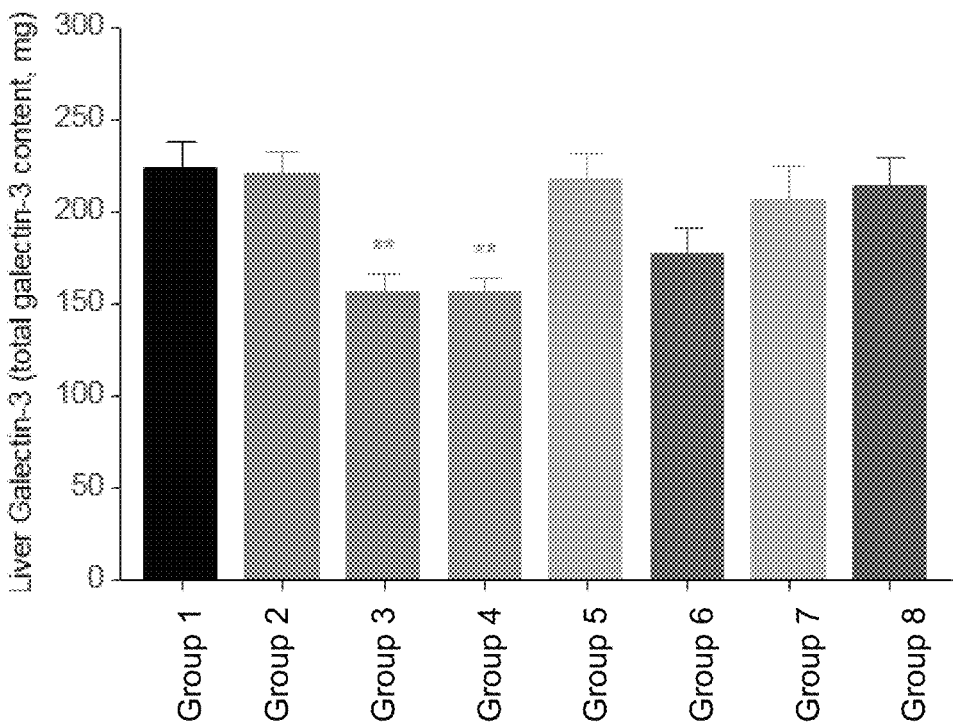
FIG. 41B is a chart showing terminal total Collagen 1A1 (Col1a1) quantified by morphometry. Values expressed as mean of n=11-13+SEM. Dunnett's test one-factor linear model. No differences at significance level 0.05 compared to Control.
Figure 42A:
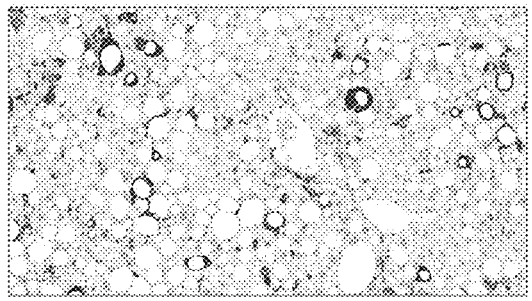
FIG. 42A is an image of liver morphology (liver stained with anti-α-smooth muscle actin (α-SMA), AbCam, cat. no. ab124964) at termination (magnification 20×, scale bar=100 μm) for Group 1.
Figure 42B:
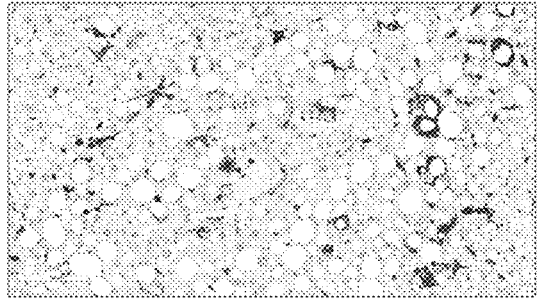
FIG. 42B is an image of liver morphology (liver stained with anti-α-smooth muscle actin (α-SMA), AbCam, cat. no. ab124964) at termination (magnification 20×, scale bar=100 μm) for Group 2.
Figure 42C:
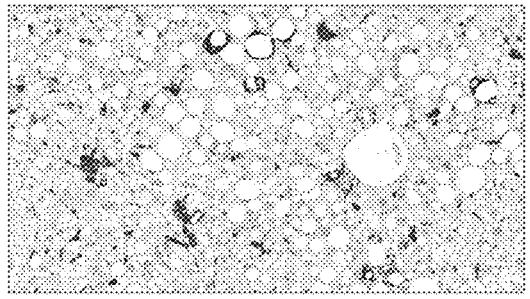
FIG. 42C is an image of liver morphology (liver stained with anti-α-smooth muscle actin (α-SMA), AbCam, cat. no. ab124964) at termination (magnification 20×, scale bar=100 μm) for r Group 3.
Figure 42D:
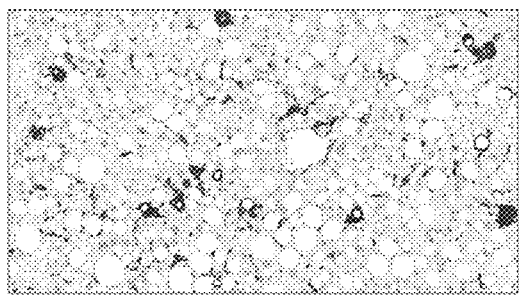
FIG. 42D is an image of liver morphology (liver stained with anti-α-smooth muscle actin (α-SMA), AbCam, cat. no. ab124964) at termination (magnification 20×, scale bar=100 μm) for Group 4.
Figure 42E:
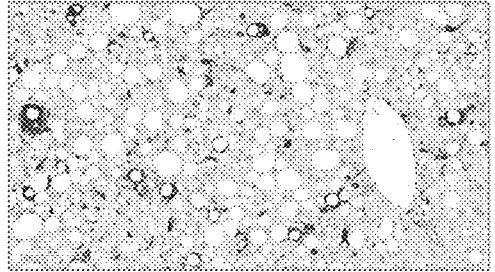
FIG. 42E is an image of liver morphology (liver stained with anti-α-smooth muscle actin (α-SMA), AbCam, cat. no. ab124964) at termination (magnification 20×, scale bar=100 μm) for Group 5.
Figure 42F:
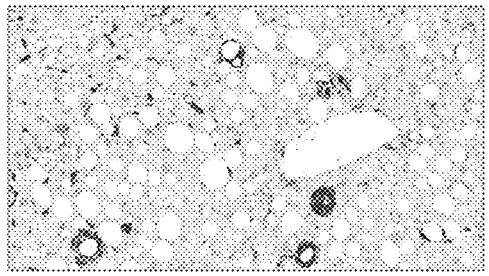
FIG. 42F is an image of liver morphology (liver stained with anti-α-smooth muscle actin (α-SMA), AbCam, cat. no. ab124964) at termination (magnification 20×, scale bar=100 μm) for Group 6.
Figure 42G:
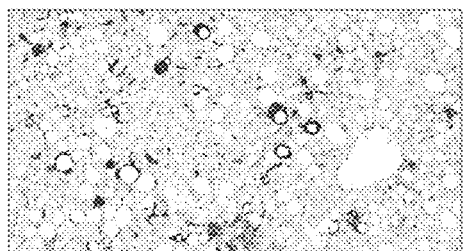
FIG. 42G is an image of liver morphology (liver stained with anti-α-smooth muscle actin (α-SMA), AbCam, cat. no. ab124964) at termination (magnification 20×, scale bar=100 μm) for Group 7.
Figure 42H:
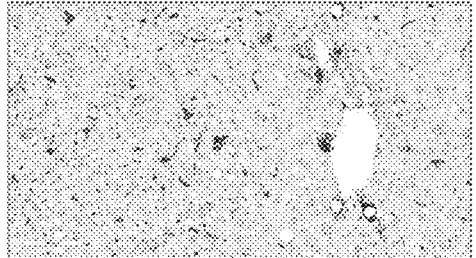
FIG. 42H is an image of liver morphology (liver stained with anti-α-smooth muscle actin (α-SMA), AbCam, cat. no. ab124964) at termination (magnification 20×, scale bar=100 μm) for Group 8.
Figure 43A:
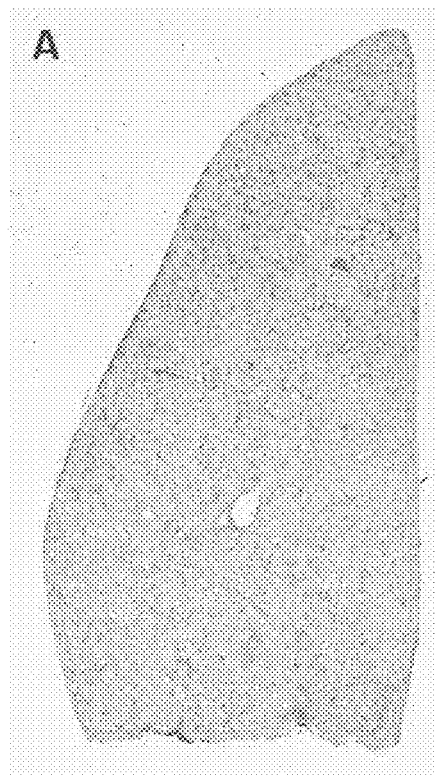
FIG. 43A is an image showing crude detection of tissue at low magnification (first step of histological quantitative assessment).
Figure 43B:
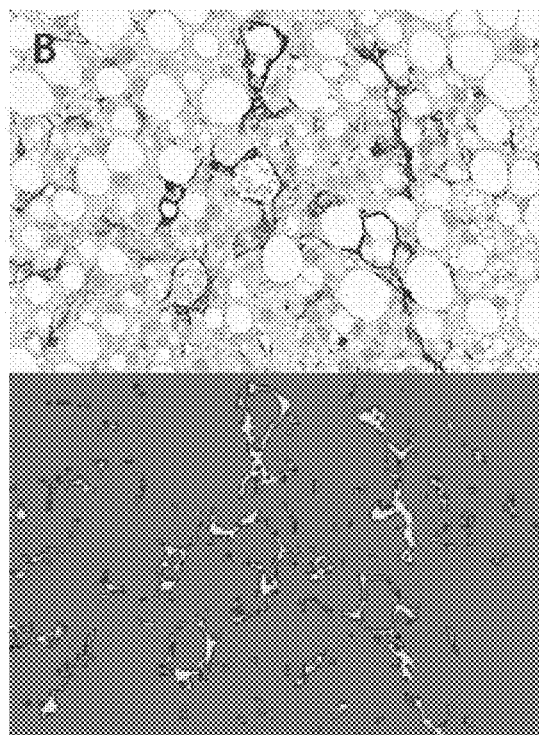
FIG. 43B is an image showing detection of α-SMA (green) and tissue (red) at high magnification.
Figure 44A:
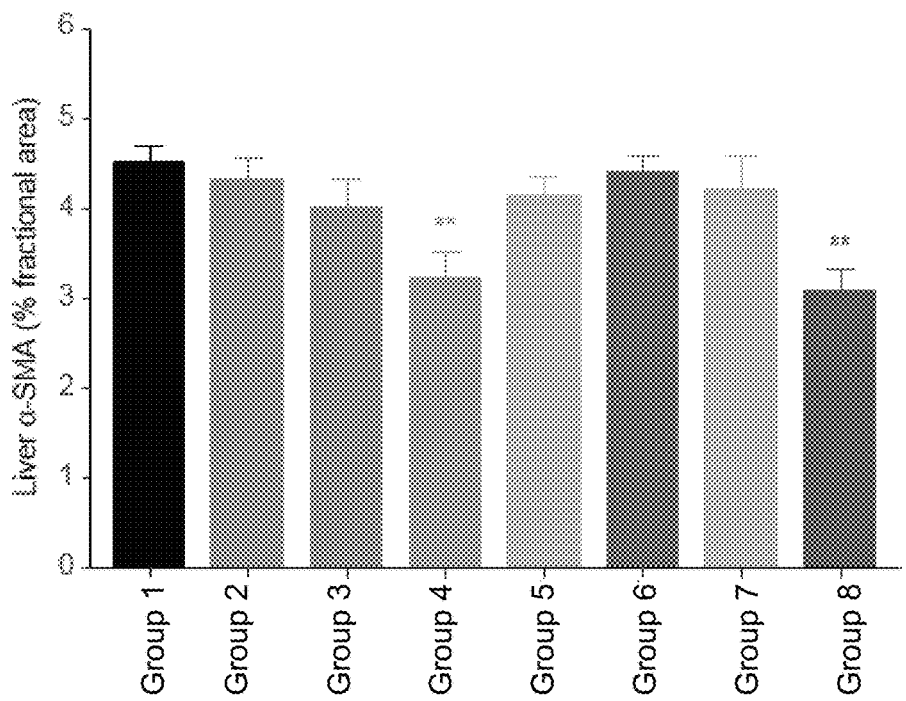
FIG. 44A is a chart showing terminal relative alpha-smooth muscle actin (α-SMA) quantified by morphometry. Values expressed as mean of n=11-13+SEM. Dunnett's test one-factor linear model. **: P<0.01 compared to Control.
Figure 44B:
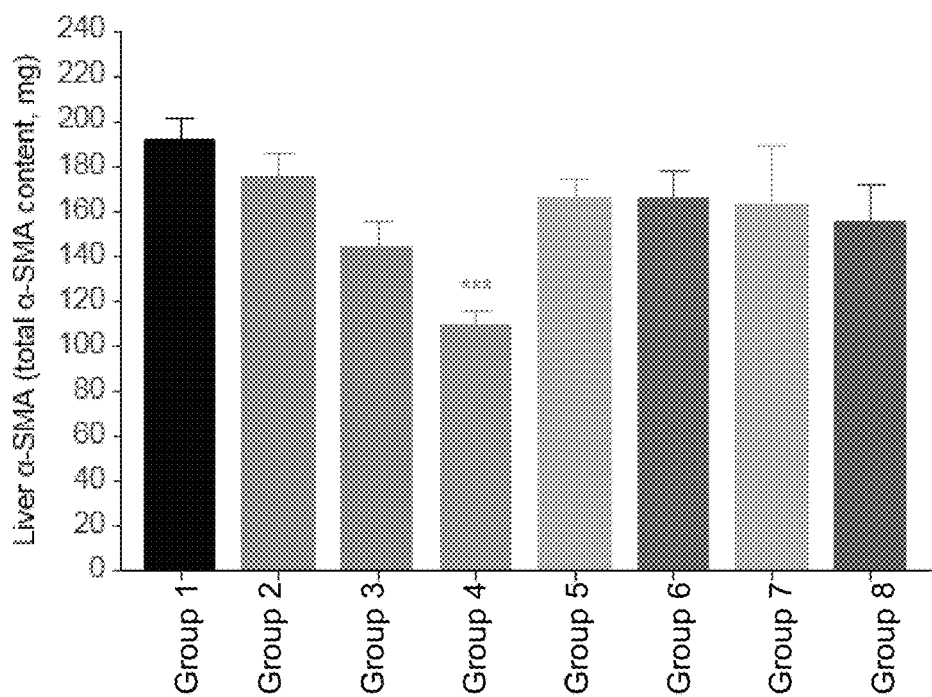
FIG. 44B is a chart showing terminal total alpha-smooth muscle actin (α-SMA) quantified by morphometry. Values expressed as mean of n=11-13+SEM. Dunnett's test one-factor linear model. ***: P<0.001 compared to Control.
Figure 45A:
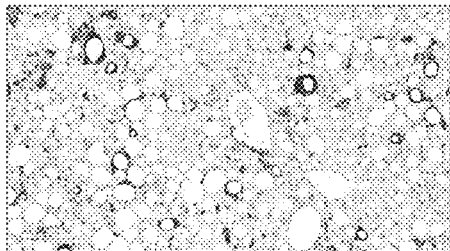
FIG. 45A is an image of liver morphology (liver stained with anti-Galectin 3, Biolegend, cat. no. 125402) at termination (magnification 20×, scale bar=100 μm) for Group 1.
Figure 45B:
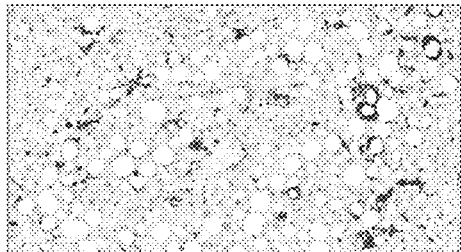
FIG. 45B is an image of liver morphology (liver stained with anti-Galectin 3, Biolegend, cat. no. 125402) at termination (magnification 20×, scale bar=100 μm) for Group 2.
Figure 45C:
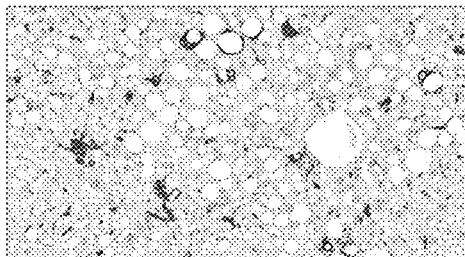
FIG. 45C is an image of liver morphology (liver stained with anti-Galectin 3, Biolegend, cat. no. 125402) at termination (magnification 20×, scale bar=100 μm) for Group 3.
Figure 45D:
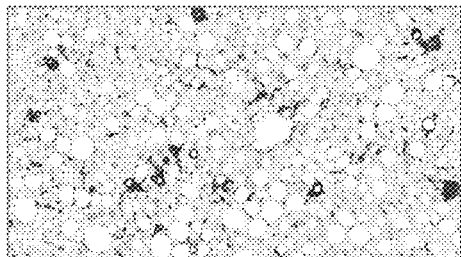
FIG. 45D is an image of liver morphology (liver stained with anti-Galectin 3, Biolegend, cat. no. 125402) at termination (magnification 20×, scale bar=100 μm) for Group 4.
Figure 45E:
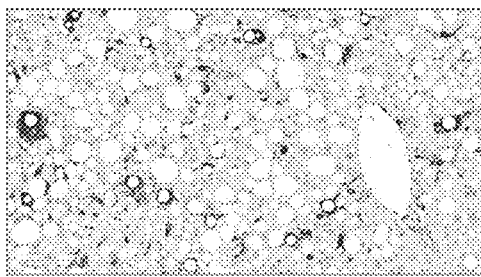
FIG. 45E is an image of liver morphology (liver stained with anti-Galectin 3, Biolegend, cat. no. 125402) at termination (magnification 20×, scale bar=100 μm) for Group 5.
Figure 45F:
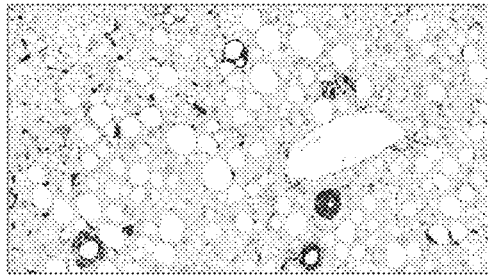
FIG. 45F is an image of liver morphology (liver stained with anti-Galectin 3, Biolegend, cat. no. 125402) at termination (magnification 20×, scale bar=100 μm) for Group 6.
Figure 45G:
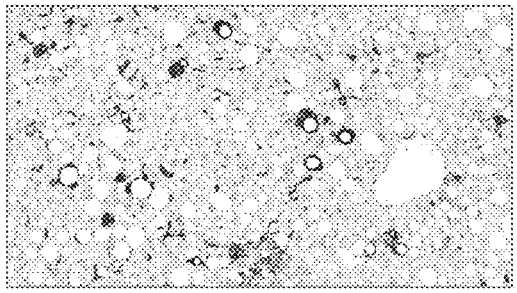
FIG. 45G is an image of liver morphology (liver stained with anti-Galectin 3, Biolegend, cat. no. 125402) at termination (magnification 20×, scale bar=100 μm) for Group 7.
Figure 45H:
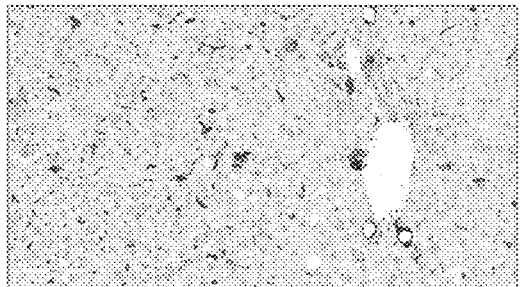
FIG. 45H is an image of liver morphology (liver stained with anti-Galectin 3, Biolegend, cat. no. 125402) at termination (magnification 20×, scale bar=100 μm) for Group 8.
Figure 46A:
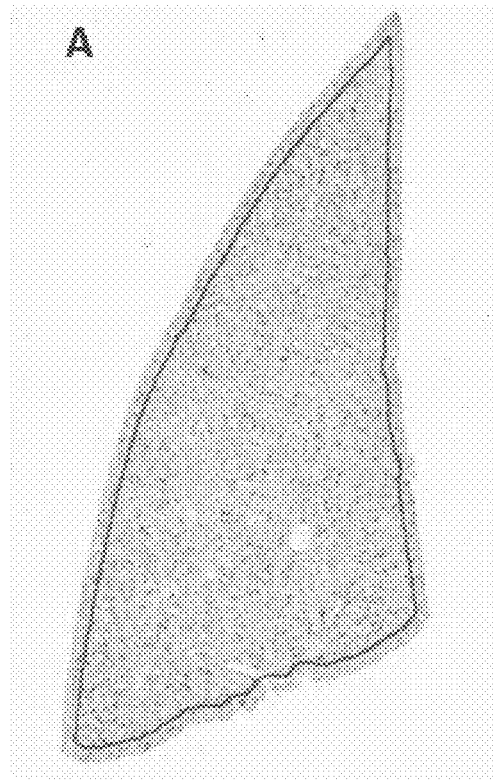
FIG. 46A is an image showing crude detection of tissue at low magnification (first step of histological quantitative assessment).
Figure 46B:
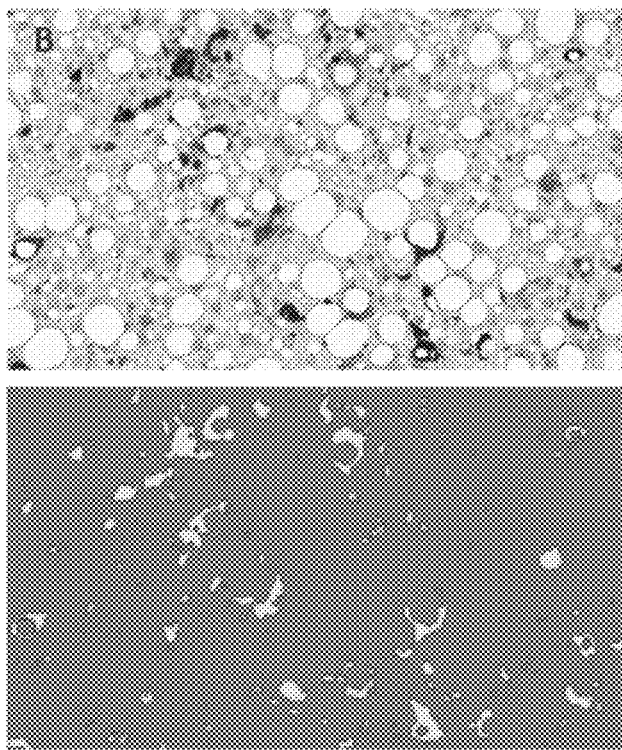
FIG. 46B is an image showing detection of galectin-3 (green) and tissue (red) at high magnification.
Figure 47A:
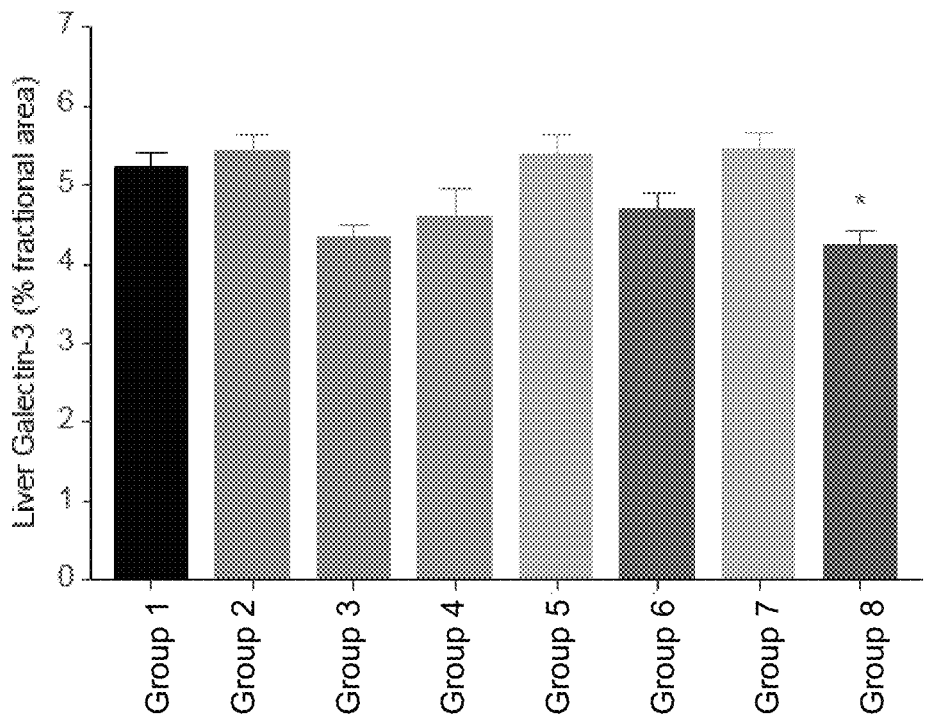
FIG. 47A is a chart showing terminal relative Galectin-3 quantified by morphometry. Values expressed as mean of n=11-13+SEM. Dunnett's test one-factor linear model. *: P<0.05 compared to Control.
Figure 47B:
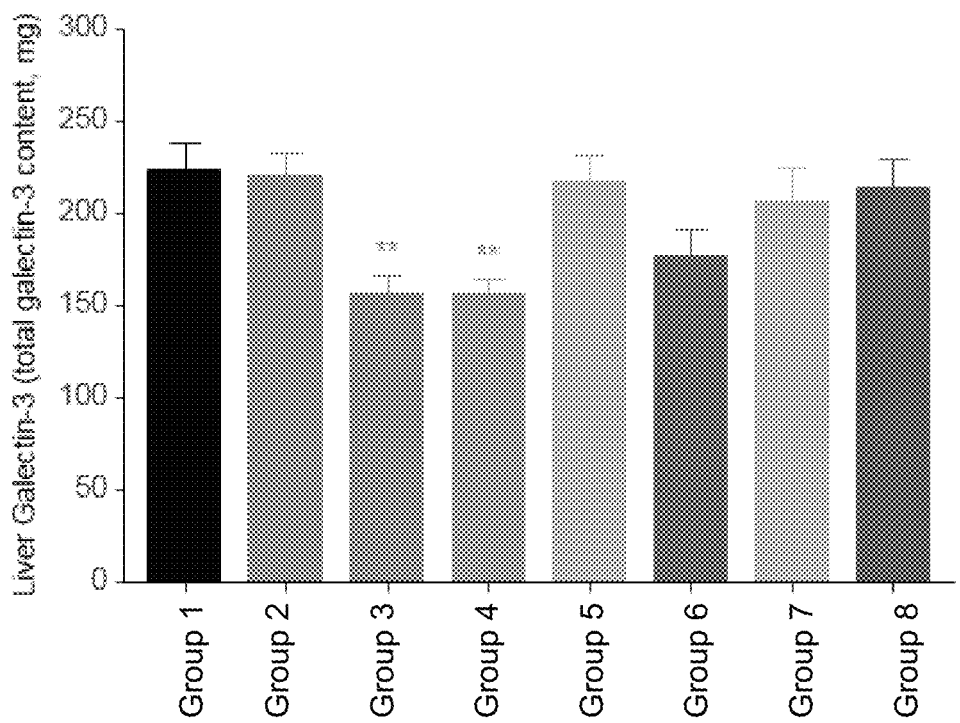
FIG. 47B is a chart showing terminal total Galectin-3 quantified by morphometry. Values expressed as mean of n=11-13+SEM. Dunnett's test one-factor linear model. **: P<0.01 compared to Control.
Figure 48A:
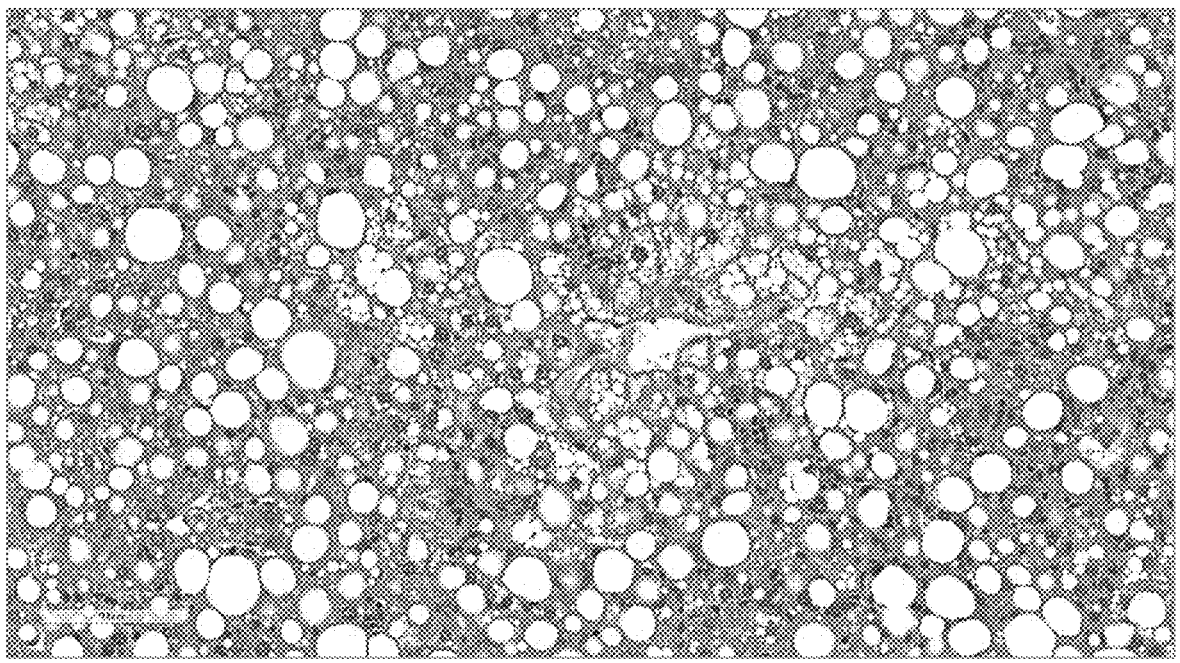
FIG. 48A is an image showing liver morphology in an DIO-NASH Control. When assessing steatosis according to the NASH CRN (Clinical Research Network) scoring criteria, the number of hepatocytes containing fatty droplets are evaluated regardless the size of the lipid vacuole. In the DIO-NASH vehicle the lipid vacuoles are normally large. As the lipid vacuoles are present in over 66% of all hepatocytes in both groups of animals they will be assessed score 3. In contrast an image analysis quantifying steatosis area fraction or a biochemical analysis of liver lipid will show a lower fraction of lipid in the Elafibranor treated animals (magnification 20×, scale bar=100 μm).
Figure 48B:
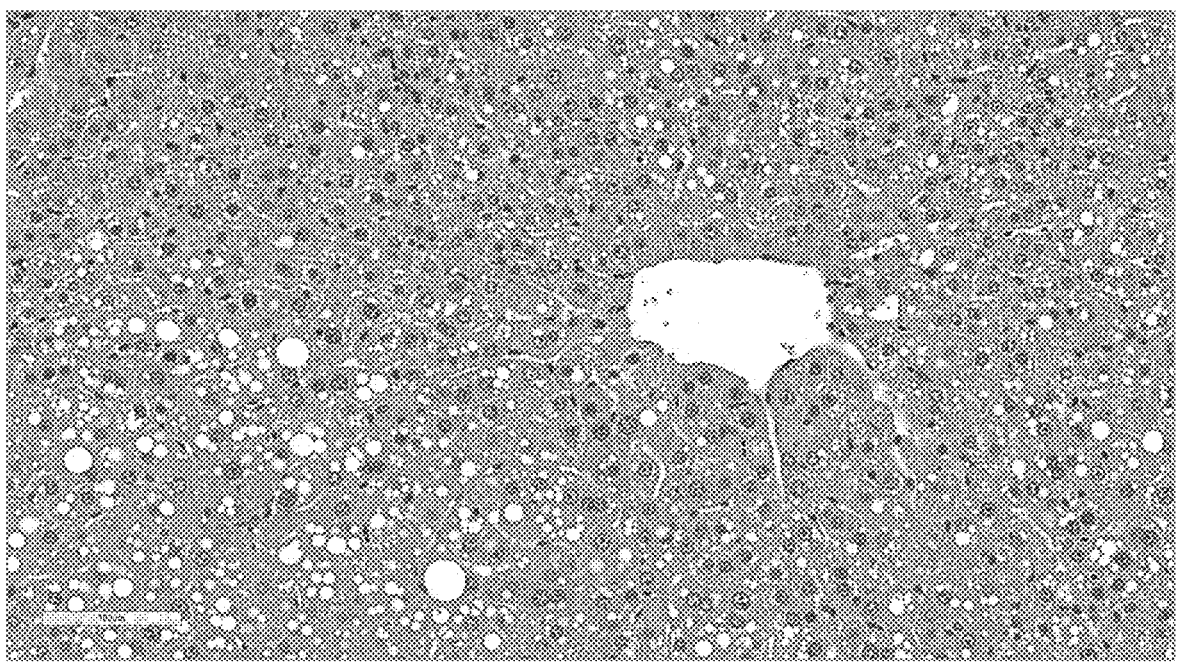
FIG. 48B is an image showing liver morphology in an Elafibranor treated animal. When assessing steatosis according to the NASH CRN (Clinical Research Network) scoring criteria, the number of hepatocytes containing fatty droplets are evaluated regardless the size of the lipid vacuole. In Elafibranor treated animal the vacuoles are smaller. As the lipid vacuoles are present in over 66% of all hepatocytes in both groups of animals they will be assessed score 3. In contrast an image analysis quantifying steatosis area fraction or a biochemical analysis of liver lipid will show a lower fraction of lipid in the Elafibranor treated animals (magnification 20×, scale bar=100 μm).
Figure 49A:
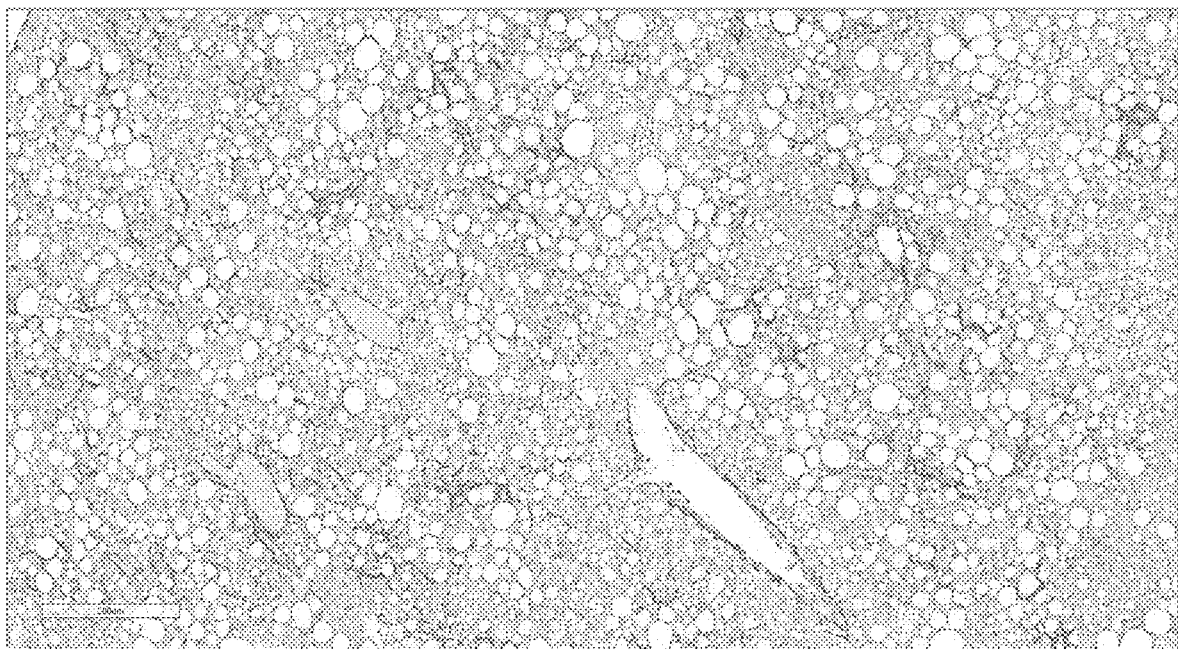
FIG. 49A is an image showing liver fibrosis (Picro Sirius red stained slides) in an DIO-NASH Control in the high end of the Collagen 1a1 (Col1a1) analysis. When assessing fibrosis according to the Brunt scoring criteria, fibrosis is assessed based on its localization. In the DIO-NASH vehicle animal fibrosis is localized in the sinusoids and portal areas without bridging. In the Elafibranor treated animal the fibrosis is finer yet still localized in both sinusoids and portal areas without bridging. In contrast, the image analysis quantifying fibrosis area fraction will show a lower fraction of fibrosis in this Elafibranor treated animal (magnification 10×, scale bar=200 μm).
Figure 49B:
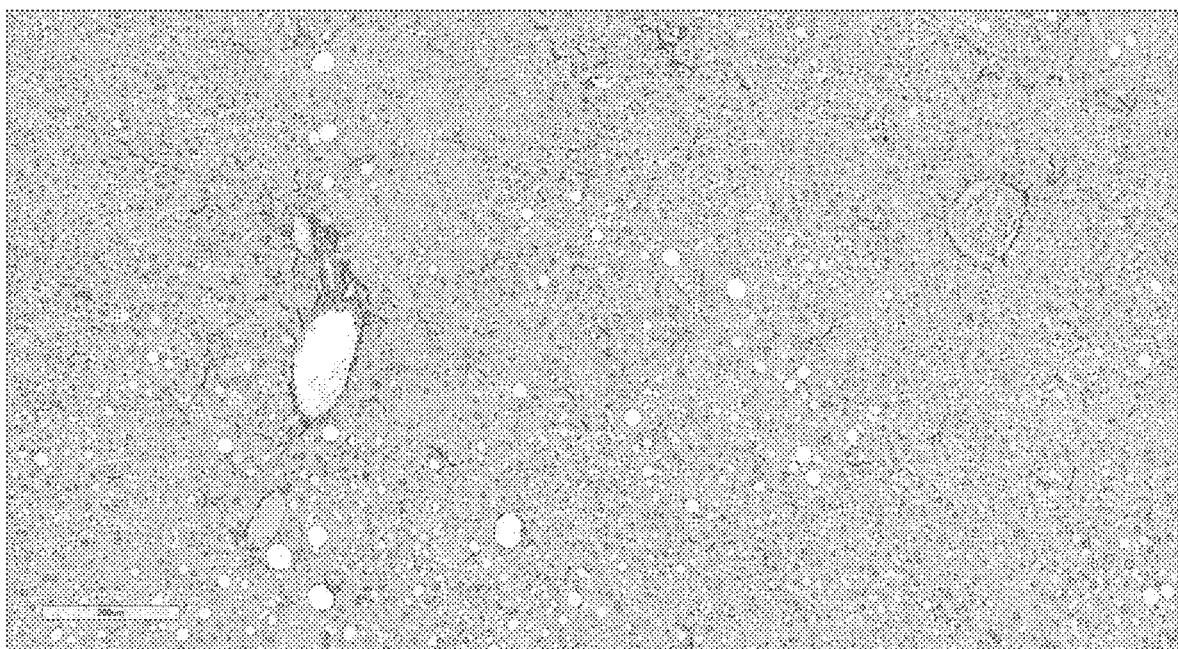
FIG. 49B is an image showing liver fibrosis (Picro Sirius red stained slides) in an Elafibranor treated animal in the low end of the Col1a1 analysis. When assessing fibrosis according to the Brunt scoring criteria, fibrosis is assessed based on its localization. In the DIO-NASH vehicle animal fibrosis is localized in the sinusoids and portal areas without bridging. In the Elafibranor treated animal the fibrosis is finer yet still localized in both sinusoids and portal areas without bridging. In contrast, the image analysis quantifying fibrosis area fraction will show a lower fraction of fibrosis in this Elafibranor treated animal (magnification 10×, scale bar=200 μm).

FIG. 6 shows that animals fed a combination of resveratrol and 1,3-butanediol had less abdominal fat than the animals in the control group. FIG. 7 shows that animals fed a combination of resveratrol with p-hydroxybutyrate or 1,3-butanediol had reduced serum triglyceride levels relative to the control group. FIG. 8 shows that animals fed a combination of resveratrol with p-hydroxybutyrate or 1,3-butanediol had reduced serum cholesterol levels relative to the control group. FIG. 9 shows that the effects shown in FIGS. 3-5 did not result from appetite suppression, as the animals in all groups had about the same daily food consumption. FIG. 10 shows that animals receiving exemplary active agent combinations, resveratrol and p-hydroxybutyrate or 1,3-butanediol, exhibited a lower average steatosis score than the control group or the animals receiving obeticholic acid, a compound currently under investigation as a potential treatment for NASH. FIG. 11 shows that animals receiving an exemplary active agent combination, resveratrol and p-hydroxybutyrate, exhibited a lower average liver inflammation score than the control group or the animals receiving obeticholic acid. FIG. 12 shows that the ballooning score was substantially the same for the animals receiving the tested regimens, with the exception of the animals receiving obeticholic acid. FIG. 13 shows that fibrosis scores were substantially the same for all tested animals. FIG. 14 shows that animals receiving an exemplary active agent combination (resveratrol and 1,3-butanediol) exhibited reduced liver weight relative to the control group or animals receiving p-hydroxybutyrate alone, 1,3-butanediol alone, or a combination of resveratrol and p-hydroxybutyrate. FIG. 15 shows that animals receiving an exemplary active agent combination (resveratrol and 1,3-butanediol) exhibited a reduced ALT level relative to the control group or animals receiving p-hydroxybutyrate alone, 1,3-butanediol alone, or a combination of resveratrol and p-hydroxybutyrate.

Example 5: In Vivo FATZO DM2/Obesity Study

Male FATZO mice (Crown Bio) of 11-12 weeks old were selected for Diabetes Mellitus Type 2 (DM2) and obesity study. Mice were randomized into 9 groups based on body weight and blood glucose level as shown below. Compounds were administered in high fat diet (HFD: D12492) and provided to mice ad libitum until study termination. Body weight was recorded at the baseline and then twice weekly thereafter. Blood glucose level was measured at 0, 15, 30, 60, 90, and 120 minutes at the end of the study. Results after 28 days are shown in the Table 3.

TABLE 3

| Compound | Weight difference VS control diet (p-value) | P Value (weight difference) | OGTT (AUC) |
| --- | --- | --- | --- |
| 4 | −1.19 g | 0.04 | 59443 |
| 14 | −1.58 g | 0.05 | 65323 |
| Rosiglitazone 0.045% in diet | +9.17 | 0.00 | 25222 |
| Control diet | 0 | | 73800 |

P-values are corrected using Benjamini-Hochberg FDR.
The data above demonstrate that conjugates of the invention may be useful for the treatment of type II diabetes, pre-diabetes, metabolic syndrome, or obesity.

Example 6: Glucose Uptake in Human Subcutaneous Adipocytes in Insulin Sensitive Model and Glucose Uptake in Human Subcutaneous Adipocytes in Insulin Resistant Model Glucose Uptake in Human Subcutaneous Adipocytes in Insulin Sensitive Model Primary human subcutaneous adipocytes (Zen Bio, Research Triangle Park, NC) were differentiated for two weeks prior to treatment. Cells were treated with indicated compounds diluted in (dimethyl-sulfoxide) DMSO in serum free medium for 24 hours in triplicate. After 24 hours, media was exchanged for assay buffer and the compounds were added again but in the presence of approximately 1 nM insulin. Glucose uptake was initiated with the addition of a cocktail containing 2-deoxyglucose and $^3$H-2-deoxyglucose and allowed to incubate for 2 hours. Cells were washed, lysed and glucose uptake was measured as counts per well. As an assay control, 100 nM of insulin was used during the 2 hours of glucose uptake. The compounds (R)—BHB and (R)-1,3-Butanediol significantly enhanced insulin-mediated glucose uptake (Table 4). Statistical changes in glucose uptake were determined by way ANOVA and compared to DMSO.

Glucose Uptake in Human Subcutaneous Adipocytes in Insulin Resistant Model

As described above, primary human subcutaneous adipocytes were differentiated for two weeks prior to treatment. To induce an insulin resistant state, cells were treated in serum free Dulbecco's Modified Eagle Medium (high glucose) and 1 M insulin for 24 hours. Cells were simultaneously treated with compounds diluted in DMSO for 24 hours. As described above, after 24 hours, media was exchanged for assay buffer and the compounds were added again but in the presence of approximately 1 nM insulin. Cells were washed and lysed after 2 hours and glucose uptake was measured. In an insulin-resistant like state, the compound (R)—BHB significantly enhanced insulin-mediated glucose uptake (Table 4). Statistical changes in glucose uptake were determined by way ANOVA and compared to DMSO.

TABLE 4

| Compound | Insulin Sensitive % DMSO | Insulin Resistant % DMSO |
| --- | --- | --- |
| DMSO | 100.0 | 100% |
| Acetate 1 mM | = | = |
| Acetate 3 mM | = | = |
| arabinose 0.5 mM | = | = |
| arabinose 1 mM | ++ | = |
| EGCG 100 nM | = | + |
| EGCG 10 μM | = | = |
| Quercetin 100 nM | = | = |
| Quercetin 1 μM | = | = |
| (R) 1,3 Butanediol 100 μM | = | = |
| (R) 1,3 Butanediol 500 μM | ++ | = |
| (R) BHB 2 mM | ++ | + |
| (R) BHB 20 mM | ++ | = |
| Butyrate 3 mM | − | + |
| Propionate 3 mM | = | = |
| Resveratrol 10 μM | = | = |
| Resveratrol 100 μM | − | − |
| Rosiglitazone 10 μM | = | = |
| Rosiglitazone 100 μM | ++ | − |
| Insulin 100 nM | +++ | + |

<50%: −
50% > ≤110%: =
110% > ≤140%: +
140% ≥ ≤200%: ++
200%>: +++

Conclusions: positives in this assay indicate that these components enhance insulin-mediated glucose uptake in insulin-resistant adipocytes, and can thereby improve glucose tolerance in type 2 Diabetes, pre-diabetes, metabolic syndrome, and obesity therapy.

Example 7: Investigating AhR Activation in Caco-2 Cells Through CYP1A1 mRNA Expression Caco-2 cells from American Type Culture Collection (ATCC) were plated in a sterile tissue culture treated 96-well plate (ThermoFisher) at $8.0 \times 10^5$ cells per well, and grown overnight at 37° C., 5% $CO_2$ in DMEM complete (Gibco) in order to achieve confluence. After the incubation medium was aspirated from the Caco-2 monolayers, tissues were then washed with 200 μL of warmed PBS solution, and subsequently 190 μL of pre-warmed growth medium was added to each well. Compounds of interest were diluted at a 20× concentration in growth medium containing 2% DMSO, and 10 μL of compound solutions were added to respective wells in triplicate. Compounds where incubated overnight at 37° C., 5% $CO_2$. 2-(1'H-indole-3'-carbonyl)-thiazole-4-carboxylic acid methyl ester (ITE) was used as the positive control for AhR activation at 1 and 100 μM concentrations. At the end of the incubation, medium was aspirated off of the Caco-2 cells, and washed with 100 μL of cold PBS solution. RNA was extracted via the TaqMan™ Gene Expression Cells-to-$C_T$™ Kit (ThermoFisher) according to the manufacturers protocol. The QuantStudio 6 Flex (Applied Biosciences) was used to analyze mRNA levels of CYP1A1 using GAPDH as the endogenous control. TaqMan™ probe sets for both genes were acquired from ThermoFisher. Samples were run in triplicate and data was analyzed using the QuantStudio software and reported as linear (Table 1) and log 2 ($\Delta\Delta C_T$) values. Statistical analysis was performed using a two-tailed t-test comparing CYP1A1 levels in the presence of each individual compound to the vehicle negative control.

Activation of AHR has been associated with immune modulation and active compounds (+, ++, +++) may be beneficial in treating a variety of inflammatory and autoimmune diseases including ulcerative colitis, multiple sclerosis, rheumatoid arthritis as well as various metabolic diseases.

TABLE 5

| | Conc. (μM) | Average CYP1A1 mRNA levels |
| --- | --- | --- |
| vehicle control | N/A | − |
| acetate | 1000.0 | − |
| acetate | 3000.0 | − |
| L-arabinose | 1000.0 | − |
| EGCG | 0.1 | − |
| EGCG | 1.0 | − |
| quercetin | 0.1 | − |
| quercetin | 1.0 | + |
| butanediol | 500.0 | − |
| beta-hydroxybutyric acid | 2000.0 | − |
| resveratrol | 100.0 | − |
| butyrate | 1000.0 | − |
| butyrate | 3000.0 | − |
| propionate | 1000.0 | − |
| propionate | 3000.0 | − |
| Indole-3-acetic acid | 500.0 | − |
| Indole-3-acetic acid | 1000.0 | − |
| Indole-3-butyric acid | 500.0 | − |
| Indole-3-butyric acid | 1000.0 | − |
| Indole-3-propionic acid | 500.0 | − |
| Indole-3-propionic acid | 1000.0 | − |
| indole | 1000.0 | + |
| Indole-3-aldehyde | 1000.0 | + |
| indole-3-carbinol | 1000.0 | + |
| Indole-3-acetic acid | 500.0 | +++ |
| Indole-3-acetic acid | 1000.0 | ++ |
| Indole-3-carboxylic acid | 1000.0 | − |
| Indole-3-acrylic acid | 10.0 | +++ |
| Indole-3-acrylic acid | 100.0 | +++ |
| Indole-3-acrylic acid | 1000.0 | +++ |
| Indole-3-pyruvic acid | 10.0 | +++ |
| Indole-3-pyruvic acid | 100.0 | +++ |
| Indole-3-pyruvic acid | 1000.0 | +++ |
| ITE 1 uM | 1.0 | +++ |
| Urolithin B | 10.0 | ++ |
| Urolithin B | 100.0 | +++ |
| Urolithin C | 10.0 | ++ |
| Urolithin C | 100.0 | ++ |
| 4-hydroxy-3-methylbenzoic acid | 10.0 | +++ |
| 4-hydroxy-3-methylbenzoic acid | 100.0 | +++ |
| Benzoic acid | 10.0 | + |
| Benzoic acid | 100.0 | + |
| Hydrocinnamic acid | 10.0 | + |
| Hydrocinnamic acid | 100.0 | + |
| L-tryptophan | 10.0 | ++ |
| L-tryptophan | 100.0 | +++ |
| D-tryptophan | 10.0 | ++ |
| D-tryptophan | 100.0 | +++ |
| L-homoserine | 5.0 | + |

TABLE 5-continued

| | Conc. (µM) | Average CYP1A1 mRNA levels |
|---|---|---|
| L-homoserine | 50.0 | + |
| L-arginine | 5.0 | + |
| L-arginine | 50.0 | + |
| Myricetin | 10.0 | + |
| Myricetin | 100.0 | ++ |
| Indole-3-lactic acid | 10.0 | + |
| Indole-3-lactic acid | 100.0 | +++ |
| 4-hydroxyphenylpyruvic acid | 10.0 | ++ |
| 4-hydroxyphenylpyruvic acid | 100.0 | +++ |
| Pterostilbene | 10.0 | ++ |
| Pterostilbene | 100.0 | ++ |
| Astaxanthine | 10.0 | + |
| Astaxanthine | 100.0 | + |
| 3,4-dihydroxyphenylacetic acid | 10.0 | + |
| 3,4-dihydroxyphenylacetic acid | 100.0 | ++++ |
| δ-tocopherol | 10.0 | + |
| δ-tocopherol | 100.0 | +++ |
| 1-methylindole-3-alanine | 10.0 | + |
| 1-methylindole-3-alanine | 100.0 | +++ |
| Piceatannol | 10.0 | + |
| Piceatannol | 100.0 | +++ |
| Kynurenine | 10.0 | + |
| Kynurenine | 100.0 | ++ |

Vehicle = baseline
− = <2-fold Vehicle
+ = >2-fold Vehicle
++ = >5-fold Vehicle
+++ = >10-fold Vehicle Example 8: Human Caco-2 Barrier Integrity Assay Caco-2 colonocytes were maintained at 37° C. and 5% $CO_2$ in Dulbecco's Modified Eagle Medium (DMEM) and supplemented with 10% FBS, 1% NEAA, 1% penicillin-streptomycin. At 70-80% confluency, cells were trypsinized and seeded in 0.4 cm² transwell collagen I coated membranes with supplemented DMEM in both apical and basolateral compartments. Cells were seeded at a density of 200,000 cells per well and maintained for 10 days to form a polarized barrier with a TransEpithelial Electrical Resistance (TEER) reading above 1000Ω. On the first day of the assay, initial TEER readings were taken and cytokines were added to the basolateral media (50 ng/mL TNFα, 25 ng/mL IFNγ and 10 ng/mL IL-1β) to reduce barrier integrity while compounds diluted in (dimethylsulfoxide) DMSO were added to the apical media in triplicate. After 48 hours, TEER readings were taken again and viability was measured by CellTiter 96® AQ$_{ueous}$ One Solution Cell Proliferation Assay (Promega). The percent change in TEER over the 48 hours was determined and normalized to the 0.1% DMSO control (Table 6). None of the compounds reduced proliferation and therefore did not alter cell viability.

TABLE 6

| | % Change in TEER from DMSO |
|---|---|
| No treatment | ++(170%) |
| DMSO + cytokines | −(100%) |
| Acetate 1 mM + cytokines | − |
| Acetate 3 mM + cytokines | − |
| Arabinose 0.5 mM + cytokines | − |
| Arabinose 1 mM + cytokines | − |
| EGCG 100 nM + cytokines | − |
| EGCG 1 µM + cytokines | − |
| Quercetin 100 nM + cytokines | − |
| Quercetin 1 µM + cytokines | + |
| Butanediol 100 µM + cytokines | − |

TABLE 6-continued

| | % Change in TEER from DMSO |
|---|---|
| Butanediol 0.5 mM + cytokines | − |
| BHB 200 µM + cytokines | + |
| BHB 2 mM + cytokines | − |
| Resveratrol 10 µM + cytokines | − |
| Resveratrol 100 µM + cytokines | +++ |
| Butyrate 1 mM + cytokines | − |
| Butyrate 3 mM + cytokines | − |
| Butyrate 5 mM + cytokines | ++ |
| Propionate 1 mM + cytokines | + |
| Propionate 3 mM + cytokines | ++ |

Statistical changes in TEER were determined by way ANOVA and compared to DMSO.
≤125%: −
125% > ≤150%: +
150% ≥ ≤200%: ++
200%>: +++

Barrier function and integrity is an important feature of a variety of diseases and can be a hallmark of a damaged GI tract. Inflammation can drive a reduction of barrier function. By improving TEER less translocation of bacteria and bacterial products occur, thus dampening the immune response and damage to the GI tract and systemic immune system. This is important for the following disease areas: type 2 diabetes, obesity, pre-diabetes, and metabolic syndrome.

Example 9: Mouse Adipocyte Lipolysis Assay

Mouse 3T3-L1 cells were obtained from ATCC and cultured in Dulbecco's Modified Eagle's medium (DMEM) containing 10% newborn calf serum (NCS) and penicillin/streptomycin (P/S) at 37° C. in an incubator with 5% $CO_2$. Once the cells became confluent, they were seeded into a tissue culture treated 96 well plate. Then differentiation was initiated by using DMEM containing 10% fetal bovine serum, P/S, IBMS, dexamethasone, and insulin. After 14 days of differentiation, cells were treated with compounds of interest. After 24 hours post-treatment, the cell viability was assessed using CellTiter-Glo Luminescent Cell Viability Assay from Promega, and lipolysis was determined using Lipolysis Assay Kit from ZenBio. No treatment had a significant effect on cell viability (>90% of DMSO control), with the exception of Sodium BHB 0.2 mM (86% of DMSO control).

TABLE 7

| | Lipolysis | |
|---|---|---|
| | Free Fatty Acids % DMSO | Glycerol % change |
| Acetic acid 1 mM | ++ | + |
| Acetic acid 3 mM | ++ | + |
| L-Arabinose 0.5 mM | ++ | + |
| L-Arabinose 1 mM | ++ | + |
| EGCG 100 nM | ++ | + |
| EGCG 1 µM | ++ | + |
| Quercetin 100 nM | ++ | + |
| Quercetin 1 µM | ++ | + |
| (R)-1,3-Butanediol 100 µM | ++ | + |
| (R)-1,3-Butanediol 0.5 mM | ++ | + |
| Sodium BHB 0.2 mM | ++ | + |
| Sodium BHB 2 mM | ++ | ++ |
| Sodium BHB 20 mM | + | ++ |
| Butyric acid 3 mM | ++ | ++ |
| Propionic acid 3 mM | +++ | ++ |
| Rosiglitazone 10 µM | +++ | ++ |

TABLE 7-continued

|  | Lipolysis | |
| --- | --- | --- |
|  | Free Fatty Acids % DMSO | Glycerol % change |
| Rosiglitazone 100 µM | +++ | +++ |
| Resveratrol 1 µM | + | + |
| Resveratrol 10 µM | = | ++ |
| Obeticholic acid 100 µM | = | = |
| DMSO | =(100%) | =(100%) |

90% > ≤100%: =
70% > ≤90%: +
50 > ≤70%: ++
50%≤: +++

Table 7 indicates compounds that reduced the release of free fatty acids and glycerol (+, ++, or +++). The lipolytic rate of white adipose tissue associated with metabolic dysfunction including insulin resistance and liver steatosis. Compounds that lower lipolysis of adipocytes may improve metabolic function including improving insulin sensitivity and reducing liver steatosis, thus improving outcomes in patients with diabetes mellitus, pre diabetes, obesity, type II diabetes, and hyperlipidemia.

Example 10: Mouse Myocyte Lipolysis Assay

Cells were obtained from ATCC and cultured in Dulbecco's Modified Eagle's medium (DMEM) containing 20% fetal bovine serum and 1% penicillin/streptomycin at 37° C. in an incubator with 5% $CO_2$. Once the cells became confluent, they were seeded into a tissue culture treated 96 well plate. The next day, the medium containing DMEM with 2% equine serum was used to start differentiation. Once cells were fully differentiated, they were treated with indicated compounds.

TABLE 8

| Treatment | Free glycerol % DMSO |
| --- | --- |
| Acetic acid 1 mM | = |
| Acetic acid 3 mM | = |
| L-Arabinose 0.5 mM | + |
| L-Arabinose 1 mM | + |
| EGCG 100 nM | + |
| EGCG 1 µM | + |
| Quercetin 100 nM | + |
| Quercetin 1 µM | + |
| (R)-1,3-Butanediol 100 µM | + |
| (R)-1,3-Butanediol 0.5 mM | + |
| Sodium BHB 0.2 mM | ++ |
| Sodium BHB 2 mM | ++ |
| Butyric acid 3 mM | +++ |
| Propionic acid 3 mM | ++ |
| Rosiglitazone 10 µM | ++ |
| Rosiglitazone 100 µM | ++ |
| Resveratrol 1 µM | + |
| Resveratrol 10 µM | ++ |
| Obeticholic acid 100 µM | = |
| DMSO | =(100.0%) |

90% > <100%: =
70% > <90%: +
50 > <70%: ++
50%<: +++

Table 8 indicates compounds that reduced the release of glycerol (+, ++, or +++). The lipolytic rate of muscle triglycerides is associated with metabolic dysfunction including insulin resistance and liver steatosis. Compounds that lower lipolysis of adipocytes may improve metabolic function including improving insulin sensitivity and reducing liver steatosis, thus improving outcomes in patients with diabetes mellitus, pre diabetes, obesity, type II diabetes, and hyperlipidemia.

Example 11: In Vivo Evaluation of an Acylated Catechin Polyphenol for Glucose Disposal and Lipidemia Methods Male DIO mice (14-15 weeks of age, n=107) were purchased from Jackson Labs (#380050). The DIO mice were prepared by feeding male C57BL/6 mice a high fat diet (HFD, Research Diets D12492) from 6-14 weeks of age. DIO mice were housed individually and maintained on the HFD through the duration of study. A twelve-hour light cycle was maintained with room temperature maintained at 22-25° C. All of the mice were acclimated to the facility for 5 days prior to starting the study.

Following 5 days of facility acclimation, DIO mice were randomized into 8 groups of 10 based on body weight and blood glucose for assignment to treatment, as shown in Table 9:

TABLE 9

| Group | Treatment |
| --- | --- |
| 1 | Control |
| 2 | Compound 4 (6%) |
| 3 | Compound 4 (2%) |
| 4 | Compound 4 (0.6%) |
| 5 | Compound 53 (5%) |
| 6 | Compound 14 (6%) |
| 7 | Resveratrol (0.78%) + 1,3 butanediol (3%) |
| 8 | Rosiglitazone 0.045% |

All treatments were administered admixed in HFD (Research Diets, New Brunswick NJ) and were provided ad libitum for 30 days. Drinking water for group 7 was supplemented with 1, 3 Butanediol at 3% concentration.

Body weight was recorded at baseline and twice weekly thereafter. Feed and water intakes were recorded each Monday, Wednesday, and Friday.

Blood samples (<3 µL) were obtained one hour post dose by tail clip at baseline and weekly thereafter for measurement of fed blood glucose by StatStrip. Additional anti-coagulated blood samples (100 µl, EDTA di-potassium salt) were obtained by tail clip one hour post-dose at baseline, day 14 and day 30. Anti-coagulated samples were quick frozen and stored on dry ice.

Fecal samples were collected 6 hours after compound administration on day 0, 14 and 27/28. Fecal samples were frozen.

Animals were subjected to a 16 hour fast for performance of an oral glucose tolerance test (OGTT) on day 28. Blood samples were obtained via tail clip just prior to (8 am) and 15, 30, 60, 90, and 120 minutes post-glucose load (2.0 g/kg, PO) for assay of whole blood glucose (StatStrip). Feed was returned following last sample.

Animals were terminated on day 30-31 using CO2 inhalation and induction of pneumothorax. Terminal blood samples were obtained by cardiac puncture. Whole blood was processed to serum and analyzed for serum cholesterol, triglycerides, high density lipoprotein (HDL), low density lipoprotein (LDL) and non-esterified fatty acids (NEFA) using AU480 clinical analyzer.

Organ weights (liver, spleen, subcutaneous fat, inguinal fat, abdominal fat, and epididymal fat) were recorded. Sections of each fat were frozen or fixed in 4% paraformaldehyde/PBS, pH 6.9; Fat samples were placed on dry ice. Fixed liver samples (4% paraformaldehyde) were sent to Premier Laboratories for H&E staining and scoring for steatosis, inflammation and fibrosis. Spleen samples were prepared in ice cold 5% bovine serum albumin (BSA) in PBS or 4% paraformaldehyde. Sections of brain, heart, lung, and small and large intestine were fixed in 10% formalin.

In parallel, twenty-seven animals (9 per dose group) were administered Compound 4 at 0.6, 2.0 and 6.0% in the diet for pharmacokinetic sampling. Three mice from each group were terminated on day 1, 14 and 28 for collection of EDTA di-potassium salt plasma by cardiac puncture. Plasma was frozen.

Results

All data are represented as group mean±SEM. Data were analyzed using JMP (SAS software). All normalizations were calculated using terminal body weight. All assigned mice completed the study.

The area under the curve (AUC) for glucose was calculated as the sum of the trapezoidal areas between the 0, 15, 30, 60, 90 and 120-minute time points corresponding to each animal from OGTT data. Baseline differences among groups were identified using Tukey-Kramer Hsd <0.05. Treatment effects compared to control were determined using Oneway ANOVA (*, $p<0.05$) followed by Dunnett's test where appropriate.

Body Weight

Body weight in sixteen week old DIO mice averaged 38.8±0.3 g and there were no significant differences among groups at baseline (38.9±1.1, 38.8±0.9, 38.8±0.9, 38.6±0.9, 38.7±0.9, 38.8±1.1, 38.8±0.9, and 38.8±0.9 g for control, Compound 4 at 6, 2 and 0.6%, Compound 43, Compound 14, Resveratrol/Butanediol and rosiglitazone, respectively).

Body weight increased compared to baseline over the course of the study in control animals and in animals administered Compound 4 (0.6-6%), Resveratrol/butanediol and rosiglitazone; in contrast, a decrease in body weight compared to baseline was noted in animals administered Compound 43 and Compound 14.

The change in body weight from baseline was significantly different compared to control in animals treated with Compound 43 (17.7±1.4 vs. −1.8±3.2%) and Compound 14 (17.7±1.4 vs. −11.9±1.3%). No other significant differences compared to control were noted (17.7±1.4, 13.5±2.0, 16.4±1.1, 15.7±1.0, 12.0±1.3 and 22.8±1.9% for control, Compound 4 at 0.6, 2.0 and 6.0%, resveratrol/butanediol and rosiglitazone, respectively).

Blood Glucose

Baseline blood glucose (fed) in fifteen week old mice averaged 170.0±2.3 mg/dL and there were no significant differences in baseline levels among groups at study start (163.0±6.0, 162.5±5.2, 170.5±5.2, 167.7±6.5, 173.2±5.9, 177.3±7.3, 172.2±5.9 and 173.5±10.0 for control, Compound 4 at 6%, 2%, and 0.6%, Compound 43, Compound 14, Resveratrol/Butanediol and rosiglitazone, respectively).

Blood glucose decreased compared to baseline values in all treatment groups. This effect was significantly larger in animals administered Compound 14 (−23.1±4.9%) and rosiglitazone (−22.8±3.7%) compared to control (−3.2±5.3%). No other significant differences compared to control were noted (−3.2±5.3, −4.3±3.0, −9.0±3.9, −15.6±3.1, −12.5±2.2 and −10.9±4.0% for control, Compound 4 at 6, 2 and 0.6%, Compound 43, and resveratrol/butanediol, respectively).

Glucose Homeostasis

Fasting blood glucose levels (time 0 from OGTT) following 28 days of compound administration in animals administered Compound 14 was significantly lower compared to control (90.3±4.0 vs. 63.1±1.9 mg/dL). No other significant effects on fasting glucose compared to control were noted (90.3±4.0, 95.1±4.4, 104.7±4.3, 107.3±5.3, 90.8±5.7, 100.5±6.7 and 91.3±2.5 for control, Compound 5 at 6, 2 and 0.6%, Compound 53, resveratrol/butanediol and rosiglitazone, respectively).

The glucose AUC (0-120 min) was significantly higher following administration of Compound 5 at 0.6% (29628.0±1791.7 mg/dL/min) and Compound 53 (30151.5±1680 mg/dL/min) compared to control (25196.3±678.8 mg/dl/min). No other significant differences compared to control were noted (25196.3±678.8, 26049.0±455.4, 27648.8±866.3, 25720.5±895.5, 28347.8±1220.9, and 24540.0±806.3 mg/dL/min for control, Compound 5 at 6 and 2%, Compound 14, resveratrol/butanediol and rosiglitazone, respectively)

Serum Chemistry

Terminal (fed) serum chemistry values are presented in Table 10. Serum cholesterol, triglycerides, LDL, and NEFA were significantly lower compared to control following administration of Compound 14. Serum LDL and NEFA were significantly lower compared to control in animals administered Compound 53 as well as after resveratrol/butanediol treatment. A significant reduction in serum cholesterol, HDL and NEFA was apparent following treatment with rosiglitazone.

Organ Weights

With regard to organ weights (% BW), no significant effects compared to control were noted from any treatment on inguinal fat mass or spleen weight. Rosiglitazone elicited a significant reduction in subcutaneous fat, abdominal fat, and liver weight compared to control. Administration of Compound 14 elicited a reduction in subcutaneous, abdominal, and epididymal fat mass compared to control while a significant reduction in abdominal fat compared to control was observed following treatment with Compound 53 and resveratrol/butanediol (Table 11). The data in Tables 10 and 11 demonstrate that compounds 14 and 53 exhibited particularly high potency in reducing metabolic markers, e.g., cholesterol level (especially, LDL level), level of triglycerides, subcutaneous fat quantity, inguinal fat quantity, and epididymal fat quantity. Accordingly, compounds 14 and 53 may be particularly useful in the treatment of metabolic disorders.

TABLE 10

Terminal (fed) Clinical chemistry

|  | Cholesterol (mg/dL) | Triglycerides (mg/dL) | HDL (mg/dL) | LDL (mg/dL) | NEFA (mEq/L) |
| --- | --- | --- | --- | --- | --- |
| Control | 188.3 ± 11.4 | 101.3 ± 3.8 | 90.5 ± 5.3 | 9.9 ± 0.7 | 1.2 ± 0.06 |
| Compound 4 (6%) | 200.4 ± 14.2 | 89.9 ± 5.7 | 91.5 ± 5.1 | 12.3 ± 0.9 | 1.1 ± 0.04 |

TABLE 10-continued

Terminal (fed) Clinical chemistry

|  | Cholesterol (mg/dL) | Triglycerides (mg/dL) | HDL (mg/dL) | LDL (mg/dL) | NEFA (mEq/L) |
|---|---|---|---|---|---|
| Compound 4 (2%) | 208.2 ± 7.2 | 91.1 ± 8.4 | 99.0 ± 3.6 | 10.7 ± 0.9 | 1.2 ± 0.06 |
| Compound 4 (0.6%) | 193.9 ± 11.0 | 97.7 ± 10.1 | 94.4 ± 4.0 | 9.2 ± 0.9 | 1.2 ± 0.04 |
| Compound 53 (5%) | 163.3 ± 10.3 | 84.8 ± 5.5 | 88.9 ± 2.7 | *6.5 ± 0.7 | *0.98 ± 0.05 |
| Compound 14 (6%) | *121.5 ± 9.4 | *64.0 ± 2.8 | 79.4 ± 4.0 | *4.9 ± 0.4 | *0.69 ± 0.03 |
| Resveratrol (0.78%) + 1,3 butanediol (3%) | 169.2 ± 10.2 | 88.0 ± 6.7 | 82.5 ± 4.2 | *6.5 ± 0.6 | *0.97 ± 0.06 |
| Rosiglitazone (0.045%) | *121.5 ± 7.3 | 91.3 ± 4.8 | *60.5 ± 3.0 | 8.0 ± 0.5 | *0.71 ± 0.04 |

*compared to control, Dunnett's ($p < 0.05$)

TABLE 11

Organ weights (% BW)

|  | Sub-cutaneous fat (% BW) | Inguinal fat (% BW) | Abdominal fat (% BW) | Epididymal fat (% BW) |
|---|---|---|---|---|
| Control | 5.2 ± 0.4 | 0.90 ± 0.07 | 2.8 ± 0.4 | 4.2 ± 0.4 |
| Compound 4 (6%) | 5.0 ± 0.6 | 0.95 ± 0.08 | 2.2 ± 0.1 | 4.7 ± 0.3 |
| Compound 4 (2%) | 5.5 ± 0.5 | 0.93 ± 0.08 | 2.4 ± 0.1 | 4.5 ± 0.2 |
| Compound 4 (0.6%) | 4.9 ± 0.4 | 0.99 ± 0.17 | 2.1 ± 0.2 | 4.7 ± 0.2 |
| Compound 53 (5%) | 4.0 ± 0.6 | 0.84 ± 0.11 | *1.9 ± 0.2 | 4.1 ± 0.4 |
| Compound 14 (6%) | *2.2 ± 0.4 | *0.40 ± 0.06 | *0.98 ± 0.2 | *2.6 ± 0.3 |
| Resveratrol (0.78%) + 1,3 butanediol (3%) | 4.8 ± 0.5 | 0.58 ± 0.04 | *1.9 ± 0.2 | 4.4 ± 0.2 |
| Rosiglitazone (0.045%) | *7.6 ± 0.5 | 0.78 ± 0.05 | *1.6 ± 0.1 | 4.1 ± 0.2 |

*compared to control, Dunnett's ($p < 0.05$)
In Table 11, BW stands for body weight.

Example 12: Human Regulatory T Cell Differentiation Assay

Peripheral blood mononuclear cells (PBMCs) from whole blood donated by health volunteers were separated by Ficoll-Paque gradient centrifugation and naïve CD4+ T cells were subsequently isolated using magnet beads (EasySep™ Human Naïve CD4+ T Cell Isolation Kit, Cambridge, MA). For regulatory T cell (Treg) differentiation assay, naïve CD4+ T cells were cultured (1-10×10$^4$ cells) in CTS OpT-mizer medium for 6 days and stimulated with 5 ng/ml TGF-β, 100 U/m IL-2, and ImmunoCult™ Human CC3/CD28/CD2 T Cell Activator; Stemcell #10990) with/without our Compounds. Cell viability was determined using a viability dye (eBioscience Fixable Viability Dye eFluor 780: ThermoFisher 65-0865-14) at 1:500 dilution. The cells were gated for Treg, defined as Live, CD11c−, CD14−, CD19−, CD8−, CD4+, CD3+, CD25+, FOXP3+. Percent (%) Tregs were calculated as percentage of CD4+, CD25+, FOXP3+ cells over total CD4+ T cells. Statistical analysis was performed with GraphPad Prism Software Using One-Way ANOVA.

TABLE 12

| Treatment | Treg induction % DMSO | Cell viability % DMSO |
|---|---|---|
| Acetic acid 1 mM | + | = |
| Acetic acid 3 mM | ++ | = |
| L-Arabinose 0.5 mM | = | = |
| L-Arabinose 1 mM | = | = |
| EGCG 100 nM | = | = |
| EGCG 1 uM | = | = |
| Quercetin 100 nM | = | = |
| Quercetin 1 uM | = | = |
| (R)-1,3-Butanediol 100 uM | = | = |
| (R)-1,3-Butanediol 0.5 mM | = | = |
| Sodium BHB 2 mM | + | = |
| Sodium BHB 20 mM | = | − |
| Butyric Acid 3 mM | − | − |
| Propionic acid 3 mM | ++ | = |
| Rosiglitazone 10 uM | = | = |
| Rosiglitazone 100 uM | = | − |
| Resveratrol 1 uM | + | − |
| Resveratrol 10 uM | + | − |
| Obeticholic acid 100 uM | + | = |
| DMSO | =(100.0) | =(100%) |

<90%: −
90% ≥ ≤110%: =
110% > ≤130%: +
130%>: ++

Table 12 shows compounds that increased the differentiation of naïve CD4+ T cells into Tregs (+, ++), or decreased the differentiation of naïve CD4+ T cells into Tregs (−). Compounds that reduce Tregs (−) may be useful for NASH and NAFLD.

Example 13. Effect of Compound Treatment on Cytokine Release from Human Peripheral Blood Monocytes (PBMCs)

Human donor blood (8 mL) was collected in sodium citrate CPT tubes and centrifuged at 1,600×g for 20 minutes at room temperature. Buffy coat containing PBMCs was collected and transferred to a 50 mL conical tube containing 30 mL of RPM 1-1640 medium at room temperature (supplemented with penicillin-streptomycin). PBMCs samples were centrifuged at 400×g for 10 minutes at 10° C. The pelleted PBMCs were washed twice in 10 ml of RPMI-1640 medium (supplemented with penicillin-streptomycin), then resuspended in RPMI-1640 medium (supplemented with penicillin-streptomycin, fetal bovine serum, and L-Glutamine). PBMCs were filtered through a 70 micron mesh to remove any cellular debris. The volume was adjusted to achieve 1.66×10$^6$ cells/mL, from which 180 μl (300,000 PBMCs) were added into each well in a 96-well plate (sterile, tissue culture treated, round bottom). PBMCs in a 96-well plate were rested for 30 minutes in a 37° C., 5% CO$_2$ incubator, then subsequently treated with 10 μl of indicated compound. After 2 hours 10 μL of LPS (O111:B4) 1 mg/mL was added to test wells. After 24 hours of incubation at 37° C., 5% $CO_2$, 100 μL of cell supernatant was collected and transferred to a 96-well plate (non-tissue treated, flat bottom). The plate was centrifuged at 350×g for 5 minutes at room temperature, and then the clear supernatant transferred to a new 96-well plate (non-tissue treated, flat bottom). The remaining cells were tested for viability using CellTiter-Glo® Luminescent Cell Viability Assay (Promega). The supernatant was analyzed for TNFα, IL-6 and IL-1β (kit LXSAHM-03; R&D Systems), using Luminex Immunoassay Technology (MAGPIX System). Cytokine levels of LPS treated DMSO control samples were set to 100%, and compound treated samples were expressed relative to this (Table 13).

TABLE 13

| Compound | Concentration (μM) | TNFα % of DMSO control | IL6 % DMSO control | IL1β % DMSO control |
|---|---|---|---|---|
| Propionate | 100 | + | + | + |
| Arabinose | 100 | + | + | = |
| butanediol | 100 | = | = | = |
| Beta-hydroxybutyrate (BHB) | 100 | − | = | − |
| Butyrate | 100 | ++ | + | − |
| Acetate | 100 | = | = | = |
| Quercetin | 100 | + | + | + |
| Resveratrol | 100 | + | + | = |

(−) ≥ 110% DMSO;
(=) 90% ≥ <110% DMSO
(+) 50% ≥ <90% DMSO
(++) < 50% DMSO

These data demonstrate that acylated active agents (e.g., those including propionate, butyrate, arabinose, quercetin, and/or resveratrol) can modulate reduce TNFα, IL6, and/or IL1β levels. Compounds that are active in this assay show anti-inflammatory activity in human monocyte cultures as shown by reduction in secreted proinflammatory cytokines. This is useful for the treatment of NAFLD and NASH.

Example 14. In Vitro Transformation and Detection of 1,3 Butane Diol

Stock solution of compound 78 was prepared at 10 mM in DMSO. FaSSIF was made by mixing sodium taurocholate (3.0 mM), lecithin (0.75 mM), and pancreatin (10 mg/mL) in prepared solution of sodium phosphate monobasic (28.4 mM), sodium hydroxide (8.7 mM), sodium chloride (105.9 mM), at pH 6.5. Compound 78 was added to FaSSIF to final concentration of 100 μM. Deuterium labeled compound d3-1,3 butanediol was spiked in the incubation mixture. Release of 1,3-butanediol was monitored via UHPLC-MSMS and comparing the retention time and corresponding fragmentation of released 1,3-butanediol to those of spiked d3-1,3-butanediol. Release of 1,3-butanediol was measured at 0 h, 2 h, and 24 h time points. At every given time point, samples were centrifuged at 14000 rpm for 10 minutes at 4° C. Supernatants were then transferred to HPLC vials and analyzed immediately.

These data demonstrate that compound 78 releases 1,3-butanediol in simulated intestinal fluids within the time period consistent with a typical residence in the gastrointestinal tract.

Example 15. Activity of Acylated Active Agents in a DIO Animal Model of NAFLD/NASH The effect of 8 weeks of treatment for the indicated compounds on metabolic liver disease in pre-biopsied, 43-week old male DIO-NASH mice was evaluated (12 animals per group). Male C57BL/6JRj mice were fed 40% fat (18% trans-fat), 40% carbohydrate (20% fructose), and 2% Cholesterol (AMLN) diet for 38 weeks. All mice entering the experiment were pre-biopsied stratified based on liver biopsy (only animals with fibrosis stage ≥1 and steatosis score ≥2 were included). Animals were randomized into groups based on Col1a1 immunostaining. Mice were treated for a total of 8 weeks of dosing (drugs in diet, ad lib). Groups: 1) NASH control, 2) compound 4, 6% in AMLN diet, 3) compound 14, 6% in AMLN diet, 4) Compound 53, 5% in AMLN diet, 5) compound 78, 1.5% in AMLN diet, 6) compound 15, 7% in AMLN diet, 7) resveratrol, 0.78% in AMLN diet, butane-1,3-diol 3% in drinking water 8) Elafibranor, 0.03% in AMLN diet. Elafibranor was supplied by the vendor. Body weight was measured daily for the entire study period. Food intake was monitored daily for first 14 days and then twice a week until study end. Day 28 collection of tail vein blood/serum and feces. Terminal plasma was collected for biomarker determination of liver transaminases (ALT, AST), triglyceride and cholesterol. Terminal liver was removed, weighed, and sampled for 1) FFPE (histology), 2) frozen (biochemistry and nucleic acid). Liver biopsy histology: pre- and post-treatment NAFLD Activity Score (HE) including Fibrosis Stage (PSR), 2) post-treatment steatosis (HE), 3) post-treatment lipid-droplet #+size (HE), 4) post-treatment Galectin-3 (IHC), 5) pre- and post-treatment Collagen 1a1 (IHC), 6) post-treatment a-SMA (IHC). Liver biochemical analysis for TG/TC/HP content.

Results of this study are shown in Table 14. Food intake was not affected by treatment with any compound (FIG. 7), but body weight was significantly reduced by all active treatments. Serum biomarkers of liver injury (liver transaminases, ALT and/or AST), were also significantly reduced by all active treatments.

TABLE 14

| Group # | Comp. | Animal model | Number of animals | Dose [% w/w in diet] | Dosing frequency | Dosing method |
|---|---|---|---|---|---|---|
| 1 | Control | DIO-NASH | 12 | NA | Ad libitum | In diet |
| 2 | 4 | DIO-NASH | 11 | 6 | Ad libitum | In diet |
| 3 | 14 | DIO-NASH | 12 | 6 | Ad libitum | In diet |
| 4 | 53 | DIO-NASH | 12 | 5 | Ad libitum | In diet |
| 5 | 78 | DIO-NASH | 12 | 1.5 | Ad libitum | In diet |
| 6 | 15 | DIO-NASH | 12 | 7 | Ad libitum | In diet |
| 7 | Resveratrol 1,3-butanediol | DIO-NASH | 13 | 0.78 3 | Ad libitum | In diet In water |
| 8 | Elafibranor | DIO-NASH | 12 | 0.03 | Ad libitum | In diet |

Example 16. Activity of Acylated Active Agents in a DIO Animal Model of NAFLD/NASH in Young Mice Species (number, sex, age/weight): C57BL/6 DIO mice (120+10 spares, male, ~18 weeks of age) from Jackson Laboratories, Stock #380050. Note: 18 week old DIO mice sent with a minimum body weight of 39 grams. Spare animals may be used to replace study animals, as required, euthanized after completion of dose administration or transferred to Testing Facility Docket 07-12.

Class of Compound: Synthetic, Small Molecule

Hazards: Unknown, use standard PPE.

Cage Side Observations (Animal Health Checks): Cage side animal's health checks will be performed at least once daily to check for general health, mortality and moribundity. Clinical Observations: Clinical observations will be performed per exception. Body Weights: Body weights for all animals will be recorded prior to Day 1 and at least twice weekly thereafter, including prior to necropsy (Day ~84).

Dose Administration: Dosing for Groups 3-8 will be provided ad libitum in the diet. Dosing for Groups 9 (Saline) and 10 (Semaglutide at 123.4 µg/kg) in a 5 mL/kg volume, will begin on Day 1, and be performed 3 times weekly for 12 weeks by SC administration. Residual Test Article: All residual high fat diets will be frozen at nominally −20° C., and at the end of the study, several pellets of the diets for groups 2-9 (in 50-ml conical tubes) will be shipped to Sponsor, and the rest will be discarded. Residual control diets (group 1) will be stored ambient, and at the end of the study, several pellets in a 50 mL conical tube will be shipped to Sponsor and the rest is discarded. Residual test material for Group 10 will be stored at nominally −70° C., and at the end of the study, an aliquot of test material will be shipped to Sponsor, and the rest will be discarded.

Fecal Pellet Collection: 2-3 fecal pellets will be collected from all animals on Day 1 at approximately 6 hours post feeding, and Days 42, and 84 (pre-euthanasia). Fecal pellets will be stored at nominally −70° C. and shipped to the Sponsor at the end of the study.

Food Consumption: Beginning on Day 1, food consumption will be measured in each Testing Facility Study No. UDI 18-01 Page 4 of 6 cage. The weight of the food removed from the cage and placed into the cage will be recorded (g) at least 3 times weekly for the duration of the study. The bedding will be examined for large pieces of chow at each measurement. Measurements will be provided in the Data Submission.

Insulin Tolerance Test (ipITT): On Day 75 (+/−2 days) an ipITT will be performed. Following an approximate 4 hour fast, 0.5 Units/kg body weight of insulin (Humulin R diluted in Humulin R sterile diluent to a concentration of 0.1 Unit/mL) will be administered at 5 mL/kg via IP injection. Blood will be collected pre-insulin challenge (t=0) and at t=15, 30, 60, 90, and 120 minutes following the insulin challenge. Whole blood glucose levels will be evaluated at all time points by a handheld glucometer and will be reported in the Data Submission. This will be scheduled on a Tuesday or Thursday to avoid Group 9/10 dosing days.

Oral Glucose Tolerance Test (oGTT) On Day 82 (+/−2 days) an oGTT will be performed. Following an approximate 4 hour fast, 2 g/kg glucose (50% Dextrose diluted in sterile water for injection to a concentration of 0.4 g/mL) will be administered at 5 mL/kg via oral gavage (PO). Blood will be collected pre-glucose challenge (t=0) and at t=15, 30, 60, 90, and 120 minutes following the glucose challenge. Whole blood glucose levels will be evaluated at all time points using a handheld glucometer and will be reported in the Data Submission. This will be scheduled on a Tuesday or Thursday to avoid Group 9/10 dosing days.

Interim Blood Collection: Whole blood (~0.125 mL) will be collected from all animals by tail snip on Days 1 (6 hours±5% post feed switch), 42 and 84 into K.2-EDTA microvettes or equivalent. Whole blood will be processed to plasma per Test Facility SOPs. Plasma will be divided into two aliquots of approximately 0.025 mL each and stored at nominally −70° C. and shipped to the Sponsor at the conclusion of the study. Exception for Group 3: Plasma will be aliquoted into tubes containing freshly prepared 300 mg/mL ascorbic acid: Sigma 95209-S0G in water (3 µL ascorbic acid/25 µL plasma).

Whole Blood for Glucose: Beginning prior to Day 1, and at least weekly thereafter, interim whole blood samples (~5 µL) will be collected and directly read using a handheld glucometer. Results will be recorded and reported in the Data submission.

Euthanasia and Terminal Blood Collection: Group 1-10 will be euthanized on ~Day 84. All animals will be euthanized by CO2 asphyxiation followed by thoracotomy and terminal blood collection. Whole blood will be collected via cardiac puncture into serum separator tube and processed to serum per facility SOPs. Serum samples will be divided into five aliquots; one with 30 µL for ALT/AST (aliquot #1), 75 µL for Lipid Panel Analysis (aliquot #2), 70 µL for TNF-a/IL-6 analysis (aliquot #3), 70 µL for TGF-–analysis (aliquot #4), and the residual serum (aliquot #5, if available) for the Sponsor. All serum samples will be stored at nominally −70° C. until analysis by the Testing Facility or shipped to the subcontractor for analysis, or Sponsor on dry ice for analysis (Sponsor's analysis will not be included in the Data Submission).

Tissue Collection: Following exsanguinations, all animals will have the whole liver and subcutaneous/abdominal fat pads harvested. Each tissue will be weighed. The left liver Testing Facility Study No. UDI 18-01 Page 5 of 6 lobe will then be placed in a cassette and fixed in 4% PF A, and stored at 2-5° C. until shipment to a subcontractor for further processing. The median and right lobe of Liver will be snapped frozen in liquid nitrogen. Samples will be stored at nominally −70° C. until shipped to the Sponsor on dry ice.

Subcutaneous and abdominal fat pads will be divided in half. Half of each pad will be placed in a cassette and fixed in 4% PF A and stored at 2-8° C. until shipped to the Sponsor at the conclusion of the study. The other half of each fat pad will be snapped frozen in liquid nitrogen. Samples will be stored at nominally −70° C. until shipped to the Sponsor on dry ice.

ALT/AST Serum Analyses: Terminal serum aliquot #1 will be measured for ALT and AST levels by ELISA by the Testing Facility and the results will be included in the Data Submission.

Lipid Panel Serum Analyses: Terminal serum aliquot #2 will be measured for HDL, LDL, triglycerides, and total cholesterol by a subcontractor and the results will be included in the Data Submission.

Serum Cytokines: Terminal serum aliquot #3 will be measured for TNF-a, TGF-/3 levels by multiplex, and terminal serum aliquot #4 IL-6 individually by a subcontractor and the results will be included in the Data Submission.

Data Submission: A data submission (Excel™) will be issued for this study, including animal assignment, individual and group means (as applicable) for times of dose administration and euthanasia, body weights, food consumption data, clinical observations, mortality (as applicable), serum chemistries, terminal collection data, and other data as applicable.

Data Retention: Data from this study will be retained at the Testing Facility for a period of 6 months from issuance of the study data. The Sponsor will be contacted to determine the disposition of the data prior to the expiration of 6 months retention period; disposition options are shipment to the Sponsor or retention by the Testing Facility (fee-based). If disposition of data is not resolved within 60 days of notification, the Testing Facility will dispose of the data.

Oral Glucose Tolerance Test (oGTT) On Day 82 (+/−2 days) an oGTT will be performed. Following an approximate 4 hour fast, 2 g/kg glucose (50% Dextrose diluted in sterile water for injection to a concentration of 0.4 g/mL) will be administered at 5 mL/kg via oral gavage (PO). Blood will be collected pre-glucose challenge (t=0) and at t=15, 30, 60, 90, and 120 minutes following the glucose challenge. Whole blood glucose levels will be evaluated at all time points using a handheld glucometer and will be reported in the Data Submission. Results are shown in Tables 15, 16, and 17.

TABLE 15

|  | % Weight change | % Difference compared to ctrl | P-value |
| --- | --- | --- | --- |
| HFD | 22.9 | ctrl |  |
| ND | −18.9 | −41.8 | 0.0001 (One-way ANOVA) |
| Compound 4 | 19 | −4 | 0.799 (One-way ANOVA) |
| Compound 14 | 16 | −7 | 0.2537 (One-way ANOVA) |
| Compound 15 | 23 | 0 | 0.9999 (One-way ANOVA) |
| Compound 53 | 10 | −13 | 0.0024 (One-way ANOVA) |
| Compound 184 | 11 | −12 | 0.0121 (One-way ANOVA) |
| Compoud 78 | 21 | −2 | 0.9935 (One-way ANOVA) |
| Saline | 26 | ctrl |  |

TABLE 16

|  | % HbA1c | P-value | Statistical method |
| --- | --- | --- | --- |
| HFD | 7.18 | ctrl |  |
| ND | 6.55 | 0.9271 | One-way ANOVA |
| Compound 4 | 4.89 | 0.0169 | One-way ANOVA |
| Compound 14 | 6.93 | 0.9994 | One-way ANOVA |
| Compound 15 | 6.50 | 0.8255 | One-way ANOVA |
| Compound 53 | 4.35 | 0.0006 | One-way ANOVA |
| Compound 184 | 5.96 | 0.2976 | One-way ANOVA |
| Compoud 78 | 6.14 | 0.4839 | One-way ANOVA |
| Saline | 5.96 | ctrl |  |
| Semaglutide | 7.90 | 0.8797 | Student's t test |

TABLE 17

|  | OGTT | P-value | P-value |
| --- | --- | --- | --- |
| HFD | 28853 |  |  |
| ND | 20182 | 0.0001 (One-way ANOVA) | <0.0001 (Student's t test) |
| Compound 4 | 25072 | 0.0665 (One-way ANOVA) | 0.0036 (Student's t test) |
| Compound 14 | 32591 | 0.0813 (One-way ANOVA) | 0.0816 (Student's t test) |
| Compound 15 | 32722 | 0.0574 (One-way ANOVA) | 0.0257 (Student's t test) |
| Compound 53 | 25779 | 0.1912 (One-way ANOVA) | 0.0131 (Student's t test) |
| Compound 184 | 27257 | 0.8100 (One-way ANOVA) | 0.1801 (Student's t test) |
| Compoud 78 | 29944 | 0.9637 (One-way ANOVA) | 0.4304 (Student's t test) |
| Saline | 33551 |  |  |
| Semaglutide | 18214 | <0.0001 (Student's t test) |  |

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of modulating a metabolic marker or a nonalcoholic fatty liver disease marker in a subject in need thereof or of ameliorating a metabolic disorder or nonalcoholic fatty liver disease in a subject in need thereof, the method comprising administering to the subject an effective amount of an active agent selected from the following structure:

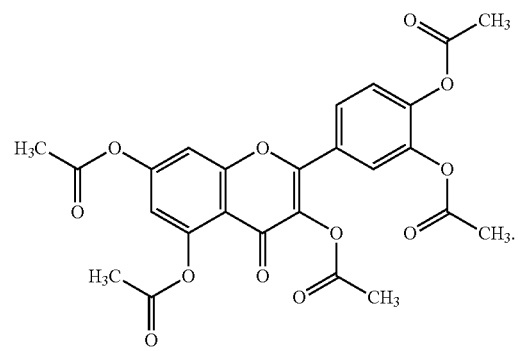 [SMILES: CC(=O)Oc1cc(OC(C)=O)c2c(=O)c(OC(C)=O)c(-c3ccc(OC(C)=O)c(OC(C)=O)c3)oc2c1]

2. The method of claim 1, wherein the method is of modulating a metabolic marker, and the metabolic marker is for an obesity disorder.

3. The method of claim 1, wherein the method is for ameliorating a metabolic disorder.

4. The method of claim 3, wherein the metabolic disorder is an obesity disorder.

5. The method of claim 1, wherein the total fat percentage, cellular adiposity, body mass index, rate of weight gain, abdominal fat quantity, ratio of white to brown fat, level of lipogenesis, or level of fat storage is reduced following the step of administering; or wherein the total fat percentage, cellular adiposity, body mass index, abdominal fat quantity, or ratio of white to brown fat is reduced following the step of administering.

6. The method of claim 1, wherein the subject is overweight or suffers from obesity, severe obesity, morbid obesity, or super obesity.

7. The method of claim 1, wherein the level of insulin, GLP-1, or PYY is increased following the administration of the active agent to the subject; or the level of blood sugar or hemoglobin A1c is reduced following the administration of the active agent to the subject; or the glucose tolerance is increased following the administration of the active agent to the subject.

8. The method of claim 1, wherein the method comprises administering the active agent to the subject orally.

9. The method of claim 8, wherein, following oral administration to the subject, the active agent is cleavable in the gastrointestinal tract of the subject.

* * * * *